(12) United States Patent
Zhou et al.

(10) Patent No.: US 7,491,735 B2
(45) Date of Patent: *Feb. 17, 2009

(54) CHEMOKINE RECEPTOR BINDING COMPOUNDS

(75) Inventors: Yuanxi Zhou, Surrey (CA); Gary J. Bridger, Bellingham, WA (US); Renato T. Skerlj, Vancouver (CA); David Bogucki, Surrey (CA); Wen Yang, Aldergrove (CA); Elyse Bourque, Langley (CA); Jonathan Langille, Langley (CA); Tong-Shuang Li, Langley (CA); Markus Metz, Delta (CA); Maria R. Di Fluri, Burnaby (CA); Siqiao Nan, ShenZhen (CN)

(73) Assignee: Genzyme Corporation, Cambridge, MA (US)

( * ) Notice: Subject to any disclaimer, the term of this patent is extended or adjusted under 35 U.S.C. 154(b) by 520 days.

This patent is subject to a terminal disclaimer.

(21) Appl. No.: 11/012,002

(22) Filed: Dec. 13, 2004

(65) Prior Publication Data

US 2005/0277670 A1 Dec. 15, 2005

Related U.S. Application Data

(60) Provisional application No. 60/528,975, filed on Dec. 11, 2003.

(51) Int. Cl.
*A61K 31/4468* (2006.01)
(52) U.S. Cl. .................. 514/318; 514/326; 546/194; 546/218
(58) Field of Classification Search .......... 514/328, 514/318, 194; 546/194, 218
See application file for complete search history.

(56) References Cited

U.S. PATENT DOCUMENTS

| | | | |
|---|---|---|---|
| 5,021,409 | A | 6/1991 | Murrer |
| 5,583,131 | A | 12/1996 | Bridger |
| 5,698,546 | A | 12/1997 | Bridger |
| 5,817,807 | A | 10/1998 | Bridger |
| 6,001,826 | A | 12/1999 | Murrer |
| 6,159,990 | A | 12/2000 | Lagu et al. |
| 6,319,932 | B1 | 11/2001 | Nerenberg et al. |
| 6,365,583 | B1 | 4/2002 | MacFarland |

FOREIGN PATENT DOCUMENTS

| | | |
|---|---|---|
| EP | 0 747 357 B1 | 1/2002 |
| EP | 1 219 605 A1 | 7/2002 |
| WO | WO-96/40136 | 12/1996 |
| WO | WO-00/56729 | 9/2000 |
| WO | WO-01/25200 | 4/2001 |
| WO | WO-02/22599 | 3/2002 |
| WO | WO-02/22600 | 3/2002 |
| WO | WO-02/34745 | 5/2002 |
| WO | WO-03/042178 | 5/2003 |

OTHER PUBLICATIONS

Thoma, et. al. "Orally Bioavailable Competitive CCR5 Antagonists" Journal of Medicinal Chemistry 2004, 47, 1939-1955.*
Martin, Yvonne C. et. al. "Do Structurally Similar Molecules Have Similar Biological Activity?" Journal of Medicinal Chemistry 2002, 45, 4350-4358.*
David R. Lide, ed., CRC Handbook of Chemistry and Physics, 88th Edition (Internet Version 2008), "http://www.hbcpnetbase.com" CRC Press/Taylor and Francis, Boca Raton, FL. "Definitions of Scientific Terms" "aryl groups" Section 2, p. 30.*
"aryl" Hawley's Condensed Chemical Dictionary, 14th Edition Hawley's Condensed Chemical Dictionary, 14th Edition, 2002, Wiley online.*
General Chemistry Glossary, online "http://antoine.frostburg.edu/cgi-bin/senese/searchglossary.cgi?query=aryl&shtml=%2Fchem" defines "aryl".*
A. D. McNaught and A. Wilkinson "Compendium of Chemical Terminology" "aryl", The Gold Book, Second Edition "http://old.iupac.org/publications/compendium/index.html" Blackwell Science, 1997.*
Pozharskii et. al. Heterocycles in Life and Society Wiley, 1997, pp. 1-6.*
Abi-Younes et al., Circ. Res. (2000) 86:131-138.
Aiuti et al., J. Exp. Med. (1997) 185:111-120.
Alkhatib et al., Science (1996) 272:1955-1958.
Arai et al., Eur. J. Haematol. (2000) 64:323-332.
Arenburg et al., J. Leukocyte Biol. (1997) 62:554-562.
Balashov et al., PNAS USA (1999) 96:6873-6878.
Blaak et al., Proc. Natl. Acad. Sci. USA (2000) 97:1269-1274.
Blanco et al., Antimircrobial. Agents and Chemother. (2000) 44:51-56.
Bleul et al., J. Exp. Med. (1998) 187:753-762.
Bleul et al., Nature (1996) 382:829-833.
Bradstock et al., Leukemia (2000) 14:882-888.
Bridger et al., Advances in Antiviral Drug Design, vol. 3, E. De Clercq (Ed.), JAI press (1999) pp. 161-229.
Bridger et al., J. Med. Chem. (1999) 42:3971-3981.
Burger et al., Blood (1999) 94:3658-3667.

(Continued)

*Primary Examiner*—Rita J Desai
*Assistant Examiner*—David K O'Dell
(74) *Attorney, Agent, or Firm*—Morrison & Foerster LLP

(57) ABSTRACT

The present invention relates to chemokine receptor binding compounds, pharmaceutical compositions and their use. More specifically, the present invention relates to modulators of chemokine receptor activity, preferably modulators of CCR5. These compounds demonstrate protective effects against infection of target cells by a human immunodeficiency virus (HIV).

6 Claims, No Drawings

OTHER PUBLICATIONS

Carroll et al., Science (1997) 276:273-276.
Cocchi et al., Science (1995) 270:1811-1815.
Connor and Ho, J. Virol. (1994) 68:4400-4408.
Deng et al., Nature (1996) 381:661-666.
Donzella et al., Nature Medicine (1998) 4:72-77.
Dragic et al., Nature (1996) 381:667-673.
Egberink et al., J. Virol. (1999) 73:6346-6352.
Eitner et al., Transplantation (1998) 66:1551-1557.
Fedyk et al., J. Leukocyte Biol. (1999) 66:667-673.
Feng et al., Science (1996) 272:872-877.
Gerard et al., Natl. Immunol. (2001) 2(2):108-115.
Gonzalo et al., J. Immunol. (2000) 165:499-508.
Gupta et al., J. Biolog. Chem. (1998) 7:4282-4287.
Ishii et al., J. Immunol. (1999) 163:3612-3620.
Lataillade et al., Blood (1999) 95:756-768.
Liu et al., Cell (1996) 86:367-377.
Luster, New Eng. J. Med. (1998) 338(7):436-445.
Maekawa et al., Internal Medicine (2000) 39:90-100.
Michael et al., J. Virol. (1998) 72:6040-6047.
Michael et al., Nature Med. (1997) 3:338-340.
Miedema et al., Immune, Rev. (1994) 140:35.
Moore et al., J. of Invest. Med. (1998) 46:113-120.
Moore et al., Trends Cardiovasc. Med. (1998) 8:51-58.
Murdoch et al., Blood (2000) 95:3032-3043.
Murphy et al., Pharmacol. Rev. (2000) 52(1):145-176.
Nagasawa et al., Nature (1996) 382:635-638.
Nagase et al., J. Immunol. (2000) 164:5935-5943.
Nanki et al., J. Immunol. (2000) 164:5010-5014.
Oberlin et al., Nature (1996) 382:833-835.
Obrien et al., Lancet (1997) 349:1219.
Panzer et al., Transplantation (2004) 78(9):1341-1350.
Peled et al., Blood (2000) 95:3289-3296.
Peled et al., Science (1999) 283:845-848.
Ponath, Exp. Opin. Invest. Drugs (1998) 7:1-18.
Ma et al., Immunity (1999) 10:463-471.
Rana et al., J. Virol. (1997) 71:3219-3227.
Robinson et al., Cancer Res. (2003) 63(23):8360-8365.
Salcedo et al., Am. J. Pathol. (1999) 154:1125-1135.
Samson et al., Nature (1996) 382:722-725.
Schols et al., Anitviral Research (1997) 35:147-156.
Schols et al., J. Exp. Med. (1997) 186:1383-1388.
Schuitemaker et al., J. Virol. (1992) 66:1354-1360.
Seghal et al., J. Surg. Oncol. (1998) 69:99-104.
Simmons et al., J. Virol. (1996) 70:8355-8360.
Simmons et al., J. Virol. (1998) 72:8453-8457.
Szekanecz et al., Seminars in Immunology (2003) 15:15-21.
Tachibana et al., Nature (1998) 393:591-594.
Tan et al., Expert Opin. Investig. Drugs (2003) 12(11):1765-1776.
Tersmette et al., J. Virol. (1988) 62:2026-2032.
Theodorou et al., Lancet (1997) 349:1219-1220.
Viardot et al., Ann. Hematol. (1998) 77:195-197.
Wyatt et al., Science (1998) 280:1884-1888.
Xia et al., J. Neurovirology (1999) 5:32-41.
Yssel et al., Clinical and Experimental Allergy (1998) 28:104-109.
Yun et al., Circulation (2004) 109(7):932-937.
Zhang et al., AIDS Res. Hum. Retroviruses (1997) 13:1357-1366.
Zhang et al., J. Virol. (1998) 72:9307-9312.
Zhang et al., J. Virol. (1999) 73:3443-3448.
Zou et al., Nature (1998) 393:591-594.
Databse CAPLUS on STN, No. 49:17187, accession No. 1955:17187.
International Search Report for PCT/US04/41865, mailed on Oct. 14, 2005, 3 pages.
Mensonides-Harsema et al., J. Med. Chem. (2000) 43:432-439.
International Search Report for PCT/US06/22897, date mailed on Mar. 29, 2007, 4 pages.

* cited by examiner

CHEMOKINE RECEPTOR BINDING COMPOUNDS

CROSS-REFERENCE TO RELATED APPLICATIONS

This application claims priority from U.S. Provisional Application Ser. No. 60/528,975, filed Dec. 11, 2003. The contents of this document are incorporated herein by reference.

TECHNICAL FIELD

This invention generally relates to novel compounds, pharmaceutical compositions and their use. More specifically, these novel compounds may be modulators of chemokine receptor activity, preferably modulators of chemokine receptor CCR5, and may further demonstrate protective effects against infection in target cells by a human immunodeficiency virus (HIV). In another aspect, the compounds in the present invention may be useful in the treatment and prevention of various inflammatory and autoimmune diseases.

BACKGROUND OF THE INVENTION

Approximately 40 human chemokines have been described that function at least in part, by modulating a complex and overlapping set of biological activities important for the movement of lymphoid cells and extravasation and tissue infiltration of leukocytes in response to inciting agents (See, for example: P. Ponath, *Exp. Opin. Invest. Drugs,* 7:1-18, 1998). These chemotactic cytokines, or chemokines, constitute a family of proteins, approximately 8-10 kDa in size, that are released by a wide variety of cells, to attract macrophages, T cells, eosinophils, basophils, and neutrophils to sites of inflammation and also play a role in the maturation of cells of the immune system. Chemokines appear to share a common structural motif that consists of 4 conserved cysteines involved in maintaining tertiary structure. There are two major subfamilies of chemokines: the "CC" or β-chemokines and the "CXC" or α-chemokines, depending on whether the first two cysteines are separated by a single amino acid, i.e., CXC or are adjacent, i.e., CC.

These chemokines bind specifically to cell-surface receptors belonging to the family of G-protein-coupled seven-transmembrane proteins which are referred to as "chemokine receptors", and mediate biological activity through these receptors. The chemokine receptor is classified based upon the chemokine that constitutes the receptor's natural ligand. Chemokine receptors of the β-chemokines are designated "CCR"; while those of the β-chemokines are designated "CXCR." These chemokine receptors include but are not limited to CCR1, CCR2, CCR2A, CCR2B, CCR3, CCR4, CCR5, CCR6, CXCR3 and CXCR4 (see for a complete review, Murphy et al. *Pharmacol. Rev.* 52(1), 145-176 (2000)).

Chemokines are considered to be principal mediators in the initiation and maintenance of inflammation (see *Chemokines in Disease* published by Humana Press (1999), Edited by C. Herbert; Murdoch et al. *Blood* 95, 3032-3043 (2000)). More specifically, chemokines have been found to play an important role in the regulation of endothelial cell function, including proliferation, migration and differentiation during angiogenesis and re-endothelialization after injury (Gupta et al., *J. Biolog. Chem.,* 7:4282-4287, 1998). Both chemokine receptors CXCR4 and CCR5 have been implicated in the etiology of infection by human immunodeficiency virus (HIV).

In most instances, HIV initially binds via its gp120 envelope protein to the CD4 receptor of the target cell. A conformational change appears to take place in the gp120 which results in its subsequent binding to a chemokine receptor, such as CCR5 (Wyatt et al., *Science,* 280:1884-1888 (1998)). HIV-1 isolates arising subsequently in the infection bind to the CXCR4 chemokine receptor. The observed binding of another related retrovirus, feline immunodeficiency virus, to a chemokine receptor without needing to bind first to the CD4 receptor, suggests that chemokine receptors may be the primordial obligate receptors for immunodeficiency retroviruses.

Following the initial binding by HIV to CD4, virus-cell fusion results, which is mediated by members of the chemokine receptor family, with different members serving as fusion cofactors for macrophage-tropic (M-tropic) and T cell linetropic (T-tropic) isolates of HIV-1 (Carroll et al., *Science,* 276: 273-276 1997; Feng et al. *Science* 272, 872-877 (1996); Bleul et al. *Nature* 382, 829-833 (1996); Oberlin et al. *Nature* 382, 833-835 (1996); Cocchi et al. *Science* 270, 1811-1815 (1995); Dragic et al. *Nature* 381, 667-673 (1996); Deng et al. Nature 381, 661-666 (1996); Alkhatib et al. *Science* 272, 1955-1958, (1996)). During the course of infection within a patient, it appears that a majority of HIV particles shift from the M-tropic to the more aggressive pathogenic T-tropic viral phenotype (Miedema et al., *Immune. Rev.,* 140:35 (1994); Blaak et al. *Proc. Natl. Acad. Sci.* 97, 1269-1274 (2000); Simmonds et al. *J. Virol.* 70, 8355-8360 (1996); Tersmette et al. *J. Virol.* 62, 2026-2032, (1988); Connor, R. I., Ho, D. D. *J. Virol.* 68, 4400-4408 (1994); Schuitemaker et al. *J. Virol.* 66, 1354-1360 (1992)). The M-tropic viral phenotype correlates with the virus' ability to enter the cell following binding of the CCR5 receptor, while the T-tropic viral phenotype correlates with viral entry into the cell following binding and membrane fusion with the CXCR4 receptor. Clinically, observations suggest that patients who possess genetic mutations in the CCR5 or CXCR4 appear resistant or less susceptible to HIV infection (Liu et al. *Cell* 86, 367-377 (1996); Samson et al. *Nature* 382, 722-725 (1996); Michael et al. *Nature Med.* 3, 338-340 (1997); Michael et al. *J. Virol.* 72, 6040-6047 (1998); Obrien et al. *Lancet* 349, 1219 (1997); Zhang et al. *AIDS Res. Hum. Retroviruses* 13, 1357-1366 (1997); Rana et al. *J. Virol.* 71, 3219-3227 (1997); Theodorou et al. *Lancet* 349, 1219-1220 (1997)). Despite the number of chemokine receptors which have been reported to mediate HIV entry into cells, CCR5 and CXCR4 appear to be the only physiologically relevant coreceptors used by a wide variety of primary clinical HIV-1 strains (Zhang et al. *J. Virol.* 72, 9307-9312 (1998); Zhang et al. *J. Virol.* 73, 3443-3448 (1999); Simmonds et al. *J. Virol.* 72, 8453-8457 (1988)). Fusion and entry of T-tropic viruses that use CXCR4 are inhibited by the natural CXC-chemokine stromal cell-derived factor-1 (SDF-1). On the other hand, fusion and entry of M-tropic viruses that use CCR5 are inhibited by the natural CC-chemokines namely, Regulated on Activation Normal T-cell Expressed and Secreted (RANTES or CCL5) and Macrophage Inflammatory proteins (MIP-1 alpha and MIP-1 beta or CCL3 and CCL4, respectively). SDF-1 is known as CXCL12 or Pre B-cell stimulating factor (PBSF).

However, the binding of chemokine receptors to their natural ligands appears to serve a more evolutionary and central role than only as mediators of HIV infection. The binding of the natural ligand, PBSF/SDF-1 to the CXCR4 chemokine receptor provides an important signaling mechanism. CXCR4 or SDF-1 knock-out mice exhibit cerebellar, cardiac and gastrointestinal tract abnormalities and die in utero (Zou et al., *Nature,* 393:591-594 (1998); Tachibana et al., *Nature,*

393:591-594 (1998); Nagasawa et al. *Nature* 382, 635-638 (1996)). CXCR4-deficient mice also display hematopoietic defects (Nagasawa et al. *Nature* 382, 635-638 (1996)). Furthermore, the migration of CXCR4 expressing leukocytes and hematopoietic progenitors to SDF-1 appears to be important for maintaining B-cell lineage and localization of CD34+ progenitor cells in bone marrow (Bleul et al. *J. Exp. Med.* 187, 753-762 (1998); Viardot et al. *Ann. Hematol.* 77, 195-197 (1998); Auiti et al. *J. Exp. Med.* 185, 111-120 (1997); Peled et al. *Science* 283, 845-848 (1999); Qing et al. *Immunity* 10, 463-471 (1999); Lataillade et al. *Blood* 95, 756-768 (1999); Ishii et al. *J. Immunol.* 163, 3612-3620 (1999); Maekawa et al. *Internal Medicine* 39, 90-100 (2000); Fedyk et al. *J. Leukocyte Biol.* 66, 667-673 (1999); Peled et al. *Blood* 95, 3289-3296 (2000)).

The signal provided by SDF-1 on binding to CXCR4 may also play an important role in tumor cell proliferation and regulation of angiogenesis associated with tumor growth (See "*Chemokines and Cancer*" published by Humana Press (1999); Edited by B. J. Rollins; Arenburg et al. *J. Leukocyte Biol.* 62, 554-562 (1997); Moore et al. *J. Invest. Med.* 46, 113-120 (1998); Moore et al. *Trends cardiovasc. Med.* 8, 51-58 (1998); Seghal et al. *J. Surg. Oncol.* 69, 99-104 (1998)). Known angiogenic growth factors VEG-F and bFGF, upregulated levels of CXCR4 in endothelial cells, and SDF-1 can induce neovascularization in vivo (Salcedo et al. *Am. J. Pathol.* 154, 1125-1135 (1999)). Furthermore, leukemia cells that express CXCR4 migrate and adhere to lymph nodes and bone marrow stromal cells that express SDF-1 (Burger et al. *Blood* 94, 3658-3667 (1999); Arai et al. *Eur. J. Haematol.* 64, 323-332 (2000); Bradstock et al. *Leukemia* 14, 882-888 (2000)).

The binding of SDF-1 to CXCR4 has also been implicated in the pathogenesis of atherosclerosis (Abi-Younes et al. *Circ. Res.* 86, 131-138 (2000)), renal allograft rejection (Eitner et al. *Transplantation* 66, 1551-1557 (1998)), asthma and allergic airway inflammation (Yssel et al. *Clinical and Experimental Allergy* 28, 104-109 (1998); *J. Immunol.* 164, 5935-5943 (2000); Gonzalo et al. *J. Immunol.* 165, 499-508 (2000)), Alzheimer's disease (Xia et al. *J. Neurovirology* 5, 32-41 (1999)) and arthritis (Nanki et al. *J. Immunol.* 164, 5010-5014 (2000)).

Platelets have also been shown to secrete the chemokine RANTES upon activation, and that the presence of RANTES on the endothelium promotes the arrest of monocytes on the inflamed endothelium, an important step in atherogenesis as the conversion of macrophages into foam cells in the subendothelium is a central process in atheroma formation (Tan, et al., *Expert Opin. Investig. Drugs,* 12(11):1765-1776 (2003)). Hence, the inhibition or prevention of the binding of RANTES, directly or indirectly, to the CCR5 receptor could potentially attenuate the development of atherosclerosis. For example, Met_RANTES has also been shown to inhibit the binding of monocytes to the activated endothelium (Tan, et al., supra).

In attempting to better understand the relationship between chemokines and their receptors, recent experiments to block the fusion, entry and replication of HIV via the CXCR4 chemokine receptor were carried out through the use of monoclonal antibodies or small molecules that appear to suggest a useful therapeutic strategy (Schols et al., *J. Exp. Med.* 186:1383-1388 (1997); Schols et al., *Antiviral Research* 35:147-156 (1997); Bridger et al. *J. Med. Chem.* 42, 3971-3981 (1999); Bridger et al. "Bicyclam Derivatives as HIV Inhibitors" in *Advances in Antiviral Drug Design* Volume 3, p 161-229; Published by JAI press (1999); Edited by E. De Clercq). Small molecules, such as bicyclams, appear to specifically bind to CXCR4 and not CCR5 (Donzella et al., *Nature Medicine,* 4:72-77 (1998)). These experiments demonstrated interference with HIV entry and membrane fusion into the target cell in vitro. More recently, bicyclams were also shown to inhibit fusion and replication of Feline Immunodeficiency Virus (FIV) that uses CXCR4 for entry (Egberink et al. *J. Virol.* 73, 6346-6352 (1999)). CCR5 blocking agents include monoclonal antibodies, some which selectively block HIV coreceptor activity but not chemokine binding, and chemokine derivatives, such as truncated versions of RANTES, Met-RANTES, and AOP-RANTES and the viral chemokine KSHV vMIP-II, all which block both chemokine and HIV interaction with CCR5 but are not selective (reviewed by Murphy et al. *Pharmacol. Rev.* 52(1), 145-176 (2000)).

Additional experiments have shown that the bicyclam dose-dependently inhibits binding of 125I-labeled SDF-1 to CXCR4 and the signal transduction (indicated by an increase in intracellular calcium) in response to SDF-1. Thus, the bicyclam also functioned as an antagonist to the signal transduction resulting from the binding of stromal derived factor or SDF-1α, the natural chemokine to CXCR4. Bicyclams also inhibited HIV gp120 (envelope)-induced apoptosis in non-HIV infected cells (Blanco et al. *Antimicrobial Agents and Chemother.* 44, 51-56 (2000)).

Passive immunization with anti-MIP-1 alpha has been shown to delay the onset and reduce the severity of collagen-induced-arthritis (CIA) in mice, where the CIA model is an established murine model representing human rheumatoid arthritis (Szekanecz, Z., et al., *AP, Seminars in Immunology,* 15 (2003), p. 15-21). Other studies have also shown that agents that block the CCR5 receptor may provide a rational approach to the treatment of multiple sclerosis. Administration of anti-MIP-1 alpha antiserum has been shown to prevent CNS infiltration by PBMC in mice with experimental allergic encephalomyelitis, a rodent model of multiple sclerosis (Balashov, K. E., et al., *Proc. Natl. Acad. Sci. USA,* Vol. 96 (1999), p. 6873-6878). Other studies involving chronic rejection of transplanted hearts or cardiac allograft vasculopathy (CAV) and acute renal allograft rejection have shown that blocking chemokine receptors such as CCR5 may provide unique therapeutic approaches in the treatment or prevention of such diseases (Yun J J, et al., Circulation, 2004, Vol. 109(7), p. 932-7, Panzer U., et al., Transplantation, 2004, Vol. 78(9), p. 1341-50). For example, antagonism of the chemokine receptors CCR1 and CCR5 with Met-RANTES attenuated CAV development by reducing mononuclear cell recruitment to the transplanted heart. Met-CCL5, an antagonist of CCR1 and CCR5, had been tested and shown to inhibit the growth of breast tumors (Robinson S C. et al, *Cancer Res.,* 2003, Vol. 63(23), p. 8360-5).

Chemokines, as indicated above, play an important role and are implicated in a wide variety of human disease such as in autoimmune disease, allograft rejection, infection, allergies, neoplasia, and vascular abnormalities. In addition to its contributory role in HIV infection, the chemokine receptor CCR5 has been associated with diseases such as the inflammatory demyelinating diseases of the central nervous system, including multiple sclerosis and experimental autoimmune encephalomyelitis, rheumatoid arthritis, intestinal inflammation, allograft rejection, asthma, and cardiovascular disease (reviewed in Gerard et al. *Natl. Immunol.* 2(2), 108-115 (2001) and Luster, A., *N. Eng. J. Med.,* 338 (7), 436-445 (1998)). The CCR5 receptor is expressed on T-lymphocytes, and macrophages and reports of CCR5 on neurons, astrocytes, capillary endothelial cells, epithelium, vascular smooth muscle, and fibroblast have been published. The natural ligands that bind to the CCR5 receptor, in addition to RANTES and MIP-1 alpha/beta, are monocyte chemoattractant protein 2 (MCP-2 or CCL8).

U.S. Pat. Nos. 5,583,131; 5,698,546; 5,817,807; 5,021,409; and 6,001,826 which are incorporated herein in their entirety by reference, disclose cyclic compounds that are active against HIV-1 and HIV-2 in in vitro tests. It was subsequently discovered and further disclosed in PCT WO 02/34745 that these compounds exhibit anti-HIV activity by binding to the chemokine receptor CXCR4 and/or CCR5 expressed on the surface of certain cells of the immune system. This competitive binding thereby protects these target cells from infection by HIV which utilize the CXCR4 receptor for entry. In addition, these compounds antagonize the binding, signaling and chemotactic effects of the natural ligand for CXCR4, the chemokine stromal cell-derived factor 1α (SDF-1). Furthermore, these compounds demonstrate protective effects against HIV infection of target cells by binding in vitro to the CCR5 receptor.

Additionally, U.S. Pat. No. 6,365,583 discloses that these cyclic polyamine antiviral agents described in the above-mentioned patents/patent applications have the effect of enhancing production of white blood cells as well as exhibiting antiviral properties. Thus, these agents are useful for controlling the side-effects of chemotherapy, enhancing the success of bone marrow transplantation, enhancing wound healing and burn treatment, as well as combating bacterial infections in leukemia.

More recently, PCT WO 00/56729, PCT WO 02/22600, PCT WO 02/22599, and PCT WO 02/34745 describe a series of heterocyclic compounds that exhibit anti-HIV activity by binding to the chemokine receptors CXCR4 and CCR5 expressed on the surface of certain cells of the immune system. This competitive binding thereby protects these target cells from infection by HIV which utilize the CXCR4 or CCR5 receptors for entry. In addition, these compounds antagonize the binding, signaling and chemotactic effects of the natural ligand for CXCR4, the chemokine stromal cell-derived factor 1α (SDF-1) and/or the natural ligand for CCR5, the chemokine RANTES.

The chemokine receptor, CXCR4 has been found to be associated with the vascularization of the gastrointestinal tract (Tachibana et al., *Nature*, 393:591-594 (1998)) as well as in hematopoiesis and cerebellar development (Zou et al., *Nature*, 393:591-594 (1998)). Interference with any of these important functions served by the binding of pre-B-cell growth-stimulating factor/stromal derived factor (PBSF/SDF-1) to the CXCR4 chemokine receptor results in lethal deficiencies in vascular development, hematopoiesis and cardiogenesis. Similarly, fetal cerebellar development appears to rely upon the effective functioning of CXCR4 in neuronal cell migration and patterning in the central nervous system. This G-protein-coupled chemokine receptor appears to play an important role in ensuring the necessary patterns of migration of granule cells in the cerebellar anlage.

Herein, we disclose compounds that have unique chemical attributes and that exhibit protective effects against HIV infection of target cells by binding to chemokine receptor CCR5. In addition, these compounds antagonize the binding, signaling and chemotactic effects of the natural ligand for CCR5, the chemokine RANTES.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are hereby incorporated in their entirety by reference herein.

DISCLOSURE OF THE INVENTION

The present invention provides novel compounds that may modulate chemokine receptors and interfere with the binding of the natural ligand thereto. The compounds of the present invention may be useful as agents demonstrating protective effects on target cells from HIV infection. In another aspect, the present invention provides novel compounds that may be useful for the treatment and prevention of inflammatory and autoimmune diseases. Embodiments of the present invention are compounds that may act as antagonists or agonists of chemokine receptors, which may be useful as agents capable of reconstituting the immune system by increasing the level of CD4$^+$ cells; as antagonist agents of apoptosis in immune cells, such as CD8$^+$ cells, and neuronal cells; as antagonist agents of migration of human bone marrow B lineage cells to stromal-derived factor 1, as well as other biological activities related to the ability of these compounds to inhibit the binding of chemokines to their receptors.

More particularly, the present invention relates to novel piperidine derivatives that may bind to chemokine receptors, preferably CCR5 receptors. In one example, the invention is directed to a compound or a pharmaceutically acceptable salt thereof, having the formula

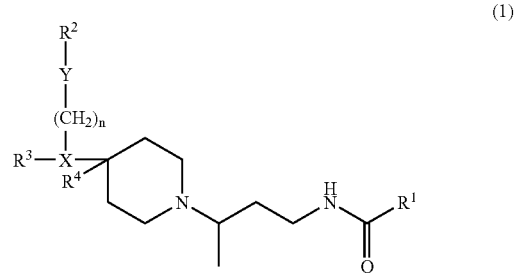

(1)

or a pharmaceutically acceptable salt thereof,
where X is carbon or nitrogen;
Y is oxygen if X is carbon, or a bond if X is nitrogen;
n is 0-1;
R$^1$ is an optionally substituted aryl or heteroaryl;
R$^2$ is an optionally substituted aryl or heteroaryl, or N=(C$_{1-6}$ alkyl);
R$^3$ is an optionally substituted aryl, heteroaryl, or a phenyl fused with a 5- or 6-membered heterocyclic ring; and
R$^4$ is hydrogen or alkyl.

In the above formula 1, X may be carbon and Y is oxygen. Alternatively, X may be nitrogen and Y is a bond.

In the above formula 1, R$^1$ may be phenyl, pyrimidinyl, pyridinyl, pyridine N-oxide, thiophenyl, isoxazolyl, or pyrazolyl, each of which is optionally substituted by one or more halogen, alkyl, amine or heteroaryl.

In the above formula 1, R$^2$ may be phenyl, pyridinyl, thiazolyl, furanyl, or thiophenyl, each of which is optionally linked to one or more C$_{1-6}$ alkyl, alkoxy, trifluoromethyl, carboxylalkyl, cyano, or halogen.

In the above formula 1, R$^3$ may be phenyl, pyridinyl, thiazolyl, oxazolyl, pyrimidinyl, indolyl, indolinyl, isoindolinyl, 1,3-benzodioxolyl, 1,4-benzodioxanyl, benzofuranyl, 2,3-dihydroxybenzofuranyl or phthalanyl, each of which is optionally linked to one or more C$_{1-6}$ alkyl, trifluoromethyl, oxotrifluoromethyl, carboxylalkyl, cyano, halogen, sulfanyl, SO$_2$R$^9$, where R$^9$ is alkyl, amine or amino alkyl, C(O)R$^{10}$, where R$^{10}$ is alkyl, amine, morpholine, NMe$_2$, N(OMe)Me, NPh, piperidine, NHMe, piperazine, NHCH$_2$C(O)OMe or PhC(O)OH, OR$^{11}$, where R$^{11}$ is H, alkyl, (CH$_2$)$_2$OMe, CH$_2$C(O)NH$_2$, CH$_2$C(O)NHNH$_2$, CH$_2$C(O)OCMe$_3$, CH$_2$C(O)OMe, CH$_2$C(O)OH, PhC(O)OH, PhC(O)NH$_2$, SO$_2$Me, C(O)Me, C(O)OMe, C(O)NEt$_2$, C(O)NMe$_2$ or

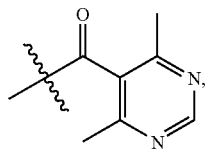

NHR$^{12}$, where R$^{12}$ is H, C(O)Me, C(O)CF$_3$, SO$_2$Me, C(O)NH$_2$, C(O)NMe$_2$ or

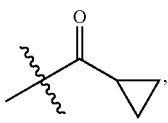

NO$_2$, CH$_2$PhC(O)OH, SOMe, CH$_2$NHC(O)Me, morpholine, CH=CHC(O)OMe, CH=CHC(O)OH,

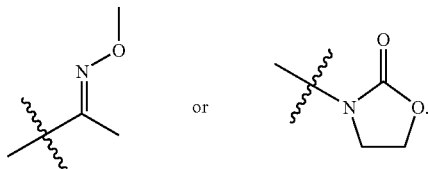

In one aspect, R$^3$ is a phenyl fused with a 5- or 6-membered heterocyclic ring. For example, R$^3$ may be indolyl, benzodioxolyl, dihydrobenzofuranyl, dihydroisobenzofuranyl, benzofuranyl, or dihydrobenzodioxinyl.

In the above formula 1, R$^4$ may be hydrogen or alkyl. In particular examples, R$^4$ is hydrogen.

In another example, the invention is directed to a compound or a pharmaceutically acceptable salt thereof, having the formula

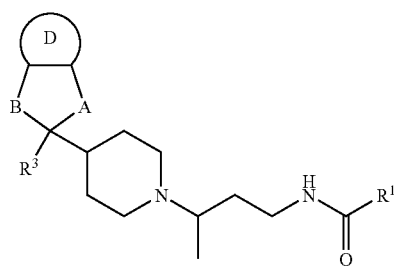

(2)

or a pharmaceutically acceptable salt thereof,
where A and B are independently CH$_2$, O, or C=NH;
Ring D is an optionally substituted 6-membered aromatic ring; and
R$^1$ and R$^3$ are independently an optionally substituted aryl or heteroaryl.

In the above formula 2, ring D may be pyridine or phenyl.

In the above formula 2, R$^1$ may be phenyl, pyrimidinyl, pyridine N-oxide or pyridinyl, each optionally substituted by one or more halogen or alkyl.

In the above formula, R$^3$ may be phenyl, which may be linked to a substituent selected from the group consisting of alkoxy, trifluoromethyl, oxotrifluoromethyl, cyano, halogen, sulfanyl, SO$_2$R$^9$ where R$^9$ is alkyl or amino alkyl, sulfinyl, carbonyl and

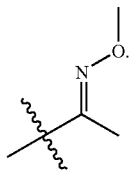

The present invention also provides pharmaceutical compositions comprising compounds having Formula 1 or 2, and a pharmaceutically acceptable carrier. Furthermore, the present invention provides methods for treating a CCR5 mediated disease in a cell, tissue or organ, comprising contacting a compound having Formula 1 or 2 with the system, thereby treating a CCR5-mediated disease. The present invention also provides methods for treating a CCR5 mediated disease in a human or animal subject, comprising administering a compound having Formula 1 or 2 with the subject, thereby treating a CCR5-mediated disease.

Examples of CCR5-mediated diseases that may be treated using the compounds of the present invention include but are not limited to HIV, an inflammatory demyelinating disease of the central nervous system, an autoimmune disease, multiple sclerosis, experimental autoimmune encephalomyelitis, psoriatic or rheumatoid arthritis, intestinal inflammation, allograft rejection, asthma, cardiovascular disease, atherosclerosis, allergic disease, allergic rhinitis, dermatitis, conjunctivitis, hypersensitivity lung disease, hypersensitivity pneumonitis, eosinophilic pneumonia, delayed-type hypersensitivity, interstitial lung disease (ILD), idiopathic pulmonary fibrosis, ILD associated with rheumatoid arthritis, systemic lupus erythematosus, ankylosing spondylitis, systemic sclerosis, Sjogren's syndrome, polymyositis, dermatomyositis, systemic anaphylaxis, myastenia gravis, juvenile onset diabetes, glomerulonephritis, autoimmune throiditis, graft rejection, allograft rejection, graft-versus-host disease, inflammatory bowel disease, Crohn's disease, ulcerative colitis, spondyloarthropathy, scleroderma; psoriasis, inflammatory dermatosis, dermatitis, eczema, atopic dermatitis, allergic contact dermatitis, urticaria, vasculitis, eosinphilic myotis, eosiniphilic fasciitis, tumor or cancer.

The compounds of Formula 1 or 2 may form hydrates or solvates, and may be in any stereoisomeric forms and mixtures of stereoisomeric forms thereof. Racemate compounds may be separated into individual isomers using known separation and purification methods. Individual optical isomers and a mixture thereof, are included in the scope of the present invention.

MODES OF CARRYING OUT THE INVENTION

In one aspect, the invention provides compounds having Formula 1 or 2 described above, which may be chemokine modulators of chemokine receptors.

In more detail, the compounds may bind chemokine receptors and interfere with the binding of the natural ligand thereto, and may demonstrate protective effects on target cells from HIV infection. The compounds may be useful as antagonists or agonists of chemokine receptors, and are thus capable of reconstituting the immune system by increasing the level of CD4+ cells; as antagonist agents of apoptosis in immune cells, such as CD8+ cells, and neuronal cells; as antagonist agents of migration of human bone marrow B lineage cells to stromal-derived factor 1, as well as other biological activities related to the ability of these compounds to inhibit the binding of chemokines to their receptors.

Chemokine antagonists that interfere in the binding of a chemokine to its receptor are useful to reconstitute the immune system by increasing the level of CD4+ cells (Biard-Piechaczyk, et al., *Immunol. Lett.*, 70: 1-3 (1999)); as antagonist agents of apoptosis in immune cells, such as CD8+ cells (Herbin, et al., *Nature* 395: 189-193, (1998)), and as antagonist agents of apoptosis in neuronal cells (Ohagen et al., *J. of Virol.*, 73: 897-906, (1999); and Hesselgesser, et al., *Curr. Biol.* 8: 595-598, (1998)). Chemokine receptor antagonist agents also inhibit the migration of human bone marrow B lineage cells to stromal-derived factor 1 (See e.g., E. Fedyk, et al., *J. of Leukocyte Biol.*, 66:667-783, (1999)).

The invention includes pharmaceutical compositions comprising a therapeutically effective amount of a compound of Formula 1 or 2 along with at least one excipient, and methods of treating diseases of the human body or the bodies of other mammals with such compositions. The term "therapeutically effective amount" means the amount of a compound of Formula 1 or 2 that will elicit the biological or medical response of a cell, tissue, organ, system, animal or human that is being sought by the researcher, veterinarian, medical doctor, or other clinician. The invention provides a method for blocking or interfering with the binding by a chemokine receptor with its natural ligand, comprising contacting of the chemokine receptor with an effective amount of the compound according to Formula 1 or 2. The present invention also provides methods of protecting target cells possessing chemokine receptors, which binding to a pathogenic agent results in disease or pathology, comprising administering to a mammalian subject a pharmaceutical composition comprising a therapeutically effective amount of the compound according to Formula 1 or 2. The invention includes the use of a compound of Formula 1 or 2 in the manufacture of a medicament for the treatment of a disease in which blocking or interfering with binding of a chemokine receptor with its natural ligand is advantageous. The compound is formulated into a composition in an amount corresponding to a therapeutically effective amount of a compound of Formula 1 or 2.

The Invention Compounds

The invention compounds are described generally by Formula 1 or 2. In one embodiment, the compounds of the present invention are of formula 1

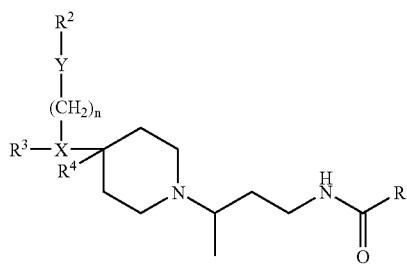

(1)

or a pharmaceutically acceptable salt thereof,
wherein X is carbon or nitrogen;
Y is O, S, SO or $SO_2$ if X is carbon, or a bond if X is nitrogen;

n is 0-3;
$R^1$ is a cyclic or acyclic alkyl or 5- or 6-membered non-aromatic heterocyclic ring, each of which is optionally substituted by one or more of cyclic alkyl, acyclic alkyl, alkene, alkyne, halogen, CN, OH, $NH_2$, $NHR^5$, or $OR^5$; or
phenyl, pyridine, pyridine N-oxide or heteroaryl, each of which is optionally substituted by one or more of cyclic or acyclic alkyl, alkene, alkyne, OH, OMe, $NH_2$, $NH(C_{1-6}$ alkyl), $N(C_{1-6}$ alkyl$)_2$, halogen, CN, $CF_3$, $OCF_3$, $NHC(O)(C_{1-6}$ alkyl), $C(O)(C_{1-6}$ alkyl), $C(O)O(C_{1-6}$ alkyl), $OC(O)(C_{1-6}$ alkyl), $C(O)OH$, $C(O)NH(C_{1-6}$ alkyl), $C(O)N(C_{1-6}$ alkyl$)_2$, $S(C_{1-6}$ alkyl), $SO_nR^6$, NHS$(O)_n(C_{1-6}$ alkyl) where n is 1 or 2; or phenyl, pyridine or pyridine N-oxide, each of which is optionally substituted by one or more of cyclic or acyclic alkyl, alkene, alkyne, halogen, CN, $NH_2$, $NH(C_{1-6}$ alkyl), $N(C_{1-6}$ alkyl$)_2$, $C(O)NH(C_{1-6}$ alkyl), $C(O)N(C_{1-6}$ alkyl$)_2$, or $C(O)O(C_{1-6}$ alkyl); or
an N-linked phenyl, pyridine, pyridine N-oxide or heteroaryl ring, each of which is optionally substituted by one or more of cyclic or acyclic alkyl, alkene, alkyne, halogen, CN, $NH_2$, $NH(C_{1-6}$ alkyl), $N(C_{1-6}$ alkyl$)_2$, $C(O)NH(C_{1-6}$ alkyl), $C(O)N(C_{1-6}$ alkyl$)_2$, or $C(O)O(C_{1-6}$ alkyl);
$R^2$ is phenyl, pyridine or heteroaryl, each of which is optionally substituted by one or more of cyclic or acyclic alkyl, alkene, alkyne, halogen, CN, $NO_2$, OH, $NH_2$, $CF_3$, $CH_2OH$, $C(O)O(C_{1-6}$ alkyl), $OR^7$, or 5- or 6-membered non aromatic heterocyclic ring; or
a $C_{1-6}$ alkyl, alkene or alkyne, $OC(O)(C_{1-6}$ alkyl), $NHC(O)(C_{1-6}$ alkyl), $NHR^8$, or a 5- or 6-membered non aromatic heterocyclic ring;
$R^3$ is phenyl, pyridine, or heteroaryl, each of which is optionally substituted by one or more of cyclic or acyclic alkyl, alkene, alkyne, halogen, CN, CHO, $CF_3$, $OCF_3$, $NO_2$, OH, $NHC(O)(C_{1-6}$ acyclic or $C_{3-6}$ cyclic alkyl), $NHC(O)CF_3$, $NHSO_2(C_{1-6}$ alkyl), $NHC(O)NH_2$, $NHC(O)(C_{1-6}$ alkyl), $C(O)NH_2$, $C(O)NHC_6H_5$, $C(O)C_6H_4C(O)OH$, $C(O)N(OC_{1-6}$ alkyl)$(C_{1-6}$ alkyl), $C(O)NHCH_2C(O)O(C_{1-6}$ alkyl), $C(O)(C_{1-6}$ alkyl), $C(O)O(C_{1-6}$ alkyl), C(O)(non-aromatic heterocylic ring), $OC(O)(C_{1-6}$ alkyl), $O(C_{1-6}$ alkyl), $O(C_{1-6}$ alkyl)$O(C_{1-6}$ alkyl), $O(C_{1-6}$ alkyl)$C(O)OH$, $OC_6H_4C(O)OH$, $OC_6H_4C(O)NH_2$, $O(C_{1-16}$ alkyl)$C(O)O(C_{1-6}$ alkyl), $O(C_{1-6}$ alkyl)$C(O)NH_2$, $O(C_{1-6}$ alkyl)$C(O)NHNH_2$, $OSO_2(C_{1-6}$ alkyl), $OC(O)O(C_{1-6}$ alkyl), $OC(O)N(C_{1-6}$ alkyl$)_2$, OC(O)(heteroaryl), COOH, $C(O)NH(C_{1-6}$ alkyl), $C(O)N(C_{1-6}$ alkyl$)_2$, $S(C_{1-6}$ alkyl), CH=NOH, CH=NO$(C_{1-6}$ alkyl), CH=N$(C_{1-6}$ alkyl), $(C_{1-6}$ alkyl)C=NOH, $(C_{1-6}$ alkyl)C=NO$(C_{1-6}$ alkyl), $(C_{1-6}$ alkyl)C=N$(C_{1-6}$ alkyl), $(C_{1-6}$ alkyl)$C_6H_4C(O)OH$, $(C_{1-6}$ alkyl)NHC(O)$(C_{1-6}$ alkyl), CH=CHC(O)O$(C_{1-6}$ alkyl), CH=CHC(O)OH, $SO_nR^6$ where n is 1 or 2; or phenyl, pyridine N-oxide, pyridine or heteroaryl each of which is optionally substituted by one or more of alkyl, alkene, alkyne, halogen, CN, $CF_3$, OH, $NH_2$, $OR^7$, $(C_{1-6}$ alkyl)$R^5$, $(C_{1-6}$ alkene)$R^5$, $(C_{1-6}$ alkyne)$R^5$, or a 5- or 6-membered non aromatic heterocyclic ring;
$R^4$ is hydrogen or $C_{1-6}$ alkyl;
$R^5$ is a $C_{1-6}$ alkyl, phenyl, pyridine, pyridine N-oxide or heteroaryl, each of which is optionally substituted by one or more of $C_{1-6}$ alkyl, OH, OMe, $NH_2$, $NH(C_{1-6}$ alkyl), $N(C_{1-6}$ alkyl$)_2$, halogen, CN, $CF_3$, $OCF_3$, $C(O)NH(C_{1-6}$ alkyl), $C(O)N(C_{1-6}$ alkyl$)_2$, $C(O)O(C_{1-6}$ alkyl), COOH, $SO_nNH(C_{1-6}$ alkyl), or $SO_n(C_{1-6}$ alkyl) where n is 1 or 2;

R[6] is C$_{1-6}$ alkyl, NH$_2$, NH(C$_{1-6}$ alkyl), N(C$_{1-6}$ alkyl)$_2$, or benzyl;

R[7] is a cyclic or acyclic alkyl, alkene, alkyne, phenyl, pyridine or heteroaryl, each of which is optionally substituted by one or more of C$_{1-6}$ alkyl, halogen, CN, NH$_2$, C(O)OH, C(O)O(C$_{1-6}$ alkyl), OH, SO$_n$NH$_2$ where n is 1 or 2, SO$_n$(C$_{1-6}$ alkyl) where n is 1 or 2, SO$_2$NH(C$_{1-6}$ alkyl), C(O)NH$_2$, C(O)NH(C$_{1-6}$ alkyl), or C(O)N(C$_{1-6}$ alkyl)$_2$; and R[8] is a C$_{1-6}$ alkyl, alkene or alkyne, OH, or OMe.

In another embodiment, the compounds of the present invention are of formula 2

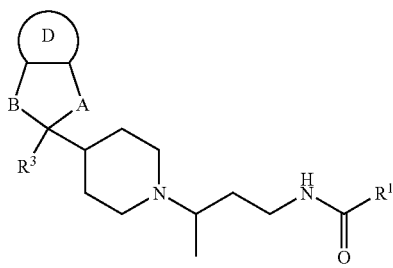

(2)

or a pharmaceutically acceptable salt thereof, wherein R[1] and R[3] are as defined in formula 1;

A and B are independently selected from C$_{1-4}$ alkyl, O, C=NH, C=O, OC(O), (O)CO, S, SO, SO$_2$, NR[8], NR[8]C(O), OC=NR[8], NOR[8], C=NR[8], or NR O where R[8] is as defined above; and Ring D is phenyl, pyridine, pyridine N-oxide or heteroaryl, each of which is optionally substituted by one or more of C$_{1-6}$ alkyl, C$_{1-6}$ alkene, C$_{1-6}$ alkyne, OH, OMe, NH$_2$, NH(C$_{1-6}$ alkyl), N(C$_{1-6}$ alkyl)$_2$, halogen, CN, CF$_3$, OCF$_3$, NHC(O)(C$_{1-6}$ alkyl), C(O)(C$_{1-6}$ alkyl), C(O)O (C$_{1-6}$ alkyl), OC(O)(C$_{1-6}$ alkyl), C(O)OH, C(O)NH(C$_{1-6}$ alkyl), C(O)N(C$_{1-6}$ alkyl)$_2$, S(C$_{1-4}$ alkyl), NHS(O)$_2$(C$_{1-6}$ alkyl), or SO$_n$R[6] where n is 1 or 2 and R[6] is as defined above.

Examples of heteroaryl substituents in the above Formula 1-2 include but are not limited to pyridine, quinoline, isoquinoline, imidazole, benzimidazole, benzotriazole, furan, morpholine, benzofuran, dihydrobenzofuran, thiazole, benzothiazole, benzodioxole, benzodioxane, oxazole, isoxazole, benzoxazole, pyrrole, indole, indoline, isoindoline, indazole, pyrrolidine, pyrrolidone, tetrahydroquinoline, tetrahydroisoquinoline, pyrazole, thiophene, isothiazole, triazole, tetrazole, oxadiazole, thiadiazole, benzopyran, pyridazine, pyrimidine, pyrazine, 1,3,5-triazine, cinnoline, tetrahydrocinnoline, quinazoline, tetrahydroquinazoline, quinoxaline, tetrahydroquinoxaline, phthalan or phthalazine.

The present invention also relates to pharmaceutical compositions comprising compounds of Formula 1 or 2, and a pharmaceutically acceptable carrier. Furthermore, the present invention relates to methods for treating a CCR5 mediated disease in a system, comprising contacting a compound of Formula 1 or 2 with a system (e.g., cell, tissue or organ), or in a subject.

Examples of piperidine compounds of the present invention include but are not limited to:

N-(3-{4-[(4-Bromophenyl)-phenoxymethyl]-piperidin-1-yl}-butyl)-2,4-dimethyl-1-oxynicotinamide (1);

N-(3-{4-[(4-Bromophenyl)-phenoxymethyl]-piperidin-1-yl}-butyl)-3,5-dichloro-isonicotinamide (2);

N-(3-{4-[(4-Bromo-phenyl)-o-tolyloxy-methyl]-piperidin-1-yl}-butyl)-3,5-dichloro-isonicotinamide (3);

2,4-Dimethyl-1-oxy-N-(3-{4-[phenoxy-(4-trifluoromethyl-phenyl)-methyl]-piperidin-1-yl}-butyl)-nicotinamide (4);

2,6-Dimethyl-N-(3-{4-[phenoxy-(4-trifluoromethyl-phenyl)-methyl]-piperidin-1-yl}-butyl)-4-pyridin-4-yl-benzamide (5);

3,5-Dichloro-N-(3-{4-[phenoxy-(4-trifluoromethyl-phenyl)-methyl]-piperidin-1-yl}-butyl)-isonicotinamide (6);

3,5-Dichloro-N-(3-{4-[(3-trifluoromethyl-phenoxy)-(4-trifluoromethyl-phenyl)-methyl]-piperidin-1-yl}-butyl)-isonicotinamide (7);

3,5-Dichloro-N-(3-{4-[(2-trifluoromethyl-phenoxy)-(4-trifluoromethyl-phenyl)-methyl]-piperidin-1-yl}-butyl)-isonicotinamide (8);

3,5-Dichloro-N-(3-{4-[(3-chloro-phenoxy)-(4-trifluoromethyl-phenyl)-methyl]-piperidin-1-yl}-butyl)-isonicotinamide (9);

3,5-Dichloro-N-(3-{4-[(2-fluoro-phenoxy)-(4-trifluoro-methyl-phenyl)-methyl]-piperidin-1-yl}-butyl)-isonicotinamide (10);

3,5-Dichloro-N-(3-{4-[(3-fluoro-phenoxy)-(4-trifluoro-methyl-phenyl)-methyl]-piperidin-1-yl}-butyl)-isonicotinamide (11);

2,6-Dimethyl-4-pyridin-4-yl-N-(3-{4-[m-tolyloxy-(4-trifluoromethyl-phenyl)-methyl]-piperidin-1-yl}-butyl)benzamide (12);

2,6-Dimethyl-4-pyridin-4-yl-N-(3-{4-[o-tolyloxy-(4-trifluoromethyl-phenyl)-methyl]-piperidin-1-yl}-butyl)-benzamide (13);

3,5-Dichloro-N-(3-{4-[(3-cyano-phenoxy)-(4-trifluoro-methyl-phenyl)-methyl]-piperidin-1-yl}-butyl)-isonicotinamide (14);

3,5-Dichloro-N-(3-{4-[ethylideneaminooxy-(4-trifluoromethyl-phenyl)-methyl]-piperidin-1-yl}-butyl)-isonicotinamide (15);

2,6-Dimethyl-N-(3(R)-{4(R)-[phenoxy-(4-trifluoromethyl-phenyl)-methyl]-piperidin-1-yl}-butyl)-4-pyridin-4-yl-benzamide (16);

2,6-Dimethyl-N-(3(S)-{4(R)-[phenoxy-(4-trifluoromethyl-phenyl)-methyl]-piperidin-1-yl}-butyl)-4-pyridin-4-yl-benzamide (17);

N-(3-{4-[(6-Chloro-pyridin-2-yloxy)-(4-trifluoromethyl-phenyl)-methyl]-piperidin-1-yl}-butyl)-2,4-dimethyl-1-oxy-nicotinamide (18);

N-(3-{4-[(6-Chloro-pyridin-2-yloxy)-(4-trifluoromethyl-phenyl)-methyl]-piperidin-1-yl}-butyl)-2,6-dimethyl-benzamide (19);

4,6-Dimethyl-pyrimidine-5-carboxylic acid (3-{4-[(6-chloro-pyridin-2-yloxy)-(4-trifluoromethyl-phenyl)-methyl]-piperidin-1-yl}-butyl)-amide (20);

N-(3-{4-[(4-Bromo-phenyl)-(pyridin-2-yloxy)-methyl]-piperidin-1-yl}-butyl)-3,5-dichloro-isonicotinamide (21);

3,5-Dichloro-N-(3-{4-[(pyridin-2-yloxy)-(4-trifluoromethyl-phenyl)-methyl]-piperidin-1-yl}-butyl)-isonicotinamide (22);

3,5-Dichloro-N-(3-{4-[(6-methyl-pyridin-2-yloxy)-(4-trifluoromethyl-phenyl)-methyl]-piperidin-1-yl}-butyl)-isonicotinamide (23);

3,5-Dichloro-N-(3-{4-[(6-ethyl-pyridin-2-yloxy)-(4-trifluoromethyl-phenyl)-methyl]-piperidin-1-yl}-butyl)-isonicotinamide (24);

3,5-Dichloro-N-(3-{4-[(6-fluoro-pyridin-2-yloxy)-(4-trifluoromethyl-phenyl)-methyl]-piperidin-1-yl}-butyl)-isonicotinamide (25);

3,5-Dichloro-N-(3-{4-[(4-trifluoromethyl-phenyl)-(6-trifluoromethyl-pyridin-2-yloxy)-methyl]-piperidin-1-yl}-butyl)-isonicotinamide (26);

3,5-Dichloro-N-(3-{4-[(6-cyano-pyridin-2-yloxy)-(4-trifluoromethyl-phenyl)-methyl]-piperidin-1-yl}-butyl)-isonicotinamide (27);

3,5-Dichloro-N-(3-{4-[(4-methanesulfonyl-phenyl)-(6-methyl-pyridin-2-yloxy)-methyl]-piperidin-1-yl}-butyl)-isonicotinamide (28);

3,5-Dichloro-N-(3-{4-[(6-chloro-pyridin-2-yloxy)-(4-methanesulfonyl-phenyl)-methyl]-piperidin-1-yl}-butyl)-isonicotinamide (29);

3,5-Dichloro-N-(3-{4-[(6-fluoro-pyridin-2-yloxy)-(4-methanesulfonyl-phenyl)-methyl]-piperidin-1-yl}-butyl)-isonicotinamide (30);

3,5-Dichloro-N-(3-{4-[(6-methyl-pyridin-2-yloxy)-(4-trifluoromethoxy-phenyl)-methyl]-piperidin-1-yl}-butyl)-isonicotinamide (31);

3,5-Dichloro-N-(3-{4-[(6-fluoro-pyridin-2-yloxy)-(4-trifluoromethoxy-phenyl)-methyl]-piperidin-1-yl}-butyl)-isonicotinamide (32);

3,5-Dichloro-N-(3-{4-[(6-chloro-pyridin-2-yloxy)-(4-trifluoromethoxy-phenyl)-methyl]-piperidin-1-yl}-butyl)-isonicotinamide (33);

3,5-Dichloro-N-(3-{4-[(6-methyl-pyridin-2-yloxy)-(4-methylsulfamoyl-phenyl)-methyl]-piperidin-1-yl}-butyl)-isonicotinamide (34);

N-(3-{4-[(R)-4-Bromophenyl)-(pyridin-2-yloxy)-methyl]-piperidin-1-yl}butyl)-3,5-dichloro-isonicotinamide (35);

N-(3-{4-[(4-Bromo-phenyl)-(3-methyl-pyridin-2-yloxy)-methyl]-piperidin-1-yl}-butyl)-3,5-dichloro-isonicotinamide (36);

3,5-Dichloro-N-(3-{4-[(4-methyl-pyridin-2-yloxy)-(4-trifluoromethyl-phenyl)-methyl]-piperidin-1-yl}-butyl)-isonicotinamide (37);

3,5-Dichloro-N-(3-{4-[(3-methyl-pyridin-2-yloxy)-(4-trifluoromethyl-phenyl)-methyl]-piperidin-1-yl}-butyl)-isonicotinamide (38);

3,5-Dichloro-N-(3-{4-[(3-chloro-pyridin-2-yloxy)-(4-trifluoromethyl-phenyl)-methyl]-piperidin-1-yl}-butyl)-isonicotinamide (39);

3,5-Dichloro-N-(3-{4-[(4-chloro-pyridin-2-yloxy)-(4-trifluoromethyl-phenyl)-methyl]-piperidin-1-yl}-butyl)-isonicotinamide (40);

6-[(1-{3-[(3,5-Dichloro-pyridine-4-carbonyl)-amino]-1-methyl-propyl}-piperidin-4-yl)-(4-trifluoromethyl-phenyl)-methoxy]-pyridine-2-carboxylic acid methyl ester (41);

3,5-Dichloro-N-(3-{4-[(4-cyano-phenyl)-(6-methyl-pyridin-2-yloxy)-methyl]-piperidin-1-yl}-butyl)-isonicotinamide (42);

3,5-Dichloro-N-(3-{4-[(6-chloro-pyridin-2-yloxy)-(4-cyano-phenyl)-methyl]-piperidin-1-yl}-butyl)-isonicotinamide (43);

3,5-Dichloro-N-(3-{4-[(4-cyano-phenyl)-(6-cyano-pyridin-2-yloxy)-methyl]-piperidin-1-yl}-butyl)-isonicotinamide (44);

3,5-Dichloro-N-(3-{4-[(4-cyano-phenyl)-(6-fluoro-pyridin-2-yloxy)-methyl]-piperidin-1-yl}-butyl)-isonicotinamide (45);

N-(3-{4-[(4-Carbamoyl-phenyl)-(6-methyl-pyridin-2-yloxy)-methyl]-piperidin-1-yl}-butyl)-3,5-dichloro-isonicotinamide (46);

4-[(1-{3-[(3,5-Dichloro-pyridine-4-carbonyl)-amino]-1-methyl-propyl}-piperidin-4-yl)-(6-methyl-pyridin-2-yloxy)-methyl]-benzoic acid methyl ester (47);

N-(3-{4-[(4-Bromo-phenyl)-(pyridin-2-yloxy)-methyl]-piperidin-1-yl}-butyl)-2,4-dimethyl-1-oxy-nicotinamide (48);

2,6-Dimethyl-4-pyridin-4-yl-N-(3-{4-[(pyridin-2-yloxy)-(4-trifluoromethyl-phenyl)-methyl]-piperidin-1-yl}-butyl)-benzamide (49);

2,6-Dimethyl-N-(3-{4-[(6-methyl-pyridin-2-yloxy)-(4-trifluoromethyl-phenyl)-methyl]-piperidin-1-yl}-butyl)-4-pyridin-4-yl-benzamide (50);

2,6-Dimethyl-N-(3(R)-{4(R)-[(6-methylpyridin-2-yloxy)-(4-trifluoromethyl-phenyl)-methyl]-piperidin-1-yl}-butyl)-4-pyridin-4-yl-benzamide (51);

2,6-Dimethyl-N-(3(S)-{4(R)-[(6-methylpyridin-2-yloxy)-(4-trifluoromethyl-phenyl)-methyl]-piperidin-1-yl}-butyl)-4-pyridin-4-yl-benzamide (52);

3,5-Dichloro-N-(3-{4-methyl-4-[(6-methyl-pyridin-2-yloxy)-(4-trifluoromethyl-phenyl)-methyl]-piperidin-1-yl}-butyl)-isonicotinamide (53);

3,5-Dichloro-N-(3-{4-[(6-fluoro-pyridin-2-yloxy)-thiazol-2-yl-methyl]-piperidin-1-yl}-butyl)-isonicotinamide (54);

3,5-Dichloro-N-(3-{4-[(6-chloro-pyridin-2-yloxy)-thiazol-2-yl-methyl]-piperidin-1-yl}-butyl)-isonicotinamide (55);

3,5-Dichloro-N-(3-{4-[(6-chloropyridin-2-yloxy)-oxazol-2-yl-methyl]-piperidin-1-yl}-butyl)-isonicotinamide (56);

3,5-Dichloro-N-(3-{4-[(6-fluoropyridin-2-yloxy)-oxazol-2-yl-methyl]-piperidin-1-yl}-butyl)-isonicotinamide (57);

3,5-Dichloro-N-(3-{4-[(6-methyl-pyridin-2-yloxy)-pyridin-3-yl-methyl]-piperidin-1-yl}-butyl)-isonicotinamide (58);

3,5-Dichloro-N-(3-{4-[(6-methyl-pyridin-2-yloxy)-pyridin-4-yl-methyl]-piperidin-1-yl}-butyl)-isonicotinamide (59);

N-(3-{4-[(4-Bromo-phenyl)-(thiazol-2-yloxy)-methyl]-piperidin-1-yl}-butyl)-3,5-dichloro-isonicotinamide (60);

3,5-Dichloro-N-(3-{4-[(thiazol-2-yloxy)-(4-trifluoromethyl-phenyl)-methyl]-piperidin-1-yl}-butyl)-isonicotinamide (61);

N-(3-{4-[(4-Bromo-phenyl)-(3-chloro-benzyl)-amino]-piperidin-1-yl}-butyl)-3,5-dichloro-isonicotinamide (62);

N-(3-{4-[Benzyl-(4-cyano-phenyl)-amino]-piperidin-1-yl}-butyl)-3,5-dichloro-isonicotinamide (63);

3,5-Dichloro-N-(3-{4-[(4-cyano-phenyl)-(3-fluoro-benzyl)-amino]-piperidin-1-yl}-butyl)-isonicotinamide (64);

3,5-Dichloro-N-(3-{4-[(3-chloro-benzyl)-(4-cyano-phenyl)-amino]-piperidin-1-yl}-butyl)-isonicotinamide (65);

3,5-Dichloro-N-(3-{4-[(4-cyano-phenyl)-(3-methyl-benzyl)-amino]-piperidin-1-yl}-butyl)-isonicotinamide (66);

N-(3-{4-[Benzyl-(4-trifluoromethyl-phenyl)-amino]-piperidin-1-yl}-butyl)-3,5-dichloro-isonicotinamide (67);

3,5-Dichloro-N-(3-{4-[(3-fluoro-benzyl)-(4-trifluoromethyl-phenyl)-amino]-piperidin-1-yl}-butyl)-isonicotinamide (68);

3,5-Dichloro-N-(3-{4-[(3-chloro-benzyl)-(4-trifluoromethyl-phenyl)-amino]-piperidin-1-yl}-butyl)-isonicotinamide (69);

N-(3-{4-[Benzyl-(4-trifluoromethoxy-phenyl)-amino]-piperidin-1-yl}-butyl)-3,5-dichloro-isonicotinamide (70);

3,5-Dichloro-N-(3-{4-[(3-methyl-benzyl)-(4-trifluoromethoxy-phenyl)-amino]-piperidin-1-yl}-butyl)-isonicotinamide (71);

3,5-Dichloro-N-(3-{4-[(3-fluoro-benzyl)-(4-methylsulfanyl-phenyl)-amino]-piperidin-1-yl}-butyl)-isonicotinamide (72);

3,5-Dichloro-N-(3-{4-[(3-chloro-benzyl)-(4-methylsulfanyl-phenyl)-amino]-piperidin-1-yl}-butyl)-isonicotinamide (73);

3,5-Dichloro-N-(3-{4-[(3-methyl-benzyl)-(4-methylsulfanyl-phenyl)-amino]-piperidin-1-yl}-butyl)-isonicotinamide (74);

3,5-Dichloro-N-(3-{4-[(3-chloro-benzyl)-(4-methanesulfonyl-phenyl)-amino]-piperidin-1-yl}-butyl)-isonicotinamide (75);
3,5-Dichloro-N-(3-{4-[(4-methanesulfonyl-phenyl)-(3-methyl-benzyl)-amino]-piperidin-1-yl}-butyl)-isonicotinamide (76);
3,5-Dichloro-N-(3-{4-[(3-fluoro-benzyl)-(4-methoxy-phenyl)-amino]-piperidin-1-yl}-butyl)-isonicotinamide (77);
3,5-Dichloro-N-(3-{4-[(3-chloro-benzyl)-(4-methoxy-phenyl)-amino]-piperidin-1-yl}-butyl)-isonicotinamide (78);
N-(3-{4-Benzyl-(4-methylsulfamoyl-phenyl)-amino]-piperidin-1-yl}-butyl)-3,5-dichloro-isonicotinamide (79);
Methanesulfonic acid 4-[benzyl-(1-{3-[(3,5-dichloro-pyridine-4-carbonyl)-amino]-1-methyl-propyl}-piperidin-4-yl)-amino]-phenyl ester (80);
N-(3-{4-[Benzyl-(4-nitro-phenyl)-amino]-piperidin-1-yl}-butyl)-3,5-dichloro-isonicotinamide (81);
3,5-Dichloro-N-(3-{4-[(3-chloro-benzyl)-(4-nitro-phenyl)-amino]-piperidin-1-yl}-butyl)-isonicotinamide (82);
N-(3-{4-[Benzyl-(4-sulfamoyl-phenyl)-amino]-piperidin-1-yl}-butyl)-3,5-dichloro-isonicotinamide (83);
4,6-Dimethyl-pyrimidine-5-carboxylic acid (3-{4-[(3-fluoro-benzyl)-(4-nitro-phenyl)-amino]-piperidin-1-yl}-butyl)-amide (84);
4-((3-Chloro-benzyl)-{1-[3-(2,6-dimethyl-benzoylamino)-1-methyl-propyl]-piperidin-4-yl}-amino)-benzoic acid methyl ester (85);
N-[3-(4-{(3-Chloro-benzyl)-[4-(morpholine-4-carbonyl)-phenyl]-amino}-piperidin-1-yl)-butyl]-2,6-dimethyl-benzamide (86);
N-(3-{4-[(3-Chloro-benzyl)-(4-dimethylcarbamoyl-phenyl)-amino]-piperidin-1-yl}-butyl)-2,6-dimethyl-benzamide (87);
N-[3-(4-{(3-Chloro-benzyl)-[4-(methoxy-methyl-carbamoyl)-phenyl]-amino}-piperidin-1-yl)-butyl]-2,6-dimethyl-benzamide (88);
N-(3-{4-[(3-Chloro-benzyl)-(4-phenylcarbamoyl-phenyl)-amino]-piperidin-1-yl}-butyl)-2,6-dimethyl-benzamide (89);
N-(3-{4-[(4-Carbamoyl-phenyl)-(3-chloro-benzyl)-amino]-piperidin-1-yl}-butyl)-2,6-dimethyl-benzamide (90);
N-(3-{4-[Benzyl-(4-dimethylcarbamoyl-phenyl)-amino]-piperidin-1-yl}-butyl)-2,6-dimethyl-4-pyridin-4-yl-benzamide (91);
N-(3-{4-[Benzyl-(4-carbamoyl-phenyl)-amino]-piperidin-1-yl}-butyl)-2,6-dimethyl-4-pyridin-4-yl-benzamide (92);
N-(3-{4-[(4-Cyano-phenyl)-(3-fluoro-benzyl)-amino]-piperidin-1-yl}-butyl)-2,4-dimethyl-1-oxy-nicotinamide (93);
N-(3-{4-[(4-Cyano-phenyl)-(3-fluoro-benzyl)-amino]-piperidin-1-yl}-butyl)-2,6-dimethyl-4-pyridin-4-yl-benzamide (94);
4,6-Dimethyl-pyrimidine-5-carboxylic acid (3-{4-[(4-cyano-phenyl)-(3-fluoro-benzyl)-amino]-piperidin-1-yl}-butyl)-amide (95);
4-{4-[Benzyl-(1-{3-[(4,6-dimethyl-pyrimidine-5-carbonyl)-amino]-1-methyl-propyl}-piperidin-4-yl)-amino]-phenoxy}-benzoic acid (96);
4-[4-(Benzyl-{1-[3-(2,6-dimethyl-benzoylamino)-1-methyl-propyl]-piperidin-4-yl}-amino)-phenoxy]-benzoic acid (97);
4-{4-[Benzyl-(1-{3-[(2,4-dimethyl-1-oxy-pyridine-3-carbonyl)-amino]-1-methyl-propyl}-piperidin-4-yl)-amino]-phenoxy}-benzoic acid (98);
4-{4-[Benzyl-(1-{1-methyl-3-[(4-methyl-pyridine-3-carbonyl)-amino]-propyl}-piperidin-4-yl)-amino]-phenoxy}-benzoic acid (99);
4-[4-(Benzyl-{1-[3-(2,6-dimethyl-benzoylamino)-1-methyl-propyl]-piperidin-4-yl}-amino)-benzyl]-benzoic acid (100);
4-[4-(Benzyl-{1-[3-(2,6-dimethyl-benzoylamino)-1-methyl-propyl]-piperidin-4-yl}-amino)-benzoyl]-benzoic acid (101);
4-{4-[Benzyl-(1-{3-[(4,6-dimethyl-pyrimidine-5-carbonyl)-amino]-1-methyl-propyl}-piperidin-4-yl)-amino]-benzyl}-benzoic acid (102);
N-(3-{4-[(4-Bromo-phenyl)-(3-cyano-benzyl)-amino]-piperidin-1-yl}-butyl)-3,5-dichloro-isonicotinamide (103);
3,5-Dichloro-N-(3-{4-[(3-cyano-benzyl)-(4-trifluoro-methyl-phenyl)-amino]-piperidin-1-yl}-butyl)-isonicotinamide (104);
3,5-Dichloro-N-(3-{4-[(3-cyano-benzyl)-(4-methylsulfanyl-phenyl)-amino]-piperidin-1-yl}-butyl)-isonicotinamide (105);
3,5-Dichloro-N-(3-{4-[(3-cyano-benzyl)-(4-cyano-phenyl)-amino]-piperidin-1-yl}-butyl)-isonicotinamide (106);
4-[(3-Cyano-benzyl)-(1-{3-[(3,5-dichloro-pyridine-4-carbonyl)-amino]-1-methyl-propyl}-piperidin-4-yl)-amino]-benzoic acid methyl ester (107);
3,5-Dichloro-N-(3-{4-[(4-chloro-phenyl)-(3-cyano-benzyl)-amino]-piperidin-1-yl}-butyl)-isonicotinamide (108);
N-(3-{4-[(3-Cyano-benzyl)-(4-dimethylcarbamoyl-phenyl)-amino]-piperidin-1-yl}-butyl)-2,6-dimethyl-benzamide (109);
N-(3-{4-[(3-Cyano-benzyl)-(4-dimethylcarbamoyl-phenyl)-amino]-piperidin-1-yl}-butyl)-2,6-dimethyl-4-pyridin-4-yl-benzamide (110);
4,6-Dimethyl-pyrimidine-5-carboxylic acid (3-{4-[(4-acetylamino-phenyl)-(3-cyano-benzyl)-amino]-piperidin-1-yl}-butyl)-amide (111);
N-(3-{4-[(4-Acetylamino-phenyl)-(3-cyano-benzyl)-amino]-piperidin-1-yl}-butyl)-2,6-dimethyl-benzamide (112);
N-[3-(4-{(3-Cyano-benzyl)-[4-(2-methoxy-ethoxy)-phenyl]-amino}-piperidin-1-yl)-butyl]-2,6-dimethyl-benzamide (113);
4,6-Dimethyl-pyrimidine-5-carboxylic acid [3-(4-{(3-cyano-benzyl)-[4-(2-methoxy-ethoxy)-phenyl]-amino}-piperidin-1-yl)-butyl]-amide (114);
N-(3-{4-[(3-Cyano-benzyl)-(4-hydrazinocarbonylmethoxy-phenyl)-amino]-piperidin-1-yl}-butyl)-2,6-dimethyl-benzamide (115);
4,6-Dimethyl-pyrimidine-5-carboxylic acid (3-{4-[(3-cyano-benzyl)-(4-hydrazinocarbonylmethoxy-phenyl)-amino]-piperidin-1-yl}-butyl)-amide (116);
N-(3-{4-[(3-Cyano-benzyl)-(4-hydroxy-phenyl)-amino]-piperidin-1-yl}-butyl)-2,6-dimethyl-benzamide (117);
4,6-Dimethyl-pyrimidine-5-carboxylic acid (3-{4-[(3-cyano-benzyl)-(4-methanesulfonylamino-phenyl)-amino]-piperidin-1-yl}-butyl)-amide (118);
4,6-Dimethyl-pyrimidine-5-carboxylic acid (3-{4-[(3-cyano-benzyl)-(4-methoxy-phenyl)-amino]-piperidin-1-yl}-butyl)-amide (119);
N-(3-{4-[(3-Cyano-benzyl)-(4-methoxy-phenyl)-amino]-piperidin-1-yl}-butyl)-2,6-dimethyl-benzamide (120);
N-(3-{4-[(3-Cyano-benzyl)-(4-methoxy-phenyl)-amino]-piperidin-1-yl}-butyl)-2,4-dimethyl-1-oxy-nicotinamide (121);
N-(3-{4-[(3-Cyano-benzyl)-(4-trifluoromethoxy-phenyl)-amino]-piperidin-1-yl}-butyl)-2,6-dimethyl-benzamide (122);

4,6-Dimethyl-pyrimidine-5-carboxylic acid (3-{4-[(3-cyano-benzyl)-(4-trifluoromethoxy-phenyl)-amino]-piperidin-1-yl}-butyl)-amide (123);

N-(3-{4-[(3-Cyano-benzyl)-(4-trifluoromethoxy-phenyl)-amino]-piperidin-1-yl}-butyl)-2,4-dimethyl-1-oxy-nicotinamide (124);

3,5-Dichloro-N-(3-{4-[(3-cyano-benzyl)-(4-methanesulfinyl-phenyl)-amino]-piperidin-1-yl}-butyl)-isonicotinamide (125);

3,5-Dichloro-N-(3-{4-[(3-cyano-benzyl)-(4-methanesulfonyl-phenyl)-amino]-piperidin-1-yl}-butyl)-isonicotinamide (126);

3,5-Dichloro-N-(3-{4-[(3-cyano-benzyl)-(4-nitro-phenyl)-amino]-piperidin-1-yl}-butyl)-isonicotinamide (127);

3,5-Dichloro-N-(3-{4-[(3-cyano-benzyl)-(4-dimethylcarbamoyl-phenyl)-amino]-piperidin-1-yl}-butyl)-isonicotinamide (128);

4,6-Dimethyl-pyrimidine-5-carboxylic acid (3-{4-[(3-cyano-benzyl)-(4-dimethylcarbamoyl-phenyl)-amino]-piperidin-1-yl}-butyl)-amide (129);

N-(3-{4-[(3-Cyano-benzyl)-(4-dimethylcarbamoyl-phenyl)-amino]-piperidin-1-yl}-butyl)-2,4-dimethyl-1-oxy-nicotinamide (130);

N-[3-(4-{(3-Cyano-benzyl)-[4-(piperidine-1-carbonyl)-phenyl]-amino}-piperidin-1-yl)-butyl]-2,6-dimethyl-benzamide (131);

N-(3-{4-[(3-Cyano-benzyl)-(4-methylcarbamoyl-phenyl)-amino]-piperidin-1-yl}-butyl)-2,6-dimethyl-benzamide (132);

4,6-Dimethyl-pyrimidine-5-carboxylic acid (3-{4-[(3-cyano-benzyl)-(4-methylcarbamoyl-phenyl)-amino]-piperidin-1-yl}-butyl)-amide (133);

N-[3-(4-{(3-Cyano-benzyl)-[4-(piperazine-1-carbonyl)-phenyl]-amino}-piperidin-1-yl)-butyl]-2,6-dimethyl-benzamide (134);

4,6-Dimethyl-pyrimidine-5-carboxylic acid [3-(4-{(3-cyano-benzyl)-[4-(piperazine-1-carbonyl)-phenyl]-amino}-piperidin-1-yl)-butyl]-amide (135);

4,6-Dimethyl-pyrimidine-5-carboxylic acid 4-[(3-cyano-benzyl)-(1-{3-[(4,6-dimethyl-pyrimidine-5-carbonyl)-amino]-1-methyl-propyl}-piperidin-4-yl)-amino]-phenyl ester (136);

Acetic acid 4-((3-cyano-benzyl)-{1-[3-(2,6-dimethyl-benzoylamino)-1-methyl-propyl]-piperidin-4-yl}-amino)-phenyl ester (137);

Acetic acid 4-[(3-cyano-benzyl)-(1-{3-[(4,6-dimethyl-pyrimidine-5-carbonyl)-amino]-1-methyl-propyl}-piperidin-4-yl)-amino]-phenyl ester (138);

Carbonic acid 4-((3-cyano-benzyl)-{1-[3-(2,6-dimethyl-benzoylamino)-1-methyl-propyl]-piperidin-4-yl}-amino)-phenyl ester methyl ester (139);

Carbonic acid 4-[(3-cyano-benzyl)-(1-{3-[(4,6-dimethyl-pyrimidine-5-carbonyl)-amino]-1-methyl-propyl}-piperidin-4-yl)-amino]-phenyl ester methyl ester (140);

Diethyl-carbamic acid 4-((3-cyano-benzyl)-{1-[3-(2,6-dimethyl-benzoylamino)-1-methyl-propyl]-piperidin-4-yl}-amino)-phenyl ester (141);

N-(3-{4-[(4-Amino-phenyl)-(3-cyano-benzyl)-amino]-piperidin-1-yl}-butyl)-2,6-dimethyl-benzamide (142);

[4-((3-Cyano-benzyl)-{1-[3-(2,6-dimethyl-benzoylamino)-1-methyl-propyl]-piperidin-4-yl}-amino)-phenoxy]-acetic acid tert-butyl ester (143);

{4-[(Cyano-benzyl)-(1-{3-[(4,6-dimethyl-pyrimidine-5-carbonyl)-amino]-1-methyl-propyl}-piperidin-4-yl)-amino]-phenoxy}-acetic acid tert-butyl ester (144);

Dimethyl-carbamic acid 4-((3-cyano-benzyl)-{1-[3-(2,6-dimethyl-benzoylamino)-1-methyl-propyl]-piperidin-4-yl}-amino)-phenyl ester (145);

Dimethyl-carbamic acid 4-[(3-cyano-benzyl)-(1-{3-[(4,6-dimethyl-pyrimidine-5-carbonyl)-amino]-1-methyl-propyl}-piperidin-4-yl)-amino]-phenyl ester (146);

[4-((3-Cyano-benzyl)-{1-[3-(2,6-dimethyl-benzoylamino)-1-methyl-propyl]-piperidin-4-yl}-amino)-phenoxy]-acetic acid methyl ester (147);

{4-[(3-Cyano-benzyl)-(1-{3-[(4,6-dimethyl-pyrimidine-5-carbonyl)-amino]-1-methyl-propyl}-piperidin-4-yl)-amino]-phenoxy}-acetic acid methyl ester (148);

[4-((3-Cyano-benzyl)-{1-[3-(2,6-dimethyl-benzoylamino)-1-methyl-propyl]-piperidin-4-yl}-amino)-phenoxy]-acetic acid (149);

{4-[(3-Cyano-benzyl)-(1-{3-[(4,6-dimethyl-pyrimidine-5-carbonyl)-amino]-1-methyl-propyl}-piperidin-4-yl)-amino]-phenoxy}-acetic acid (150);

N-(3-{4-[(3-Cyano-benzyl)-(4-methylsulfamoyl-phenyl)-amino]-piperidin-1-yl}-butyl)-2,6-dimethyl-benzamide (151);

4,6-Dimethyl-pyrimidine-5-carboxylic acid (3-{4-[(3-cyano-benzyl)-(4-methylsulfamoyl-phenyl)-amino]-piperidin-1-yl}-butyl)-amide (152);

N-[3-(4-{(3-Cyano-benzyl)-[4-(cyclopropanecarbonyl-amino)-phenyl]-amino}-piperidin-1-yl)-butyl]-2,6-dimethyl-benzamide (153);

4,6-Dimethyl-pyrimidine-5-carboxylic acid [3-(4-{(3-cyano-benzyl)-[4-(cyclopropanecarbonyl-amino)-phenyl]-amino}-piperidin-1-yl)-butyl]-amide (154);

N-[3-(4-{(3-Cyano-benzyl)-[4-(3,3-dimethyl-ureido)-phenyl]-amino}-piperidin-1-yl)-butyl]-2,6-dimethyl-benzamide (155);

N-[3-(4-{(3-Cyano-benzyl)-[4-(2,2,2-trifluoro-acetylamino)-phenyl]-amino}-piperidin-1-yl)-butyl]-2,6-dimethyl-benzamide (156);

4,6-Dimethyl-pyrimidine-5-carboxylic acid [3-(4-{(3-cyano-benzyl)-[4-(2,2,2-trifluoro-acetylamino)-phenyl]-amino}-piperidin-1-yl)-butyl]-amide (157);

N-(3-{4-[(3-Cyano-benzyl)-(4-ureido-phenyl)-amino]-piperidin-1-yl}-butyl)-2,6-dimethyl-benzamide (158);

4,6-Dimethyl-pyrimidine-5-carboxylic acid (3-{4-[(3-cyano-benzyl)-(4-ureido-phenyl)-amino]-piperidin-1-yl}-butyl)-amide (159);

N-[3-(4-{(3-Cyano-benzyl)-[4-(2-oxo-oxazolidin-3-yl)-phenyl]-amino}-piperidin-1-yl)-butyl]-2,6-dimethyl-benzamide (160);

4,6-Dimethyl-pyrimidine-5-carboxylic acid [3-(4-{(3-cyano-benzyl)-[4-(2-oxo-oxazolidin-3-yl)-phenyl]-amino}-piperidin-1-yl)-butyl]-amide (161);

4-{4-[(3-Cyano-benzyl)-(1-{3-[(4,6-dimethyl-pyrimidine-5-carbonyl)-amino]-1-methyl-propyl}-piperidin-4-yl)-amino]-phenoxy}-benzoic acid (162);

4-{4-[{1-[3-(2-Chloro-6-methyl-benzoylamino)-1-methyl-propyl]-piperidin-4-yl}-(3-cyano-benzyl)-amino]-phenoxy}-benzoic acid (163);

4,6-Dimethyl-pyrimidine-5-carboxylic acid (3-{4-[(4-carbamoyl-phenyl)-(3-cyano-benzyl)-amino]-piperidin-1-yl}-butyl)-amide (164);

N-(3-{4-[(4-Carbamoyl-phenyl)-(3-cyano-benzyl)-amino]-piperidin-1-yl}-butyl)-2-chloro-6-methyl-benzamide (165);

N-(3-{4-[(4-Carbamoyl-phenyl)-(3-cyano-benzyl)-amino]-piperidin-1-yl}-butyl)-2,6-dimethyl-4-pyridin-4-yl-benzamide (166);

4,6-Dimethyl-pyrimidine-5-carboxylic acid [3-(4-{(3-cyano-benzyl)-[4-(morpholine-4-carbonyl)-phenyl]-amino}-piperidin-1-yl)-butyl]-amide (167);

4,6-Dimethyl-pyrimidine-5-carboxylic acid (3-{4-[(3-cyano-benzyl}-(4-sulfamoyl-phenyl)-amino]-piperidine-1-yl}-butyl)-amide (168);

Methanesulfonic acid 4-[(3-cyano-benzyl)-(1-{3-[(4,6-dimethyl-pyrimidine-5-carbonyl)-amino]-1-methyl-propyl}-piperidin-4-yl)-amino]-phenyl ester (169);

Methanesulfonic acid 4-[(3-cyano-benzyl)-(1-{3-[(2,4-dimethyl-1-oxy-pyridine-3-carbonyl)-amino]-1-methyl-propyl}-piperidin-4-yl)-amino]-phenyl ester (170);

4,6-Dimethyl-pyrimidine-5-carboxylic acid (3-{4-[[4-(acetylamino-methyl)-phenyl]-(3-cyano-benzyl)-amino]-piperidin-1-yl}-butyl)-amide (171);

N-(3-{4-[[4-(Acetylamino-methyl)-phenyl]-(3-cyano-benzyl)-amino]-piperidin-1-yl}-butyl)-2,4-dimethyl-1-oxy-nicotinamide (172);

4,6-Dimethyl-pyrimidine-5-carboxylic acid (3-{4-[(4-acetyl-phenyl)-(3-cyano-benzyl)-amino]-piperidin-1-yl}-butyl)-amide (173);

N-(3-{4-[(4-Acetyl-phenyl)-(3-cyano-benzyl)-amino]-piperidin-1-yl}-butyl)-2,4-dimethyl-1-oxy-nicotinamide (174);

{4-[(3-Cyano-benzyl)-(1-{3-[(4,6-dimethyl-pyrimidine-5-carbonyl)-amino]-1-methyl-propyl}-piperidin-4-yl)-amino]-benzoylamino}-acetic acid methyl ester (175);

N-[3-(4-{(3-Cyano-benzyl)-[4-(1-methoxyimino-ethyl)-phenyl]-amino}-piperidin-1-yl)-butyl]-2,4-dimethyl-1-oxy-nicotinamide (176);

N-(3-{4-[(3-Cyano-benzyl)-(1H-indol-5-yl)-amino]-piperidin-1-yl}-butyl)-2,6-dimethyl-benzamide (177);

4,6-Dimethyl-pyrimidine-5-carboxylic acid (3-{4-[(3-cyano-benzyl)-(1H-indol-5-yl)-amino]-piperidin-1-yl}-butyl)-amide (178);

4,6-Dimethyl-pyrimidine-5-carboxylic acid (3-{4-[benzo[1,3]dioxol-5-yl-(3-cyano-benzyl)-amino]-piperidin-1-yl}-butyl)-amide (179);

N-(3-{4-[Benzo[1,3]dioxol-5-yl-(3-cyano-benzyl)-amino]-piperidin-1-yl}-butyl)-2,6-dimethyl-benzamide (180);

4,6-Dimethyl-pyrimidine-5-carboxylic acid (3-{4-[(3-cyano-benzyl)-(2,3-dihydro-benzofuran-5-yl)-amino]-piperidin-1-yl}-butyl)-amide (181);

N-(3-{4-[(3-Cyano-benzyl)-(2,3-dihydro-benzofuran-5-yl)-amino]-piperidin-1-yl}-butyl)-2,6-dimethyl-benzamide (182);

N-(3-{4-[(3-Cyano-benzyl)-(1,3-dihydro-isobenzofuran-5-yl)-amino]-piperidin-1-yl}-butyl)-2,6-dimethyl-benzamide (183);

4,6-Dimethyl-pyrimidine-5-carboxylic acid (3-{4-[benzofuran-5-yl-(3-cyano-benzyl)-amino]-piperidin-1-yl}-butyl)-amide (184);

N-(3-{4-[Benzofuran-5-yl-(3-cyano-benzyl)-amino]-piperidin-1-yl}-butyl)-2,6-dimethyl-benzamide (185);

4,6-Dimethyl-pyrimidine-5-carboxylic acid (3-{4-[(3-cyano-benzyl)-(3,4-dimethoxy-phenyl)-amino]-piperidin-1-yl}-butyl)-amide (186);

N-(3-{4-[(3-Cyano-benzyl)-(3,4-dimethoxy-phenyl)-amino]-piperidin-1-yl}-butyl)-2,6-dimethyl-benzamide (187);

4,6-Dimethyl-pyrimidine-5-carboxylic acid (3-{4-[(3-cyano-benzyl)-(2,3-dihydro-benzo[1,4]dioxin-6-yl)-amino]-piperidin-1-yl}-butyl)-amide (188);

2-Chloro-N-(3-{4-[(3-cyano-benzyl)-(2,3-dihydro-benzo[1,4]dioxin-6-yl)-amino]-piperidin-1-yl}-butyl)-6-methyl-benzamide (189);

N-(3-{4-[(3-Cyano-benzyl)-(2,3-dihydro-benzo[1,4]dioxin-6-yl)-amino]-piperidin-1-yl}-butyl)-2,6-dimethyl-benzamide (190);

4,6-Dimethyl-pyrimidine-5-carboxylic acid (3-{4-[(3-cyano-benzyl)-(6-methoxy-pyridin-3-yl)-amino]-piperidin-1-yl}-butyl)-amide (191);

N-(3-{4-[(3-Cyano-benzyl)-(6-methoxy-pyridin-3-yl)-amino]-piperidin-1-yl}-butyl)-2,6-dimethyl-benzamide (192);

N-(3-{4-[(2-Acetyl-2,3-dihydro-1H-isoindol-5-yl)-(3-cyano-benzyl)-amino]-piperidin-1-yl}-butyl)-2,6-dimethyl-benzamide (193);

N-(3-{4-[(3-Cyano-benzyl)-(2,3-dihydro-1H-indol-5-yl)-amino]-piperidin-1-yl}-butyl)-2,6-dimethyl-benzamide (194);

3,5-Dichloro-N-(3-{4-[(5-chloro-2-fluoro-benzyl)-(4-cyano-phenyl)-amino]-piperidin-1-yl}-butyl)-isonicotinamide (195);

N-(3-{4-[(5-Chloro-2-fluoro-benzyl)-(4-cyano-phenyl)-amino]-piperidin-1-yl}-butyl)-2,4-dimethyl-1-oxy-nicotinamide (196);

4,6-Dimethyl-pyrimidine-5-carboxylic acid (3-{4-[(5-chloro-2-fluoro-benzyl)-(4-cyano-phenyl)-amino]-piperidin-1-yl}-butyl)-amide (197);

3,5-Dichloro-N-(3-{4-[(5-chloro-2-fluoro-benzyl)-(4-chloro-phenyl)-amino]-piperidin-1-yl}-butyl)-isonicotinamide (198);

4,6-Dimethyl-pyrimidine-5-carboxylic acid (3-{4-[(5-chloro-2-fluoro-benzyl)-(4-dimethylcarbamoyl-phenyl)-amino]-piperidin-1-yl}-butyl)-amide (199);

N-(3-{4-[(5-Chloro-2-fluoro-benzyl)-(4-dimethylcarbamoyl-phenyl)-amino]-piperidin-1-yl}-butyl)-2,4-dimethyl-1-oxy-nicotinamide (200);

4,6-Dimethyl-pyrimidine-5-carboxylic acid (3-{4-[(5-chloro-2-fluoro-benzyl)-(4-methoxy-phenyl)-amino]-piperidin-1-yl}-butyl)-amide (201);

N-(3-{4-[(5-Chloro-2-fluoro-benzyl)-(4-methoxy-phenyl)-amino]-piperidin-1-yl}-butyl)-2,4-dimethyl-1-oxy-nicotinamide (202);

4,6-Dimethyl-pyrimidine-5-carboxylic acid [3-(4-{(5-chloro-2-fluoro-benzyl)-[4-(2-methoxy-ethoxy)-phenyl]-amino}-piperidin-1-yl)-butyl]-amide (203);

N-[3-(4-{(5-Chloro-2-fluoro-benzyl)-[4-(2-methoxy-ethoxy)-phenyl]-amino}-piperidin-1-yl)-butyl]-2,4-dimethyl-1-oxy-nicotinamide (204);

4,6-Dimethyl-pyrimidine-5-carboxylic acid (3-{4-[(4-acetylamino-phenyl)-(5-chloro-2-fluoro-benzyl)-amino]-piperidin-1-yl}-butyl)-amide (205);

N-(3-{4-[(4-Acetylamino-phenyl)-(5-chloro-2-fluoro-benzyl)-amino]-piperidin-1-yl}-butyl)-2,4-dimethyl-1-oxy-nicotinamide (206);

4,6-Dimethyl-pyrimidine-5-carboxylic acid (3-{4-[(4-carbamoyl-phenyl)-(5-chloro-2-fluoro-benzyl)-amino]-piperidin-1-yl}-butyl)-amide (207);

N-(3-{4-[(4-Carbamoyl-phenyl)-(5-chloro-2-fluoro-benzyl)-amino]-piperidin-1-yl}-butyl)-2-chloro-6-methyl-benzamide (208);

4,6-Dimethyl-pyrimidine-5-carboyxlic acid (3-{4-[(5-chloro-2-fluoro-benzyl)-(4-sulfamoyl-phenyl)-amino]-piperidine-1-yl}-butyl)-amide (209);

2-Chloro-N-(3-{4-[(5-chloro-2-fluoro-benzyl)-(4-sulfamoyl-phenyl)-amino]-piperidin-1-yl}-butyl)-6-methyl-benzamide (210);

4,6-Dimethyl-pyrimidine-5-carboxylic acid (3-{4-[(4-acetyl-phenyl)-(5-chloro-2-fluoro-benzyl)-amino]-piperidin-1-yl}-butyl)-amide (211);

N-(3-{4-[(4-Acetyl-phenyl)-(5-chloro-2-fluoro-benzyl)-amino]-piperidin-1-yl}-butyl)-2,4-dimethyl-1-oxy-nicotinamide (212);

3-[(5-Chloro-2-fluoro-benzyl)-(1-{3-[(4,6-dimethyl-pyrimidine-5-carbonyl)-amino]-1-methyl-propyl}-piperidin-4-yl)-amino]-benzoic acid methyl ester (213);

4,6-Dimethyl-pyrimidine-5-carboxylic acid (3-{4-[(5-chloro-2-fluoro-benzyl)-(3-methylcarbamoyl-phenyl)-amino]-piperidin-1-yl}-butyl)-amide (214);

4,6-Dimethyl-pyrimidine-5-carboxylic acid (3-{4-[(5-chloro-2-fluoro-benzyl)-(2,3-dihydro-benzo[1,4]dioxin-6-yl)-amino]-piperidin-1-yl}-butyl)-amide (215);

N-(3-{4-[(5-Chloro-2-fluoro-benzyl)-(2,3-dihydro-benzo[1,4]dioxin-6-yl)-amino]-piperidin-1-yl}-butyl)-2,6-dimethyl-benzamide (216);

N-(3-{4-[(5-Chloro-2-fluoro-benzyl)-(2,3-dihydro-benzo[1,4]dioxin-6-yl)-amino]-piperidin-1-yl}-butyl)-3,5-dimethyl-1-oxy-isonicotin-amide (217);

4,6-Dimethyl-pyrimidine-5-carboxylic acid (3-{4-[benzo[1,3]dioxol-5-yl-(5-chloro-2-fluoro-benzyl)-amino]-piperidin-1-yl}-butyl)-amide (218);

3,5-Dichloro-N-(3-{4-[(5-cyano-2-fluoro-benzyl)-(4-cyano-phenyl)-amino]-piperidin-1-yl}-butyl)-isonicotinamide (219);

N-(3-{4-[(4-Bromo-phenyl)-(5-cyano-2-fluoro-benzyl)-amino]-piperidin-1-yl}-butyl)-2,4-dimethyl-1-oxy-nicotinamide (220);

4,6-Dimethyl-pyrimidine-5-carboxylic acid (3-{4-[(5-cyano-2-fluoro-benzyl)-(4-methoxy-phenyl)-amino]-piperidin-1-yl}-butyl)-amide (221);

N-(3-{4-[(5-Cyano-2-fluoro-benzyl)-(4-methoxy-phenyl)-amino]-piperidin-1-yl}-butyl)-2,4-dimethyl-1-oxy-nicotinamide (222);

4,6-Dimethyl-pyrimidine-5-carboxylic acid [3-(4-{(5-cyano-2-fluoro-benzyl)-[4-(2-methoxy-ethoxy)-phenyl]-amino}-piperidin-1-yl)-butyl]-amide (223);

N-[3-(4-{(5-Cyano-2-fluoro-benzyl)-[4-(2-methoxy-ethoxy)-phenyl]-amino}-piperidin-1-yl)-butyl]-2,4-dimethyl-1-oxy-nicotinamide (224);

4,6-Dimethyl-pyrimidine-5-carboxylic acid (3-{4-[(4-acetylamino-phenyl)-(5-cyano-2-fluoro-benzyl)-amino]-piperidin-1-yl}-butyl)-amide (225);

N-(3-{4-[(4-Acetylamino-phenyl)-(5-cyano-2-fluoro-benzyl)-amino]-piperidin-1-yl}-butyl)-2,4-dimethyl-1-oxy-nicotinamide (226);

(E)-3-{4-[(5-Cyano-2-fluoro-benzyl)-(1-{3-[(4,6-dimethyl-pyrimidine-5-carbonyl)-amino]-1-methyl-propyl}-piperidin-4-yl)-amino]-phenyl}-acrylic acid methyl ester (227);

4-{4-[(5-Cyano-2-fluoro-benzyl)-(1-{3-[(4,6-dimethyl-pyrimidine-5-carbonyl)-amino]-1-methyl-propyl}-piperidin-4-yl)-amino]-phenoxy}-benzoic acid (228);

4-[4-((5-Cyano-2-fluoro-benzyl)-{1-[3-(2,6-dimethyl-benzoylamino)-1-methyl-propyl]-piperidin-4-yl}-amino)-phenoxy]-benzoic acid (229);

N—((R)-3-{4-[(5-Cyano-2-fluoro-benzyl)-(4-methoxy-phenyl)-amino]-piperidin-1-yl}-butyl)-3,5-dimethyl-isonicotinamide (230);

4,6-Dimethyl-pyrimidine-5-carboxylic acid ((R)-3-{4-[(4-acetyl-phenyl)-(5-cyano-2-fluoro-benzyl)-amino]-piperidin-1-yl}-butyl)-amide (231);

N—((R)-3-{4-[(4-Acetyl-phenyl)-(5-cyano-2-fluoro-benzyl)-amino]-piperidin-1-yl}-butyl)-2,4-dimethyl-nicotinamide (232);

4,6-Dimethyl-pyrimidine-5-carboxylic acid ((R)-3-{4-[(5-cyano-2-fluoro-benzyl)-(4-hydroxy-phenyl)-amino]-piperidin-1-yl}-butyl)-amide (233);

4,6-Dimethyl-pyrimidine-5-carboxylic acid (3-{4-[(5-cyano-2-fluoro-benzyl)-(4-ureido-phenyl)-amino]-piperidin-1-yl}-butyl)-amide (234);

{4-[(5-Cyano-2-fluoro-benzyl)-(1-{(R)-3-[(4,6-dimethyl-pyrimidine-5-carbonyl)-amino]-1-methyl-propyl}-piperidin-4-yl)-amino]-phenoxy}-acetic acid tert-butyl ester (235);

{4-[(5-Cyano-2-fluoro-benzyl)-(1-{(R)-3-[(2,4-dimethyl-1-oxy-pyridine-3-carbonyl)-amino]-1-methyl-propyl}-piperidin-4-yl)-amino]-phenoxy}-acetic acid (236);

{4-[(5-Cyano-2-fluoro-benzyl)-(1-{(R)-3-[(4,6-dimethyl-pyrimidine-5-carbonyl)-amino]-1-methyl-propyl}-piperidin-4-yl)-amino]-phenoxy}-acetic acid methyl ester (237);

{4-[(5-Cyano-2-fluoro-benzyl)-(1-{(R)-3-[(4,6-dimethyl-pyrimidine-5-carbonyl)-amino]-1-methyl-propyl}-piperidin-4-yl)-amino]-phenoxy}-acetic acid (238);

4,6-Dimethyl-pyrimidine-5-carboxylic acid ((R)-3-{4-[(4-carbamoylmethoxy-phenyl)-(5-cyano-2-fluoro-benzyl)-amino]-piperidin-1-yl}-butyl)-amide (239);

(E)-3-{4-[(5-Cyano-2-fluoro-benzyl)-(1-{3-[(4,6-dimethyl-pyrimidine-5-carbonyl)-amino]-1-methyl-propyl}-piperidin-4-yl)-amino]-phenyl}-acrylic acid (240);

(E)-3-{4-[(5-Cyano-2-fluoro-benzyl)-(1-{3-[(2,4-dimethyl-1-oxy-pyridine-3-carbonyl)-amino]-1-methyl-propyl}-piperidin-4-yl)-amino]-phenyl}-acrylic acid (241);

4,6-Dimethyl-pyrimidine-5-carboxylic acid (3-{4-[benzo[1,3]dioxol-5-yl-(5-cyano-2-fluoro-benzyl)-amino]-piperidin-1-yl}-butyl)-amide (242);

N-(3-{4-[Benzo[1,3]dioxol-5-yl-(5-cyano-2-fluoro-benzyl)-amino]-piperidin-1-yl}-butyl)-2,4-dimethyl-1-oxy-nicotinamide (243);

N-(3-{4-[(5-Cyano-2-fluoro-benzyl)-(1H-indol-5-yl)-amino]-piperidin-1-yl}-butyl)-2,4-dimethyl-1-oxy-nicotinamide (244);

4,6-Dimethyl-pyrimidine-5-carboxylic acid (3-{4-[(5-cyano-2-fluoro-benzyl)-(1H-indol-5-yl)-amino]-piperidin-1-yl}-butyl)-amide (245);

4,6-Dimethyl-pyrimidine-5-carboxylic acid ((R)-3-{4-[(6-acetylamino-pyridin-3-yl)-(5-cyano-2-fluoro-benzyl)-amino]-piperidin-1-yl}-butyl)-amide (246);

3,5-Dichloro-N-(3-{4-[2-(4-trifluoromethoxy-phenyl)-2,3-dihydro-benzofuran-2-yl]-piperidin-1-yl}-butyl)-isonicotinamide (247);

3,5-Dichloro-N-(3-{4-[2-(4-trifluoromethyl-phenyl)-2,3-dihydrobenzofuran-2-yl]-piperidin-1-yl}-butyl)-isonicotinamide (248);

3,5-Dichloro-N-(3-{4-[2-(4-methanesulfonyl-phenyl)-2,3-dihydro-benzofuran-2-yl]-piperidin-1-yl}-butyl)-isonicotinamide (249);

3,5-Dichloro-N-(3-{4-[2-(4-methylsulfamoyl-phenyl)-2,3-dihydro-benzofuran-2-yl]-piperidin-1-yl}-butyl)-isonicotinamide (250);

3,5-Dichloro-N-(3-{4-[4-fluoro-2-(4-trifluoromethyl-phenyl)-2,3-dihydro-benzofuran-2-yl]-piperidin-1-yl}-butyl)-isonicotinamide (251);

3,5-Dichloro-N-(3-{4-[4-fluoro-2-(4-trifluoromethoxy-phenyl)-2,3-dihydro-benzofuran-2-yl]-piperidin-1-yl}-butyl)-isonicotinamide (252);

3,5-Dichloro-N-(3-{4-[4-fluoro-2-(4-methanesulfonyl-phenyl)-2,3-dihydro-benzofuran-2-yl]-piperidin-1-yl}-butyl)-isonicotinamide (253);

3,5-Dichloro-N-(3-{4-[4-fluoro-2-(4-methylsulfamoyl-phenyl)-2,3-dihydro-benzofuran-2-yl]-piperidin-1-yl}-butyl)-isonicotinamide (254);

3,5-Dichloro-N-(3-{4-[6-fluoro-2-(4-trifluoromethyl-phenyl)-2,3-dihydro-benzofuran-2-yl]-piperidin-1-yl}-butyl)-isonicotinamide (255);

N-(3-{4-[2-(4-Methanesulfonyl-phenyl)-2,3-dihydro-benzofuran-2-yl]-piperidin-1-yl}-butyl)-2,4-dimethyl-1-oxy-nicotinamide (256);

4,6-Dimethyl-pyrimidine-5-carboxylic acid (3-{4-[4-fluoro-2-(4-trifluoromethyl-phenyl)-2,3-dihydro-benzofuran-2-yl]-piperidin-1-yl}-butyl)-amide (257);

3,5-Dichloro-N-(3-{4-[1-imino-2-(4-trifluoromethyl-phenyl)-indan-2-yl]-piperidin-1-yl}-butyl)-isonicotinamide (258);

4,6-Dimethyl-pyrimidine-5-carboxylic acid (3-{4-[1-imino-2-(4-trifluoromethyl-phenyl)-indan-2-yl]-piperidin-1-yl}-butyl)-amide (259);

N-(3-{4-[1-Imino-2-(4-trifluoromethyl-phenyl)-indan-2-yl]-piperidin-1-yl}-butyl)-2,4-dimethyl-1-oxy-nicotinamide (260);

N-(3-{4-[2-(4-Bromo-phenyl)-benzo[1,3]dioxol-2-yl]-piperidin-1-yl}-butyl)-3,5-dichloro-isonicotinamide (261);

N-(3-{4-[2-(4-Bromo-phenyl)-benzo[1,3]dioxol-2-yl]-piperidin-1-yl}-butyl)-2,4-dimethyl-1-oxy-nicotinamide (262);

4,6-Dimethyl-pyrimidine-5-carboxylic acid (3-{4-[2-(4-bromo-phenyl)-benzo[1,3]dioxol-2-yl]-piperidin-1-yl}-butyl)-amide (263);

3,5-Dichloro-N-(3-{4-[2-(4-trifluoromethyl-phenyl)-benzo[1,3]dioxol-2-yl]-piperidin-1-yl}-butyl)-isonicotinamide (264);

2,4-Dimethyl-1-oxy-N-(3-{4-[2-(4-trifluoromethyl-phenyl)-benzo [1,3]dioxol-2-yl]-piperidin-1-yl}-butyl)-nicotinamide (265);

4,6-Dimethyl-pyrimidine-5-carboxylic acid (3-{4-[2-(4-trifluoromethyl-phenyl)-benzo[1,3]dioxol-2-yl]-piperidin-1-yl}-butyl)-amide (266);

2,6-Dimethyl-N-(3-{4-[2-(4-trifluoromethyl-phenyl)-benzo[1,3]dioxol-2-yl]-piperidin-1-yl}-butyl)-benzamide (267);

2,4-Dimethyl-N-(3-{4-[2-(4-trifluoromethyl-phenyl)-benzo[1,3]dioxol-2-yl]-piperidin-1-yl}-butyl)-nicotinamide (268);

2-Chloro-6-methyl-N-(3-{4-[2-(4-trifluoromethyl-phenyl)-benzo[1,3]dioxol-2-yl]-piperidin-1-yl}-butyl)-benzamide (269);

3,5-Dimethyl-N-(3-{4-[2-(4-trifluoromethyl-phenyl)-benzo[1,3]dioxol-2-yl]-piperidin-1-yl}-butyl)-isonicotinamide (270);

3,5-Dichloro-N-(3-{4-[2-(4-methylsulfanyl-phenyl)-benzo[1,3]dioxol-2-yl]-piperidin 1-yl}-butyl)-isonicotinamide (271);

3,5-Dichloro-N-(3-{4-[2-(4-methanesulfinyl-phenyl)-benzo[1,3]dioxol-2-yl]-piperidin-1-yl}-butyl)-isonicotinamide (272);

3,5-Dichloro-N-(3-{4-[2-(4-methanesulfonyl-phenyl)-benzo[1,3]dioxol-2-yl]-piperidin-1-yl}-butyl)-isonicotinamide (273);

N-(3-{4-[2-(4-Methanesulfonyl-phenyl)-benzo[1,3]dioxol-2-yl]-piperidin-1-yl}-butyl)-2,4-dimethyl-nicotinamide (274);

3,5-Dichloro-N-(3-{4-[2-(4-trifluoromethoxy-phenyl)-benzo[1,3]dioxol-2-yl]-piperidin-1-yl}-butyl)-isonicotinamide (275);

2,4-Dimethyl-N-(3-{4-[2-(4-trifluoromethoxy-phenyl)-benzo[1,3]dioxol-2-yl]-piperidin-1-yl}-butyl)-nicotinamide (276);

4,6-Dimethyl-pyrimidine-5-carboxylic acid (3-{4-[2-(4-cyano-phenyl)-benzo[1,3]dioxol-2-yl]-piperidin-1-yl}-butyl)-amide (277);

N-(3-{4-[2-(4-Cyano-phenyl)-benzo[1,3]dioxol-2-yl]-piperidin-1-yl}-butyl)-2,4-dimethyl-1-oxy-nicotinamide (278);

N-(3-{4-[2-(4-Cyano-phenyl)-benzo[1,3]dioxol-2-yl]-piperidin-1-yl}-butyl)-2,6-dimethyl-benzamide (279);

4,6-Dimethyl-pyrimidine-5-carboxylic acid (3-{4-[2-(4-chloro-phenyl)-benzo[1,3]dioxol-2-yl]-piperidin-1-yl}-butyl)-amide (280);

N-(3-{4-[2-(4-Chloro-phenyl)-benzo[1,3]dioxol-2-yl]-piperidin-1-yl}-butyl)-2,4-dimethyl-1-oxy-nicotinamide (281);

4,6-Dimethyl-pyrimidine-5-carboxylic acid (3-{4-[2-(4-acetyl-phenyl)-benzo[1,3]dioxol-2-yl]-piperidin-1-yl}-butyl)-amide (282);

4,6-Dimethyl-pyrimidine-5-carboxylic acid [3-(4-{2-[4-(1-methoxyimino-ethyl)-phenyl]-benzo[1,3]dioxol-2-yl}-piperidin-1-yl)-butyl]-amide (283);

N-(3-{4-[2-(4-Methoxy-phenyl)-benzo[1,3]dioxol-2-yl]-piperidin-1-yl}-butyl)-2,4-dimethyl-nicotinamide (284);

4,6-Dimethyl-pyrimidine-5-carboxylic acid (3-{4-[2-(4-methoxy-phenyl)-benzo[1,3]dioxol-2-yl]-piperidin-1-yl}-butyl)-amide (285);

3,5-Dichloro-N-(3-{4-[5-fluoro-2-(4-trifluoromethyl-phenyl)-benzo[1,3]dioxol-2-yl]-piperidin-1-yl}-butyl)-isonicotinamide (286);

3,5-Dichloro-N-(3-{4-[4-fluoro-2-(4-trifluoromethyl-phenyl)-benzo[1,3]dioxol-2-yl]-piperidin-1-yl}-butyl)-isonicotinamide (287);

3,5-Dichloro-N-(3-{4-[5-fluoro-2-(4-methanesulfonyl-phenyl)-benzo[1,3]dioxol-2-yl]-piperidin-1-yl}-butyl)-isonicotinamide (288);

N-(3-{4-[5-Fluoro-2-(4-methoxy-phenyl)-benzo[1,3]dioxol-2-yl]-piperidin-1-yl}-butyl)-2,4-dimethyl-nicotinamide (289);

4,6-Dimethyl-pyrimidine-5-carboxylic acid (3-{4-[(4-methoxy-phenyl)-thiophen-3-ylmethyl-amino]-piperidin-1-yl}-butyl)-amide (290);

4,6-Dimethyl-pyrimidine-5-carboxylic acid (3-{4-[thiophen-3-ylmethyl-(4-trifluoromethoxy-phenyl)-amino]-piperidin-1-yl}-butyl)-amide (291);

4,6-Dimethyl-pyrimidine-5-carboxylic acid ((R)-3-{4-[(4-chloro-phenyl)-thiophen-3-ylmethyl-amino]-piperidin-1-yl}-butyl)-amide (292);

4,6-Dimethyl-pyrimidine-5-carboxylic acid ((R)-3-{4-[(4-acetyl-phenyl)-thiophen-3-ylmethyl-amino]-piperidin-1-yl}-butyl)-amide (293);

4,6-Dimethyl-pyrimidine-5-carboxylic acid [(R)-3-(4-{[4-(1-methoxyimino-ethyl)-phenyl]-thiophen-3-ylmethyl-amino}-piperidin-1-yl)-butyl]-amide (294);

4,6-Dimethyl-pyrimidine-5-carboxylic acid (3-{4-[thiophen-3-ylmethyl-(4-trifluoromethyl-phenyl)-amino-piperidin-1-yl}-butyl)-amide (295);

4,6-Dimethyl-pyrimidine-5-carboxylic acid ((R)-3-{4-[(4-hydroxy-phenyl)-thiophen-3-ylmethyl-amino]-piperidin-1-yl}-butyl)-amide (296);

{4-[(1-{(R)-3-[(4,6-Dimethyl-pyrimidine-5-carbonyl)-amino]-1-methyl-propyl}-piperidin-4-yl)-thiophen-3-ylmethyl-amino]-phenoxy}-acetic acid (297);

4,6-Dimethyl-pyrimidine-5-carboxylic acid ((R)-3-{4-[(4-carbamoylmethoxy-phenyl)-thiophen-3-ylmethyl-amino]-piperidin-1-yl}-butyl)-amide (298);

4-[(1-{(R)-3-[(4,6-Dimethyl-pyrimidine-5-carbonyl)-amino]-1-methyl-propyl}-piperidin-4-yl)-thiophen-3-ylmethyl-amino]-benzoic acid methyl ester (299);

4,6-Dimethyl-pyrimidine-5-carboxylic acid (3-{4-[(4-carbamoyl-phenyl)-thiophen-3-ylmethyl-amino]-piperidin-1-yl}-butyl)-amide (300);

4,6-Dimethyl-pyrimidine-5-carboxylic acid ((R)-3-{4-[(4-bromo-phenyl)-thiophen-3-ylmethyl-amino]-piperidin-1-yl}-butyl)-amide (301);

4-{4-[(1-{(R)-3-[(4,6-Dimethyl-pyrimidine-5-carbonyl)-amino]-1-methyl-propyl}-piperidin-4-yl)-thiophen-3-ylmethyl-amino]-phenoxy}-benzoic acid (302);

4,6-Dimethyl-pyrimidine-5-carboxylic acid [(R)-3-(4-{[4-(4-carbamoyl-phenoxy)-phenyl]-thiophen-3-ylmethyl-amino}-piperidin-1-yl)-butyl]-amide (303);

4,6-Dimethyl-pyrimidine-5-carboxylic acid ((R)-3-{4-[(4-fluoro-phenyl)-thiophen-3-ylmethyl-amino]-piperidin-1-yl}-butyl)-amide (304);

4,6-Dimethyl-pyrimidine-5-carboxylic acid ((R)-3-{4-[(4-ethoxy-phenyl)-thiophen-3-ylmethyl-amino]-piperidin-1-yl}-butyl)-amide (305);

4,6-Dimethyl-pyrimidine-5-carboxylic acid (3-{4-[(4-cyano-phenyl)-thiophen-3-ylmethyl-amino]-piperidin-1-yl}-butyl)-amide (306);

4,6-Dimethyl-pyrimidine-5-carboxylic acid ((R)-3-{4-[(4-methylsulfanyl-phenyl)-thiophen-3-ylmethyl-amino]-piperidin-1-yl}-butyl)-amide (307);

4,6-Dimethyl-pyrimidine-5-carboxylic acid ((R)-3-{4-[(4-methanesulfonyl-phenyl)-thiophen-3-ylmethyl-amino]-piperidin-1-yl}-butyl)-amide (308);

3,5-Dimethyl-N-((R)-3-{4-[thiophen-3-ylmethyl-(4-trifluoromethoxy-phenyl)-amino]-piperidin-1-yl}-butyl)-isonicotinamide (309);

2,6-Dimethyl-N-((R)-3-{4-[thiophen-3-ylmethyl-(4-trifluoromethoxy-phenyl)-amino]-piperidin-1-yl}-butyl)-benzamide (310);

2-Chloro-6-methyl-N-((R)-3-{4-[thiophen-3-ylmethyl-(4-trifluoromethoxy-phenyl)-amino]-piperidin-1-yl}-butyl)-benzamide (311);

3,5-Dimethyl-isoxazole-4-carboxylic acid ((R)-3-{4-[thiophen-3-ylmethyl-(4-trifluoromethoxy-phenyl)-amino]-piperidin-1-yl}-butyl)-amide (312);

1,3,5-Trimethyl-1H-pyrazole-4-carboxylic acid ((R)-3-{4-[thiophen-3-ylmethyl-(4-trifluoromethoxy-phenyl)-amino]-piperidin-1-yl}-butyl)-amide (313);

2,4-Dimethyl-1-oxy-N-((R)-3-{4-[thiophen-3-ylmethyl-(4-trifluoromethoxy-phenyl)-amino]-piperidin-1-yl}-butyl)-nicotinamide (314);

2,6-Dimethyl-4-pyridin-4-yl-N-((R)-3-{4-[thiophen-3-ylmethyl-(4-trifluoromethoxy-phenyl)-amino]-piperidin-1-yl}-butyl)-benzamide (315);

2,4-Dimethyl-N-((R)-3-{4-[thiophen-3-ylmethyl-(4-trifluoromethoxy-phenyl)-amino]-piperidin-1-yl}-butyl)-nicotinamide (316);

2,4-Dimethyl-thiophene-3-carboxylic acid ((R)-3-{4-[thiophen-3-ylmethyl-(4-trifluoromethoxy-phenyl)-amino]-piperidin-1-yl}-butyl)-amide (317);

N—((R)-3-{4-[(4-Methoxy-phenyl)-thiophen-3-ylmethyl-amino]-piperidin-1-yl}-butyl)-2,6-dimethyl-benzamide (318);

2-Chloro-N-((R)-3-{4-[(4-methoxy-phenyl)-thiophen-3-ylmethyl-amino]-piperidin-1-yl}-butyl)-6-methyl-benzamide (319);

1,3,5-Trimethyl-1H-pyrazole-4-carboxylic acid ((R)-3-{4-[(4-methoxy-phenyl)-thiophen-3-ylmethyl-amino]-piperidin-1-yl}-butyl)-amide (320);

N—((R)-3-{4-[(4-Methoxy-phenyl)-thiophen-3-ylmethyl-amino]-piperidin-1-yl}-butyl)-2,4-dimethyl-nicotinamide (321);

N—((R)-3-{4-[(4-Methoxy-phenyl)-thiophen-3-ylmethyl-amino]-piperidin-1-yl}-butyl)-2,4-dimethyl-1-oxy-nicotinamide (322);

3,5-Dichloro-N-((R)-3-{4-[(4-methoxy-phenyl)-thiophen-3-ylmethyl-amino]-piperidin-1-yl}-butyl)-isonicotinamide (323);

3,5-Dimethyl-isoxazole-4-carboxylic acid ((R)-3-{4-[(4-methoxy-phenyl)-thiophen-3-ylmethyl-amino]-piperidin-1-yl}-butyl)-amide (324);

N—((R)-3-{4-[(4-Methoxy-phenyl)-thiophen-3-ylmethyl-amino]-piperidin-1-yl}-butyl)-3,5-dimethyl-isonicotinamide (325);

2,4-Dimethyl-thiophene-3-carboxylic acid ((R)-3-{4-[(4-methoxy-phenyl)-thiophen-3-ylmethyl-amino]-piperidin-1-yl}-butyl)-amide (326);

4,6-Dimethyl-pyrimidine-5-carboxylic acid {3-[4-(pyridin-3-yl-thiophen-3-ylmethyl-amino)-piperidin-1-yl]-butyl}-amide (327);

4,6-Dimethyl-pyrimidine-5-carboxylic acid ((R)-3-{4-[(6-acetylamino-pyridin-3-yl)-thiophen-3-ylmethyl-amino]-piperidin-1-yl}-butyl)-amide (328);

4,6-Dimethyl-pyrimidine-5-carboxylic acid (3-{4-[(6-chloro-pyridin-3-yl)-thiophen-3-ylmethyl-amino]-piperidin-1-yl}-butyl)-amide (329);

4,6-Dimethyl-pyrimidine-5-carboxylic acid (3-{4-[(6-bromo-pyridin-3-yl)-thiophen-3-ylmethyl-amino]-piperidin-1-yl}-butyl)-amide (330);

4,6-Dimethyl-pyrimidine-5-carboxylic acid ((R)-3-{4-[(6-ethoxy-pyridin-3-yl)-thiophen-3-ylmethyl-amino]-piperidin-1-yl}-butyl)-amide (331);

2,6-Dimethyl-N-{3-[4-(pyridin-3-yl-thiophen-3-ylmethyl-amino)-piperidin-1-yl]-butyl}-benzamide (332);

2-Chloro-6-methyl-N-{3-[4-(pyridin-3-yl-thiophen-3-ylmethyl-amino)-piperidin-1-yl]-butyl}-benzamide (333);

2,4-Dimethyl-N-{3-[4-(pyridin-3-yl-thiophen-3-ylmethyl-amino)-piperidin-1-yl]-butyl}-nicotinamide (334);

2,4-Dimethyl-1-oxy-N-{3-[4-(pyridin-3-yl-thiophen-3-ylmethyl-amino)-piperidin-1-yl]-butyl}-nicotinamide (335);

3,5-Dichloro-N-{3-[4-(pyridin-3-yl-thiophen-3-ylmethyl-amino)-piperidin-1-yl]-butyl}-isonicotinamide (336);

3,5-Dimethyl-N-{3-[4-(pyridin-3-yl-thiophen-3-ylmethyl-amino)-piperidin-1-yl]-butyl}-isonicotinamide (337);

2,4-Dimethyl-thiophene-3-carboxylic acid {3-[4-(pyridin-3-yl-thiophen-3-ylmethyl-amino)-piperidin-1-yl]-butyl}-amide (338);

4,6-Dimethyl-pyrimidine-5-carboxylic acid {3-[4-(pyrimidin-5-yl-thiophen-3-ylmethyl-amino)-piperidin-1-yl]-butyl}-amide (339);

2,4-Dimethyl-1-oxy-N-{3-[4-(pyrimidin-5-yl-thiophen-3-ylmethyl-amino)-piperidin-1-yl]-butyl}-nicotinamide (340);

2,6-Dimethyl-N-{3-[4-(pyrimidin-5-yl-thiophen-3-ylmethyl-amino)-piperidin-1-yl]-butyl}-benzamide (341);

4,6-Dimethyl-pyrimidine-5-carboxylic acid ((R)-3-{4-[(4-methoxy-phenyl)-(4-methyl-thiophen-3-ylmethyl)-amino]-piperidin-1-yl}-butyl)-amide (342);

4,6-Dimethyl-pyrimidine-5-carboxylic acid ((R)-3-{4-[(4-bromo-thiophen-3-ylmethyl)-(4-methoxy-phenyl)-amino]-piperidin-1-yl}-butyl)-amide (343);

4,6-Dimethyl-pyrimidine-5-carboxylic acid ((R)-3-{4-[(4-methoxy-phenyl)-(4-methoxy-thiophen-3-ylmethyl)-amino]-piperidin-1-yl}-butyl)-amide (344);

4,6-Dimethyl-pyrimidine-5-carboxylic acid {(R)-3-[4-(benzo[1,3]dioxol-5-yl-thiophen-3-ylmethyl-amino)-piperidin-1-yl]-butyl}-amide (345);

4,6-Dimethyl-pyrimidine-5-carboxylic acid ((R)-3-{4-[(2,3-dihydro-benzo[1,4]dioxin-6-yl)-thiophen-3-ylmethyl-amino]-piperidin-1-yl}-butyl)-amide (346);

4,6-Dimethyl-pyrimidine-5-carboxylic acid (3-{4-[(4-methoxy-phenyl)-thiophen-2-ylmethyl-amino]-piperidin-1-yl}-butyl)-amide (347);

4,6-Dimethyl-pyrimidine-5-carboxylic acid (3-{4-[(4-methoxy-phenyl)-(3-methyl-thiophen-2-ylmethyl)-amino]-piperidin-1-yl}-butyl)-amide (348);

4,6-Dimethyl-pyrimidine-5-carboxylic acid (3-{4-[(5-chloro-thiophen-2-ylmethyl)-(4-methoxy-phenyl)-amino]-piperidin-1-yl}-butyl)-amide (349);

4,6-Dimethyl-pyrimidine-5-carboxylic acid (3-{4-[furan-2-ylmethyl-(4-methoxy-phenyl)-amino]-piperidin-1-yl}-butyl)-amide (350);

4,6-Dimethyl-pyrimidine-5-carboxylic acid (3-{4-[(4-methoxy-phenyl)-(4-methyl-pyridin-3-ylmethyl)-amino]-piperidin-1-yl}-butyl)-amide (351);

4,6-Dimethyl-pyrimidine-5-carboxylic acid (3-{4-[(4-bromo-phenyl)-(4-methyl-pyridin-3-ylmethyl)-amino]-piperidin-1-yl}-butyl)-amide (352);

4,6-Dimethyl-pyrimidine-5-carboxylic acid (3-{4-[(4-methyl-pyridin-3-ylmethyl)-p-tolyl-amino]-piperidin-1-yl}-butyl)-amide (353);

4,6-Dimethyl-pyrimidine-5-carboxylic acid ((R)-3-{4-[(4-methyl-pyridin-3-ylmethyl)-(4-methylsulfanyl-phenyl)-amino]-piperidin-1-yl}-butyl)-amide (354);

4,6-Dimethyl-pyrimidine-5-carboxylic acid (3-{4-[(4-carbamoyl-phenyl)-(4-methyl-pyridin-3-ylmethyl)-amino]-piperidin-1-yl}-butyl)-amide (355);

4,6-Dimethyl-pyrimidine-5-carboxylic acid ((R)-3-{4-[(4-methyl-pyridin-3-ylmethyl)-(4-trifluoromethoxy-phenyl)-amino]-piperidin-1-yl}-butyl)-amide (356);

N-(3-{4-[(4-Methoxy-phenyl)-(4-methyl-pyridin-3-ylmethyl)-amino]-piperidin-1-yl}-butyl)-3,5-dimethyl-isonicotinamide (357);

N—((R)-3-{4-[(4-Methoxy-phenyl)-(4-methyl-pyridin-3-ylmethyl)-amino]-piperidin-1-yl}-butyl)-2,6-dimethyl-benzamide (358);

N—((R)-3-{4-[(4-Methoxy-phenyl)-(4-methyl-pyridin-3-ylmethyl)-amino]-piperidin-1-yl}-butyl)-2,4-dimethyl-nicotinamide (359);

2-Amino-N-((R)-3-{4-[(4-methoxy-phenyl)-(4-methyl-pyridin-3-ylmethyl)-amino]-piperidin-1-yl}-butyl)-6-methyl-benzamide (360);

2-Chloro-N-((R)-3-{4-[(4-methoxy-phenyl)-(4-methyl-pyridin-3-ylmethyl)-amino]-piperidin-1-yl}-butyl)-6-methyl-benzamide (361);

3,5-Dichloro-N-((R)-3-{4-[(4-methoxy-phenyl)-(4-methyl-pyridin-3-ylmethyl)-amino]-piperidin-1-yl}1-butyl)-isonicotinamide (362);

N—((R)-3-{4-[(4-Methoxy-phenyl)-(4-methyl-pyridin-3-ylmethyl)-amino]-piperidin-1-yl}-butyl)-2,6-dimethyl-4-pyridin-4-yl-benzamide (363);

2,4-Dimethyl-thiophene-3-carboxylic acid ((R)-3-{4-[(4-methoxy-phenyl)-(4-methyl-pyridin-3-ylmethyl)-amino]-piperidin-1-yl}-butyl)-amide (364);

N—((R)-3-{1-[(4-methyl-pyridin-3-ylmethyl)-amino]-piperidin-1-yl}-butyl)-2,4-dimethyl-1-oxy-nicotinamide (365);

N-(3-{4-[(4-Carbamoyl-phenyl)-(4-methyl-pyridin-3-ylmethyl)-amino]-piperidin-1-yl}-butyl)-2,4-dimethyl-nicotinamide (366);

N—((R)-3 {4-[(4-Carbamoylmethoxy-phenyl)-(4-methyl-pyridin-3-ylmethyl)-amino]-piperidin-1-yl}-butyl)-2,4-dimethyl-nicotinamide (367);

Methanesulfonic acid 4-[(1-{(R)-3-[(2,4-dimethyl-pyridine-3-carbonyl)-amino]-1-methyl-propyl}-piperidin-4-yl)-(4-methyl-pyridin-3-ylmethyl)-amino]-phenyl ester (368);

2,4-Dimethyl-N-(3-{4-[(4-methyl-pyridin-3-ylmethyl)-(4-morpholin-4-yl-phenyl)-amino]-piperidin-1-yl}-butyl)-nicotinamide (369);

N-(3-{4-[(4-Methoxy-phenyl)-pyridin-3-ylmethyl-amino]-piperidin-1-yl}-butyl)-2,6-dimethyl-benzamide (370); and 2,4-Dimethyl-N-(3-{4-[(4-methyl-pyridin-3-ylmethyl)-p-tolyl-amino]-piperidin-1-yl}-butyl)-1-oxy-nicotinamide (371).

The present invention also relates to pharmaceutical compositions comprising a piperidine derivative including but not limited to compounds 1-371, and a pharmaceutically acceptable carrier. Furthermore, the present invention relates to methods for treating a CCR5 mediated disease in a system, comprising contacting a piperidine derivative, including but not limited to compounds 1-371, with the system. In one embodiment, the system is a cell or tissue. The present invention also relates to methods for treating a CCR5 mediated disease in a subject, comprising administering a piperidine derivative, including but not limited to compounds 1-371, to the subject. The subject may be human or an animal.

Moreover, the compounds may be supplied as "pro-drugs" or protected forms, which release the compound after administration to a subject. The terms "administration" and or administering" as used herein should be understood to mean providing a compound of the invention to the subject in need of treatment. For example, the compound may carry a protective group which is split off by hydrolysis in body fluids, e.g., in the bloodstream, thus releasing the active compound or is oxidized or reduced in body fluids to release the compound. A discussion of pro-drugs may be found in "Smith and Williams' Introduction to the Principles of Drug Design," H. J. Smith, Wright, Second Edition, London (1988).

The compounds of the present invention may be administered in the form of pharmaceutically acceptable salts that are non-toxic. The term "pharmaceutically acceptable salt" as used herein means an active ingredient comprising compounds of Formula 1 or 2 used in the form of a salt thereof, particularly where the salt form confers on the active ingredient improved pharmacokinetic properties as compared to the free form of the active ingredient or other previously disclosed salt form. The term "pharmaceutically acceptable salt" encompasses all acceptable salts including but not limited to acetate, lactobionate, benzenesulfonate, laurate, benzoate, malate, bicarbonate, maleate, bisulfate, mandelate, bitartarate, mesylate, borate, methylbromide, bromide, methylnitrite, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutame, stearate, glycollylarsanilate, sulfate, hexylresorcinate, subacetate, hydradamine, succinate, hydrobromide, tannate, hydrochloride, tartrate, hydroxynaphthoate, teoclate, iodide, tosylate, isothionate, triethiodide, lactate, panoate, valerate, and the like.

Pharmaceutically acceptable salts of the compounds of the present invention can be used as a dosage for modifying solubility or hydrolysis characteristics, or can be used in sustained release or pro-drug formulations. Also, pharmaceutically acceptable salts of the compounds of this invention may include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

All of the compounds of the invention contain at least one chiral center. The invention includes mixtures of stereoisomers, individual stereoisomers, and enantiomeric mixtures, and mixtures of multiple stereoisomers. In short, the compound may be supplied in any desired degree of chiral purity.

Utility and Administration

In one aspect, the invention is directed to compounds of Formula 1 or 2 that may modulate chemokine receptor activity. Chemokine receptors include but are not limited to CCR1, CCR2, CCR3, CCR4, CCR5, CXCR3, and CXCR4.

In one embodiment, the invention provides compounds of Formula 1 or 2 that may demonstrate protective effects on target cells from HIV infection by binding specifically to the chemokine receptor, thus affecting the binding of a natural ligand to the CCR5 and/or CXCR4 of a target cell.

In another embodiment, the compounds of the present invention may be useful as agents which affect chemokine receptors, such as CCR1, CCR2, CCR3, CCR4, CCR5, CXCR3, CXCR4 where such chemokine receptors have been correlated as being important mediators of many inflammatory as well as immunoregulatory diseases.

Other diseases that are also implicated with chemokines as mediators include angiogenesis, and tumorigenesis such as brain, and breast tumors. Thus, a compound that modulates the activity of such chemokine receptors is useful for the treatment or prevention of such diseases.

As used herein, the terms "modulators and/or modulation" encompass antagonist/antagonism, agonist/agonism, partial antagonist/partial antagonism, and or partial agonist/partial agonism, i.e., inhibitors, and activators. The compounds of Formula 1 or 2 described herein may possess biological activity such that they are able to modulate CCR5 chemokine receptor activity and consequent or associated pathogenic processes subsequently mediated by the CCR5 receptor and its natural ligands. In one embodiment, compounds of Formula 1 or 2 demonstrate a protective effect against HIV infection by inhibiting the binding of HIV to a chemokine receptor of a target cell such as CCR5 and/or CXCR4. Such modulation is obtained by a method which comprises contacting a target cell with an effective amount of the compound to inhibit the binding of the virus to the chemokine receptor. As used herein, the terms "modulation and/or modulation" encompass modulating activity in all types and subtypes of CCR5 receptors of a target cell, in any tissues of a particular patient where they are found, and in any cell components comprising those tissues that the target cell may be located.

Compounds that inhibit chemokine receptor activity and function may be used for the treatment of diseases that are associated with inflammation, including but not limited to, inflammatory or allergic diseases such as asthma, allergic rhinitis, hypersensitivity lung diseases, hypersensitivity pneumonitis, eosinophilic pneumonias, delayed-type hypersensitivity, atherosclerosis, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, multiple sclerosis, systemic lupus erythematosus, myastenia gravis, juvenile onset diabetes; glomerulonephritis, autoimmune throiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinphilic myotis, eosiniphilic fasciitis; and cancers.

In addition, compounds that activate or promote chemokine receptor function are used for the treatment of diseases associated with immunosuppression, such as in individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; or immunosuppression due to congenital deficiency in receptor function or other causes. Compounds that activate or promote chemokine receptor function are also used for the treatment of infectious diseases, such as parasitic diseases, including but not limited to helminth infections, such as nematodes (round worms); Trichuriasis, Enterobiasis, Ascariasis, Hookworm, Strongyloidiasis, Trichinosis, filariasis; trematodes; visceral worms, visceral larva migtrans (e.g., Toxocara), eosinophilic gastroenteritis (e.g., *Anisaki* spp., *Phocanema* ssp.), cutaneous larva migrans (*Ancylostona braziliense, Ancylostoma caninum*); the malaria-causing protozoan *Plasmodium vivax*, Human cytomegalovirus, *Herpesvirus saimiri*, and Kaposi's sarcoma herpesvirus, also known as human herpesvirus 8, and poxvirus *Moluscum contagiosum*.

Compounds of the present invention may be used in combination with any other active agents or pharmaceutical compositions where such combined therapy is useful to modulate chemokine receptor activity and thereby prevent and treat inflammatory and immunoregulatory diseases.

Furthermore, the compounds may be used in combination with one or more agents useful in the prevention or treatment of HIV. Examples of such agents include:

(1) nucleotide reverse transcriptase inhibitor such as tenofovir disoproxil fumarate; lamivudine/zidovudine; abacavir/lamivudine/zidovudine; emtricitabine; amdoxovir; alovudine; DPC-817; SPD-756; SPD-754; GS7340; ACH-126,443 (beta)-L-F d4C; didanosine, zalcitabine, stavudine, adefovir, adefovir dipivoxil, fozivudine todoxil, etc.;

(2) non-nucleotide reverse transcriptase inhibitor (including an agent having anti-oxidation activity such as immunocal, oltipraz, etc.) such as nevirapine, delavirdine, efavirenz, loviride, immunocal, oltipraz, TMC-125; DPC-083; capravarine; calanolide A; SJ-3366 series, etc.;

(3) protease inhibitors such as saquinavir, lopinavir/ritonavir, atazanavir, fosamprenavir, tipranavir, TMC-114, DPC-684, indinavir, nelfinavir, amprenavir, palinavir, lasinavir, etc.;

(4) entry inhibitors such as T-20; T-1249; PRO-542; PRO-140; TNX-355; BMS-806 series; and 5-Helix;

(5) CCR5-receptor inhibitors such as Sch-C (or SCH351125); Sch-D (or SCH350634); TAK779; UK 427,857 and TAK 449; or CXCR4-receptor inhibitors such as T22, T134, T140, 18 amino acid analogs of polyphemusin II, ALX40-4C, ALK40-4C, AMD3100 and AMD070;

(6) Integrase inhibitors such as L-870,810; GW-810781 (S-1360); and (7) Budding inhibitors such as PA-344; and PA-457.

Combinations of compounds of the present invention with HIV agents are not limited to the above examples, but include the combination with any agent useful for the treatment of HIV. Combinations the compounds of the invention and other HIV agents may be administered separately or in conjunction. The administration of one agent may be prior to, concurrent to, or subsequent to the administration of other agent(s).

The compounds according to the present invention may be administered by oral, intramuscular, intraperitoneal, intravenous, intracisternal injection or infusion, subcutaneous injection, transdermal or transmucosal administration or by implant. They may also be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

The compounds of the invention may be used to treat animals, including mice, rats, horses, cattle, sheep, dogs, cats, and monkeys. However, compounds of the invention can also be used in other species, such as avian species (e.g., chickens). The compounds of the invention may also be effective for use in humans. The term "subject" or alternatively referred to herein as "patient" is intended to be referred to an animal, preferably a mammal, most preferably a human, who has been the object of treatment, observation or experiment. However, the compounds, methods and pharmaceutical compositions of the present invention may be used in the treatment of animals.

The invention also relates to a pharmaceutical composition comprising a pharmaceutically acceptable carrier or diluent and an effective amount of compound of Formula 1 or 2. The compounds may be administered alone or as a mixture with a pharmaceutically acceptable carrier (e.g., solid formulations such as tablets, capsules, granules, powders, etc.; liquid formulations such as syrups, injections, etc.). The compounds may be administered orally or non-orally. Examples of non-oral formulations include injections. drops, suppositories, pessaryies.

In the treatment or prevention of conditions which require chemokine receptor modulation, an appropriate dosage level will generally be about 0.01 to 500 mg per kg subject body weight per day, and can be administered in singe or multiple doses. Preferably, the dosage level will be about 0.1 to about 250 mg/kg per day. It will be understood that the specific dose level and frequency of dosage for any particular patient may be varied and will depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

In another aspect of the present invention, a compound of Formula 1 or 2 may be used in screening assays for compounds which modulate the activity of chemokine receptors, preferably CCR5 receptors. The ability of a test compound to inhibit gp120 and CD4/CCR5-dependent cell-cell fusion may be measured using a cell fusion assay known in the art.

The compounds of Formula 1 or 2 as disclosed herein may be useful for isolating receptor mutants, which can then be made into screening tools for the discovery of even more potent compounds, following procedures described herein and procedures known in the art. The compounds of Formula 1 or 2 may also be useful in establishing or characterizing the binding sites of other ligands, including compounds other than those of Formula 1 or 2 to chemokine receptors, e.g., by competitive inhibition. The compounds of the present invention may also be useful for the evaluation of putative specific modulators of various chemokine receptors. As appreciated in the art, thorough evaluation of specific agonists and antagonists of the above chemokine receptors has been hampered by the lack of availability of non-peptidyl (metabolically resistant) compounds with high binding affinity for these receptors. Thus, the compounds of this invention are commercial products to be sold for these purposes.

The invention is further described by means of examples, but not in any limitative sense.

Experimental

General Procedures

General procedure A: Reductive Amination with NaBH(OAc)$_3$

To a stirred solution of the amine (1 equivalent) in $CH_2Cl_2$ (concentration ~0.2M) at room temperature were added the carbonyl compound (1-2 equivalents), glacial AcOH (0-2 equivalents) and sodium triacetoxyborohydride (NaBH(OAc)$_3$) (~1.5-3 equivalents) and the resultant solution was stirred at room temperature. In a standard workup, the reaction mixture was poured into either saturated aqueous $NaHCO_3$ or 1N NaOH. The phases were separated and the aqueous extracted with $CH_2Cl_2$. The combined organic extracts were dried ($Na_2SO_4$ or $MgSO_4$), filtered and concentrated under reduced pressure. The crude material was purified by flash column chromatography on silica gel or by recrystallization.

General procedure B: Reductive Amination with NaCNBH$_3$

To a stirred solution of the amine (1 equivalent) in MeOH (concentration ~0.1M) at room temperature were added the carbonyl compound (1-3 equivalents), glacial AcOH (0-1 equivalents) and sodium cyanoborohydride (NaCNBH$_3$) (~1.5-3 equivalents) and the resultant solution was heated to reflux. In a standard workup, the reaction mixture was concentrated under reduced pressure and diluted with saturated aqueous $NaHCO_3$. The aqueous was extracted with $CH_2Cl_2$ and the combined organic extracts were dried ($Na_2SO_4$ or $MgSO_4$), filtered and concentrated under reduced pressure. The crude material was purified by flash column chromatography on silica gel or by recrystallization.

General Procedure C: Boc deprotection with TFA

The Boc-protected amine was dissolved in $CH_2Cl_2$ (~4 mL/mmol) and trifluoroacetic acid (TFA) (~2 mL/mmol) was added. The mixture was stirred at room temperature for 0.5-5 hours. In a standard work-up, the mixture was neutralized with saturated aqueous $NaHCO_3$ or 1N NaOH and the aqueous extracted with $CH_2Cl_2$. The combined extracts were dried ($Na_2SO_4$ or $MgSO_4$), filtered and concentrated under reduced pressure. The crude material was used in the next reaction as is or was purified by flash column chromatography on silica gel.

General Procedure D: Phthalimide Deprotection

To a solution of the phthalimide-protected amine in EtOH (0.05-0.2M) was added hydrazine hydrate (~10 equivalents). The resulting mixture was stirred at room temperature overnight or heated at 40-50° C. for 2-16 hours. In a standard work-up, the mixture was concentrated under reduced pressure, diluted with $CH_2Cl_2$ and filtered. The filtrate was concentrated under reduced pressure and purified by flash column chromatography on silica gel.

General Procedure E: EDCI coupling

To a stirred solution of a primary or secondary amine (1 equivalent), a carboxylic acid (1.1-2.0 equivalents), 1-hydroxy-benzotriazole hydrate (HOBT) (1.1-2.0 equivalents) and diisopropylethylamine (DIPEA) or N-methylmorpholine (NMM) (1.5-3 equivalents) in $CH_2Cl_2$ or DMF (concentration ~0.05-1.5M) was added 1-[3-(dimethylamino)propyl]-3-ethylcarbodiimide hydrochloride (EDCI) (1.1-2.0 equivalents). The solution was stirred at room temperature for 1-3 days and concentrated in vacuo. In a standard work-up, the mixture was diluted with $CH_2Cl_2$ or EtOAc and washed consecutively with saturated aqueous $NaHCO_3$ and brine. The organic layer was dried ($Na_2SO_4$ or $MgSO_4$), filtered and concentrated under reduced pressure. The crude material was purified by flash column chromatography or by radial chromatography on silica gel.

General Procedure F: Coupling with the Acid Chloride

To a stirred suspension of a carboxylic acid (2 equivalents) in $CH_2Cl_2$ (concentration ~0.1-0.2M) were added DMF (1-5 drops) followed by oxalyl chloride (6 equivalents) and the resultant mixture was stirred at room temperature for 1-2 hours. The mixture was concentrated under reduced pressure and the acid chloride was dried in vacuo for 10-45 minutes. To the acid chloride was added a solution of the amine (1 equivalent) and $Et_3N$ (1.5-2 equivalents) in THF (concentration ~0.1-0.2M) and the mixture was stirred at room temperature for 1-18 hours. In a standard work-up, the mixture was diluted with $CH_2Cl_2$ or EtOAc and washed consecutively with saturated aqueous $NaHCO_3$ and brine. The organic layer was dried ($Na_2SO_4$ or $MgSO_4$), filtered and concentrated under reduced pressure. The crude material was purified by flash column chromatography or by radial chromatography on silica gel.

General Procedure G: Reaction of Alcohols with MsCl

To a stirred solution of the alcohol (1 equivalent) and $Et_3N$ (1.5-2 equivalents) in $CH_2Cl_2$ (or THF) (concentration ~0.1M) at room temperature (or 0° C.) was added methanesulfonyl chloride (MsCl) (~1.5 equivalents) and the reaction was stirred at room temperature for 0.5-2 hours. In a standard work-up, the reaction mixture was poured into either saturated aqueous $NaHCO_3$ or saturated aqueous $NH_4Cl$. The phases were separated and the aqueous extracted with $CH_2Cl_2$. The combined organic layers were dried ($Na_2SO_4$ or $MgSO_4$), filtered and concentrated under reduced pressure. The crude material was either purified by flash column chromatography or used without further purification in the next step.

General Procedure H: N-Alkylation with Mesylates, Alkyl or Benzyl Halides

To a solution of the amine (1 equivalent), the mesylate or alkyl or benzyl halide (1-2 equivalents) in $CH_3CN$ or DMF (concentration ~0.1-0.3M) were added DIPEA or $K_2CO_3$ (1.5-2 equivalents) and KI (0-0.2 equivalents) and the mixture was stirred at 50-90° C. for 2-72 hours. In a standard work-up, the reaction was cooled to room temperature, concentrated under reduced pressure, diluted with $CH_2Cl_2$ and washed with either saturated aqueous $NaHCO_3$ or brine. The aqueous was extracted with $CH_2Cl_2$ and the combined organic extracts were dried ($Na_2SO_4$ or $MgSO_4$), filtered and concentrated under reduced pressure. The crude material was purified by flash column chromatography on silica gel.

General Procedure I: Michael Addition with Crotononitrile

A solution of the amine (1 equivalent) and crotononitrile (2-4 equivalents) in MeOH (concentration ~0.1-0.3M) was heated at 50-60° C. overnight. The mixture was concentrated under reduced pressure and used in the next reaction as is or was purified by flash column chromatography on silica gel.

General Procedure J: Hydrogenation of Nitrile with Raney Nickel

The nitrile (1 equivalent) was dissolved in $NH_3$ saturated MeOH (concentration ~0.05-0.2M), treated with Raney nickel (excess), and placed under 45 psi $H_2$ on a Parr shaker for 1-8 hours. In a standard work-up the mixture was diluted with MeOH and filtered through Celite®. The cake was washed with MeOH and the combined filtrate was concentrated under reduced pressure. The crude material was purified by flash column chromatography on silica gel.

General Procedure K: Ester Hydrolysis

To a solution of the ester (1 equivalent) in MeOH (or 1:1 $THF/I_2O$) was added 10N NaOH (excess) (or LiOH) and the mixture was heated at 40-60° C. for 3-24 hours. The mixture was acidified with 4-6N HCl to pH~5-6 and extracted with $CH_2Cl_2$, $CHCl_3$ or $MeOH/CH_2Cl_2$. The combined organic extracts were dried ($MgSO_4$ or $Na_2SO_4$), filtered and concentrated under reduced pressure. The crude acid was used as is or was purified by flash column chromatography on silica gel.

Intermediates

The preparation of various intermediates used in preparing the present compounds is described below. The intermediates 4-formyl-piperidine-1-carboxylic acid tert-butyl ester, 2-(3-oxo-butyl)-isoindole-1,3-dione; and 3-(bromomethyl) thiophene were prepared according to procedures desribed in literature. (Shu, Min; et al., *Bioorg Med. Chem. Lett.*, 14, 4, 2004, 947-952; Pave, Gregoire; et al., *Syn. Lett.*, 7, 2003, 987-990; and Moustrou, Corinne; et al., *Helv. Chim. Acta.*, 78, 1995, 1887-1893, respectively).

4-(4-Bromo-benzoyl)-piperidine-1-carboxylic acid tert-butyl ester. To a solution of 1-[4-(4-bromo-benzoyl)-piperidin-1-yl]-2,2,2-trifluoroethanone (11.6 g, 31.9 mmol) (Palani A.; et al., *J. Med. Chem.*, 2001, 44, 3339-3342) in MeOH (60 mL) and $H_2O$ (15 mL) at room temperature was added $K_2CO_3$ (10.0 g, 72.5 mmol) and the mixture was stirred for 16 hours to give (4-bromophenyl)-piperidin-4-yl-methanone as a pale yellow solid (7.81 g, 96%) following work-up and purification.

To a solution of the above amine (28.9 g, 108 mmol) in $CH_2Cl_2$ (200 mL) and $Et_3N$ (22.5 mL, 162 mmol) at room temperature was added a solution of $Boc_2O$ (25.8 g, 119 mmol) in $CH_2Cl_2$ dropwise and the mixture was stirred at room temperature for 2 hours. The solvents were removed in vacuo and the residue was crystallized (EtOAc/Hexanes) to give 4-(4-bromobenzoyl)-piperidine-1-carboxylic acid tert-butyl ester as a white solid (29.5 g). The mother liquor was purified by column chromatography to give further product (9.4 g) as a white solid (combined yield: 38.9 g, 98%). $^1H$ NMR ($CDCl_3$) δ 1.46 (s, 9H), 1.61-1.75 (m, 2H), 1.82 (d, 2H, J=10.5 Hz), 2.89 (t, 2H, J=12.0 Hz), 3.34 (tt, 1H, J=10.8, 3.9 Hz), 4.16 (br s, 2H), 7.62 (d, 2H, J=8.7 Hz), 7.81 (d, 2H, J=8.7 Hz).

4-[(4-Bromo-phenyl)-hydroxymethyl]-piperidine-1-carboxylic acid tert-butyl ester.

To a solution of 4-(4-bromobenzoyl)-piperidine-1-carboxylic acid tert-butyl ester (1.47 g, 4.00 mmol) in absolute EtOH (25 mL) was added $NaBH_4$ (227 mg, 6.00 mmol). The mixture was stirred at room temperature for 2 hours. Standard work-up and purification gave 4-[(4-bromo-phenyl)-hydroxymethyl]-piperidine-1-carboxylic acid tert-butyl ester as a white solid (1.480 g, 100%). $^1H$ NMR ($CDCl_3$) δ 1.07-1.27 (m, 2H), 1.62-1.72 (m, 1H), 1.88 (d, 1H, J=13.2 Hz), 2.35 (d, 1H, J=3.3 Hz), 2.50-2.65 (m, 2H), 4.04-4.13 (m, 2H), 4.33 (dd, 1H, J=7.2, 3.3 Hz), 7.16 (d, 2H, J=8.4 Hz), 7.45 (d, 2H, J=8.4 Hz).

4-[Hydroxy-(4-trifluoromethylphenyl)-methyl]-piperidine-1-carboxylic acid tert-butyl ester. To a −78° C. solution of 1-bromo-4-trifluoromethylbenzene (32.9 g, 146 mmol) in anhydrous THF (500 mL) was added n-BuLi (2.5M in Hexanes, 63.4 mL, 158 mmol) dropwise. The mixture was stirred at −78° C. for 1 hour. TMEDA (22.1 mL, 146 mmol) was added followed by 4-formyl-piperidine-1-carboxylic acid tert-butyl ester (26.0 g, 122 mmol) and the mixture was stirred at −78° C. for 1.5 hours. Saturated aqueous $NH_4Cl$ (5000 mL) was added and the mixture was warmed to room temperature. The phases were separated and the aqueous phase was extracted with EtOAc (2×300 mL). The combined organic extracts were dried ($MgSO_4$), filtered and concentrated in vacuo. The crude material was crystallized ($CH_2Cl_2$/Hexanes) to give 4-[hydroxy-(4-trifluoromethylphenyl)-methyl]-piperidine-1-carboxylic acid tert-butyl ester as a white solid (29.0 g). The mother liquor was purified by column chromatography to give further product (3.8 g) as a white solid (combined yield: 32.8 g, 75%). $^1$H NMR ($CDCl_3$) δ 1.15-1.32 (m, 3H), 1.44 (s, 9H), 1.68-1.81 (m, 1H), 1.89 (d, 1H, J=13.8 Hz), 1.98 (br s, 1H), 2.54-2.68 (m, 2H), 4.12 (br s, 2H), 7.43 (d, 2H, J=8.7 Hz), 7.62 (d, 2H, J=8.7 Hz).

4-(4-Trifluoromethyl-benzoyl)-piperidine-1-carboxylic acid tert-butyl ester. To a solution of 4-[hydroxy-(4-trifluoromethylphenyl)-methyl]-piperidine-1-carboxylic acid tert-butyl ester (1.07 g, 2.98 mmol) in $CH_2Cl_2$ (15 mL) were added PCC (1.93 g, 8.94 mmol) and $SiO_2$ (3.86 g) and the mixture was stirred at room temperature for 75 minutes. The mixture was filtered through a silica gel plug (1:4, EtOAc/Hexanes) to afford 4-(4-trifluoromethyl-benzoyl)-piperidine-1-carboxylic acid tert-butyl ester (800 mg, 75%) as a white solid. $^1$H NMR ($CDCl_3$) δ 1.47 (s, 9H), 1.68-1.75 (m, 2H), 1.85 (d, 2H, J=12.0 Hz), 2.91 (t, 2H, J=11.4 Hz), 3.36-3.43 (m, 1H), 4.13-4.19 (m, 2H), 7.75 (d, 2H, J=8.1 Hz), 8.03 (d, 2H, J=8.1 Hz).

4-Fluoro-3-hydroxymethyl-benzonitrile. To a stirred solution of 5-bromo-2-fluorobenzaldehyde (9.2 g, 45 mmol) in DMF (5 mL) was added CuCN (4.8 g, 54 mmol) and the mixture was heated at 100° C. for 2 hours and at 130° C. overnight. The mixture was cooled to room temperature, added to a solution of $FeCl_2$ (11 g) in conc. HCl (100 mL) and $H_2O$ (500 mL) and stirred at room temperature for 30 minutes. The aqueous was extracted with $CH_2Cl_2$ (4×200 mL) and the combined organic extracts were dried ($Na_2SO_4$), filtered and concentrated under reduced pressure. The crude material was purified to afford 5-cyano-2-fluorobenzaldehyde as a yellow solid (5.0 g, 75%).

To a stirred solution of the above aldehyde (5.0 g, 33.5 mmol) in MeOH (330 mL) cooled to 0° C. was added $NaBH_4$ (1.51 g, 40 mmol) and the mixture was stirred at 0° C. for 1 hour. Standard work-up and purification afforded 4-fluoro-3-hydroxymethyl-benzonitrile (4.9 g, 98%) as an off-white solid. $^1$H NMR ($CDCl_3$) δ 1.95 (br s, 1H), 4.81 (s, 2H), 7.13-7.19 (m, 1H), 7.60-7.62 (m, 1H), 7.83-7.85 (m, 1H).

(R)-3-(4-Oxo-piperidin-1-yl)-butyronitrile. As described in literature (Stanfield; et al., *JOC.*, 1981, 46, 4799-800), a solution of Boc-D-Ala-OH (50.0 g, 0.264 mol) in THF (250 mL) was added dropwise to a 0° C. solution of $BH_3$-THF (1.0M in THF, 380 mL, 380 mmol). The mixture was stirred for 2 hours at 0° C. and quenched with a 10% solution of AcOH in MeOH (200 mL). The mixture was concentrated under reduced pressure, diluted with EtOAc (500 mL) and washed with 1N HCl (150 mL). The aqueous was extracted with EtOAc (100 mL) and the combined organic extracts were washed consecutively with $H_2O$ (150 mL) and 1N $NH_4HCO_3$ (150 mL). The organic layer was dried ($Na_2SO_4$), filtered and concentrated in vacuo to give ((S)-2-hydroxy-1-methyl-ethyl)-carbamic acid tert-butyl ester as a colourless oil (43.6 g) that was used in the next step without further purification.

Using standard procedure G the above alcohol gave methanesulfonic acid (S)-2-tert-butoxycarbonylamino-propyl ester as an orange crystalline solid (48.34 g, 76% over 2 steps).

To the above mesylate (48.34 g, 0.190 mol) in DMSO (100 mL) was added NaCN (27.93 g, 0.570 mol) followed by DMSO (75 mL) and the mixture was heated at 45° C. for 18 hours. The mixture was cooled to room temperature, quenched with $H_2O$ (200 mL) and extracted with $Et_2O$ (3×200 mL). The combined organic layers were washed with brine (3×120 mL) and the combined aqueous layers were extracted with $Et_2O$ (200 mL). The organic layers were dried ($Na_2SO_4$), filtered and concentrated under reduced pressure. The resulting orange oil was dissolved in $^iPr_2O$ (45 mL) and warmed to 60° C. Heptane (130 mL) was added and the mixture was cooled to room temperature and concentrated under reduced pressure. The precipitate was collected by filtration and the filtrate was concentrated under reduced pressure and purified by flash column chromatography on silica gel (49:1, MeOH/$CH_2Cl_2$) to give ((S)-2-cyano-1-methyl-ethyl)-carbamic acid tert-butyl ester as a pale orange solid (combined yield: 22 g, 63%).

To a solution of the above carbamate (21.43 g, 0.116 mol) in $CH_3CN$ (58 mL) and EtOAc (29 mL) was added methanesulfonic acid (9.0 mL, 0.23 mol) (Allen, et al. U.S. 2003/0065207A1). The mixture was diluted with $CH_3CN$ (20 mL) to facilitate stirring and the mixture was heated to 70° C. for 1 hour. The mixture was cooled to room temperature and placed in an ice bath for 20 minutes with stirring. The resulting solid with isolated via filtration and then dissolved in $NH_4OH$ (50 mL). The aqueous phase was extracted with $CH_2Cl_2$ (4×120 mL) and the combined organic extracts were dried ($Na_2SO_4$), filtered and concentrated under reduced pressure to afford (S)-3-amino-butyronitrile as a pale yellow liquid (6.87 g, 90%).

To a solution of 1-ethyl-4-piperidone (21.0 g, 0.165 mol) in acetone (175 mL) cooled to 10° C. was added a solution of MeI (12.3 mL, 0.198 mmol) in acetone (15 mL) dropwise. The mixture was stirred at room temperature overnight and the precipitate was isolated by filtration, washed with acetone and dried in vacuo to give 1-ethyl-1-methyl-4-oxo-piperidinium iodide as a pale yellow solid (42.03 g, 95%).

To a solution of the above amine (6.85 g, 81.5 mmol) in EtOH (150 mL) heated to 100° C. was added a solution of the above piperidone salt (32.9 g, 122 mmol) in $H_2O$ (150 mL) dropwise. The resulting solution was stirred at reflux for 1 hour and then slowly cooled to room temperature. The mixture was concentrated under reduced pressure, diluted with saturated aqueous $NaHCO_3$ (120 mL) and extracted with $CH_2Cl_2$ (4×150 mL). The combined organic extracts were washed with $H_2O$ (150 mL) and the organic layer was dried ($Na_2SO_4$), filtered and concentrated under reduced pressure to give (R)-3-(4-oxo-piperidin-1-yl)-butyronitrile as an orange liquid (11.74 g, 87%). $^1$H NMR ($CDCl_3$) δ 1.22 (d, 3H, J=6.0 Hz), 2.38-2.59 (m, 6H), 2.82-2.83 (m, 4H), 3.20-3.27 (m, 1H).

EXAMPLE 1

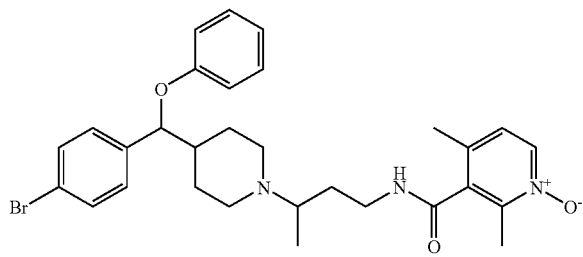

COMPOUND 1: N-(3-{4-[(4-Bromophenyl)-phenoxymethyl]-piperidin-1-yl}-butyl)-2,4-dimethyl-1-oxynicotinamide To a solution of 4-[(4-bromophenyl)-hydroxymethyl]-piperidine-1-carboxylic acid tert-butyl ester (370 mg, 1.00 mmol), phenol (141 mg, 1.50 mmol) and $Ph_3P$ (393 mg, 1.50 mmol) in THF (6 mL) at room temperature was added DIAD (0.295 mL, 1.50 mmol) dropwise. The mixture was stirred at room temperature for 2.5 hours. Aqueous work-up and purification gave 4-[(4-bromophenyl)-phenoxymethyl]-piperidine-1-carboxylic acid tert-butyl ester as a colorless oil (213 mg, 48%).

Using general procedure C with the above compound (213 mg, 0.48 mmol), then general procedure B with the resulting amine, 2-(3-oxo-butyl)-isoindole-1,3-dione (156 mg, 0.72 mmol) and $CH(OMe)_3$ (0.15 mL) and then using general procedure D gave 3-{4-[(4-bromophenyl)-phenoxymethyl]-piperidin-1-yl}-butylamine as a colorless oil (79 mg, 40% over 3 steps).

Using general procedure E, the above primary amine (24.0 mg, 0.058 mmol) and 2,4-dimethyl-1-oxynicotinic acid (11.0 mg, 0.063 mmol) gave COMPOUND 1 as a white foam (26.8 mg, 82%). $^1H$ NMR ($CDCl_3$) δ 0.84-1.10 (m, 1H), 1.00 (d, 3H, J=6.3 Hz), 1.26 (br d, 1H, J=9.9 Hz), 1.53-1.66 (m, 2H), 1.84 (br s, 1H), 2.05 (br d, 2H, J=11.4 Hz), 2.28 and 2.29 (s, 3H), 2.40 (s, 3H), 2.27-2.49 (m, 2H), 2.67-2.85 (m, 3H), 3.35 (m, 1H), 3.75 (m, 1H), 4.36 (t, 1H, J=7.5 Hz), 6.75 (d, 2H, J=7.5 Hz), 6.76-6.90 (m, 2H), 7.19 (t, 4H, J=8.1 Hz), 7.43 (d, 2H, J=8.1 Hz), 7.95 and 7.99 (d, 1H, J=6.6 Hz), 9.10 and 9.17 (br s, 1H). $^{13}C$ NMR ($CDCl_3$) δ 13.3, 13.4, 18.4, 28.7, 29.0, 29.4, 29.7, 30.8, 31.1, 39.5, 42.9, 44.3, 51.8, 59.9, 60.0, 83.6, 83.9, 115.96, 116.00, 121.05, 121.09, 121.6, 124.9, 128.6, 129.4, 131.7, 133.6, 136.9, 138.1, 139.0, 145.5, 145.6, 157.9, 158.1, 165.3, 165.5. ES-MS m/z 568 (M+H). Anal. Calcd. for $C_{30}H_{36}BrN_3O_3 \cdot 0.6CH_2Cl_2 \cdot 0.2C_6H_{14}$: C, 60.17; H, 6.25; N, 6.62; Br, 12.59. Found. C, 60.35; H, 6.27; N, 6.94; Br, 12.53.

EXAMPLE 2

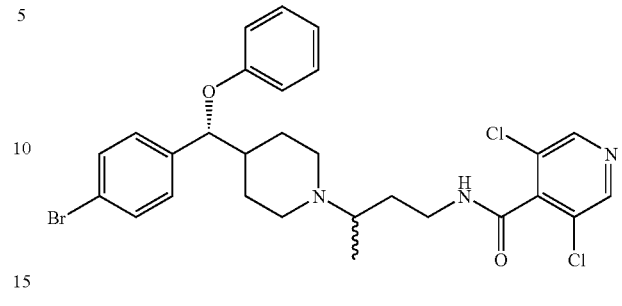

COMPOUND 2: N-(3-{4-[(4-Bromophenyl)-phenoxymethyl]-piperidin-1-yl}-butyl)-3,5-dichloro-isonicotinamide To a solution of (−)-DIP-chloride™ (6.42 g, 20.0 mmol) in THF (10 mL) at 0° C. was added 4-(4-bromobenzoyl)-piperidine-1-carboxylic acid tert-butyl ester (3.68 g, 10.0 mmol). The mixture was stirred at room temperature for 29 hours. Aqueous work-up and purification gave (S)-4-[(4-bromophenyl)-hydroxymethyl]-piperidine-1-carboxylic acid tert-butyl ester (ee 78% determined by both chiral HPLC and Mosher ester) as a crystalline solid (2.22 g, 54%). This material was recrystallized ($CH_2Cl_2$/hexane) three times to provide (S)-4-[(4-bromophenyl)-hydroxymethyl]-piperidine-1-carboxylic acid tert-butyl ester as a white solid (1.29 g, 35%) with ee of 96%.

To a solution of the above alcohol (370 mg, 1.00 mmol), phenol (141 mg, 1.50 mmol) and $Ph_3P$ (393 mg, 1.50 mmol) in THF (6 mL) at room temperature was added DIAD (0.295 mL, 1.50 mmol) dropwise. The mixture was stirred at room temperature for 3 hours. Aqueous work-up and purification gave (R)-4-[(4-bromophenyl)-phenoxymethyl]-piperidine-1-carboxylic acid tert-butyl ester as a colorless oil (257 mg, 58%).

Using general procedure C with the above carbamate, then general procedure B with the resulting amine and 2-(3-oxo-butyl)-isoindole-1,3-dione (157 mg, 0.724 mmol) and then using general procedure D gave 3-{4-[(-(R)-4-bromophenyl)phenoxymethyl]-piperidin-1-yl}-butylamine as a colorless oil (96 mg, 48% over 3 steps).

Using general procedure F, 3,5-dichloroisonicotinic acid (64.5 mg, 0.336 mmol) and the above amine (70.0 mg, 0.168 mmol) gave COMPOUND 2 as a white foam (90 mg, 91%). $^1H$ NMR ($CDCl_3$) δ 0.45-85 (m, 1H), 0.95 (d, 3H, J=6.6 Hz), 1.19 (br d, 1H, J=12.6 Hz), 1.45-1.65 (m, 2H), 1.71-1.82 (m, 1H), 1.92-2.02 (m, 2H), 2.33-2.41 (m, 1H), 2.64-2.89 (m, 3H), 3.27-3.35 (m, 1H), 3.82-3.93 (m, 1H), 4.18 (t, 1H, J=6.8 Hz), 6.70 (d, 2H, J=8.1 Hz), 6.88 and 6.89 (t, 1H, J=7.2 Hz), 7.02 and 7.03 (d, 2H, J=8.4 Hz), 7.16-7.22 (m, 2H), 7.42 (d, 2H, J=8.4 Hz), 8.50 and 8.54 (s, 2H), 9.31 and 9.43 (d, 1H, J=5.1 Hz). $^{13}C$ NMR ($CDCl_3$) δ 13.7, 29.0, 29.1, 29.8, 30.1, 30.3, 30.5, 40.7, 40.8, 43.2, 44.1, 44.2, 52.4, 52.5, 61.0, 84.0, 84.1, 116.35, 116.43, 121.5, 121.6, 122.0, 128.78, 128.80, 129.6, 129.8, 132.0, 139.4, 143.9, 148.0, 158.3, 158.4, 161.77, 161.83. ES-MS m/z 592 (M+H). Anal. Calcd. for $C_{28}H_{30}BrCl_2N_3O_2$: C, 56.87; H, 5.11; N, 7.11; Br, 13.51; Cl, 11.99. Found. C, 56.81; H, 5.10; N, 7.07; Br, 13.17; Cl, 12.24.

EXAMPLE 3

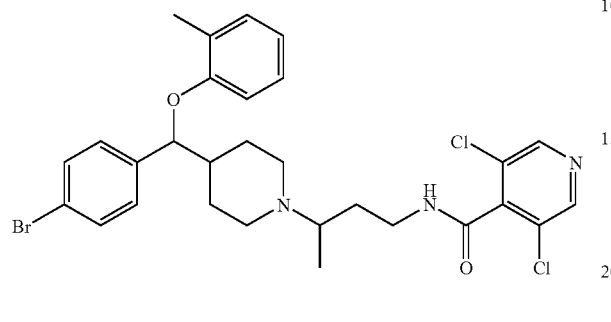

COMPOUND 3: N-(3-{4-[(4-Bromo-phenyl)-o-tolyloxy-methyl]-piperidin-1-yl}-butyl)-3,5-dichloro-isonicotinamide To a solution of 4-[(4-bromo-phenyl)-hydroxy-methyl]-piperidine-1-carboxylic acid tert-butyl ester (740 mg, 2.00 mmol), m-cresol (0.31 mL, 3.00 mmol), Ph₃P (786 mg, 3.00 mmol) and THF (13 mL) cooled to 0° C. was added DIAD (0.59 mL, 3.00 mmol) dropwise. The reaction mixture was stirred at room temperature overnight to give a colourless syrup after aqueous work-up and purification.

Using general procedure C with the above substrate, then general procedure B with the resulting amine and 2-(3-oxo-butyl)-isoindole-1,3-dione (203 mg, 1.00 mmol) and then using general procedure D afforded 3-{4-[(4-bromo-phenyl)-o-tolyloxy-methyl]-piperidin-1-yl}-butylamine as a colourless syrup (81 mg, 10% over 4 steps).

Using general procedure F, 3,5-dichloroisonicotinic acid (45 mg, 0.24 mmol) and the above amine (51 mg, 0.12 mmol) afforded COMPOUND 3 as a white solid (34 mg, 48%). ¹H NMR (CDCl₃) δ 0.34-0.99 (m, 2H), 0.96, 0.97 (d, 3H, J=6.6 Hz), 1.12-1.20 (m, 1H), 1.46-1.56 (m, 1H), 1.58-2.05 (m, 3H), 2.07-2.16 (m, 1H), 2.22 (s, 3H), 2.28-2.50 (m, 1H), 2.61-2.93 (m, 3H), 3.27-3.40 (m, 1H), 3.81-3.96 (m, 1H), 4.14, 4.17 (d, 1H, J=8.4 Hz), 6.46 (d, 1H, J=8.1 Hz), 6.78 (dd, 1H, J=7.5, 7.5 Hz), 6.98-7.04 (m, 3H), 7.09 (d, 1H, J=7.2 Hz), 7.42 (d, 2H, J=8.1 Hz), 8.52, 8.56 (s, 2H), 9.18, 9.39 (d, 1H, J=5.4 Hz). ¹³C NMR (CDCl₃) δ 13.60, 13.72, 16.95, 28.92, 29.70, 29.89, 30.16, 30.69, 40.64, 40.80, 43.24, 44.16, 52.34, 52.54, 60.93, 61.09, 83.42, 83.62, 112.84, 112.97, 120.89, 122.00, 127.05, 127.34, 128.79, 129.69, 131.09, 132.04, 139.44, 143.88, 148.01, 155.91, 155.99, 161.69, 161.86. ES-MS m/z 604 (M+H). Anal. Calcd. for $C_{29}H_{32}N_3O_2BrCl_2$: C, 57.54; H, 5.33; N, 6.94; Cl, 11.71; Br, 13.20. Found. C, 57.51; H, 5.31; N, 6.94; Cl, 11.99; Br, 12.99.

Scheme 1 describes the preparation of Examples 4-14, using various general procedures previously described, and reagents listed below.

Scheme 1

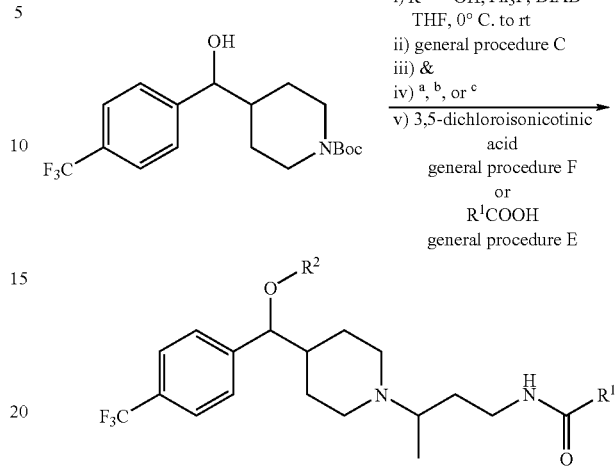

i) R²—OH, Ph₃P, DIAD THF, 0° C. to rt
ii) general procedure C
iii) &
iv) a, b, or c
v) 3,5-dichloroisonicotinic acid
general procedure F
or
R¹COOH
general procedure E

| Example | R²—OH | R¹COOH |
|---|---|---|
| 4[a] | phenol | 2,4-dimethyl-1-oxy-nicotinic acid |
| 5[a] | phenol | 2,6-dimethyl-4-pyridin-4-yl-benzoic acid |
| 6[a] | phenol | 3,5-dichloroisonicotinic acid |
| 7[a] | 3-(trifluoromethyl)phenol | 3,5-dichloroisonicotinic acid |
| 8[a] | 2-(trifluoromethyl)phenol | 3,5-dichloroisonicotinic acid |
| 9[b] | 3-chlorophenol | 3,5-dichloroisonicotinic acid |
| 10[b] | 2-fluorophenol | 3,5-dichloroisonicotinic acid |
| 11[b] | 3-fluorophenol | 3,5-dichloroisonicotinic acid |
| 12[c] | m-cresol | 2,6-dimethyl-4-pyridin-4-yl-benzoic acid |
| 13[c] | o-cresol | 2,6-dimethyl-4-pyridin-4-yl-benzoic acid |
| 14[c] | 3-cyanophenol | 3,5-dichloroisonicotinic acid |

[a]iii) general procedure I, iv) general procedure J
[b]iii) general procedure I, iv) BH₃—Me₂S, THF, reflux
[c]iii) 2-(3-oxo-butyl-isoindole-1,3-dione, general procedure B, iv) general procedure D

EXAMPLE 4

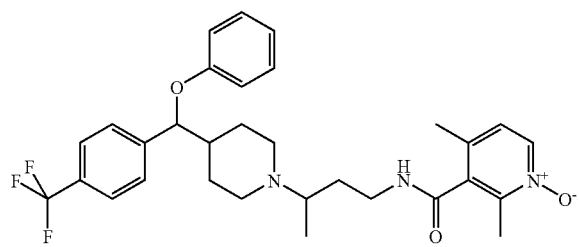

COMPOUND 4: 2,4-Dimethyl-1-oxy-N-(3-{4-[phenoxy-(4-trifluoromethyl-phenyl)-methyl]-piperidin-1-yl}-butyl)-nicotinamide White solid. ¹H NMR (CDCl₃) δ 0.50-0.92 (m, 2H), 0.96 (d, 3H, J=6.6 Hz), 1.16-1.24 (m, 1H), 1.46-1.83 (m, 3H), 1.89-2.08 (m, 2H), 2.28, 2.29 (s, 3H), 2.31-2.48 (m, 1H), 2.51

(s, 3H), 2.59-2.87 (m, 3H), 3.24-3.38 (m, 1H), 3.77-3.91 (m, 1H), 4.32, 4.37 (d, 1H, J=7.8 Hz), 6.74-6.93 (m, 4H), 7.18-7.23 (m, 2H), 7.44 (d, 2H, J=8.1 Hz), 7.58 (d, 2H, J=8.1 Hz), 7.97, 8.02 (d, 1H, J=6.6 Hz), 9.09, 9.18 (br s, 1H). $^{13}$C NMR (CDCl$_3$) δ 13.35, 13.44, 15.26, 18.38, 28.70, 29.37, 29.47, 30.91, 31.17, 39.68, 43.00, 44.24, 51.74, 59.73, 59.88, 76.63, 77.05, 77.47, 86.67, 83.95, 115.88, 115.94, 121.14, 121.18, 124.05 (q, J=272 Hz), 124.83, 125.47, 127.23, 129.42, 129.88 (q, J=32 Hz), 133.64, 133.72, 137.01, 138.04, 144.25, 145.50, 145.60, 157.94, 158.05, 165.23, 165.36. ES-MS m/z 556 (M+H). Anal. Calcd. for C$_{31}$H$_{36}$N$_3$O$_3$F$_3$.0.2H$_2$O.0.2CH$_2$Cl$_2$: C, 65.03; H, 6.44; N, 7.29; F, 9.89. Found. C, 65.10; H, 6.46; N, 7.29; F, 9.88.

EXAMPLE 5

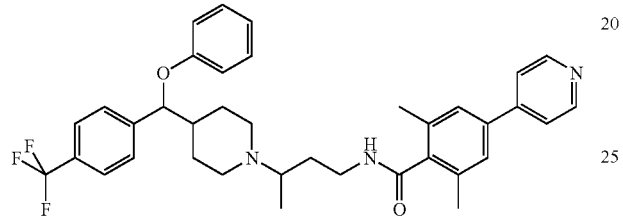

COMPOUND 5: 2,6-Dimethyl-N-(3-{4-[phenoxy-(4-trifluoromethyl-phenyl)-methyl]-piperidin-1-yl}-butyl)-4-pyridin-4-yl-benzamide White solid. $^1$H NMR (CDCl$_3$) δ 0.47-1.09 (m, 3H), 0.95, 0.96 (d, 3H, J=6.0 Hz), 1.48-1.64 (m, 2H), 1.68-2.11 (m, 3H), 2.23-2.46 (m, 1H), 2.43, 2.44 (s, 6H), 2.57-2.91 (m, 3H), 3.26-3.38 (m, 1H), 3.85-3.96 (m, 1H), 4.09-4.13 (d, 1H, J=8.1 Hz), 6.45-6.50 (m, 2H), 6.78-6.85 (m, 1H), 6.93-7.01 (m, 2H), 7.09-7.14 (m, 2H), 7.36 (d, 2H, J=10.5 Hz), 7.42-7.48 (m, 4H), 8.61-8.64 (m, 2H), 8.80 (br s, 1H). $^{13}$C NMR (CDCl$_3$) δ 13.25, 13.33, 19.42, 28.20, 28.68, 29.17, 29.86, 30.68, 30.80, 39.85, 43.04, 43.84, 43.94, 52.08, 52.17, 60.52, 60.64, 83.61, 83.79, 115.70, 115.91, 121.12, 121.28, 124.16 (q, J=306 Hz), 125.32, 125.82, 126.86, 129.29, 129.92 (q, J=32 Hz), 135.34, 135.40, 137.75, 139.63, 144.17, 147.36, 150.39, 150.43, 157.58, 157.72, 169.19, 169.34. ES-MS m/z 616 (M+H). Anal. Calcd. for C$_{37}$H$_{40}$N$_3$O$_2$F$_3$.0.5H$_2$O: C, 71.13; H, 6.61; N, 6.73; F, 9.12. Found. C, 71.05; H, 6.55; N, 6.66; F, 9.48.

EXAMPLE 6

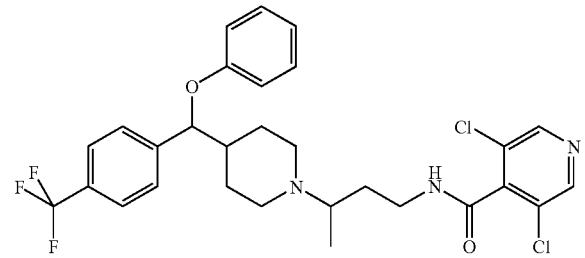

COMPOUND 6: 3,5-Dichloro-N-(3-{4-[phenoxy-(4-trifluoromethyl-phenyl)-methyl]-piperidin-1-yl}-butyl)-isonicotinamide White solid. $^1$H NMR (CDCl$_3$) δ 0.49-0.93 (m, 2H), 0.96 (d, 3H, J=6.6 Hz), 1.15-1.22 (m, 1H), 1.45-1.72 (m, 2H), 1.73-2.04 (m, 3H), 2.30-2.46 (m, 1H), 2.64-2.92 (m, 3H), 3.28-3.38 (m, 1H), 3.86-3.96 (m, 1H), 4.26-4.31 (m, 1H), 6.71 (d, 2H, J=7.8 Hz), 6.87-6.93 (m, 1H), 7.17-7.28 (m, 4H), 7.57 (d, 2H, J=8.1 Hz), 8.52, 8.55 (s, 2H), 9.29, 9.38 (d, 1H, J=5.7 Hz). $^{13}$C NMR (CDCl$_3$) δ 13.27, 28.55, 28.70, 29.50, 29.97, 30.14, 40.32, 40.39, 42.86, 43.70, 43.79, 52.02, 52.12, 60.68, 83.53, 83.75, 115.90, 115.98, 121.26, 121.32, 124.00 (q, J=272 Hz), 125.47, 125.51, 126.98, 129.29, 129.47, 129.97 (q, J=32 Hz), 143.51, 144.11, 147.63, 157.79, 157.92, 161.42. ES-MS m/z 580 (M+H). Anal. Calcd. for C$_{29}$H$_{30}$N$_3$Cl$_2$O$_2$F$_3$.0.1CH$_2$Cl$_2$: C, 59.34; H, 5.17; N, 7.13; Cl, 13.24; F, 9.68. Found. C, 59.17; H, 5.18; N, 7.07; Cl, 13.38; F, 9.84.

EXAMPLE 7

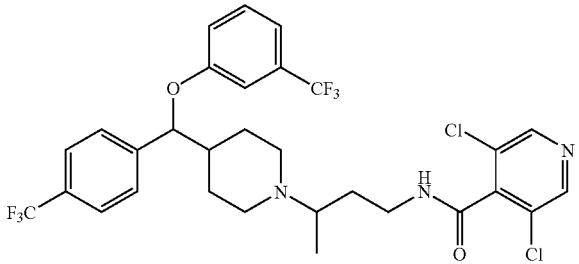

COMPOUND 7: 3,5-Dichloro-N-(3-{4-[(3-trifluoromethyl-phenoxy)-(4-trifluoromethyl-phenyl)-methyl]-piperidin-1-yl}-butyl)-isonicotinamide White powder. $^1$H NMR (CDCl$_3$) δ 0.52-1.01 (m, 2H), 0.96 (d, 3H, J=6.6 Hz), 1.15-1.26 (m, 1H), 1.46-1.57 (m, 1H), 1.60-1.83 (m, 2H), 1.87-2.04 (m, 2H), 2.31-2.46 (m, 1H), 2.64-2.94 (m, 3H), 3.27-3.40 (m, 1H), 3.82-3.95 (m, 1H), 4.32 and 4.33 (d, 1H, J=7.5 Hz), 6.81 (d, 1H, J=8.1 Hz), 7.03 (s, 1H), 7.12-7.18 (m, 1H), 7.24-7.32 (m, 3H), 7.59 (d, 2H, J=8.4 Hz), 8.52 and 8.54 (s, 2H), 9.20 and 9.27 (br d, 1H, J=5.0 Hz). $^{13}$C NMR (CDCl$_3$) δ 13.10 and 13.16, 28.25 and 28.47, 29.23, 30.04 and 30.11, 40.00 and 40.05, 42.62 and 42.66, 43.61 and 43.73, 51.73 and 51.78, 60.23 and 60.31, 83.76 and 83.88, 113.23 and 113.25 (q, J=3.9 Hz), 117.75 and 117.80 (q, J=3.8 Hz), 118.34 and 118.38, 123.68 (q, J=272 Hz), 123.80 (q, J=271 Hz), 125.55 (q, J=3.8 Hz), 126.80 and 126.86, 129.17 and 129.20, 129.96, 130.12 and 130.14 (q, J=32.5 Hz), 131.73 and 131.74 (q, J=32.4 Hz), 143.10 (q, J=1.3 Hz), 143.35 and 143.37, 147.45, 157.72 and 157.82, 161.31. ESI-MS m/z 648 (MH)$^+$, 650 (MH+2)$^+$. Anal. Calcd.

for C$_{30}$H$_{29}$Cl$_2$F$_6$N$_3$O$_2$.0.2C$_4$H$_{10}$O.0.1CH$_2$Cl$_2$: C, 55.25; H, 4.68; N, 6.25; Cl, 11.61; F, 16.97. Found. C, 55.22; H, 4.49; N, 6.54; Cl, 11.57; F, 16.66.

EXAMPLE 8

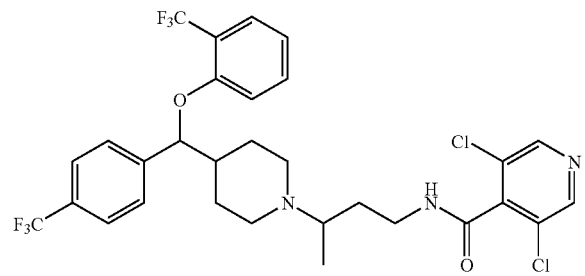

COMPOUND 8: 3,5-Dichloro-N-(3-{4-[(2-trifluoromethyl-phenoxy)-(4-trifluoromethyl-phenyl)-methyl]-piperidin-1-yl}-butyl)-isonicotinamide White powder. $^1$H NMR (CDCl$_3$) δ 0.41-0.93 (m, 2H), 0.96 and 0.97 (d, 3H, J=6.3 Hz), 1.09-1.19 (m, 1H), 1.47-2.19 (m, 5H), 2.29-2.51 (m, 1H), 2.61-2.95 (m, 3H), 3.27-3.41 (m, 1H), 3.81-3.95 (m, 1H), 4.27 and 4.32 (d, 1H, J=8.3 Hz), 6.60 (d, 1H, J=8.7 Hz), 6.93 (dd, 1H, J=7.7, 7.7 Hz), 7.27-7.35 (m, 3H), 7.54 (d, 1H, J=8.1 Hz), 7.58 (d, 2H, J=8.1 Hz), 8.53 and 8.57 (s, 2H), 9.15 and 9.36 (br s, 1H). $^{13}$C NMR (CDCl$_3$) δ 13.14 and 13.28, 28.32 and 29.01, 29.05 and 29.68, 29.89 and 30.34, 40.08 and 40.20, 42.61 and 42.70, 43.62 and 43.66, 51.78 and 51.99, 60.38 and 60.46, 83.19 and 83.36, 113.21 and 113.26, 118.81 (q, J=30.4 Hz), 120.05 and 120.07, 123.70 (q, J=272 Hz), 123.84 (q, J=272 Hz), 125.62 and 125.64 (q, J=3.8 Hz), 127.02 and 127.05, 127.22 (q, J=5.4 Hz), 129.36 and 129.40, 130.32 (q, J=32.4 Hz), 133.10, 142.91 (q, J=1.3 Hz), 143.50 and 143.52, 147.53 and 147.55, 154.97 (q, J=1.9 Hz), 161.26 and 161.38. ESI-MS m/z 648 (MH)$^+$, 650 (MH+2)$^+$. Anal. Calcd. for C$_{30}$H$_{29}$Cl$_2$F$_6$N$_3$O$_2$: C, 55.57; H, 4.51; N, 6.48; Cl, 10.93; F, 17.58. Found. C, 55.42; H, 4.44; N, 6.35; Cl, 10.66; F, 17.24.

EXAMPLE 9

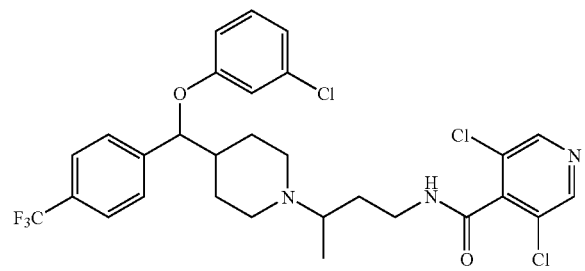

COMPOUND 9: 3,5-Dichloro-N-(3-{4-[(3-chlorophenoxy)-(4-trifluoromethyl-phenyl)-methyl]-piperidin-1-yl}-butyl)-isonicotinamide White powder. $^1$H NMR (CDCl$_3$) δ 0.51-0.92 (m, 2H), 0.96 (d, 3H, J=6.6 Hz), 1.15-1.24 (m, 1H), 1.47-2.04 (m, 5H), 2.30-2.46 (m, 1H), 2.64-2.92 (m, 3H), 3.28-3.39 (m, 1H), 3.84-3.96 (m, 1H), 4.26 and 4.29 (d, 1H, J=6.9 Hz), 6.55 (dd, 1H, J=8.4, 2.7 Hz), 6.75 (s, 1H), 6.89 (ddd, 1H, J=8.0, 2.2, 2.2 Hz), 7.11 (ddd, 1H, J=8.1, 8.1, 2.0 Hz), 7.25 (d, 2H, J=8.1 Hz), 7.58 (d, 2H, J=8.1 Hz), 8.55 and 8.57 (s, 2H), 9.20 and 9.30 (br d, 1H, J=4.2 Hz). $^{13}$C NMR (CDCl$_3$) δ 13.19 and 13.22, 28.30 and 28.59, 29.23 and 29.36, 30.03 and 30.18, 40.17 and 40.23, 42.70 and 42.75, 43.64 and 43.75, 51.88 and 51.96, 60.47 and 60.52, 83.78 and 83.96, 113.73 and 113.81, 116.65 and 116.68, 121.48 and 121.53, 123.87 (q, J=272 Hz), 125.56 (q, J=3.6 Hz), 126.84 and 126.88, 129.23 and 129.26, 130.14 and 130.16 (q, J=32.6 Hz), 130.22, 134.79, 143.33 (q, J=1.2 Hz), 143.40 and 143.43, 147.58, 158.43 and 158.53, 161.35 and 161.36. ESI-MS m/z 614 (MH)$^+$, 616 (MH+2)$^+$, 618 (MH+4)$^+$. Anal. Calcd. for C$_{29}$H$_{29}$Cl$_3$F$_3$N$_3$O$_2$: C, 56.64; H, 4.75; N, 6.83; Cl, 17.30; F, 9.27. Found. C, 56.41; H, 4.67; N, 6.71; Cl, 17.19; F, 9.09.

EXAMPLE 10

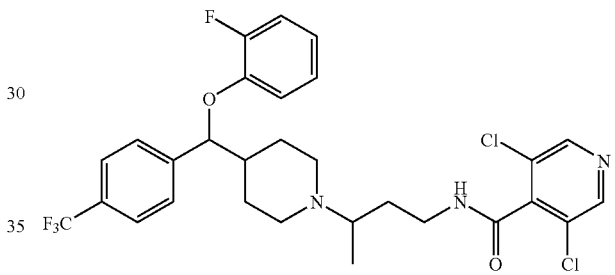

COMPOUND 10: 3,5-Dichloro-N-(3-{4-[(2-fluorophenoxy)-(4-trifluoro-methyl-phenyl)-methyl]-piperidin-1-yl}-butyl)-isonicotinamide White powder. $^1$H NMR (CDCl$_3$) δ 0.43-1.18 (m, 2H), 0.957 and 0.963 (d, 3H, J=6.6 Hz), 1.45-1.56 (m, 1H), 1.63-2.18 (m, 5H), 2.29-2.49 (m, 1H), 2.61-2.97 (m, 3H), 3.27-3.39 (m, 1H), 3.85-3.95 (m, 1H), 4.21 and 4.25 (d, 1H, J=8.3 Hz), 6.60-6.66 (m, 1H), 6.82-6.94 (m, 2H), 7.00-7.08 (m, 1H), 7.27 and 7.29 (d, 2H, J=7.9 Hz), 7.57 (d, 2H, J=7.9 Hz), 8.51 and 8.53 (s, 2H), 9.38 and 9.53 (br s, 1H). $^{13}$C NMR (CDCl$_3$) δ 13.19, 28.48 and 28.72, 29.23 and 29.51, 29.74 and 30.05, 40.15 and 40.27, 42.56, 43.55 and 43.65, 51.75 and 51.87, 60.49 and 60.53, 85.54 and 85.81, 116.35 (d, J=18.4 Hz), 117.74 and 117.76 (d, J=9.8 Hz), 122.06 and 122.12 (d, J=6.9 Hz), 123.86 (q, J=272 Hz), 124.14 (d, J=4.0 Hz), 125.40 (q, J=3.6 Hz), 127.08, 129.16 and 129.19, 130.12 (q, J=32.8 Hz), 143.40 (q, J=1.5 Hz), 145.47 (d, J=7.5 Hz), 145.56 and 145.66, 147.48, 153.2 (d, J=245 Hz), 161.27 and 161.36. ESI-MS m/z 598 (MH)$^+$, 600 (MH+2)$^+$. Anal. Calcd. for C$_{29}$H$_{29}$Cl$_2$F$_4$N$_3$O$_2$.0.2H$_2$O: C, 57.85; H, 4.92; N, 6.98; Cl, 11.78; F, 12.62. Found. C, 57.82; H, 4.72; N, 6.92; Cl, 12.01; F, 12.25.

EXAMPLE 11

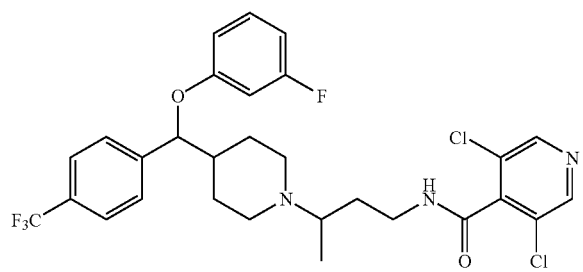

COMPOUND 11: 3,5-Dichloro-N-(3-{4-[(3-fluoro-phenoxy)-(4-trifluoro-methyl-phenyl)-methyl]-piperidin-1-yl}-butyl)-isonicotinamide White foam. $^1$H NMR (CDCl$_3$) δ 0.51-1.04 (m, 2H), 0.96 (d, 3H, J=6.6 Hz), 1.14-1.26 (m, 1H), 1.46-2.05 (m, 5H), 2.30-2.46 (m, 1H), 2.64-2.95 (m, 3H), 3.28-3.40 (m, 1H), 3.84-3.94 (m, 1H), 4.27 and 4.29 (d, 1H, J=6.8 Hz), 6.41-6.51 (m, 2H), 6.56-6.66 (m, 1H), 7.09-7.18 (m, 1H), 7.26 (d, 2H, J=8.0 Hz), 7.58 (d, 2H, J=8.0 Hz), 8.53 and 8.56 (s, 2H), 9.18 and 9.28 (br s, 1H). $^{13}$C NMR (CDCl$_3$) δ 13.17 and 13.20, 28.36 and 28.52, 29.26 and 29.28, 30.01 and 30.17, 40.07 and 40.14, 42.68 and 42.72, 43.66 and 43.76, 51.80 and 51.88, 60.37 and 60.40, 83.77 and 83.94, 103.66 and 103.69 (d, J=24.8 Hz), 108.06 and 108.11 (d, J=21.3 Hz), 111.29 and 111.36 (d, J=2.9 Hz), 123.86 (q, J=272 Hz), 125.52 (q, J=3.7 Hz), 126.83 and 126.87, 129.19 and 129.22, 130.08 (q, J=32.4 Hz), 130.18 (d, J=10.0 Hz), 143.41 (q, J=1.7 Hz), 147.53, 158.97 and 159.11 (d, J=7.8 Hz), 161.33 and 161.35, 163.34 (d, J=245 Hz). ESI-MS m/z 598 (MH)$^+$, 600 (MH+2)$^+$. Anal. Calcd. for C$_{29}$H$_{29}$Cl$_2$F$_4$N$_3$O$_2$.0.2C$_3$H$_7$NO.0.1CH$_2$Cl$_2$: C, 57.39; H, 4.96; N, 7.21; Cl, 12.55; F, 12.23. Found. C, 57.62; H, 4.97; N, 6.92; Cl, 12.39; F, 11.89.

EXAMPLE 12

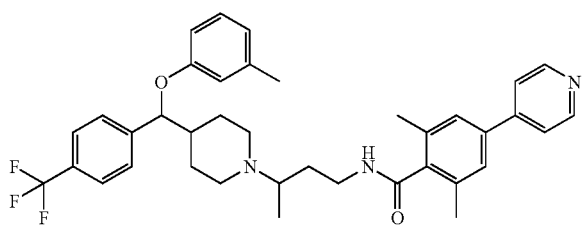

COMPOUND 12: 2,6-Dimethyl-4-pyridin-4-yl-N-(3-{4-[m-tolyloxy-(4-trifluoromethyl-phenyl)-methyl]-piperidin-1-yl}-butyl)benzamide White foam. $^1$H NMR (CDCl$_3$) δ 0.52-1.10 (m, 2H), 0.95 and 0.96 (d, 3H, J=6.3 Hz), 1.50-1.60 (m, 2H), 1.70-2.10 (m, 4H), 2.17 and 2.20 (s, 3H), 2.21-2.39 (m, 1H), 2.43 (s, 6H), 2.65-2.93 (m, 3H), 3.30 (m, 1H), 3.90 (m, 1H), 4.14 and 4.16 (d, 1H, J=7.2 Hz), 6.18 (t, 1H, J=9 Hz), 6.48 (s, 1H), 6.65 (t, 1H, J=7.5 Hz), 6.79 and 6.83 (t, 1H, J=7.1 Hz), 7.11 and 7.12 (d, 2H, J=7.8 Hz), 7.29-7.47 (m, 6H), 8.60 (td, 2H, J=4.2, 1.8 Hz), 8.68 (m, 1H). $^{13}$C NMR (CDCl$_3$) δ 13.6, 13.7, 19.8, 21.8, 28.6, 29.0, 29.6, 30.2, 31.1, 31.3, 40.2, 43.5, 44.3, 44.4, 52.4, 52.5, 60.8, 60.9, 83.9, 84.0, 112.4, 112.7, 117.5, 117.7, 121.7, 122.4, 122.5, 124.2 (q, J=230 Hz), 125.7, 126.2, 127.2, 129.4, 130.1 (q, J=34.7 Hz), 135.68, 135.74, 138.1, 138.2, 139.8, 139.9, 144.7, 147.8, 150.72, 150.76, 158.0, 158.2, 169.6, 169.8. ES-MS m/z 630 (M+H). Anal. Calcd. for C$_{38}$H$_{42}$F$_3$N$_3$O$_2$.0.3CH$_2$Cl$_2$: C, 70.21; H, 6.55; N, 6.41; F, 8.70. Found. C, 70.07; H, 6.47; N, 6.39; F, 8.35.

EXAMPLE 13

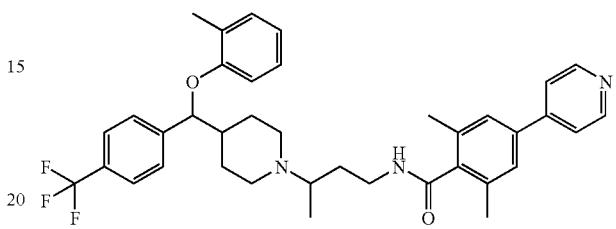

COMPOUND 13: 2,6-Dimethyl-4-pyridin-4-yl-N-(3-{4-[o-tolyloxy-(4-trifluoromethyl-phenyl)-methyl]-piperidin-1-yl}-butyl)-benzamide White foam. $^1$H NMR (CDCl$_3$) δ 0.50-0.85 (m, 1H), 0.95 (t, 3H, J=6.5 Hz), 1.50-1.64 (m, 2H), 1.70-2.20 (m, 3H), 2.21 (s, 3H), 2.22-2.47 (m, 2H), 2.41 (s, 3H), 2.43 (s, 3H), 2.65-2.90 (m, 3H), 3.30 (m, 1H), 3.90 (m, 1H), 4.13 (t, 1H, J=7.5 Hz), 6.01 and 6.05 (d, 1H, J=8.1 Hz), 6.50-6.74 (m, 2H), 7.04 (t, 1H, J=5.4 Hz), 7.11 (d, 2H, J=7.8 Hz), 7.37 (d, 2H, J=9.6 Hz), 7.43-7.50 (m, 4H), 8.63 (d, 2H, J=6.3 Hz), 8.75 and 8.80 (d, 1H, J=6.3 Hz). $^{13}$C NMR (CDCl$_3$) δ 13.6, 13.8, 19.8, 28.6, 29.5, 29.7, 30.7, 30.9, 31.3, 40.2, 40.3, 43.5, 44.2, 44.4, 52.4, 52.6, 60.8, 61.0, 83.4, 83.6, 112.4, 112.7, 120.85, 120.91, 125.7, 126.2, 126.9, 127.2, 130.3 (q, J=31.8 Hz), 131.1, 135.77, 135.81, 138.09, 138.14, 140.0, 144.7, 147.7, 150.8, 155.6, 155.8, 169.5, 169.8. ES-MS m/z 630 (M+H). Anal. Calcd. for C$_{38}$H$_{42}$F$_3$N$_3$O$_2$.0.4CH$_2$Cl$_2$: C, 69.49; H, 6.50; N, 6.33; F, 8.59. Found. C, 69.34; H, 6.56; N, 6.39; F, 8.63.

EXAMPLE 14

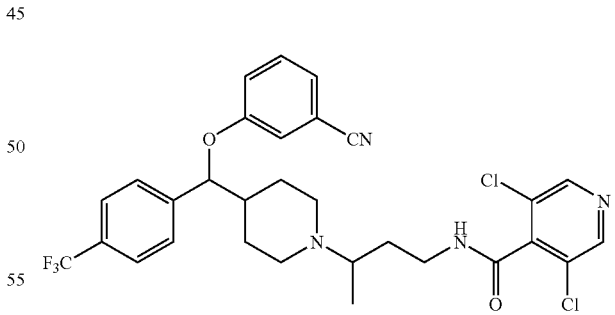

COMPOUND 14: 3,5-Dichloro-N-(3-{4-[(3-cyano-phenoxy)-(4-trifluoro-methyl-phenyl)-methyl]-piperidin-1-yl}-butyl)-isonicotinamide White powder. $^1$H NMR (CDCl$_3$) δ 0.55-1.01 (m, 2H), 0.96 (d, 3H, J=6.6 Hz), 1.16-1.26 (m, 1H), 1.47-1.58 (m, 1H), 1.60-1.84 (m, 2H), 1.87-2.05 (m, 2H), 2.31-2.46 (m, 1H), 2.64-2.93 (m, 3H), 3.28-3.40 (m, 1H), 3.81-3.93 (m, 1H), 4.31 and 4.33 (d, 1H, J=6.8 Hz), 6.90-6.95 (m, 1H), 6.98 (s, 1H), 7.17-7.33 (m, 4H), 7.60 (d, 2H, J=8.1 Hz), 8.52 and 8.55 (s, 2H), 9.05 and 9.13 (br s, 1H). $^{13}$C NMR (CDCl$_3$) δ 13.11 and 13.15, 28.19 and 28.42, 29.03 and 29.13, 30.12 and 30.18, 39.84 and 39.88, 42.58 and 42.64, 43.64 and 43.74, 51.57 and 51.61, 59.99 and 60.06, 83.84 and 83.98, 113.06 and 113.07, 118.29, 119.15, 120.31 and 120.34, 123.70 (q, J=272 Hz), 124.79 and 124.84, 125.59 (q, J=3.9 Hz), 126.74 and 126.77, 129.11 and 129.13, 130.20 (q, J=32.5 Hz), 130.30, 142.65, 143.25 and 143.27, 147.39 and 147.40, 157.64 and 157.72, 161.23 and 161.25. ESI-MS m/z 605 (MH)$^+$, 607 (MH+2)$^+$. Anal. Calcd. for C$_{30}$H$_{29}$Cl$_2$F$_3$N$_4$O$_2$: C, 59.51; H, 4.83; N, 9.25; Cl, 11.71; F, 9.41. Found. C, 59.17; H, 4.85; N, 9.27; Cl, 11.76; F, 9.52.

EXAMPLE 15

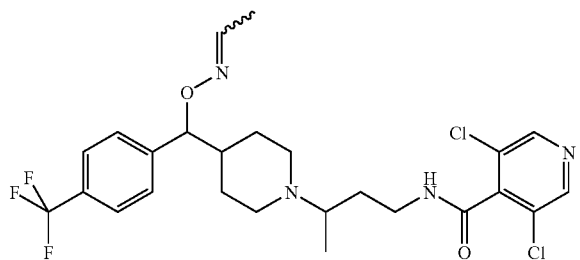

COMPOUND 15: 3,5-Dichloro-N-(3-{4-[ethylidene-aminooxy-(4-trifluoromethyl-phenyl)-methyl]-piperidin-1-yl}-butyl)-isonicotinamide Using general procedure C with 4-[hydroxy-(4-trifluoromethyl-phenyl)-methyl]-piperidine-1-carboxylic acid tert-butyl ester (500 mg, 1.39 mmol), then general procedure I with the resulting amine followed by using general procedure J afforded [1-(3-amino-1-methyl-propyl)-piperidin-4-yl]-(4-trifluoromethyl-phenyl)-methanol as a colourless syrup (195 mg, 42% over 3 steps).

Using general procedure F, 3,5-dichloroisonicotinic acid (225 mg, 1.17 mmol) and the amine from above (195 mg, 0.59 mmol) afforded 3,5-dichloro-N-(3-{4-[hydroxy-(4-trifluoromethyl-phenyl)-methyl]-piperidin-1-yl}-butyl)-isonicotinamide as a white solid (203 mg, 69%).

To a solution of the alcohol from above (203 mg, 0.40 mmol), N-hydroxyphthalimide (98 mg, 0.60 mmol) and Ph$_3$P (158 mg, 0.60 mmol) in THF (3 mL) cooled to 0° C. was added DIAD (119 μL, 0.60 mmol) dropwise. The reaction mixture was stirred at room temperature for 3.5 hours to afford 3,5-dichloro-N-(3-{4-[(1,3-dioxo-1,3-dihydro-isoindol-2-yloxy)-(4-trifluoromethyl-phenyl)-methyl]-piperidin-1-yl}-butyl)-isonicotinamide as a white solid (75 mg, 29%) after work-up and purification.

Using general procedure D with the above substrate (75 mg, 0.12 mmol) and then using general procedure A with the resulting amine and acetaldehyde (6 μL, 0.11 mmol) afforded COMPOUND 15 (28 mg, 45% over 2 steps). $^1$H NMR (CDCl$_3$) δ 0.38-0.81 (m, 2H), 0.93-0.97 (m, 3H), 1.06-1.20 (m, 1H), 1.45-1.57 (m, 2H), 1.72-2.02 (m, 6H), 2.27-2.46 (m, 1H), 2.59-2.90 (m, 3H), 3.25-3.40 (m, 1H), 3.81-3.96 (m, 1H), 4.27-4.37 (m, 1H), 6.60-6.73, 7.41-7.30 (m, 1H), 7.15-7.22 (m, 2H), 7.56 (d, 2H, J=8.1 Hz), 8.57 (s, 2H), 8.98, 9.14, 9.27 (br s, 1H). $^{13}$C NMR (CDCl$_3$) δ 12.03, 13.16, 13.29, 15.21, 28.45, 28.66, 28.84, 29.29, 29.57, 29.88, 29.97, 30.24, 30.45, 40.28, 40.37, 41.11, 41.34, 43.92, 51.81, 52.00, 60.40, 60.58, 60.72, 87.64, 88.36, 124.17 (q, J=272 Hz), 125.17, 127.31, 129.13, 129.34 (q, J=32 Hz), 143.34, 145.18, 147.61, 147.77, 161.44, 161.57. ES-MS m/z 545 (M+H). Anal. Calcd. for C$_{25}$H$_{29}$N$_4$Cl$_2$F$_3$O$_2$.0.1H$_2$O.0.2CH$_2$Cl$_2$: C, 53.65; H, 5.29; N, 9.93; Cl, 15.08; F, 10.10. Found. C, 53.76; H, 5.29; N, 9.77; Cl, 15.07; F, 9.89.

EXAMPLE 16

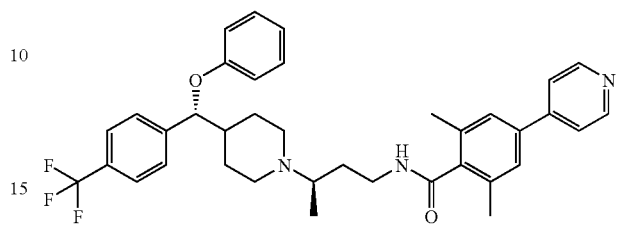

COMPOUND 16: 2,6-Dimethyl-N-(3 (R)-{4(R)-[phenoxy-(4-trifluoromethyl-phenyl)-methyl]-piperidin-1-yl}-butyl)-4-pyridin-4-yl-benzamide To a solution of (−)-DIP-chloride™ (3.45 g, 10.8 mmol) in THF (6 mL) at 0° C. was added a solution of 4-(4-trifluoromethylbenzoyl)-piperidine-1-carboxylic acid tert-butyl ester (1.92 g, 5.38 mmol) in THF (2 mL). The mixture was stirred at room temperature for 18 hours. Aqueous work-up and purification gave 4(S)-[(4-trifluoromethyl-phenyl)-hydroxy-methyl]-piperidine-1-carboxylic acid tert-butyl ester (ee 82% determined by Mosher ester) as a white crystalline solid (989 mg, 51%) and 4(S)-[hydroxy-(4-trifluoromethyl-phenyl)-methyl]-piperidine (ee 82% determined by Mosher ester after conversion to 4-[(4-trifluoromethyl-phenyl)-hydroxy-methyl]-piperidine-1-carboxylic acid tert-butyl ester) as a white crystalline solid (571 mg, 41%). 4(S)-[Hydroxy-(4-trifluoromethyl-phenyl)-methyl]-piperidine (1.00 g) was recrystallized (EtOAc/hexane) five times to provide a white solid (0.64 g) with 97% ee. 4(S)-[Hydroxy-(4-trifluoromethyl-phenyl)-methyl]-piperidine and 4(S)-[(4-trifluoromethyl-phenyl)-hydroxy-methyl]-piperidine-1-carboxylic acid tert-butyl ester could be interconverted by protection and deprotection of the Boc group in quantitative yield.

To a solution of 4(S)-[(4-trifluoromethyl-phenyl)-hydroxy-methyl]-piperidine-1-carboxylic acid tert-butyl ester (314 mg, 0.875 mmol), phenol (210 mg, 2.01 mmol) and Ph$_3$P (383 mg, 1.31 mmol) in THF (8 mL) at room temperature was added DIAD (0.258 mL, 1.31 mmol) dropwise. The mixture was stirred at room temperature for 6 hours. Work-up and purification gave 4(R)-[phenoxy-(4-trifluoromethyl-phenyl)-methyl]-piperidine-1-carboxylic acid tert-butyl ester as a white foam (347 mg, 91%).

Using general procedure C, the above amine (347 mg, 0.798 mmol) gave 4(R)-[phenoxy-(4-trifluoromethyl-phenyl)-methyl]-piperidine (ee 96.3% determined by chiral HPLC) as a colorless oil (267 mg, 100%).

Using general procedure G, methyl-(S)-lactate (63 mg, 0.61 mmol) gave the mesylate as a colorless oil. A solution of the above amine (135 mg, 0.403 mmol) in dry CH$_3$CN (1.5 mL) was added to the above mesylate followed by 2,2,6,6-tetramethylpiperidine (77 mg, 0.54 mmol). The mixture was heated at reflux for 3.5 hours. Aqueous work-up and purification gave the methyl ester, which was subsequently reduced with LiAlH$_4$ (1.0M in THF, 0.48 mL, 0.48 mmol) to give 2(R)-{4(R)-[phenoxy-(4-trifluoromethyl-phenyl)-methyl]-piperidin-1-yl}-propan-1-ol (de 94% determined by chiral HPLC) as a colorless oil (103 mg, 65% over 2 steps) after a Feiser work-up and purification.

Using general procedure G, the above alcohol (102 mg, 0.260 mmol) gave the chloride, which was subsequently dissolved in DMSO (1.5 mL) followed by the addition of NaCN (26 mg, 0.52 mmol). The reaction was heated at 140° C. for 1 hour. Aqueous work-up and purification gave the nitrile, which was subsequently reduced with $BH_3$-THF (1.0M in THF, 0.63 mL, 0.63 mmol) in THF (1.5 mL) at reflux and treated with MeOH then ethylenediamine (0.5 mL) to give 3(R)-{4(R)-[phenoxy-(4-trifluoromethyl-phenyl)-methyl]-piperidin-1-yl}-butylamine as a colorless oil (59 mg, 57% over 2 steps) after work-up and purification.

Using general procedure E, the above amine (59 mg, 0.15 mmol) and 2,6-dimethyl-4-pyridin-4-yl-benzoic acid (40 mg, 0.17 mmol) gave COMPOUND 16 as a white foam (87 mg, 97%). $^1$H NMR ($CDCl_3$) δ 0.55-0.65 (m, 1H), 0.95 (d, 3H, J=6.6 Hz), 0.94-1.02 (m, 1H), 1.50-1.60 (m, 2H), 1.65-1.80 (m, 1H), 1.89 (t, 2H, J=12 Hz), 2.20 (d, 1H, J=12 Hz), 2.38-2.44 (m, 1H), 2.43 (s, 6H), 2.75 (d, 2H, J=9.9 Hz), 2.85 (m, 1H), 3.32 (m, 1H), 3.82-3.90 (m, 1H), 4.10 (d, 1H, J=8.1 Hz), 6.47 (d, 2H, J=8.1 Hz), 6.80 (t, 1H, J=6.3 Hz), 6.96 (t, 2H, J=8.0 Hz), 7.12 (d, 2H, J=7.8 Hz), 7.38 (s, 2H), 7.46 (d, 4H, J=8.1 Hz), 8.62 (d, 2H, J=6.0 Hz), 8.79 (br s, 1H). $^{13}$C NMR ($CDCl_3$) δ 13.3, 19.4, 28.2, 29.9, 30.7, 39.9, 43.0, 43.8, 52.2, 60.7, 83.6, 115.7, 121.1, 121.3, 124.2 (q, J=308 Hz), 125.3, 125.4, 125.8, 126.9, 129.3, 129.9 (q, J=32 Hz), 135.4, 137.7, 139.6, 144.2, 147.3, 150.4, 157.6, 169.2. ES-MS m/z 616 (M+H). Anal. Calcd. for $C_{37}H_{40}F_3N_3O_2 \cdot 0.4 CH_2Cl_2$: C, 69.14; H, 6.33; N, 6.47; F, 8.77. Found. C, 69.12; H, 6.43; N, 6.44; F, 8.66.

EXAMPLE 17

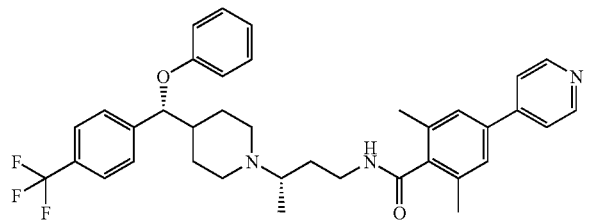

COMPOUND 17: 2,6-Dimethyl-N-(3(S)-{4(R)-[phenoxy-(4-trifluoromethyl-phenyl)-methyl]-piperidin-1-yl}-butyl)-4-pyridin-4-yl-benzamide To a solution of 4(S)-[(4-trifluoromethyl-phenyl)-hydroxy-methyl]-piperidine-1-carboxylic acid tert-butyl ester (see EXAMPLE 16) (314 mg, 0.875 mmol), phenol (210 mg, 2.01 mmol) and $Ph_3P$ (383 mg, 1.31 mmol) in THF (8 mL) at room temperature was added DIAD (0.258 mL, 1.31 mmol) dropwise. Standard work-up and purification gave 4(R)-[phenoxy-(4-trifluoromethyl-phenyl)-methyl]-piperidine-1-carboxylic acid tert-butyl ester as a white foam (347 mg, 91%).

Using general procedure C, the above carbamate (347 mg, 0.798 mmol) gave 4(R)-[phenoxy-(4-trifluoromethyl-phenyl)-methyl]-piperidine (ee 96.3% determined by chiral HPLC) as a colorless oil (267 mg, 100%).

Using general procedure G, methyl-(R)-lactate (63 mg, 0.61 mmol) gave the mesylate as a colorless oil. A solution of the above amine (135 mg, 0.403 mmol) in dry $CH_3CN$ (1.5 mL) was added to the above mesylate followed by 2,2,6,6-tetramethylpiperidine (77 mg, 0.54 mmol). The mixture was heated at reflux for 3 hours. Work-up and purification gave the methyl ester, which was subsequently reduced with $LiAlH_4$ (1.0M in THF, 0.40 mL, 0.40 mmol) to give 2(S)-{4(R)-[phenoxy-(4-trifluoromethyl-phenyl)-methyl]-piperidin-1-yl}-propan-1-ol (de 89% determined by chiral HPLC) as a colorless oil (71 mg, 51% over 2 steps) following a Feiser work-up and purification.

Using general procedure G the above alcohol (71 mg, 0.18 mmol) gave the chloride, which was subsequently dissolved in DMSO (1 mL) followed by the addition of NaCN (18 mg, 0.36 mmol). The reaction was heated at 140° C. for 1 hour. Work-up and purification gave the nitrile, which was subsequently reduced with $BH_3$-THF (1.0M, 0.41 mL, 0.41 mmol) in THF (1 mL) at reflux and treated with MeOH then ethylenediamine (0.5 mL) to give 3(R)-{4(R)-[phenoxy-(4-trifluoromethyl-phenyl)-methyl]-piperidin-1-yl}-butylamine as a colorless oil (43.5 mg, 59% over 2 steps) after work-up and purification.

Using general procedure E, the above amine (43 mg, 0.11 mmol) and 2,6-dimethyl-4-pyridin-4-yl-benzoic acid (29 mg, 0.13 mmol) gave COMPOUND 17 as a white foam (64 mg, 98%). $^1$H NMR ($CDCl_3$) δ 0.76-0.90 (m, 1H), 0.96 (d, 3H, J=6.3 Hz), 1.05 (d, 1H, J=11.7 Hz), 1.49-1.60 (m, 2H), 1.77-1.84 (m, 1H), 2.01 (t, 2H, J=10.7 Hz), 2.31 (t, 1H, J=10.8 Hz), 2.42 (s, 6H), 2.63 (d, 1H, J=8.4 Hz), 2.80-2.90 (m, 2H), 3.32 (t, 1H, J=11.6 Hz), 3.83-3.93 (m, 1H), 4.15 (d, 1H, J=7.8 Hz), 6.49 (d, 2H, J=7.8 Hz), 6.82 (t, 1H, J=7.4 Hz), 6.98 (t, 2H, J=8.0 Hz), 7.12 (d, 2H, J=7.8 Hz), 7.34 (s, 2H), 7.41-7.47 (m, 4H), 8.60 (d, 2H, J=6.0 Hz), 8.80 (br s, 1H). $^{13}$C NMR ($CDCl_3$) δ 13.3, 19.4, 28.6, 29.2, 30.6, 39.9, 43.1, 43.9, 52.1, 60.5, 83.8, 115.9, 121.2, 121.3, 124.2 (q, J=308 Hz), 125.3, 125.4, 125.8, 126.8, 129.3, 129.9 (q, J=32 Hz), 135.3, 137.7, 139.6, 144.2, 147.4, 150.4, 157.7, 169.3. ES-MS m/z 616 (M+H). Anal. Calcd. for $C_{37}H_{40}F_3N_3O_2 \cdot 0.4 CH_2Cl_2$: C, 69.14; H, 6.33; N, 6.47; F, 8.77. Found. C, 69.10; H, 6.47; N, 6.37; F, 8.58.

Scheme 2 describes the preparation of Examples 18-20, using general procedures E, and reagents listed below.

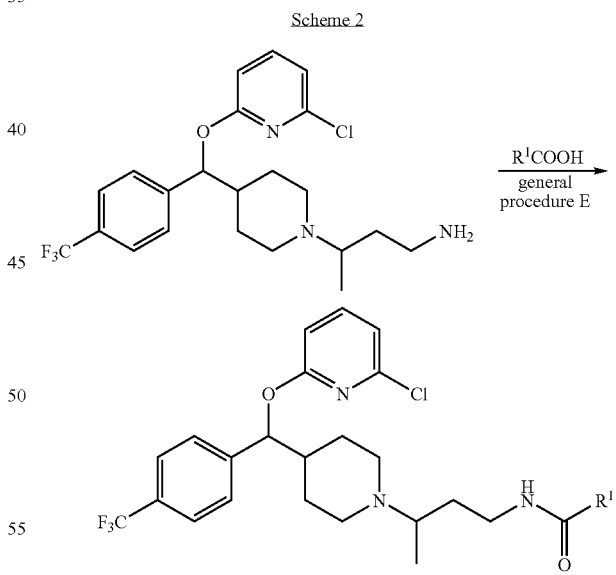

| Example | $R^1$COOH |
|---|---|
| 18 | 2,4-dimethyl-1-oxy-nicotinic acid |
| 19 | 2,6-dimethylbenzoic acid |
| 20 | 4,6-dimethyl-pyrimidine-5-carboxylic acid |

EXAMPLE 18

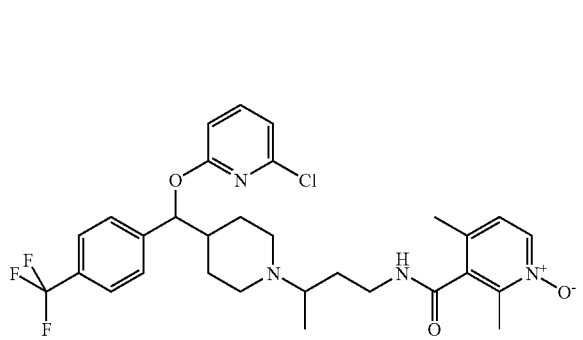

COMPOUND 18: N-(3-{4-[(6-Chloro-pyridin-2-yloxy)-(4-trifluoromethyl-phenyl)-methyl]-piperidin-1-yl}-butyl)-2,4-dimethyl-1-oxy-nicotinamide To a suspension of NaH (60% in mineral oil, 56 mg, 1.4 mmol) in DMF (2.3 mL) was added 4-[hydroxy-(4-trifluoromethyl-phenyl)-methyl]-piperidine-1-carboxylic acid tert-butyl ester (250 mg, 0.696 mmol) followed by 2,6-dichloro-pyridine (309 mg, 2.09 mmol). The mixture was heated to 90° C. for 2 h then concentrated in vacuo. Aqueous work-up and purification gave 4-[(6-chloro-pyridin-2-yloxy)-(4-trifluoromethyl-phenyl)-methyl]-piperidine-1-carboxylic acid tert-butyl ester as a colourless foam (313 mg, 95%).

Using general procedure C with the carbamate from above (313 mg, 0.665 mmol), then general procedure B with the resulting amine and 2-(3-oxo-butyl)-isoindole-1,3-dione (121 mg, 0.557 mmol) and then using general procedure D gave a 1:1 diastereomeric mixture of 3-{4-[(6-chloro-pyridin-2-yloxy)-(4-trifluoromethyl-phenyl)-methyl]-piperidin-1-yl}-butylamine as a colourless oil (48 mg, 39% over 3 steps).

COMPOUND 18 was isolated as a white solid. $^1$H NMR (CDCl$_3$) δ 0.42-0.86 (m, 2H), 0.95, 0.96 (d, 3H, J=6.6 Hz), 1.08-1.18 (m, 1H), 1.45-1.55 (m, 1H), 1.63-1.83 (m, 2H), 1.87-2.06 (m, 2H), 2.27-2.45 (m, 1H), 2.31, 2.32 (s, 3H), 2.49 (s, 3H), 2.56-2.87 (m, 3H), 3.23-3.35 (m, 1H), 3.79-3.90 (m, 1H), 5.20, 5.23 (d, 1H, J=9.3 Hz), 6.62, 6.64 (d, 1H, J=3.6 Hz), 6.85 (dd, 1H, J=7.5, 1.2 Hz), 7.05, 7.09 (d, 1H, J=6.6 Hz), 7.43-7.52 (m, 3H), 7.54-7.61 (m, 2H), 8.35 (d, 1H, J=6.3 Hz), 9.31 (br s, 1H). $^{13}$C NMR (CDCl$_3$) δ 13.73, 15.54, 15.63, 28.78, 29.36, 29.56, 30.15, 30.91, 40.23, 41.91, 41.98, 44.23, 52.13, 52.19, 60.62, 81.11, 81.24, 109.79, 117.21, 125.46, 125.73, 128.12, 130.04, 133.56, 133.72, 137.23, 139.07, 141.32, 143.94, 146.11, 148.49, 162.85, 165.69. ES-MS m/z 591 (M+H). Anal. Calcd. for C$_{30}$H$_{34}$N$_4$ClO$_3$F$_3$.0.8CH$_4$O: C, 59.99; H, 6.08; N, 9.08; Cl, 5.75; F, 9.24. Found. C, 59.85; H, 6.11; N, 9.24; Cl, 5.61; F, 9.55.

EXAMPLE 19

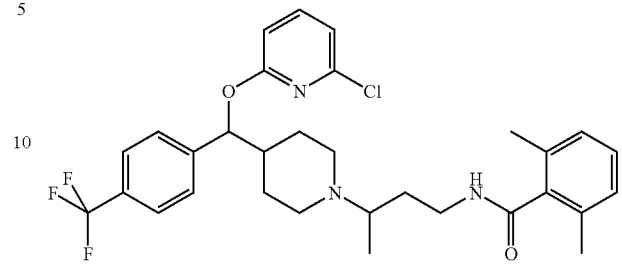

COMPOUND 19: N-(3-{4-[(6-Chloro-pyridin-2-yloxy)-(4-trifluoromethyl-phenyl)-methyl]-piperidin-1-yl}-butyl)-2,6-dimethyl-benzamide White solid. $^1$H NMR (CDCl$_3$) δ 0.24-0.86 (m, 2H), 0.87-0.99 (m, 3H), 1.41-2.02 (m, 6H), 2.22-2.46 (m, 7H), 2.50-2.88 (m, 3H), 3.19-3.34 (m, 1H), 3.80-3.94 (m, 1H), 5.04, 5.07 (d, 1H, J=6.3 Hz), 6.57 (d, 1H, J=8.1 Hz), 6.84 (dd, 1H, J=7.2, 0.9 Hz), 7.06 (d, 1H, J=7.5 Hz), 7.11 (d, 1H, J=7.5 Hz), 7.30-7.41 (m, 3H), 7.43-7.49 (m, 1H), 7.43-7.49 (m, 1H), 7.55 (d, 2H, J=8.1 Hz), 8.93, 9.00 (br s, 1H). ES-MS m/z 574 (M+H).

EXAMPLE 20

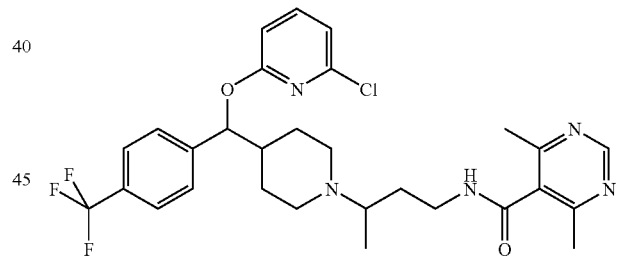

COMPOUND 20: 4,6-Dimethyl-pyrimidine-5-carboxylic acid (3-{4-[(6-chloro-pyridin-2-yloxy)-(4-trifluoromethyl-phenyl)-methyl]-piperidin-1-yl}-butyl)-amide White solid. $^1$H NMR (CDCl$_3$) δ 0.43-0.85 (m, 2H), 0.95, 0.96 (d, 3H, J=6.3 Hz), 1.08-1.21 (m, 1H), 1.44-2.04 (m, 5H), 2.30-2.47 (m, 1H), 2.53, 2.54 (s, 6H), 2.59-2.87 (m, 3H), 3.24-3.36 (m, 1H), 3.81-3.93 (m, 1H), 5.12, 5.23 (d, 1H, J=7.8 Hz), 6.64 (dd, 1H, J=10.5, 8.4 Hz), 6.82 (dd, 1H, J=7.2, 2.1 Hz), 7.37-7.51 (m, 3H), 7.55 (d, 2H, J=8.1 Hz), 9.12, 9.19 (s, 1H), 8.96, 9.27 (br s, 1H). ES-MS m/z 576 (M+H).

Scheme 3 describes the preparation of Examples 21-40, using various general procedures previously described, and reagents listed below.

Scheme 3

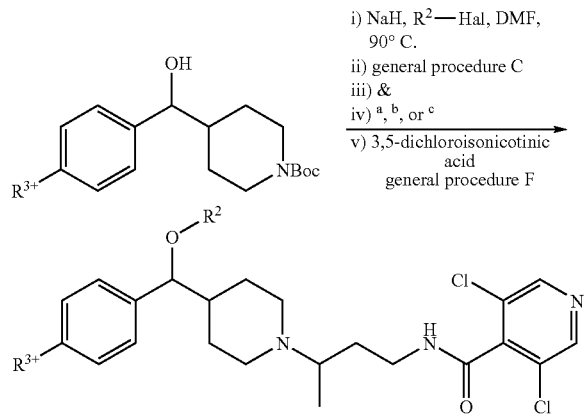

i) NaH, R²—Hal, DMF, 90° C.
ii) general procedure C
iii) &
iv) a, b, or c
v) 3,5-dichloroisonicotinic acid
general procedure F

| Example | R³* | R²—Hal |
|---------|-----|--------|
| 21[a] | Br | 2-bromopyridine |
| 22[b] | CF₃ | 2-bromopyridine |
| 23[b] | CF₃ | 6-chloro-2-picoline |
| 24[b] | CF₃ | 2-chloro-6-ethylpyridine (Choppin, Sabine; et al., Org. Lett., 2, 6, 2000, 803-806) |
| 25[c] | CF₃ | 2,6-difluoropyridine |
| 26[c] | CF₃ | 2-chloro-6-(trifluoromethyl)pyridine |
| 27[c] | CF₃ | 2-chloro-6-cyanopyridine (Sakamoto, Takao; et al., Chem. Pharm. Bull., 33, 2, 1985, 565-571) |
| 28[c] | SO₂Me | 2-bromo-6-picoline |
| 29[c] | SO₂Me | 2,6-dichloropyridine |
| 30[c] | SO₂Me | 2,6-difluoropyridine |
| 31[b] | OCF₃ | 2-bromo-6-picoline |
| 32[a] | OCF₃ | 2,6-difluoropyridine |
| 33[a] | OCF₃ | 2,6-dichloropyridine |
| 34[c] | SO₂NHMe | 2-bromo-6-picoline |
| 35[c] | Br | 2-chloropyridine |
| 36[a] | Br | 2-bromo-3-picoline |
| 37[b] | CF₃ | 2-bromo-4-picoline |
| 38[b] | CF₃ | 2-bromo-3-picoline |
| 39[c] | CF₃ | 2,3-dichloropyridine |
| 40[c] | CF₃ | 2,4-dichloropyridine (Choppin, Sabine; et al., Eur. J. Org. Chem., 3, 2001, 603-606) |

[a]iii) general procedure I, iv) BH₃—Me₂S, THF, reflux
[b]iii) general procedure I, iv) general procedure J
[c]iii) 2-(3-oxo-butyl-isoindole-1,3-dione, general procedure B, iv) general procedure D

EXAMPLE 21

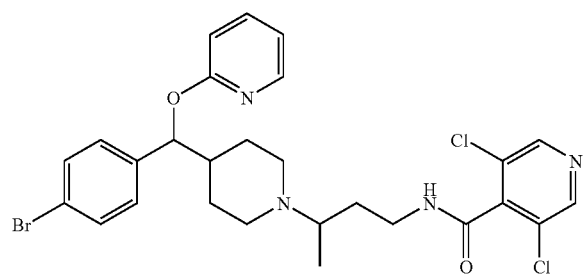

COMPOUND 21: N-(3-{4-[(4-Bromo-phenyl)-(pyridin-2-yloxy)-methyl]-piperidin-1-yl}-butyl)-3,5-dichloro-isonicotinamide White foam. ¹H NMR (CDCl₃) δ 0.43-0.83 (m, 1H), 0.96 (d, 3H, J=6.3 Hz), 1.17-1.28 (m, 1H), 1.45-1.57 (m, 1H), 1.59-2.06 (m, 5H), 2.30-2.47 (m, 1H), 2.61-2.92 (m, 3H), 3.26-3.40 (m, 1H), 3.80-3.94 (m, 1H), 5.34 (d, 1H, J=8.1 Hz), 6.65 (dd, 1H, J=8.4, 0.9 Hz), 6.78-6.83 (m, 1H), 7.10 and 7.11 (d, 2H, J=8.4 Hz), 7.40 (d, 2H, J=8.4 Hz), 7.49-7.56 (m, 1H), 8.06-8.10 (m, 1H), 8.56 and 8.57 (s, 2H), 9.16 and 9.33 (br s, 1H). ¹³C NMR (CDCl₃) δ 13.18 and 13.23, 28.52 and 28.68, 29.28 and 29.48, 29.85 and 30.24, 40.21, 41.78, 43.77 and 43.85, 51.94 and 52.09, 60.52 and 60.66, 79.22, 111.02 and 111.06, 116.93, 121.27, 128.82 and 128.85, 129.01 and 129.04, 131.29, 138.59, 139.32 and 139.33, 146.90, 147.66, 161.48 and 161.59, 162.92 and 162.95. ESI-MS m/z 591 (MH)⁺, 593 (MH+2)⁺, 595 (MH+4)⁺. Anal. Calcd. for $C_{27}H_{29}BrCl_2N_4O_2$: C, 54.75; H, 4.93; N, 9.46; Cl, 11.97. Found. C, 54.54; H, 5.01; N, 9.42; Cl, 12.05.

EXAMPLE 22

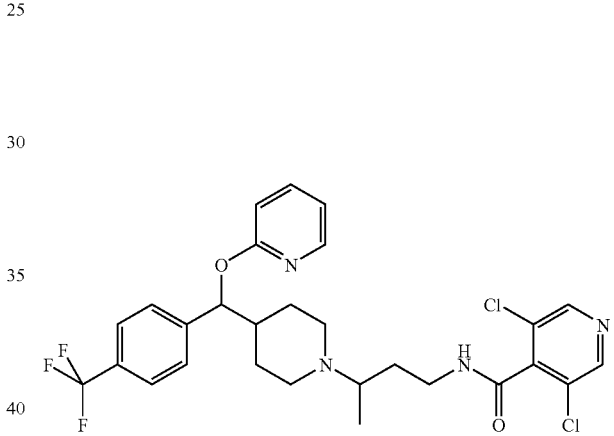

COMPOUND 22: 3,5-Dichloro-N-(3-{4-[(pyridin-2-yloxy)-(4-trifluoromethyl-phenyl)-methyl]-piperidin-1-yl}-butyl)-isonicotinamide White solid. ¹H NMR (CDCl₃) δ 0.49-1.01 (m, 2H), 0.95 (d, 3H, J=6.6 Hz), 1.14-1.26 (m, 1H), 1.45-1.55 (m, 1H), 1.62-2.04 (m, 4H), 2.30-2.45 (m, 1H), 2.61-2.90 (m, 3H), 3.27-3.38 (m, 1H), 3.83-3.94 (m, 1H), 5.45 (d, 1H, J=7.8 Hz), 6.68 (dd, 1H, J=8.4, 0.8 Hz), 6.79-6.83 (m, 1H), 7.34 (dd, 2H, J=8.1, 3.3 Hz), 7.50-7.57 (m, 3H), 8.06-8.09 (m, 1H), 8.57 (s, 2H), 9.11, 9.27 (d, 1H, J=4.5 Hz). ¹³C NMR (CDCl₃) δ 13.62, 28.96, 29.07, 29.80, 30.33, 30.68, 40.61, 40.71, 42.33, 44.20, 44.29, 52.31, 52.45, 60.89, 60.98, 79.57, 111.44, 111.48, 117.45, 124.49 (q, J=272 Hz), 127.75, 129.48, 129.95 (q, J=32 Hz), 139.07, 143.73, 144.91, 147.29, 148.07, 161.87, 161.96, 163.26. ES-MS m/z 581 (M+H). Anal. Calcd. for $C_{28}H_{29}N_4Cl_2O_2F_3 \cdot 0.06CH_2Cl_2$: C, 57.46; H, 5.00; N, 9.55; Cl, 12.81; F, 9.72. Found. C, 57.33; H, 4.97; N, 9.57; Cl, 12.71; F, 9.62.

EXAMPLE 23

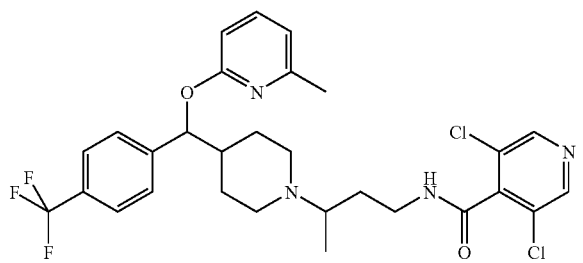

COMPOUND 23: 3,5-Dichloro-N-(3-{4-[(6-methyl-pyridin-2-yloxy)-(4-trifluoromethyl-phenyl)-methyl]-piperidin-1-yl}-butyl)-isonicotinamide White solid. $^1$H NMR (CDCl$_3$) δ0.37-1.02 (m, 2H), 0.95 (dd, 3H, J=6.6, 1.8 Hz), 1.09-1.18 (m, 1H), 1.43-1.55 (m, 1H), 1.63-2.04 (m, 4H), 2.27-2.46 (m, 1H), 2.39 (s, 3H), 2.58-2.90 (m, 3H), 3.25-3.39 (m, 1H), 3.80-3.95 (m, 1H), 5.29 (dd, 1H, J=8.4, 1.8 Hz), 6.44 (d, 1H, J=8.4 Hz), 6.65 (d, 1H, J=7.2 Hz), 7.32-7.42 (m, 3H), 7.53 (d, 2H, J=8.1 Hz), 8.56, 8.58 (s, 2H), 9.27, 9.44 (d, 1H, J=6.0 Hz). $^{13}$C NMR (CDCl$_3$) δ 13.21, 13.31, 24.05, 28.60, 28.98, 29.38, 29.74, 29.83, 30.22, 40.30, 40.42, 41.69, 43.73, 51.92, 52.09, 60.55, 60.74, 79.41, 107.24, 116.06, 124.13 (q, J=272 Hz), 125.05, 125.10, 127.60, 129.14, 129.50 (q, J=32 Hz), 138.88, 143.40, 144.66, 147.65, 156.30, 161.41, 161.56, 162.20. ES-MS m/z 595 (M+H). Anal. Calcd. for C$_{29}$H$_{31}$Cl$_2$F$_3$N$_4$O$_2$: C, 58.49; H, 5.25; N, 9.41; Cl, 11.91; F, 9.57. Found. C, 58.32; H, 5.19; N, 9.37; Cl, 12.11; F, 9.35.

EXAMPLE 24

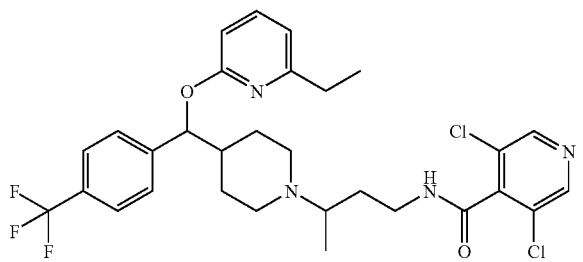

COMPOUND 24: 3,5-Dichloro-N-(3-{4-[(6-ethyl-pyridin-2-yloxy)-(4-trifluoromethyl-phenyl)-methyl]-piperidin-1-yl}-butyl)-isonicotinamide White foam. $^1$H NMR (CDCl$_3$) δ 0.39-0.82 (m, 3H), 0.95 (m, 7H), 1.13 (m, 8H), 1.50 (m, 2H), 1.69-2.05 (m, 8H), 2.38 (m, 2H), 2.57-2.90 (m, 10H), 3.32 (m, 2H), 3.88 (m, 2H), 5.30 (d, 2H, J=7.5 Hz), 6.46 (2d, 2H, J=8.1 Hz), 6.64 (2d, 2H, J=7.5 Hz), 7.33 (d, 2H, J=7.8 Hz), 7.34 (d, 2H, J=7.8 Hz), 7.42 (m, 2H), 7.53 (d, 4H, J=7.8 Hz), 8.55 (s, 2H), 8.57 (s, 2H), 9.23 (d, 1H, J=5.7 Hz), 9.41 (d, 1H, J=3.6 Hz). $^{13}$C NMR (CDCl$_3$) δ 13.19, 13.29, 28.63, 29.01, 29.39, 29.81, 29.89, 30.33, 30.81, 40.27, 40.40, 41.76, 43.84, 51.94, 52.09, 60.54, 60.74, 79.48, 107.58, 114.77, 125.00, 125.05, 127.56, 127.60, 129.15, 138.88, 143.40, 144.94, 147.65, 161.25, 161.41, 161.59, 162.26. ES-MS m/z 609 (M+H). Anal. Calcd. for C$_{30}$H$_{33}$N$_4$Cl$_2$F$_3$O$_2$: C, 59.12; H, 5.46; N, 9.19; Cl, 11.63; F, 9.35. Found. C, 59.00; H, 5.56; N, 9.10; Cl, 11.80; F, 9.17.

EXAMPLE 25

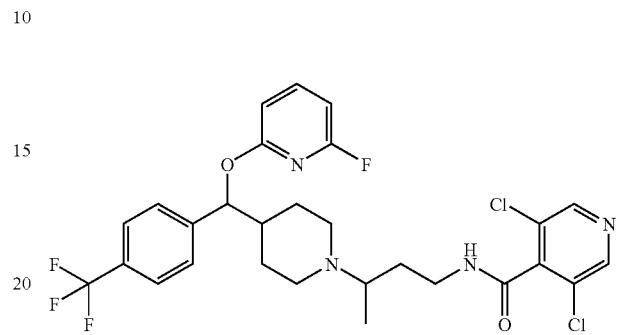

COMPOUND 25: 3,5-Dichloro-N-(3-{4-[(6-fluoro-pyridin-2-yloxy)-(4-trifluoromethyl-phenyl)-methyl]-piperidin-1-yl}-butyl)-isonicotinamide White foam. $^1$H NMR (CDCl$_3$) δ 0.43-0.83 (m, 3H), 0.97 (m, 7H), 1.17 (m, 2H), 1.50 (m, 2H), 1.66-2.03 (m, 8H), 2.37 (m, 2H), 2.64 (m, 1H), 2.80 (m, 5H), 3.33 (m, 2H), 3.87 (m, 2H), 5.30 (m, 2H), 6.43 (m, 2H), 6.54 (m, 2H), 7.34 (m, 4H), 7.60 (m, 6H), 8.62 (s, 4H), 9.12 (d, 1H, J=4.8 Hz), 9.31 (d, 1H, J=4.5 Hz). $^{13}$C NMR (CDCl$_3$) δ 13.28, 28.55, 28.66, 29.29, 29.42, 29.85, 30.30, 40.22, 40.36, 41.62, 43.67, 43.79, 51.82, 51.98, 60.50, 60.64, 80.29, 100.49, 100.96, 107.23, 122.23, 125.27, 125.32, 125.84, 127.51, 129.10, 129.71, 130.14, 142.80, 142.90, 143.34, 143.58, 147.78, 160.27, 161.47, 161.60, 161.85, 162.03, 163.47. ES-MS m/z 599 (M+H). Anal. Calcd. for C$_{28}$H$_{28}$N$_4$Cl$_2$F$_4$O$_2$: C, 56.10; H, 4.71; N, 9.35; Cl, 11.83; F, 12.68. Found. C, 56.05; H, 4.75; N, 9.30; Cl, 12.00; F, 12.43.

EXAMPLE 26

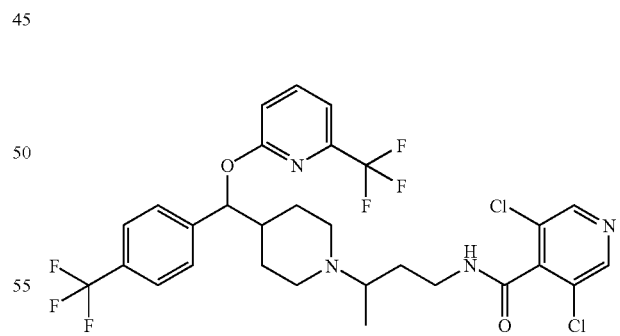

COMPOUND 26: 3,5-Dichloro-N-(3-{4-[(4-trifluoromethyl-phenyl)-(6-trifluoromethyl-pyridin-2-yloxy)-methyl]-piperidin-1-yl}-butyl)-isonicotinamide White foam. $^1$H NMR (CDCl$_3$) δ 0.34-0.82 (m, 3H), 0.95 (m, 7H), 1.11 (m, 2H), 1.50 (m, 2H), 1.67-2.06 (m, 8H), 2.39 (m, 2H), 2.63 (m, 1H), 2.74-2.91 (m, 5H), 3.32 (m, 2H), 3.87

(m, 2H), 5.33 (m, 2H), 6.86 (m, 2H), 7.19 (m, 2H), 7.37 (m, 4H), 7.54 (d, 4H, J=8.1 Hz), 7.67 (m, 2H), 8.56 (s, 2H), 8.58 (s, 2H), 9.17 (d, 1H, J=6.3 Hz), 9.40 (d, 1H, J=4.2 Hz). $^{13}$C NMR (CDCl$_3$) δ 13.19, 13.32, 28.42, 29.04, 29.18, 29.70, 29.86, 30.34, 40.22, 40.40, 41.16, 43.64, 51.74, 51.90, 60.46, 60.73, 80.66, 113.60, 114.58, 125.15, 125.20, 127.88, 129.12, 139.73, 143.32, 143.47, 147.65, 161.41, 161.63, 162.68. ES-MS m/z 649 (M+H). Anal. Calcd. for C$_{29}$H$_{28}$N$_4$Cl$_2$F$_6$O$_2$: C, 53.63; H, 4.35; N, 8.63; Cl, 10.92; F, 17.55. Found. C, 53.63; H, 4.36; N, 8.81; Cl, 11.06; F, 17.44.

EXAMPLE 27

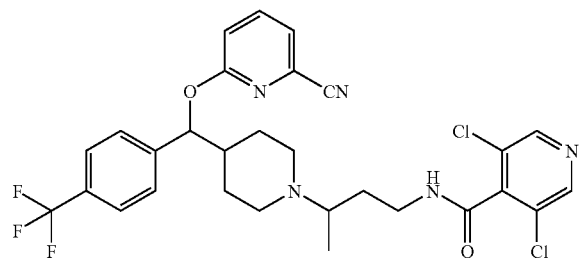

COMPOUND 27: 3,5-Dichloro-N-(3-{4-[(6-cyano-pyridin-2-yloxy)-(4-trifluoromethyl-phenyl)-methyl]-piperidin-1-yl}-butyl)-isonicotinamide White foam. $^1$H NMR (CDCl$_3$) δ 0.47-0.78 (m, 3H), 0.92 (m, 7H), 1.19 (m, 2H), 1.51 (m, 2H), 1.69-2.04 (m, 8H), 2.38 (m, 2H), 2.65 (m, 1H), 2.73-2.88 (m, 5H), 3.33 (m, 2H), 3.86 (m, 2H), 5.41 (m, 2H), 6.93 (d, 2H, J=8.4 Hz), 7.26 (m, 2H), 7.35 (m, 4H), 7.56 (d, 4H, J=8.1 Hz), 7.65 (m, 2H), 8.59 (s, 2H), 8.61 (s, 2H), 9.03 (d, 1H, J=4.8 Hz), 9.12 (d, 1H, J=4.5 Hz). $^{13}$C NMR (CDCl$_3$) δ 13.26, 28.51, 28.68, 29.24, 29.44, 30.09, 30.30, 40.16, 40.23, 41.41, 43.71, 43.80, 51.72, 60.41, 60.48, 80.58, 116.09, 117.09, 122.53, 125.33, 127.57, 129.08, 130.28, 139.50, 143.16, 143.25, 147.66, 147.70, 161.49, 161.56, 162.99. ES-MS m/z 628 (M+Na). Anal. Calcd. for C$_{29}$H$_{28}$N$_5$Cl$_2$F$_3$O$_2$: C, 57.43; H, 4.65; N, 11.55; Cl, 11.69; F, 9.40. Found. C, 57.20; H, 4.65; N, 11.54; Cl, 11.50; F, 9.20.

EXAMPLE 28

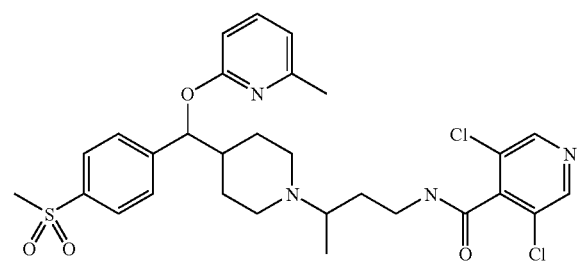

COMPOUND 28: 3,5-Dichloro-N-(3-{4-[(4-methanesulfonyl-phenyl)-(6-methyl-pyridin-2-yloxy)-methyl]-piperidin-1-yl}-butyl)-isonicotinamide A mixture of 4-(4-bromo-benzoyl)-piperidine-1-carboxylic acid tert-butyl ester (3.68 g, 10.0 mmol), NaSMe (1.05 g, 15.0 mmol) and DMF (100 mL) was heated at 75° C. for 3 hours to give 4-(4-methylsulfanyl-benzoyl)-piperidine-1-carboxylic acid tert-butyl ester as a white solid (3.37 g, 100%) following work-up.

To solution of the above sulfide (1.2 g, 3.58 mmol) in MeOH (58 mL) cooled to 0° C. was added OXONE® (4.40 g, 7.15 mmol) and the mixture was stirred at 0° C. for 4 hours to afford 4-(4-methanesulfonyl-benzoyl)-piperidine-1-carboxylic acid tert-butyl ester as a white solid (802 mg, 61%) after basic work-up and purification.

The above ketone (810 mg, 2.20 mmol) was reduced with NaBH$_4$ (84 mg, 2.20 mmol) to afford 4-[hydroxy-(4-methanesulfonyl-phenyl)-methyl]-piperidine-1-carboxylic acid tert-butyl ester (760 mg, 94%) as a white foam after work-up and purification.

COMPOUND 28 was isolated as a white foam. $^1$H NMR (CDCl$_3$) δ 0.39-0.84 (m, 1H), 0.94, 0.96 (d, 3H, J=6.7 Hz), 1.07-1.17 (m, 1H), 1.42-1.59 (m, 1H), 1.59-1.83 (m, 3H), 1.88-2.01 (m, 2H), 2.25-2.46 (m, 1H), 2.39 (s, 3H), 2.59-2.93 (m, 3H), 3.03 (s, 3H), 3.20-3.41 (m, 1H), 3.77-3.95 (m, 1H), 5.32 (d, 1H, J=7.0 Hz), 6.43-6.49 (m, 1H), 6.66 (d, 1H, J=7.0 Hz), 7.36-7.46 (m, 3H), 7.84 (d, 2H, J=8.3 Hz), 8.57, 8.59 (s, 2H), 9.22, 9.38 (br s, 1H). $^{13}$C NMR (CDCl$_3$) δ 13.22, 13.31, 24.04, 28.57, 28.83, 29.35, 29.75, 30.22, 40.25, 40.36, 41.65, 43.71, 44.41, 51.83, 52.01, 53.45, 60.49, 60.67, 79.11, 107.32, 116.17, 127.24, 128.19, 129.13, 138.96, 139.34, 143.37, 147.20, 147.63, 156.24, 161.38, 161.54, 162.00. ES-MS m/z 607 (M+H). Anal. Calcd. for C$_{29}$H$_{34}$Cl$_2$N$_4$O$_4$S.0.3CH$_2$Cl$_2$.0.4H$_2$O: C, 55.14; H, 5.59; N, 8.78; Cl, 14.44; S, 5.02. Found. C, 55.31; H, 5.71; N, 8.97; Cl, 14.23; S, 4.92.

EXAMPLE 29

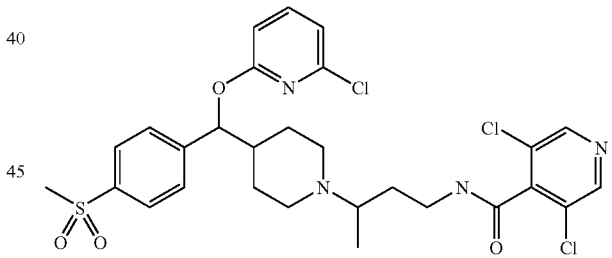

COMPOUND 29: 3,5-Dichloro-N-(3-{4-[(6-chloro-pyridin-2-yloxy)-(4-methanesulfonyl-phenyl)-methyl]-piperidin-1-yl}-butyl)-isonicotinamide White foam. $^1$H NMR (CDCl$_3$) δ 0.33-0.85 (m, 2H), 0.94 (d, 3H, J=6.1 Hz), 1.06-1.21 (m, 1H), 1.41-1.60 (m, 1H), 1.61-1.99 (m, 4H), 2.25-2.46 (m, 1H), 2.55-2.89 (m, 3H), 3.03 (s, 3H), 3.23-3.42 (m, 1H), 3.76-3.92 (m, 1H), 5.29-5.38 (m, 1H), 6.60 (d, 1H, J=8.2 Hz), 6.85 (d, 1H, J=7.4 Hz), 7.36-7.55 (m, 3H), 7.85 (d, 2H, J=8.3 Hz), 8.61, 8.62 (s, 2H), 9.08, 9.29 (br s, 1H). $^{13}$C NMR (CDCl$_3$) δ 13.64, 13.71, 28.86, 29.02, 29.60, 29.80, 30.25, 30.76, 40.49, 40.64, 41.82, 44.05, 44.15, 44.78, 52.09, 52.26, 60.69, 60.87, 80.50, 109.58, 117.38, 127.80, 128.60, 129.49, 140.14, 141.37, 143.72, 146.41, 148.13, 148.60, 161.83, 161.99, 162.62. ES-MS m/z 649 (M+Na). Anal. Calcd. for $C_{28}H_{31}Cl_3N_4O_4S \cdot 0.6CH_2Cl_2 \cdot 0.1H_2O$: C, 50.61; H, 4.81; N, 8.25; Cl, 21.94; S, 4.72. Found. C, 50.45; H, 4.73; N, 8.21; Cl, 22.10; S, 4.65.

EXAMPLE 30

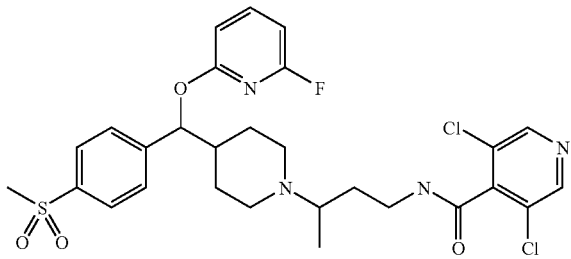

COMPOUND 30: 3,5-Dichloro-N-(3-{4-[(6-fluoro-pyridin-2-yloxy)-(4-methanesulfonyl-phenyl)-methyl]-piperidin-1-yl}-butyl)-isonicotinamide White foam. $^1$H NMR (CDCl$_3$) δ 0.41-0.93 (m, 2H), 0.96 (d, 3H, J=6.6 Hz), 1.10-1.21 (m, 1H), 1.47-2.02 (m, 5H), 2.28-2.49 (m, 1H), 2.57-2.90 (m, 3H), 3.03 (s, 3H), 3.24-3.42 (m, 1H), 3.78-3.92 (m, 1H), 5.27-5.37 (m, 1H), 6.45 (d, 1H, J=7.6 Hz), 6.57 (d, 1H, J=7.8 Hz), 7.41, 7.43 (d, 2H, J=3.9 Hz), 7.57-7.70 (m, 1H), 7.88 (d, 2H, J=8.2 Hz), 8.62 (s, 2H), 9.06, 9.25 (br s, 1H). $^{13}$C NMR (CDCl$_3$) δ 13.65, 14.59, 21.46, 28.91, 29.66, 30.31, 30.73, 40.54, 40.67, 42.01, 44.05, 44.17, 44.79, 52.13, 52.30, 60.80, 60.93, 80.44, 101.03, 101.50, 107.67, 127.85, 128.45, 129.48, 140.19, 143.30, 143.41, 143.71, 146.42, 148.15, 160.61, 161.85, 161.97, 162.23, 163.81. ES-MS m/z 609 (M+H). Anal. Calcd. for $C_{28}H_{31}Cl_2FN_4O_4S \cdot 0.1CH_2Cl_2 \cdot 0.1H_2O$: C, 54.45; H, 5.11; N, 9.04; Cl, 12.58; F, 3.07; S, 5.17. Found. C, 54.45; H, 5.17; N, 8.88; Cl, 12.71; F, 2.88; S, 4.98.

EXAMPLE 31

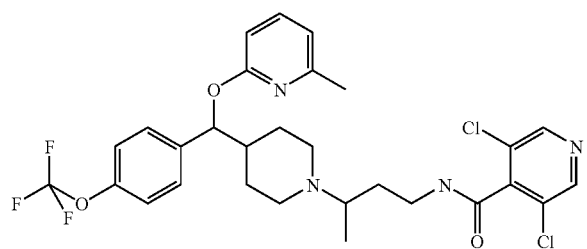

COMPOUND 31: 3,5-Dichloro-N-(3-{4-[(6-methyl-pyridin-2-yloxy)-(4-trifluoromethoxy-phenyl)-methyl]-piperidin-1-yl}-butyl)-isonicotinamide To a solution of 1-bromo-4-(trifluoromethoxy)benzene (1.88 g, 7.80 mmol) in THF (16 mL) at −78° C. was added n-BuLi (1.9M in hexanes, 4.1 mL, 7.8 mmol), and the solution was stirred at −78° C. for 30 minutes. A solution of 4-formyl-piperidine-1-carboxylic acid tert-butyl ester (1.50 g, 7.03 mmol) in THF (2 mL) was added dropwise, and the mixture was stirred at −78° C. for 45 minutes then allowed to warm to room temperature over 1 h. Work-up and purification gave 4-[hydroxy-(4-trifluoromethoxy-phenyl)-methyl]-piperidine-1-carboxylic acid tert-butyl ester as colourless crystals (1.75 g, 66%).

COMPOUND 31 was isolated as a white solid. $^1$H NMR (CDCl$_3$) δ 0.29-0.80 (m, 1H), 0.94, 0.96 (d, 3H, J=2.3 Hz), 1.08-1.17 (m, 1H), 1.43-1.56 (m, 1H), 1.62-2.05 (m, 5H), 2.26-2.40 (m, 1H), 2.41 (s, 3H), 2.57-2.92 (m, 3H), 3.22-3.41 (m, 1H), 3.79-3.96 (m, 1H), 5.19, 5.21 (d, 1H, J=3.5 Hz), 6.42 (d, 1H, J=8.3 Hz), 6.65 (d, 1H, J=5.6 Hz), 7.11 (d, 2H, J=8.2 Hz), 7.22-7.29 (m, 2H), 7.36-7.43 (m, 1H), 8.56, 8.58 (s, 2H), 9.36, 9.56 (br s, 1H). $^{13}$C NMR (CDCl$_3$) δ 13.59, 13.70, 24.46, 28.99, 29.50, 29.78, 30.02, 30.36, 30.56, 40.71, 40.84, 42.11, 44.13, 52.30, 52.46, 53.82, 60.95, 61.15, 79.71, 107.58, 116.36, 119.11, 120.91, 122.51, 129.08, 129.52, 139.23, 139.53, 143.80, 148.02, 148.75, 156.69, 161.78, 161.96, 162.69. ES-MS m/z 611 (M+H). Anal. Calcd. for $C_{29}H_{31}Cl_2F_3N_4O_3$: C, 56.96; H, 5.11; N, 9.16; Cl, 11.6; F, 9.32. Found. C, 57.04; H, 5.14; N, 9.20; Cl, 11.77; F, 9.39.

EXAMPLE 32

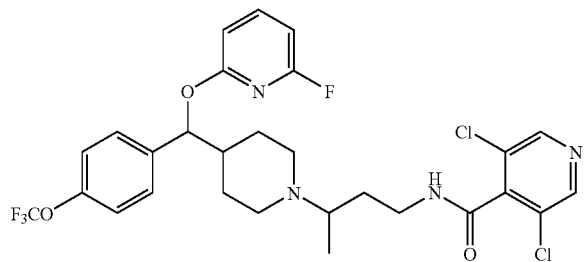

COMPOUND 32: 3,5-Dichloro-N-(3-{4-[(6-fluoro-pyridin-2-yloxy)-(4-trifluoromethoxy-phenyl)-methyl]-piperidin-1-yl}-butyl)-isonicotinamide White solid. $^1$H NMR (CDCl$_3$) δ 0.35-1.02 (m, 2H), 0.96 (d, 3H, J=6.6 Hz), 1.10-1.21 (m, 1H), 1.44-1.57 (m, 1H), 1.61-2.06 (m, 4H), 2.28-2.47 (m, 1H), 2.59-2.92 (m, 3H), 3.25-3.40 (m, 1H), 3.80-3.94 (m, 1H), 5.23 and 5.24 (d, 1H, J=8.0 Hz), 6.41-6.45 (m, 1H), 6.52 (d, 1H, J=7.8 Hz), 7.14 (d, 2H, J=8.4 Hz), 7.25 and 7.27 (d, 2H, J=8.4 Hz), 7.56-7.65 (m, 1H), 8.63 (s, 2H), 9.21 and 9.43 (br s, 1H). $^{13}$C NMR (CDCl$_3$) δ 13.17 and 13.24, 28.44 and 28.71, 29.19 and 29.48, 29.64 and 30.19, 40.13 and 40.29, 41.46 and 41.51, 43.57 and 43.71, 51.72 and 51.89, 60.40 and 60.57, 80.09 and 80.12, 100.52 (d, J=35.2 Hz), 107.17 and 107.20 (d, J=5.1 Hz), 120.34 (q, J=258 Hz), 120.66, 128.57, 128.98 and 129.02, 138.06 and 138.09, 142.73 (d, J=8.2 Hz), 143.26 and 143.29, 147.72, 148.55 (q, J=2.1 Hz), 161.80 and 161.82 (d, J=241 Hz), 161.42 and 161.58, 161.87 and 162.05. ESI-MS m/z 615 (MH)$^+$, 617 (MH+2)$^+$. Anal. Calcd. for $C_{28}H_{28}Cl_2F_4N_4O_3$: C, 54.64; H, 4.59; N, 9.10; Cl, 11.52. Found. C, 54.53; H, 4.61; N, 9.01; Cl, 11.63.

EXAMPLE 33

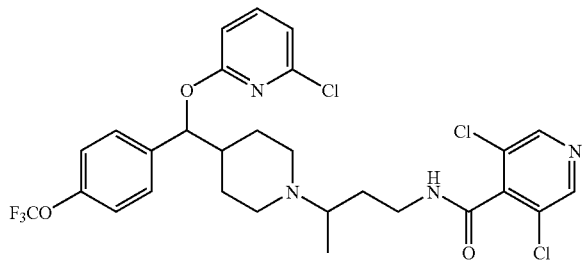

COMPOUND 33: 3,5-Dichloro-N-(3-{4-[(6-chloro-pyridin-2-yloxy)-(4-trifluoromethoxy-phenyl)-methyl]-piperidin-1-yl}-butyl)-isonicotinamide White solid. $^1$H NMR (CDCl$_3$) δ 0.29-1.01 (m, 2H), 0.956 and 0.960 (d, 3H, J=6.6 Hz), 1.07-1.18 (m, 1H), 1.44-2.05 (m, 5H), 2.29-2.47 (m, 1H), 2.57-2.92 (m, 3H), 3.24-3.40 (m, 1H), 3.80-3.95 (m, 1H), 5.23 and 5.26 (d, 1H, J=6.8 Hz), 6.56 and 6.57 (d, 1H, J=8.1 Hz), 6.85 and 6.86 (d, 1H, J=7.5 Hz), 7.14 (d, 2H, J=8.4 Hz), 7.24-7.29 (m, 2H), 7.47 and 7.48 (dd, 1H, J=8.1, 7.4 Hz), 8.66 (s, 2H), 9.27 and 9.52 (br s, 1H). $^{13}$C NMR (CDCl$_3$) δ 13.17 and 13.27, 28.43 and 28.84, 29.19 and 29.61, 29.62 and 30.24, 40.16 and 40.32, 41.33 and 41.39, 43.57 and 43.70, 51.74 and 51.93, 60.42 and 60.64, 80.17 and 80.22, 109.08 and 109.11, 116.68 and 116.71, 120.30 (q, J=261 Hz), 120.63, 128.73, 129.03 and 129.07, 138.04 and 138.07, 140.77, 143.31 and 143.33, 147.73 and 147.75, 148.20 and 148.22, 148.58 (q, J=1.3 Hz), 161.40 and 161.58, 162.46. ESI-MS m/z 631 (MH)$^+$, 633 (MH+2)$^+$, 635 (MH+4)$^+$. Anal. Calcd. for C$_{28}$H$_{28}$Cl$_3$F$_3$N$_4$O$_3$: C, 53.22; H, 4.47; N, 8.87; Cl, 16.83. Found. C, 53.30; H, 4.45; N, 8.82; Cl, 16.71.

EXAMPLE 34

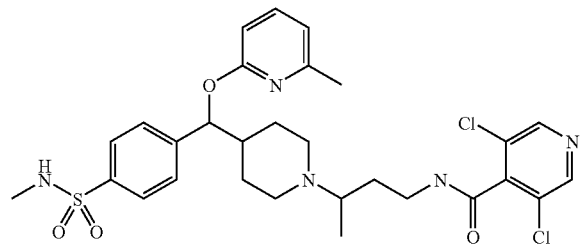

COMPOUND 34: 3,5-Dichloro-N-(3-{4-[(6-methyl-pyridin-2-yloxy)-(4-methylsulfamoyl-phenyl)-methyl]-piperidin-1-yl}-butyl)-isonicotinamide To a solution of 4-bromo-N-methyl-benzenesulfonamide (Marvel; Smith, J. Am. Chem. Soc., 45, 1923, 2697) (1.00 g, 4.00 mmol) in THF (35 mL) at −78° C. was added MeLi (4.00 mmol) and the solution was stirred at −78° C. for 15 minutes. n-BuLi (1.95M in hexanes, 2.05 mL, 4.00 mmol) was then added. After the solution was stirred at −78° C. for 45 minutes, TMEDA (1.20 mL, 8.00 mmol) was added followed by a solution of 4-formyl-piperidine-1-carboxylic acid tert-butyl ester (4.76 g, 22.30 mmol) in THF (5 mL), and the mixture was stirred at −78° C. for 1 hour. Work-up and purification gave 4-[hydroxy-(4-methylsulfamoyl-phenyl)-methyl]-piperidine-1-carboxylic acid tert-butyl ester (622 mg, 41%) as a white foam.

COMPOUND 34 was isolated as a white foam. $^1$H NMR (CDCl$_3$) δ 0.42-0.84 (m, 1H), 0.96 (d, 3H, J=6.4 Hz), 1.09-1.21 (m, 1H), 1.41-1.59 (m, 1H), 1.65-2.02 (m, 5H), 2.28-2.50 (m, 1H), 2.38 (s, 3H), 2.64 (d, 3H, J=4.8 Hz), 2.70-2.94 (m, 3H), 3.23-3.44 (m, 1H), 3.79-3.95 (m, 1H), 4.48-4.56 (m, 1H), 5.33 (d, 1H, J=8.2 Hz), 6.46 (d, 1H, J=8.0 Hz), 6.66 (d, 1H, J=7.3 Hz), 7.37-7.47 (m, 3H), 7.76 (d, 2H, J=7.9 Hz), 8.56, 8.57 (s, 2H), 9.23, 9.40 (br s, 1H). $^{13}$C NMR (CDCl$_3$) δ 13.59, 13.69, 14.59, 21.45, 24.43, 28.91, 29.22, 29.80, 30.07, 30.19, 30.65, 40.60, 42.10, 44.17, 52.26, 52.42, 60.85, 61.03, 79.56, 107.70, 116.51, 127.44, 128.33, 129.53, 138.71, 139.32, 143.76, 146.33, 148.01, 156.63, 161.82, 161.97, 162.48. ES-MS m/z 611 (M+H). Anal. Calcd. for C$_{29}$H$_{35}$Cl$_2$N$_5$O$_4$S.0.3C$_4$H$_8$O$_2$.0.4H$_2$O: C, 55.44; H, 5.89; N, 10.70; S, 4.90. Found. C, 55.41; H, 5.80; N, 10.81; S, 4.67.

EXAMPLE 35

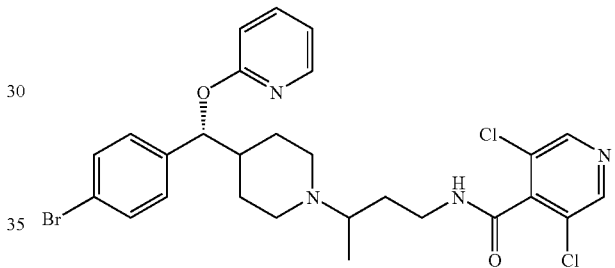

COMPOUND 35: N-(3-{4-[(R)-4-Bromophenyl)-(pyridin-2-yloxy)-methyl]-piperidin-1-yl}butyl)-3,5-dichloro-isonicotinamide To a solution of (+)-DIP-chloride™ (6.42 g, 20.0 mmol) in THF (10 mL) at 0° C. was added 4-(4-bromobenzoyl)-piperidine-1-carboxylic acid tert-butyl ester (3.68 g, 10.0 mmol). The mixture was stirred at room temperature for 29 hours to give (R)-4-[(4-bromophenyl)-hydroxymethyl]-piperidine-1-carboxylic acid tert-butyl ester (ee 82% determined by both chiral HPLC and Mosher ester) as a crystalline solid (2.22 g, 54%) following work-up and purification. This material was recrystallized (CH$_2$Cl$_2$/hexane) five times to provide a white solid (1.27 g, 35%) with 95% ee.

COMPOUND 35 was isolated as a white foam. $^1$H NMR (CDCl$_3$) δ 0.45-85 (m, 1H), 0.95 (d, 3H, J=6.6 Hz), 1.22 (br d, 1H, J=12 Hz), 1.51 (m, 1H), 1.66-1.98 (m, 5H), 2.30-2.45 (m, 1H), 2.60-2.90 (m, 3H), 3.31 (m, 1H), 3.80-3.90 (m, 1H), 5.33 (d, 1H, J=7.1 Hz), 6.64 (d, 1H, J=8.4 Hz), 6.80 (m, 1H), 7.09 and 7.10 (d, 2H, J=8.1 Hz), 7.40 (d, 2H, J=8.4 Hz), 7.48-7.55 (m, 1H), 8.08 (t, 1H, J=2.4 Hz), 8.56 and 8.56 (s, 2H), 9.17 and 9.34 (d, 1H, J=4.5 Hz). $^{13}$C NMR (CDCl$_3$) δ 13.2, 13.3, 28.6, 28.7, 29.4, 29.6, 29.9, 30.2, 40.2, 40.3, 41.8, 43.8, 43.9, 51.9, 52.1, 60.5, 60.6, 79.3, 111.0, 116.9, 121.3, 128.8, 129.1, 131.3, 138.6, 139.4, 143.3, 146.9, 147.7, 161.5, 161.6, 163.0. ES-MS m/z 593 (M+H). Anal. Calcd. for C$_{27}$H$_{29}$BrCl$_2$N$_4$O$_2$·0.3CH$_2$Cl$_2$: C, 53.07; H, 4.83; N, 9.07; Br, 12.93; Cl, 14.92. Found. C, 53.13; H, 4.80; N, 9.02; Br, 12.83; Cl, 14.78.

EXAMPLE 36

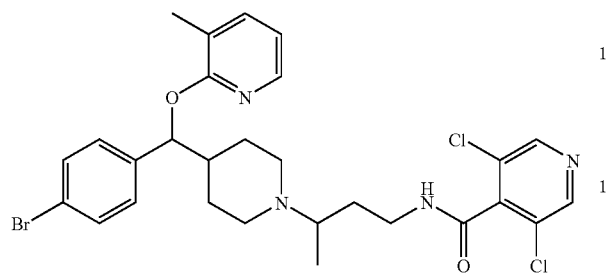

COMPOUND 36: N-(3-{4-[(4-Bromo-phenyl)-(3-methyl-pyridin-2-yloxy)-methyl]-piperidin-1-yl}-butyl)-3,5-dichloro-isonicotinamide Off-white foam. $^1$H NMR (CDCl$_3$) δ 0.45-1.12 (m, 2H), 0.97 (d, 3H, J=5.4 Hz), 1.17-1.28 (m, 1H), 1.45-1.58 (m, 1H), 1.66-1.85 (m, 2H), 1.88-2.09 (m, 2H), 2.16 (s, 3H), 2.25-2.47 (m, 1H), 2.61-2.93 (m, 3H), 3.25-3.42 (m, 1H), 3.75-3.92 (m, 1H), 5.42 and 5.45 (d, 1H, J=6.6 Hz), 6.71 (apparent t, 1H, J=5.6 Hz), 7.11 and 7.13 (d, 2H, J=8.4 Hz), 7.32 (d, 1H, J=7.2 Hz), 7.39 (d, 2H, J=8.4 Hz), 7.90 (s, 1H), 8.54 (s, 2H), 8.96 and 9.19 (br s, 1H). $^{13}$C NMR (CDCl$_3$) δ 13.10 and 13.23, 15.88 and 15.89, 28.33 and 29.03, 28.94 and 29.54, 29.91 and 30.50, 39.90 and 40.04, 41.72 and 41.77, 43.94, 51.77 and 52.01, 60.22 and 60.44, 78.76 and 78.81, 116.73 and 116.74, 120.42 and 120.45, 121.17, 128.81 and 128.85, 128.90 and 128.94, 131.20, 138.46 and 138.48, 139.63 and 139.66, 143.14 and 143.16, 143.96, 147.65, 160.96 and 160.98. ESI-MS m/z 605 (MH)$^+$, 607 (MH+2)$^+$, 609 (MH+4)$^+$. Anal. Calcd. for C$_{28}$H$_{31}$BrCl$_2$N$_4$O$_2$·0.2CH$_2$Cl$_2$: C, 54.33; H, 5.08; N, 8.99; Br, 12.82. Found. C, 54.51; H, 5.17; N, 8.72; Br, 12.44.

EXAMPLE 37

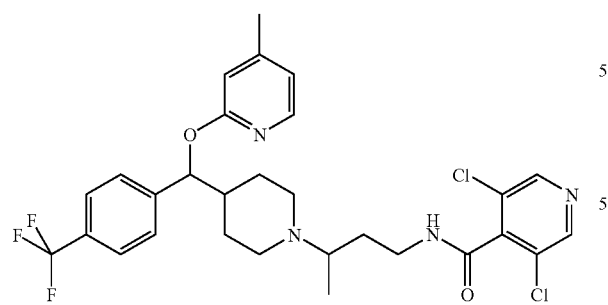

COMPOUND 37: 3,5-Dichloro-N-(3-{4-[(4-methyl-pyridin-2-yloxy)-(4-trifluoromethyl-phenyl)-methyl]-piperidin-1-yl}-butyl)-isonicotinamide White solid. $^1$H NMR (CDCl$_3$) δ 0.5-1.06 (m, 2H), 0.95 (d, 3H, J=6.6 Hz), 1.18-1.26 (m, 1H), 1.45-1.56 (m, 1H), 1.62-1.87 (m, 3H), 1.89-2.03 (m, 1H), 2.28 (s, 3H), 2.29-2.43 (m, 1H), 2.61-2.89 (m, 3H), 3.27-3.37 (m, 1H), 3.83-3.93 (m, 1H), 5.46 (d, 1H, J=7.8 Hz), 6.50 (s, 1H), 6.64 (d, 1H, J=5.1 Hz), 7.32 (dd, 2H, J=8.1, 2.1 Hz), 7.53 (d, 2H, J=8.1 Hz), 7.92 (dd, 1H, J=5.4, 2.4 Hz), 8.57, 8.57 (s, 2H), 9.10, 9.25 (d, 1H, J=5.1 Hz). $^{13}$C NMR (CDCl$_3$) δ 13.24, 20.87, 28.45, 28.72, 29.26, 29.46, 29.99, 30.31, 40.25, 40.34, 41.99, 43.82, 43.92, 51.98, 52.11, 60.55, 60.62, 77.03, 111.18, 118.61, 124.54 (q, J=270 Hz), 125.10, 127.30, 129.08, 129.50 (q, J=32 Hz), 143.34, 144.68, 146.41, 147.70, 150.04, 161.51, 161.60, 163.17. ES-MS m/z 595 (M+H). Anal. Calcd. for C$_{29}$H$_{31}$N$_4$O$_2$Cl$_2$F$_3$: C, 58.49; H, 5.25; N, 9.41; Cl, 11.91; F, 9.57. Found. C, 58.69; H, 5.21; N, 9.46; Cl, 11.71; F, 9.63.

EXAMPLE 38

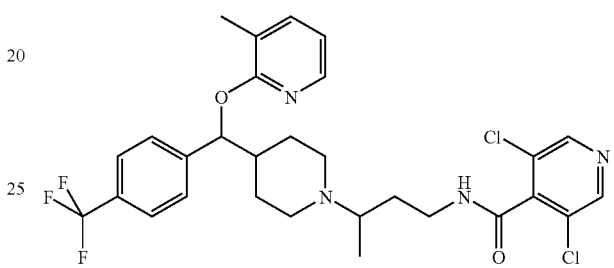

COMPOUND 38: 3,5-Dichloro-N-(3-{4-[(3-methyl-pyridin-2-yloxy)-(4-trifluoromethyl-phenyl)-methyl]-piperidin-1-yl}-butyl)-isonicotinamide White solid. $^1$H NMR (CDCl$_3$) δ 0.45-1.11 (m, 2H), 0.95, 0.96 (d, 3H, J=6.6 Hz), 1.15-1.26 (m, 1H), 1.46-1.57 (m, 1H), 1.66-1.83 (m, 2H), 1.89-2.07 (m, 2H), 2.18 (s, 3H), 2.29-2.47 (m, 1H), 2.60-2.91 (m, 3H), 3.26-3.40 (m, 1H), 3.79-3.94 (m, 1H), 5.49, 5.51 (d, 1H, J=8.4 Hz), 6.71-6.75 (m, 1H), 7.33-7.38 (m, 3H), 7.53 (d, 2H, J=8.1 Hz), 7.89-7.93 (m, 1H), 8.56 (s, 2H), 8.92, 9.17 (d, 1H, J=5.1 Hz). $^{13}$C NMR (CDCl$_3$) δ 13.17, 13.30, 15.92, 28.64, 29.10, 29.29, 29.67, 29.95, 30.57, 40.09, 40.25, 41.91, 41.98, 43.94, 51.80, 52.05, 60.31, 60.53, 77.04, 116.90, 120.44, 124.13 (q, J=272 Hz), 125.07, 125.12, 127.45, 128.99, 129.04, 129.52 (q, J=32 Hz), 138.61, 143.27, 144.01, 144.84, 147.70, 160.93, 161.47, 161.65. ES-MS m/z 595 (M+H). Anal. Calcd. for C$_{29}$H$_{31}$N$_4$O$_2$Cl$_2$F$_3$·0.1H$_2$O·0.1CH$_2$Cl$_2$: C, 57.70; H, 5.22; N, 9.25; Cl, 12.88; F, 9.41. Found. C, 57.54; H, 5.27; N, 9.27; Cl, 13.25; F, 9.18.

EXAMPLE 39

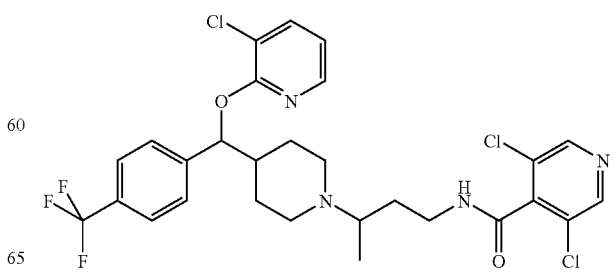

COMPOUND 39: 3,5-Dichloro-N-(3-{4-[(3-chloro-pyridin-2-yloxy)-(4-trifluoromethyl-phenyl)-methyl]-piperidin-1-yl}-butyl)-isonicotinamide White solid. $^1$H NMR (CDCl$_3$) δ 0.46-1.08 (m, 2H), 0.96, 0.97 (d, 3H, J=6.6 Hz), 1.16-1.27 (m, 1H), 1.47-1.61 (m, 1H), 1.72-2.09 (m, 4H), 2.30-2.50 (m, 1H), 2.61-2.93 (m, 3H), 3.25-3.40 (m, 1H), 3.81-3.97 (m, 1H), 5.40, 5.44 (d, 1H, J=8.4 Hz), 6.78-6.83 (m, 1H), 7.35-7.40 (m, 2H), 7.54-7.61 (m, 3H), 7.96-7.99 (m, 1H), 8.54, 8.55 (s, 2H), 9.03, 9.24 (br s, 1H). $^{13}$C NMR (CDCl$_3$) δ 13.57, 13.68, 28.98, 29.30, 29.62, 29.84, 30.33, 30.88, 40.52, 40.67, 42.15, 42.23, 44.18, 52.18, 52.39, 60.78, 60.97, 80.91, 81.03, 118.14, 118.72, 124.46 (q, J=272 Hz), 125.56, 125.60, 127.78, 127.82, 129.47, 130.18 (q, J=32 Hz), 138.80, 143.70, 144.34, 145.02, 148.03, 158.51, 161.82, 161.99. ES-MS m/z 615 (M+H). Anal. Calcd. for C$_{28}$H$_{28}$N$_4$Cl$_3$F$_3$O$_2$: C, 54.60; H, 4.58; N, 9.10; Cl, 17.27; F, 9.25. Found. C, 54.57; H, 4.59; N, 9.09; Cl, 16.97; F, 9.32.

EXAMPLE 40

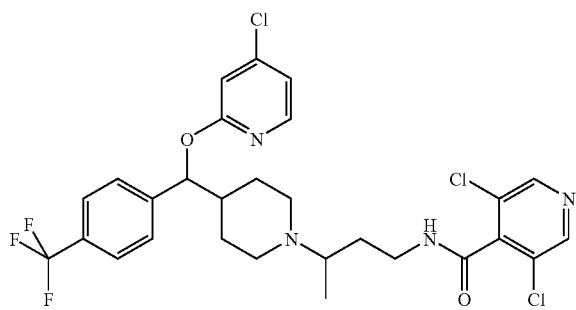

COMPOUND 40: 3,5-Dichloro-N-(3-{4-[(4-chloro-pyridin-2-yloxy)-(4-trifluoromethyl-phenyl)-methyl]-piperidin-1-yl}-butyl)-isonicotinamide White solid. $^1$H NMR (CDCl$_3$) δ 0.45-0.91 (m, 2H), 0.96 (d, 3H, J=6.6 Hz), 1.15-1.27 (m, 2H), 1.46-2.04 (m, 4H), 2.30-2.45 (m, 1H), 2.62-2.90 (m, 3H), 3.27-3.38 (m, 1H), 3.83-3.94 (m, 1H), 5.40 (d, 1H, J=8.1 Hz), 6.73 (s, 1H), 6.84 (d, 1H, J=4.8 Hz), 7.29-7.33 (m, 2H), 7.55 (d, 2H, J=8.1 Hz), 7.95-7.99 (m, 1H), 8.58 (s, 2H), 9.14, 9.29 (br s, 1H). $^{13}$C NMR (CDCl$_3$) δ 13.24, 28.59, 29.37, 29.96, 30.28, 30.94, 40.26, 41.77, 43.72, 51.90, 52.03, 60.56, 79.95, 111.24, 117.88, 122.25 (q, J=272 Hz), 125.26, 127.34, 129.13, 129.81 (q, J=32 Hz), 143.34, 143.95, 145.55, 147.56, 147.68, 161.46, 163.66. ES-MS m/z 615 (M+H).

EXAMPLE 41

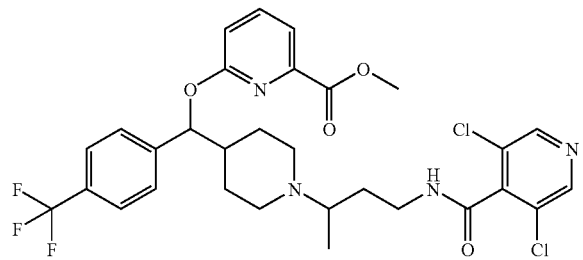

COMPOUND 41: 6-[(1-{3-[(3,5-Dichloro-pyridine-4-carbonyl)-amino]-1-methyl-propyl}-piperidin-4-yl)-(4-trifluoromethyl-phenyl)-methoxy]-pyridine-2-carboxylic acid methyl ester To saturated HCl/MeOH (4 mL) at 0° C. was added a solution of COMPOUND 27 (165 mg, 0.272 mmol) in MeOH (1 mL), and the mixture was stirred at room temperature for 45 minutes. Work-up and purification gave a 1:1 diastereomeric mixture of COMPOUND 41 (122 mg, 70%). $^1$H NMR (CDCl$_3$) δ 0.35-0.62 (m, 2H), 0.70-0.83 (m, 1H), 0.95 (m, 7H), 1.12 (m, 2H), 1.49 (m, 2H), 1.67-2.05 (m, 8H), 2.29-2.46 (m, 2H), 2.61 (m, 1H), 2.73-2.89 (m, 5H), 3.32 (m, 2H), 3.86 (m, 2H), 3.98 (s, 6H), 5.42 (d, 2H, J=8.7 Hz), 6.85 (m, 2H), 7.42 (m, 4H), 7.53 (d, 4H, J=8.1 Hz), 7.64 (m, 4H), 8.62 (s, 2H), 8.63 (s, 2H), 9.20 (d, 1H, J=5.7 Hz), 9.41 (d, 1H, J=4.8 Hz). $^{13}$C NMR (CDCl$_3$) δ 13.22, 13.32, 28.45, 28.96, 29.22, 29.77, 30.28, 40.22, 40.35, 41.21, 43.66, 43.74, 51.83, 52.00, 52.54, 60.46, 60.65, 80.23, 115.00, 118.85, 125.10, 127.96, 129.03, 139.33, 143.29, 143.84, 145.36, 147.79, 161.47, 161.63, 162.42, 165.39. ES-MS m/z 641 (M+H). Anal. Calcd. for C$_{30}$H$_{31}$N$_4$Cl$_2$F$_3$O$_4$·0.2CH$_2$Cl$_2$: C, 55.25; H, 4.82; N, 8.53; Cl, 12.96; F, 8.68. Found. C, 55.10; H, 4.76; N, 8.44; Cl, 13.27; F, 8.46.

EXAMPLE 42

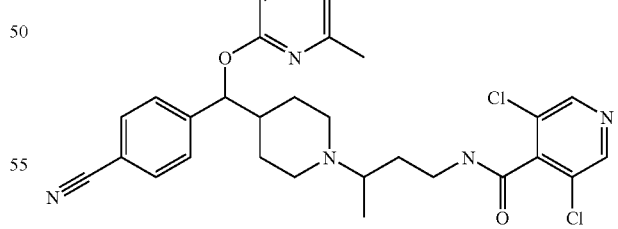

COMPOUND 42: 3,5-Dichloro-N-(3-{4-[(4-cyano-phenyl)-(6-methyl-pyridin-2-yloxy)-methyl]-piperidin-1-yl}-butyl)-isonicotinamide To a solution of 4-[(4-bromo-phenyl)-(6-methyl-pyridin-2-yloxy)-methyl]-piperidine-1-carboxylic acid tert-butyl ester (2.00 g, 4.33 mmol) and zinc cyanide (305 mg, 2.60 mmol) in DMF (20 mL) under nitrogen was added DPPF (48 mg, 0.087 mmol) and Pd$_2$(dba)$_3$ (40 mg, 0.043 mmol). The resulting suspension was warmed to 130° C. and stirred for 5 hours. Standard work-up and purification gave 4-[(4-cyano-phenyl)-(6-methyl-pyridin-2-yloxy)-methyl]-piperidine-1-carboxylic acid tert-butyl ester (1.4 g, 79%) as a yellow solid.

Using general procedure C with the above carbamate (1.2 g, 2.95 mmol), then general procedure B with the resulting amine and 2-(3-oxo-butyl)-isoindole-1,3-dione (1.2 g, 5.60 mmol) followed by general procedure D afforded 4-[[1-(3-amino-1-methyl-propyl)-piperidin-4-yl]-(6-methyl-pyridin-2-yloxy)-methyl]-benzonitrile (500 mg, 40% over 4 steps) as a white foam.

Using general procedure F, 3,5-dichloroisonicotinic acid (301 mg, 1.58 mmol) and the above amine (300 mg, 0.79 mmol) gave a diastereomeric mixture of COMPOUND 42 (285 mg, 65%) as a white foam. $^1$H NMR (CDCl$_3$) δ 0.38-0.82 (m, 1H), 0.96 (d, 3H, J=6.5 Hz), 1.09-1.22 (m, 1H), 1.40-2.03 (m, 5H), 2.27-2.50 (m, 1H), 2.37 (s, 3H), 2.57-2.93 (m, 4H), 3.23-3.43 (m, 1H), 3.79-3.97 (m, 1H), 5.25-5.34 (m, 1H), 6.45 (d, 1H, J=9.0 Hz), 6.65 (d, 1H, J=7.4 Hz), 7.28-7.36 (m, 2H), 7.37-7.45 (m, 1H), 7.56 (d, 2H, J=8.4 Hz), 8.56, 8.57 (s, 2H), 9.14, 9.32 (br s, 1H). $^{13}$C NMR (CDCl$_3$) δ 11.17, 11.25, 21.96, 26.51, 26.75, 27.28, 27.78, 28.23, 38.20, 39.57, 41.68, 50.01, 58.46, 58.63, 77.18, 105.28, 109.10, 114.14, 116.77, 125.90, 127.11, 129.94, 136.90, 141.32, 144.19, 145.58, 154.18, 159.49, 159.93. ES-MS m/z 553 (M+H). Anal. Calcd. for C$_{29}$H$_{31}$Cl$_2$N$_5$O$_2$.0.2CH$_2$Cl$_2$.0.3H$_2$O: C, 61.01; H, 5.61; N, 12.19; Cl, 14.80. Found. C, 61.03; H, 5.61; N, 11.96; Cl, 14.91.

4-[(6-chloro-pyridin-2-yloxy)-(4-cyano-phenyl)-methyl]-piperidine-1-carboxylic acid tert-butyl ester (236 mg, 24%) and 4-[(4-cyano-phenyl)-(6-cyano-pyridin-2-yloxy)-methyl]-piperidine-1-carboxylic acid tert-butyl ester (200 mg, 21%) as pale yellow solids.

Using general procedure C with 4-[(6-chloro-pyridin-2-yloxy)-(4-cyano-phenyl)-methyl]-piperidine-1-carboxylic acid tert-butyl ester (236 mg, 0.55 mmol), then general procedure B with the resulting amine and 2-(3-oxo-butyl)-isoindole-1,3-dione (203 mg, 0.93 mmol) and then using general procedure D afforded 4-[[1-(3-amino-1-methyl-propyl)-piperidin-4-yl]-(6-chloro-pyridin-2-yloxy)-methyl]-benzonitrile as a colourless syrup (65 mg, 37% over 3 steps).

Using general procedure F, 3,5-dichloroisonicotinic acid (77 mg, 0.40 mmol) and the amine from above (80 mg, 0.20 mmol) afforded COMPOUND 43 (98 mg, 85%). $^1$H NMR (CDCl$_3$) δ 0.38-1.00 (m, 2H), 0.95 (d, 3H, J=6.3 Hz), 1.10-1.17 (m, 1H), 1.45-1.56 (m, 1H), 1.66-2.03 (m, 4H), 2.29-2.45 (m, 1H), 2.59-2.90 (m, 3H), 3.26-3.39 (m, 1H), 3.79-3.93 (m, 1H), 5.29-5.32 (m, 1H), 6.59 (dd, 1H, J=8.1, 1.5 Hz), 6.86 (dd, 1H, J=7.5, 1.5 Hz), 7.32-7.36 (m, 2H), 7.46-7.52 (m, 1H), 7.59 (d, 2H, J=7.8 Hz), 8.62 (s, 2H), 9.09, 9.30 (br s, 1H). $^{13}$C NMR (CDCl$_3$) δ 13.24, 13.31, 28.46, 28.65, 29.20, 29.44, 29.82, 30.34, 40.16, 40.31, 41.33, 43.63, 43.74, 51.75, 51.92, 60.40, 60.56, 80.22, 109.13, 111.59, 117.01, 118.67, 128.00, 129.09, 132.16, 140.96, 143.33, 145.01, 147.74, 148.21, 161.42, 161.57, 162.19. ES-MS m/z 572 (M+H). Anal. Calcd. for C$_{28}$H$_{28}$N$_5$Cl$_3$O$_2$.0.1CH$_2$Cl$_2$: C, 58.05; H, 4.89; N, 12.05; Cl, 19.51. Found. C, 58.08; H, 4.93; N, 11.95; Cl, 19.27.

EXAMPLE 43

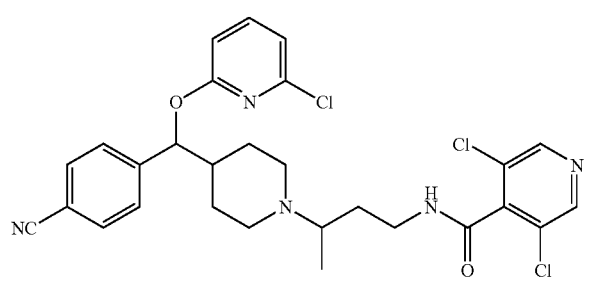

COMPOUND 43: 3,5-Dichloro-N-(3-{4-[(6-chloro-pyridin-2-yloxy)-(4-cyano-phenyl)-methyl]-piperidin-1-yl}-butyl)-isonicotinamide To a solution of 4-[(4-bromo-phenyl)-hydroxy-methyl]-piperidine-1-carboxylic acid tert-butyl ester (1.03 g, 2.78 mmol) in DMF (14 mL) was added NaH (60% in mineral oil, 278 mg, 6.95 mmol) and the mixture was stirred at room temperature for 10 minutes. 2,6-Dichloropyridine (1.23 g, 8.34 mmol) was added and the mixture was heated at 70° C. for 3 hours. Standard work-up and purification afforded 4-[(4-bromo-phenyl)-(6-chloro-pyridin-2-yloxy)-methyl]-piperidine-1-carboxylic acid tert-butyl ester as an off white solid (1.28 g, 96%).

The above bromide (1.10 g, 2.28 mmol), Zn(CN)$_2$ (161 mg, 1.37 mmol), DPPF (126 mg, 0.23 mmol) and degassed DMF (12 mL) were flushed with N$_2$ and heated to 60° C. Pd$_2$(dba)$_3$ (104 mg, 0.11 mmol) was added and the mixture was heated at 130° C. overnight. Work-up and purification afforded

EXAMPLE 44

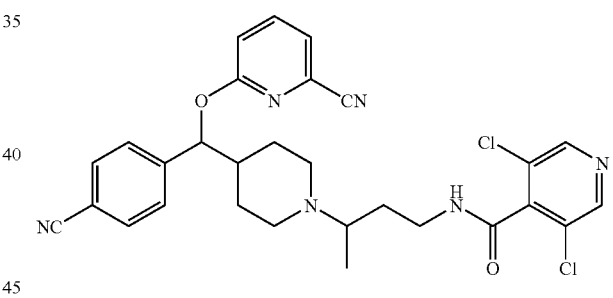

COMPOUND 44: 3,5-Dichloro-N-(3-{4-[(4-cyano-phenyl)-(6-cyano-pyridin-2-yloxy)-methyl]-piperidin-1-yl}-butyl)-isonicotinamide Using general procedure C with 4-[(4-cyano-phenyl)-(6-cyano-pyridin-2-yloxy)-methyl]-piperidine-1-carboxylic acid tert-butyl ester (see EXAMPLE 43) (200 mg, 0.48 mmol), then general procedure B with the resulting amine and 2-(3-oxo-butyl)-isoindole-1,3-dione (168 mg, 0.77 mmol) and then using general procedure D afforded 6-[[1-(3-amino-1-methyl-propyl)-piperidin-4-yl]-(4-cyano-phenyl)-methoxy]-pyridine-2-carbonitrile as a colourless syrup (40 mg, 22% over 3 steps).

Using general procedure F, 3,5-dichloroisonicotinic acid (40 mg, 0.21 mmol) and the amine from above (40 mg, 0.10 mmol) afforded COMPOUND 44 (27 mg, 47%). $^1$H NMR (CDCl$_3$) δ 0.49-0.97 (m, 2H), 0.96 (d, 3H, J=6.3 Hz), 1.15-1.23 (m, 1H), 1.45-1.56 (m, 1H), 1.67-1.89 (m, 3H), 1.91-2.06 (m, 1H), 2.30-2.45 (m, 1H), 2.62-2.90 (m, 3H), 3.28-3.39 (m, 1H), 3.80-3.91 (m, 1H), 5.38-5.42 (m, 1H), 6.94 (d, 1H, J=8.1 Hz), 7.26-7.36 (m, 3H), 7.61 (d, 2H, J=7.8 Hz), 7.64-7.70 (m, 1H), 8.57, 8.60 (s, 2H), 8.90, 8.99 (br s, 1H). $^{13}$C NMR (CDCl$_3$) δ 13.27, 28.55, 29.21, 29.30, 30.23, 30.42, 40.07, 40.13, 41.39, 43.77, 43.84, 51.68, 51.76, 60.30, 80.45, 111.81, 116.06, 116.11, 116.98, 118.55, 122.67, 127.90, 129.09, 130.27, 132.24, 139.63, 143.24, 144.59, 147.64, 161.47, 161.52, 162.83. ES-MS m/z 563 (M+H). Anal. Calcd. for C$_{29}$H$_{28}$N$_6$Cl$_2$O$_2$.0.1CH$_2$Cl$_2$: C, 61.11; H, 4.97; N, 14.69; Cl, 13.64. Found. C, 60.96; H, 5.03; N, 14.39; Cl, 13.81.

EXAMPLE 45

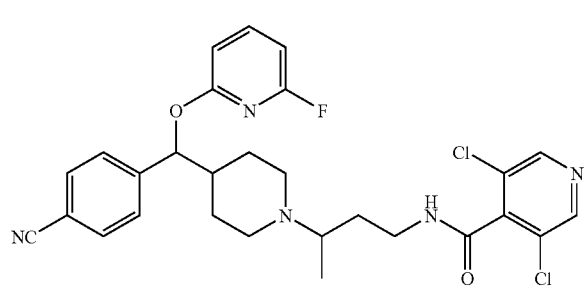

COMPOUND 45: 3,5-Dichloro-N-(3-{4-[(4-cyano-phenyl)-(6-fluoro-pyridin-2-yloxy)-methyl]-piperidin-1-yl}-butyl)-isonicotinamide To a solution of 4-[(4-bromo-phenyl)-hydroxy-methyl]-piperidine-1-carboxylic acid tert-butyl ester (1.36 g, 3.67 mmol) in DMF (18 mL) was added NaH (60% in mineral oil, 367 mg, 9.17 mmol) and the mixture was stirred at room temperature for 10 minutes. 2,6-Difluoropyridine (1.00 mL, 11.0 mmol) was added and the mixture was heated at 70° C. overnight. Work-up and purification gave 4-[(4-bromo-phenyl)-(6-fluoro-pyridin-2-yloxy)-methyl]-piperidine-1-carboxylic acid tert-butyl ester as an off-white solid (1.60 g, 94%).

The above bromide (1.60 g, 3.44 mmol), Zn(CN)$_2$ (242 mg, 2.06 mmol), DPPF (382 mg, 0.69 mmol) and degassed DMF (17 mL) were flushed with N$_2$. Pd$_2$(dba)$_3$ (311 mg, 0.34 mmol) was added and the mixture was heated at 130° C. overnight. Aqueous work-up and purification afforded 4-[(4-cyano-phenyl)-(6-fluoro-pyridin-2-yloxy)-methyl]-piperidine-1-carboxylic acid tert-butyl ester as a yellow solid (1.12 mg, 78%).

Using general procedure C with the above substrate (1.12 g, 2.72 mmol), then general procedure B with the resulting amine and 2-(3-oxo-butyl)-isoindole-1,3-dione (893 mg, 4.11 mmol) followed by general procedure D afforded 4-[[1-(3-amino-1-methyl-propyl)-piperidin-4-yl]-(6-fluoro-pyridin-2-yloxy)-methyl]-benzonitrile as a colourless syrup (270 mg, 27% over 3 steps).

Using general procedure F, 3,5-dichloroisonicotinic acid (216 mg, 1.12 mmol) and the amine from above (215 mg, 0.56 mmol) afforded COMPOUND 45 (203 mg, 65%). $^1$H NMR (CDCl$_3$) δ 0.44-0.98 (m, 2H), 0.96 (d, 3H, J=6.6 Hz), 1.13-1.21 (m, 1H), 1.47-1.57 (m, 1H), 1.63-2.04 (m, 4H), 2.30-2.44 (m, 1H), 2.62-2.88 (m, 3H), 3.28-3.39 (m, 1H), 3.82-3.93 (m, 1H), 5.27-5.31 (m, 1H), 6.43-6.47 (m, 1H), 6.56 (d, 1H, J=7.8 Hz), 7.33, 7.34 (d, 2H, J=8.1 Hz), 7.58-7.65 (m, 3H), 8.62 (s, 2H), 9.04-9.23 (br s, 1H). $^{13}$C NMR (CDCl$_3$) δ 13.28, 28.51, 29.22, 29.28, 29.88, 30.32, 40.14, 40.27, 41.50, 41.54, 43.65, 43.78, 51.73, 51.89, 60.38, 60.50, 80.11, 100.64, 101.11, 107.25, 111.58, 118.65, 127.85, 129.05, 129.09, 132.17, 142.91, 143.02, 143.31, 145.02, 147.72, 161.44, 161.56, 161.78 (d, J=242 Hz), 161.79. ES-MS m/z 556 (M+H). Anal. Calcd. for C$_{28}$H$_{28}$N$_5$Cl$_2$FO$_2$.0.1H$_2$O.0.16CH$_2$Cl$_2$: C, 59.17; H, 5.03; N, 12.25; Cl, 14.34; F, 3.32. Found. C, 59.21; H, 5.08; N, 12.37; Cl, 14.36; F, 3.15.

EXAMPLE 46

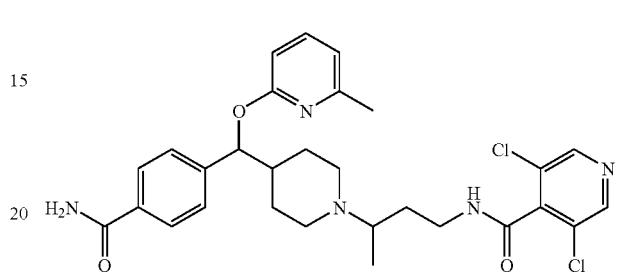

COMPOUND 46: N-(3-{4-[(4-Carbamoyl-phenyl)-(6-methyl-pyridin-2-yloxy)-methyl]-piperidin-1-yl}-butyl)-3,5-dichloro-isonicotinamide To a solution of COMPOUND 42 (100 mg, 0.18 mmol) in MeOH (2 mL) was added 10% NaOH (2 mL). The resulting mixture was heated at 50° C. overnight. Work-up and purification afforded a diastereomeric mixture of COMPOUND 46 (32 mg, 31%) as a white foam. $^1$H NMR (CDCl$_3$) δ 0.32-0.82 (m, 1H), 0.93-0.98 (m, 3H), 1.17-1.26 (m, 2H), 1.41-1.57 (m, 1H), 1.69-1.81 (m, 2H), 1.89-1.98 (m, 2H), 2.26-2.49 (m, 1H), 2.37 (s, 3H), 2.61-2.92 (m, 3H), 3.22-3.41 (m, 1H), 3.78-3.96 (m, 1H), 5.31 (d, 1H, J=7.5 Hz), 5.62, 6.27 (br s, 2H), 6.42 (d, 1H, J=7.8 Hz), 6.64 (d, 1H, J=7.5 Hz), 7.27-7.33 (m, 2H), 7.35-7.43 (m, 1H), 7.70 (d, 2H, J=7.9 Hz), 8.53, 8.55 (s, 2H), 9.26, 9.43 (br s, 1H). $^{13}$C NMR (CDCl$_3$) δ 13.21, 13.32, 24.05, 28.33, 29.01, 29.10, 29.70, 29.89, 30.16, 40.30, 40.40, 41.71, 43.81, 51.98, 52.15, 60.56, 60.76, 79.56, 107.22, 116.02, 127.27, 127.45, 129.11, 132.52, 138.86, 143.35, 144.54, 147.54, 156.28, 161.42, 161.58, 162.24, 169.40. ES-MS m/z 572 (M+H). Anal. Calcd. for C$_{29}$H$_{33}$Cl$_2$N$_5$O$_3$.0.5CH$_2$Cl$_2$.0.3H$_2$O: C, 57.30; H, 5.64; N, 11.33; Cl, 17.20. Found. C, 57.17; H, 5.65; N, 11.26; Cl, 17.27.

EXAMPLE 47

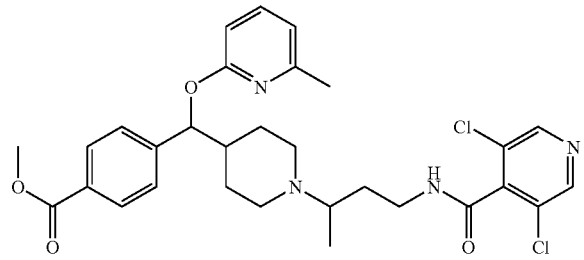

COMPOUND 47: 4-[(1-{3-[(3,5-Dichloro-pyridine-4-carbonyl)-amino]-1-methyl-propyl}-piperidin-4-yl)-(6-methyl-pyridin-2-yloxy)-methyl]-benzoic acid methyl ester To a solution of COMPOUND 42 (40 mg, 0.07 mmol) in HCl/MeOH (3 mL), was added H$_2$O (3 drops). The resulting mixture was heated at 80° C. overnight to afford a diastereomeric mixture of COMPOUND 47 (22 mg, 51%) as a white foam following work-up and purification. $^1$H NMR (CDCl$_3$) δ 0.37-0.82 (m, 1H), 0.87-1.02 (m, 3H), 1.07-1.23 (m, 1H), 1.44-1.58 (m, 1H), 1.63-2.00 (m, 5H), 2.28-2.47 (m, 1H), 2.37 (s, 3H), 2.53-2.94 (m, 3H), 3.22-3.40 (m, 1H), 3.76-3.93 (m, 1H), 3.88 (s, 3H), 5.27 (d, 1H, J=8.0 Hz), 6.42 (d, 1H, J=8.5 Hz), 6.63 (d, 1H, J=7.1 Hz), 7.27-7.32 (m, 2H), 7.38, 7.39 (dd, 1H, J=7.6, 7.6 Hz), 7.94 (d, 2H, J=8.4 Hz), 8.56, 8.57 (s, 2H), 9.24, 9.39 (br s, 1H). $^{13}$C NMR (CDCl$_3$) δ 13.58, 13.69, 24.42, 28.95, 29.36, 29.74, 30.15, 30.28, 30.60, 40.69, 40.79, 42.09, 44.14, 52.46, 60.97, 61.16, 80.11, 107.57, 116.38, 127.63, 127.67, 129.50, 129.62, 129.82, 139.21, 143.75, 146.18, 148.04, 156.68, 161.81, 161.97, 162.66, 167.31. ES-MS m/z 585 (M+H). Anal. Calcd. for C$_{29}$H$_{34}$Cl$_2$N$_4$O$_4$.0.3CH$_2$Cl$_2$: C, 59.56; H, 5.71; N, 9.17. Found. C, 59.39; H, 5.76; N, 8.91.

EXAMPLE 48

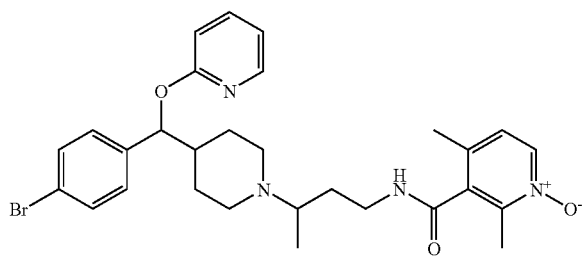

COMPOUND 48: N-(3-{4-[(4-Bromo-phenyl)-(pyridin-2-yloxy)-methyl]-piperidin-1-yl}-butyl)-2,4-dimethyl-1-oxy-nicotinamide Using general procedure E, 3-{4-[(4-bromo-phenyl)-(pyridin-2-yloxy)-methyl]-piperidin-1-yl}-butylamine (see EXAMPLE 21) (116 mg, 0.28 mmol) and 2,4-dimethyl-1-oxynicotinic acid (61 mg, 0.36 mmol) gave COMPOUND 48 as a pale yellow foam (144 mg, 92%). $^1$H NMR (CDCl$_3$) δ 0.62-1.00 (m, 1H), 0.96 (d, 3H, J=6.9 Hz), 1.22-1.32 (m, 1H), 1.47-1.58 (m, 1H), 1.61-2.07 (m, 5H), 2.28 and 2.29 (s, 3H), 2.32-2.49 (m, 1H), 2.44 (s, 3H), 2.58-2.84 (m, 3H), 3.26-3.38 (m, 1H), 3.72-3.84 (m, 1H), 5.34 and 5.37 (d, 1H, J=8.3 Hz), 6.68-6.71 (m, 1H), 6.77-6.82 (m, 1H), 6.88 and 6.92 (d, 1H, J=6.5 Hz), 7.195 and 7.203 (d, 2H, J=8.4 Hz), 7.41 (d, 2H, J=8.4 Hz), 7.49-7.56 (m, 1H), 8.04-8.07 (m, 1H), 8.10 and 8.12 (d, 1H, J=5.1 Hz), 9.01 (br s, 1H). $^{13}$C NMR (CDCl$_3$) δ 13.28 and 13.32, 14.86 and 14.88, 18.26 and 18.28, 28.48 and 28.60, 29.03 and 29.16, 31.52 and 31.58, 38.95 and 38.96, 42.03 and 42.06, 44.61, 51.24 and 51.27, 58.75 and 58.79, 79.35 and 79.41, 111.05, 116.73, 120.98, 124.70, 128.77, 131.06, 133.97, 136.82, 137.86, 138.47, 139.42 and 139.43, 145.32 and 145.37, 146.64 and 146.66, 162.88, 165.18 and 165.21. ESI-MS m/z 567 (MH)$^+$, 569 (MH+2)$^+$. Anal. Calcd. for C$_{29}$H$_{35}$BrN$_4$O$_3$.1.0CH$_2$Cl$_2$: C, 55.23; H, 5.72; N, 8.59; Br, 12.25. Found. C, 55.48; H, 5.81; N, 8.66; Br, 11.98.

EXAMPLE 49

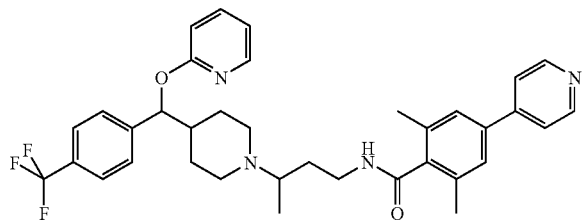

COMPOUND 49: 2,6-Dimethyl-4-pyridin-4-yl-N-(3-{4-[(pyridin-2-yloxy)-(4-trifluoromethyl-phenyl)-methyl]-piperidin-1-yl}-butyl)-benzamide Using general procedure E, 3-{4-[(pyridin-2-yloxy)-(4-trifluoromethyl-phenyl)-methyl]-piperidin-1-yl}-butylamine (75 mg, 0.18 mmol) (see EXAMPLE 22) and 2,6-dimethyl-4-pyridin-4-yl-benzoic acid (46 mg, 0.20 mmol) gave COMPOUND 49 as a white solid (56 mg, 50%). $^1$H NMR (CDCl$_3$) δ 0.46-1.09 (m, 2H), 0.94 (dd, 3H, J=6.6, 3.6 Hz), 1.44-2.05 (m, 5H), 2.24-2.46 (m, 1H), 2.40 (s, 3H), 2.41 (s, 3H), 2.54-2.89 (m, 4H), 3.23-3.40 (m, 1H), 3.77-3.94 (m, 1H), 5.23-5.31 (m, 1H), 6.60 (dd, 1H, J=8.4, 3.6 Hz), 6.54 (dd, 1H, J=11.7, 4.8 Hz), 7.17 (d, 2H, J=8.1 Hz), 7.36-7.44 (m, 5H), 5.54-5.57 (m, 2H), 7.84, 7.79 (dd, 1H, J=4.8, 1.2 Hz), 8.57, 8.73 (d, 1H, J=5.7 Hz), 8.61, 8.63 (s, 2H). $^{13}$C NMR (CDCl$_3$) δ 13.22, 13.39, 19.40 (2 carbons), 28.23, 28.80, 29.09, 29.77, 30.52, 31.09, 39.72, 39.85, 42.21, 43.98, 51.97, 52.14, 60.25, 60.55, 79.55, 79.63, 111.01, 116.96, 121.67, 124.05 (q, J=272 Hz), 124.91, 124.95, 126.05, 126.07, 127.25, 129.46 (q, J=32 Hz), 135.18, 138.06, 138.16, 138.54, 139.39, 144.59, 144.67, 146.64, 147.88, 150.27, 162.79, 162.82, 169.26, 169.52. ES-MS m/z 617 (M+H). Anal. Calcd. for C$_{36}$H$_{39}$F$_3$N$_4$O$_2$: C, 68.76; H, 6.36; N, 8.88; F, 9.04. Found. C, 68.54; H, 6.31; N, 8.75; F, 9.26.

EXAMPLE 50

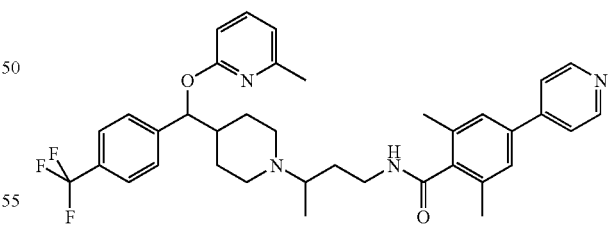

COMPOUND 50: 2,6-Dimethyl-N-(3-{4-[(6-methyl-pyridin-2-yloxy)-(4-trifluoromethyl-phenyl)-methyl]-piperidin-1-yl}-butyl)-4-pyridin-4-yl-benzamide Using general procedure E, 3-{4-[(6-methyl-pyridin-2-yloxy)-(4-trifluoromethyl-phenyl)-methyl]-piperidin-1-yl}-butylamine (see EXAMPLE 23) (40 mg, 0.10 mmol) and 2,6-dimethyl-4-pyridin-4-yl-benzoic acid (24 mg, 0.11 mmol) afforded COMPOUND 50 (30 mg, 50%). $^1$H NMR (CDCl$_3$) δ 0.50-1.10 (m, 2H), 0.95, 0.96 (d, 3H, J=6.1 Hz), 1.47-2.06 (m, 5H), 2.20, 2.22 (s, 3H), 2.26-2.45 (m, 1H), 2.42 (s, 6H), 2.56-2.87 (m, 4H), 3.24-3.41 (m, 1H), 3.76-3.94 (m, 1H), 5.16, 5.23 (d, 1H, J=8.1 Hz), 6.29 (dd, 1H, J=8.4, 4.5 Hz), 6.57 (dd, 1H, J=7.5, 2.7 Hz), 7.18-7.24 (m, 3H), 7.36-7.40 (m, 4H), 7.50 (d, 2H, J=4.8 Hz), 8.35, 8.47 (br s, 1H), 8.61-8.64 (m, 2H). $^{13}$C NMR (CDCl$_3$) δ 13.17, 13.39, 19.42, 23.99, 24.03, 28.26, 28.90, 29.08, 29.87, 30.78, 31.32, 39.58, 39.69, 42.28, 44.06, 44.16, 51.95, 52.10, 60.03, 60.38, 79.67, 79.83, 106.97, 107.01, 116.03, 121.47, 124.06 (q, J=272 Hz), 124.88, 124.92, 125.93, 127.35, 129.43 (q, J=32 Hz), 135.25, 137.90, 137.97, 138.77, 139.38, 144.73, 147.70, 150.32, 156.19, 162.20, 169.26, 169.54. ES-MS m/z 631 (M+H). Anal. Calcd. for C$_{37}$H$_{41}$F$_3$N$_4$O$_2$: C, 70.06; H, 6.58; N, 8.83; F, 8.98. Found. C, 70.15; H, 6.50; N, 8.79; F, 8.78.

EXAMPLE 51

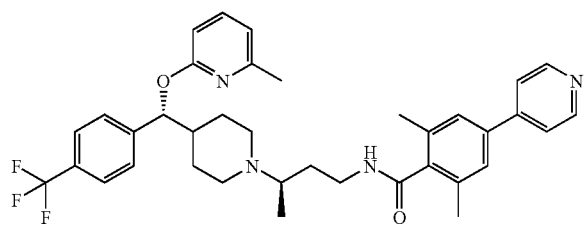

COMPOUND 51: 2,6-Dimethyl-N-(3 (R)-{4(R)-[(6-methylpyridin-2-yloxy)-(4-trifluoromethyl-phenyl)-methyl]-piperidin-1-yl}-butyl)-4-pyridin-4-yl-benzamide To a solution of 4(S)-[(4-trifluoromethyl-phenyl)-hydroxy-methyl]-piperidine-1-carboxylic acid tert-butyl ester (see EXAMPLE 16) (443 mg, 1.23 mmol), 2-hydroxy-6-methylpyridine (269 mg, 2.47 mmol) and Ph$_3$P (646 mg, 2.47 mmol) in THF (10 mL) at room temperature was added DIAD (0.49 mL, 2.47 mmol) dropwise. The mixture was stirred at room temperature for 2 hours to give 4(R)-[(6-methyl-pyridin-2-yloxy)-(4-trifluoromethyl-phenyl)-methyl]-piperidine-1-carboxylic acid tert-butyl ester as a white foam (416 mg, 75%) following work-up and purification.

Using general procedure C, the above carbamate (560 mg, 1.24 mmol) gave (R)-2-methyl-6-[piperidin-4-yl-(4-trifluoromethyl-phenyl)-methoxy]-pyridine (ee 96.5% determined by chiral HPLC) as a colorless oil (436 mg, 100%).

Using general procedure G, methyl-(S)-lactate (98 mg, 0.944 mmol) gave (S)-2-methanesulfonyloxy-propionic acid methyl ester as a colorless oil (172 mg, 100%).

A solution of the above piperidine (240 mg, 0.629 mmol) in dry CH$_3$CN (2 mL) was added to the above mesylate followed by 2,2,6,6-tetramethylpiperidine (127 mg, 0.900 mmol). The mixture was heated at reflux for 15 hours to give the methyl ester (263 mg, 0.603 mmol), which was subsequently reduced with LiAlH$_4$ (1.0 M in THF, 0.905 mL, 0.905 mmol) in Et$_2$O (4 mL) to give 2(R)-{4(R)-[(6-methylpyridin-2-yloxy)-(4-trifluoromethyl-phenyl)-methyl]-piperidin-1-yl}-propan-1-ol (de 95% determined by chiral HPLC) as a colorless oil (209 mg, 75% over 2 steps) following a Feiser work-up and purification.

Using general procedure G the above alcohol (195 mg, 0.478 mmol) gave the chloride, which was subsequently dissolved in DMSO (2.5 mL) followed by the addition of NaCN (47 mg, 0.95 mmol). The reaction was heated at 140° C. for 1 hour to give the nitrile (140 mg, 0.336 mmol), which was subsequently reduced with BH$_3$-THF (1.0M in THF, 1.01 mL, 1.01 mmol) in THF (2 mL) at reflux and treated with MeOH then ethylenediamine (1 mL) to give 3(R)-{4(R)-[(6-methylpyridin-2-yloxy)-(4-trifluoromethyl-phenyl)-methyl]-piperidin-1-yl}-butylamine as a colorless oil (121 mg, 64% over 2 steps) following work-up and purification.

Using general procedure E, the above amine (58 mg, 0.14 mmol) and 2,6-dimethyl-4-pyridin-4-yl-benzoic acid (37.5 mg, 0.165 mmol) gave COMPOUND 51 as a white foam (80.8 mg, 93%). $^1$H NMR (CDCl$_3$) δ 0.55-0.65 (m, 1H), 0.94 (d, 3H, J=6.3 Hz), 1.04 (br d, 2H, J=10.5 Hz), 1.45-1.80 (m, 3H), 1.87-2.01 (m, 2H), 2.19 (s, 3H), 2.36-2.41 (m, 1H), 2.41 (s, 6H), 2.69-2.82 (m, 3H), 3.20-3.35 (m, 1H), 3.80-3.90 (m, 1H), 5.18 (d, 1H, J=8.4 Hz), 6.28 (d, 1H, J=8.1 Hz), 6.55 (d, 1H, J=7.2 Hz), 7.17-7.29 (m, 3H), 7.35-7.40 (m, 4H), 7.48 (d, 2H, J=6.0 Hz), 8.35 (br s, 1H), 8.60 (d, 2H, J=6.0 Hz). $^{13}$C NMR (CDCl$_3$) δ 13.5, 19.8, 24.4, 28.6, 30.2, 31.7, 39.9, 42.6, 44.5, 52.5, 60.7, 80.2, 107.4, 116.4, 121.9, 125.3, 126.4, 127.7, 129.8 (q, J=32 Hz), 135.6, 138.4, 139.2, 139.7, 145.1, 148.1, 150.7, 156.6, 162.5, 169.7. ES-MS m/z 632 (M+H). Anal. Calcd. for C$_{37}$H$_{41}$F$_3$N$_4$O$_2$.0.4CH$_2$Cl$_2$: C, 67.58; H, 6.34; N, 8.43; F, 8.57. Found. C, 67.46; H, 6.35; N, 8.27; F, 8.31.

EXAMPLE 52

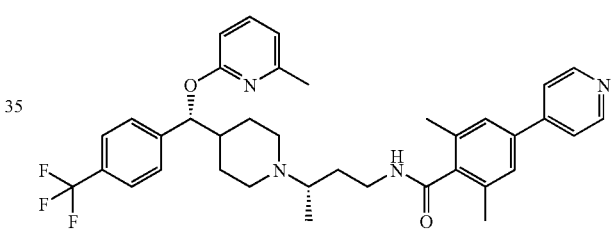

COMPOUND 52: 2,6-Dimethyl-N-(3(S)-{4(R)-[(6-methylpyridin-2-yloxy)-(4-trifluoromethyl-phenyl)-methyl]-piperidin-1-yl}-butyl)-4-pyridin-4-yl-benzamide Using general procedure G, methyl-(R)-lactate (98 mg, 0.944 mmol) gave the mesylate as a colorless oil (172 mg, 100%).

A solution of (R)-2-methyl-6-[piperidin-4-yl-(4-trifluoromethyl-phenyl)-methoxy]-pyridine (see EXAMPLE 51) (240 mg, 0.629 mmol) in dry CH$_3$CN (2 mL) was added to the above mesylate followed by 2,2,6,6-tetramethylpiperidine (127 mg, 0.900 mmol). The mixture was heated at reflux for 15 hours to give the methyl ester (212 mg, 0.486 mmol), which was subsequently reduced with LiAlH$_4$ (1.0 M in THF, 0.73 mL, 0.73 mmol) in Et$_2$O (2.5 mL) to give 2(S)-{4(R)-[(6-methylpyridin-2-yloxy)-(4-trifluoromethyl-phenyl)-methyl]-piperidin-1-yl}-propan-1-ol (de 87% determined by chiral HPLC) as a colorless oil (183 mg, 76% over 2 steps) following a Feiser work-up and purification.

Using general procedure G, the above alcohol (172 mg, 0.422 mmol) gave the chloride, which was subsequently dissolved in DMSO (2 mL) followed by the addition of NaCN (41 mg, 0.84 mmol). The reaction was heated at 140° C. for 1 hour to give the nitrile (128 mg, 0.307 mmol), which was subsequently reduced with BH₃-THF (1.0M in THF, 0.92 mL, 0.92 mmol) in THF (1.8 mL) at reflux and treated with MeOH then ethylenediamine (1 mL) to give 3(S)-{4(R)-[(6-methylpyridin-2-yloxy)-(4-trifluoromethyl-phenyl)-methyl]-piperidin-1-yl}-butylamine as a colorless oil (109 mg, 61% over 2 steps) following work-up and purification.

Using general procedure E, the above amine (65 mg, 0.14 mmol) and 2,6-dimethyl-4-pyridin-4-yl-benzoic acid (42 mg, 0.19 mmol) gave COMPOUND 52 as a white foam (95 mg, 98%). ¹H NMR (CDCl₃) δ 0.72-1.09 (m, 3H), 0.95 (d, 3H, J=6.3 Hz), 1.48-1.85 (m, 3H), 1.93-2.04 (m, 2H), 2.21 (s, 3H), 2.30 (t, 1H, J=10.6 Hz), 2.40 (s, 6H), 2.59 (d, 1H, J=10.8 Hz), 2.76-2.86 (m, 2H), 3.31-3.40 (m, 1H), 3.75-3.83 (m, 1H), 5.24 (d, 1H, J=8.1 Hz), 6.29 (d, 1H, J=8.1 Hz), 6.56 (d, 1H, J=7.2 Hz), 7.18-7.29 (m, 3H), 7.34-7.39 (m, 4H), 7.48 (d, 2H, J=6.0 Hz), 8.47 (br s, 1H), 8.60 (d, 2H, J=5.7 Hz). ¹³C NMR (CDCl₃) δ 13.8, 19.8, 24.4, 29.3, 29.4, 31.2, 40.0, 42.7, 44.6, 52.3, 60.4, 80.0, 107.4, 116.4, 121.9, 125.3, 126.3, 127.7, 129.8 (q, J=32 Hz), 135.6, 138.3, 139.2, 139.8, 145.1, 148.1, 150.7, 156.6, 162.6, 170.0. ES-MS m/z 653 (M+Na). Anal. Calcd. for C₃₇H₄₁F₃N₄O₂.0.4CH₂Cl₂: C, 67.58; H, 6.34; N, 8.43; F, 8.57. Found. C, 67.74; H, 6.38; N, 8.25; F, 8.34.

EXAMPLE 53

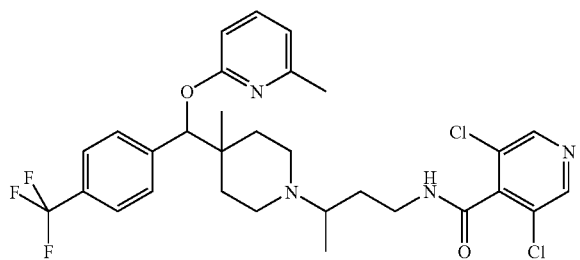

COMPOUND 53: 3,5-Dichloro-N-(3-{4-methyl-4-[(6-methyl-pyridin-2-yloxy)-(4-trifluoromethyl-1)-phenyl)-methyl]-piperidin-1-yl}-butyl)-isonicotinamide To 4-(4-trifluoromethyl-benzoyl)-piperidine-1-carboxylic acid tert-butyl ester (650 mg, 1.82 mmol) in DMF (14 mL) was added to NaH (60% in mineral oil, 153 mg, 6.37 mmol) and the mixture was heated at 50° C. for 30 minutes. MeI (0.47 mL, 7.64 mmol) was added and the mixture was heated at 50° C. for an additional 3 hours to afford 4-methyl-4-(4-trifluoromethyl-benzoyl)-piperidine-1-carboxylic acid tert-butyl ester as a colourless oil (390 mg, 58%) following work-up and purification.

The ketone from above (390 mg, 1.05 mmol) in MeOH (5 mL) was reduced with NaBH₄ (79 mg, 2.1 mmol) to afford a white solid (348 mg) after work-up.

To the alcohol from above (310 mg, 0.83 mmol) in DMF (4.0 mL) was added NaH (60% in mineral oil, 83 mg, 2.08 mmol) and the mixture was stirred at room temperature for 10 minutes. 6-Chloro-2-picoline (0.27 mL, 2.50 mmol) was added and the mixture heated at 70° C. for 3.5 hours. Standard work-up and purification afforded 4-methyl-4-[(6-methyl-pyridin-2-yloxy)-(4-trifluoromethyl-phenyl)-methyl]-piperidine-1-carboxylic acid tert-butyl ester as a white solid (263 mg, 54% over 2 steps).

Using general procedure C with the above substrate (260 mg, 0.56 mmol), then general procedure I with the resulting amine and then using general procedure J afforded 3-{4-methyl-4-[(6-methyl-pyridin-2-yloxy)-(4-trifluoromethyl-phenyl)-methyl]-piperidin-1-yl}-butylamine as a colourless syrup (124 mg, 51% over 3 steps).

Using general procedure F, 3,5-dichloroisonicotinic acid (62 mg, 0.32 mmol) and the amine from above (70 mg, 0.16 mmol) afforded COMPOUND 53 (53 mg, 54%). ¹H NMR (CDCl₃) δ 0.82, 0.83 (s, 3H), 0.84-1.00 (m, 1H), 1.03 (d, 3H, J=5.7 Hz), 1.04-1.29 (m, 2H), 1.34-1.59 (m, 2H), 1.72-1.89 (m, 1H), 2.20-2.34 (m, 1H), 2.35 (s, 3H), 2.46-2.63 (m, 2H), 2.66-2.87 (m, 1H), 2.80-2.90 (m, 1H), 3.29-3.40 (m, 1H), 3.85-3.96 (m, 1H), 5.30-5.45 (m, 1H), 6.45 (d, 1H, J=8.1 Hz), 6.64 (d, 1H, J=7.2 Hz), 7.24-7.28 (m, 2H), 7.38-7.44 (m, 1H), 7.50 (d, 2H, J=8.1 Hz), 8.55, 8.56 (s, 2H), 9.38, 9.46 (br s, 1H). ¹³C NMR (CDCl₃) δ 13.33, 13.39, 17.73, 24.08, 29.74, 29.99, 34.82, 35.11, 35.21, 36.21, 40.28, 40.34, 41.45, 45.70, 60.50, 60.56, 81.87, 107.26, 116.07, 124.16 (q, J=272 Hz), 124.41, 124.46, 128.34, 129.08, 129.47, 138.83, 142.86, 143.36, 147.63, 156.33, 161.51, 161.58, 162.15. ES-MS m/z 609 (M+H). Anal. Calcd. for C₃₀H₃₃N₄Cl₂F₃O₂: C, 59.12; H, 5.46; N, 9.19; Cl, 11.63; F, 9.35. Found. C, 58.92; H, 5.44; N, 9.08; Cl, 11.89; F, 9.23.

Scheme 4 describes the preparation of Examples 54-59, using various general procedures previously described, and reagents listed below.

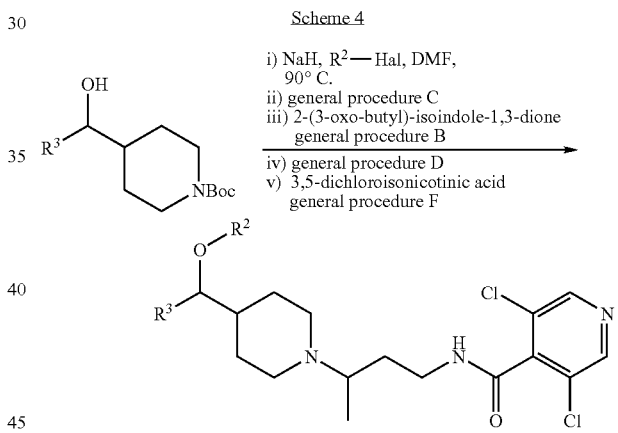

Scheme 4 i) NaH, R²—Hal, DMF, 90° C.
ii) general procedure C
iii) 2-(3-oxo-butyl)-isoindole-1,3-dione general procedure B
iv) general procedure D
v) 3,5-dichloroisonicotinic acid general procedure F

| Example | R³ | R²—Hal |
|---|---|---|
| 54 | thiazol-2-yl | 2,6-difluoropyridine |
| 55 | thiazol-2-yl | 2,6-dichloropyridine |
| 56 | oxazol-2-yl | 2,6-dichloropyridine |

-continued

| Example | R³ | R²—Hal |
|---|---|---|
| 57 | 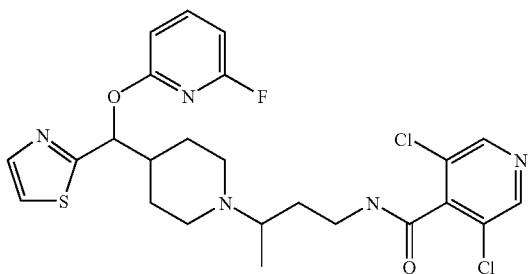 (oxazole) | 2,6-difluoropyridine |
| 58 | (3-pyridyl) | 2-chloro-6-methylpyridine |
| 59 | (4-pyridyl) | 2-chloro-6-methylpyridine |

EXAMPLE 54

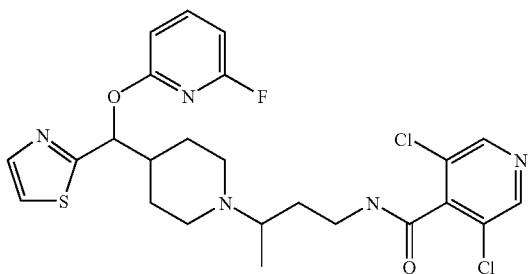

COMPOUND 54: 3,5-Dichloro-N-(3-{4-[(6-fluoro-pyridin-2-yloxy)-thiazol-2-yl-methyl]-piperidin-1-yl}-butyl)-isonicotinamide 2-(Trimethylsilyl)thiazole (1.0 g, 6.36 mmol) and 4-formyl-cyclohexanecarboxylic acid tert-butyl ester (1.63 g, 7.63 mmol) were stirred at room temperature for 4 hours. THF (50 mL) and TBAF (1M in THF, 7.6 mL, 7.6 mmol) were added and the mixture stirred for an additional hour. Standard work-up and purification afforded 4-(hydroxy-thiazol-2-yl-methyl)-piperidine-1-carboxylic acid tert-butyl ester as a beige syrup (940 mg, 50%).

COMPOUND 54 was isolated as a white foam. $^1$H NMR (CDCl$_3$) δ 0.62-0.86 (m, 1H), 0.96 (d, 3H, J=6.6 Hz), 0.99-1.17 (m, 1H), 1.46-1.65 (m, 2H), 1.68-2.14 (m, 4H), 2.34-2.52 (m, 1H), 2.64-2.91 (m, 3H), 3.23-3.41 (m, 1H), 3.78-3.94 (m, 1H), 5.86 (dd, 1H, J=6.7, 3.1 Hz), 6.50 (dd, 1H, J=7.9, 5.4 Hz), 6.63 (d, 1H, J=7.9 Hz), 7.25 (d, 1H, J=3.0 Hz), 7.63-7.75 (m, 2H), 8.53 (s, 2H), 8.98 (br s, 1H). $^{13}$C NMR (CDCl$_3$) δ 13.61, 14.59, 28.05, 28.75, 28.83, 29.46, 30.67, 40.56, 41.66, 44.26, 52.21, 60.89, 101.53, 102.00, 107.71, 119.41, 129.29, 143.15, 143.49, 143.59, 148.09, 160.60, 161.88, 162.03, 163.81, 169.51, 169.67. ES-MS m/z 539 (M+H). Anal. Calcd. for C$_{24}$H$_{26}$Cl$_2$FN$_5$O$_2$S.0.4H$_2$O: C, 52.83; H, 4.95; N, 12.83; Cl, 12.99; S, 5.88. Found. C, 52.91; H, 4.99; N, 12.54; Cl, 13.28; S, 5.49.

EXAMPLE 55

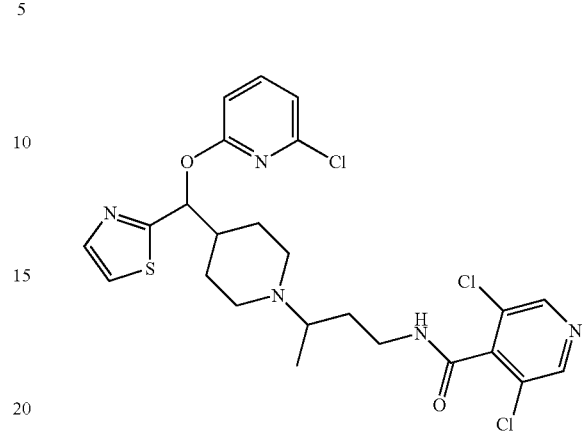

COMPOUND 55: 3,5-Dichloro-N-(3-{4-[(6-chloro-pyridin-2-yloxy)-thiazol-2-yl-methyl]-piperidin-1-yl}-butyl)-isonicotinamide White foam. $^1$H NMR (CDCl$_3$) δ 0.62-1.13 (m, 2H), 0.96 (d, 3H, J=6.6 Hz), 1.44-1.62 (m, 2H), 1.66-1.87 (m, 2H), 1.96-2.20 (m, 2H), 2.34-2.49 (m, 1H), 2.62-2.90 (m, 3H), 3.21-3.39 (m, 1H), 3.76-3.94 (m, 1H), 5.91 (dd, 1H, J=6.4, 3.0 Hz), 6.67 (d, 1H, J=8.5 Hz), 6.92 (d, 1H, J=7.5 Hz), 7.25 (d, 1H, J=2.9 Hz), 7.51-7.58 (m, 1H), 7.73 (d, 1H, J=3.2 Hz), 8.53, 8.54 (s, 2H), 8.94 (br s, 1H). $^{13}$C NMR (CDCl$_3$) δ 13.63, 14.59, 28.08, 28.76, 28.86, 29.46, 30.73, 40.49, 41.50, 44.33, 52.17, 60.80, 109.59, 109.64, 117.84, 119.47, 129.27, 141.51, 143.09, 143.50, 148.06, 148.63, 162.00, 162.49, 169.42, 169.56. ES-MS m/z 556 (M+H). Anal. Calcd. for C$_{24}$H$_{26}$Cl$_3$N$_5$O$_2$S.0.2CH$_2$Cl$_2$.0.3H$_2$O: C, 50.53; H, 4.71; N, 12.13; Cl, 20.88; S, 5.55. Found. C, 50.35; H, 4.81; N, 11.76; Cl, 20.76; S, 5.37.

EXAMPLE 56

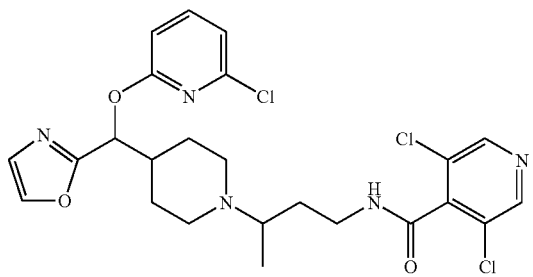

COMPOUND 56: 3,5-Dichloro-N-(3-{4-[(6-chloro-pyridin-2-yloxy)-oxazol-2-yl-methyl]-piperidin-1-yl}-butyl)-isonicotinamide To a solution of oxazole (420 mg, 6.08 mmol) in THF (15 mL) was added BH$_3$-THF (1.0M in THF, 6.69 mL, 6.69 mmol). The mixture was stirred at room temperature for 1 hour. After cooling to −78° C., t-BuLi (1.7M, 4.29 mL, 7.30 mmol) was introduced to the mixture and stirred at this temperature for 30 min. 4-Formyl-piperidine-1-carboxylic acid tert-butyl ester (1.30 g, 6.08 mmol) was added dropwise and the mixture was stirred at −78° C. for 3 hours. Work-up and purification gave 4-(hydroxy-oxazol-2-yl-methyl)-piperidine-1-carboxylic acid tert-butyl ester as a white foam (1.227 g, 71%).

COMPOUND 56 was isolated as a white foam. $^1$H NMR (CDCl$_3$) δ 0.55-1.04 (m, 2H), 0.98 (d, 3H, J=6.6 Hz), 1.42-1.63 (m, 3H), 1.72-1.82 (m, 2H), 2.01-2.09 (m, 1H), 2.43 (td, 1H, J=11.4, 2.1 Hz), 2.70-2.88 (m, 3H), 3.39 (m, 1H), 3.84 (m, 1H), 5.67 (d, 1H, J=6.3 Hz), 6.69 (d, 1H, J=8.1 Hz), 6.92 (d, 1H, J=7.5 Hz), 7.04 (s, 1H), 7.55 (t, 1H, J=7.8 Hz), 7.57 (s, 1H), 8.55 and 8.56 (s, 2H), 8.79 (br s, 1H). $^{13}$C NMR (CDCl$_3$) δ 13.66, 13.70, 28.3, 28.5, 28.9, 29.1, 40.3, 44.4, 44.5, 51.8, 51.9, 60.4, 60.5, 73.6, 73.7, 109.5, 109.6, 117.7, 127.6, 129.2, 139.1, 141.5, 143.4, 148.0, 148.1, 148.5, 162.0, 162.1, 162.2, 162.9. ES-MS m/z 540 (M+H). Anal. Calcd. for $C_{24}H_{26}Cl_3N_5O_3 \cdot 0.5H_2O \cdot 0.1C_6H_{14}$: C, 53.26; H, 5.14; N, 12.58; Cl, 19.11. Found. C, 53.10; H, 5.05; N, 12.45; Cl, 18.83.

EXAMPLE 57

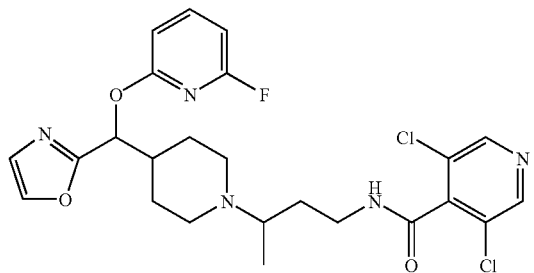

COMPOUND 57: 3,5-Dichloro-N-(3-{4-[(6-fluoro-pyridin-2-yloxy)-oxazol-2-yl-methyl]-piperidin-1-yl}-butyl)-isonicotinamide White foam. $^1$H NMR (CDCl$_3$) δ 0.55-1.04 (m, 2H), 0.99 (d, 3H, J=6.3 Hz), 1.41-1.63 (m, 3H), 1.80 (m, 2H), 2.01-2.09 (m, 1H), 2.44 (t, 1H, J=11.4 Hz), 2.70-2.89 (m, 3H), 3.35 (m, 1H), 3.84 (m, 1H), 5.60 (d, 1H, J=7.5 Hz), 6.50 (d, 1H, J=7.2 Hz), 6.64 (d, 1H, J=8.4 Hz), 7.05 (s, 1H), 7.57 (s, 1H), 7.68 (q, 1H, J=8.1 Hz), 8.55 and 8.56 (s, 2H), 8.85 (br s, 1H). $^{13}$C NMR (CDCl$_3$) δ 13.7, 28.3, 28.4, 28.9, 29.0, 30.7, 30.8, 40.2, 44.4, 51.8, 51.9, 60.4, 60.5, 73.61, 73.65, 101.4, 101.8, 107.6, 127.6, 129.2, 139.1, 143.4, 143.5, 148.03, 148.07, 161.8, 162.05, 162.09 (d, J=241 Hz), 163.7. ES-MS m/z 523 (M+H). Anal. Calcd. for $C_{24}H_{26}Cl_2FN_5O_3 \cdot 0.3H_2O$: C, 54.62; H, 5.08; N, 13.27; Cl, 13.43; F, 3.60. Found. C, 54.82; H, 5.06; N, 13.09; Cl, 13.14; F, 3.44.

EXAMPLE 58

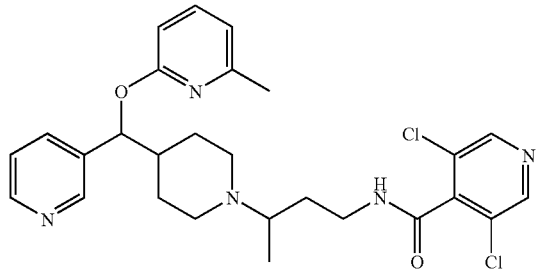

COMPOUND 58: 3,5-Dichloro-N-(3-{4-[(6-methyl-pyridin-2-yloxy)-pyridin-3-yl-methyl]-piperidin-1-yl}-butyl)-isonicotinamide To a cold (−78° C.) solution of 2-bromo pyridine (800 mg, 5.06 mmol) in freshly distilled THF (15 mL) was added LDA (2.0 M, 2.8 mL, 6.5 mmol). The mixture was stirred under N$_2$ for 30 min. A solution of 4-formyl-piperidine-1-carboxylic acid tert-butyl ester (500 mg, 2.34 mmol) was added slowly to maintain the bath temperature below −70° C. The reaction was stirred at below −70° C. for 30 min, warmed to −20° C. within 60 min, and quenched with saturated aqueous NH$_4$Cl (10 mL). Work-up and purification gave 4-[(2-bromo-pyridin-3-yl)-hydroxy-methyl]-piperidine-1-carboxylic acid tert-butyl ester (470 mg, 50%) as a colourless oil.

To a solution of the above alcohol (470 mg, 1.27 mmol) in MeOH (4 ml) in a Parr flask was added 10% Pd/C (80 mg) under N$_2$. The mixture was hydrogenated at room temperature under 1.5 atm H$_2$ for 1 h. 3N NaOH (5 mL) was added and the mixture was extracted with CHCl$_3$ (20 mL×2). The combined organic solution was filtered through a short pad of Celite® to give 4-(hydroxy-pyridin-3-yl-methyl)-piperidine-1-carboxylic acid tert-butyl ester (270 mg, 72%) as a colourless oil.

COMPOUND 58 was isolated as a white foam. $^1$H NMR (CDCl$_3$) δ 0.48-0.80 (m, 2H), 0.96 (d, 3H, J=6.0 Hz), 1.15-1.25 (m, 1H), 1.30-2.05 (m, 5H), 2.25-2.50 (m, 4H), 2.80-2.98 (m, 3H), 3.25-3.54 (m, 1H), 3.75-3.98 (m, 1H), 5.25-5.28 (m, 1H), 6.43 (d, 1H, J=9.0 Hz), 6.65 (d, 1H, J=6.0 Hz), 7.20-7.25 (m, 1H), 7.30-7.48 (m, 1H), 7.59 (d, 1H, J=6.0 Hz), 8.45 (d, 1H, J=6.0 Hz), 8.50 (d, 1H, J=3.0 Hz), 8.55 (s, 1H), 8.58 (s, 1H), 9.25 (s, 0.5H), 9.48 (s, 0.5H). $^{13}$C NMR (CDCl$_3$) δ 13.62, 13.71, 24.42, 28.82, 29.35, 29.58, 30.20, 30.60, 40.53, 40.61, 41.78, 42.69, 44.17, 52.17, 52.32, 60.80, 60.97, 78.19, 78.24, 107.72, 116.45, 123.65, 129.47, 135.27, 136.35, 139.28, 143.69, 148.03, 149.17, 149.67, 156.65, 161.90, 162.04, 162.45. ES-MS m/z 550 (M+Na). Anal.

Calcd. for $C_{27}H_{31}Cl_2N_5O_2 \cdot 0.5CH_2Cl_2 \cdot 0.3C_4H_8O_2$: C, 57.70; H, 5.80; N, 11.72; Cl, 17.80. Found. C, 57.61; H, 5.70; N, 11.97; Cl, 17.63.

EXAMPLE 59

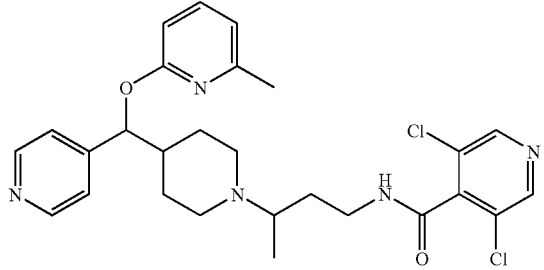

COMPOUND 59: 3,5-Dichloro-N-(3-{4-[(6-methyl-pyridin-2-yloxy)-pyridin-4-yl-methyl]-piperidin-1-yl}-butyl)-isonicotinamide To a cold (−90° C.) solution of 3-bromo pyridine (741 mg, 4.7 mmol) in freshly distilled THF (18 ml) was added LDA (2.0M, 2.6 mL, 5.2 mmol). The mixture was stirred under $N_2$ for 20 min. A solution of 4-formyl-piperidine-1-carboxylic acid tert-butyl ester (500 mg, 2.34 mmol) was added slowly to maintain the bath temperature below −80° C. The reaction was continued at below −80° C. for 30 min, warmed to −20° C. within 30 min and quenched with saturated aqueous $NH_4Cl$ (10 mL). Work-up and purification gave 4-[(3-bromo-pyridin-4-yl)-hydroxy-methyl]-piperidine-1-carboxylic acid tert-butyl ester (610 mg, 70%) as colourless oil.

To a solution of the above alcohol (610 mg, 1.6 mmol) in MeOH (5 mL) in a Parr flask was added 10% Pd/C (100 mg) under $N_2$. The mixture was hydrogenated at room temperature under 1.5 atm $H_2$ for 1 h. 3N NaOH (5 mL) was added and the mixture was extracted with $CHCl_3$ (20 mL×2). The solution was filtered through a short pad of Celite® to give the 4-(hydroxy-pyridin-4-yl-methyl)-piperidine-1-carboxylic acid tert-butyl ester (380 mg, 81%) as a colourless oil.

COMPOUND 59 was isolated as a white foam. $^1$H NMR ($CDCl_3$) δ 0.80-1.05 (m, 2H), 0.97 (d, 3H, J=12.0 Hz), 1.20-1.25 (m, 1H), 1.50-1.60 (m, 1H), 1.59 (s, 3H), 1.80-2.10 (m, 4H), 2.27-2.50 (m, 2H), 2.36 (s, 3H), 2.80-2.99 (m, 3H), 3.25-3.48 (m, 1H), 3.74-3.96 (m, 1H), 5.31 (d, 1H, J=9.0 Hz)), 6.44 (d, 1H, J=9.0 Hz), 6.63 (d, 1H, J=6.0 Hz), 7.11 (d, 1H, J=6.0 Hz), 7.36-7.42 (m, 1H), 8.46 (d, 2H, J=6.0 Hz), 8.50 (s, 1H), 8.53 (s, 1H), 9.15 (s, 0.5H), 9.25 (s, 0.5H). $^{13}$C NMR ($CDCl_3$) δ 13.60, 13.66, 24.40, 28.88, 29.66, 30.31, 30.68, 40.57, 41.79, 44.18, 52.32, 52.46, 60.86, 61.01, 78.92, 107.67, 116.61, 122.58, 122.64, 129.50, 139.35, 143.70, 148.03, 150.03, 156.64, 161.30, 162.36. ES-MS m/z 550 (M+Na). Anal. Calcd. for $C_{27}H_{31}Cl_2N_5O_2 \cdot 0.05CH_2Cl_2 \cdot 0.4C_4H_8O_2$: C, 60.59; H, 6.09; N, 12.33; Cl, 13.11. Found. C, 60.60; H, 6.06; N, 12.40; Cl, 13.21.

EXAMPLE 60

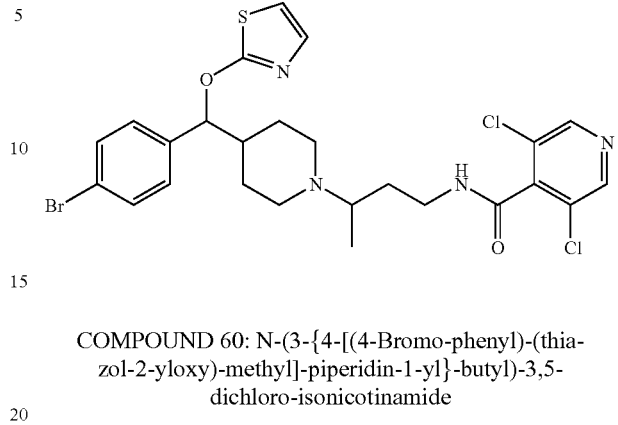

COMPOUND 60: N-(3-{4-[(4-Bromo-phenyl)-(thia-zol-2-yloxy)-methyl]-piperidin-1-yl}-butyl)-3,5-dichloro-isonicotinamide Using general procedure 1,4-[2-(4-bromophenyl)-1,3-di-oxolan-2-yl]-piperidine (Palani A., et al. J. Med. Chem., 2002, 45, 3143-3160) (3.26 g, 10.4 mmol) gave the nitrile (1.37 g, 3.62 mmol), which was subsequently reduced with $BH_3$-$Me_2S$ (2.0M in THF, 8.0 mL, 16 mmol) in THF (30 mL) at reflux and treated with MeOH then 6M HCl (16 mL) to give the crude amine following standard work-up.

The resulting colourless oil was dissolved into EtOAc (6 mL) and 6M HCl (18 mL) and the solution was stirred at room temperature for a further 21 hours. The reaction was made basic by the addition of 20% NaOH and was extracted with $CH_2Cl_2$ (25 mL×5). The organic solution was dried ($Na_2SO_4$), filtered and concentrated under reduced pressure. Purification gave the ketone-amine (628 mg, 1.85 mmol), which was subsequently reduced with $NaBH_4$ (215 mg, 5.68 mmol) in MeOH (10 mL) to give the crude amino-alcohol as a white foam (552 mg, 44% over 2 steps) following work-up.

To a 0° C. solution of this material and $NEt_3$ (0.34 mL, 2.4 mmol) in $CH_2Cl_2$ (11 mL) under nitrogen was added TFAA (0.30 mL, 2.1 mmol) and the reaction was stirred at 0° C. for 30 minutes. Standard work-up and purification gave N-(3-{4-[(4-bromo-phenyl)-hydroxy-methyl]-piperidin-1-yl}-butyl)-2,2,2-trifluoro-acetamide as a white foam (455 mg, 64%).

To a mixture of the above TFA-alcohol (206 mg, 0.47 mmol) and NaH (60% in mineral oil, 45 mg, 1.1 mmol) in DMF (1.8 mL) under nitrogen was added 2-bromothiazole (0.06 mL, 0.7 mmol) and the reaction was stirred at 60° C. for 2 hours to give N-(3-{4-[(4-bromo-phenyl)-(thiazol-2-yloxy)-methyl]-piperidin-1-yl}-butyl)-2,2,2-trifluoro-acetamide as a brown oil (81.2 mg, 33%) following work-up and purification.

A solution of the above acetamide (81.2 mg, 0.16 mmol) and $K_2CO_3$ (114 mg, 0.82 mmol) in MeOH (2 mL) and $H_2O$ (0.5 mL) was stirred at room temperature for 6 hours to give 3-{4-[(4-bromo-phenyl)-(thiazol-2-yloxy)-methyl]-piperidin-1-yl}-butylamine as a colourless oil (40.3 mg, 60%) following standard work-up and purification.

Using general procedure F, 3,5-dichloroisonicotinic acid (28 mg, 0.14 mmol) and the above primary amine (40.3 mg, 0.095 mmol) gave a diastereomeric mixture of COMPOUND 60 as a white foam (25.8 mg, 45%). $^1$H NMR ($CDCl_3$) δ 0.42-1.03 (m, 2H), 0.95 (d, 3H, J=6.6 Hz), 1.16-1.25 (m, 1H), 1.46-1.56 (m, 1H), 1.64-2.04 (m, 4H), 2.30-2.44 (m, 1H), 2.60-2.91 (m, 3H), 3.26-3.38 (m, 1H), 3.81-3.92 (m, 1H), 5.09 and 5.10 (d, 1H, J=7.8 Hz), 6.62 and 6.63 (d, 1H, J=2.9 Hz), 7.05-7.10 (m, 3H), 7.45 (d, 2H, J=8.4 Hz), 8.59 (s, 2H), 8.99 and 9.13 (br s, 1H). $^{13}$C NMR (CDCl$_3$) δ 13.23, 28.36 and 28.53, 29.12 and 29.42, 30.06 and 30.34, 40.14 and 40.24, 41.81, 43.66 and 43.77, 51.77 and 51.85, 60.48 and 60.52, 86.40 and 86.46, 111.23, 122.13 and 122.16, 128.70 and 128.75, 129.03 and 129.05, 131.60, 137.01, 137.45, 143.26 and 143.28, 147.72, 161.47 and 161.54, 173.96 and 173.98. ESI-MS m/z 597 (MH)$^+$, 599 (MH+2)$^+$, 601 (MH+4)$^+$. Anal. Calcd. for $C_{25}H_{27}BrCl_2N_4O_2S·0.6CH_2Cl_2$: C, 47.35; H, 4.38; N, 8.63; Br, 12.31. Found. C, 47.36; H, 4.56; N, 8.67; Br, 12.15.

EXAMPLE 61

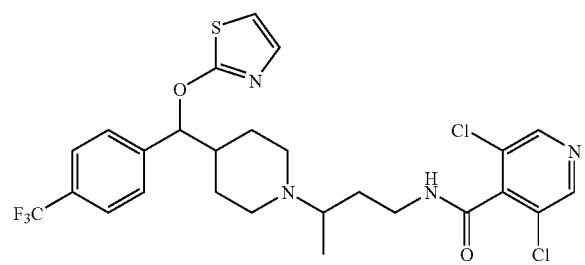

COMPOUND 61: 3,5-Dichloro-N-(3-{4-[(thiazol-2-yloxy)-(4-trifluoro-methyl-phenyl)-methyl]-piperidin-1-yl}-butyl)-isonicotinamide Using general procedure C, 4-[hydroxy-(4-trifluoromethyl-phenyl)-methyl]-piperidine-1-carboxylic acid tert-butyl ester (907 mg, 2.54 mmol) gave piperidin-4-yl-(4-trifluoromethyl-phenyl)-methanone as a white solid (635 mg, 97%).

Using general procedure I, the crude secondary amine (631 mg, 2.45 mmol) gave the nitrile (338 mg, 1.04 mmol), which was subsequently reduced with BH$_3$-Me$_2$S (2.0M in THF, 3.0 mL, 6.0 mmol) in THF (10 mL) at reflux and treated with MeOH then 6M HCl (6 mL) to give [1-(3-amino-1-methyl-propyl)-piperidin-4-yl]-(4-trifluoromethyl-phenyl)-methanol as a white foam (269 mg, 70% over 2 steps) following work-up and purification.

A solution of the amino alcohol (269 mg, 0.81 mmol) and NEt$_3$ (0.17 mL, 1.2 mmol) in CH$_2$Cl$_2$ (5.5 mL) was cooled to 0° C. under nitrogen and TFAA (0.17 mL, 1.2 mmol) was added. The reaction was stirred at 0° C. for 1 hour to give 2,2,2-trifluoro-N-(3-{4-[hydroxy-(4-trifluoromethyl-phenyl)-methyl]-piperidin-1-yl}-butyl)-acetamide as a pale yellow foam (302 mg, 87%) following standard work-up and purification.

To a solution of the above alcohol (302 mg, 0.71 mmol) and 2-bromothiazole (0.10 mL, 1.1 mmol) in DMF (2.5 mL) under nitrogen was added NaH (60% in mineral oil, 86 mg, 2.2 mmol). The mixture was warmed to 60° C. and stirred for 2 hours to give 2,2,2-trifluoro-N-(3-{4-[(thiazol-2-yloxy)-(4-trifluoromethyl-phenyl)-methyl]-piperidin-1-yl}-butyl)-acetamide as a light brown oil (98.4 mg, 27%) following work-up and purification.

A mixture of the trifluoroacetamide (98.4 mg, 0.19 mmol) and K$_2$CO$_3$ (130 mg, 0.94 mmol) in MeOH (2.5 mL) and H$_2$O (0.5 mL) was stirred at room temperature for 4 hours. Standard work-up and purification gave 3-{4-[(thiazol-2-yloxy)-(4-trifluoromethyl-phenyl)-methyl]-piperidin-1-yl}-butylamine as a yellow oil (63.7 mg, 81%).

Using general procedure F, 3,5-dichloroisonicotinic acid (37 mg, 0.19 mmol) and the primary amine (63.7 mg, 0.15 mmol) gave a diastereomeric mixture of COMPOUND 61 as a white powder (49.0 mg, 54%). $^1$H NMR (CDCl$_3$) δ 0.51-1.07 (m, 2H), 0.96 (d, 3H, J=6.6 Hz), 1.17-1.27 (m, 1H), 1.47-1.60 (m, 1H), 1.68-2.05 (m, 4H), 2.31-2.45 (m, 1H), 2.62-2.92 (m, 3H), 3.28-3.40 (m, 1H), 3.81-3.93 (m, 1H), 5.25 (d, 1H, J=8.1 Hz), 6.63 and 6.64 (d, 1H, J=3.6 Hz), 7.05 and 7.06 (d, 1H, J=3.6 Hz), 7.33 (d, 2H, J=7.8 Hz), 7.59 (d, 2H, J=7.8 Hz), 8.60 (s, 2H), 8.89 and 9.02 (br s, 1H). $^{13}$C NMR (CDCl$_3$) δ 13.19 and 13.21, 28.28 and 28.40, 29.13, 30.13 and 30.34, 40.03 and 40.12, 41.88 and 41.90, 43.64 and 43.79, 51.68 and 51.74, 60.33, 86.09 and 86.12, 111.33, 123.90 (q, J=272 Hz), 125.37 (q, J=3.9 Hz), 127.20 and 127.25, 128.99 and 129.02, 130.20 and 130.23 (q, J=32.4 Hz), 136.93, 142.52 (q, J=1.3 Hz), 143.21 and 143.24, 147.69, 161.44 and 161.48, 173.82 and 173.84. ESI-MS m/z 587 (MH)$^+$, 589 (MH+2)$^+$. Anal. Calcd. for $C_{26}H_{27}Cl_2F_3N_4O_2S$: C, 53.16; H, 4.63; N, 9.54; Cl, 12.07. Found. C, 52.83; H, 4.71; N, 9.40; Cl, 12.07.

Scheme 5 describes the preparation of Examples 62-79, using various general procedures previously described, and reagents listed below.

Scheme 5

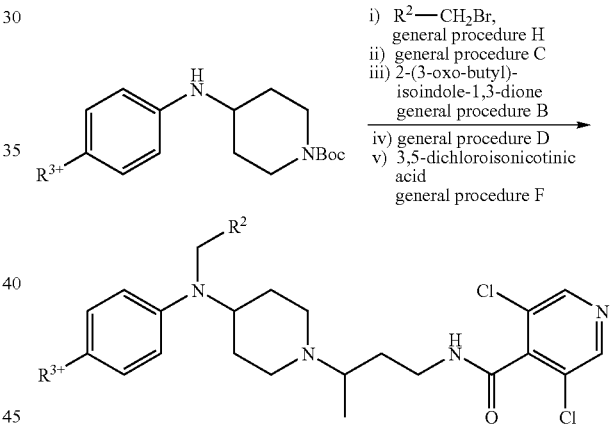

i) R$^2$—CH$_2$Br, general procedure H
ii) general procedure C
iii) 2-(3-oxo-butyl)-isoindole-1,3-dione general procedure B
iv) general procedure D
v) 3,5-dichloroisonicotinic acid general procedure F

| Example | R$^3$* | R$^2$—CH$_2$Br |
| --- | --- | --- |
| 62 | Br | 3-chlorobenzyl bromide |
| 63 | CN | benzyl bromide |
| 64 | CN | 3-fluorobenzyl bromide |
| 65 | CN | 3-chlorobenzyl bromide |
| 66 | CN | 3-methylbenzyl bromide |
| 67 | CF$_3$ | benzyl bromide |
| 68 | CF$_3$ | 3-fluorobenzyl bromide |
| 69 | CF$_3$ | 3-chlorobenzyl bromide |
| 70 | OCF$_3$ | benzyl bromide |
| 71 | OCF$_3$ | 3-methylbenzyl bromide |
| 72 | SMe | 3-fluorobenzyl bromide |
| 73 | SMe | 3-chlorobenzyl bromide |
| 74 | SMe | 3-methylbenzyl bromide |
| 75 | SO$_2$Me | 3-chlorobenzyl bromide |
| 76 | SO$_2$Me | 3-methylbenzyl bromide |
| 77 | OMe | 3-fluorobenzyl bromide |
| 78 | OMe | 3-chlorobenzyl bromide |
| 79 | SO$_2$NHMe | benzyl bromide |

EXAMPLE 62

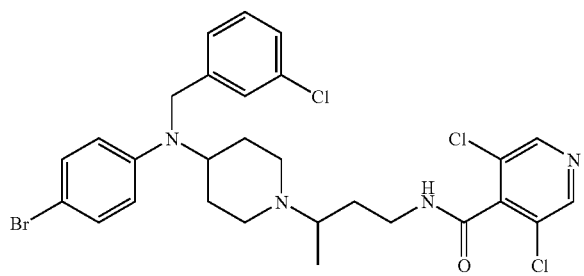

COMPOUND 62: N-(3-{4-[(4-Bromo-phenyl)-(3-chloro-benzyl)-amino]-piperidin-1-yl}-butyl)-3,5-dichloro-isonicotinamide Using general procedure A, 4-bromoaniline (1.23 g, 7.13 mmol) and 1-Boc-4-piperidone (1.42 g, 7.13 mmol) afforded 4-(4-bromo-phenylamino)-piperidine-1-carboxylic acid tert-butyl ester (6.5 g, 53%).

COMPOUND 62 was isolated as a white solid. $^1$H NMR (CDCl$_3$) δ 1.01 (d, 3H, J=6.2 Hz), 1.07-1.30 (m, 1H), 1.46-1.61 (m, 1H), 1.66-1.91 (m, 4H), 2.18 (t, 1H, J=11.4 Hz), 2.57 (t, 1H, J=11.4 Hz), 2.73-2.99 (m, 3H), 3.34 (t, 1H, J=10.1 Hz), 3.60 (t, 1H, J=11.4 Hz), 3.79 (s, 2H), 3.79-3.93 (m, 1H), 6.43 (d, 2H, J=8.7 Hz), 7.00-7.31 (m, 6H), 8.48 (s, 2H), 8.91 (s, 1H). $^{13}$C NMR (CDCl$_3$) δ 13.8, 29.6, 30.1, 30.7, 40.6, 42.9, 43.9, 48.7, 49.4, 52.4, 56.3, 60.7, 109.6, 115.3, 124.7, 126.5, 127.5, 129.5, 130.3, 132.3, 135.0, 142.0, 143.6, 147.7, 148.0, 161.8. ES-MS m/z 625 (M+2)$^+$. Anal. Calcd. for C$_{28}$H$_{30}$N$_4$Cl$_3$OBr.0.4CH$_2$Cl$_2$: C, 51.78; H, 4.71; N, 8.50; Cl, 20.45. Found. C, 51.85; H, 4.69; N, 8.40; Cl, 20.37.

EXAMPLE 63

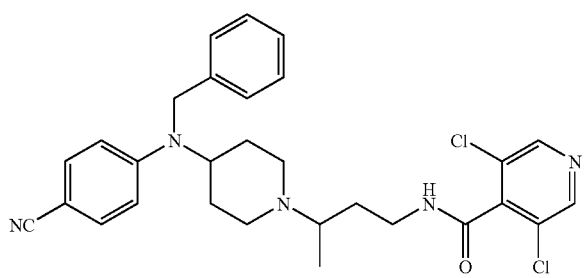

COMPOUND 63: N-(3-{4-[Benzyl-(4-cyano-phenyl)-amino]-piperidin-1-yl}-butyl)-3,5-dichloro-isonicotinamide A mixture of 4-amino-piperidine-1-carboxylic acid tert-butyl ester (Willoughby, Christopher A.; *Bioorg. Med. Chem. Lett.*, 13, 3, 2003, 427-432) (311 mg, 1.55 mmol), 4-bromobenzonitrile (237 mg, 1.30 mmol), Pd$_2$(dba)$_3$ (21 mg, 0.023 mmol), (±)-BINAP (48 mg, 0.077 mmol) and t-BuONa (136 mg, 1.42 mmol) in freshly degassed toluene (4.5 mL) was stirred at 85° C. under argon for 2 hours. Work-up and purification gave 4-(4-cyano-phenylamino)-piperidine-1-carboxylic acid tert-butyl ester as an orange solid (324 mg, 83%).

COMPOUND 63 was isolated as a white powder. $^1$H NMR (CDCl$_3$) δ 1.02 (d, 3H, J=6.6 Hz), 1.03-1.17 (m, 1H), 1.19-1.33 (m, 1H), 1.52-1.62 (m, 1H), 1.73-1.87 (m, 3H), 2.16-2.25 (m, 1H), 2.55-2.63 (m, 1H), 2.78-2.98 (m, 3H), 3.30-3.42 (m, 1H), 3.67-3.78 (m, 1H), 3.81-3.91 (m, 1H), 3.98 (s, 2H), 6.56 (d, 2H, J=8.7 Hz), 7.12 (d, 2H, J=6.9 Hz), 7.23-7.39 (m, 5H), 8.47 (s, 2H), 8.66 (br s, 1H). $^{13}$C NMR (CDCl$_3$) δ 13.34, 29.30, 30.07, 30.41, 39.85, 43.43, 48.23, 51.69, 55.53, 59.88, 98.15, 112.33, 120.25, 125.68, 127.02, 128.66, 128.94, 133.41, 137.82, 143.05, 147.55, 151.23, 161.40. ESI-MS m/z 536 (MH)$^+$, 538 (MH+2)$^+$. Anal. Calcd. for C$_{29}$H$_{31}$Cl$_2$N$_5$O.0.1CH$_2$Cl$_2$: C, 64.13; H, 5.77; N, 12.85; Cl, 14.31. Found. C, 64.08; H, 5.72; N, 12.52; Cl, 14.36.

EXAMPLE 64

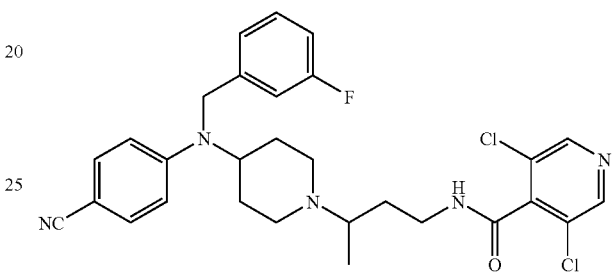

COMPOUND 64: 3,5-Dichloro-N-(3-{4-[(4-cyano-phenyl)-(3-fluoro-benzyl)-amino]-piperidin-1-yl}-butyl)-isonicotinamide White foam. $^1$H NMR (CDCl$_3$) δ 1.03 (d, 3H, J=6.6 Hz), 1.02-1.15 (m, 1H), 1.32-1.18 (m, 1H), 1.51-1.62 (m, 1H), 1.73-1.87 (m, 3H), 2.17-2.26 (m, 1H), 2.55-2.64 (m, 1H), 2.79-2.99 (m, 3H), 3.32-3.42 (m, 1H), 3.68-3.78 (m, 1H), 3.80-3.90 (m, 1H), 3.96 (s, 2H), 6.55 (d, 2H, J=8.9 Hz), 6.79-6.85 (m, 1H), 6.92-6.99 (m, 2H), 7.27-7.35 (m, 1H), 7.39 (d, 2H, J=8.9 Hz), 8.48 (s, 2H), 8.61 (br s, 1H). $^{13}$C NMR (CDCl$_3$) δ 13.35, 29.34, 30.26, 30.53, 39.84, 43.48, 47.95, 51.68, 55.59, 59.84, 98.69, 112.44, 112.76 (d, J=21.9 Hz), 114.05 (d, J=21.1 Hz), 120.10, 121.36 (d, J=2.8 Hz), 129.00, 130.34 (d, J=8.5 Hz), 133.51, 140.92 (d, J=6.3 Hz), 143.08, 147.57, 151.05, 161.41, 163.15 (d, J=246 Hz). ESI-MS m/z 554 (MH)$^+$, 556 (MH+2)$^+$. Anal. Calcd. for C$_{29}$H$_{30}$Cl$_2$FN$_5$O.0.3H$_2$O: C, 62.21; H, 5.51; N, 12.51; Cl, 12.66. Found. C, 62.26; H, 5.48; N, 12.26; Cl, 12.85.

EXAMPLE 65

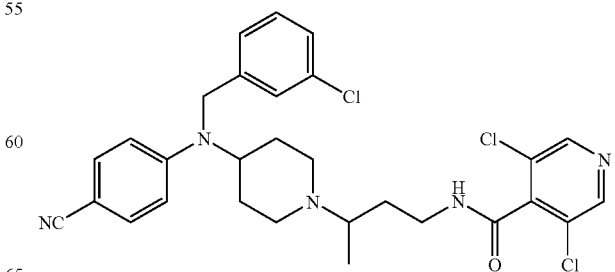

COMPOUND 65: 3,5-Dichloro-N-(3-{4-[(3-chloro-benzyl)-(4-cyano-phenyl)-amino]-piperidin-1-yl}-butyl)-isonicotinamide White foam. $^1$H NMR(CDCl$_3$) δ 1.01-1.15 (m, 1H), 1.03 (d, 3H, J=6.6 Hz), 1.17-1.31 (m, 1H), 1.52-1.67 (m, 1H), 1.73-1.86 (m, 3H), 2.17-2.25 (m, 1H), 2.55-2.64 (m, 1H), 2.81-2.97 (m, 3H), 3.32-3.42 (m, 1H), 3.67-3.90 (m, 2H), 3.95 (s, 2H), 6.56 (d, 2H, J=9.0 Hz), 7.01-7.06 (m, 1H), 7.11 (s, 1H), 7.21-7.31 (m, 2H), 7.39 (d, 2H, J=9.0 Hz), 8.49 (s, 2H), 8.61 (br s, 1H). $^{13}$C NMR (CDCl$_3$) δ 13.39, 29.36, 30.34, 30.49, 40.02, 43.45, 47.99, 51.79, 55.60, 60.05, 98.92, 112.47, 120.11, 123.99, 125.88, 127.43, 129.08, 130.09, 133.61, 134.80, 140.32, 143.14, 147.64, 151.08, 161.41. ESI-MS m/z 570 (MH)$^+$, 572 (MH+2)$^+$, 574 (MH+4)$^+$. Anal. Calcd. for C$_{29}$H$_{30}$Cl$_3$N$_5$O.0.4H$_2$O.0.2C$_4$H$_{10}$O: C, 60.36; H, 5.58; N, 11.81. Found. C, 60.36; H, 5.27; N, 11.56.

EXAMPLE 66

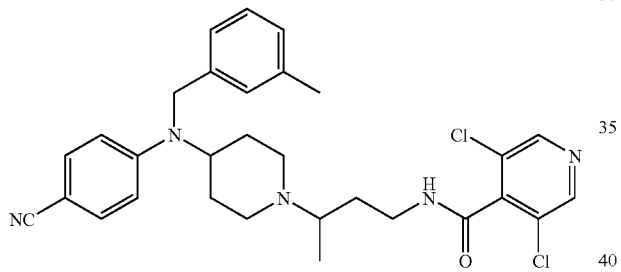

COMPOUND 66: 3,5-Dichloro-N-(3-{4-[(4-cyano-phenyl)-(3-methyl-benzyl)-amino]-piperidin-1-yl}-butyl)-isonicotinamide White powder. $^1$H NMR (CDCl$_3$) δ 1.02 (d, 3H, J=6.6 Hz), 1.02-1.16 (m, 1H), 1.18-1.32 (m, 1H), 1.51-1.65 (m, 1H), 1.72-1.86 (m, 3H), 2.16-2.24 (m, 1H), 2.35 (s, 3H), 2.55-2.63 (m, 1H), 2.78-2.97 (m, 3H), 3.31-3.41 (m, 1H), 3.67-3.77 (m, 1H), 3.80-3.90 (m, 1H), 3.94 (s, 2H), 6.56 (d, 2H, J=8.9 Hz), 6.88-6.94 (m, 2H), 7.07 (d, 1H, J=7.5 Hz), 7.21 (dd, 1H, J=7.5, 7.5 Hz), 7.37 (d, 2H, J=8.9 Hz), 8.48 (s, 2H), 8.68 (br s, 1H). $^{13}$C NMR (CDCl$_3$) δ 13.31, 21.43, 29.25, 30.18, 30.47, 39.77, 43.47, 48.29, 51.64, 55.49, 59.74, 98.01, 112.29, 120.26, 122.71, 126.26, 127.73, 128.50, 128.91, 133.38, 137.86, 138.33, 143.03, 147.52, 151.33, 161.41. ESI-MS m/z 550 (MH)$^+$, 552 (MH+2)$^+$. Anal. Calcd. for C$_{30}$H$_{33}$Cl$_2$N$_5$O.0.1CH$_2$Cl$_2$: C, 64.67; H, 5.99; N, 12.53; Cl, 13.95. Found. C, 64.56; H, 5.92; N, 12.49; Cl, 13.56.

EXAMPLE 67

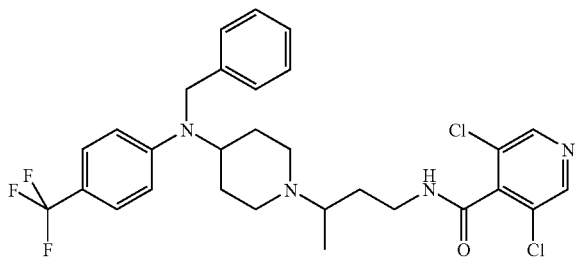

COMPOUND 67: N-(3-{4-[Benzyl-(4-trifluoromethyl-phenyl)-amino]-piperidin-1-yl}-butyl)-3,5-dichloro-isonicotinamide Using general procedure A, 4-trifluoromethylaniline (2.02 g, 12.5 mmol) and 1-Boc-4-piperidone (2.5 g, 12.5 mmol) afforded 4-(4-trifluoromethyl-phenylamino)-piperidine-1-carboxylic acid tert-butyl ester (1.71 g, 40%).

COMPOUND 67 was isolated as a white solid. $^1$H NMR (CDCl$_3$) δ 1.03 (d, 3H, J=6.5 Hz), 1.00-1.33 (m, 2H), 1.48-1.67 (m, 1H), 1.71-1.95 (m, 3H), 2.21 (t, 1H, J=11.3 Hz), 2.60 (t, 1H, J=11.9 Hz), 2.77-3.01 (m, 3H), 3.29-2.43 (m, 1H), 3.66-3.80 (m, 1H), 3.82-3.93 (m, 1H), 3.94 (s, 2H), 6.60 (d, 2H, J=8.8 Hz), 7.11-7.39 (m, 7H), 8.48 (s, 2H), 8.82 (s, 1H). $^{13}$C NMR (CDCl$_3$) δ 13.8, 29.7, 30.7, 40.6, 43.9, 48.9, 52.4, 56.0, 60.7, 112.4, 126.3, 126.8, 127.3, 129.1, 129.4, 139.1, 148.1, 151.1, 161.9. ES-MS t/z 580 (M+2)$^+$. Anal. Calcd. for C$_{29}$H$_{31}$N$_4$Cl$_2$OF$_3$.0.2CH$_2$Cl$_2$: C, 58.80; H, 5.31; N, 9.39. Found. C, 58.95; H, 5.32; N, 9.27.

EXAMPLE 68

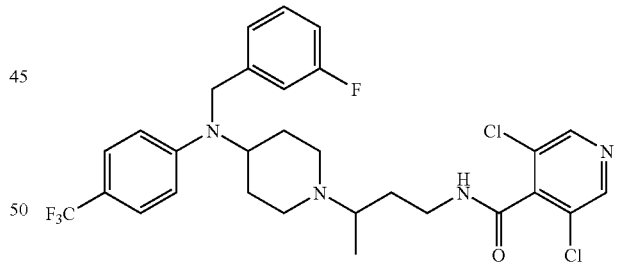

COMPOUND 68: 3,5-Dichloro-N-(3-{4-[(3-fluoro-benzyl)-(4-trifluoro-methyl-phenyl)-amino]-piperidin-1-yl}-butyl)-isonicotinamide White powder. $^1$H NMR (CDCl$_3$) δ 0.97-1.12 (m, 1H), 1.03 (d, 3H, J=6.6 Hz), 1.15-1.29 (m, 1H), 1.51-1.61 (m, 1H), 1.73-1.88 (m, 3H), 2.17-2.27 (m, 1H), 2.56-2.65 (m, 1H), 2.79-2.99 (m, 3H), 3.31-3.41 (m, 1H), 3.68-3.78 (m, 1H), 3.82-3.91 (m, 1H), 3.91 (s, 2H), 6.58 (d, 2H, J=8.7 Hz), 6.84-6.99 (m, 3H), 7.24-7.38 (m, 1H), 7.36 (d, 2H, J=8.7 Hz), 8.48 (s, 2H), 8.79 (br d, 1H). $^{13}$C NMR (CDCl$_3$) δ 13.34, 29.27, 30.29, 30.39, 39.96, 43.46, 48.08 (d, J=1.7 Hz), 51.80, 55.53, 60.03, 112.02, 112.82 (d, J=21.7 Hz), 113.84 (d, J=21.2 Hz), 118.46 (q, J=32.8 Hz), 121.45 (d, J=2.9 Hz), 124.71 (q, J=270 Hz), 126.43 (q, J=3.8 Hz), 128.99, 130.19 (d, J=8.7 Hz), 141.70 (d, J=6.7 Hz), 143.12, 147.55, 150.50 (q, J=1.1 Hz), 161.38, 163.14 (d, J=247 Hz). ESI-MS m/z 597 (MH)$^+$, 599 (MH+2)$^+$. Anal. Calcd. for $C_{29}H_{30}Cl_2F_4N_4O \cdot 0.3H_2O$: C, 57.78; H, 5.12; N, 9.29; Cl, 11.76; F, 12.60. Found. C, 57.91; H, 5.06; N, 9.22; Cl, 11.84; F, 12.25.

EXAMPLE 69

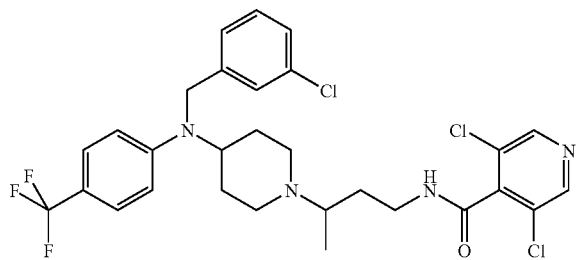

COMPOUND 69: 3,5-Dichloro-N-(3-{4-[(3-chloro-benzyl)-(4-trifluoromethyl-phenyl)-amino]-piperidin-1-yl}-butyl)-isonicotinamide White solid. $^1$H NMR (CDCl$_3$) δ 0.96-1.29 (m, 2H), 1.03 (d, 3H, J=6.6 Hz), 1.46-1.51 (m, 1H), 1.72-1.88 (m, 3H), 2.16-2.26 (m, 1H), 2.56-2.66 (m, 1H), 2.78-2.99 (m, 3H), 3.30-3.42 (m, 1H), 3.66-3.78 (m, 1H), 3.82-3.93 (m, 3H), 6.58 (d, 2H, J=8.7 Hz), 7.06 (d, 1H, J=6.6 Hz), 7.15 (s, 1H), 7.21-7.30 (m, 2H), 7.36 (d, 2H, J=8.7 Hz), 8.49 (s, 2H), 8.80 (br s, 1H). $^{13}$C NMR (CDCl$_3$) δ 13.41, 29.31, 31.40, 40.09, 43.50, 48.18, 51.90, 55.57, 60.17, 122.09, 118.62 (q, J=32 Hz), 124.13, 124.43, 124.84 (q, J=270 Hz), 126.00, 126.55 (q, J=3 Hz), 127.24, 129.08, 130.01, 134.70, 141.13, 143.18, 147.64, 150.57, 161.45. ES-MS m/z 613 (M+H). Anal. Calcd. for $C_{29}H_{30}N_4Cl_3OF_3 \cdot 0.1CH_2Cl_2$: C, 56.15; H, 4.89; N, 9.00; Cl, 18.23. Found. C, 55.86; H, 4.82; N, 8.94; Cl, 18.03.

EXAMPLE 70

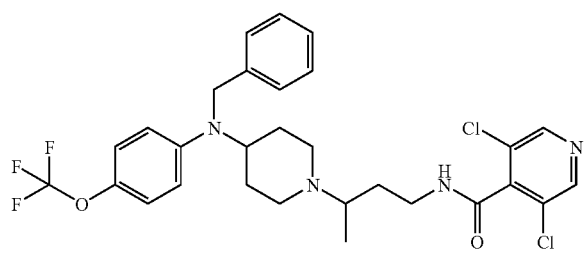

COMPOUND 70: N-(3-{4-[Benzyl-(4-trifluoromethoxy-phenyl)-amino]-piperidin-1-yl}-butyl)-3,5-dichloro-isonicotinamide Using general procedure A, 4-trifluoromethoxy-phenylamine (354 mg, 2.00 mmol) and 1-Boc-4-piperidone (418 mg, 2.10 mmol) gave 4-(4-trifluoromethoxy-phenylamino)-piperidine-1-carboxylic acid tert-butyl ester (692 mg, 96%) as a white crystalline solid.

COMPOUND 70 was isolated as a white foam. $^1$H NMR (CDCl$_3$) δ 1.02 (d, 3H, J=6.6 Hz), 1.18-1.25 (m, 2H), 1.51-1.58 (m, 2H), 1.72-1.82 (m, 3H), 2.18 (t, 1H, J=11.7 Hz), 2.58 (t, 1H, J=11.4 Hz), 2.80-2.96 (m, 3H), 3.34 (t, 1H, J=11.4 Hz), 3.63 (t, 1H, J=11.4 Hz), 3.85 (s, 2H), 6.53 (d, 2H, J=9.0 Hz), 6.97 (d, 2H, J=8.7 Hz), 7.17-7.35 (m, 5H), 8.47 (s, 2H), 8.96 (br s, 1H). $^{13}$C NMR (CDCl$_3$) δ 13.7, 29.6, 30.7, 40.4, 44.0, 49.3, 52.4, 56.3, 60.6, 113.8, 121.1 (q, J=254 Hz), 122.5, 126.4, 127.2, 129.0, 129.4, 139.7, 140.4, 143.6, 147.8, 148.0, 161.9. ES-MS m/z 596 (M+H). Anal. Calcd. for $C_{29}H_{31}Cl_2F_3N_4O_2$: C, 57.98; H, 5.47; N, 8.90; Cl, 13.51; F, 9.05. Found. C, 58.07; H, 5.33; N, 9.03; Cl, 13.21; F, 8.91.

EXAMPLE 71

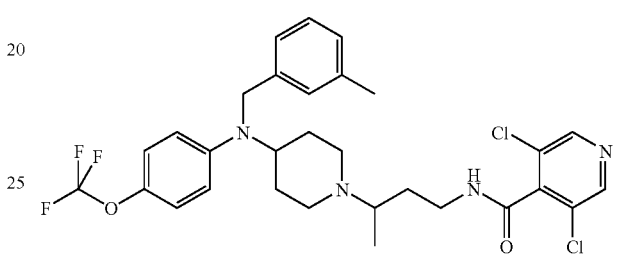

COMPOUND 71: 3,5-Dichloro-N-(3-{4-[(3-methyl-benzyl)-(4-trifluoromethoxy-phenyl)-amino]-piperidin-1-yl}-butyl)-isonicotinamide White solid. $^1$H NMR (CDCl$_3$) δ 0.95-1.26 (m, 2H), 1.02 (d, 3H, J=6.6 Hz), 1.52-1.58 (m, 1H), 1.81-1.85 (m, 3H), 2.18 (t, 1H, J=11.4 Hz), 2.36 (s, 3H), 2.58 (t, 1H, J=11.4 Hz), 2.79-2.95 (m, 3H), 3.30-3.38 (m, 1H), 3.58-3.67 (m, 1H), 3.83 (s, 2H), 3.84-3.89 (m, 1H), 6.53 (d, 2H, J=9.3 Hz), 6.96-7.07 (m, 5H), 7.18-7.24 (m, 1H), 8.48 (s, 2H), 8.95 (br s, 1H). $^{13}$C NMR (CDCl$_3$) δ 13.76, 21.94, 29.61, 30.68, 30.76, 40.63, 43.90, 49.33, 52.51, 56.25, 60.78, 113.66, 119.37, 122.55, 123.47, 126.98, 127.97, 128.86, 129.41, 138.63, 139.75, 140.33, 143.58, 147.88, 148.08, 161.89. ES-MS m/z 609 (M+H). Anal. Calcd. for $C_{30}H_{33}N_4Cl_2O_2F_3$: C, 59.12; H, 5.46; N, 9.19; Cl, 11.63; F, 9.35. Found. C, 59.25; H, 5.52; N, 9.09; Cl, 11.46; F, 9.44.

EXAMPLE 72

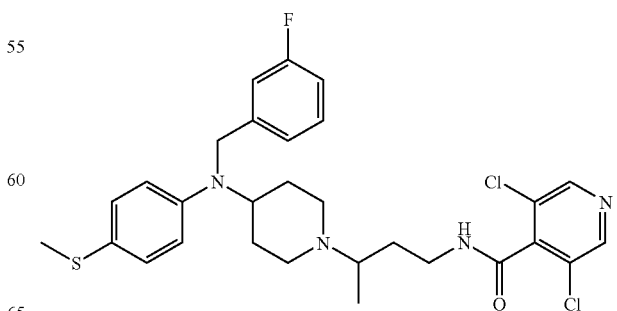

COMPOUND 72: 3,5-Dichloro-N-(3-{4-[(3-fluoro-benzyl)-(4-methylsulfanyl-phenyl)-amino]-piperidin-1-yl}-butyl)-isonicotinamide Using general procedure A, 4-(methylthio)aniline (250 μL, 2.01 mmol) and 1-Boc-4-piperidone (400 mg, 2.01 mmol) afforded 4-(4-methylsulfanyl-phenylamino)-piperidine-1-carboxylic acid tert-butyl ester (502 mg, 77%).

COMPOUND 72 was isolated as a white solid. $^1$H NMR (CDCl$_3$) δ 0.96-1.18 (m, 2H), 1.02 (d, 3H, J=6.6 Hz), 1.53-1.58 (m, 1H), 1.74-1.81 (m, 3H), 2.18 (t, 1H, J=11.1 Hz), 2.38 (s, 3H), 2.58 (t, 1H, J=10.5 Hz), 2.79-2.96 (m, 3H), 3.30-3.38 (m, 1H), 3.63-3.67 (m, 1H), 3.81 (s, 2H), 3.86-3.92 (m, 1H), 6.52 (d, 2H, J=8.4 Hz), 6.88-7.01 (m, 3H), 7.16 (d, 2H, J=8.4 Hz), 7.26-7.33 (m, 1H), 8.48 (s, 2H), 8.98 (br s, 1H). $^{13}$C NMR (CDCl$_3$) δ 13.79, 19.11, 29.69, 30.71, 30.81, 40.58, 43.92, 48.80, 52.45, 56.24, 60.72, 113.47 (d, J=22 Hz), 114.06 (d, J=21 Hz), 114.37, 122.08, 124.85, 129.45, 130.46 (d, J=8 Hz), 131.37, 143.08 (d, J=6 Hz), 143.60, 147.45, 148.02, 161.85, 163.60 (d, J=246 Hz). ES-MS m/z 575 (M+H). Anal. Calcd. for C$_{29}$H$_{33}$N$_4$OSCl$_2$F.0.1CH$_2$Cl$_2$: C, 59.84; H, 5.73; N, 9.59; S, 5.49; Cl, 13.35; F, 3.25. Found. C, 59.57; H, 5.77; N, 9.35; S, 5.30; Cl, 13.75; F, 3.12.

EXAMPLE 73

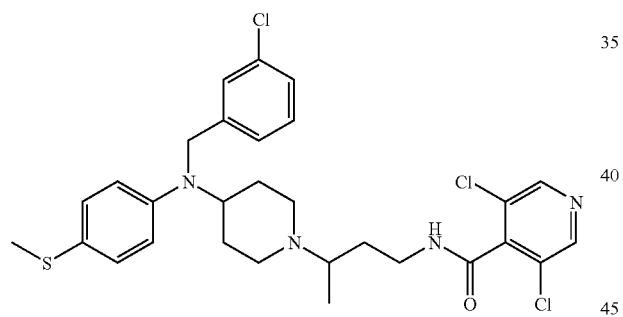

COMPOUND 73: 3,5-Dichloro-N-(3-{4-[(3-chloro-benzyl)-(4-methylsulfanyl-phenyl)-amino]-piperidin-1-yl}-butyl)-isonicotinamide White solid. $^1$H NMR (CDCl$_3$) δ 0.96-1.25 (m, 2H), 1.02 (d, 3H, J=6.3 Hz), 1.53-1.58 (m, 1H), 1.78-1.81 (m, 3H), 2.18 (t, 1H, J=11.4 Hz), 2.38 (s, 3H), 2.58 (t, 1H, J=10.8 Hz), 2.79-2.96 (m, 3H), 3.31-3.59 (m, 1H), 3.59-3.65 (m, 1H), 3.79 (s, 2H), 3.86-3.90 (m, 1H), 6.52 (d, 2H, J=8.7 Hz), 7.07-7.28 (m, 6H), 8.49 (s, 2H), 8.97 (br s, 1H). $^{13}$C NMR (CDCl$_3$) δ 13.78, 19.09, 29.63, 30.70, 40.57, 43.92, 48.85, 52.46, 56.18, 60.74, 114.37, 124.72, 124.95, 126.59, 127.41, 129.46, 130.24, 131.37, 131.62, 134.95, 142.43, 143.59, 147.44, 148.04, 161.86. ES-MS m/z 591 (M+H). Anal. Calcd. for C$_{29}$H$_{33}$N$_4$OSCl$_3$: C, 58.84; H, 5.62; N, 9.46; S, 5.42; Cl, 17.97. Found. C, 59.03; H, 5.75; N, 9.27; S, 5.29; Cl, 17.74.

EXAMPLE 74

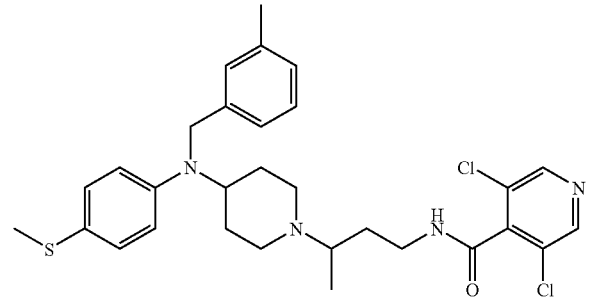

COMPOUND 74: 3,5-Dichloro-N-(3-{4-[(3-methyl-benzyl)-(4-methylsulfanyl-phenyl)-amino]-piperidin-1-yl}-butyl)-isonicotinamide White solid. $^1$H NMR (CDCl$_3$) δ 0.98-1.23 (m, 2H), 1.02 (d, 3H, J=6.3 Hz), 1.53-1.58 (m, 1H), 1.76-1.82 (m, 3H), 2.18 (t, 1H, J=11.1 Hz), 2.35 (s, 3H), 2.38 (s, 3H), 2.58 (t, 1H, J=11.4 Hz), 2.78-2.96 (m, 3H), 3.31-3.38 (m, 1H), 3.59-3.65 (m, 1H), 3.81 (s, 2H), 3.86-3.91 (m, 1H), 6.53 (d, 2H, J=8.7 Hz), 6.96-7.05 (m, 3H), 7.15-7.22 (m, 3H), 8.48 (s, 2H), 9.00 (br s, 1H). $^{13}$C NMR (CDCl$_3$) δ 13.78, 19.31, 21.96, 30.69, 30.77, 40.61, 43.94, 49.20, 52.54, 56.00, 60.78, 114.06, 123.52, 124.11, 127.03, 127.87, 128.79, 129.41, 131.57, 138.53, 140.04, 143.57, 147.91, 148.07, 161.91. ES-MS m/z 571 (M+H). Anal. Calcd. for C$_{30}$H$_{36}$N$_4$OSCl$_2$: C, 63.04; H, 6.35; N, 9.80; S, 5.61; Cl, 12.40. Found. C, 62.95; H, 6.36; N, 9.60; S, 5.40; Cl, 12.51.

EXAMPLE 75

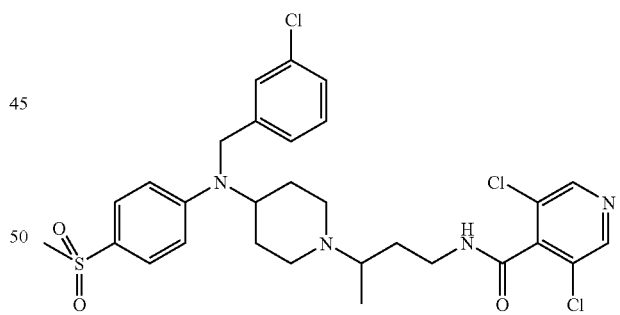

COMPOUND 75: 3,5-Dichloro-N-(3-{4-[(3-chloro-benzyl)-(4-methanesulfonyl-phenyl)-amino]-piperidin-1-yl}-butyl)-isonicotinamide Using general procedure A, 1-Boc-4-piperidone (2.01 g, 10.09 mmol) and 4-(methanesulfonyl)aniline hydrochloride (1.69 g, 8.13 mmol) afforded 4-(4-methanesulfonyl-phenylamino)-piperidine-1-carboxylic acid tert-butyl ester as a white solid (1.44 g, 50%).

COMPOUND 75 was isolated as a white solid. $^1$H NMR (CDCl$_3$) δ 0.97-1.30 (m, 2H), 1.04 (d, 3H, J=6.3 Hz), 1.57-

1.58 (m, 1H), 1.73-1.82 (m, 3H), 2.23 (t, 1H, J=11.4 Hz), 2.61 (t, 1H, J=11.1 Hz), 2.82-2.93 (m, 3H), 2.99 (s, 3H), 3.34-3.42 (m, 1H), 3.76-3.87 (m, 2H), 3.96 (s, 2H), 6.61 (d, 2H, J=8.7 Hz), 7.05 (d, 1H, J=6.9 Hz), 7.12 (s, 1H), 7.26-7.32 (m, 2H), 7.66 (d, 2H, J=8.7 Hz), 8.50 (s, 2H), 8.61 (br s, 1H). $^{13}$C NMR (CDCl$_3$) δ 13.44, 29.38, 30.38, 30.51, 40.06, 43.47, 44.97, 48.10, 51.83, 55.78, 60.11, 112.11, 124.07, 125.91, 127.47, 129.11, 129.27, 130.13, 134.83, 140.30, 147.67, 152.01, 161.43. ES-MS m/z 623 (M+H). Anal. Calcd. for C$_{29}$H$_{33}$N$_4$Cl$_3$O$_3$S.0.2CH$_2$Cl$_2$: C, 54.71; H, 5.25; N, 8.74; Cl, 18.80; S, 5.00. Found. C, 54.49; H, 5.32; N, 8.61; Cl, 18.60; S, 5.14.

EXAMPLE 76

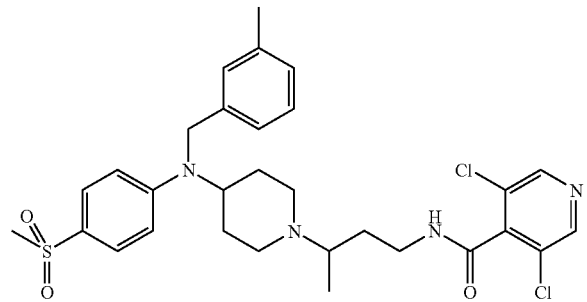

COMPOUND 76: 3,5-Dichloro-N-(3-{4-[(4-methanesulfonyl-phenyl)-(3-methyl-benzyl)-amino]-piperidin-1-yl}-butyl)-isonicotinamide White solid. $^1$H NMR (CDCl$_3$) δ 1.02-1.32 (m, 2H), 1.03 (d, 3H, J=6.3 Hz), 1.55-1.58 (m, 1H), 1.75-1.84 (m, 3H), 2.22 (t, 1H, J=11.7 Hz) 2.36 (s, 3H), 2.61 (t, 1H, J=11.7 Hz), 2.81-2.93 (m, 3H), 2.98 (s, 3H), 3.36-3.42 (m, 1H), 3.75-3.96 (m, 2H), 3.96 (s, 2H), 6.63 (d, 2H, J=8.7 Hz), 6.91-6.93 (m, 2H), 7.08 (d, 1H, J=7.2 Hz), 7.20 (d, 1H, J=6.9 Hz), 7.64 (d, 2H, J=8.4 Hz), 8.49 (s, 2H), 8.70 (br s, 1H). $^{13}$C NMR (CDCl$_3$) δ 13.42, 21.56, 29.34, 30.36, 30.47, 40.10, 43.47, 44.98, 48.49, 51.90, 55.73, 60.18, 111.99, 122.85, 126.40, 126.84, 127.90, 128.64, 129.15, 137.90, 138.49, 143.15, 147.70, 152.34, 161.48. ES-MS m/z 603 (M+H). Anal. Calcd. for C$_{30}$H$_{36}$N$_4$Cl$_2$O$_3$S.0.2CH$_2$Cl$_2$.0.3H$_2$O: C, 57.94; H, 5.96; N, 8.95; Cl, 13.59; S, 5.12. Found. C, 58.31; H, 6.12; N, 8.98; Cl, 13.22; S, 4.92.

EXAMPLE 77

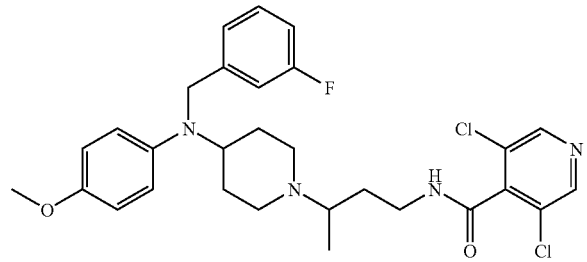

COMPOUND 77: 3,5-Dichloro-N-(3-{4-[(3-fluoro-benzyl)-(4-methoxy-phenyl)-amino]-piperidin-1-yl}-butyl)-isonicotinamide Using general procedure A, 4-methoxyphenylamine (246 mg, 2.00 mmol) and 1-Boc-4-piperidone (418 mg, 2.10 mmol) gave 4-(4-methoxyphenylamino)-piperidine-1-carboxylic acid tert-butyl ester as a pale yellow oil (612 mg, 100%).

COMPOUND 77 was isolated as a white solid. $^1$H NMR (CDCl$_3$) δ 0.94-1.20 (m, 2H), 1.00 (d, 3H, J=6.6 Hz), 1.50-1.56 (m, 1H), 1.78-1.82 (m, 3H), 2.14 (t, 1H, J=12.0 Hz), 2.55 (t, 1H, J=12.0 Hz), 2.78-2.93 (m, 3H), 3.29-3.48 (m, 2H), 3.71 (s, 3H), 3.76 (s, 2H), 3.85-3.91 (m, 1H), 6.57 (d, 2H, J=7.5 Hz), 6.72 (d, 2H, J=7.5 Hz), 6.86-6.96 (m, 2H), 7.01 (d, 1H, J=7.5 Hz), 7.22-7.30 (m, 1H), 8.47 (s, 2H), 9.09 (br s, 1H). $^1$H NMR (CDCl$_3$) δ 13.75, 29.79, 30.60, 30.93, 40.69, 43.91, 49.83, 52.51, 56.02, 57.71, 60.86, 113.74, 114.02, 114.96, 116.55, 117.09, 122.48, 129.42, 130.17, 130.28, 143.04, 143.66, 143.75, 148.02, 152.81, 161.88, 165.18. ES-MS m/z 559 (M+H). Anal. Calcd. for C$_{29}$H$_{33}$N$_4$Cl$_2$O$_2$F: C, 62.25; H, 5.94; N, 10.01; Cl, 12.67; F, 3.40. Found. C, 62.08; H, 5.97; N, 9.95; Cl, 12.60; F, 3.27.

EXAMPLE 78

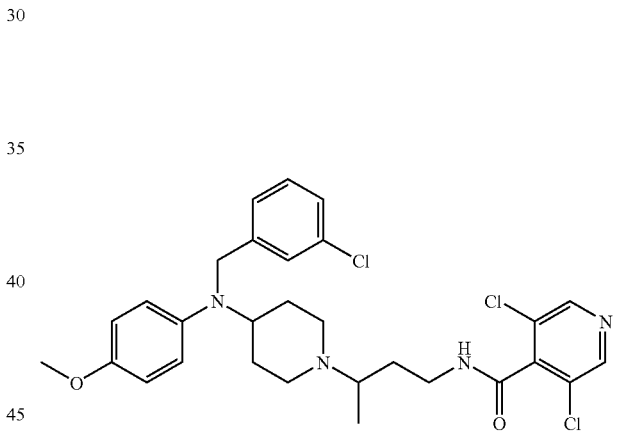

COMPOUND 78: 3,5-Dichloro-N-(3-{4-[(3-chloro-benzyl)-(4-methoxy-phenyl)-amino]-piperidin-1-yl}-butyl)-isonicotinamide White solid. $^1$H NMR (CDCl$_3$) δ 0.94-1.18 (m, 2H), 1.00 (d, 3H, J=6.3 Hz), 1.51-1.56 (m, 1H), 1.78-1.81 (m, 3H), 2.14 (t, 1H, J=10.8 Hz), 2.54 (d, 1H, J=11.1 Hz), 2.78-2.95 (m, 3H), 3.29-3.47 (m, 2H), 3.71 (s, 3H), 3.74 (s, 2H), 3.85-3.92 (m, 1H), 6.57 (d, 2H, J=9.0 Hz), 6.73 (d, 2H, J=9.0 Hz), 7.10-7.12 (m, 1H), 7.17-7.23 (m, 3H), 8.48 (s, 2H), 9.09 (br s, 1H). $^{13}$C NMR (CDCl$_3$) δ 13.35, 29.37, 30.18, 30.52, 40.30, 43.49, 49.46, 52.10, 55.62, 57.26, 60.47, 114.58, 116.67, 124.75, 126.64, 126.83, 129.03, 129.65, 134.37, 142.63, 143.20, 147.62, 152.43, 161.48. ES-MS m/z 575 (M+H).

EXAMPLE 79

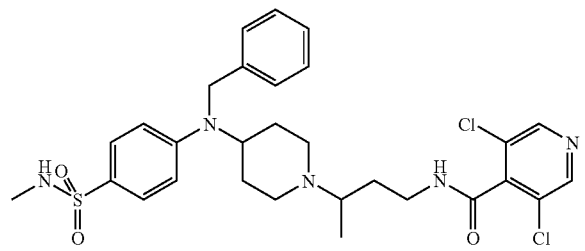

COMPOUND 79: N-(3-{4-Benzyl-(4-methylsulfamoyl-phenyl)-amino]-piperidin-1-yl}-butyl)-3,5-dichloro-isonicotinamide Using general procedure A, 4-amino-N-methyl-benzenesulfonamide (Andrewes; King; Walker, *Proc. R. Soc. London B.*, 133, 1946, 20-30) (320 mg, 1.72 mmol) and 1-Boc-4-piperidone (377 mg, 1.89 mmol) afforded a white solid (440 mg).

COMPOUND 79 was isolated as a white solid. $^1$H NMR (CDCl$_3$) δ 1.03 (d, 3H, J=6.6 Hz), 1.08-1.28 (m, 2H), 1.56 (m, 1H), 1.78 (m, 3H), 2.22 (t, 1H, J=11.4 Hz), 2.58 (d, 3H, J=5.4 Hz), 2.60 (m, 1H), 2.80-2.96 (m, 3H), 2.36 (m, 1H), 3.71-3.88 (m, 2H), 3.99 (s, 2H), 4.31 (q, 1H, J=5.4 Hz), 6.60 (d, 2H, J=9.0 Hz), 7.14 (d, 2H, J=6.9 Hz), 7.23-7.36 (m, 3H), 7.57 (d, 2H, J=9.0 Hz), 8.47 (s, 2H), 8.72 (br s, 1H). $^{13}$C NMR (CDCl$_3$) δ 13.43, 29.31, 30.33, 30.47, 39.97, 43.56, 48.48, 51.78, 53.47, 55.68, 59.99, 111.93, 124.79, 125.83, 127.05, 128.71, 129.06, 138.17, 143.13, 147.63, 151.63, 161.52. ES-MS m/z 604 (M+H). Anal. Calcd. for C$_{29}$H$_{35}$N$_5$Cl$_2$O$_3$S.0.4CH$_2$Cl$_2$: C, 55.30; H, 5.65; N, 10.97; Cl, 15.55; S, 5.02. Found. C, 55.18; H, 5.51; N, 10.80; Cl, 15.73; S, 5.00.

Anal. Calcd. for C$_{29}$H$_{33}$N$_4$Cl$_3$O$_2$: C, 60.48; H, 5.77; N, 9.73; Cl, 18.47. Found. C, 60.49; H, 5.81; N, 9.64; Cl, 18.45.

EXAMPLE 80

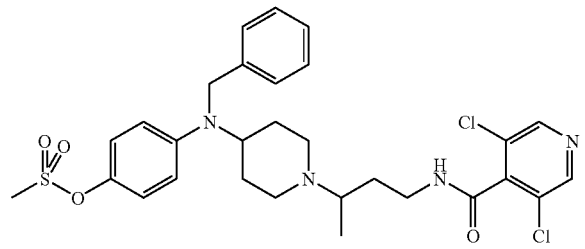

COMPOUND 80: Methanesulfonic acid 4-[benzyl-(1-{3-[(3,5-dichloro-pyridine-4-carbonyl)-amino]-1-methyl-propyl}-piperidin-4-yl)-amino]-phenyl ester Using general procedure H, 4-(4-methoxyphenylamino)-piperidine-1-carboxylic acid tert-butyl ester (see EXAMPLE 77) (612 mg, 2.00 mmol) and benzyl bromide (410 mg, 2.40 mmol) gave 4-[benzyl-(4-methoxyphenyl)-amino]-piperidine-1-carboxylic acid tert-butyl ester as a colorless oil (688 mg, 87%).

Using general procedure C with the above carbamate (303 mg, 0.765 mmol), then general procedure B with the resulting amine and 2-(3-oxo-butyl)-isoindole-1,3-dione (320 mg, 1.47 mmol) and then using general procedure D gave [1-(3-amino-1-methylpropyl)-piperidin-4-yl]-benzyl-(4-methoxyphenyl)-amine as a colorless oil (190 mg, 68% over 3 steps).

Using general procedure F, 3,5-dichloroisonicotinic acid (184 mg, 0.959 mmol) and the above amine (176 mg, 0.479 mmol) gave N-(3-{4-[benzyl-(4-methoxyphenyl)-amino]-piperidin-1-yl}-butyl)-3,5-dichloro-isonicotinamide as a white foam (243 mg, 94%).

To a solution of the above substrate (124 mg, 0.229 mmol) in CH$_2$Cl$_2$ (2 mL) cooled to −78° C. was added BBr$_3$ (1.0M in CH$_2$Cl$_2$, 0.92 mL, 0.92 mmol). The mixture was warmed to room temperature and stirred for 1 hour. 6N HCl was added and the mixture stirred at room temperature overnight to afford N-(3-{4-[benzyl-(4-hydroxy-phenyl)-amino]-piperidin-1-yl}-butyl)-3,5-dichloro-isonicotinamide as a white solid (107 mg, 89%) following basic work-up and purification.

Using general procedure G, the above alcohol (43 mg, 0.082 mmol) afforded COMPOUND 80 as a white solid (42 mg, 80%). $^1$H NMR (CDCl$_3$) δ 0.88-1.25 (m, 2H), 1.28 (d, 3H, J=6.3 Hz), 1.57 (m, 1H), 1.82 (m, 3H), 2.19 (t, 1H, J=10.8 Hz), 2.59 (t, 1H, J=11.1 Hz), 2.81-2.96 (m, 3H), 3.06 (s, 3H), 3.35 (m, 1H), 3.64 (m, 1H), 3.86 (m, 3H), 6.54 (d, 2H, J=9.0 Hz), 7.02 (d, 2H, J=9.0 Hz), 7.18 (d, 2H, J=7.2 Hz), 7.22-7.35 (m, 3H), 8.47 (s, 2H), 8.93 (br s, 1H). $^{13}$C NMR (CDCl$_3$) δ 13.36, 29.21, 30.34, 36.78, 40.10, 43.55, 48.85, 52.05, 55.88, 60.29, 113.49, 122.69, 125.99, 126.20, 126.65, 126.86, 128.61, 129.01, 139.14, 139.90, 143.16, 147.65, 147.73, 161.50. ES-MS m/z 605 (M+H). Anal. Calcd. for C$_{29}$H$_{34}$N$_4$Cl$_2$O$_4$S.CH$_2$Cl$_2$.0.3H$_2$O: C, 53.71; H, 5.45; N, 8.46; Cl, 17.14; S, 4.84. Found. C, 53.61; H, 5.34; N, 8.32; Cl, 17.21; S, 4.90.

EXAMPLE 81

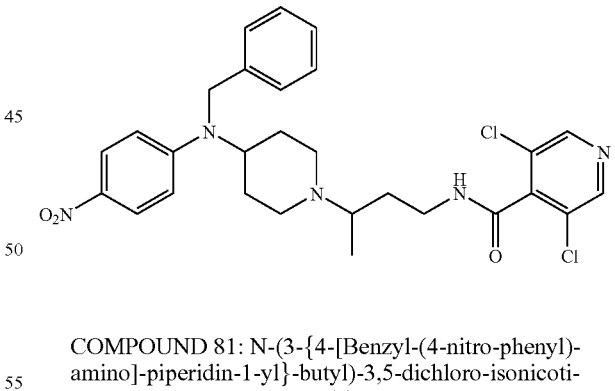

COMPOUND 81: N-(3-{4-[Benzyl-(4-nitro-phenyl)-amino]-piperidin-1-yl}-butyl)-3,5-dichloro-isonicotinamide Using general procedure A, benzylamine (1.2 mL, 11 mmol) and 1-Boc-4-piperidone (2.0 g, 10 mmol) gave 4-benzylamino-piperidine-1-carboxylic acid tert-butyl ester as a white solid (2.93 g, 100%).

A solution of the above amine (500 mg, 1.72 mmol), 1-iodo-4-nitrobenzene (408 mg, 1.64 mmol), Pd$_2$(dba)$_3$, (±)BINAP and toluene was purged with N$_2$ and then heated to 100° C. for 24 h to afford 4-[benzyl-(4-nitro-phenyl)-amino]-piperidine-1-carboxylic acid tert-butyl ester as a yellow foam (250 mg, 37%) following aqueous work-up and purification.

Using general procedure C with the above carbamate (100 mg, 0.24 mmol), then general procedure B with the resulting amine and 2-(3-oxo-butyl)-isoindole-1,3-dione (107 mg, 0.49 mmol) and then using general procedure D afforded [1-(3-amino-1-methyl-propyl)-piperidin-4-yl]-benzyl-(4-nitro-phenyl)-amine (79 mg, 86% over 3 steps).

Using general procedure F, 3,5-dichloroisonicotinic acid (60 mg, 0.31 mmol) and the above amine (79 mg, 0.21 mmol) afforded COMPOUND 81 as a yellow solid (45 mg, 38%). $^1$H NMR (CDCl$_3$) δ 1.03 (d, 3H, J=6.6 Hz), 1.09-1.36 (m, 2H), 1.55-1.60 (m, 1H), 1.76-1.91 (m, 3H), 2.27 (t, 1H, J=11.4 Hz), 2.61 (t, 1H, J=11.4 Hz), 2.82-2.97 (m, 3H), 3.33-3.41 (m, 1H), 3.77-3.87 (m, 2H), 4.07 (s, 2H), 6.55 (d, 2H, J=9.6 Hz), 7.12 (d, 2H, J=7.2 Hz), 7.27-7.37 (m, 3H), 8.02 (d, 2H, J=8.4 Hz), 8.48 (s, 2H), 8.56 (br s, 1H). $^{13}$C NMR (CDCl$_3$) δ 13.80, 29.89, 30.81, 30.96, 40.38, 43.87, 48.91, 52.18, 56.55, 60.42, 111.75, 126.14, 126.49, 127.68, 129.25, 129.44, 137.78, 137.96, 143.52, 148.08, 153.62, 161.86. ES-MS m/z 556 (M+H). Anal. Calcd. for C$_{28}$H$_{31}$N$_5$Cl$_2$O$_3$.0.6CH$_2$Cl$_2$.0.2C$_4$H$_{10}$O: C, 56.75; H, 5.54; N, 11.25; Cl, 18.23. Found. C, 56.71; H, 5.33; N, 11.17; Cl, 18.05.

EXAMPLE 82

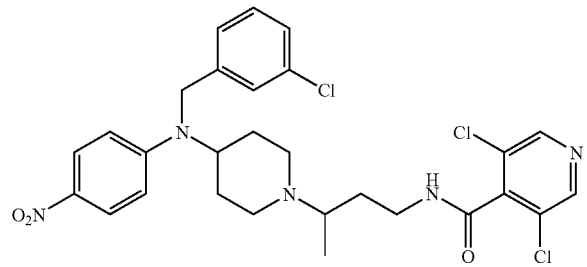

COMPOUND 82: 3,5-Dichloro-N-(3-{4-[(3-chloro-benzyl)-(4-nitro-phenyl)-amino]-piperidin-1-yl}-butyl)-isonicotinamide Using general procedure A, 3-chlorobenzylamine (0.27 mL, 2.2 mmol) and 1-Boc-4-piperidone (484 mg, 2.4 mmol) afforded 4-(3-chloro-benzylamino)-piperidine-1-carboxylic acid tert-butyl ester as a colourless oil (640 mg, 89%).

The above secondary amine (640 mg, 1.80 mmol), 1-iodo-4-nitrobenzene (899 mg, 3.61 mmol), sodium tert-butoxide (243 mg, 2.53 mmol), (+/−) BINAP (224 mg, 0.36 mmol), Pd$_2$(dba)$_3$ (165 mg, 0.18 mmol) and toluene (4.0 mL) were flushed with N$_2$ for 5 minutes. The mixture was heated at 100° C. overnight to afford an orange/brown solid (500 mg) following aqueous work-up and purification.

Using general procedure C with the above substrate, then general procedure B with the resulting amine and 2-(3-oxo-butyl)-isoindole-1,3-dione (427 mg, 1.97 mmol) and then using general procedure D afforded [1-(3-amino-1-methyl-propyl)-piperidin-4-yl]-(3-chloro-benzyl)-(4-nitro-phenyl)-amine as a yellow solid (215 mg, 29% over 4 steps).

Using general procedure F, 3,5-dichloroisonicotinic acid (46 mg, 0.24 mmol) and the above amine (50 mg, 0.12 mmol) afforded COMPOUND 82 as a yellow solid (61 mg, 86%). $^1$H NMR (CDCl$_3$) δ 1.04 (d, 3H, J=6.3 Hz), 1.06-1.35 (m, 2H), 1.52-1.63 (m, 1H), 1.73-1.89 (m, 3H), 2.18-2.28 (m, 1H), 2.56-2.67 (m, 1H), 2.80-3.00 (m, 3H), 3.32-3.44 (m, 1H), 3.74-3.90 (m, 2H), 4.03 (s, 2H), 6.54 (d, 2H, J=7.00 Hz), 7.00-7.05 (m, 1H), 7.10 (s, 1H), 7.23-7.32 (m, 2H), 8.04 (d, 2H, J=9.3 Hz), 8.46-8.54 (m, 3H). $^{13}$C NMR (CDCl$_3$) δ 13.45, 29.49, 30.38, 30.65, 39.86, 43.50, 48.16, 51.64, 56.15, 59.81, 111.42, 124.00, 125.88, 126.11, 127.55, 129.07, 130.19, 134.86, 137.80, 139.84, 143.11, 147.64, 153.03, 161.47. ES-MS m/z 590 (M+H). Anal. Calcd. for C$_{28}$H$_{30}$N$_5$Cl$_3$O$_3$.0.3CH$_2$Cl$_2$: C, 55.14; H, 5.00; N, 11.36; Cl, 20.71. Found. C, 55.34; H, 4.92; N, 11.32; Cl, 20.66.

EXAMPLE 83

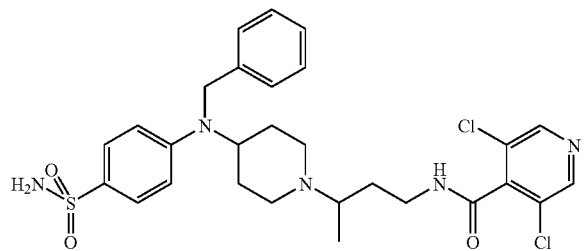

COMPOUND 83: N-(3-{4-[Benzyl-(4-sulfamoyl-phenyl)-amino]-piperidin-1-yl}-butyl)-3,5-dichloro-isonicotinamide Using general procedure A, 1-Boc-4-piperidone (1.00 g, 5.03 mmol) and 4-amino-N,N-dibenzyl-benzenesulfonamide (Mikhura, I. V.; et al., *Russ. J. Org. Chem.*, 36, 1, 2002, 64-68) (1.53 g, 4.34 mmol) afforded 4-(4-dibenzylsulfamoyl-phenylamino)-piperidine-1-carboxylic acid tert-butyl ester as a white solid (1.27 g, 55%).

Using general procedure H with the above aniline (970 mg, 1.81 mmol) and benzyl bromide (0.66 mL, 5.52 mmol) followed by general procedure C afforded N,N-dibenzyl-4-(benzyl-piperidin-4-yl-amino)-benzenesulfonamide as a white solid (679 mg, 72% over 2 steps).

Using general procedure B with the above amine (679 mg, 1.29 mmol) and 2-(3-oxo-butyl)-isoindole-1,3-dione (877 mg, 4.04 mmol) and then using general procedure D afforded 4-{[1-(3-amino-1-methyl-propyl)-piperidin-4-yl]-benzyl-amino}-N,N-dibenzyl-benzenesulfonamide as a white solid (461 mg, 60% over 2 steps).

To the above amine (122 mg, 0.204 mmol) was added conc. H$_2$SO$_4$ (2 mL) and the mixture was stirred at room temperature for 1.5 hours. The mixture was poured onto ice (~20 mL), neutralized with Na$_2$CO$_3$ (s, ~5 g), diluted with H$_2$O (20 mL) and extracted with CH$_2$Cl$_2$ (5×25 mL). The combined organic extracts were dried (Na$_2$SO$_4$), filtered and concentrated under reduced pressure to give 4-{[1-(3-amino-1-methyl-propyl)-piperidin-4-yl]-benzyl-amino}-benzenesulfonamide as a yellow solid (66 mg, 78%).

Using general procedure F, 3,5-dichloroisonicotinic acid (87 mg, 0.45 mmol) and the above amine (58 mg, 0.14 mmol) afforded the desired product and N-{3-[4-(benzyl-{4-[(3,5-dichloro-pyridine-4-carbonyl)-sulfamoyl]-phenyl}-amino)-piperidin-1-yl]-butyl}-3,5-dichloro-isonicotinamide.

To the above amide in THF (1 mL) was added 6N HCl (1 mL) and the mixture was heated at 60° C. overnight to afford COMPOUND 83 as a white solid (27 mg, 29% over 2 steps) following work-up and purification. $^1$H NMR (CDCl$_3$) δ 0.96-1.32 (m, 2H), 1.03 (d, 3H, J=6.6 Hz), 1.51-1.57 (m, 1H), 1.75-1.90 (m, 3H), 2.22 (t, 1H, J=11.7 Hz), 2.61 (t, 1H, J=10.8

Hz), 2.81-2.97 (m, 3H), 3.32-3.40 (m, 1H), 3.71-3.79 (m, 1H), 3.84-3.90 (m, 1H), 3.98 (s, 2H), 4.60 (s, 2H), 6.60 (d, 2H, J=9.0 Hz), 7.14 (d, 2H, J=7.2 Hz), 7.29-7.36 (m, 3H), 7.65 (d, 2H, J=9.0 Hz), 8.48 (s, 2H), 8.71 (br s, 1H). $^{13}$C NMR (CDCl$_3$) δ 13.80, 29.75, 30.76, 30.87, 40.44, 43.91, 48.84, 52.26, 56.15, 60.51, 112.35, 126.24, 127.49, 128.69, 129.13, 129.44, 138.45, 143.54, 148.05, 152.01, 161.89. ES-MS m/z 590 (M+H). Anal. Calcd. for $C_{28}H_{35}N_5O_3SCl_2.0.9CH_2Cl_2.0.4H_2O$: C, 51.48; H, 5.32; N, 10.39; S, 4.76; Cl, 19.98. Found. C, 51.37; H, 5.18; N, 10.04; S, 4.58; Cl, 20.37.

EXAMPLE 84

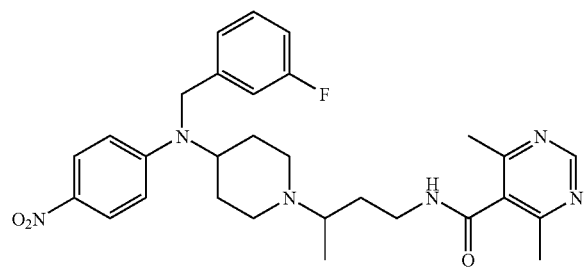

COMPOUND 84: 4,6-Dimethyl-pyrimidine-5-carboxylic acid (3-{4-[(3-fluoro-benzyl)-(4-nitro-phenyl)-amino]-piperidin-1-yl}-butyl)-amide Using general procedure A, 3-fluorobenzylamine (0.25 mL, 2.2 mmol) and 1-Boc-4-piperidone (482 mg, 2.4 mmol) afforded 4-(3-fluoro-benzylamino)-piperidine-1-carboxylic acid tert-butyl ester as a colourless oil (620 mg, 91%).

The above secondary amine (620 mg, 2.0 mmol), 1-iodo-4-nitrobenzene (996 mg, 4.0 mmol), sodium tert-butoxide (269 mg, 2.8 mmol), (+/−) BINAP (246 mg, 0.4 mmol), Pd$_2$(dba)$_3$ (183 mg, 0.2 mmol) and toluene (4.0 mL) were flushed with N$_2$ for 5 minutes. The mixture was heated at 100° C. overnight to afford 4-[(3-fluoro-benzyl)-(4-nitro-phenyl)-amino]-piperidine-1-carboxylic acid tert-butyl ester as an orange/brown solid (354 mg, ~41%) following aqueous work-up and purification.

Using general procedure C with the above substrate (354 mg, 0.82 mmol), then general procedure B with the resulting amine and 2-(3-oxo-butyl)-isoindole-1,3-dione (356 mg, 1.64 mmol) and then using general procedure D afforded [1-(3-amino-1-methyl-propyl)-piperidin-4-yl]-(3-fluoro-benzyl)-(4-nitro-phenyl)-amine as a yellow solid (198 mg, 60% over 3 steps).

Using general procedure E, the above amine (50 mg, 0.13 mmol) and 4,6-dimethyl-pyrimidine-5-carboxylic acid (21 mg, 0.14 mmol) afforded COMPOUND 84 as a yellow solid (57 mg, 85%). $^1$H NMR (CDCl$_3$) δ 0.96-1.29 (m, 2H), 1.03 (d, 3H, J=6.6 Hz), 1.52-1.61 (m, 1H), 1.70-1.85 (m, 3H), 2.16-2.28 (m, 1H), 2.52 (s, 6H), 2.55-2.66 (m, 1H), 2.74-2.95 (m, 3H), 3.29-3.41 (m, 1H), 3.72-3.88 (m, 2H), 4.09 (s, 2H), 6.55 (d, 2H, J=9.0 Hz), 6.85-7.03 (m, 3H), 7.27-7.36 (m, 1H), 8.04 (d, 2H, J=9.0 Hz), 8.26 (br s, 1H), 8.92 (s, 1H). $^{13}$C NMR (CDCl$_3$) δ 13.48, 21.97, 29.34, 30.35, 31.01, 39.83, 43.53, 48.25, 51.72, 56.12, 59.95, 111.32, 112.90 (d, J=22 Hz), 114.23 (d, J=21 Hz), 121.47, 126.16, 130.48 (d, J=8 Hz), 130.81, 137.80, 140.60 (d, J=7 Hz), 153.19, 157.63, 163.12, 163.21 (d, J=247 Hz), 166.33. ES-MS m/z 535 (M+H). Anal. Calcd. for $C_{29}H_{35}N_6O_3F.0.8CH_2Cl_2$: C, 59.40; H, 6.12; N, 13.95; F, 3.15. Found. C, 59.26; H, 6.02; N, 13.98; F, 3.15.

EXAMPLE 85

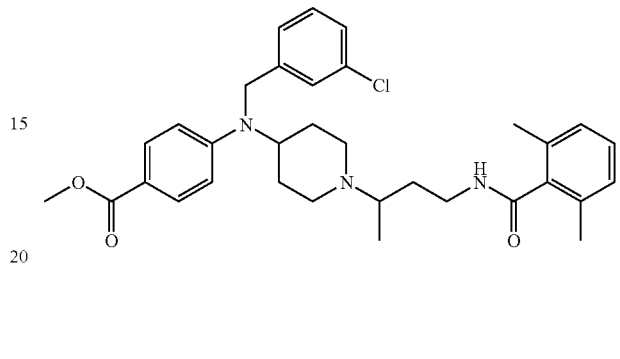

COMPOUND 85: 4-((3-Chloro-benzyl)-{1-[3-(2,6-dimethyl-benzoylamino)-1-methyl-propyl]-piperidin-4-yl}-amino)-benzoic acid methyl ester Using general procedure A, methyl 4-aminobenzoate (380 mg, 2.51 mmol) and 1-Boc-4-piperidone (500 g, 2.51 mmol) afforded 4-(4-methoxycarbonyl-phenylamino)-piperidine-1-carboxylic acid tert-butyl ester (643 mg, 77%).

Using general procedure H, the above aniline (590 mg, 1.77 mmol) and 3-chlorobenzyl bromide (348 μL, 2.65 mmol) afforded 4-[(3-chloro-benzyl)-(4-methoxycarbonyl-phenyl)-amino]-piperidine-1-carboxylic acid tert-butyl ester (452 mg, 56%).

Using general procedure C with the above carbamate (452 mg, 0.98 mmol), then using general procedure B with the resulting amine and 2-(3-oxo-butyl)-isoindole-1,3-dione (428 mg, 1.97 mmol) followed by general procedure D afforded 4-[[1-(3-amino-1-methyl-propyl)-piperidin-4-yl]-(3-chloro-benzyl)-amino]-benzoic acid methyl ester (295 mg, 70% over 3 steps).

Using general procedure E, the above amine (295 mg, 0.69 mmol) and 2,6-dimethylbenzoic acid (113 mg, 0.75 mmol) afforded COMPOUND 85 as a white solid (290 mg, 75%). $^1$H NMR (CDCl$_3$) δ 0.99 (d, 3H, J=6.3 Hz), 1.00-1.21 (m, 2H), 1.48-1.54 (m, 1H), 1.70-1.76 (m, 3H), 2.17 (t, 1H, J=11.1 Hz), 2.30 (s, 6H), 2.56 (t, 1H, J=10.8 Hz), 2.74-2.90 (m, 3H), 3.23-3.31 (m, 1H), 3.66-3.75 (m, 1H), 3.78-3.90 (m, 1H), 3.80 (s, 3H), 3.86 (s, 2H), 6.53 (d, 2H, J=9.0 Hz), 6.95-7.01 (m, 3H), 7.06-7.11 (m, 2H), 7.20-7.23 (m, 2H), 7.80 (d, 2H, J=8.7 Hz), 8.35 (br s, 1H). $^{13}$C NMR (CDCl$_3$) δ 13.59, 13.85, 19.54, 29.41, 29.81, 30.69, 31.34, 34.02, 40.18, 43.95, 48.56, 49.10, 51.94, 52.41, 53.87, 56.16, 58.61, 60.87, 112.04, 118.42, 124.59, 126.55, 126.95, 127.43, 127.78, 128.88, 130.24, 131.35, 131.75, 132.13, 134.42, 134.89, 138.98, 141.94, 152.30, 167.51, 170.29. ES-MS m/z 562 (M+H). Anal. Calcd. for $C_{33}H_{40}N_3ClO_3.0.2CH_2Cl_2$: C, 68.86; H, 7.03; N, 7.26. Found. C, 68.73; H, 7.00; N, 7.26.

EXAMPLE 86

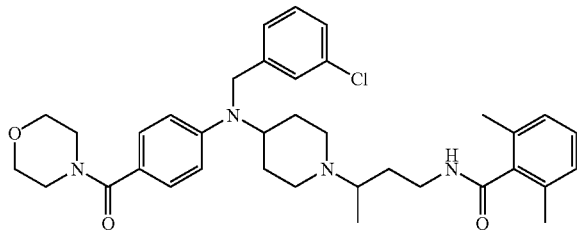

COMPOUND 86: N-[3-(4-{(3-Chloro-benzyl)-[4-(morpholine-4-carbonyl)-phenyl]-amino}-piperidin-1-yl)-butyl]-2,6-dimethyl-benzamide Using general procedure K, COMPOUND 85 (273 mg, 0.485 mmol) afforded 4-((3-chloro-benzyl)-{1-[3-(2,6-dimethyl-benzoylamino)-1-methyl-propyl]-piperidin-4-yl}-amino)-benzoic acid (280 mg).

Using general procedure E, the above acid (40 mg) and morpholine (71 µL, 0.080 mmol) gave COMPOUND 86 as a white solid (24 mg, 53%). $^1$H NMR (CDCl$_3$) δ 0.91-1.21 (m, 2H), 0.99 (d, 3H, J=6.3 Hz), 1.49-1.54 (m, 1H), 1.70-1.74 (m, 3H), 2.16 (t, 1H, J=11.1 Hz), 2.30 (s, 6H), 2.55 (t, 1H, J=11.4 Hz), 2.74-2.90 (m, 3H), 3.24-3.31 (m, 1H), 3.62-3.65 (m, 9H), 3.82 (s, 2H), 3.83-3.88 (m, 1H), 6.53 (d, 2H, J=8.7 Hz), 6.95 (d, 2H, J=7.5 Hz), 7.01-7.11 (m, 3H), 7.19-7.25 (m, 4H), 8.35-8.36 (m, 1H). $^{13}$C NMR (CDCl$_3$) δ 13.81, 19.54, 29.33, 30.65, 31.34, 40.20, 43.98, 46.15, 48.66, 52.50, 56.20, 60.90, 67.35, 112.45, 123.18, 124.66, 126.60, 127.36, 127.75, 128.87, 129.79, 130.20, 134.41, 134.87, 138.96, 142.35, 150.27, 170.30, 171.16. ES-MS m/z 617 (M+H). Anal. Calcd. for C$_{36}$N$_{45}$N$_4$ClO$_3$.0.2CH$_2$Cl$_2$: C, 68.56; H, 7.21; N, 8.83. Found. C, 68.65; H, 7.21; N, 8.90.

EXAMPLE 87

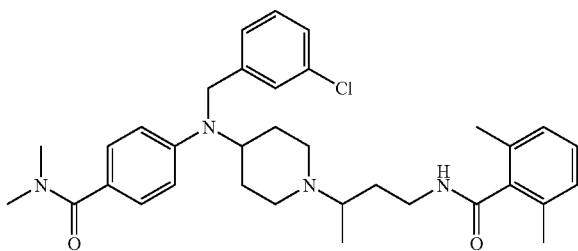

COMPOUND 87: N-(3-{4-[(3-Chloro-benzyl)-(4-dimethylcarbamoyl-phenyl)-amino]-piperidin-1-yl}-butyl)-2,6-dimethyl-benzamide Using general procedure E, 4-((3-chloro-benzyl)-{1-[3-(2,6-dimethyl-benzoylamino)-1-methyl-propyl]-piperidin-4-yl}-amino)-benzoic acid (see EXAMPLE 86) (40 mg, 0.074) and dimethylamine (2.0M in THF, 56 µL, 0.11 mmol) afforded COMPOUND 87 as a white solid (31 mg, 71%). $^1$H NMR (CDCl$_3$) δ 0.89-1.20 (m, 2H), 1.00 (d, 3H, J=6.3 Hz), 1.50-1.54 (m, 1H), 1.70-1.83 (m, 3H), 2.16 (t, 1H, J=11.1 Hz), 2.30 (s, 6H), 2.56 (t, 1H, J=12.0 Hz), 2.74-2.90 (m, 3H), 3.03 (s, 6H), 3.24-3.31 (m, 1H), 3.62-3.69 (m, 1H), 3.81 (s, 2H), 3.84-3.91 (m, 1H), 6.52 (d, 2H, J=8.4 Hz), 6.96 (d, 2H, J=7.5 Hz), 7.02-7.12 (m, 3H), 7.21-7.28 (m, 4H), 8.39 (br s, 1H). $^{13}$C NMR (CDCl$_3$) δ 13.81, 19.54, 29.32, 30.67, 31.31, 40.24, 43.98, 48.67, 52.54, 56.18, 60.96, 112.31, 124.37, 124.68, 126.63, 127.30, 127.77, 128.88, 129.70, 130.16, 134.41, 134.83, 138.96, 142.53, 149.98, 170.32, 172.18. ES-MS m/z 575 (M+H). Anal. Calcd. for C$_{34}$H$_{43}$N$_4$ClO$_2$.0.5CH$_2$Cl$_2$: C, 67.09; H, 7.18; N, 9.07. Found. C, 66.75; H, 7.12; N, 8.94.

EXAMPLE 88

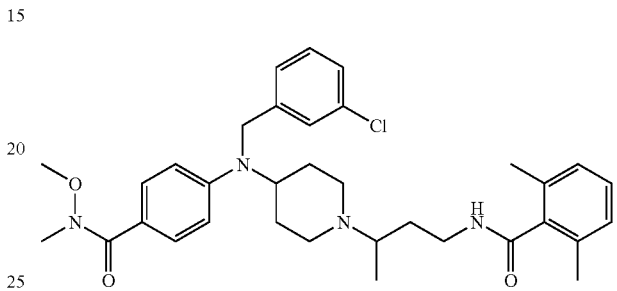

COMPOUND 88: N-[3-(4-{(3-Chloro-benzyl)-[4-(methoxy-methyl-carbamoyl)-phenyl]-amino}-piperidin-1-yl)-butyl]-2,6-dimethyl-benzamide Using general procedure E, 4-((3-chloro-benzyl)-{1-[3-(2,6-dimethyl-benzoylamino)-1-methyl-propyl]-piperidin-4-yl}-amino)-benzoic acid (see EXAMPLE 86) (40 mg, 0.074) and N,O-dimethylhydroxylamine hydrochloride (11 mg, 0.11 mmol) afforded COMPOUND 88 as a white solid (36 mg, 84%). $^1$H NMR (CDCl$_3$) δ 0.91-1.21 (m, 2H), 1.00 (d, 3H, J=6.3 Hz), 1.50-1.54 (m, 1H), 1.71-1.88 (m, 3H), 2.17 (t, 1H, J=11.4 Hz), 2.30 (s, 6H), 2.56 (t, 1H, J=11.4 Hz), 2.74-2.90 (m, 3H), 3.24-3.30 (m, 1H), 3.30 (s, 3H), 3.57 (s, 3H), 3.65-3.72 (m, 1H), 3.84 (s, 2H), 3.84-3.90 (m, 1H), 6.52 (d, 2H, J=8.7 Hz), 6.96 (d, 2H, J=7.5 Hz), 7.02-7.11 (m, 3H), 7.21-7.26 (m, 2H), 7.62 (d, 2H, J=8.4 Hz), 8.39 (br s, 1H). $^{13}$C NMR (CDCl$_3$) δ 13.82, 19.54, 29.37, 30.69, 31.32, 34.49, 40.23, 43.97, 48.64, 52.50, 56.07, 60.93, 61.16, 111.89, 121.77, 124.65, 126.60, 127.34, 127.77, 128.88, 130.19, 131.09, 134.41, 134.85, 138.97, 142.35, 150.90, 169.94, 170.31. ES-MS m/z 591 (M+H). Anal. Calcd. for C$_{34}$H$_{43}$N$_4$ClO$_3$.0.3CH$_2$Cl$_2$: C, 66.84; H, 7.13; N, 9.09. Found. C, 66.87; H, 7.06; N, 8.94.

EXAMPLE 89

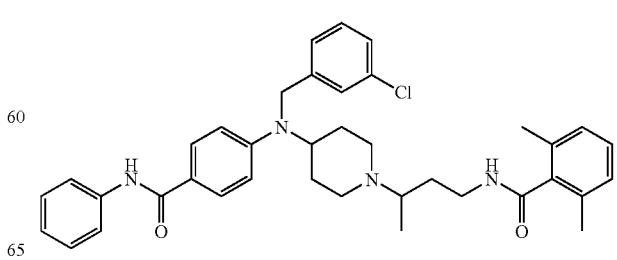

COMPOUND 89: N-(3-{4-[(3-Chloro-benzyl)-(4-phenylcarbamoyl-phenyl)-amino]-piperidin-1-yl}-butyl)-2,6-dimethyl-benzamide Using general procedure E, 4-((3-chloro-benzyl)-{1-[3-(2,6-dimethyl-benzoylamino)-1-methyl-propyl]-piperidin-4-yl}-amino)-benzoic acid (see EXAMPLE 86) (40 mg, 0.074) and aniline (8 μL, 0.08 mmol) afforded COMPOUND 89 as a white solid (32 mg, 71%). $^1$H NMR (CDCl$_3$) δ 0.93-1.25 (m, 2H), 1.01 (d, 3H, J=6.3 Hz), 1.51-1.55 (m, 1H), 1.72-1.76 (m, 3H), 2.19 (t, 1H, J=11.1 Hz), 2.31 (s, 6H), 2.58 (t, 1H, J=11.1 Hz), 2.76-2.92 (m, 3H), 3.25-3.32 (m, 1H), 3.67-3.75 (m, 1H), 3.87 (s, 2H), 3.87-3.93 (m, 1H), 6.57 (d, 2H, J=8.7 Hz), 6.95-7.12 (m, 6H), 7.23-7.32 (m, 4H), 7.60 (d, 2H, J=7.8 Hz), 7.68 (d, 2H, J=8.4 Hz), 7.76 (s, 1H), 8.35 (br s, 1H). $^{13}$C NMR (CDCl$_3$) δ 13.85, 19.55, 29.42, 30.70, 31.35, 40.22, 43.96, 48.59, 52.47, 56.25, 60.92, 112.50, 120.35, 122.88, 124.35, 124.61, 126.60, 127.47, 127.78, 128.89, 129.13, 129.37, 130.27, 134.44, 134.95, 138.80, 138.97, 142.01, 151.51, 165.65, 170.31. ES-MS m/z 623 (M+H). Anal. Calcd. for C$_{38}$H$_{43}$N$_4$ClO$_2$.0.2CH$_2$Cl$_2$: C, 71.65; H, 6.83; N, 8.75. Found. C, 71.64; H, 6.81; N, 8.84.

EXAMPLE 90

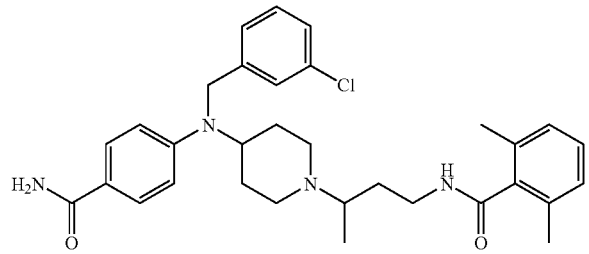

COMPOUND 90: N-(3-{4-[(4-Carbamoyl-phenyl)-(3-chloro-benzyl)-amino]-piperidin-1-yl}-butyl)-2,6-dimethyl-benzamide Using general procedure E (Wang, W.; McMurray, J. S. Tetrahedron Lett., 1999, 40, 2501-2504) 4-((3-chloro-benzyl)-{1-[3-(2,6-dimethyl-benzoylamino)-1-methyl-propyl]-piperidin-4-yl}-amino)-benzoic acid (see EXAMPLE 86) (90 mg, 0.16 mmol) and NH$_4$Cl (22 mg, 0.41 mmol) gave COMPOUND 90 as a white solid (64.1 mg, 0.12 mmol, 71%). $^1$H NMR (CDCl$_3$) δ 0.95-1.09 (m, 1H), 1.01 (d, 3H, J=6.6 Hz), 1.10-1.25 (m, 1H), 1.48-1.58 (m, 1H), 1.68-1.83 (m, 3H), 2.13-2.24 (m, 1H), 2.31 (s, 6H), 2.52-2.63 (m, 1H), 2.73-2.94 (m, 3H), 3.23-3.34 (m, 1H), 3.64-3.76 (m, 1H), 3.83-3.93 (m, 1H), 3.85 (s, 2H), 5.67 (br s, 2H), 6.55 (d, 2H, J=8.4 Hz), 6.94-7.04 (m, 3H), 7.06-7.13 (m, 2H), 7.20-7.27 (m, 2H), 7.61 (d, 2H, J=8.4 Hz), 8.34 (br d, 1H, J=5.1 Hz). $^{13}$C NMR (CDCl$_3$) δ 13.37, 19.05, 28.90, 30.19, 30.84, 39.72, 43.48, 48.09, 51.94, 55.68, 60.37, 111.78, 120.97, 124.13, 126.10, 126.93, 127.29, 128.40, 129.07, 129.77, 133.95, 134.40, 138.46, 141.59, 151.10, 169.07, 169.83. ESI-MS m/z 547 (MH)$^+$, 549 (MH+2)$^+$. Anal. Calcd. for C$_{32}$H$_{39}$ClN$_4$O$_2$.0.7CH$_2$Cl$_2$.0.3H$_2$O: C, 64.18; H, 6.75; N, 9.15; Cl, 13.90. Found. C, 64.11; H, 6.58; N, 9.11; Cl, 13.99.

EXAMPLE 91

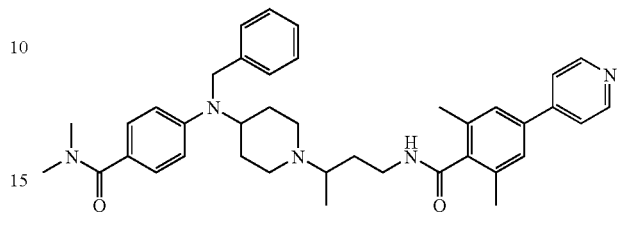

COMPOUND 91: N-(3-{4-[Benzyl-(4-dimethylcarbamoyl-phenyl)-amino]-piperidin-1-yl}-butyl)-2,6-dimethyl-4-pyridin-4-yl-benzamide Using general procedure H with 4-(4-methoxycarbonyl-phenylamino)-piperidine-1-carboxylic acid tert-butyl ester (see EXAMPLE 85) (1.0 g) and benzylbromide (0.54 mL, 4.50 mmol) and then using general procedure C afforded 4-(benzyl-piperidin-4-yl-amino)-benzoic acid methyl ester as a white solid (620 mg, 63% over 2 steps).

Using general procedure B with the above secondary amine (620 mg, 1.91 mmol) and 2-(3-oxo-butyl)-isoindole-1,3-dione (830 mg, 3.82 mmol) and then using general procedure D afforded 4-{[1-(3-amino-1-methyl-propyl)-piperidin-4-yl]-benzyl-amino}-benzoic acid methyl ester as a white solid (120 mg, 16% over 2 steps).

Using general procedure E with the above amine (120 mg, 0.30 mmol) and 2,6-dimethyl-4-pyridin-4-yl-benzoic acid (76 mg, 0.33 mmol) and then using general procedure K afforded 4-(benzyl-{1-[3-(2,6-dimethyl-4-pyridin-4-yl-benzoylamino)-1-methyl-propyl]-piperidin-4-yl}-amino)-benzoic acid as a yellow solid (160 mg, 88% over 2 steps).

Using general procedure E, the above acid (60 mg, 0.10 mmol) and dimethylamine (2M, 153 μL, 0.31 mmol) afforded COMPOUND 91 as a white solid (49 mg, 78%). $^1$H NMR (CDCl$_3$) δ 1.00 (d, 3H, J=6.0 Hz), 1.00-1.33 (m, 2H), 1.49-1.60 (m, 1H), 1.68-1.82 (m, 3H), 2.11-2.23 (m, 1H), 2.39 (s, 6H), 2.49-2.60 (m, 1H), 2.71-2.92 (m, 3H), 3.01 (s, 6H), 3.25-3.37 (m, 1H), 3.60-3.72 (m, 1H), 3.79-3.92 (m, 3H), 6.47 (d, 2H, J=8.1 Hz), 6.86-6.92 (m, 2H), 7.12-7.19 (m, 3H), 7.23 (d, 2H, J=8.1 Hz), 7.29 (s, 2H), 7.45 (d, 2H, J=3.9 Hz), 8.26 (br s, 1H), 8.63 (d, 2H, J=4.5 Hz). $^{13}$C NMR (CDCl$_3$) δ 13.83, 19.75, 29.40, 30.81, 31.64, 40.05, 44.16, 48.65, 52.47, 56.10, 60.59, 112.07, 121.91, 123.95, 126.25, 126.47, 127.03, 128.83, 129.71, 135.63, 138.47, 139.63, 139.91, 148.03, 150.14, 150.75, 169.76, 172.25. ES-MS m/z 618 (M+H). Anal. Calcd. for C$_{39}$H$_{47}$N$_5$O$_2$.1.0CH$_2$Cl$_2$: C, 68.36; H, 7.03; N, 9.97. Found. C, 68.16; H, 7.02; N, 10.04.

EXAMPLE 92

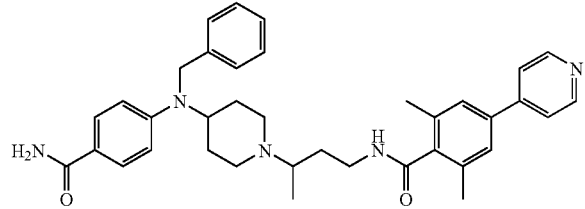

COMPOUND 92: N-(3-{4-[Benzyl-(4-carbamoyl-phenyl)-amino]-piperidin-1-yl}-butyl)-2,6-dimethyl-4-pyridin-4-yl-benzamide Using general procedure E, 4-(benzyl-{1-[3-(2,6-dimethyl-4-pyridin-4-yl-benzoylamino)-1-methyl-propyl]-piperidin-4-yl}-amino)-benzoic acid (see EXAMPLE 91) (60 mg, 0.10 mmol) and ammonium chloride (22 mg, 0.41 mmol) afforded COMPOUND 92 as a white solid (43 mg, 71%). $^1$H NMR (CDCl$_3$) δ 1.02 (d, 3H, J=5.7 Hz), 1.06-1.35 (m, 2H), 1.51-1.62 (m, 1H), 1.69-1.86 (m, 3H), 2.13-2.31 (m, 1H), 2.40 (s, 6H), 2.52-2.63 (m, 1H), 2.73-2.94 (m, 3H), 3.20-3.40 (m, 2H), 3.62-3.71 (m, 1H), 3.89 (s, 2H), 5.79 (br s, 2H), 6.49 (d, 2H, J=8.1 Hz), 6.84-6.93 (m, 2H), 7.12-7.22 (m, 3H), 7.25-7.33 (m, 2H), 7.41-7.48 (m, 2H), 7.57 (d, 2H, J=8.1 Hz), 8.20 (br s, 1H), 8.60-8.67 (m, 2H). $^{13}$C NMR (CDCl$_3$) δ 13.45, 19.34, 29.05, 30.40, 31.30, 39.60, 43.73, 48.18, 51.98, 55.72, 60.12, 111.66, 120.60, 121.49, 125.76, 126.06, 126.75, 128.51, 129.11, 135.24, 138.06, 139.02, 139.21, 147.61, 150.35, 151.34, 169.08, 169.34. ES-MS m/z 590 (M+H).

Scheme 6 describes the preparation of Examples 93-95, using general procedure E, and reagents listed below.

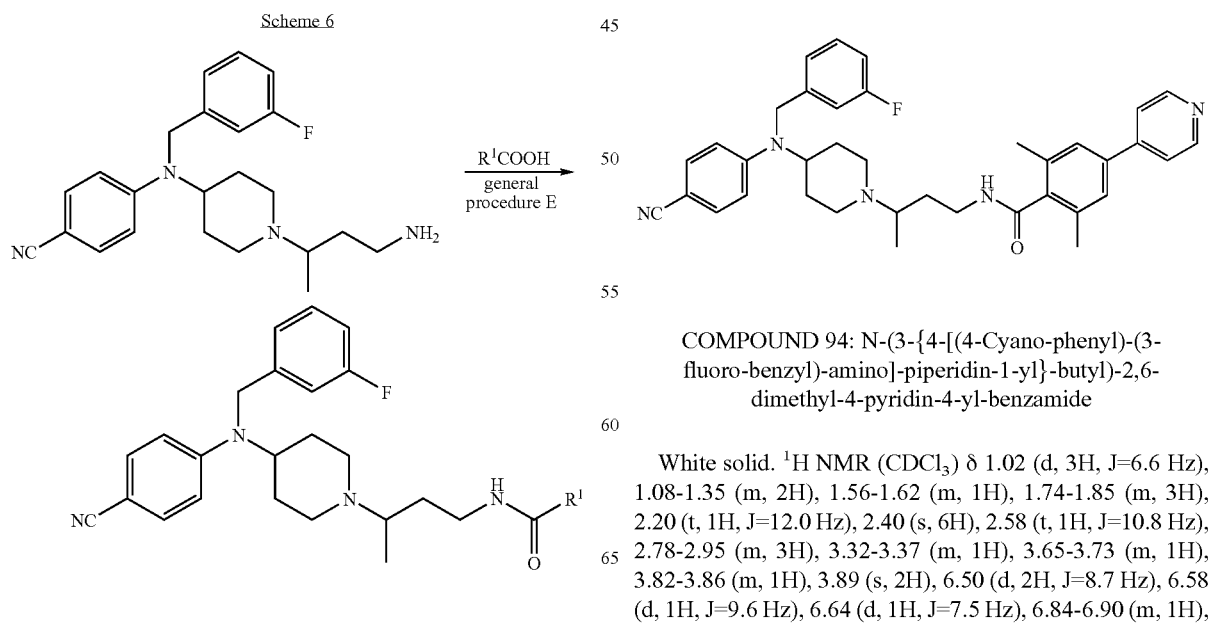

Scheme 6

| Example | R$^1$COOH |
|---|---|
| 93 | 2,4-dimethyl-1-oxy-nicotinic acid |
| 94 | 2,6-dimethyl-4-pyridin-4-yl-benzoic acid |
| 95 | 4,6-dimethyl-pyrimidine-5-carboxylic acid |

EXAMPLE 93

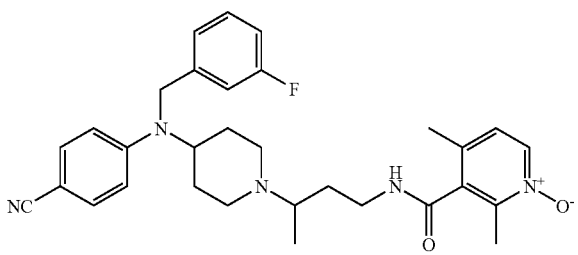

COMPOUND 93: N-(3-{4-[(4-Cyano-phenyl)-(3-fluoro-benzyl)-amino]-piperidin-1-yl}-butyl)-2,4-dimethyl-1-oxy-nicotinamide White foam. $^1$H NMR (CDCl$_3$) δ 1.04 (d, 3H, J=6.6 Hz), 1.21-1.48 (m, 2H), 1.56-1.69 (m, 1H), 1.74-1.88 (m, 3H), 2.20-2.28 (m, 1H), 2.29 (s, 3H), 2.39 (s, 3H), 2.54-2.63 (m, 1H), 2.76-2.94 (m, 3H), 3.35-3.47 (m, 1H), 3.65-3.81 (m, 2H), 4.26 (s, 2H), 6.60 (d, 2H, J=8.9 Hz), 6.84-7.03 (m, 4H), 7.27-7.34 (m, 1H), 7.40 (d, 2H, J=8.9 Hz), 7.96 (d, 1H, J=6.6 Hz), 8.38 (br s, 1H). ESI-MS m/z 530 (MH)$^+$.

EXAMPLE 94

COMPOUND 94: N-(3-{4-[(4-Cyano-phenyl)-(3-fluoro-benzyl)-amino]-piperidin-1-yl}-butyl)-2,6-dimethyl-4-pyridin-4-yl-benzamide White solid. $^1$H NMR (CDCl$_3$) δ 1.02 (d, 3H, J=6.6 Hz), 1.08-1.35 (m, 2H), 1.56-1.62 (m, 1H), 1.74-1.85 (m, 3H), 2.20 (t, 1H, J=12.0 Hz), 2.40 (s, 6H), 2.58 (t, 1H, J=10.8 Hz), 2.78-2.95 (m, 3H), 3.32-3.37 (m, 1H), 3.65-3.73 (m, 1H), 3.82-3.86 (m, 1H), 3.89 (s, 2H), 6.50 (d, 2H, J=8.7 Hz), 6.58 (d, 1H, J=9.6 Hz), 6.64 (d, 1H, J=7.5 Hz), 6.84-6.90 (m, 1H), 7.11-7.19 (m, 1H), 7.31 (s, 2H), 7.37 (d, 2H, J=8.4 Hz), 7.47 (d, 2H, J=5.1 Hz), 7.95 (br s, 1H), 8.67 (d, 2H, J=4.8 Hz). ES-MS m/z 590 (M+H).

EXAMPLE 95

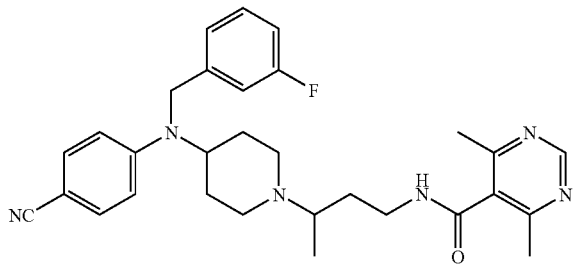

COMPOUND 95: 4,6-Dimethyl-pyrimidine-5-carboxylic acid (3-{4-[(4-cyano-phenyl)-(3-fluoro-benzyl)-amino]-piperidin-1-yl}-butyl)-amide White solid. $^1$H NMR (CDCl$_3$) δ 1.02 (d, 3H, J=6.3 Hz), 1.53-1.67 (m, 2H), 1.69-1.85 (m, 4H), 2.16-2.27 (m, 1H), 2.52-2.27 (m, 1H), 2.76-2.96 (m, 3H), 3.39-3.50 (m, 1H), 3.66-3.86 (m, 2H), 4.58 (s, 2H), 6.65 (d, 2H, J=8.4 Hz), 6.88-6.99 (m, 2H), 7.03 (d, 1H, J=7.5 Hz), 7.22-7.37 (m, 2H), 7.42 (d, 2H, J=8.4 Hz), 8.02 (br s, 1H), 8.30 (d, 1H, J=3.6 Hz), 8.53 (dd, 1H, J=8.7, 8.7 Hz). ES-MS m/z 515 (M+H).

Scheme 7 describes the preparation of Examples 96-99, using various general procedures previously described, and reagents listed below.

Scheme 7

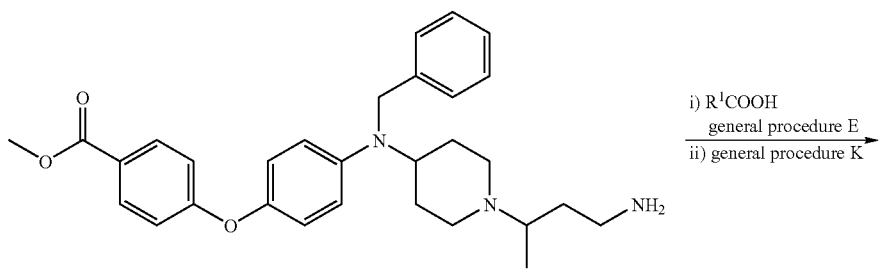

i) R$^1$COOH
general procedure E
ii) general procedure K

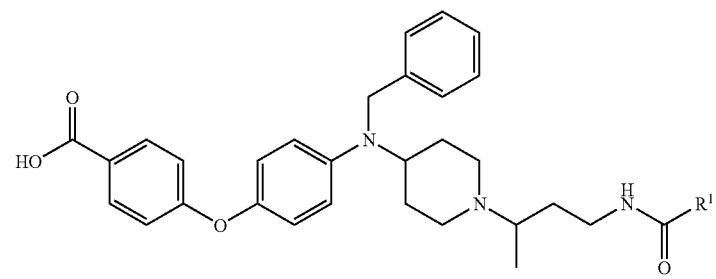

| Example | R¹COOH |
|---|---|
| 96 | 4,6-dimethyl-pyrimidine-5-carboxylic acid |
| 97 | 2,6-dimethylbenzoic acid |
| 98 | 2,4-dimethyl-1-oxy-nicotinic acid |
| 99 | 4-methylnicotinic acid |

EXAMPLE 96

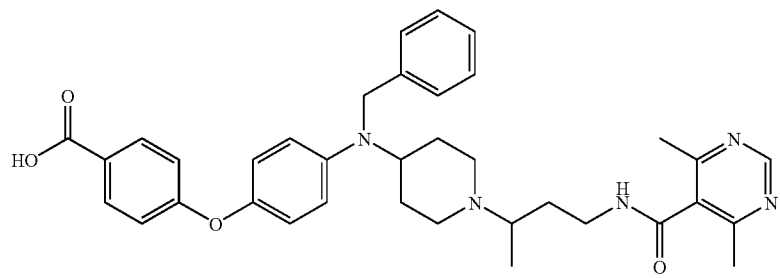

COMPOUND 96: 4-{4-[Benzyl-(1-{3-[(4,6-dimethyl-pyrimidine-5-carbonyl)-amino]-1-methyl-propyl}-piperidin-4-yl)-amino]-phenoxy}-benzoic acid Using general procedure A, 4-(4-aminophenoxy)-benzoic acid methyl ester (Fokin; et al., Chem. Abstr., 72, 12294, 1970) (556 mg, 2.29 mmol) and 1-Boc-4-piperidone (478 mg, 2.40 mmol) gave 4-[4-(4-methoxycarbonyl-phenoxy)-phenylamino]-piperidine-1-carboxylic acid tert-butyl ester (917 mg, 94%) as a crystalline solid.

Using general procedure H, the above aniline (550 mg, 1.29 mmol) and benzyl bromide (265 mg, 1.55 mmol) gave 4-{benzyl-[4-(4-methoxycarbonyl-phenoxy)-phenyl]-amino}-piperidine-1-carboxylic acid tert-butyl ester (660 mg, 99%) as a colorless oil.

Using general procedure C with the above carbamate (660 mg, 1.28 mmol), then general procedure B with the resulting amine and 2-(3-oxo-butyl)-isoindole-1,3-dione (522 mg, 2.40 mmol) and then using general procedure D gave 4-(4-{[1-(3-amino-1-methyl-propyl)-piperidin-4-yl]-benzyl-amino}-phenoxy)-benzoic acid methyl ester (341 mg, 56% over 3 steps) as a colorless oil.

COMPOUND 96 was isolated as an off-white solid. ¹H NMR (CDCl₃) δ 1.15 (d, 3H, J=5.4 Hz), 1.61-1.79 (m, 3H), 1.82-2.17 (m, 3H), 2.39-2.52 (m, 1H), 2.48 (s, 6H), 2.67-2.79 (m, 1H), 2.95-3.14 (m, 2H), 3.21-3.47 (m, 2H), 3.56-3.77 (m, 2H), 4.11-4.22 (m, 2H), 6.69 (d, 2H, J=7.8 Hz), 6.78-6.88 (m, 4H), 7.16-7.31 (m, 5H), 7.68 (d, 2H, J=7.5 Hz), 8.74 (br s, 1H), 8.86 (s, 1H). ES-MS m/z 608 (M+H).

EXAMPLE 97

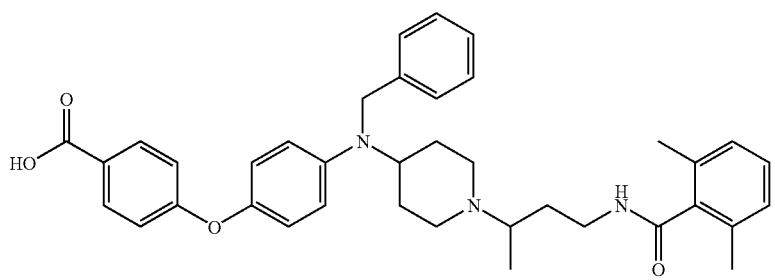

COMPOUND 97: 4-[4-(Benzyl-{1-[3-(2,6-dimethyl-benzoylamino)-1-methyl-propyl]-piperidin-4-yl}-amino)-phenoxy]-benzoic acid White solid. $^1$H NMR (CD$_3$OD) δ 1.40 (d, 3H, J=6.6 Hz), 1.80-1.93 (m, 1H), 1.96-2.21 (m, 5H), 2.29 (s, 6H), 3.12-3.26 (m, 2H), 3.36-3.60 (m, 5H), 4.03-4.14 (m, 1H), 4.44 (s, 2H), 6.82-6.89 (m, 6H), 7.04 (d, 2H, J=7.5 Hz), 7.14-7.21 (m, 2H), 7.24-7.30 (m, 4H), 7.90 (d, 2H, J=8.4 Hz). ES-MS m/z 606 (M+H).

EXAMPLE 98

COMPOUND 98: 4-{4-[Benzyl-(1-{3-[(2,4-dimethyl-1-oxy-pyridine-3-carbonyl)-amino]-1-methyl-propyl}-piperidin-4-yl)-amino]-phenoxy}-benzoic acid Beige solid. $^1$H NMR (MeOH-d$_4$) δ1.19 (d, 3H, J=6.6 Hz), 1.65-1.87 (m, 3H), 1.92-2.05 (m, 3H), 2.33 (s, 3H), 2.46 (s, 3H), 2.58-2.68 (m, 1H), 2.74-2.84 (m, 1H), 2.95-3.12 (m, 3H), 3.38-3.58 (m, 2H), 3.78-3.89 (m, 1H), 4.40 (s, 2H), 6.76-6.87 (m, 6H), 7.14-7.21 (m, 1H), 7.23-7.31 (m, 5H), 7.81-7.91 (m, 2H), 8.23 (d, 1H, J=6.0 Hz). ESI-MS m/z 623 (MH)$^+$.

EXAMPLE 99

COMPOUND 99: 4-{4-[Benzyl-(1-{1-methyl-3-[(4-methyl-pyridine-3-carbonyl)-amino]-propyl}-piperidin-4-yl)-amino]-phenoxy}-benzoic acid White solid. $^1$H NMR (CD$_3$OD) δ 1.34 (d, 3H, J=6.6 Hz), 1.75-1.87 (m, 1H), 1.94-2.20 (m, 5H), 2.45 (s, 3H), 2.97-3.19 (m, 2H), 3.39-3.60 (m, 5H), 3.94-4.06 (m, 1H), 4.41 (s, 2H), 6.77-6.86 (m, 6H), 7.12-7.28 (m, 5H), 7.33 (d, 1H, J=5.1 Hz), 7.87 (d, 2H, J=8.1 Hz), 8.43 (d, 1H, J=4.2 Hz), 8.52 (s, 1H). ES-MS m/z 593 (M+H).

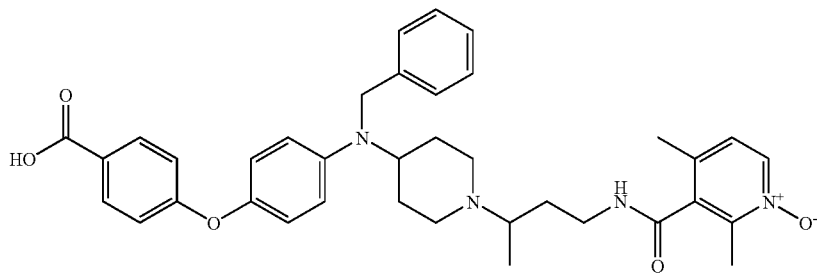

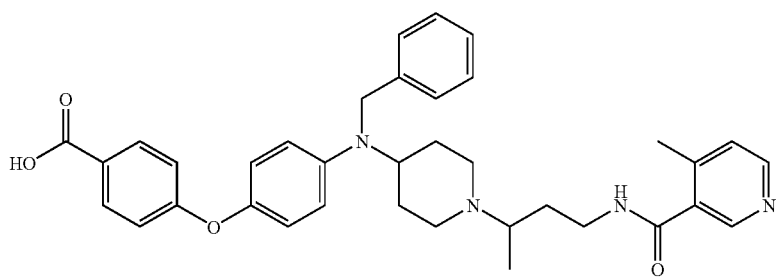

EXAMPLE 100

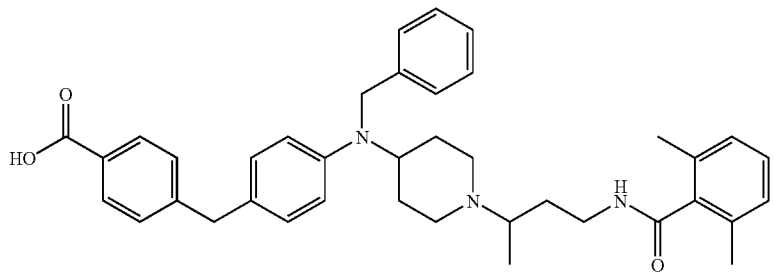

COMPOUND 100: 4-[4-(Benzyl-{1-[3-(2,6-dimethyl-benzoylamino)-1-methyl-propyl]-piperidin-4-yl}-amino)-benzyl]-benzoic acid A solution of 4-(4-nitro-benzoyl)-benzoic acid (Dinsmore, Christopher J.; et al., *Bioorg. Med. Chem. Lett.*, 7, 10, 1997, 1345-1348) (4.00 g, 14.7 mmol) and sulfuric acid (1.2 mL) in MeOH (40 mL) was heated at reflux for 18 h. The mixture was filtered and after work-up gave 4-(4-nitro-benzoyl)-benzoic acid methyl ester as a yellow solid (3.97 g, 94%).

The above substrate (3.23 g, 11.3 mmol) in MeOH (40 mL) was flushed with $N_2$ in a Parr flask. 10% Pd/C (200 mg) was added and the mixture was hydrogenated at 45 psi $H_2$ for 20 h. The mixture was filtered through Celite® and concentrated to give 4-(4-amino-benzyl)-benzoic acid methyl ester as pink crystals (660 mg, 24%) and 4-[(4-amino-phenyl)-hydroxymethyl]-benzoic acid methyl ester as yellow crystals (2.07 g, 71%) following purification.

Using general procedure A, 4-(4-amino-benzyl)-benzoic acid methyl ester (0.66 g, 2.7 mmol) and 1-Boc-4-piperidone (545 mg, 2.74 mmol) gave 4-[4-(4-methoxycarbonyl-benzyl)-phenylamino]-piperidine-1-carboxylic acid tert-butyl ester as a yellow foam (434 mg, 36%).

Using general procedure H, the above amine (434 mg, 1.02 mmol) and benzyl bromide (0.18 mL, 1.5 mmol) gave 4-{benzyl-[4-(4-methoxycarbonyl-benzyl)-phenyl]-amino}-piperidine-1-carboxylic acid tert-butyl ester as a yellow foam (444 mg, 84%).

Using general procedure C with the carbamate from above (444 mg, 0.863 mmol), and then general procedure B with the resulting amine and 2-(3-oxo-butyl)-isoindole-1,3-dione (375 mg, 1.73 mmol) and then using general procedure D gave 4-(4-{[1-(3-amino-1-methyl-propyl)-piperidin-4-yl]-benzyl-amino}-benzyl)-benzoic acid methyl ester as a yellow oil (146 mg, 35% over 3 steps).

Using general procedure E, the above amine (124 mg, 0.255 mmol) and 2,6-dimethylbenzoic acid (46 mg, 0.31 mmol) gave 4-[4-(benzyl-{1-[3-(2,6-dimethyl-benzoylamino)-1-methyl-propyl]-piperidin-4-yl}-amino)-benzyl]-benzoic acid methyl ester as a yellow foam (133 mg, 84%).

Using general procedure K, the above methyl ester (106 mg, 0.172 mmol) gave COMPOUND 100 as a yellow foam (100 mg, 96%). $^1$H NMR (CD$_3$OD) δ 1.34 (d, 3H, J=6.3 Hz), 1.76-2.18 (m, 6H), 2.26 (s, 6H), 3.06 (m, 2H), 3.30-3.57 (m, 5H), 3.81 (s, 2H), 3.99 (m, 1H), 4.24 (s, 2H), 6.67 (d, 2H, J=8.4 Hz), 6.94 (d, 2H, J=8.1 Hz), 7.01 (d, 2H, J=7.5 Hz), 7.13 (m, 8H), 7.81 (d, 2H, J=7.8 Hz). $^{13}$C NMR (CDCl$_3$) δ 13.15, 19.67, 27.34, 27.96, 31.79, 37.91, 41.27, 45.13, 50.13, 51.34, 54.91, 59.36, 114.18, 126.62, 126.98, 127.80, 128.82, 128.92, 129.85, 130.06, 130.29, 130.92, 134.35, 138.23, 140.59, 146.48, 147.58, 171.27, 171.81. ES-MS t/z 604 (M+H). Anal. Calcd. for $C_{39}H_{45}N_3O_3 \cdot 0.6CH_2Cl_2$: C, 72.64; H, 7.11; N, 6.42. Found. C, 72.30; H, 7.11; N, 6.45.

EXAMPLE 101

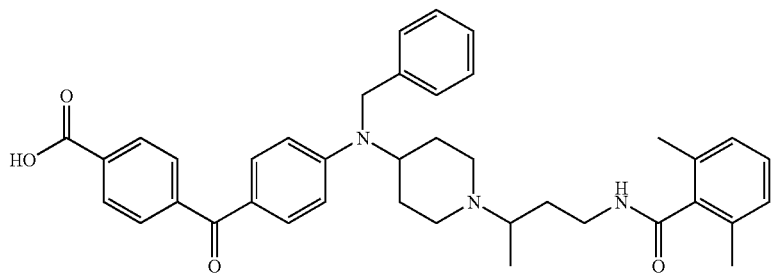

COMPOUND 101: 4-[4-(Benzyl-{1-[3-(2,6-dimethyl-benzoylamino)-1-methyl-propyl]-piperidin-4-yl}-amino)-benzoyl]-benzoic acid Using general procedure A, 4-[(4-amino-phenyl)-hydroxy-methyl]-benzoic acid methyl ester (see EXAMPLE 100) (1.40 g, 5.44 mmol) and 1-Boc-4-piperidone (1.63 g, 8.18 mmol) gave 4-{4-[hydroxy-(4-methoxycarbonyl-phenyl)-methyl]-phenylamino}-piperidine-1-carboxylic acid tert-butyl ester as a pale solid (2.04 g, 85%).

Using general procedure H, the above amine (2.04 g, 4.63 mmol) and benzyl bromide (0.77 mL, 6.5 mmol) gave the alcohol (444 mg, 0.837 mmol), which was subsequently oxidized with MnO$_2$ (85%, 856 mg, 8.37 mmol) in CH$_2$Cl$_2$ (8.4 mL) to give 4-{benzyl-[4-(4-methoxycarbonyl-benzoyl)-phenyl]-amino}-piperidine-1-carboxylic acid tert-butyl ester as a yellow foam (381 mg, 13% over 2 steps) following filtration through Celite®.

Using general procedure C with the carbamate from above (381 mg, 0.721 mmol), then general procedure I with the resulting amine followed by general procedure J gave the crude primary amine that was used in the next reaction without purification.

The above substrate (249 mg) and $MnO_2$ (85%, 227 mg, 2.21 mmol) in $CH_2Cl_2$ (9 mL) were stirred at room temperature for 4 days. The mixture was filtered through Celite®V and concentrated to give 4-(4-{[1-(3-amino-1-methyl-propyl)-piperidin-4-yl]-benzyl-amino}-benzoyl)-benzoic acid methyl ester as a yellow foam (92 mg, 25% over 4 steps) following purification.

Using general procedure E with the above amine (46 mg, 0.092 mmol) and 2,6-dimethylbenzoic acid (17 mg, 0.11 mmol) followed by general procedure K with the resulting ester gave COMPOUND 101 as a yellow powder (22 mg, 48% over 2 steps). $^1$H NMR ($CDCl_3$+$CD_3OD$) δ 1.05 (d, 3H, J=5.7 Hz), 1.52 (m, 3H), 1.76-1.97 (m, 3H), 2.19 (s, 6H), 2.39 (m, 1H), 2.67 (m, 1H), 2.91 (m, 3H), 3.26 (m, 1H), 3.61 (m, 1H), 3.85 (m, 1H), 4.11 (s, 2H), 6.54 (d, 2H, J=8.1 Hz), 6.89 (d, 2H, J=7.2 Hz), 7.02 (m, 3H), 7.16 (m, 3H), 7.53 (m, 4H), 7.95 (d, 2H, J=6.9 Hz). $^{13}$C NMR ($CDCl_3$+$CD_3OD$) δ 13.20, 19.10, 28.29, 29.09, 31.02, 38.54, 44.54, 51.27, 55.08, 59.79, 111.77, 125.19, 125.99, 127.06, 127.53, 128.75, 128.89, 129.02, 129.31, 133.02, 134.06, 137.80, 137.95, 138.65, 141.26, 152.68, 171.24, 173.21, 195.46. ES-MS m/z 618 (M+H). Anal. Calcd. for $C_{39}H_{43}N_3O_4 \cdot 0.8CH_2Cl_2$: C, 69.71; H, 6.56; N, 6.13. Found. C, 69.61; H, 6.48; N, 6.05.

58.93, 114.26, 126.48, 126.91, 128.73, 128.87, 129.96, 130.02, 130.82, 131.69, 140.33, 146.24, 147.43, 157.34, 163.70, 167.59, 172.17. ES-MS m/z 606 (M+H). Anal. Calcd. for $C_{37}H_{43}N_5O_3 \cdot 0.7CH_2Cl_2$: C, 68.07; H, 6.73; N, 10.53. Found. C, 68.09; H, 6.66; N, 10.49.

Scheme 8 describes the preparation of Examples 103-124, using various general procedures previously described, and reagents listed below.

Scheme 8

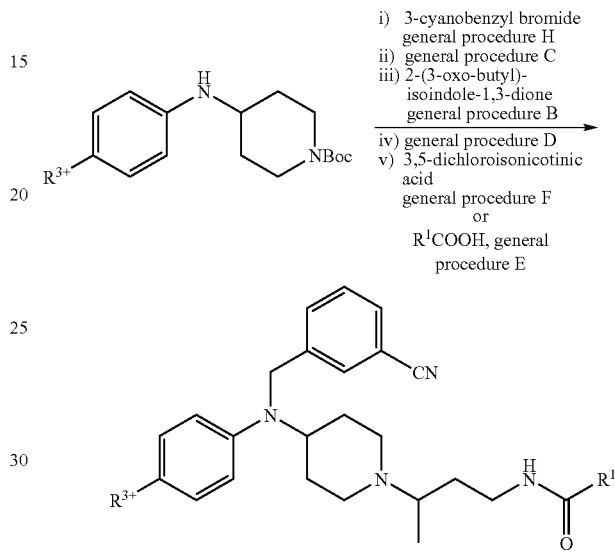

i) 3-cyanobenzyl bromide
general procedure H
ii) general procedure C
iii) 2-(3-oxo-butyl)-isoindole-1,3-dione
general procedure B
iv) general procedure D
v) 3,5-dichloroisonicotinic acid
general procedure F
or
$R^1COOH$, general procedure E

EXAMPLE 102

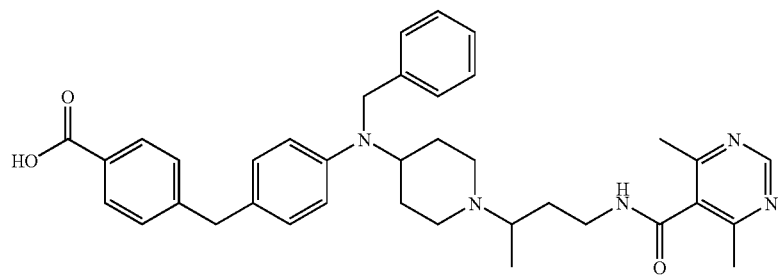

COMPOUND 102: 4-{4-[Benzyl-(1-{3-[(4,6-dimethyl-pyrimidine-5-carbonyl)-amino]-1-methyl-propyl}-piperidin-4-yl)-amino]-benzyl}-benzoic acid Using general procedure E with 4-(4-{[1-(3-amino-1-methyl-propyl)-piperidin-4-yl]-benzyl-amino}-benzyl)-benzoic acid methyl ester (see EXAMPLE 100) (79 mg, 0.16 mmol) and 4,6-dimethyl-pyrimidine-5-carboxylic acid (30 mg, 0.20 mmol) followed by general procedure K with the resulting ester gave COMPOUND 102 as a yellow powder (59 mg, 70% over 2 steps). $^1$H NMR ($CDCl_3$+$CD_3OD$) δ 1.20 (d, 3H, J=6.0 Hz), 1.68 (m, 1H), 1.90 (m, 4H), 2.13 (m, 1H), 2.40 (s, 6H), 2.61 (m, 1H), 2.81 (m, 1H), 3.09-3.37 (m, 4H), 3.54 (m, 1H), 3.80 (m, 3H), 4.23 (s, 2H), 6.55 (d, 2H, J=7.8 Hz), 6.90 (d, 2H, J=7.8 Hz), 7.09 (m, 7H), 7.71 (d, 2H, J=7.5 Hz), 8.77 (s, 1H). $^1$H NMR ($CDCl_3$+$CD_3OD$) δ 12.71, 21.99, 27.18, 27.54, 31.62, 37.35, 41.10, 45.34, 50.14, 51.13, 54.40,

| Example | R$^{3*}$ | R$^1$COOH |
|---|---|---|
| 103 | Br | 3,5-dichloroisonicotinic acid |
| 104 | CF$_3$ | 3,5-dichloroisonicotinic acid |
| 105 | SMe | 3,5-dichloroisonicotinic acid |
| 106 | CN | 3,5-dichloroisonicotinic acid |
| 107 | COOMe | 3,5-dichloroisonicotinic acid |
| 108 | Cl | 3,5-dichloroisonicotinic acid |
| 109 | CONMe$_2$ | 2,6-dimethylbenzoic acid |
| 110 | CONMe$_2$ | 2,6-dimethyl-4-pyridin-4-yl-benzoic acid |
| 111 | NHCOMe | 4,6-dimethyl-pyrimidine-5-carboxylic acid |
| 112 | NHCOMe | 2,6-dimethylbenzoic acid |
| 113 | O(CH$_2$)$_2$OMe | 2,6-dimethylbenzoic acid |
| 114 | O(CH$_2$)$_2$OMe | 4,6-dimethyl-pyrimidine-5-carboxylic acid |
| 115 | OCH$_2$CONHNH$_2$ | 2,6-dimethylbenzoic acid |
| 116 | OCH$_2$CONHNH$_2$ | 4,6-dimethyl-pyrimidine-5-carboxylic acid |

-continued

| Example | R³* | R¹COOH |
|---|---|---|
| 117 | OH | 2,6-dimethylbenzoic acid |
| 118 | NHSO₂Me | 4,6-dimethyl-pyrimidine-5-carboxylic acid |
| 119 | OMe | 4,6-dimethyl-pyrimidine-5-carboxylic acid |
| 120 | OMe | 2,6-dimethylbenzoic acid |
| 121 | OMe | 2,4-dimethyl-1-oxy-nicotinc acid |
| 122 | OCF₃ | 2,6-dimethylbenzoic acid |
| 123 | OCF₃ | 4,6-dimethyl-pyrimidine-5-carboxylic acid |
| 124 | OCF₃ | 2,4-dimethyl-1-oxy-nicotinc acid |

EXAMPLE 103

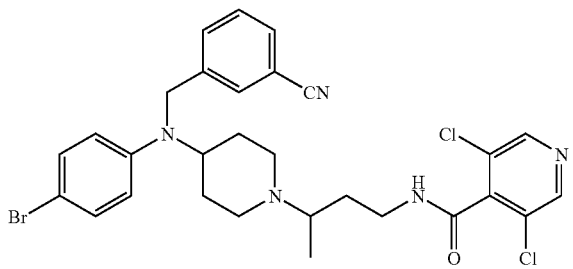

COMPOUND 103: N-(3-{4-[(4-Bromo-phenyl)-(3-cyano-benzyl)-amino]-piperidin-1-yl}-butyl)-3,5-dichloro-isonicotinamide White solid. ¹H NMR (CDCl₃) δ 1.02 (d, 3H, J=6.6 Hz), 1.07-1.28 (m, 1H), 1.49-1.61 (m, 1H), 1.65-1.89 (m, 4H), 2.19 (t, 1H, J=11.3 Hz), 2.58 (t, 1H, J=11.3 Hz), 2.76-2.98 (m, 3H), 3.36 (t, 1H, J=10.0 Hz), 3.61 (t, 1H, J=11.7 Hz), 3.84 (s, 2H), 3.82-3.92 (m, 1H), 6.42 (d, 2H, J=6.6 Hz), 7.20 (d, 2H, J=8.8 Hz), 7.40-7.58 (m, 4H), 8.45 (s, 2H), 8.79 (s, 1H). ¹³C NMR (CDCl₃) δ 13.8, 29.8, 30.8, 40.5, 43.9, 48.5, 52.3, 56.7, 60.6, 110.2, 113.2, 115.4, 115.7, 119.2, 129.5, 129.8, 130.1, 131.2, 132.4, 141.5, 143.6, 147.3, 148.0, 161.8. ES-MS m/z 616 (M+2)⁺. Anal. Calcd. for $C_{29}H_{30}N_5Cl_2OBr \cdot 0.2CH_2Cl_2$: C, 55.46; H, 4.85; N, 11.07; Cl, 13.45. Found. C, 55.69; H, 4.98; N, 10.95; Cl, 13.38.

EXAMPLE 104

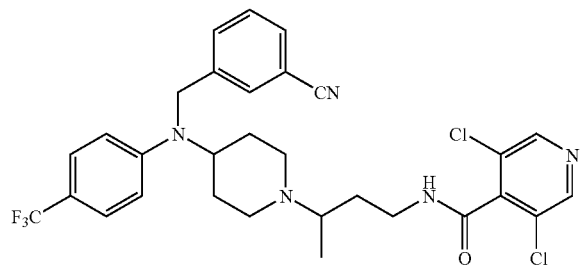

COMPOUND 104: 3,5-Dichloro-N-(3-{4-[(3-cyano-benzyl)-(4-trifluoro-methyl-phenyl)-amino]-piperidin-1-yl}-butyl)-isonicotinamide White powder. ¹H NMR (CDCl₃) δ 0.98-1.12 (m, 1H), 1.04 (d, 3H, J=6.6 Hz), 1.15-1.29 (m, 1H), 1.52-1.63 (m, 1H), 1.74-1.88 (m, 3H), 2.18-2.27 (m, 1H), 2.57-2.60 (m, 1H), 2.80-2.99 (m, 3H), 3.32-3.43 (m, 1H), 3.70-3.92 (m, 2H), 3.95 (s, 2H), 6.56 (d, 2H, J=8.7 Hz), 7.38 (d, 2H, J=8.7 Hz), 7.43-7.49 (m, 3H), 7.54-7.59 (m, 1H), 8.48 (s, 2H), 8.67 (br s, 1H). ¹³C NMR (CDCl₃) δ 13.36, 29.33, 30.34, 30.49, 39.87, 43.47, 47.88, 51.73, 55.72, 59.88, 112.19, 112.77, 118.68, 119.02 (q, J=32.6 Hz), 124.65 (q, J=270 Hz), 126.58 (q, J=3.7 Hz), 129.07, 129.44, 129.49, 130.53, 130.82, 140.55, 143.14, 147.50, 150.20 (q, J=1.2 Hz), 161.33. ESI-MS m/z 604 (MH)⁺, 606 (MH+2)⁺. Anal. Calcd. for $C_{30}H_{30}Cl_2F_3N_5O \cdot 0.3H_2O$: C, 59.08; H, 6.05; N, 11.48; Cl, 11.63. Found. C, 59.13; H, 5.10; N, 11.22; Cl, 11.87.

EXAMPLE 105

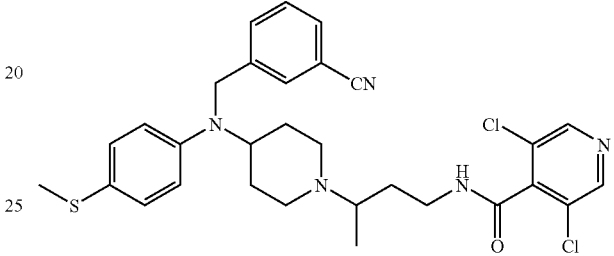

COMPOUND 105: 3,5-Dichloro-N-(3-{4-[(3-cyano-benzyl)-(4-methylsulfanyl-phenyl)-amino]-piperidin-1-yl}-butyl)-isonicotinamide White solid. ¹H NMR (CDCl₃) δ 0.97-1.21 (m, 2H), 1.02 (d, 2H, J=6.6 Hz), 1.51-1.57 (m, 1H), 1.78-1.82 (m, 3H), 2.19 (t, 1H, J=11.4 Hz), 2.39 (s, 3H), 2.59 (t, 1H, J=10.8 Hz), 2.80-2.96 (m, 3H), 3.31-3.39 (m, 1H), 3.60-3.67 (m, 1H), 3.84 (s, 2H), 3.84-3.89 (m, 1H), 6.50 (d, 2H, J=9.0 Hz), 7.16 (d, 2H, J=8.7 Hz), 7.42-7.58 (m, 4H), 8.47 (s, 2H), 8.87 (br s, 1H). ¹³C NMR (CDCl₃) δ 13.41, 18.52, 29.38, 30.33, 30.51, 40.21, 43.49, 48.18, 52.02, 56.23, 60.32, 112.70, 113.99, 114.38, 118.91, 125.33, 129.15, 129.36, 129.82, 130.70, 130.85, 141.44, 143.26, 146.59, 147.58, 161.38. ES-MS m/z 582 (M+H). Anal. Calcd. for $C_{30}H_{33}N_5OSCl_2 \cdot 0.4H_2O$: C, 61.09; H, 5.78; N, 11.87; S, 5.44; Cl, 12.02. Found. C, 61.05; H, 5.74; N, 12.13; S, 5.22; Cl, 12.20.

EXAMPLE 106

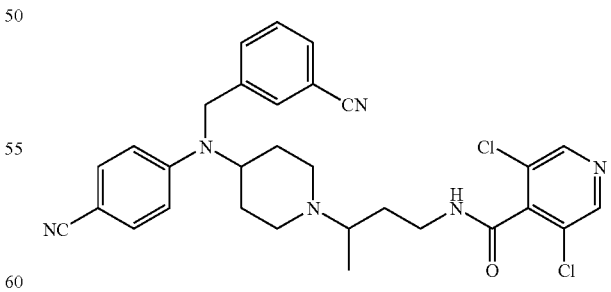

COMPOUND 106: 3,5-Dichloro-N-(3-{4-[(3-cyano-benzyl)-(4-cyano-phenyl)-amino]-piperidin-1-yl}-butyl)-isonicotinamide Using general procedure A, 4-aminobenzonitrile (1.19 g, 10.1 mmol) and 1-Boc-4-piperidone (2.05 g, 10.3 mmol)

gave 4-(4-cyano-phenylamino)-piperidine-1-carboxylic acid tert-butyl ester as a white solid (1.58 g, 52%).

COMPOUND 106 was isolated as a white powder. $^1$H NMR (CDCl$_3$) δ 1.04 (d, 3H, J=6.6 Hz), 1.03-1.16 (m, 1H), 1.19-1.32 (m, 1H), 1.52-1.63 (m, 1H), 1.74-1.87 (m, 3H), 2.19-2.27 (m, 1H), 2.57-2.66 (m, 1H), 2.79-3.00 (m, 3H), 3.34-3.44 (m, 1H), 3.71-3.89 (m, 2H), 4.01 (s, 2H), 6.54 (d, 2H, J=9.0 Hz), 7.39-7.52 (m, 5H), 7.56-7.61 (m, 1H), 8.46 (br s, 1H), 8.48 (s, 2H). $^{13}$C NMR (CDCl$_3$) δ 13.35, 29.35, 30.25, 30.64, 39.64, 43.46, 47.74, 51.50, 55.67, 59.55, 99.15, 112.49, 112.83, 118.55, 119.88, 129.03, 129.27, 129.60, 130.40, 130.95, 133.59, 139.84, 143.04, 147.47, 150.77, 161.34. ESI-MS m/z 561 (MH)$^+$, 563 (MH+2)$^+$. Anal. Calcd. for C$_{30}$H$_{30}$Cl$_2$N$_6$O.0.4CH$_2$Cl$_2$: C, 61.32; H, 5.21; N, 14.11; Cl, 16.67. Found. C, 61.27; H, 5.11; N, 13.74; Cl, 16.64.

EXAMPLE 107

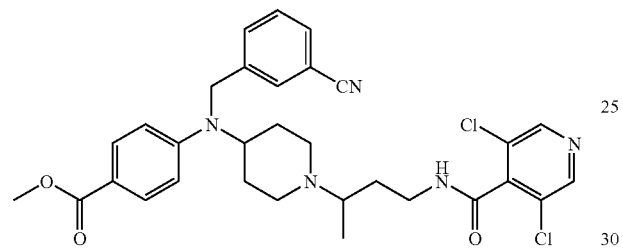

COMPOUND 107: 4-[(3-Cyano-benzyl)-(1-{3-[(3,5-dichloro-pyridine-4-carbonyl)-amino]-1-methyl-propyl}-piperidin-4-yl)-amino]-benzoic acid methyl ester White solid. $^1$H NMR (CDCl$_3$) δ 0.97-1.25 (m, 2H), 1.03 (d, 3H, J=6.6 Hz), 1.54-1.59 (m, 1H), 1.69-1.82 (m, 3H), 2.23 (t, 1H, J=11.1 Hz), 2.61 (t, 1H, J=10.8 Hz), 2.81-2.96 (m, 3H), 3.33-3.41 (m, 1H), 3.76-3.87 (m, 2H), 3.83 (s, 3H), 3.99 (s, 2H), 6.52 (d, 2H, J=9.0 Hz), 7.43-7.49 (m, 3H), 7.54-7.61 (m, 1H), 7.82 (d, 2H, J=9.0 Hz), 8.47 (s, 2H), 8.64 (br s, 1H). $^{13}$C NMR (CDCl$_3$) δ 13.83, 29.87, 30.90, 40.42, 43.08, 43.90, 48.26, 52.03, 52.22, 56.09, 60.44, 112.21, 113.26, 119.13, 129.54, 129.92, 130.98, 131.28, 131.87, 140.95, 143.59, 147.99, 151.78, 161.80, 167.39. ES-MS m/z 595 (M+2). Anal. Calcd. for C$_{31}$H$_{33}$N$_5$Cl$_2$O$_3$.0.4CH$_2$Cl$_2$: C, 60.01; H, 5.42; N, 11.14. Found. C, 59.91; H, 5.38; N, 10.84.

EXAMPLE 108

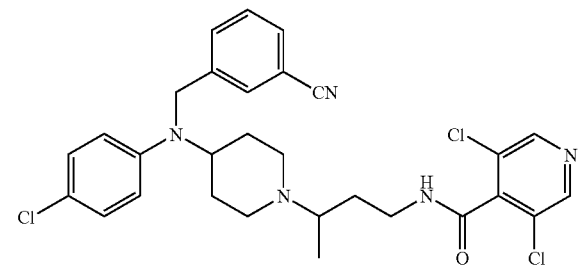

COMPOUND 108: 3,5-Dichloro-N-(3-{4-[(4-chloro-phenyl)-(3-cyano-benzyl)-amino]-piperidin-1-yl}-butyl)-isonicotinamide Using general procedure A, 4-chloroaniline (640 mg, 5.0 mmol) and 1-Boc-4-piperidone (1.0 g, 5.0 mmol) afforded 4-(4-chloro-phenylamino)-piperidine-1-carboxylic acid tert-butyl ester (1.21 g, 78%).

COMPOUND 108 was isolated as a white solid. $^1$H NMR (CDCl$_3$) δ 0.94-1.22 (m, 2H), 1.02 (d, 3H, J=6.3 Hz), 1.53-1.57 (m, 1H), 1.78-1.82 (m, 3H), 2.19 (t, 1H, J=11.4 Hz), 2.59 (t, 1H, J=10.8 Hz), 2.80-2.96 (m, 3H), 3.32-3.40 (m, 1H), 3.57-3.65 (m, 1H), 3.83 (s, 2H), 3.83-3.90 (m, 1H), 6.47 (d, 2H, J=8.7 Hz), 7.08 (d, 2H, J=8.4 Hz), 7.46 (m, 3H), 7.54 (br s, 1H), 8.46 (s, 2H), 8.82 (br s, 1H). $^{13}$C NMR (CDCl$_3$) δ 13.41, 29.36, 30.40, 40.11, 43.51, 48.16, 51.93, 56.41, 60.17, 112.72, 114.89, 118.85, 122.69, 129.13, 129.41, 129.75, 130.78, 141.16, 143.22, 146.54, 147.56, 161.38. ES-MS m/z 570 (M+H). Anal. Calcd. for C$_{29}$H$_{30}$N$_5$Cl$_3$O.0.1CH$_2$Cl$_2$.0.1C$_3$H$_7$NO: C, 60.18; H, 5.31; N, 12.17; Cl, 19.34. Found. C, 60.26; H, 5.41; N, 12.04; Cl, 19.05.

EXAMPLE 109

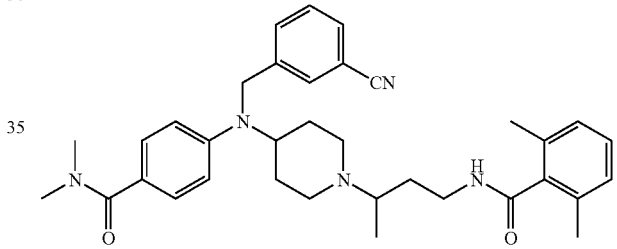

COMPOUND 109: N-(3-{4-[(3-Cyano-benzyl)-(4-dimethylcarbamoyl-phenyl)-amino]-piperidin-1-yl}-butyl)-2,6-dimethyl-benzamide Using general procedure A, 4-amino-N,N-dimethyl-benzamide (Schiemenz, G. P.; Stein, G., *Tetrahedron,* 26, 1970, 2007-2026) (619 mg, 3.77 mmol) and 1-Boc-4-piperidone (901 mg, 4.52 mmol) gave 4-(4-dimethylcarbamoyl-phenylamino)-piperidine-1-carboxylic acid tert-butyl ester as a white solid (1.31 g).

COMPOUND 109 was isolated as a white solid. $^1$H NMR (CDCl$_3$) δ 0.93-1.21 (m, 2H), 1.00 (d, 3H, J=6.6 Hz), 1.51-1.55 (m, 1H), 1.70-1.75 (m, 3H), 2.18 (t, 1H, J=11.1 Hz), 2.31 (s, 6H), 2.57 (t, 1H, J=11.7 Hz), 2.75-2.91 (m, 3H), 3.03 (s, 6H), 3.25-3.33 (m, 1H), 3.64-3.71 (m, 1H), 3.82-3.91 (m, 1H), 3.86 (s, 2H), 6.50 (d, 2H, J=8.4 Hz), 6.95 (d, 2H, J=7.5 Hz), 7.02-7.07 (m, 1H), 7.25-7.28 (m, 2H), 7.41-7.42 (m, 3H), 7.52-7.55 (m, 1H), 8.29 (br s, 1H). $^{13}$C NMR (CDCl$_3$) δ 13.82, 19.55, 29.42, 30.73, 31.40, 40.17, 43.98, 48.31, 52.46, 56.43, 60.85, 112.56, 113.02, 119.29, 124.95, 127.70, 128.80, 129.72, 130.20, 131.00, 131.14, 134.51, 139.03, 142.01, 149.62, 170.23, 172.05. ES-MS m/z 566 (M+H).

EXAMPLE 110

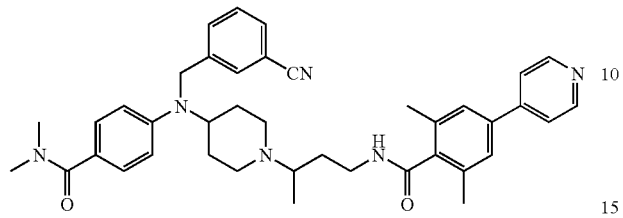

COMPOUND 110: N-(3-{4-[(3-Cyano-benzyl)-(4-dimethylcarbamoyl-phenyl)-amino]-piperidin-1-yl}-butyl)-2,6-dimethyl-4-pyridin-4-yl-benzamide White solid. $^1$H NMR (CDCl$_3$) δ 0.97-1.27 (m, 5H), 1.53-1.60 (m, 1H), 1.70-1.98 (m, 3H), 2.16-2.24 (m, 1H), 2.40 (s, 6H), 2.54-2.61 (m, 1H), 2.77-2.93 (m, 3H), 3.02 (s, 6H), 3.31-3.38 (m, 1H), 3.65-3.73 (m, 1H), 3.85 (br s, 3H), 6.45 (d, 2H, J=8.1 Hz), 7.08-7.10 (m, 1H), 7.22-7.31 (m, 6H), 7.42-7.48 (m, 3H), 8.10 (br s, 1H), 8.65 (s, 2H). $^{13}$C NMR (CDCl$_3$) δ 13.83, 19.77, 29.49, 30.80, 31.74, 39.94, 44.15, 48.15, 52.31, 56.36, 60.42, 112.49, 113.00, 119.16, 121.74, 125.06, 126.34, 129.74, 129.93, 130.88, 130.94, 131.38, 135.76, 138.36, 139.67, 141.74, 147.78, 149.52, 150.91, 169.66, 171.99. ES-MS m/z 643 (M+H). Anal. Calcd. for C$_{40}$H$_{46}$N$_6$O$_2$.1.2CH$_2$Cl$_2$: C, 66.44; H, 6.55; N, 11.28. Found. C, 66.43; H, 6.55; N, 11.24.

EXAMPLE 111

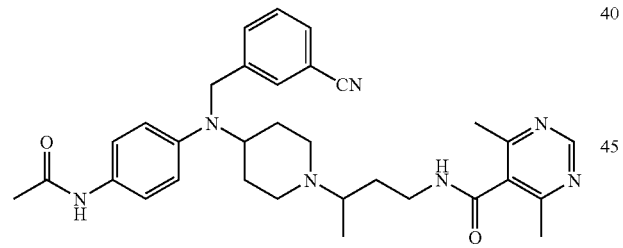

COMPOUND 111: 4,6-Dimethyl-pyrimidine-5-carboxylic acid (3-{4-[(4-acetylamino-phenyl)-(3-cyano-benzyl)-amino]-piperidin-1-yl}-butyl)-amide Using general procedure A, N-(4-amino-phenyl)-acetamide (Gowda, D. Channe; Gowda, Shankare, *Indian J. Chem. Sect.*, 39, 9, 2000, 709-711) (675 mg, 4.49 mmol) and 1-Boc-4-piperidone (938 mg, 4.71 mmol) gave 4-(4-acetylamino-phenylamino)-piperidine-1-carboxylic acid tert-butyl ester as a white solid (923 mg, 62%).

COMPOUND 111 was isolated as a white foam. $^1$H NMR (CDCl$_3$) δ 0.85-1.08 (m, 2H), 1.02 (d, 3H, J=6.3 Hz), 1.49-1.59 (m, 1H), 1.75-1.79 (m, 3H), 2.12 (s, 3H), 2.17 (t, 1H, J=10.8 Hz), 2.51 (s, 6H), 2.57 (t, 1H, J=12.0 Hz), 2.74-2.85 (m, 3H), 3.29-3.36 (m, 1H), 3.54-3.61 (m, 1H), 3.83-3.89 (m, 3H), 6.52 (d, 2H, J=8.4 Hz), 6.99 (br s, 1H), 7.22-7.26 (m, 2H), 7.40-7.45 (m, 1H), 7.51-7.56 (m, 3H), 8.65-8.67 (m, 1H), 8.85 (s, 1H). $^{13}$C NMR (CDCl$_3$) δ 12.18, 20.62, 22.81, 27.99, 29.08, 29.53, 38.59, 42.42, 47.16, 50.58, 54.71, 55.41, 111.09, 113.09, 117.69, 120.69, 127.71, 128.00, 128.70, 129.26, 129.55, 129.81, 140.60, 143.81, 145.99, 156.16, 161.77, 165.04, 167.13. ES-MS m/z 554 (M+H). Anal. Calcd. for C$_{32}$H$_{39}$N$_7$O$_2$.0.9H$_2$O: C, 67.44; H, 7.22; N, 17.20. Found. C, 67.47; H, 7.15; N, 17.09.

EXAMPLE 112

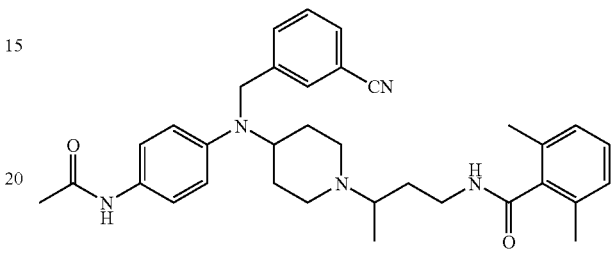

COMPOUND 112: N-(3-{4-[(4-Acetylamino-phenyl)-(3-cyano-benzyl)-amino]-piperidin-1-yl}-butyl)-2,6-dimethyl-benzamide White foam. $^1$H NMR (CDCl$_3$) δ 0.94-1.18 (m, 2H), 1.00 (d, 3H, J=6.6 Hz), 1.50-1.59 (m, 1H), 1.69-1.83 (m, 3H), 2.11 (s, 3H), 2.15 (t, 1H, J=10.8 Hz), 2.31 (s, 6H), 2.55 (t, 1H, J=11.1 Hz), 2.74-2.90 (m, 3H), 3.24-3.31 (m, 1H), 3.53-3.59 (m, 1H), 3.76 (s, 2H), 3.85-3.90 (m, 1H), 6.50 (d, 2H, J=8.7 Hz), 6.92-7.03 (m, 4H), 7.21 (d, 2H, J=8.7 Hz), 7.42-7.44 (m, 3H), 7.51 (br s, 1H), 8.40-8.42 (m, 1H). $^{13}$C NMR (CDCl$_3$) δ 13.84, 19.54, 24.46, 29.40, 30.69, 31.25, 40.26, 44.01, 48.66, 52.54, 57.36, 60.92, 112.76, 114.70, 119.42, 122.40, 127.68, 128.81, 129.32, 129.60, 130.47, 130.84, 131.48, 134.45, 138.93, 142.67, 145.52, 168.88, 170.35. ES-MS m/z 552 (M+H). Anal. Calcd. for C$_{34}$H$_{41}$N$_5$O$_2$.0.7H$_2$O: C, 72.36; H, 7.57; N, 12.41. Found. C, 72.36; H, 7.44; N, 12.30.

EXAMPLE 113

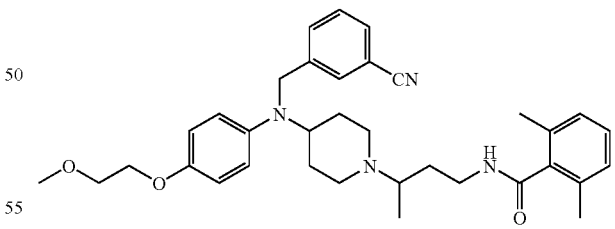

COMPOUND 113: N-[3-(4-{(3-Cyano-benzyl)-[4-(2-methoxy-ethoxy)-phenyl]-amino}-piperidin-1-yl)-butyl]-2,6-dimethyl-benzamide Using general procedure A, 4-(2-methoxy-ethoxy)-phenylamine (Ishidate; Maruyoma, *Chem. Abstr.*, 1952, 8810) (1.15 g, 6.84 mmol) and 1-Boc-4-piperidone (1.36 g, 6.83 mmol) afforded 4-[4-(2-methoxy-ethoxy)-phenylamino]-piperidine-1-carboxylic acid tert-butyl ester (2.08 g, 86%).

Anal. Calcd. for C$_{35}$H$_{43}$N$_5$O$_2$.0.3CH$_2$Cl$_2$: C, 71.71; H, 7.43; N, 11.85. Found. C, 71.57; H, 7.46; N, 11.63.

COMPOUND 113 was isolated as a white solid. ¹H NMR (CDCl₃) δ 0.88-1.16 (m, 2H), 0.98 (d, 3H, J=6.3 Hz), 1.49-1.54 (m, 1H), 1.69-1.78 (m, 3H), 2.11 (t, 1H, J=11.4 Hz), 2.30 (s, 6H), 2.52 (t, 1H, J=10.8 Hz), 2.72-2.88 (m, 3H), 3.22-3.31 (m, 1H), 3.37-3.45 (m, 1H), 3.41 (s, 3H), 3.68 (t, 2H, J=4.8 Hz), 3.71 (s, 2H), 3.85-3.89 (m, 1H), 4.00 (t, 2H, J=4.5 Hz), 6.52 (d, 2H, J=8.1 Hz), 6.74 (d, 2H, J=7.8 Hz), 6.91-6.96 (m, 3H), 7.38-7.50 (m, 4H), 8.45-8.46 (m, 1H). ¹³C NMR (CDCl₃) δ 13.39, 19.14, 29.08, 30.34, 30.91, 39.87, 43.61, 48.78, 52.20, 58.08, 59.16, 60.57, 67.76, 71.15, 112.33, 115.56, 116.60, 119.07, 127.25, 128.35, 129.02, 130.35, 130.39, 131.27, 134.05, 138.63, 142.54, 142.72, 151.65, 169.87. ES-MS m/z 569 (M+H). Anal. Calcd. for C₃₅H₄₄N₄O₃: C, 73.91; H, 7.80; N, 9.85. Found. C, 73.67; H, 7.81; N, 9.76.

EXAMPLE 114

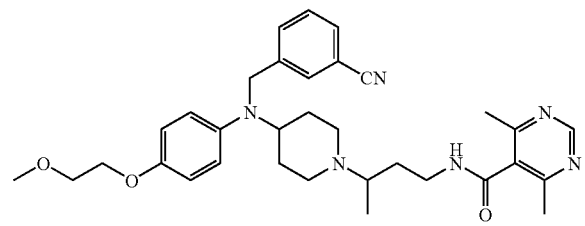

COMPOUND 114: 4,6-Dimethyl-pyrimidine-5-carboxylic acid [3-(4-{(3-cyano-benzyl)-[4-(2-methoxy-ethoxy)-phenyl]-amino}-piperidin-1-yl)-butyl]-amide White solid. ¹H NMR (CDCl₃) δ 0.86-1.10 (m, 2H), 1.00 (d, 3H, J=5.7 Hz), 1.54 (d, 1H, J=12.0 Hz), 1.74-1.78 (m, 3H), 2.14 (t, 1H, J=12.0 Hz), 2.50 (s, 6H), 2.54 (t, 1H, J=12.0 Hz), 2.72-2.84 (m, 3H), 3.27-3.38 (m, 2H), 3.36 (s, 3H), 3.68 (t, 2H, J=4.2 Hz), 3.82 (m, 3H), 4.01 (t, 2H, J=4.5 Hz), 6.54 (d, 2H, J=8.1 Hz), 6.74 (d, 2H, J=8.1 Hz), 7.37-7.42 (m, 1H), 7.47-7.54 (m, 3H), 8.72 (br s, 1H), 8.82 (s, 1H). ¹³C NMR (CDCl₃) δ 13.39, 21.95, 29.24, 30.45, 30.63, 40.10, 43.58, 49.13, 52.06, 57.80, 59.17, 60.38, 67.76, 71.14, 112.40, 115.62, 116.59, 117.10, 119.06, 129.13, 130.38, 130.48, 130.87, 131.37, 142.10, 142.52, 152.00, 157.53, 163.05, 166.32. ES-MS m/z 571 (M+H). Anal. Calcd. for C₃₃H₄₂N₆O₃.0.3CH₂Cl₂: C, 67.08; H, 7.20; N, 14.10. Found. C, 67.26; H, 7.35; N, 14.19.

EXAMPLE 115

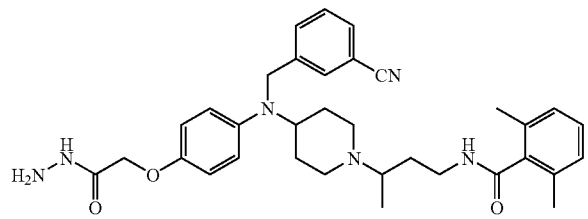

COMPOUND 115: N-(3-{4-[(3-Cyano-benzyl)-(4-hydrazinocarbonylmethoxy-phenyl)-amino]-piperidin-1-yl}-butyl)-2,6-dimethyl-benzamide Using general procedure A, (4-amino-phenoxy)-acetic acid methyl ester (Oguchi, Minoru; et al., *J. Med. Chem.*, 43, 16, 2000, 3052-3066) (860 mg, 4.72 mmol) and 1-Boc-4-piperidone (941 mg, 4.72 mmol) afforded 4-[4-(2-oxo-propoxy)-phenylamino]-piperidine-1-carboxylic acid tert-butyl ester (1.66 g, 96%).

COMPOUND 115 was isolated as a white solid. ¹H NMR (CDCl₃) δ 0.86-1.91 (m, 5H), 1.51-1.55 (m, 1H), 1.70-1.74 (m, 3H), 2.09-2.19 (m, 1H), 2.30 (s, 6H), 2.51-2.58 (m, 1H), 2.76-2.87 (m, 3H), 3.25-3.32 (m, 1H), 3.44-3.50 (m, 1H), 3.74 (s, 2H), 3.86 (br s, 3H), 4.45 (s, 2H), 6.53 (d, 2H, J=9.0 Hz), 6.71 (d, 2H, J=9.0 Hz), 6.91-7.00 (m, 3H), 7.38-7.52 (m, 4H), 7.71 (s, 1H), 8.37 (br s, 1H). ¹³C NMR (CDCl₃) δ 13.78, 19.57, 29.39, 30.65, 31.42, 40.17, 44.09, 48.96, 52.52, 58.12, 60.87, 68.04, 112.89, 116.00, 116.48, 127.67, 128.79, 129.56, 130.61, 130.90, 131.52, 134.48, 142.55, 144.05, 150.13, 169.29. ES-MS m/z 583 (M+H). Anal. Calcd. for C₃₄H₄₂N₆O₃.0.3CH₂Cl₂.0.2C₆H₁₄: C, 68.17; H, 7.32; N, 13.44. Found. C, 68.22; H, 7.31; N, 13.35.

EXAMPLE 116

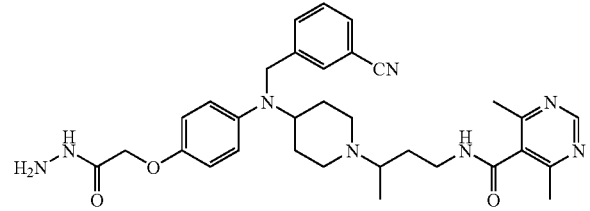

COMPOUND 116: 4,6-Dimethyl-pyrimidine-5-carboxylic acid (3-{4-[(3-cyano-benzyl)-(4-hydrazinocarbonylmethoxy-phenyl)-amino]-piperidin-1-yl}-butyl)-amide White solid. ¹H NMR (CDCl₃) δ 0.87-1.01 (m, 5H), 1.52-1.57 (m, 1H), 1.75-1.78 (m, 3H), 2.10-2.17 (m, 1H), 2.49 (s, 6H), 2.49-2.58 (m, 1H), 2.73-2.84 (m, 3H), 3.24-3.42 (m, 2H), 3.85-3.88 (m, 5H), 4.47 (s, 2H), 6.55 (d, 2H, J=7.5 Hz), 6.71 (d, 2H, J=7.5 Hz), 7.39-7.55 (m, 4H), 7.88 (br s, 1H), 8.66 (br s, 1H), 8.84 (s, 1H). ¹³C NMR (CDCl₃) δ 13.79, 22.30, 29.58, 30.74, 31.07, 38.68, 40.41, 44.00, 49.61, 52.40, 57.91, 60.67, 68.07, 112.86, 115.97, 117.36, 119.38, 129.62, 130.61, 130.98, 131.20, 131.64, 142.16, 143.73, 150.65, 157.88, 163.44, 166.66, 169.27. ES-MS m/z 585 (M+H). Anal. Calcd. for C₃₂H₄₀N₈O₃.0.3CH₂Cl₂.0.08C₆H₁₄: C, 63.80; H, 6.81; N, 18.16. Found. C, 63.66; H, 6.85; N, 18.14.

EXAMPLE 117

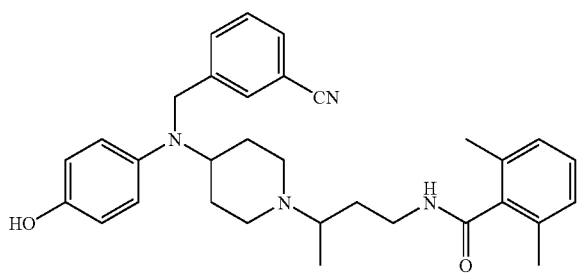

COMPOUND 117: N-(3-{4-[(3-Cyano-benzyl)-(4-hydroxy-phenyl)-amino]-piperidin-1-yl}-butyl)-2,6-dimethyl-benzamide Using general procedure A, 1-Boc-4-piperidone (2.52 g, 12.66 mmol) and acetic acid 4-amino-phenyl ester (Bargota, Rakesh S.; et al., Bioorg. Med. Chem. Lett., 13, 10, 2003, 1623-1626) (2.95 g, 19.52 mmol) afforded 4-(4-acetoxy-phenylamino)-piperidine-1-carboxylic acid tert-butyl ester as a white solid (3.41 g, 76%).

COMPOUND 117 was isolated as a white solid. $^1$H NMR (CDCl$_3$) δ 0.92-1.13 (m, 2H), 0.98 (d, 3H, J=6.3 Hz), 1.50-1.54 (m, 1H), 1.69-1.73 (m, 3H), 2.11 (t, 1H, J=10.8 Hz), 2.31 (s, 6H), 2.51 (t, 1H, J=11.1 Hz), 2.72-2.88 (m, 3H), 3.24-3.37 (m, 2H), 3.69 (s, 2H), 3.87-3.90 (m, 1H), 4.80 (br s, 1H), 5.30 (s, 1H), 6.49 (d, 2H, J=8.4 Hz), 6.63 (d, 2H, J=8.1 Hz), 6.93-6.96 (m, 3H), 7.36-7.51 (m, 4H), 8.48 (br s, 1H). $^{13}$C NMR (CDCl$_3$) δ 13.38, 19.14, 29.08, 30.29, 30.83, 36.56, 39.93, 43.64, 48.99, 52.15, 58.49, 60.52, 112.26, 115.95, 117.52, 119.10, 127.26, 128.42, 128.98, 130.32, 130.53, 131.40, 134.05, 138.42, 142.17, 142.59, 148.97, 170.09. ES-MS m/z 511 (M+H). Anal. Calcd. for C$_{32}$H$_{38}$N$_4$O$_2$.0.8H$_2$O: C, 73.45; H, 7.59; N, 10.71. Found. C, 73.52; H, 7.51; N, 11.06.

EXAMPLE 118

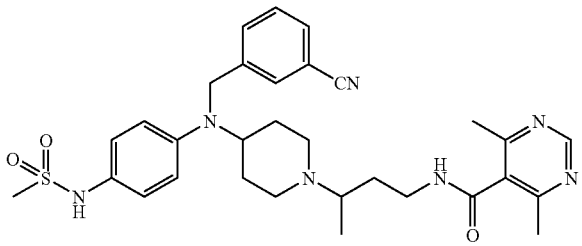

COMPOUND 118: 4,6-Dimethyl-pyrimidine-5-carboxylic acid (3-{4-[(3-cyano-benzyl)-(4-methanesulfonylamino-phenyl)-amino]-piperidin-1-yl}-butyl)-amide To a solution of 4-nitroaniline (5.04 g, 36.5 mmol) in CH$_2$Cl$_2$ (100 ml) cooled to 0° C. were added Et$_3$N (6.61 mL, 47.4 mmol) and MsCl (3.39 mL, 43.8 mmol) and the mixture was stirred at room temperature overnight to give dimethane-sulfonyl-(4-nitro-phenyl)-amine as a yellow solid (10.46 g, 98%) following work-up.

The above substrate (9.2 g, 31 mmol), MeOH (100 mL) and 1N NaOH (150 mL) were stirred at room temperature for 2 hours to give N-(4-nitro-phenyl)-methanesulfonamide as a yellow solid (6.35 g, 94%) following an acidic work-up.

Using general procedure H, the above substrate (1.51 g, 6.98 mmol) and bromomethyl methyl ether (0.86 mL, 10.5 mmol) gave N-methoxymethyl-N-(4-nitro-phenyl)-methanesulfonamide (1.75 g, 96%).

A solution of the above substrate (1.72 g, 6.60 mmol) in MeOH (40 ml) was flushed with N$_2$ in a Parr flask. 10% Pd/C (175 mg) was added and the mixture was hydrogenated at 30 psi H$_2$ for 1 hour. The mixture was filtered through Celite®, the cake was rinsed with MeOH and the combined filtrate was concentrated under reduced pressure to give N-(4-amino-phenyl)-N-methoxymethyl-methanesulfonamide as a white solid (1.47 g, 97%).

Using general procedure A, the above aniline (1.47 g, 6.38 mmol) and 1-Boc-4-piperidone (1.33 g, 6.70 mmol) afforded 4-[4-(methanesulfonyl-methoxymethyl-amino)-phenylamino]-piperidine-1-carboxylic acid tert-butyl ester as a white solid (2.17 g, 83%).

COMPOUND 118 was isolated as a white foam. $^1$H NMR (CDCl$_3$) δ 0.86-1.15 (m, 2H), 1.02 (d, 3H, J=5.4 Hz), 1.49-1.58 (m, 1H), 1.75-1.79 (m, 3H), 2.18 (t, 1H, J=11.7 Hz), 2.51 (s, 6H), 2.58 (t, 1H, J=11.7 Hz), 2.75-2.92 (m, 3H), 2.92 (s, 3H), 3.33-3.37 (m, 1H), 3.59-3.65 (m, 1H), 3.76-3.88 (m, 1H), 3.89 (s, 2H), 6.09 (br s, 1H), 6.51 (d, 2H, J=7.8 Hz), 7.05 (d, 2H, J=7.5 Hz), 7.46-7.55 (m, 4H), 8.60 (br s, 1H), 8.88 (s, 1H). $^{13}$C NMR (CDCl$_3$) δ 13.86, 22.33, 29.57, 30.78, 31.11, 39.18, 40.45, 43.95, 48.76, 52.33, 56.55, 60.61, 112.99, 114.44, 119.34, 125.71, 126.68, 129.81, 130.19, 131.10, 131.28, 141.87, 147.25, 157.91, 163.53, 166.66. ES-MS m/z 590 (M+H). Anal. Calcd. for C$_{31}$H$_{39}$N$_7$O$_3$S.0.3H$_2$O.0.3CH$_2$Cl$_2$: C, 60.57; H, 6.53; N, 15.80; S, 5.17. Found. C, 60.63; H, 6.64; N, 15.66; S, 5.12.

EXAMPLE 119

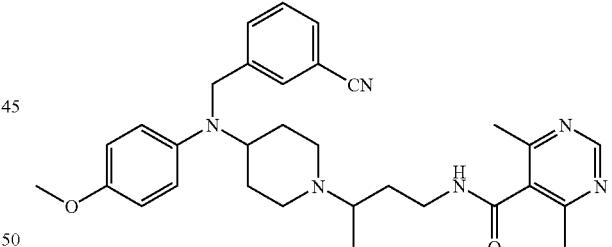

COMPOUND 119: 4,6-Dimethyl-pyrimidine-5-carboxylic acid (3-{4-[(3-cyano-benzyl)-(4-methoxy-phenyl)-amino]-piperidin-1-yl}-butyl)-amide Using general procedure A, 4-methoxyphenylamine (246 mg, 2.00 mmol) and 1-Boc-4-piperidone (418 mg, 2.10 mmol) gave 4-(4-methoxy-phenylamino)-piperidine-1-carboxylic acid tert-butyl ester as a pale yellow oil (612 mg, 100%).

COMPOUND 119 was isolated as a white solid. $^1$H NMR (CDCl$_3$) δ 0.80-1.13 (m, 2H), 1.00 (d, 3H, J=6.3 Hz), 1.49-1.57 (m, 1H), 1.71-1.81 (m, 3H), 2.07-2.19 (m, 1H), 2.47-2.59 (m, 1H), 2.52 (s, 6H), 2.70-2.90 (m, 3H), 3.25-3.46 (m, 2H), 3.72 (s, 3H), 3.80 (s, 2H), 3.82-3.92 (m, 1H), 6.57 (d, 2H, J=9.3 Hz), 6.73 (d, 2H, J=9.0 Hz), 7.37-7.58 (m, 4H), 8.75 (br s, 1H), 8.83 (s, 1H). ES-MS m/z 527 (M+H).

EXAMPLE 120

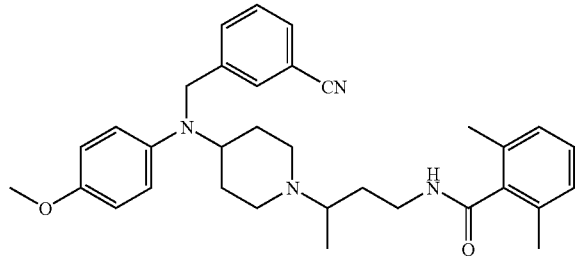

COMPOUND 120: N-(3-{4-[(3-Cyano-benzyl)-(4-methoxy-phenyl)-amino]-piperidin-1-yl}-butyl)-2,6-dimethyl-benzamide White solid. $^1$H NMR (CDCl$_3$) δ 0.87-1.19 (m, 2H), 0.99 (d, 3H, J=6.3 Hz), 1.47-1.58 (m, 1H), 1.48-1.66 (m, 3H), 2.06-2.17 (m, 1H), 2.31 (s, 6H), 2.46-2.58 (m, 1H), 2.70-2.91 (m, 3H), 3.21-3.46 (m, 2H), 3.65-3.74 (m, 5H), 3.84-3.95 (m, 1H), 6.55 (d, 2H, J=8.7 Hz), 6.71 (d, 2H, J=8.7 Hz), 6.89-7.01 (m, 1H), 7.35-7.52 (m, 4H), 8.44 (br s, 1H). ES-MS m/z 525 (M+H).

EXAMPLE 121

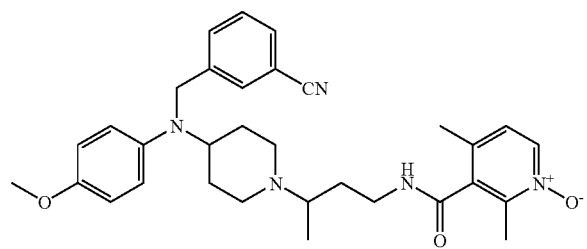

COMPOUND 121: N-(3-{4-[(3-Cyano-benzyl)-(4-methoxy-phenyl)-amino]-piperidin-1-yl}-butyl)-2,4-dimethyl-1-oxy-nicotinamide White solid. $^1$H NMR (CDCl$_3$) δ 0.94-1.28 (m, 2H), 1.00 (d, 3H, J=6.6 Hz), 1.51-1.63 (m, 1H), 1.71-1.85 (m, 3H), 2.10-2.20 (m, 1H), 2.29 (s, 3H), 2.44 (s, 3H), 2.47-2.58 (m, 1H), 2.71-2.89 (m, 3H), 3.28-3.50 (m, 2H), 3.72 (s, 3H), 3.73-3.84 (m, 1H), 3.99 (m, 2H), 6.61 (d, 2H, J=8.7 Hz), 6.73 (d, 2H, J=8.7 Hz), 6.84 (d, 1H, J=6.6 Hz), 7.41 (dd, 1H, J=7.8, 7.2 Hz), 7.55 (s, 1H), 7.60 (d, 1H, J=7.8 Hz), 7.92 (d, 1H, J=6.6 Hz), 8.66 (br s, 1H). ES-MS m/z 542 (M+H).

EXAMPLE 122

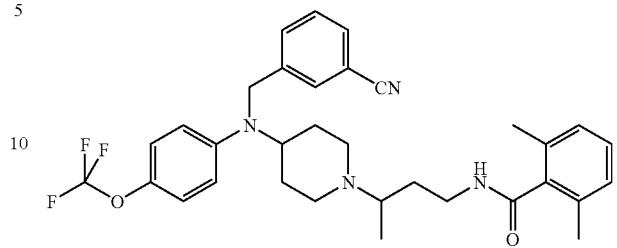

COMPOUND 122: N-(3-{4-[(3-Cyano-benzyl)-(4-trifluoromethoxy-phenyl)-amino]-piperidin-1-yl}-butyl)-2,6-dimethyl-benzamide Using general procedure A, 4-(trifluoromethoxy)aniline (2.09 g, 11.8 mmol) and 1-Boc-4-piperidone (2.6 g, 13.0 mmol) afforded 4-(4-trifluoromethoxy-phenylamino)-piperidine-1-carboxylic acid tert-butyl ester (2.56 g, 60%).

COMPOUND 122 was isolated as a white solid. $^1$H NMR (CDCl$_3$) δ 0.91-1.23 (m, 2H), 1.00 (d, 3H, J=6.4 Hz), 1.47-1.57 (m, 1H), 1.69-1.81 (m, 3H), 2.16 (t, 1H, J=11.7 Hz), 2.31 (s, 6H), 2.56 (t, 1H, J=12.0 Hz), 2.74-2.91 (m, 3H), 3.25-3.33 (m, 1H), 3.55-3.65 (m, 1H), 3.81 (s, 2H), 3.82-3.92 (m, 1H), 6.49 (d, 2H, J=8.8 Hz), 6.93-7.05 (m, 5H), 7.40-7.46 (m, 3H), 7.51-7.56 (m, 1H), 8.31 (br s, 1H). ES-MS m/z 579 (M+H).

EXAMPLE 123

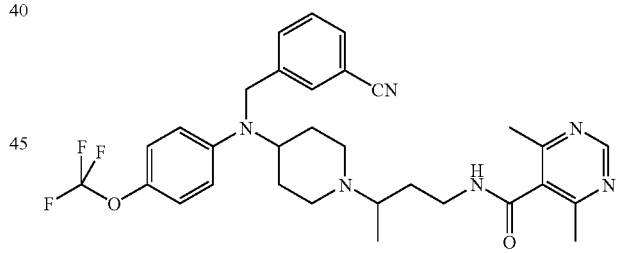

COMPOUND 123: 4,6-Dimethyl-pyrimidine-5-carboxylic acid (3-{4-[(3-cyano-benzyl)-(4-trifluoromethoxy-phenyl)-amino]-piperidin-1-yl}-butyl)-amide White solid. $^1$H NMR (CDCl$_3$) δ 0.88-1.15 (m, 2H), 1.02 (d, 3H, J=6.0 Hz), 1.48-1.57 (m, 1H), 1.71-1.81 (m, 3H), 2.18 (t, 1H, J=11.7 Hz), 2.51 (s, 6H), 2.58 (t, 1H, J=11.4 Hz), 2.75-2.89 (m, 3H), 3.29-3.37 (m, 1H), 3.58-3.65 (m, 1H), 3.82-3.89 (m, 1H), 3.90 (s, 2H), 6.50 (d, 2H, J=9.3 Hz), 7.00 (d, 2H, J=8.4 Hz), 7.43-7.58 (m, 4H), 8.56 (br s, 1H), 8.87 (s, 1H). ES-MS m/z 581 (M+H).

EXAMPLE 124

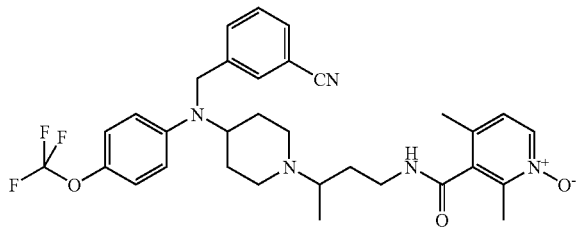

COMPOUND 124: N-(3-{4-[(3-Cyano-benzyl)-(4-trifluoromethoxy-phenyl)-amino]-piperidin-1-yl}-butyl)-2,4-dimethyl-1-oxy-nicotinamide White solid. $^1$H NMR (CD$_3$OD) δ 1.12-1.20 (m, 3H), 1.35-1.39 (m, 1H), 1.64-1.78 (m, 3H), 1.90-1.96 (m, 3H), 2.34 (s, 3H), 2.46 (s, 3H), 2.89-3.07 (m, 3H), 3.42-3.58 (m, 2H), 3.87-3.96 (m, 1H), 4.51 (s, 2H), 6.76 (d, 2H, J=8.8 Hz), 7.05 (d, 2H, J=8.6 Hz), 7.30 (d, 1H, J=7.3 Hz), 7.49 (d, 1H, J=7.0 Hz), 7.57-7.62 (m, 3H), 8.25 (d, 1H, J=6.2 Hz). ES-MS m/z 596 (M+H).

EXAMPLE 125

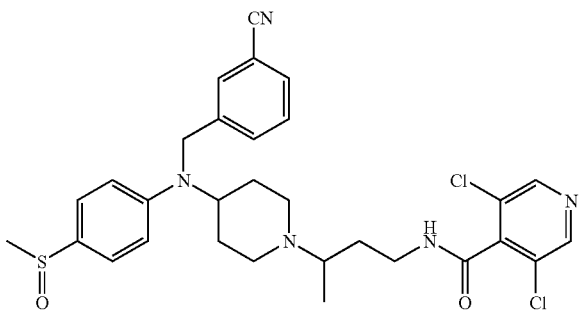

COMPOUND 125: 3,5-Dichloro-N-(3-{4-[(3-cyano-benzyl)-(4-methanesulfinyl-phenyl)-amino]-piperidin-1-yl}-butyl)-isonicotinamide To a solution of 4-[(3-cyano-benzyl)-(4-methylsulfanyl-phenyl)-amino]-piperidine-1-carboxylic acid tert-butyl ester (see EXAMPLE 105) (484 mg, 1.1 mmol) in MeOH (20 mL) cooled to 0° C. was added OXONE® (680 mg, 1.1 mmol) and the mixture was stirred at 0° C. for 1.5 hours. Work-up and purification afforded 4-[(3-cyano-benzyl)-(4-methanesulfonyl-phenyl)-amino]-piperidine-1-carboxylic acid tert-butyl ester (166 mg, 32%) as a white solid and 4-[(3-cyano-benzyl)-(4-methanesulfinyl-phenyl)-amino]-piperidine-1-carboxylic acid tert-butyl ester (264 mg, 53%) as a white solid.

Using general procedure C with 4-[(3-cyano-benzyl)-(4-methanesulfinyl-phenyl)-amino]-piperidine-1-carboxylic acid tert-butyl ester (260 mg, 0.57 mmol), then general procedure B with the resulting amine and 2-(3-oxo-butyl)-isoindole-1,3-dione (270 mg, 1.2 mmol) followed by general procedure D afforded 3-{[[1-(3-amino-1-methyl-propyl)-piperidin-4-yl]-(4-methanesulfinyl-phenyl)-amino]-methyl}-benzonitrile as a white solid (133 mg, 55% over 3 steps).

Using general procedure F, 3,5-dichloroisonicotinic acid (117 mg, 0.61 mmol) and the above amine (130 mg, 0.31 mmol) afforded COMPOUND 125 as a white solid (77 mg, 42%). $^1$H NMR (CDCl$_3$) δ 1.01-1.24 (m, 2H), 1.04 (d, 3H, J=6.3 Hz), 1.55-1.60 (m, 1H), 1.79-1.82 (m, 3H), 2.23 (t, 1H, J=11.7 Hz), 2.62 (t, 1H, J=11.4 Hz), 2.67 (s, 3H), 2.82-2.97 (m, 3H), 3.33-3.40 (m, 1H), 3.76-3.86 (m, 2H), 3.96 (s, 2H), 6.62 (d, 2H, J=8.4 Hz), 7.43-7.56 (m, 5H), 8.47 (s, 2H), 8.65 (br s, 1H). $^{13}$C NMR (CDCl$_3$) δ 13.46, 26.45, 30.46, 30.53, 40.02, 43.52, 43.70, 47.97, 51.84, 53.44, 55.91, 60.05, 112.89, 113.18, 118.78, 126.69, 129.17, 129.54, 130.62, 130.93, 132.46, 140.53, 143.23, 147.59, 150.32, 161.39. ES-MS m/z 598 (M+H). Anal. Calcd. for C$_{30}$H$_{33}$N$_5$Cl$_2$O$_2$S.0.5CH$_2$Cl$_2$: C, 57.15; H, 5.35; N, 10.92; Cl, 16.59; S, 5.00. Found. C, 57.22; H, 5.27; N, 10.98; Cl, 16.30; S, 4.93.

EXAMPLE 126

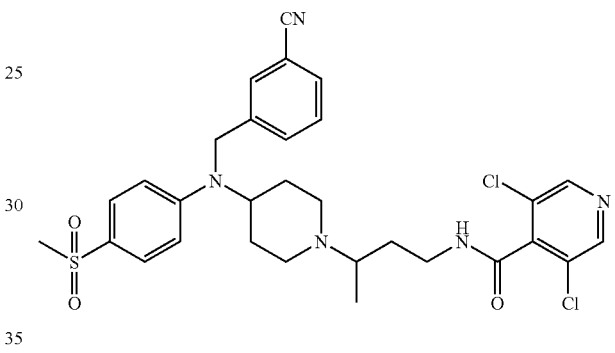

COMPOUND 126: 3,5-Dichloro-N-(3-{4-[(3-cyano-benzyl)-(4-methanesulfonyl-phenyl)-amino]-piperidin-1-yl}-butyl)-isonicotinamide Using general procedure C with 4-[(3-cyano-benzyl)-(4-methanesulfonyl-phenyl)-amino]-piperidine-1-carboxylic acid tert-butyl ester (see EXAMPLE 125) (166 mg, 0.35 mmol), then general procedure B with the resulting amine and 2-(3-oxo-butyl)-isoindole-1,3-dione (147 mg, 0.68 mmol) and then using general procedure D gave 3-{[[1-(3-amino-1-methyl-propyl)-piperidin-4-yl]-(4-methanesulfonyl-phenyl)-amino]-methyl}-benzonitrile as a white solid (94 mg, 61% over 3 steps).

Using general procedure F, 3,5-dichloroisonicotinic acid (79 mg, 0.41 mmol) and the above amine (91 mg, 0.21 mmol) afforded COMPOUND 126 as a white solid (70 mg, 55%). $^1$H NMR (CDCl$_3$) δ 1.02-1.31 (m, 2H), 1.04 (d, 3H, J=6.3 Hz), 1.54-1.59 (m, 1H), 1.77-1.81 (m, 3H), 2.24 (t, 1H, J=11.4 Hz), 2.63 (t, 1H, J=11.1 Hz), 2.83-2.94 (m, 3H), 2.99 (s, 3H), 3.36-3.41 (m, 1H), 3.78-3.85 (m, 2H), 4.03 (s, 2H), 6.59 (d, 2H, J=8.4 Hz), 7.40-7.60 (m, 4H), 7.67 (d, 2H, J=8.4 Hz), 8.48 (br s, 3H). $^{13}$C NMR (CDCl$_3$) δ 13.46, 29.46, 30.41, 30.66, 39.91, 43.50, 44.99, 47.86, 51.72, 53.44, 55.91, 59.90, 112.20, 113.00, 118.69, 127.95, 129.16, 129.38, 129.72, 130.55, 131.08, 139.85, 143.17, 147.61, 151.69, 161.40. ES-MS m/z 614 (M+H). Anal. Calcd. for C$_{30}$H$_{33}$N$_5$Cl$_2$O$_3$S.0.5CH$_2$Cl$_2$: C, 55.75; H, 5.22; N, 10.66; Cl, 16.19; S, 4.88. Found. C, 55.85; H, 5.18; N, 10.69; Cl, 15.95; S, 4.85.

EXAMPLE 127

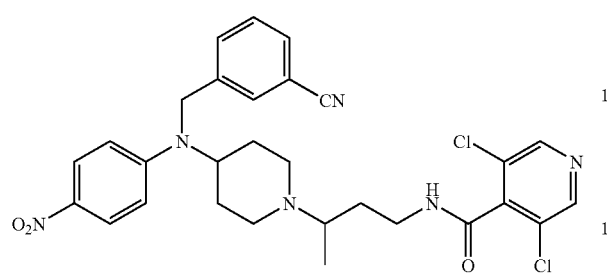

COMPOUND 127: 3,5-Dichloro-N-(3-{4-[(3-cyano-benzyl)-(4-nitro-phenyl)-amino]-piperidin-1-yl}-butyl)-isonicotinamide 4-Amino-piperidine-1-carboxylic acid tert-butyl ester (see EXAMPLE 63) (400 mg, 2.0 mmol) and 3-cyanobenzaldehyde (262 mg, 2.0 mmol) in MeOH (6 mL) were stirred at room temperature overnight. NaBH$_4$ (151 mg, 4.0 mmol) was added and the mixture was stirred for an additional 30 minutes to give the crude material after work-up.

The above secondary amine (480 mg), 1-iodo-4-nitrobenzene (416 mg, 1.67 mmol), sodium tert-butoxide (205 mg, 2.13 mmol), (+/−) BINAP (93 mg, 0.15 mmol), Pd$_2$(dba)$_3$ (70 mg, 0.076 mmol) and toluene (3.5 mL) were flushed with N$_2$ for 5 minutes. The mixture was heated at 100° C. for 20 hours. A second aliquot of 1-iodo-4-nitrobenzene (416 mg, 1.67 mmol) was added and the mixture heated at 100° C. for 3 days to afford 4-[(3-cyano-benzyl)-(4-nitro-phenyl)-amino]-piperidine-1-carboxylic acid tert-butyl ester as a yellow solid (170 mg, 26%) after aqueous work-up and purification.

Using general procedure C with the above substrate (170 mg, 0.39 mmol), then general procedure B with the resulting amine and 2-(3-oxo-butyl)-isoindole-1,3-dione (129 mg, 0.59 mmol) followed by general procedure D afforded 3-{[[1-(3-amino-1-methyl-propyl)-piperidin-4-yl]-(4-nitro-phenyl)-amino]-methyl}-benzonitrile as a yellow solid (41 mg, 26% over 3 steps).

Using general procedure F, 3,5-dichloroisonicotinic acid (38 mg, 0.20 mmol) and the above amine (41 mg, 0.10 mmol) afforded COMPOUND 127 as a yellow solid (38 mg, 66%). $^1$H NMR (CDCl$_3$) δ 1.04 (d, 3H, J=6.3 Hz), 1.06-1.37 (m, 2H), 1.52-1.61 (m, 1H), 1.73-1.89 (m, 3H), 2.19-2.30 (m, 1H), 2.57-2.68 (m, 1H), 2.80-3.00 (m, 3H), 3.33-3.46 (m, 1H), 3.76-3.89 (m, 2H), 4.10 (s, 2H), 6.52 (d, 2H, J=9.0 Hz), 7.37-7.62 (m, 4H), 8.05 (d, 2H, J=8.7 Hz), 8.34 (br s, 1H), 8.48 (s, 2H). $^{13}$C NMR (CDCl$_3$) δ 13.47, 29.57, 30.42, 30.80, 39.74, 43.52, 47.99, 51.57, 56.27, 59.64, 111.52, 113.06, 118.55, 126.17, 129.14, 129.32, 129.78, 130.46, 131.17, 138.11, 139.46, 143.13, 147.60, 152.75, 161.43. ES-MS m/z 581 (M+H). Anal. Calcd. for C$_{29}$H$_{30}$N$_6$Cl$_2$O$_3$.0.1CH$_2$Cl$_2$: C, 59.24; H, 5.16; N, 14.24; Cl, 13.22. Found. C, 59.10; H, 5.19; N, 14.13; Cl, 13.39.

EXAMPLE 128

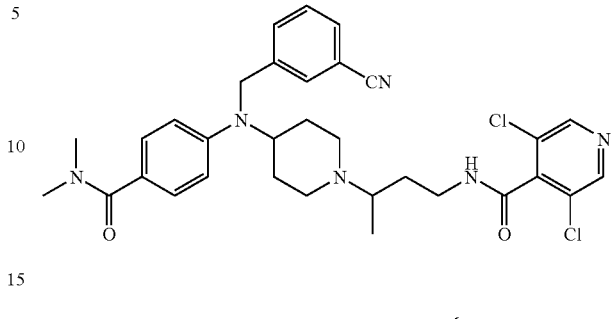

COMPOUND 128: 3,5-Dichloro-N-(3-{4-[(3-cyano-benzyl)-(4-dimethylcarbamoyl-phenyl)-amino]-piperidin-1-yl}-butyl)-isonicotinamide Using general procedure K with COMPOUND 107 (36 mg, 0.06 mmol) followed by general procedure E with the resulting acid and dimethylamine (2.0M in THF, 31 μL, 0.062 mmol) afforded COMPOUND 128 as a white solid (18 mg, 50% over 2 steps). $^1$H NMR (CDCl$_3$) δ 0.96-1.25 (m, 2H), 1.29 (d, 3H, J=5.7 Hz), 1.54-1.58 (m, 1H), 1.71-1.80 (m, 3H), 2.17-2.25 (m, 1H), 2.56-2.64 (m, 1H), 2.81-2.95 (m, 3H), 3.03 (s, 6H), 3.33-3.40 (m, 1H), 3.70-3.87 (m, 2H), 3.92 (s, 2H), 6.51 (d, 2H, J=8.7 Hz), 7.26-7.28 (m, 2H), 7.46-7.55 (m, 4H), 8.47 (s, 2H), 8.76 (br s, 1H). $^{13}$C NMR (CDCl$_3$) δ 13.81, 29.79, 30.85, 40.47, 43.94, 48.36, 52.30, 56.17, 60.52, 112.38, 112.61, 113.15, 119.26, 125.14, 129.54, 129.75, 129.84, 130.05, 131.11, 131.17, 141.47, 147.98, 149.42, 172.01. ES-MS m/z 607 (M+H). Anal. Calcd. for C$_{32}$H$_{36}$N$_6$Cl$_2$O$_2$.0.6CH$_2$Cl$_2$: C, 59.46; H, 5.69; N, 12.76. Found. C, 59.52; H, 5.64; N, 12.41.

EXAMPLE 129

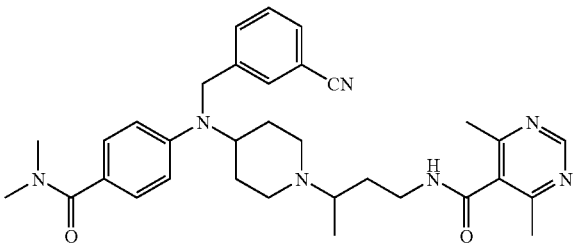

COMPOUND 129: 4,6-Dimethyl-pyrimidine-5-carboxylic acid (3-{4-[(3-cyano-benzyl)-(4-dimethylcarbamoyl-phenyl)-amino]-piperidin-1-yl}-butyl)-amide Using general procedure E with 4-[[1-(3-amino-1-methyl-propyl)-piperidin-4-yl]-(3-cyano-benzyl)-amino]-benzoic acid methyl ester (see EXAMPLE 107) (300 mg, 0.71 mmol) and 4,6-dimethyl-pyrimidine-5-carboxylic acid (119 mg, 0.78 mmol) followed by general procedure K with the resulting ester afforded 4-[(3-cyano-benzyl)-(1-{3-[(4,6-dimethylpyrimidine-5-carbonyl)-amino]-1-methyl-propyl}-piperidin-4-yl)-amino]-benzoic acid as a white solid (260 mg, 74%).

Using general procedure E, the above acid (50 mg, 0.09 mmol) and dimethylamine (2M, 167 μL, 0.33 mmol) afforded COMPOUND 129 as a white solid (45 mg, 87%). $^1$H NMR (CDCl$_3$) δ 0.86-1.17 (m, 2H), 1.02 (d, 3H, J=6.6 Hz), 1.51-1.62 (m, 1H), 1.71-1.83 (m, 3H), 2.14-2.25 (m, 1H), 2.51 (s, 6H), 2.54-2.64 (m, 1H), 2.71-2.92 (m, 3H), 3.04 (s, 6H), 3.24-3.39 (m, 1H), 3.65-3.91 (m, 2H), 3.96 (s, 2H), 6.51 (d, 2H, J=8.7 Hz), 7.25-7.31 (m, 2H), 7.42-7.58 (m, 4H), 8.56 (br s, 1H), 8.89 (s, 1H). $^{13}$C NMR (CDCl$_3$) δ 13.85, 22.36, 29.60, 30.83, 31.11, 40.50, 43.90, 48.46, 52.40, 56.09, 60.73, 112.45, 113.10, 118.24, 125.16, 129.79, 130.14, 131.18, 141.68, 149.59, 157.98, 163.52, 166.64, 172.02. ES-MS m/z 568 (M+H). Anal. Calcd. for C$_{33}$H$_{41}$N$_7$O$_2$.0.1CH$_2$Cl$_2$.0.2H$_2$O: C, 68.57; H, 7.23; N, 16.91. Found. C, 68.77; H, 7.38; N, 16.51.

EXAMPLE 130

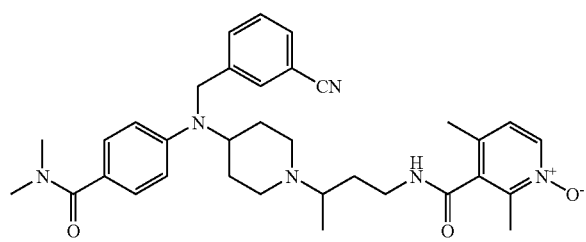

COMPOUND 130: N-(3-{4-[(3-Cyano-benzyl)-(4-dimethylcarbamoyl-phenyl)-amino]-piperidin-1-yl}-butyl)-2,4-dimethyl-1-oxy-nicotinamide Using general procedure E with 4-[[1-(3-amino-1-methyl-propyl)-piperidin-4-yl]-(3-cyano-benzyl)-amino]-benzoic acid methyl ester (see EXAMPLE 107) (200 mg, 0.48 mmol) and 2,4-dimethyl-1-oxy-nicotinic acid (87 mg, 0.52 mmol) followed by general procedure K with the resulting ester afforded 4-[(3-cyano-benzyl)-(1-{3-[(2,4-dimethyl-1-oxy-pyridine-3-carbonyl)-amino]-1-methyl-propyl}-piperidin-4-yl)-amino]-benzoic acid as a yellow solid (180 mg, 70%).

Using general procedure E, the above acid (50 mg, 0.09 mmol) and dimethylamine (2M, 138 μL, 0.28 mmol) afforded COMPOUND 130 as a white solid (36 mg, 60%). $^1$H NMR (CDCl$_3$) δ 0.97 (d, 3H, J=6.6 Hz), 1.15-1.40 (m, 2H), 1.47-1.62 (m, 1H), 1.68-1.86 (m, 3H), 2.12-2.32 (m, 1H), 2.23 (s, 3H), 2.26 (s, 3H), 2.46-2.56 (m, 1H), 2.67-2.85 (m, 3H), 2.97 (s, 6H), 3.28-3.41 (m, 1H), 3.54-3.76 (m, 2H), 4.21 (s, 2H), 6.49 (d, 2H, J=9.0 Hz), 6.80 (d, 1H, J=6.6 Hz), 7.22 (d, 2H, J=7.8 Hz), 7.34-7.53 (m, 4H), 7.84 (d, 1H, J=6.6 Hz), 8.59 (br s, 1H). $^{13}$C NMR (CDCl$_3$) δ 13.93, 15.54, 18.84, 29.87, 30.71, 32.38, 39.45, 44.63, 48.66, 51.89, 56.41, 59.20, 112.50, 112.97, 119.33, 124.92, 125.27, 129.76, 129.84, 130.13, 131.03, 131.39, 134.48, 137.27, 138.30, 141.88, 145.88, 149.71, 165.75, 172.08. ES-MS m/z 583 (M+H).

EXAMPLE 131

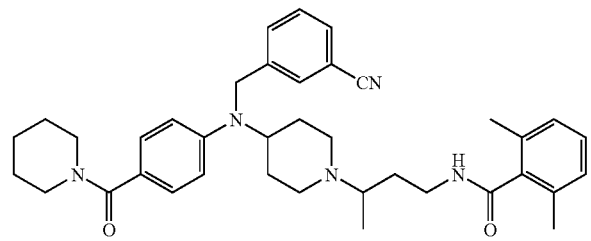

COMPOUND 131: N-[3-(4-{(3-Cyano-benzyl)-[4-(piperidine-1-carbonyl)-phenyl]-amino}-piperidin-1-yl)-butyl]-2,6-dimethyl-benzamide Using general procedure F with 2,6-dimethylbenzoic acid (93 mg, 0.62 mmol) and 4-[[1-(3-amino-1-methyl-propyl)-piperidin-4-yl]-(3-cyano-benzyl)-amino]-benzoic acid methyl ester (see EXAMPLE 107) (130 mg, 0.31 mmol) followed by general procedure K with the resulting ester afforded 4-((3-cyano-benzyl)-{1-[3-(2,6-dimethyl-benzoylamino)-1-methyl-propyl]-piperidin-4-yl}-amino)-benzoic acid as a white solid (107 mg, 64% over 2 steps).

Using general procedure E, the above acid (49 mg, 0.090 mmol) and piperidine (15 μL, 0.14 mmol) afforded COMPOUND 131 as a white solid (33 mg, 59%). $^1$H NMR (CDCl$_3$) δ 0.94-1.20 (m, 2H), 1.01 (d, 3H, J=6.6 Hz), 1.56-1.81 (m, 10H), 2.18 (t, 1H, J=11.7 Hz), 2.31 (s, 6H), 2.57 (t, 1H, J=12.0 Hz), 2.75-2.92 (m, 3H), 3.25-3.32 (m, 1H), 3.52 (br s, 4H), 3.64-3.71 (m, 1H), 3.85 (s, 2H), 3.85-3.91 (m, 1H), 6.50 (d, 2H, J=8.4 Hz), 6.95 (d, 2H, J=4.5 Hz), 7.03-7.08 (m, 1H), 7.22-7.26 (m, 2H), 7.42-7.46 (m, 3H), 7.54 (d, 1H, J=7.2 Hz), 8.29 (br s, 1H). $^{13}$C NMR (CDCl$_3$) δ 13.43, 19.15, 24.70, 26.13, 29.02, 30.33, 31.00, 39.77, 43.59, 48.06, 52.07, 56.04, 60.45, 112.26, 112.60, 118.91, 124.75, 127.30, 128.40, 129.08, 129.31, 129.81, 130.59, 130.76, 134.11, 138.64, 141.67, 149.18, 169.83, 170.51. ES-MS m/z 606 (M+H). Anal. Calcd. for C$_{38}$H$_{47}$N$_5$O$_2$.0.4CH$_2$Cl$_2$: C, 72.09; H, 7.53; N, 10.95. Found. C, 72.46; H, 7.53; N, 11.04.

EXAMPLE 132

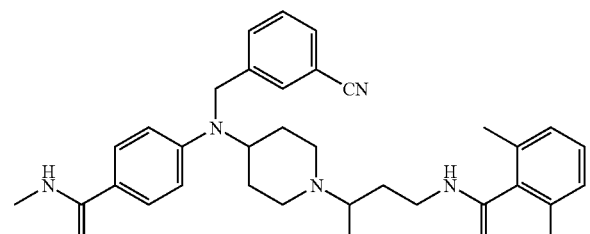

COMPOUND 132: N-(3-{4-[(3-Cyano-benzyl)-(4-methylcarbamoyl-phenyl)-amino]-piperidin-1-yl}-butyl)-2,6-dimethyl-benzamide Using general procedure E, 4-((3-cyano-benzyl)-{1-[3-(2,6-dimethyl-benzoylamino)-1-methyl-propyl]-piperidin-4- yl}-amino)-benzoic acid (see EXAMPLE 131) (30 mg, 0.056 mmol) and methylamine hydrochloride (19 mg, 0.28 mmol) afforded COMPOUND 132 as a white solid (22 mg, 72%). $^1$H NMR (CDCl$_3$) δ 1.01 (d, 3H, J=6.3 Hz), 1.15-1.26 (m, 1H), 1.52-1.75 (m, 4H), 2.15-2.37 (m, 2H), 2.31 (s, 6H), 2.59 (t, 1H, J=11.1 Hz), 2.76-2.88 (m, 3H), 2.96 (d, 3H, J=4.2 Hz), 3.20-3.33 (m, 1H), 3.67-3.74 (m, 1H), 3.85-3.89 (m, 1H), 3.89 (s, 2H), 5.91 (br s, 1H), 6.52 (d, 2H, J=8.4 Hz), 6.96 (d, 2H, J=7.2 Hz), 7.04-7.09 (m, 1H), 7.41-7.46 (m, 3H), 7.54-7.57 (m, 3H), 8.25 (br s, 1H). $^{13}$C NMR (CDCl$_3$) δ 13.85, 19.54, 27.07, 29.47, 30.73, 31.40, 40.13, 43.97, 48.36, 52.39, 56.37, 60.80, 112.55, 113.05, 119.20, 123.36, 127.70, 128.80, 128.86, 129.76, 130.13, 131.07, 134.52, 139.01, 141.73, 150.81, 168.13, 170.24. ES-MS m/z 552 (M+H). Anal. Calcd. for C$_{34}$H$_{41}$N$_5$O$_2$.0.9H$_2$O: C, 71.90; H, 7.60; N, 12.33. Found. C, 71.72; H, 7.71; N, 12.72.

EXAMPLE 133

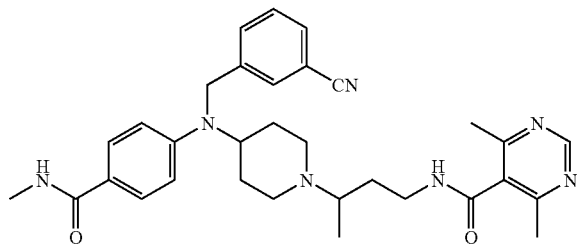

COMPOUND 133: 4,6-Dimethyl-pyrimidine-5-carboxylic acid (3-{4-[(3-cyano-benzyl)-(4-methylcarbamoyl-phenyl)-amino]-piperidin-1-yl}-butyl)-amide Using general procedure E with 4,6-dimethyl-pyrimidine-5-carboxylic acid (71 mg, 0.46 mmol) and 4-[[1-(3-amino-1-methyl-propyl)-piperidin-4-yl]-(3-cyano-benzyl)-amino]-benzoic acid methyl ester (see EXAMPLE 107) (130 mg, 0.31 mmol) followed by general procedure K with the resulting ester gave 4-[(3-cyano-benzyl)-(1-{3-[(4,6-dimethyl-pyrimidine-5-carbonyl)-amino]-1-methyl-propyl}-piperidin-4-yl)-amino]-benzoic acid as a brown solid (105 mg, 64% over 2 steps).

Using general procedure E, the above acid (52 mg, 0.10 mmol) and methylamine hydrochloride (32 mg, 0.48 mmol) afforded COMPOUND 133 as a white solid (31 mg, 58%) after an aqueous work-up. $^1$H NMR (CDCl$_3$) δ 0.91-1.13 (m, 2H), 1.03 (d, 3H, J=6.6 Hz), 1.49-1.64 (m, 1H), 1.76-1.79 (m, 3H), 2.21 (t, 1H, J=11.1 Hz), 2.51 (s, 6H), 2.60 (t, 1H, J=11.4 Hz), 2.75-2.90 (m, 3H), 2.96 (d, 3H, J=4.8 Hz), 3.29-3.38 (m, 1H), 3.70-3.87 (m, 2H), 3.87 (s, 2H), 5.95-5.96 (m, 1H), 6.53 (d, 2H, J=8.7 Hz), 7.43-7.59 (m, 6H), 8.52-8.53 (m, 1H), 8.90 (s, 1H). $^{13}$C NMR (CDCl$_3$) δ 12.49, 20.94, 25.65, 28.26, 29.34, 29.88, 38.83, 42.64, 47.03, 50.79, 54.67, 58.99, 111.06, 111.67, 117.80, 122.08, 127.52, 128.45, 128.65, 129.75, 140.01, 149.41, 156.51, 162.09, 165.30, 166.72. ES-MS m/z 554 (M+H). Anal. Calcd. for C$_{32}$H$_{39}$N$_7$O$_2$.0.4CH$_2$Cl$_2$: C, 66.22; H, 6.83; N, 16.68. Found. C, 66.17; H, 7.14; N, 16.53.

EXAMPLE 134

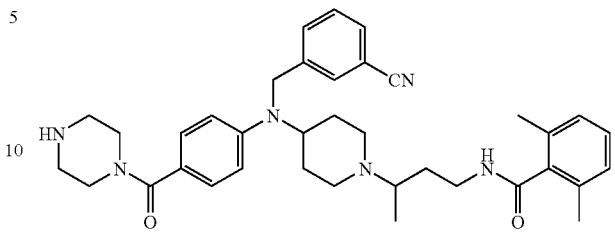

COMPOUND 134: N-[3-(4-{(3-Cyano-benzyl)-[4-(piperazine-1-carbonyl)-phenyl]-amino}-piperidin-1-yl)-butyl]-2,6-dimethyl-benzamide Using general procedure E, 4-((3-cyano-benzyl)-{1-[3-(2,6-dimethyl-benzoylamino)-1-methyl-propyl]-piperidin-4-yl}-amino)-benzoic acid (see EXAMPLE 131) (60 mg, 0.11 mmol) and piperazine (29 mg, 0.33 mmol) afforded COMPOUND 134 as a white solid (23 mg, 34%). $^1$H NMR (CDCl$_3$) δ 0.98-1.18 (m, 2H), 1.01 (d, 3H, J=6.6 Hz), 1.51-1.55 (m, 1H), 1.70-1.82 (m, 3H), 2.18 (t, 1H, J=11.1 Hz), 2.31 (s, 6H), 2.58 (t, 1H, J=11.1 Hz), 2.76-2.92 (m, 7H), 3.26-3.33 (m, 1H), 3.58-3.72 (m, 5H), 3.87 (m, 3H), 6.51 (d, 2H, J=8.7 Hz), 6.95 (d, 2H, J=7.5 Hz), 7.03-7.08 (m, 1H), 7.23-7.26 (m, 2H), 7.42-7.47 (m, 3H), 7.55 (d, 1H, J=6.6 Hz), 8.26 (br s, 1H). $^{13}$C NMR (CDCl$_3$) δ 13.82, 19.55, 29.41, 30.70, 31.42, 40.14, 43.98, 46.66, 48.43, 52.45, 56.42, 60.83, 112.64, 113.03, 119.29, 124.40, 127.70, 128.79, 129.72, 130.18, 131.01, 131.12, 134.51, 139.03, 141.94, 149.74, 170.22, 171.00. ES-MS m/z 607 (M+H). Anal. Calcd. for C$_{37}$H$_{46}$N$_6$O$_2$.CH$_2$Cl$_2$: C, 70.10; H, 7.36; N, 13.12. Found. C, 69.89; H, 7.48; N, 13.02.

EXAMPLE 135

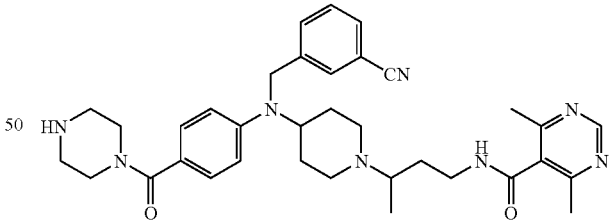

COMPOUND 135: 4,6-Dimethyl-pyrimidine-5-carboxylic acid [3-(4-{(3-cyano-benzyl)-[4-(piperazine-1-carbonyl)-phenyl]-amino}-piperidin-1-yl)-butyl]-amide Using general procedure E, 4-[(3-cyano-benzyl)-(1-{3-[(4,6-dimethyl-pyrimidine-5-carbonyl)-amino]-1-methyl-propyl}-piperidin-4-yl)-amino]-benzoic acid (see EXAMPLE 133) (54 mg, 0.10 mmol) and piperazine (26 mg, 0.30 mmol) afforded COMPOUND 135 as a white solid (19 mg, 31%). ¹H NMR (CDCl₃) δ 0.83-1.13 (m, 2H), 1.03 (d, 3H, J=6.3 Hz), 1.49-1.79 (m, 5H), 2.20 (t, 1H, J=11.7 Hz), 2.51 (s, 6H), 2.60 (t, 1H, J=10.8 Hz), 2.76-2.86 (m, 7H), 3.29-3.37 (m, 1H), 3.58-3.72 (m, 4H), 3.82-3.88 (m, 1H), 3.96 (s, 2H), 6.52 (d, 2H, J=8.7 Hz), 7.25-7.26 (m, 2H), 7.44-7.56 (m, 4H), 8.54 (br s, 1H), 8.90 (s, 1H). ¹³C NMR (CDCl₃) δ 13.46, 21.97, 29.16, 30.38, 30.82, 39.97, 41.22, 42.71, 43.57, 46.25, 48.11, 51.94, 55.66, 60.20, 112.14, 112.70, 118.91, 124.15, 129.38, 129.45, 129.70, 130.77, 130.90, 141.23, 149.34, 157.56, 163.12, 166.27, 170.60. ES-MS m/z 609 (M+H). Anal. Calcd. for C$_{35}$H$_{44}$N$_8$O$_2$.0.5CH$_2$Cl$_2$.0.1H$_2$O: C, 65.29; H, 6.98; N, 17.16. Found. C, 65.22; H, 7.12; N, 16.78.

EXAMPLE 136

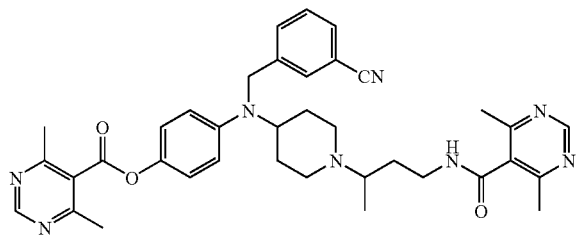

COMPOUND 136: 4,6-Dimethyl-pyrimidine-5-carboxylic acid 4-[(3-cyano-benzyl)-(1-{3-[(4,6-dimethyl-pyrimidine-5-carbonyl)-amino]-1-methyl-propyl}-piperidin-4-yl)-amino]-phenyl ester Using general procedure E, 3-{[[1-(3-amino-1-methyl-propyl)-piperidin-4-yl]-(4-hydroxy-phenyl)-amino]-methyl}-benzonitrile (see EXAMPLE 117) (929 mg, 2.43 mmol) and 4,6-dimethyl-pyrimidine-5-carboxylic acid (1.11 g, 7.28 mmol) afforded COMPOUND 136 as a white solid (1.036 g, 65%). ¹H NMR (CDCl₃) δ 0.94-1.13 (m, 2H), 1.03 (d, 3H, J=6.3 Hz), 1.50-1.59 (m, 1H), 1.78-1.85 (m, 3H), 2.20 (t, 1H, J=11.7 Hz), 2.52 (s, 6H), 2.59 (t, 1H, J=12.0 Hz), 2.65 (s, 6H), 2.70-2.87 (m, 3H), 3.31-3.38 (m, 1H), 3.63-3.67 (m, 1H), 3.85-3.89 (m, 1H), 3.93 (s, 2H), 6.61 (d, 2H, J=9.0 Hz), 7.03 (d, 2H, J=9.0 Hz), 7.44-7.59 (m, 4H), 8.56 (br s, 1H), 8.87 (s, 1H), 9.01 (s, 1H). ¹³C NMR (CDCl₃) δ 13.84, 22.35, 23.40, 29.61, 30.81, 31.18, 40.42, 43.97, 48.84, 52.41, 56.90, 60.63, 113.10, 114.30, 114.54, 119.27, 122.20, 126.52, 129.81, 130.23, 131.14, 131.29, 141.81, 141.97, 147.02, 157.95, 158.63, 163.49, 164.86, 166.55, 166.66. ES-MS m/z 647 (M+H). Anal. Calcd. for C$_{37}$H$_{42}$N$_8$O$_3$.0.8H$_2$O: C, 67.21; H, 6.65; N, 16.95. Found. C, 67.20; H, 6.46; N, 16.70.

EXAMPLE 137

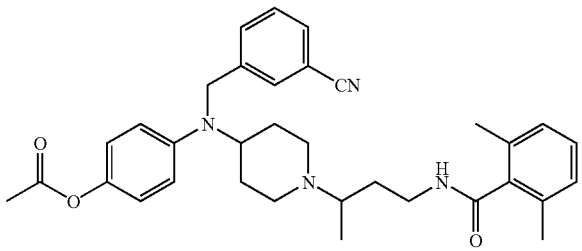

COMPOUND 137: Acetic acid 4-((3-cyano-benzyl)-{1-[3-(2,6-dimethyl-benzoylamino)-1-methyl-propyl]-piperidin-4-yl}-amino)-phenyl ester To a solution of COMPOUND 117 (51 mg, 0.10 mmol) in CH$_2$Cl$_2$ (2 mL) were added Et$_3$N (0.04 mL, 0.29 mmol) followed by acetic anhydride (0.02 mL, 0.21 mmol) and the mixture was stirred at room temperature overnight to afford COMPOUND 137 as a white solid (48 mg, 85%) following work-up and purification. ¹H NMR (CDCl₃) δ 0.97-1.18 (m, 2H), 1.00 (d, 3H, J=6.3 Hz), 1.50-1.58 (m, 1H), 1.70-1.74 (m, 3H), 2.15 (t, 1H, J=11.1 Hz), 2.24 (s, 3H), 2.31 (s, 6H), 2.55 (t, 1H, J=10.5 Hz), 2.74-2.87 (m, 3H), 3.24-3.31 (m, 1H), 3.57-3.63 (m, 1H), 3.77 (s, 2H), 3.85-3.91 (m, 1H), 6.51 (d, 2H, J=8.4 Hz), 6.84 (d, 2H, J=8.1 Hz), 6.93-7.05 (m, 3H), 7.43-7.52 (m, 4H), 8.38 (br s, 1H). ¹³C NMR (CDCl₃) δ 14.53, 20.27, 22.20, 30.06, 31.46, 32.06, 40.96, 44.70, 49.60, 53.28, 57.84, 61.68, 113.66, 115.15, 120.06, 123.21, 128.42, 129.52, 130.36, 131.08, 131.64, 132.01, 135.21, 139.77, 143.16, 143.23, 147.35, 170.96, 171.27. ES-MS m/z 533 (M+H). Anal. Calcd. for C$_{34}$H$_{40}$N$_4$O$_3$.0.6H$_2$O: C, 72.47; H, 7.37; N, 9.94. Found. C, 72.38; H, 7.25; N, 9.83.

EXAMPLE 138

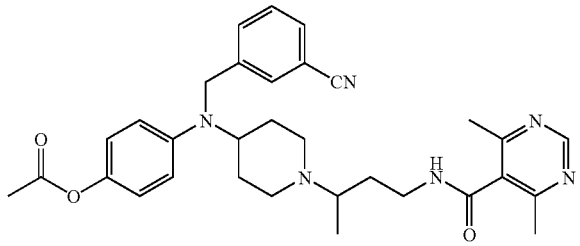

COMPOUND 138: Acetic acid 4-[(3-cyano-benzyl)-(1-{3-[(4,6-dimethyl-pyrimidine-5-carbonyl)-amino]-1-methyl-propyl}-piperidin-4-yl)-amino]-phenyl ester To a solution of COMPOUND 136 (870 mg, 1.39 mmol) in MeOH (14 mL) was added 10N NaOH (1.4 mL, 14 mmol) and the mixture was heated at 40° C. overnight to afford 4,6-dimethyl-pyrimidine-5-carboxylic acid (3-{4-[(3-cyanobenzyl)-(4-hydroxy-phenyl)-amino]-piperidin-1-yl}-butyl)-amide as a pink solid (400 mg, 53%) following an acidic work-up and purification.

To a solution of the above phenol (45 mg, 0.087 mmol) in CH$_2$Cl$_2$ (2 mL) were added Et$_3$N (0.04 mL, 0.29 mmol) followed by acetic anhydride (0.02 mL, 0.21 mmol) and the mixture was stirred at room temperature overnight to afford COMPOUND 138 as a white solid (43 mg, 80%) following work-up and purification. $^1$H NMR (CDCl$_3$) δ 0.82-1.12 (m, 5H), 1.54-1.58 (m, 1H), 1.76-1.79 (m, 3H), 2.18 (t, 1H, J=11.7 Hz), 2.25 (s, 3H), 2.51 (s, 6H), 2.57 (t, 1H, J=10.5 Hz), 2.74-2.86 (m, 3H), 3.30-3.36 (m, 1H), 3.56-3.62 (m, 1H), 3.82-3.87 (m, 1H), 3.89 (s, 2H), 6.53 (d, 2H, J=8.1 Hz), 6.87 (d, 2H, J=8.4 Hz), 7.41-7.46 (m, 1H), 7.52-7.55 (m, 3H), 8.60 (br s, 1H), 8.86 (s, 1H). $^{13}$C NMR (CDCl$_3$) δ 12.37, 20.06, 20.93, 28.06, 29.26, 29.75, 38.92, 42.58, 47.57, 50.96, 55.43, 59.14, 111.59, 113.16, 117.91, 121.16, 128.32, 128.89, 129.64, 129.83, 129.94, 140.71, 141.26, 145.13, 156.53, 162.07, 165.32, 169.07. ES-MS m/z 555 (M+H). Anal. Calcd. for C$_{32}$H$_{38}$N$_6$O$_3$·0.8CH$_2$Cl$_2$: C, 63.27; H, 6.41; N, 13.50. Found. C; 63.46; H, 6.39; N, 13.29.

EXAMPLE 139

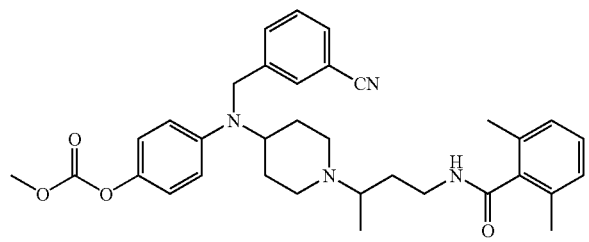

COMPOUND 139: Carbonic acid 4-((3-cyano-benzyl)-{1-[3-(2,6-dimethyl-benzoylamino)-1-methyl-propyl]-piperidin-4-yl}-amino)-phenyl ester methyl ester To a solution of COMPOUND 117 (43 mg, 0.083 mmol) in CH$_2$Cl$_2$ (2 mL) were added Et$_3$N (0.04 mL, 0.29 mmol) followed by methyl chloroformate (14 μL, 0.19 mmol) and the mixture was stirred at room temperature overnight to afford COMPOUND 139 as a white solid (41 mg, 86%) following work-up and purification. $^1$H NMR (CDCl$_3$) δ 0.91-1.14 (m, 2H), 1.00 (d, 3H, J=6.0 Hz), 1.50-1.55 (m, 1H), 1.70-1.74 (m, 3H), 2.15 (t, 1H, J=12.0 Hz), 2.31 (s, 6H), 2.55 (t, 1H, J=10.8 Hz), 2.74-2.91 (m, 3H), 3.24-3.32 (m, 1H), 3.57-3.63 (m, 1H), 3.78 (s, 2H), 3.86 (s, 3H), 3.86-3.90 (m, 1H), 6.51 (d, 2H, J=8.1 Hz), 6.92-7.05 (m, 5H), 7.43-7.53 (m, 4H), 8.37-8.38 (m, 1H). $^{13}$C NMR (CDCl$_3$) δ 13.80, 19.54, 29.34, 30.72, 31.34, 40.23, 43.96, 48.84, 52.54, 55.68, 57.14, 60.94, 112.96, 114.36, 119.30, 122.04, 127.69, 128.78, 129.65, 130.33, 130.94, 131.25, 134.49, 139.04, 142.38, 143.01, 146.78, 155.24, 170.23. ES-MS m/z 569 (M+H). Anal. Calcd. for C$_{34}$H$_{40}$N$_4$O$_4$·0.5H$_2$O: C, 70.69; H, 7.15; N, 9.70. Found. C, 70.64; H, 7.02; N, 9.65.

EXAMPLE 140

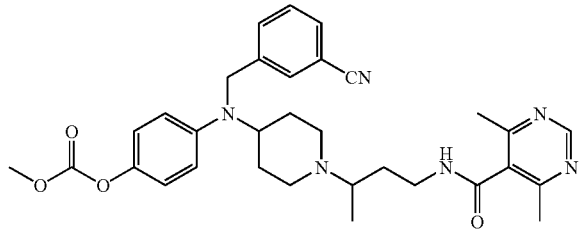

COMPOUND 140: Carbonic acid 4-[(3-cyano-benzyl)-(1-{3-[(4,6-dimethyl-pyrimidine-5-carbonyl)-amino]-1-methyl-propyl}-piperidin-4-yl)-amino]-phenyl ester methyl ester To a solution of COMPOUND 138 (41 mg, 0.080 mmol) in CH$_2$Cl$_2$ (2 mL) were added Et$_3$N (0.04 mL, 0.29 mmol) followed by methyl chloroformate (15 μL, 0.19 mmol) and the mixture was stirred at room temperature overnight to afford COMPOUND 140 as a white solid (33 mg, 66%) following work-up and purification. $^1$H NMR (CDCl$_3$) δ 0.90-1.14 (m, 2H), 1.02 (d, 3H, J=6.0 Hz), 1.53-1.59 (m, 1H), 1.76-1.79 (m, 3H), 2.17 (t, 1H, J=11.7 Hz), 2.51 (s, 6H), 2.57 (t, 1H, J=10.8 Hz), 2.74-2.86 (m, 3H), 3.33-3.39 (m, 1H), 3.56-3.61 (m, 1H), 3.86-3.89 (m, 6H), 6.53 (d, 2H, J=9.0 Hz), 6.95 (d, 2H, J=8.4 Hz), 7.44-7.46 (m, 1H), 7.52-7.55 (m, 4H), 8.60 (br s, 1H), 8.86 (s, 1H). $^{13}$C NMR (CDCl$_3$) δ 13.84, 22.35, 29.58, 30.79, 31.13, 40.45, 43.97, 48.93, 52.42, 55.70, 56.89, 60.65, 113.04, 114.45, 119.31, 122.12, 129.76, 130.28, 131.09, 131.32, 142.01, 143.22, 146.71, 155.19, 157.95, 163.49, 166.69. ES-MS m/z 571 (M+H). Anal. Calcd. for C$_{32}$H$_{38}$N$_6$O$_4$·0.7CH$_2$Cl$_2$: C, 62.33; H, 6.30; N, 13.34. Found. C, 62.25; H, 6.34; N, 13.44.

EXAMPLE 141

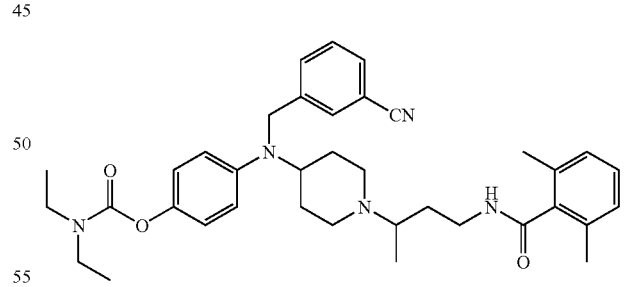

COMPOUND 141: Diethyl-carbamic acid 4-((3-cyano-benzyl)-{1-[3-(2,6-dimethyl-benzoylamino)-1-methyl-propyl]-piperidin-4-yl}-amino)-phenyl ester To a solution of COMPOUND 117 (42 mg, 0.082 mmol) in DMF (1 mL) were added K$_2$CO$_3$ (40 mg, 0.29 mmol) followed by diethylcarbamoyl chloride (20 μL, 0.16 mmol) and the mixture was stirred at room temperature overnight to afford COMPOUND 141 as a white solid (35 mg, 67%) following work-up and purification. $^1$H NMR (CDCl$_3$) δ 0.93-1.01 (m, 1H), 1.00 (d, 3H, J=5.7 Hz), 1.10-1.18 (m, 7H), 1.50-1.58 (m, 1H), 1.70-1.73 (m, 3H), 2.14 (t, 1H, J=10.8 Hz), 2.31 (s, 6H), 2.54 (t, 1H, J=11.4 Hz), 2.73-2.88 (m, 3H), 3.15-3.36 (m, 5H), 3.50-3.56 (m, 1H), 3.74 (s, 2H), 3.87-3.93 (m, 1H), 6.51 (d, 2H, J=7.2 Hz), 6.87 (d, 2H, J=7.8 Hz), 6.95-6.99 (m, 3H), 7.41-7.50 (m, 4H), 8.44 (br s, 1H). $^{13}$C NMR (CDCl$_3$) δ 13.80, 14.59, 19.53, 29.33, 30.74, 31.32, 36.87, 40.26, 42.17, 42.56, 43.96, 48.78, 52.59, 57.57, 60.99, 112.84, 114.95, 119.36, 122.75, 127.68, 128.77, 129.55, 130.48, 130.83, 131.43, 134.47, 139.03, 142.64, 143.52, 146.07, 155.18, 170.24. ES-MS m/z 610 (M+H). Anal. Calcd. for C$_{37}$H$_{47}$N$_5$O$_3$.0.8H$_2$O: C, 71.19; H, 7.85; N, 11.22. Found. C, 71.09; H, 7.68; N, 11.16.

EXAMPLE 142

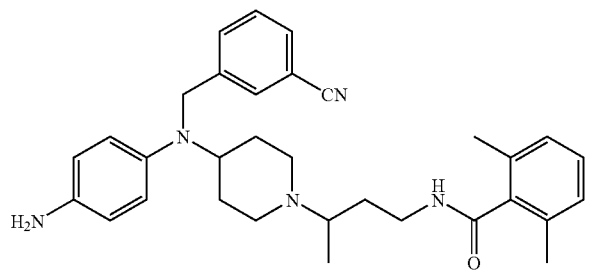

COMPOUND 142: N-(3-{4-[(4-Amino-phenyl)-(3-cyano-benzyl)-amino]-piperidin-1-yl}-butyl)-2,6-dimethyl-benzamide To a solution of COMPOUND 112 (59 mg, 0.11 mmol) in MeOH (1 mL) was added 6N HCl (2 mL) and the solution was stirred at room temperature for 26 hours to afford COMPOUND 142 as a white solid (36 mg, 67%) following a basic work-up and purification. $^1$H NMR (CDCl$_3$) δ 0.91-1.12 (m, 2H), 0.98 (d, 3H, J=6.0 Hz), 1.51 (m, 1H), 1.68-1.75 (m, 3H), 2.09 (t, 1H, J=10.8 Hz), 2.31 (s, 6H), 2.49 (t, 1H, J=10.8 Hz), 2.71-2.83 (m, 3H), 3.22-3.34 (m, 2H), 3.67 (s, 2H), 3.88 (m, 1H), 6.50 (m, 4H), 6.93 (m, 3H), 7.34-7.48 (m, 4H), 8.48 (br s, 1H). $^{13}$C NMR (CDCl$_3$) δ 13.36, 19.14, 29.10, 30.33, 30.92, 39.85, 43.62, 48.98, 52.18, 58.75, 60.55, 112.21, 116.34, 118.09, 127.24, 128.35, 128.91, 130.24, 130.63, 131.00, 131.49, 134.03, 138.60, 138.93, 141.24, 142.75, 169.89. ES-MS m/z 510 (M+H). Anal. Calcd. for C$_{32}$H$_{39}$N$_5$O.0.1CH$_2$Cl$_2$.0.2C$_6$H$_{14}$: C, 74.70; H, 7.91; N, 13.08. Found. C, 74.89; H, 7.77; N, 13.20.

EXAMPLE 143

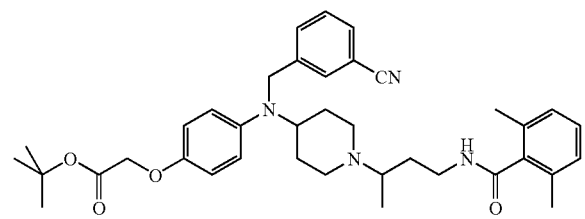

COMPOUND 143: [4-((3-Cyano-benzyl)-{1-[3-(2,6-dimethyl-benzoylamino)-1-methyl-propyl]-piperidin-4-yl}-amino)-phenoxy]-acetic acid tert-butyl ester Using general procedure A, (4-amino-phenoxy)-acetic acid tert-butyl ester (Renodon-Corniere, Axelle; et al., J. Med. Chem., 45, 4, 2002, 944-954) (4.84 g, 21.6 mmol) and 1-Boc-4-piperidone (3.4 g, 17.1 mmol) afforded 4-(4-tert-butoxycarbonylmethoxy-phenylamino)-piperidine-1-carboxylic acid tert-butyl ester (6.6 g, 95%).

Using general procedure H, the above aniline (6.6 mg, 14.9 mmol) and 3-cyanobenzyl bromide (3.1 g, 15.8 mmol) afforded 4-[(4-tert-butoxycarbonylmethoxy-phenyl)-(3-cyano-benzyl)-amino]-piperidine-1-carboxylic acid tert-butyl ester (6.78 g, 87%).

The above carbamate (5.1 g, 9.74 mmol) was treated with a solution of EtOAc (40 mL) saturated with HCl. The mixture was stirred at room temperature for 3 h then concentrated under reduced pressure to give the crude material after work-up.

Using general procedure B with the above amine and 2-(3-oxo-butyl)-isoindole-1,3-dione (3.38 g, 15.6 mmol) and then using general procedure D afforded {4-[[1-(3-amino-1-methyl-propyl)-piperidin-4-yl]-(3-cyano-benzyl)-amino]-phenoxy}-acetic acid tert-butyl ester (800 mg, 44%).

Using general procedure E, the above amine (440 mg, 0.89 mmol) and 2,6-dimethylbenzoic acid (148 mg, 0.99 mmol) afforded COMPOUND 143 as a white solid (430 mg, 77%). $^1$H NMR (CDCl$_3$) δ 0.87-1.15 (m, 2H), 0.96 (d, 3H, J=6.0 Hz), 1.43 (s, 9H), 1.43-1.51 (m, 1H), 1.67-1.75 (m, 3H), 2.10 (t, 1H, J=11.4 Hz), 2.28 (s, 6H), 2.49 (t, 1H, J=11.4 Hz), 2.70-2.86 (m, 3H), 3.21-3.28 (m, 1H), 3.38-3.45 (m, 1H), 3.70 (s, 2H), 3.81-3.85 (m, 1H), 3.36 (s, 2H), 6.50 (d, 2H, J=8.1 Hz), 6.68 (d, 2H, J=7.8 Hz), 6.91-6.97 (m, 3H), 7.34-7.47 (m, 4H), 8.46 (br s, 1H). ES-MS m/z 625 (M+H).

EXAMPLE 144

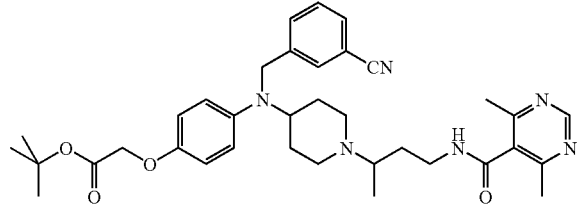

COMPOUND 144: {4-[(Cyano-benzyl)-(1-{3-[(4,6-dimethyl-pyrimidine-5-carbonyl)-amino]-1-methyl-propyl}-piperidin-4-yl)-amino]-phenoxy}-acetic acid tert-butyl ester Using general procedure E, {4-[[1-(3-amino-1-methyl-propyl)-piperidin-4-yl]-(3-cyano-benzyl)-amino]-phenoxy}-acetic acid tert-butyl ester (see EXAMPLE 143) (356 mg, 0.72 mmol) and 4,6-dimethyl-pyrimidine-5-carboxylic acid (121 mg, 0.80 mmol) afforded COMPOUND 144 as a white solid (340 mg, 75%). $^1$H NMR (CDCl$_3$) δ 0.93-1.15 (m, 5H), 1.39 (s, 9H), 1.45-50 (m, 1H), 1.69-1.73 (m, 3H), 2.09 (t, 1H, J=11.1 Hz), 2.43 (s, 6H), 2.47-2.51 (m, 1H), 3.67-3.77 (m, 3H), 3.26-3.43 (m, 2H), 3.63-3.74 (m, 1H), 3.82 (s, 2H), 4.33 (s, 2H), 6.49 (d, 2H, J=7.8 Hz), 6.66 (d, 2H, J=7.8 Hz), 7.32-7.48 (m, 4H), 8.63 (br s, 1H), 8.76 (s, 1H). ES-MS m/z 627 (M+H).

EXAMPLE 145

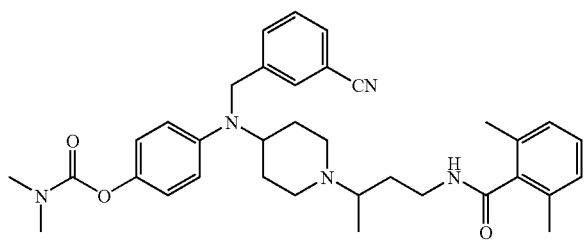

COMPOUND 145: Dimethyl-carbamic acid 4-((3-cyano-benzyl)-{1-[3-(2,6-dimethyl-benzoylamino)-1-methyl-propyl]-piperidin-4-yl}-amino)-phenyl ester To a solution of COMPOUND 117 (42 mg, 0.082 mmol) in DMF (1 mL) were added $K_2CO_3$ (36 mg, 0.26 mmol) followed by dimethylcarbamoyl chloride (15 μL, 0.16 mmol) and the mixture was stirred at room temperature overnight to afford COMPOUND 145 as a white solid (41 mg, 84%) following work-up and purification. $^1$H NMR (CDCl$_3$) δ 0.93-1.13 (m, 2H), 0.99 (d, 3H, J=6.3 Hz), 1.50-1.58 (m, 1H), 1.70-1.81 (m, 3H), 2.14 (t, 1H, J=11.4 Hz), 2.31 (s, 6H), 2.54 (t, 1H, J=12.0 Hz), 2.73-3.05 (m, 9H), 3.23-3.28 (m, 1H), 3.51-5.56 (m, 1H), 3.75 (s, 2H), 3.87-3.93 (m, 1H), 6.50 (d, 2H, J=7.8 Hz), 6.86 (d, 2H, J=8.1 Hz), 6.93-7.00 (m, 3H), 7.42-7.50 (m, 4H), 8.42-8.44 (m, 1H). $^{13}$C NMR (CDCl$_3$) δ 13.80, 19.53, 29.34, 30.75, 31.32, 36.75, 36.87, 37.04, 38.99, 40.24, 43.97, 48.81, 52.57, 57.43, 60.97, 112.84, 114.79, 119.36, 122.74, 127.68, 128.77, 129.57, 130.45, 130.83, 131.40, 134.47, 139.04, 142.64, 143.47, 146.18, 155.88, 162.90, 170.23. ES-MS m/z 582 (M+H). Anal. Calcd. for $C_{35}H_{43}N_5O_3 \cdot 1.0H_2O$: C, 70.09; H, 7.56; N, 11.68. Found. C, 70.35; H, 7.56; N, 11.95.

EXAMPLE 146

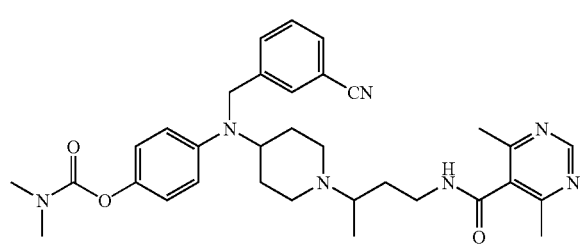

COMPOUND 146: Dimethyl-carbamic acid 4-[(3-cyano-benzyl)-(1-{3-[(4,6-dimethyl-pyrimidine-5-carbonyl)-amino]-1-methyl-propyl}-piperidin-4-yl)-amino]-phenyl ester To a solution of COMPOUND 138 (43 mg, 0.084 mmol) in DMF (1 mL) were added $K_2CO_3$ (38 mg, 0.27 mmol) followed by dimethylcarbamoyl chloride (15 μL, 0.16 mmol) and the mixture was stirred at room temperature overnight to afford COMPOUND 146 as a white solid (27 mg, 53%) following work-up and purification. $^1$H NMR (CDCl$_3$) δ 0.86-1.13 (m, 2H), 1.02 (d, 3H, J=6.6 Hz), 1.52-1.59 (m, 1H), 1.75-1.79 (m, 3H), 2.16 (t, 1H, J=11.4 Hz), 2.52 (s, 6H), 2.57 (t, 1H, J=10.5 Hz), 2.73-2.88 (m, 3H), 2.98 (s, 3H), 3.05 (s, 3H), 3.28-3.36 (m, 1H), 3.53-3.60 (m, 1H), 3.83-3.87 (m, 1H), 3.87 (s, 2H), 6.53 (d, 2H, J=9.0 Hz), 6.88 (d, 2H, J=9.0 Hz), 7.40-7.45 (m, 1H), 7.50-7.56 (m, 3H), 8.65-8.66 (m, 1H), 8.84 (s, 1H). $^{13}$C NMR (CDCl$_3$) δ 14.72, 23.24, 30.49, 31.68, 32.01, 37.66, 37.95, 41.32, 44.90, 49.82, 53.32, 58.14, 61.53, 113.83, 115.91, 120.24, 123.71, 130.55, 131.32, 131.88, 132.15, 132.37, 143.13, 144.63, 146.97, 156.73, 158.83, 164.36, 167.61. ES-MS m/z 584 (M+H). Anal. Calcd. for $C_{33}H_{41}N_7O_3 \cdot 1.4H_2O$: C, 65.09; H, 7.25; N, 16.10. Found. C, 65.27; H, 6.88; N, 15.76.

EXAMPLE 147

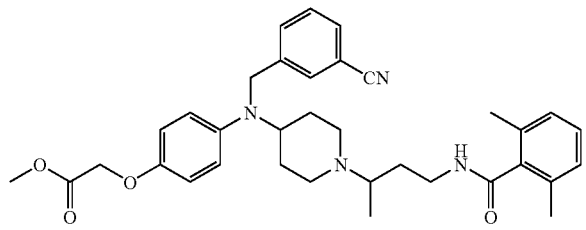

COMPOUND 147: [4-((3-Cyano-benzyl)-{1-[3-(2,6-dimethyl-benzoylamino)-1-methyl-propyl]-piperidin-4-yl}-amino)-phenoxy]-acetic acid methyl ester To a solution of COMPOUND 117 (102 mg, 0.20 mmol) in DMF (1 mL) were added $K_2CO_3$ (86 mg, 0.62 mmol) followed by methyl bromoacetate (40 μL, 0.42 mmol) and the mixture was stirred at room temperature overnight to afford COMPOUND 147 as a tan solid (97 mg, 82%) following work-up and purification. $^1$H NMR (CDCl$_3$) δ 0.90-1.13 (m, 2H), 0.99 (d, 3H, J=6.3 Hz), 1.49-1.54 (m, 1H), 1.69-1.81 (m, 3H), 2.12 (t, 1H, J=12.0 Hz), 2.31 (s, 6H), 2.53 (t, 1H, J=11.7 Hz), 2.73-2.88 (m, 3H), 3.24-3.31 (m, 1H), 3.41-3.49 (m, 1H), 3.71 (s, 2H), 3.78 (s, 3H), 3.86-3.90 (m, 1H), 4.52 (s, 2H), 6.51 (d, 2H, J=8.1 Hz), 6.73 (d, 2H, J=8.4 Hz), 6.94-7.00 (m, 3H), 7.42-7.50 (m, 4H), 8.42 (br s, 1H). $^{13}$C NMR (CDCl$_3$) δ 13.79, 19.51, 29.43, 30.68, 31.28, 40.19, 44.01, 49.03, 52.51, 58.07, 60.86, 66.52, 112.73, 116.20, 116.37, 119.42, 127.62, 128.72, 129.51, 130.61, 130.78, 131.56, 134.42, 139.02, 142.79, 143.83, 150.85, 162.90, 170.14, 170.22. ES-MS m/z 583 (M+H). Anal. Calcd. for $C_{35}H_{422}N_4O_4 \cdot 0.3H_2O$: C, 71.48; H, 7.30; N, 9.53. Found. C, 71.42; H, 7.23; N, 9.40.

EXAMPLE 148

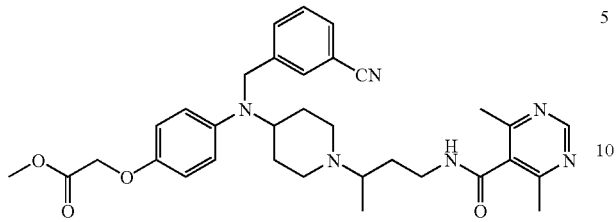

COMPOUND 148: {4-[(3-Cyano-benzyl)-(1-{3-[(4,6-dimethyl-pyrimidine-5-carbonyl)-amino]-1-methyl-propyl}-piperidin-4-yl)-amino]-phenoxy}-acetic acid methyl ester To a solution of COMPOUND 138 (105 mg, 0.205 mmol) in DMF (1 mL) were added $K_2CO_3$ (87 mg, 0.63 mmol) followed by methyl bromoacetate (40 μL, 0.42 mmol) and the mixture was stirred at room temperature overnight to afford COMPOUND 148 as a tan solid (81 mg, 66%) following work-up and purification. $^1$H NMR (CDCl$_3$) δ 0.86-1.03 (m, 5H), 1.52-1.60 (m, 1H), 1.74-1.78 (m, 3H), 2.14 (t, 1H, J=11.4 Hz), 2.51 (s, 6H), 2.51-2.59 (m, 1H), 2.72-2.88 (m, 3H), 3.29-3.48 (m, 2H), 3.78-3.83 (m, 6H), 4.53 (s, 2H), 6.53 (d, 2H, J=8.4 Hz), 6.75 (d, 2H, J=8.1 Hz), 7.40-7.44 (m, 1H), 7.49-7.54 (m, 3H), 8.71 (br s, 1H), 8.84 (s, 1H). $^{13}$C NMR (CDCl$_3$) δ 11.37, 19.90, 27.17, 28.32, 28.69, 37.93, 41.60, 46.92, 49.93, 50.15, 55.37, 58.15, 64.12, 110.38, 113.84, 114.32, 116.98, 127.17, 128.17, 128.50, 128.83, 129.20, 139.97, 141.27, 148.72, 155.46, 161.02, 164.27, 167.71. ES-MS m/z 585 (M+H). Anal. Calcd. for $C_{33}H_{40}N_6O_4 \cdot 0.7H_2O$: C, 66.36; H, 6.99; N, 14.07. Found. C, 66.32; H, 6.83; N, 13.71.

EXAMPLE 149

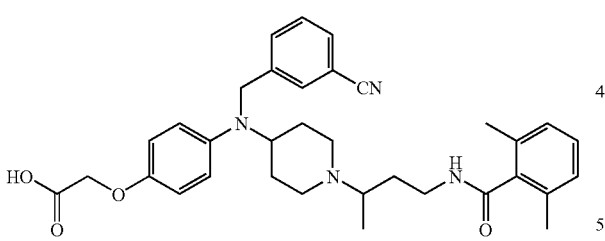

COMPOUND 149: [4-((3-Cyano-benzyl)-{1-[3-(2,6-dimethyl-benzoylamino)-1-methyl-propyl]-piperidin-4-yl}-amino)-phenoxy]-acetic acid To a solution of COMPOUND 143 in CH$_2$Cl$_2$ (2 mL) was added anisole (0.1 mL, 0.92 mmol) followed by TFA (2 mL) and the solution was stirred at room temperature for 90 minutes to afford COMPOUND 149 as a white solid (200 mg, 52%) after a basic work-up and purification. $^1$H NMR (CD$_3$OD) δ 1.29 (d, 3H, J=6.3 Hz), 1.76-1.89 (m, 5H), 2.07-2.28 (m, 1H), 2.28 (s, 6H), 2.86-3.03 (m, 2H), 3.19-3.27 (m, 3H), 3.37-3.51 (m, 2H), 3.67-3.75 (m, 1H), 4.19 (s, 2H), 4.24 (s, 2H), 6.76 (s, 4H), 7.02 (d, 2H, J=7.5 Hz), 7.11-7.16 (m, 1H), 7.36-7.41 (m, 1H), 7.48-7.55 (m, 3H). $^{13}$C NMR (CD$_3$OD) δ 12.82, 18.45, 27.43, 31.16, 36.74, 46.73, 49.61, 50.48, 56.06, 59.61, 67.86, 112.19, 115.51, 118.98, 119.18, 127.52, 128.96, 129.51, 130.55, 130.77, 132.17, 134.23, 137.73, 142.53, 142.92, 152.96, 172.43, 176.24. ES-MS m/z 569 (M+H). Anal. Calcd. for $C_{34}H_{40}N_4O_4 \cdot 0.6CH_2Cl_2$: C, 67.06; H, 6.70; N, 9.04. Found. C, 66.95; H, 6.64; N, 8.91.

EXAMPLE 150

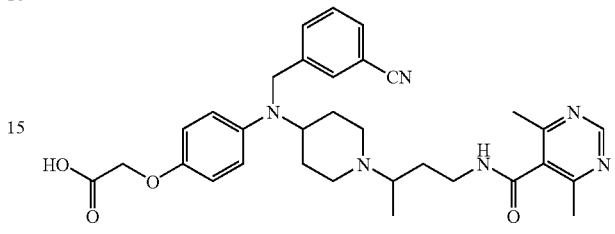

COMPOUND 150: {4-[(3-Cyano-benzyl)-(1-{3-[(4,6-dimethyl-pyrimidine-5-carbonyl)-amino]-1-methyl-propyl}-piperidin-4-yl)-amino]-phenoxy}-acetic acid To a solution of COMPOUND 144 in CH$_2$Cl$_2$ (2 mL) was added anisole (0.1 mL, 0.92 mmol) followed by TFA (2 mL) and the solution was stirred at room temperature for 2 h to afford COMPOUND 150 as a white solid (210 mg, 70%) following work-up and purification. $^1$H NMR (CDCl$_3$) δ 1.21 (m, 3H), 1.62-1.71 (m, 5H), 2.17 (m, 1H), 2.43 (s, 6H), 2.58 (m, 1H), 2.82 (m, 1H), 3.03-3.07 (m, 2H), 3.44-3.52 (m, 4H), 3.67-3.72 (m, 1H), 3.93-3.99 (m, 1H), 4.12 (s, 2H), 6.46 (m, 2H), 6.66 (m, 2H), 7.26-7.39 (m, 4H), 8.58 (br s, 1H), 8.82 (s, 1H). $^{13}$C NMR (CDCl$_3$) δ 12.35, 22.47, 25.26, 27.15, 31.92, 36.99, 44.70, 50.89, 54.47, 58.49, 67.56, 112.73, 115.53, 116.55, 119.35, 129.79, 130.30, 130.68, 130.99, 131.49, 142.57, 152.35, 157.67, 163.47, 167.77, 175.61. ES-MS m/z 571 (M+H). Anal. Calcd. for $C_{32}H_{38}N_6O_4 \cdot 1.3CH_2Cl_2$: C, 58.72; H, 6.01; N, 12.34. Found. C, 58.81; H, 6.08; N, 12.28.

EXAMPLE 151

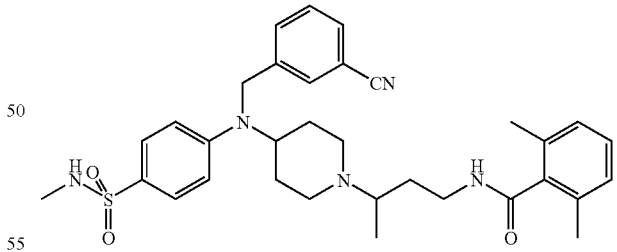

COMPOUND 151: N-(3-{4-[(3-Cyano-benzyl)-(4-methylsulfamoyl-phenyl)-amino]-piperidin-1-yl}-butyl)-2,6-dimethyl-benzamide Using general procedure A, 4-amino-N-benzyl-N-methyl-benzenesulfonamide (Mikhura, I. V.; et al., *Russ. J. Org. Chem.*, 36, 1, 2000, 64-68) (852 mg, 3.09 mmol) and 1-Boc-4-piperidone (677 mg, 3.40 mmol) afforded 4-[4-(benzyl-methyl-sulfamoyl)-phenylamino]-piperidine-1-carboxylic acid tert-butyl ester as a white solid (796 mg, 64%).

Using general procedure H with the above amine (790 mg, 1.72 mmol) and α-bromo-m-tolunitrile (660 mg, 3.37 mmol) and then using general procedure C gave N-benzyl-4-[(3-cyano-benzyl)-piperidin-4-yl-amino]-N-methyl-benzenesulfonamide as a white foam (202 mg, 25% over 2 steps).

The above amine (100 mg, 0.21 mmol) and conc. $H_2SO_4$ (2 mL) were stirred at room temperature for 2 hours. The mixture was poured over ice, neutralized with 10N NaOH to pH-12 and extracted with $CHCl_3$ (2×20 mL) and EtOAc (3×20 mL). The combined organic extracts were dried ($Na_2SO_4$), filtered and concentrated under reduced pressure to give 4-[(3-cyano-benzyl)-piperidin-4-yl-amino]-N-methyl-benzenesulfonamide as a white solid (31 mg, 38%) following purification.

Using general procedure B with the above amine (160 mg, 0.417 mmol) and 2-(3-oxo-butyl)-isoindole-1,3-dione (181 mg, 0.833 mmol) and then using general procedure D afforded 4-[[1-(3-amino-1-methyl-propyl)-piperidin-4-yl]-(3-cyano-benzyl)-amino]-N-methyl-benzenesulfonamide as a white solid (105 mg, 55% over 2 steps).

Using general procedure E, the above amine (42 mg, 0.092 mmol) and 2,6-dimethylbenzoic acid (15 mg, 0.10 mmol) gave COMPOUND 151 as a white solid (49 mg, 89%). $^1$H NMR (CDCl$_3$) δ 0.98-1.24 (m, 2H), 1.01 (d, 3H, J=6.3 Hz), 1.53 (m, 1H), 1.70-1.75 (m, 3H), 2.19 (t, 1H, J=11.1 Hz), 2.30 (s, 6H), 2.56-2.61 (m, 4H), 2.76-2.92 (m, 3H), 3.30 (t, 1H, J=10.8 Hz), 3.72 (t, 1H, J=10.2 Hz), 3.81-3.87 (m, 1H), 3.94 (s, 2H), 4.40 (d, 1H, J=4.98 Hz), 6.55 (d, 2H, J=8.4 Hz), 6.96 (d, 2H, J=7.2 Hz), 7.05-7.10 (m, 1H), 7.38-7.48 (m, 3H), 7.55-7.60 (m, 3H), 8.16 (br s, 1H). $^{13}$C NMR (CDCl$_3$) δ 13.49, 19.17, 29.08, 29.35, 30.28, 31.08, 39.67, 43.55, 48.01, 51.87, 56.04, 60.29, 112.11, 112.79, 118.77, 125.78, 127.33, 128.43, 129.23, 129.56, 130.61, 130.86, 134.16, 138.63, 140.64, 151.25, 169.83. ES-MS m/z 588 (M+H). Anal. Calcd. for $C_{33}H_{41}N_5O_3S \cdot 0.3CH_2Cl_2$: C, 65.22; H, 6.84; N, 11.42; S, 5.23. Found. C, 65.36; H, 6.84; N, 11.21; S, 5.13.

EXAMPLE 152

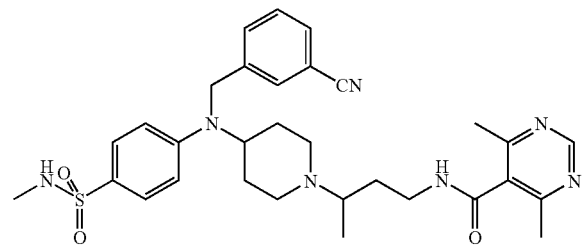

COMPOUND 152: 4,6-Dimethyl-pyrimidine-5-carboxylic acid (3-{4-[(3-cyano-benzyl)-(4-methylsulfamoyl-phenyl)-amino]-piperidin-1-yl}-butyl)-amide Using general procedure E, 4-[[1-(3-amino-1-methyl-propyl)-piperidin-4-yl]-(3-cyano-benzyl)-amino]-N-methyl-benzenesulfonamide (see EXAMPLE 151) (63 mg, 0.14 mmol) and 4,6-dimethyl-pyrimidine-5-carboxylic acid (23 mg, 0.15 mmol) gave COMPOUND 152 as a white solid (72 mg, 89%). $^1$H NMR (CDCl$_3$) δ 1.00-1.17 (m, 2H), 1.02 (d, 3H, J=5.4 Hz), 1.55 (m, 1H), 1.74-1.78 (m, 3H), 2.21 (t, 1H, J=10.5 Hz), 2.50 (s, 6H), 2.58-2.62 (m, 4H), 2.75-2.85 (m, 3H), 3.34 (m, 1H), 3.77 (m, 2H), 4.05 (s, 2H), 4.44 (d, 1H, J=4.2 Hz), 6.56 (d, 2H, J=8.1 Hz), 7.47-7.72 (m, 5H), 8.35 (br s, 1H), 8.90 (s, 1H). $^{13}$C NMR (CDCl$_3$) δ 13.52, 21.97, 28.92, 29.32, 30.31, 31.00, 39.75, 43.60, 48.08, 51.64, 55.73, 59.82, 112.00, 112.78, 118.79, 125.81, 129.25, 129.48, 129.64, 130.70, 130.88, 130.95, 140.36, 151.29, 157.53, 163.15, 166.30. ES-MS m/z 590 (M+H). Anal. Calcd. for $C_{31}H_{39}N_7O_3S \cdot 0.6CH_2Cl_2$: C, 59.24; H, 6.32; N, 15.30; S, 5.00. Found. C, 59.35; H, 6.37; N, 15.18; S, 4.87.

EXAMPLE 153

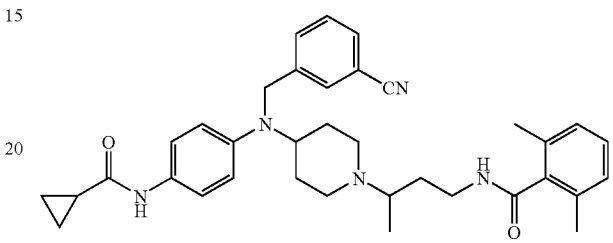

COMPOUND 153: N-[3-(4-{(3-Cyano-benzyl)-[4-(cyclopropanecarbonyl-amino)-phenyl]-amino}-piperidin-1-yl)-butyl]-2,6-dimethyl-benzamide To a solution of COMPOUND 142 (61 mg, 0.12 mmol) in $CH_2Cl_2$ (1 mL) and $Et_3N$ (33 μL, 0.24 mmol) was added cyclopropanecarbonyl chloride (17 μL, 0.18 mmol) and the solution was stirred at room temperature for 4 hours to afford COMPOUND 153 as a white solid (69 mg, 100%) following work-up and purification. $^1$H NMR (CDCl$_3$) δ 0.75-0.83 (m, 2H), 1.01 (m, 6H), 1.01-1.16 (m, 1H), 1.42-1.61 (m, 2H), 1.61-1.77 (m, 3H), 2.15 (t, 1H, J=11.1 Hz), 2.30 (s, 6H), 2.55 (t, 1H, J=10.8 Hz), 2.74-2.86 (m, 3H), 3.28 (t, 1H, J=11.1 Hz), 3.54 (m, 1H), 3.76 (s, 2H), 3.85 (m, 1H), 6.50 (d, 2H, J=6.49 (d, 2H, J=8.4 Hz), 6.91-6.99 (m, 3H), 7.24 (d, 2H, J=9.3 Hz), 7.36-7.44 (m, 4H), 7.50 (br s, 1H), 8.40 (br s, 1H). $^{13}$C NMR (CDCl$_3$) δ 7.98, 8.39, 13.77, 15.72, 19.54, 29.29, 30.57, 31.31, 40.14, 44.03, 48.66, 52.46, 57.39, 60.82, 112.78, 114.85, 119.40, 122.01, 127.67, 128.79, 129.56, 129.66, 130.50, 130.82, 131.47, 134.45, 138.91, 142.66, 145.31, 170.35, 172.09. ES-MS m/z 578 (M+H). Anal. Calcd. for $C_{36}H_{43}N_5O_2 \cdot 0.3CH_2Cl_2$: C, 72.28; H, 7.28; N, 11.61. Found. C, 72.57; H, 7.38; N, 11.30.

EXAMPLE 154

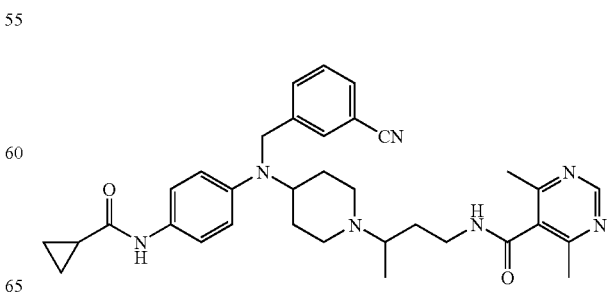

COMPOUND 154: 4,6-Dimethyl-pyrimidine-5-carboxylic acid [3-(4-{(3-cyano-benzyl)-[4-(cyclopropanecarbonyl-amino)-phenyl]-amino}-piperidin-1-yl)-butyl]-amide To a solution of COMPOUND 111 (880 mg, 1.59 mmol) in MeOH (10 mL) was added 6N HCl (20 mL) and the solution was stirred at room temperature for 18 hours and heated at 40° C. for 3 hours to give 4,6-dimethyl-pyrimidine-5-carboxylic acid (3-{4-[(4-amino-phenyl)-(3-cyano-benzyl)-amino]-piperidin-1-yl}-butyl)-amide as a white solid (813 mg, 100%) following a basic work-up.

To a solution of the above aniline (51 mg, 0.10 mmol) in $CH_2Cl_2$ (1 mL) and $Et_3N$ (28 μL, 0.20 mmol) was added cyclopropanecarbonyl chloride (14 μL, 0.15 mmol) and the solution was stirred at room temperature for 16 hours to afford COMPOUND 154 as a white solid (56 mg, 96%) following work-up and purification. $^1$H NMR (CDCl$_3$) δ 0.74-0.79 (m, 2H), 0.98-1.15 (m, 7H), 1.43 (m, 1H), 1.56 (m, 1H), 1.74-1.79 (m, 3H), 2.19 (m, 1H), 2.50 (s, 6H), 2.58 (m, 1H), 2.75-2.87 (m, 3H), 3.32 (m, 1H), 3.57 (m, 1H), 3.82 (m, 1H), 3.89 (s, 2H), 6.52 (d, 2H, J=8.4 Hz), 7.26 (m, 3H), 7.39-7.44 (m, 1H), 7.49-7.53 (m, 3H), 8.64 (br s, 1H), 8.85 (s, 1H). $^{13}$C NMR (CDCl$_3$) δ 7.64, 13.36, 15.44, 21.95, 29.04, 30.17, 30.77, 39.86, 43.64, 48.46, 51.94, 56.68, 60.10, 112.48, 114.66, 118.98, 121.61, 129.27, 129.43, 130.06, 130.58, 130.84, 131.12, 141.85, 144.86, 157.51, 163.09, 166.38, 171.62. ES-MS m/z 580 (M+H). Anal. Calcd. for $C_{34}H_{41}N_7O_2 \cdot 0.45CH_2Cl_2$: C, 66.96; H, 6.83; N, 15.87. Found. C, 66.99; H, 7.02; N, 15.55.

EXAMPLE 155

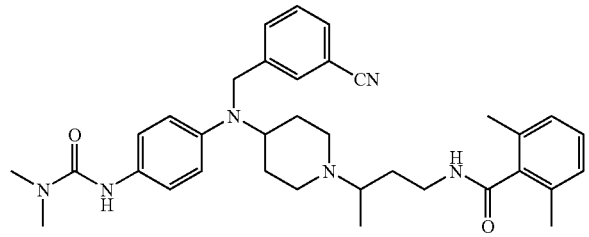

COMPOUND 155: N-[3-(4-{(3-Cyano-benzyl)-[4-(3,3-dimethyl-ureido)-phenyl]-amino}-piperidin-1-yl)-butyl]-2,6-dimethyl-benzamide A mixture of COMPOUND 142 (61 mg, 0.12 mmol), $K_2CO_3$ (50 mg, 0.36 mmol) and dimethylcarbamoyl chloride (23 μL, 0.24 mmol) in DMF (1 mL) was stirred at room temperature for 76 hours to afford COMPOUND 155 as a white solid (53 mg, 76%) following work-up and purification. $^1$H NMR (CDCl$_3$) δ 0.93-1.17 (m, 2H), 0.99 (d, 3H, J=6.0 Hz), 1.49-1.59 (m, 1H), 1.69-1.78 (m, 3H), 2.14 (t, 1H, J=11.1 Hz), 2.31 (s, 6H), 2.54 (t, 1H, J=10.8 Hz), 2.73-2.85 (m, 3H), 2.98 (s, 6H), 3.27 (t, 1H, J=10.5 Hz), 3.52 (m, 1H), 3.73 (s, 2H), 3.90 (m, 1H), 6.04 (s, 1H), 6.50 (d, 2H, J=8.1 Hz), 6.94-6.99 (m, 3H), 7.09 (d, 2H, J=8.1 Hz), 7.39-7.58 (m, 4H), 8.44 (br s, 1H). $^{13}$C NMR (CDCl$_3$) δ 13.81, 19.54, 29.38, 30.74, 31.29, 36.79, 40.28, 43.97, 48.67, 52.61, 57.72, 61.01, 112.75, 115.27, 119.44, 122.87, 127.66, 128.76, 129.49, 130.39, 130.59, 130.76, 131.54, 134.46, 139.03, 142.81, 144.99, 156.69, 170.24. ES-MS m/z 581 (M+H). Anal. Calcd. for $C_{35}H_{44}N_6O_2 \cdot 0.2CH_2Cl_2$: C, 70.73; H, 7.49; N, 14.06. Found. C, 70.74; H, 7.57; N, 13.74.

EXAMPLE 156

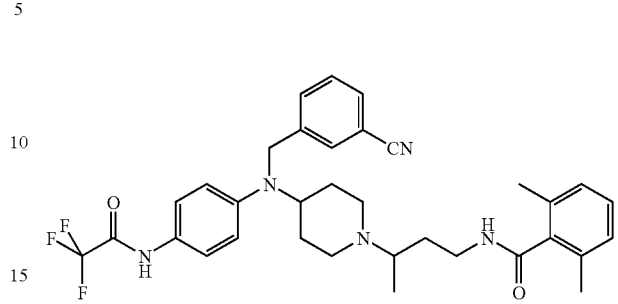

COMPOUND 156: N-[3-(4-{(3-Cyano-benzyl)-[4-(2,2,2-trifluoro-acetylamino)-phenyl]-amino}-piperidin-1-yl)-butyl]-2,6-dimethyl-benzamide To a solution of COMPOUND 142 (61 mg, 0.12 mmol) in $CH_2Cl_2$ (1 mL) and $Et_3N$ (28 μL, 0.20 mmol) was added TFAA (21 μL, 0.15 mmol) and the solution was stirred at room temperature for 2.5 hours to afford COMPOUND 156 as a white solid (54 mg, 89%) following work-up and purification. $^1$H NMR (CDCl$_3$) δ 1.00-1.25 (m, 5H), 1.52-1.61 (m, 1H), 1.70-1.76 (m, 3H), 2.17 (m, 1H), 2.30 (s, 6H), 2.57 (m, 1H), 2.75-2.87 (m, 3H), 3.29 (m, 1H), 3.61 (m, 1H), 3.81-3.90 (m, 3H), 6.52 (d, 2H, J=6.9 Hz), 6.94-6.99 (m, 3H), 7.26-7.31 (m, 2H), 7.42 (s, 3H), 7.53 (br s, 1H), 7.81 (s, 1H), 8.34 (br s, 1H). $^{13}$C NMR (CDCl$_3$) δ 13.82, 19.51, 29.43, 30.71, 31.29, 40.23, 43.95, 48.49, 52.50, 57.03, 60.91, 112.94, 114.14, 116.17 (q, J=300 Hz), 119.30, 122.70, 125.87, 127.67, 128.79, 129.70, 130.29, 130.98, 131.28, 134.49, 138.95, 142.15, 146.85, 154.99 (q, J=37 Hz), 170.26. ES-MS m/z 606 (M+H). Anal. Calcd. for $C_{34}H_{38}N_5O_2F_3 \cdot 0.2CH_2Cl_2$: C, 65.97; H, 6.22; N, 11.25; F, 9.15. Found. C, 66.21; H, 6.26; N, 11.16; F, 9.05.

EXAMPLE 157

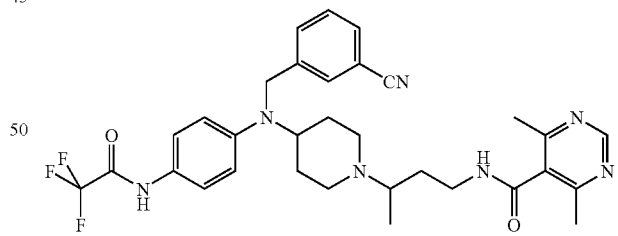

COMPOUND 157: 4,6-Dimethyl-pyrimidine-5-carboxylic acid [3-(4-{(3-cyano-benzyl)-[4-(2,2,2-trifluoro-acetylamino)-phenyl]-amino}-piperidin-1-yl)-butyl]-amide To a solution of 4,6-dimethyl-pyrimidine-5-carboxylic acid (3-{4-[(4-amino-phenyl)-(3-cyano-benzyl)-amino]-piperidin-1-yl}-butyl)-amide (see EXAMPLE 154) (51 mg, 0.10 mmol) in $CH_2Cl_2$ (1 mL) and $Et_3N$ (28 μL, 0.20 mmol) was added TFAA (21 μL, 0.15 mmol) and the solution was stirred at room temperature for 3 hours. Standard work-up and purification afforded COMPOUND 157 as a white solid (57 mg, 94%). ¹H NMR (CDCl₃) δ 0.88-1.15 (m, 2H), 1.02 (d, 3H, J=6.6 Hz), 1.57 (m, 1H), 1.74-1.80 (m, 3H), 2.19 (t, 1H, J=12.0 Hz), 2.51 (s, 6H), 2.59 (t, 1H, J=11.4 Hz), 2.75-2.86 (m, 3H), 3.33 (m, 1H), 3.63 (m, 1H), 3.84-3.92 (m, 1H), 3.92 (s, 2H), 6.55 (d, 2H, J=8.4 Hz), 7.32 (d, 2H, J=8.4 Hz), 7.43-7.52 (m, 4H), 7.76 (s, 1H), 8.58 (br s, 1H), 8.87 (s, 1H). ¹³C NMR (CDCl₃) δ 13.84, 22.31, 29.63, 30.80, 31.09, 40.45, 43.95, 48.59, 52.36, 56.68, 60.63, 113.00, 114.16, 116.28 (q, J=289 Hz), 119.27, 121.70, 126.01, 129.80, 130.21, 131.12, 131.30, 141.76, 146.82, 154.93 (q, J=37 Hz), 157.91, 163.50, 166.66. ES-MS m/z 608 (M+H). Anal. Calcd. for C₃₂H₃₆N₇O₂F₃.0.3CH₂Cl₂: C, 61.27; H, 5.83; N, 15.49; F, 9.00. Found. C, 61.33; H, 5.90; N, 15.36; F, 8.74.

EXAMPLE 158

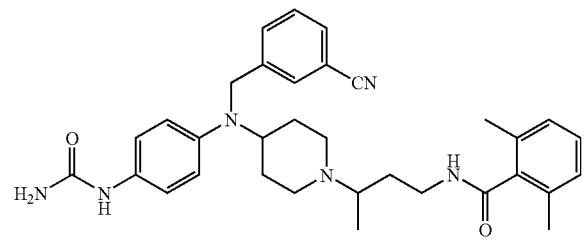

COMPOUND 158: N-(3-{4-[(3-Cyano-benzyl)-(4-ureido-phenyl)-amino]-piperidin-1-yl}-butyl)-2,6-dimethyl-benzamide To a solution of COMPOUND 142 (61 mg, 0.12 mmol) in toluene (1 mL) was added phosgene (20% in toluene, 82 μL, 0.15 mmol) and the resultant slurry was stirred at room temperature for 1 hour. The mixture was concentrated under reduced pressure and the residue was dissolved in DMF (1 mL). To the solution were added ammonium chloride (33 mg, 0.62 mmol) and DIPEA (120 μL, 0.69 mmol) and the mixture was stirred at room temperature for 17 hours to afford COMPOUND 158 as a white solid (24 mg, 36%) following work-up and purification. ¹H NMR (CDCl₃) δ 1.00-1.15 (m, 5H), 1.55 (m, 1H), 1.71 (m, 3H), 2.16 (m, 1H), 2.30 (s, 6H), 2.56 (m, 1H), 2.75-2.87 (m, 3H), 3.29 (m, 1H), 3.57 (m, 1H), 3.79-3.90 (m, 3H), 4.63 (s, 2H), 6.41 (s, 1H), 6.50 (d, 2H, J=7.8 Hz), 6.92-7.04 (m, 5H), 7.43 (s, 3H), 7.52 (br s, 1H), 8.38 (br s, 1H). ¹³C NMR (CDCl₃) δ 13.81, 19.54, 29.41, 30.68, 31.30, 40.24, 43.99, 48.69, 52.49, 57.30, 60.85, 112.86, 114.97, 119.39, 125.05, 127.70, 128.84, 129.63, 130.41, 130.90, 131.39, 134.47, 138.87, 142.42, 146.09, 158.05, 170.39. ES-MS m/z 553 (M+H). Anal. Calcd. for C₃₃H₄₀N₆O₂.0.85CH₂Cl₂.0.1C₆H₁₄: C, 65.31; H, 6.86; N, 13.27. Found. C, 65.38; H, 6.66; N, 13.07.

EXAMPLE 159

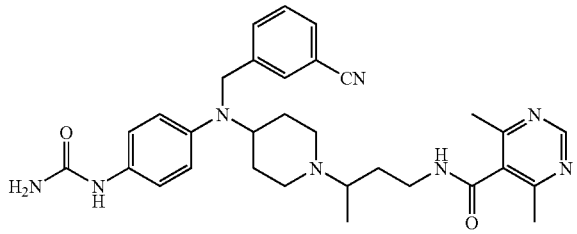

COMPOUND 159: 4,6-Dimethyl-pyrimidine-5-carboxylic acid (3-{4-[(3-cyano-benzyl)-(4-ureido-phenyl)-amino]-piperidin-1-yl}-butyl)-amide To a solution of 4,6-dimethyl-pyrimidine-5-carboxylic acid (3-{4-[(4-amino-phenyl)-(3-cyano-benzyl)-amino]-piperidin-1-yl}-butyl)-amide (see EXAMPLE 154) (54 mg, 0.10 mmol) in toluene (1 mL) was added phosgene (20% in toluene, 82 μL, 0.15 mmol) and the resultant slurry was stirred at room temperature for 3.5 hours. The mixture was concentrated under reduced pressure and the residue was dissolved in DMF (1 mL). To the solution were added ammonium chloride (28 mg, 0.53 mmol) and DIPEA (110 μL, 0.64 mmol) and the mixture was stirred at room temperature for 25 hours. Standard work-up and purification afforded COMPOUND 159 as a white solid (23 mg, 39%). ¹H NMR (CDCl₃) δ 0.90-1.10 (m, 5H), 1.54 (d, 1H, J=13.5 Hz), 1.74-1.83 (m, 3H), 2.17 (t, 1H, J=11.1 Hz), 2.50 (s, 6H), 2.56 (t, 1H, J=11.1 Hz), 2.73-2.84 (m, 3H), 3.31 (m, 1H), 3.56 (m, 1H), 3.82-3.89 (m, 1H), 3.89 (s, 2H), 4.72 (s, 2H), 6.51 (d, 2H, J=8.1 Hz), 6.58 (s, 1H), 7.05 (d, 2H, J=8.1 Hz), 7.41-7.56 (m, 4H), 8.62 (br s, 1H), 8.85 (s, 1H). ¹³C NMR (CDCl₃) δ 13.44, 21.94, 29.21, 30.42, 30.73, 40.05, 43.58, 48.57, 51.99, 53.45, 56.55, 60.24, 112.55, 117.73, 118.98, 125.26, 128.41, 129.36, 129.93, 130.67, 130.88, 131.02, 141.60, 145.94, 157.52, 157.75, 163.11, 166.29. ES-MS m/z 555 (M+H). Anal. Calcd. for C₃₁H₃₈N₈O₂.0.8CH₂Cl₂: C, 61.34; H, 6.41; N, 18.00. Found. C, 61.52; H, 6.49; N, 17.93.

EXAMPLE 160

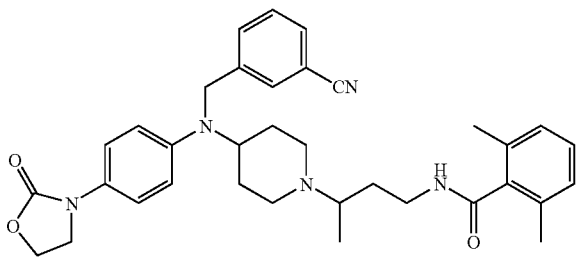

COMPOUND 160: N-[3-(4-{(3-Cyano-benzyl)-[4-(2-oxo-oxazolidin-3-yl)-phenyl]-amino}-piperidin-1-yl)-butyl]-2,6-dimethyl-benzamide To a solution of COMPOUND 142 (51 mg, 0.10 mmol) in $CH_2Cl_2$ (1 mL) was added 2-chloro-ethylchloroformate (12 μL, 0.12 mmol) followed by $Et_3N$ (21 μL, 0.15 mmol) and the solution was stirred at room temperature for 18.5 hours to afford the crude substrate after work-up.

To the above substrate (70 mg) in DMF (2 mL) was added NaH (60% in mineral oil, 15 mg, 0.25 mmol) and the mixture was heated at 90° C. for 2.5 hours to afford COMPOUND 160 as a white solid (52 mg, 90%) following work-up and purification. $^1$H NMR ($CDCl_3$) δ 0.98-1.20 (m, 2H), 1.00 (d, 3H, J=6.3 Hz), 1.50-1.60 (m, 1H), 1.70-1.78 (m, 3H), 2.15 (t, 1H, J=11.1 Hz), 2.31 (s, 6H), 2.56 (t, 1H, J=11.1 Hz), 2.75-2.91 (m, 3H), 3.28 (t, 1H, J=11.7 Hz), 3.58 (m, 1H), 3.77 (s, 2H), 3.86-3.93 (m, 1H), 3.95 (t, 2H, J=7.8 Hz), 4.43 (t, 2H, J=7.8 Hz), 6.56 (d, 2H, J=8.4 Hz), 6.92-7.03 (m, 3H), 7.26 (m, 2H), 7.43 (m, 3H), 7.52 (br s, 1H), 8.37 (br S, 1H). $^{13}$C NMR ($CDCl_3$) δ 13.43, 19.14, 29.01, 30.32, 30.95, 39.82, 43.59, 45.79, 48.17, 52.14, 53.46, 60.53, 61.32, 112.51, 114.31, 118.96, 120.69, 127.27, 128.37, 128.83, 129.23, 130.01, 130.51, 130.96, 134.08, 138.64, 142.01, 145.28, 155.73, 169.83. ES-MS m/z 580 (M+H). Anal. Calcd. for $C_{35}H_{41}N_5O_3 \cdot 0.2CH_2Cl_2$: C, 70.85; H, 6.99; N, 11.74. Found. C, 70.89; H, 7.07; N, 11.57.

EXAMPLE 161

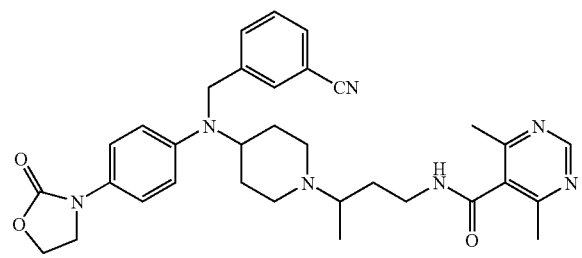

COMPOUND 161: 4,6-Dimethyl-pyrimidine-5-carboxylic acid [3-(4-{(3-cyano-benzyl)-[4-(2-oxo-oxazolidin-3-yl)-phenyl]-amino}-piperidin-1-yl)-butyl]-amide To a solution of 4,6-dimethyl-pyrimidine-5-carboxylic acid (3-{4-[(4-amino-phenyl)-(3-cyano-benzyl)-amino]-piperidin-1-yl}-butyl)-amide (see EXAMPLE 154) (51 mg, 0.10 mmol) in $CH_2Cl_2$ (1 mL) was added 2-chloro-ethylchloroformate (12 μL, 0.12 mmol) followed by $Et_3N$ (21 μL, 0.15 mmol) and the solution was stirred at room temperature for 18.5 hours to afford the crude substrate after work-up.

To the above substrate (73 mg) in DMF (2 mL) was added NaH (60% in mineral oil, 15 mg, 0.25 mmol) and the mixture was heated at 90° C. for 2 hours to afford COMPOUND 161 as a white solid (49 mg, 84%) following work-up and purification. $^1$H NMR ($CDCl_3$) δ 0.90-1.10 (m, 2H), 1.02 (d, 3H, J=6.3 Hz), 1.54-1.61 (m, 1H), 1.77 (m, 3H), 2.18 (t, 1H, J=11.7 Hz), 2.51 (s, 6H), 2.58 (t, 1H, J=11.4 Hz), 2.74-2.86 (m, 3H), 3.30 (m, 1H), 3.60 (m, 1H), 3.88 (m, 3H), 3.97 (t, 2H, J=8.1 Hz), 4.44 (t, 2H, J=8.4 Hz), 6.57 (d, 2H, J=9.0 Hz), 7.28 (d, 2H, J=10.5 Hz), 7.41-7.46 (m, 1H), 7.51-7.57 (m, 3H), 8.65 (m, 1H), 8.85 (s, 1H). $^{13}$C NMR ($CDCl_3$) δ 13.46, 21.95, 29.24, 30.40, 30.75, 40.01, 43.62, 45.75, 48.28, 51.99, 56.62, 60.21, 61.32, 112.57, 114.40, 118.96, 120.62, 129.07, 129.33, 129.96, 130.64, 130.89, 131.02, 141.65, 145.15, 155.69, 157.51, 163.09, 166.29. ES-MS m/z 582 (M+H). Anal. Calcd. for $C_{33}H_{39}N_7O_3 \cdot 0.15CH_2Cl_2$: C, 66.98; H, 6.66; N, 16.49. Found. C, 67.03; H, 6.70; N, 16.27.

EXAMPLE 162

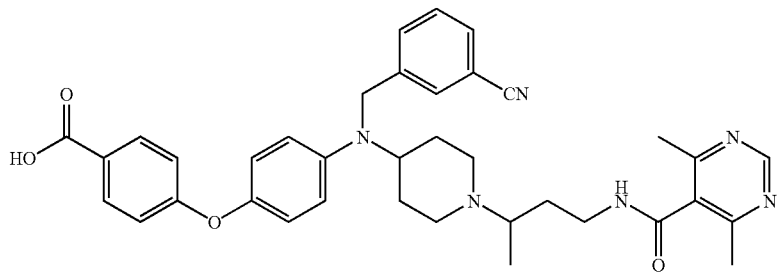

COMPOUND 162: 4-{4-[(3-Cyano-benzyl)-(1-{3-[(4,6-dimethyl-pyrimidine-5-carbonyl)-amino]-1-methyl-propyl}-piperidin-4-yl)-amino]-phenoxy}-benzoic acid Using general procedure H, 4-[4-(4-methoxycarbonyl-phenoxy)-phenylamino]-piperidine-1-carboxylic acid tert-butyl ester (see EXAMPLE 96) (440 mg, 1.07 mmol) and 3-cyanobenzyl bromide (314 mg, 1.6 mmol) afforded 4-{(3-cyano-benzyl)-[4-(4-methoxycarbonyl-phenoxy)-phenyl]-amino}-piperidine-1-carboxylic acid tert-butyl ester as a white solid (520 mg, 90%).

Using general procedure C with the above substrate (520 mg, 0.96 mmol), then general procedure B with 2-(3-oxo-butyl)-isoindole-1,3-dione (413 mg, 1.90 mmol) and then using general procedure D afforded 4-{4-[[1-(3-amino-1-methyl-propyl)-piperidin-4-yl]-(3-cyano-benzyl)-amino]-phenoxy}-benzoic acid methyl ester as a white solid (218 mg, 44% over 3 steps).

Using general procedure E with the above primary amine (80 mg, 0.16 mmol) and 4,6-dimethyl-pyrimidine-5-carboxylic acid (26 mg, 0.17 mmol) followed by general procedure K afforded COMPOUND 162 as a white solid (25 mg, 25% over 2 steps). $^1$H NMR ($CD_3OD$) δ 1.40 (d, 3H, J=6.0 Hz), 1.78-1.94 (m, 1H), 2.03-2.15 (m, 4H), 2.15-2.29 (m, 1H), 2.48 (s, 6H), 3.06-3.27 (m, 2H), 3.32-3.61 (m, 5H), 3.99-4.12 (m, 1H), 4.46 (s, 2H), 6.80 (d, 2H, J=8.4 Hz), 6.86

(s, 4H), 7.38-7.46 (m, 1H), 7.49-7.61 (m, 3H), 7.87 (d, 2H, J=8.1 Hz), 8.86 (s, 1H). $^{13}$C NMR (CD$_3$OD) δ 14.19, 22.40, 28.54, 28.70, 32.64, 38.07, 51.10 (2 carbons), 56.32, 61.15, 113.81, 117.56, 118.92, 120.25, 122.70, 130.25, 131.05, 131.85, 132.08 (2 carbons), 132.90, 133.18, 143.95, 146.90, 149.93, 158.66, 163.43, 165.09, 169.54, 173.58. ES-MS m/z 633 (M+H). Anal. Calcd. for C$_{37}$H$_{40}$N$_6$O$_4$.1.2CH$_2$Cl$_2$: C, 62.45; H, 5.82; N, 11.44. Found. C, 62.56; H, 5.95; N, 11.40.

EXAMPLE 163

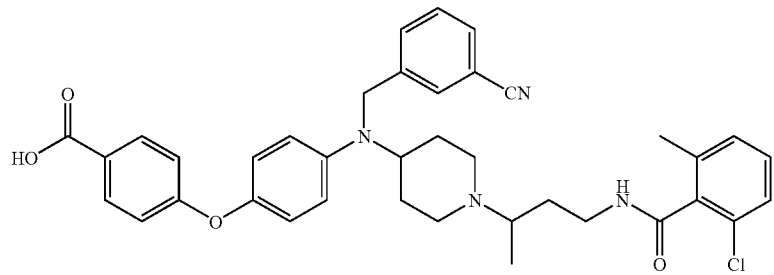

COMPOUND 163: 4-{4-[{1-[3-(2-Chloro-6-methyl-benzoylamino)-1-methyl-propyl]-piperidin-4-yl}-(3-cyano-benzyl)-amino]-phenoxy}-benzoic acid Using general procedure E with 4-{4-[[1-(3-amino-1-methyl-propyl)-piperidin-4-yl]-(3-cyano-benzyl)-amino]-phenoxy}-benzoic acid methyl ester (see EXAMPLE 162) (80 mg, 0.16 mmol) and 2-chloro-6-methyl benzoic acid (29 mg, 0.17 mmol) followed by general procedure K afforded COMPOUND 163 as a white solid (42 mg, 41% over 2 steps). $^1$H NMR (CD$_3$OD) δ 1.39 (d, 3H, J=6.6 Hz), 1.79-2.07 (m, 3H), 2.08-2.21 (m, 3H), 2.34 (s, 3H), 3.06-3.26 (m, 2H), 3.34-3.64 (m, 5H), 3.98-4.10 (m, 1H), 4.48 (s, 2H), 6.86 (d, 2H, J=8.4 Hz), 6.92 (s, 4H), 7.19-7.30 (m, 3H), 7.44-7.51 (m, 1H), 7.55-7.65 (m, 3H), 7.91 (d, 2H, J=8.4 Hz). $^{13}$C NMR (CD$_3$OD) δ 14.26, 19.87, 28.36, 28.48, 32.53, 37.62, 51.11, 56.02, 61.37, 113.82, 117.65, 119.02, 120.25, 122.79, 128.23, 128.90, 130.28, 131.07, 131.75, 131.85, 131.92, 132.11, 133.03, 133.18, 138.02, 138.59, 143.83, 146.92, 149.84, 163.81, 171.08, 172.17. ES-MS m/z 651 (M+H). Anal. Calcd. for C$_{38}$H$_{39}$N$_4$ClO$_4$.0.5CH$_2$Cl$_2$.1.7H$_2$O: C, 63.84; H, 6.04; N, 7.74; Cl, 9.79. Found. C, 63.70; H, 6.08; N, 7.64; Cl, 9.92.

EXAMPLE 164

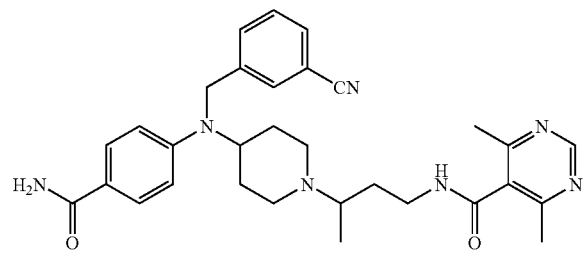

COMPOUND 164: 4,6-Dimethyl-pyrimidine-5-carboxylic acid (3-{4-[(4-carbamoyl-phenyl)-(3-cyano-benzyl)-amino]-piperidin-1-yl}-butyl)-amide Using general procedure H, 4-(4-methoxycarbonyl-phenylamino)-piperidine-1-carboxylic acid tert-butyl ester (see EXAMPLE 85) (331 mg, 0.99 mmol) and 3-(bromomethyl) benzonitrile (300 mg, 1.53 mmol) gave impure product as a white foam (299 mg).

Using general procedure C with the impure carbamate, then general procedure B with the resulting amine and 2-(3-oxo-butyl)-isoindole-1,3-dione (252 mg, 1.16 mmol) and then using general procedure D gave 4-[[1-(3-amino-1-methyl-propyl)-piperidin-4-yl]-(3-cyano-benzyl)-amino]-benzoic acid methyl ester as a white foam (146 mg, 35% over 4 steps).

Using general procedure E with the primary amine (73 mg, 0.17 mmol) and 4,6-dimethylpyrimidine-5-carboxylic acid (37 mg, 0.24 mmol) followed by general procedure K with the resulting ester gave 4-[(3-cyano-benzyl)-(1-{3-[(4,6-dimethyl-pyrimidine-5-carbonyl)-amino]-1-methyl-propyl}-piperidin-4-yl)-amino]-benzoic acid as a beige solid (43.4 mg, 46% over 2 steps).

Using general procedure E, the crude carboxylic acid (43.4 mg, 0.080 mmol) and NH$_4$Cl (11 mg, 0.21 mmol) gave COMPOUND 164 as an off-white foam (23.7 mg, 55%). $^1$H NMR (CDCl$_3$) δ 0.98-1.21 (m, 2H), 1.03 (d, 3H, J=6.6 Hz), 1.51-1.62 (m, 1H), 1.70-1.86 (m, 3H), 2.17-2.28 (m, 1H), 2.51 (s, 6H), 2.55-2.66 (m, 1H), 2.72-2.93 (m, 3H), 3.30-3.40 (m, 1H), 3.70-3.87 (m, 2H), 4.04 (s, 2H), 5.80 (br s, 2H), 6.55 (d, 2H, J=8.6 Hz), 7.43-7.57 (m, 4H), 7.63 (d, 2H, J=8.6 Hz), 8.47 (br s, 1H), 8.90 (s, 1H). $^{13}$C NMR (CDCl$_3$) δ 13.45, 21.91, 29.26, 30.36, 30.80, 39.90, 43.53, 47.97, 51.81, 55.64, 60.06, 111.94, 112.71, 118.75, 121.60, 129.22, 129.46, 129.58, 130.67, 130.78, 130.83, 140.79, 150.87, 157.53, 163.09, 166.23, 168.84. ESI-MS m/z 540 (MH)$^+$. Anal. Calcd. for C$_{31}$H$_{37}$N$_7$O$_2$.0.8CH$_2$Cl$_2$: C, 62.86; H, 6.40; N, 16.14. Found. C, 62.61; H, 6.59; N, 16.27.

EXAMPLE 165

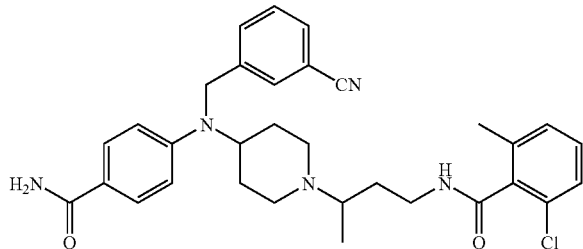

COMPOUND 165: N-(3-{4-[(4-Carbamoyl-phenyl)-(3-cyano-benzyl)-amino]-piperidin-1-yl}-butyl)-2-chloro-6-methyl-benzamide Using general procedure E with 4-[[1-(3-amino-1-methyl-propyl)-piperidin-4-yl]-(3-cyano-benzyl)-amino]-benzoic acid methyl ester (see EXAMPLE 164) (73 mg, 0.17 mmol) and 2-chloro-6-methylbenzoic acid (43 mg, 0.25 mmol) followed by general procedure K with the resulting ester gave 4-[{1-[3-(2-chloro-6-methyl-benzoylamino)-1-methyl-propyl]-piperidin-4-yl}-(3-cyano-benzyl)-amino]-benzoic acid as a beige solid (44.5 mg, 46% over 2 steps).

Using general procedure E, the crude carboxylic acid (44.5 mg, 0.080 mmol) and NH$_4$Cl (12 mg, 0.22 mmol) gave COMPOUND 165 as a white foam (20.9 mg, 47%). $^1$H NMR (CDCl$_3$) δ 1.02 (d, 3H, J=6.0 Hz), 1.03-1.17 (m, 1H), 1.19-1.32 (m, 1H), 1.49-1.60 (m, 1H), 1.70-1.88 (m, 3H), 2.16-2.26 (m, 1H), 2.36 (s, 3H), 2.54-2.65 (m, 1H), 2.78-2.99 (m, 3H), 3.27-3.39 (m, 1H), 3.70-3.91 (m, 2H), 3.98 (s, 2H), 5.79 (br s, 2H), 6.54 (d, 2H, J=8.6 Hz), 7.04-7.14 (m, 3H), 7.36-7.48 (m, 3H), 7.52-7.58 (m, 1H), 7.62 (d, 2H, J=8.6 Hz), 8.33 (br s, 1H). $^{13}$C NMR (CDCl$_3$) δ 13.38, 19.32, 29.27, 30.33, 30.84, 39.82, 43.54, 47.96, 51.87, 55.96, 60.17, 112.06, 112.71, 118.69, 121.50, 126.54, 128.39, 129.18, 129.43, 129.63, 130.56, 130.72, 137.19, 137.54, 141.05, 150.86, 166.71, 168.83. ESI-MS m/z 558 (MH)$^+$, 560 (MH+2)$^+$. Anal. Calcd. for C$_{32}$H$_{36}$ClN$_5$O$_2$.0.9CH$_2$Cl$_2$: C, 62.27; H, 6.00; N, 11.04. Found. C, 62.25; H, 5.94; N, 11.04.

EXAMPLE 166

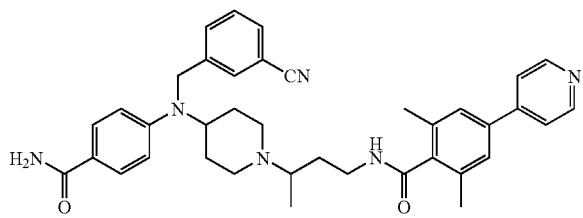

COMPOUND 166: N-(3-{4-[(4-Carbamoyl-phenyl)-(3-cyano-benzyl)-amino]-piperidin-1-yl}-butyl)-2,6-dimethyl-4-pyridin-4-yl-benzamide Using general procedure E with 4-[[1-(3-amino-1-methyl-propyl)-piperidin-4-yl]-(3-cyano-benzyl)-amino]-benzoic acid methyl ester (see EXAMPLE 107) (100 mg, 0.24 mmol) and 2,6-dimethyl-4-pyridin-4-yl-benzoic acid (59 mg, 0.26 mmol) followed by general procedure K with the resulting ester afforded 4-((3-cyano-benzyl)-{1-[3-(2,6-dimethyl-4-pyridin-4-yl-benzoylamino)-1-methyl-propyl]-piperidin-4-yl}-amino)-benzoic acid as a white solid (92 mg, 58% over 2 steps).

Using general procedure E, the above acid (44 mg, 0.07 mmol) and ammonium chloride (15 mg, 0.0.28 mmol) afforded COMPOUND 166 as a white solid (31 mg, 71%). $^1$H NMR (CDCl$_3$) δ 0.92-1.32 (m, 2H), 1.02 (d, 3H, J=6.0 Hz), 1.51-1.62 (m, 1H), 1.69-1.83 (m, 3H), 2.14-2.27 (m, 1H), 2.39 (s, 6H), 2.53-2.64 (m, 1H), 2.74-2.95 (m, 3H), 3.29-3.41 (m, 1H), 3.67-3.88 (m, 2H), 3.90 (s, 2H), 5.81 (br s, 2H), 6.47 (d, 2H, J=8.4 Hz), 7.10 (d, 1H, J=7.5 Hz), 7.18 (s, 1H), 7.22-7.33 (m, 3H), 7.41-7.49 (m, 3H), 7.60 (d, 2H, J=7.8 Hz), 8.02 (br s, 1H), 8.65 (d, 2H, J=4.5 Hz). $^{13}$C NMR (CDCl$_3$) δ 13.50, 19.37, 29.20, 30.43, 31.42, 39.48, 43.75, 47.70, 51.83, 55.93, 59.92, 111.95, 112.70, 118.65, 121.33, 121.58, 125.95, 129.26, 129.43, 130.39, 130.65, 135.39, 137.95, 139.29, 140.94, 147.37, 150.53, 150.83, 168.88, 169.26. ES-MS m/z 615 (M+H). Anal. Calcd. for C$_{38}$H$_{42}$N$_6$O$_2$.1.2H$_2$O: C, 65.69; H, 6.24; N, 11.73. Found. C, 65.94; H, 6.24; N, 11.70.

EXAMPLE 167

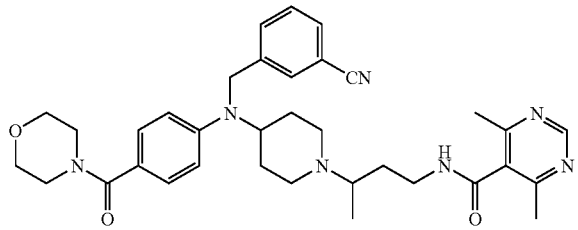

COMPOUND 167: 4,6-Dimethyl-pyrimidine-5-carboxylic acid [3-(4-{(3-cyano-benzyl)-[4-(morpholine-4-carbonyl)-phenyl]-amino}-piperidin-1-yl)-butyl]-amide Using general procedure E, 4-[(3-cyano-benzyl)-(1-{3-[(4,6-dimethyl-pyrimidine-5-carbonyl)-amino]-1-methyl-propyl}-piperidin-4-yl)-amino]-benzoic acid (see EXAMPLE 129) (50 mg, 0.09 mmol) and morpholine (29 μL, 0.33 mmol) afforded COMPOUND 167 as a white solid (48 mg, 87%). $^1$H NMR (CDCl$_3$) δ 0.84-1.18 (m, 2H), 1.03 (d, 3H, J=6.6 Hz), 1.50-1.60 (m, 1H), 1.70-1.84 (m, 3H), 2.14-2.26 (m, 1H), 2.51 (s, 6H), 2.53-2.65 (m, 1H), 2.71-2.92 (m, 3H), 3.27-3.39 (m, 1H), 3.57-3.92 (m, 10H), 3.96 (s, 2H), 6.52 (d, 2H, J=8.4 Hz), 7.25-7.30 (m, 2H), 7.43-7.59 (m, 4H), 8.54 (br s, 1H), 8.90 (s, 1H). $^{13}$C NMR (CDCl$_3$) δ 13.84, 22.36, 29.54, 30.83, 31.12, 40.49, 43.87, 48.45, 52.39, 56.04, 60.76, 67.36, 77.61, 112.53, 113.14, 123.98, 129.89, 130.08, 131.17, 141.51, 149.88, 157.99, 163.53, 166.57, 171.00. ES-MS m/z 610 (M+H). Anal. Calcd. for C$_{35}$H$_{43}$N$_7$O$_3$.0.2CH$_2$Cl$_2$.0.1H$_2$O: C, 67.26; H, 6.99; N, 15.60. Found. C, 67.44; H, 7.12; N, 15.30.

EXAMPLE 168

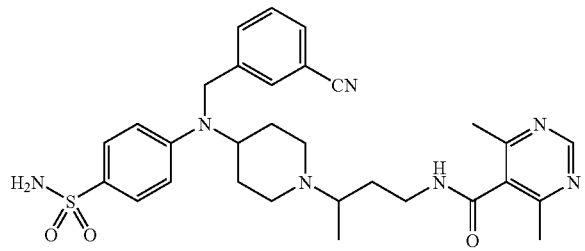

COMPOUND 168: 4,6-Dimethyl-pyrimidine-5-carboxylic acid (3-{4-[(3-cyano-benzyl 1-(4-sulfamoyl-phenyl)-amino]-piperidine-1-yl}-butyl)-amide Using general procedure A, 4-amino-N,N-dibenzyl-benzenesulfonamide (see EXAMPLE 83) (4.30 g, 12.20 mmol) and 1-Boc-4-piperidone (4.86 g, 24.40 mmol) afforded 4-(4-dibenzylsulfamoyl-phenylamino)-piperidine-1-carboxylic acid tert-butyl ester as a white foam (3.84 g, 59%).

Using general procedure H, the amine (1.37 g, 2.56 mmol) and α-bromo-m-tolunitrile (1.51 g, 7.68 mmol) afforded a yellow oil as a mixture of starting amine/product (1:1).

Using general procedure C with the above amine, then general procedure B with the resulting amine and 2-(3-oxo-butyl)-isoindole-1,3-dione (313 mg, 1.44 mmol) and then using general procedure D afforded 4-[[1-(3-amino-1-methyl-propyl)-piperidin-4-yl]-(3-cyano-benzyl)-amino]-N,N-dibenzyl-benzenesulfonamide as a white foam (170 mg, 11% over 4 steps).

Using general procedure E, the amine (126 mg, 0.20 mmol) and 4,6-dimethyl-pyrimidine-5-carboxylic acid (40 mg, 0.26 mmol) afforded 4,6-dimethyl-pyrimidine-5-carboxylic acid (3-{4-[(3-cyano-benzyl)-(4-dibenzylsulfamoyl-phenyl)-amino]-piperidin-1-yl}-butyl)-amide as a pale yellow foam (146 mg, 100%).

A solution of the above amine (146 mg, 0.19 mmol) in $H_2SO_4$ (conc) (1.5 mL) was stirred for 1 h. Then the mixture was poured into ice (20 mL), basified with $Na_2CO_3$ (s) to pH-9, and extracted with $CH_2Cl_2$ (12×20 mL). The combined organic layers were dried ($MgSO_4$), filtered, and concentrated to afford COMPOUND 168 as a pale yellow foam (48 mg, 44%) after purification. $^1$H NMR (CDCl$_3$) δ 1.02 (d, 3H, J=6.3 Hz), 1.11-1.25 (m, 1H), 1.54-1.59 (m, 4H), 2.22 (t, 1H, J=11.4 Hz), 2.50 (s, 6H), 2.60 (t, 1H, J=11.1 Hz), 2.75-2.90 (m, 3H), 3.34 (br s, 1H), 3.71-3.83 (m, 2H), 4.06 (s, 2H), 4.85 (s, 2H), 6.56 (d, 2H, J=8.7 Hz), 7.46-7.57 (m, 4H), 7.66 (d, 2H, J=8.7 Hz), 8.32 (br s, 1H), 8.89 (s, 1H). $^{13}$C NMR (CDCl$_3$) δ 13.38, 21.97, 29.28, 30.34, 30.92, 39.88, 43.55, 47.97, 51.75, 53.45, 60.01, 112.06, 112.85, 118.76, 128.52, 129.09, 129.36, 129.51, 129.65, 130.71, 130.86, 130.98, 140.23, 151.23, 151.57, 163.16, 166.28. ES-MS m/z 598 [M+H]$^+$. Anal. Calcd. for $C_{30}H_{37}N_7O_3S \cdot 0.9CH_2Cl_2$: C, 56.91; H, 6.00; N, 15.03; S, 4.92. Found. C, 56.83; H, 6.03; N, 14.88; S, 4.87.

EXAMPLE 169

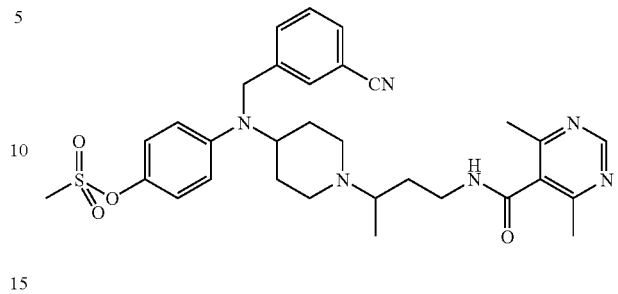

COMPOUND 169: Methanesulfonic acid 4-[(3-cyano-benzyl)-(1-{3-[(4,6-dimethyl-pyrimidine-5-carbonyl)-amino]-1-methyl-propyl}-piperidin-4-yl)-amino]-phenyl ester Using general procedure A, 4-aminophenol (2.0 g, 18.3 mmol) and 1-Boc-4-piperidone (3.64 mg, 18.3 mmol) gave the alcohol which was subsequently treated with TBDMSCl (2.76 g, 18.3 mmol), imidazole (1.50 g, 22 mmol) and DMF (40 mL) to afford 4-[4-(tert-butyl-dimethyl-silanyloxy)-phenylamino]-piperidine-1-carboxylic acid tert-butyl ester (6.7 g, 63% over 2 steps) following work-up and purification.

Using general procedure H, the above aniline (2.1 g, 5.16 mmol) and 3-cyanobenzyl bromide (1.52 g, 7.74 mmol) gave 4-[[4-(tert-butyl-dimethyl-silanyloxy)-phenyl]-(3-cyano-benzyl)-amino]-piperidine-1-carboxylic acid tert-butyl ester (2.70 g, 100%).

Using general procedure C with the above carbamate (2.7 g, 5.16 mmol), then general procedure B with the resulting amine and 2-(3-oxo-butyl)-isoindole-1,3-dione (2.24 g, 10.3 mmol) and then using general procedure D afforded 3-({[1-(3-amino-1-methyl-propyl)-piperidin-4-yl]-[4-(tert-butyl-dimethyl-silanyloxy)-phenyl]-amino}-methyl)-benzonitrile (810 mg, 32% over 3 steps).

To the above amine (810 mg, 1.64 mmol) in $CH_2Cl_2$ (20 mL) was added Boc$_2$O (360 mg, 1.65 mmol) and the mixture was stirred at room temperature for 15 minutes. The mixture was concentrated under reduced pressure and the residue was dissolved in THF (10 mL) and TBAF (10M in THF, 2.0 mL, 2.0 mmol) was added. The mixture was stirred at room temperature for 3 h and concentrated under reduced pressure to give (3-{4-[(3-cyano-benzyl)-(4-hydroxy-phenyl)-amino]-piperidin-1-yl}-butyl)-carbamic acid tert-butyl ester (740 mg, 94% over 2 steps) following work-up and purification.

Using general procedure G with the above alcohol (740 mg, 1.55 mmol) followed by general procedure C afforded methanesulfonic acid 4-[[1-(3-amino-1-methyl-propyl)-piperidin-4-yl]-(3-cyano-benzyl)-amino]-phenyl ester (360 mg, 51% over 2 steps).

Using general procedure E, the above amine (120 mg, 0.26 mmol) and 4,6-dimethyl-pyrimidine-5-carboxylic acid (44 mg, 0.29 mmol) afforded COMPOUND 169 as a white solid (92 mg, 60%). $^1$H NMR (CDCl$_3$) δ 0.88-1.15 (m, 2H), 1.02 (d, 3H, J=6.0 Hz), 1.53-1.60 (m, 1H), 1.75-1.79 (m, 3H), 2.18 (t, 1H, J=12.0 Hz), 2.51 (s, 6H), 2.58 (t, 1H, J=12.0 Hz), 2.58-2.86 (m, 3H), 3.07 (s, 3H), 3.28-3.37 (m, 1H), 3.59-3.66 (m, 1H), 3.82-3.89 (m, 1H), 3.91 (s, 2H), 6.52 (d, 2H, J=8.4

Hz), 7.06 (d, 2H, J=8.4 Hz), 7.44-7.56 (m, 4H), 8.54 (br s, 1H), 8.87 (s, 1H). $^{13}$C NMR (CDCl$_3$) δ 13.84, 22.35, 29.54, 30.79, 31.12, 37.26, 40.49, 43.89, 48.80, 52.40, 56.63, 60.74, 114.32, 123.35, 129.87, 130.11, 131.20, 141.60, 147.71, 157.97, 163.52, 166.63. ES-MS m/z 591 (M+H). Anal. Calcd. for C$_{31}$H$_{38}$N$_6$O$_4$S.0.2CH$_2$Cl$_2$: C, 61.66; H, 6.37; N, 13.83; S, 5.28. Found. C, 61.80; H, 6.39; N, 13.82; S, 5.24.

EXAMPLE 170

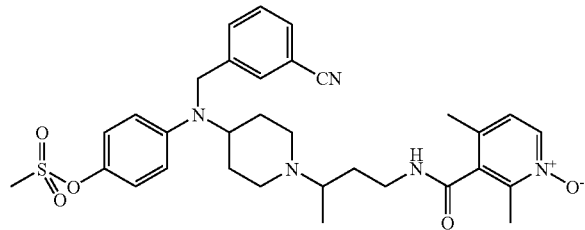

COMPOUND 170: Methanesulfonic acid 4-[(3-cyano-benzyl)-(1-{3-[(2,4-dimethyl-1-oxy-pyridine-3-carbonyl)-amino]-1-methyl-propyl}-piperidin-4-yl)-amino]-phenyl ester Using general procedure E, methanesulfonic acid 4-[[1-(3-amino-1-methyl-propyl)-piperidin-4-yl]-(3-cyano-benzyl)-amino]-phenyl ester (see EXAMPLE 169) (120 mg, 0.26 mmol) and 2,4-dimethyl-1-oxy-nicotinic acid (53 mg, 0.32 mmol) afforded COMPOUND 170 as a white solid (110 mg, 69%). $^1$H NMR (CDCl$_3$) δ 1.02-1.28 (m, 5H), 1.53-1.63 (m, 1H), 1.78-1.82 (m, 3H), 2.21 (t, 1H, J=12.0 Hz), 2.29 (s, 3H), 2.44 (s, 3H), 2.58 (t, 1H, J=12.0 Hz), 2.76-2.85 (m, 3H), 3.08 (s, 3H), 3.37 (m, 1H), 3.65-3.77 (m, 2H), 4.12 (s, 2H), 6.55 (d, 2H, J=7.8 Hz), 6.88 (d, 1H, J=6.3 Hz), 7.06 (d, 2H, J=8.1 Hz), 7.44-7.62 (m, 4H), 7.97 (d, 1H, J=6.3 Hz), 8.42 (br s, 1H). $^{13}$C NMR (CDCl$_3$) δ 13.96, 15.44, 18.86, 29.89, 30.56, 32.71, 37.22, 39.11, 44.86, 49.10, 51.67, 56.93, 58.72, 112.98, 114.19, 119.31, 123.28, 125.34, 129.87, 130.11, 131.07, 131.31, 134.98, 137.37, 138.14, 140.73, 141.90, 145.80, 147.91, 165.75. ES-MS m/z 606 (M+H). Anal. Calcd. for C$_{32}$H$_{39}$N$_5$O$_5$S.0.6CH$_2$Cl$_2$: C, 59.62; H, 6.17; N, 10.66; S, 4.88. Found. C, 59.43; H, 6.22; N, 10.46; S, 4.79.

EXAMPLE 171

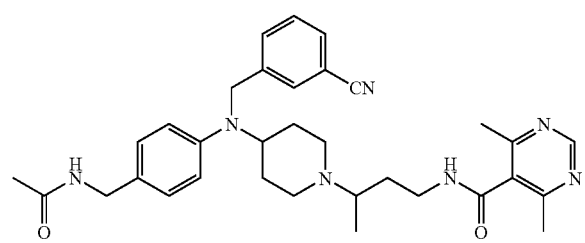

COMPOUND 171: 4,6-Dimethyl-pyrimidine-5-carboxylic acid (3-{4-[[4-(acetylamino-methyl)-phenyl]-(3-cyano-benzyl)-amino]-piperidin-1-yl}-butyl)-amide Using general procedure A with 1-CBZ-4-piperidone (3.00 g, 12.86 mmol) and 2-(4-amino-benzyl)-isoindole-1,3-dione (Vamecq, Joseph; et al., J. Med. Chem., 43, 7, 2000, 1311-1319) (1.62 g, 6.42 mmol), then general procedure H with the resulting amine and 3-cyanobenzyl bromide (1.68 g, 8.59 mmol) and then using general procedure D afforded 4-[(4-aminomethyl-phenyl)-(3-cyano-benzyl)-amino]-piperidine-1-carboxylic acid benzyl ester as a white solid (1.95 g, 67% over 3 steps).

To a solution of the above amine (462 mg, 1.02 mmol) in CH$_2$Cl$_2$ (10 mL) were added Et$_3$N (0.45 mL, 3.23 mmol) followed by acetic anhydride (0.20 mL, 2.12 mmol) and the mixture was stirred at room temperature overnight to afford 4-[[4-(acetylamino-methyl)-phenyl]-(3-cyano-benzyl)-amino]-piperidine-1-carboxylic acid benzyl ester as a white solid (463 mg, 91%) following work-up and purification.

To a solution of the above substrate (445 mg, 0.90 mmol) in EtOH (9 mL) were added ammonium formate (695 mg, 11.01 mmol) followed by 10% Pd/C (215 mg) and the mixture was stirred at room temperature for 2 hours. Standard work-up and purification afforded N-{4-[(3-cyano-benzyl)-piperidin-4-yl-amino]-benzyl}-acetamide as a white solid (154 mg, 47%).

Using general procedure B with the above amine (146 mg, 0.403 mmol) and 2-(3-oxo-butyl)-isoindole-1,3-dione (285 mg, 1.31 mmol) and then using general procedure D afforded N-{4-[[1-(3-amino-1-methyl-propyl)-piperidin-4-yl]-(3-cyano-benzyl)-amino]-benzyl}-acetamide as a white solid (108 mg, 62% over 2 steps).

Using general procedure E, the above amine (48 mg, 0.11 mmol) and 4,6-dimethyl-pyrimidine-5-carboxylic acid (27 mg, 0.18 mmol) afforded COMPOUND 171 as a white solid (49 mg, 72%). $^1$H NMR (CDCl$_3$) δ 0.87-1.25 (m, 2H), 1.02 (d, 3H, J=6.3 Hz), 1.54-1.59 (m, 1H), 1.75-1.78 (m, 3H), 1.98 (s, 3H), 2.18 (t, 1H, J=12.3 Hz), 2.50 (s, 6H), 2.58 (t, 1H, J=11.4 Hz), 2.73-2.85 (m, 3H), 3.27-3.35 (m, 1H), 3.50-3.66 (m, 1H), 3.80-3.90 (m, 1H), 3.90 (s, 2H), 4.28 (d, 2H, J=4.5 Hz), 5.69 (br s, 1H), 6.52 (d, 2H, J=7.5 Hz), 7.08 (d, 2H, J=7.5 Hz), 7.42-7.58 (m, 4H), 8.65 (br s, 1H), 8.86 (s, 1H). $^{13}$C NMR (CDCl$_3$) δ 13.46, 20.27, 21.31, 21.92, 23.25, 29.20, 30.43, 30.74, 33.96, 38.09, 40.03, 43.18, 43.60, 44.85, 45.52, 48.45, 51.14, 52.01, 52.17, 53.46, 56.16, 56.92, 60.23, 112.53, 113.92, 118.99, 124.70, 127.38, 127.88, 128.39, 128.54, 129.31, 129.90, 130.61, 130.89, 130.96, 138.18, 139.71, 141.72, 147.53, 157.48, 162.95, 163.07, 166.25, 166.43, 169.74. ES-MS m/z 568 (M+H). Anal. Calcd. for C$_{33}$H$_{41}$N$_7$O$_2$.2.0H$_2$O: C, 65.65; H, 7.51; N, 16.24. Found. C, 65.78; H, 7.16; N, 16.05.

EXAMPLE 172

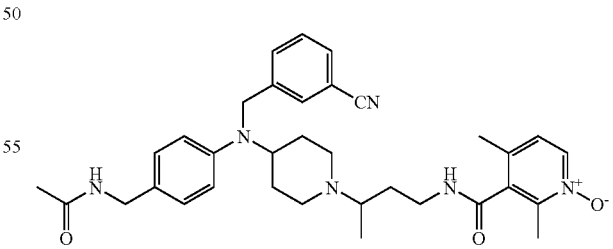

COMPOUND 172: N-(3-{4-[[4-(Acetylamino-methyl)-phenyl]-(3-cyano-benzyl)-amino]-piperidin-1-yl}-butyl)-2,4-dimethyl-1-oxy-nicotinamide Using general procedure E, N-{4-[[1-(3-amino-1-methyl-propyl)-piperidin-4-yl]-(3-cyano-benzyl)-amino]-benzyl}- acetamide (see EXAMPLE 171) (51 mg, 0.12 mmol) and 2,4-dimethyl-1-oxy-nicotinic acid (29 mg, 0.18 mmol) afforded COMPOUND 172 as a white solid (27 mg, 33%). $^1$H NMR (CDCl$_3$) δ 0.96-1.25 (m, 2H), 1.02 (d, 3H, J=6.0 Hz), 1.53-1.61 (m, 1H), 1.71-1.81 (m, 3H), 1.99 (s, 3H), 2.16-2.25 (m, 1H), 2.29 (s, 3H), 2.46 (s, 3H), 2.57 (t, 1H, J=12.6 Hz), 2.74-2.84 (m, 3H), 3.31-3.38 (m, 1H), 3.58-3.81 (m, 2H), 7.09 (s, 2H), 4.28 (d, 2H, J=4.5 Hz), 5.73 (br s, 1H), 6.54 (d, 2H, J=7.2 Hz), 3.87 (d, 1H, J=6.0 Hz), 7.07 (d, 2H, J=7.2 Hz), 7.45-7.53 (m, 3H), 7.63 (d, 1H, J=7.5 Hz), 7.98 (d, 1H, J=6.0 Hz), 8.47 (br s, 1H). $^{13}$C NMR (CDCl$_3$) δ 13.90, 15.54, 18.82, 20.62, 21.73, 23.67, 29.86, 30.73, 32.22, 35.13, 38.21, 39.60, 43.56, 44.58, 48.99, 51.52, 52.02, 56.85, 59.43, 112.86, 114.30, 119.42, 125.23, 127.63, 128.23, 128.76, 129.11, 129.66, 129.75, 130.30, 130.94, 131.54, 134.44, 137.24, 138.32, 142.29, 145.90, 148.00, 165.72, 170.17. ES-MS m/z 583 (M+H). Anal. Calcd. for C$_{34}$H$_{42}$N$_6$O$_3$·1.3CH$_2$Cl$_2$: C, 61.17; H, 6.49; N, 12.12. Found. C, 61.32; H, 6.45; N, 11.88.

EXAMPLE 173

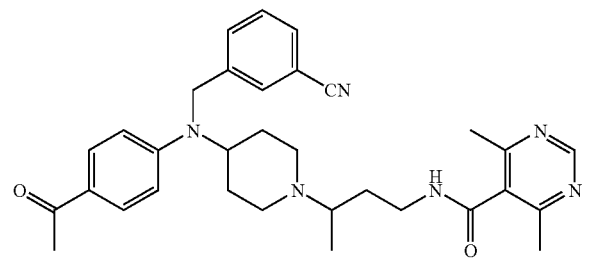

COMPOUND 173: 4,6-Dimethyl-pyrimidine-5-carboxylic acid (3-{4-[(4-acetyl-phenyl)-(3-cyano-benzyl)-amino]-piperidin-1-yl}-butyl)-amide A mixture of 4'-aminoacetophenone (1.45 g, 10.7 mmol), ethylene glycol (2.00 g, 32.2 mmol), and p-TsOH.H$_2$O (2.45 g, 12.9 mmol) in toluene (30 mL) were heated to reflux under a Dean-Stark trap for 3.5 h. Basic work-up and purification gave 4-(2-methyl-[1,3]dioxolan-2-yl)-phenylamine as colourless crystals (0.67 g, 35%).

Using general procedure A, the amine from above (388 mg, 2.16 mmol) and I-Boc-4-piperidone (518 mg, 2.60 mmol) gave 4-[4-(2-methyl-[1,3]dioxolan-2-yl)-phenylamino]-piperidine-1-carboxylic acid tert-butyl ester as colourless crystals (283 mg, 36%).

Using general procedure H, the above aniline (690 mg, 1.90 mmol) and 3-cyanobenzyl bromide (1.12 g, 5.71 mmol) afforded a beige solid (907 mg).

A solution of the above carbamate (907 mg) in 6N HCl (20 mL) was heated at 40° C. for 2 hours to give 3-{[(4-acetyl-phenyl)-piperidin-4-yl-amino]-methyl}-benzonitrile as a white solid (410 mg, 65% over 2 steps) following basic work-up and purification.

Using general procedure B with the above amine (410 mg, 1.23 mmol) and 2-(3-oxo-butyl)-isoindole-1,3-dione (670 mg, 3.1 mmol) and then using general procedure D afforded a pale brown solid.

To the above amine in THF (4 mL) was added Boc$_2$O (350 mg, 1.60 mmol) and the mixture was stirred at room temperature for 1 hour to afford (3-{4-[(4-acetyl-phenyl)-(3-cyano-benzyl)-amino]-piperidin-1-yl}-butyl)-carbamic acid tert-butyl ester as a white solid (271 mg, 44% over 3 steps) following work-up and purification.

Using general procedure C, the above substrate (270 mg, 0.54 mmol) gave 3-({(4-acetyl-phenyl)-[1-(3-amino-1-methyl-propyl)-piperidin-4-yl]-amino}-methyl)-benzonitrile as a white solid (209 mg, 97%).

Using general procedure E, the above amine (104 mg, 0.26 mmol) and 4,6-dimethyl-pyrimidine-5-carboxylic acid (59 mg, 0.39 mmol) afforded COMPOUND 173 as a white solid (102 mg, 73%). $^1$H NMR (CDCl$_3$) δ 0.97-1.15 (m, 2H), 1.03 (d, 3H, J=6.6 Hz), 1.55-1.60 (m, 1H), 1.76-1.79 (m, 3H), 2.22 (t, 1H, J=12.0 Hz), 2.48 (s, 3H), 2.52 (s, 6H), 2.61 (t, 1H, J=12.0 Hz), 2.76-2.95 (m, 3H), 3.30-3.39 (m, 1H), 3.78-3.85 (m, 2H), 4.04 (s, 2H), 6.54 (d, 2H, J=8.4 Hz), 7.45-7.55 (m, 4H), 7.79 (d, 2H, J=8.4 Hz), 8.44 (br s, 1H), 8.92 (s, 1H). $^{13}$C NMR (CDCl$_3$) δ 13.89, 22.34, 26.42, 29.75, 30.79, 31.35, 40.20, 43.98, 48.33, 52.13, 56.05, 60.30, 111.99, 113.17, 119.13, 127.14, 129.94, 131.08, 131.26, 140.99, 152.12, 157.93, 163.50, 166.68. ES-MS m/z 539 (M+H). Anal. Calcd. for C$_{32}$H$_{38}$N$_6$O$_2$·0.5CH$_2$Cl$_2$: C, 67.17; H, 6.76; N, 14.46. Found. C, 66.97; H, 6.89; N, 14.80.

EXAMPLE 174

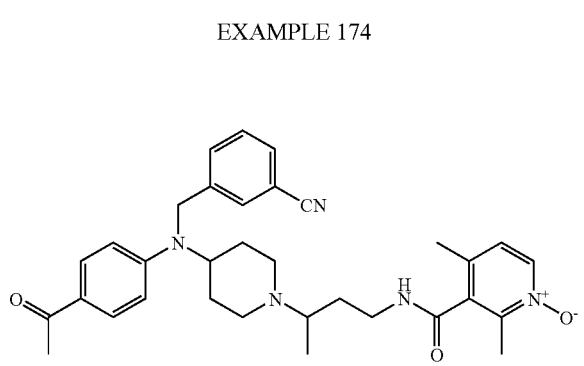

COMPOUND 174: N-(3-{4-[(4-Acetyl-phenyl)-(3-cyano-benzyl)-amino]-piperidin-1-yl}-butyl)-2,4-dimethyl-1-oxy-nicotinamide Using general procedure E, 3-({(4-acetyl-phenyl)-[1-(3-amino-1-methyl-propyl)-piperidin-4-yl]-amino}-methyl)-benzonitrile (see EXAMPLE 173) (102 mg, 0.25 mmol) and 2,4-dimethyl-1-oxy-nicotinic acid (63 mg, 0.38 mmol) afforded COMPOUND 174 as a white solid (85 mg, 61%). $^1$H NMR (CDCl$_3$) δ 1.04 (d, 3H, J=5.1 Hz), 1.14-1.39 (m, 2H), 1.53-1.62 (m, 1H), 1.79-1.83 (m, 3H), 2.26 (t, 1H, J=12.3 Hz), 2.30 (s, 3H), 2.42 (s, 3H), 2.48 (s, 3H), 2.61 (t, 1H, J=11.4 Hz), 2.77-2.90 (m, 3H), 3.40 (br s, 1H), 3.70-3.83 (m, 2H), 4.28 (s, 2H), 6.57 (d, 2H, J=7.5 Hz), 6.89 (d, 1H, J=6.0 Hz), 7.44-7.60 (m, 4H), 7.83 (d, 2H, J=7.8 Hz), 7.98 (d, 1H, J=6.0 Hz), 8.36 (br s, 1H). $^{13}$C NMR (CDCl$_3$) δ 13.99, 15.49, 18.87, 26.42, 30.05, 30.71, 32.71, 39.19, 44.72, 48.57, 51.67, 56.44, 58.79, 112.04, 113.12, 119.18, 125.32, 127.03, 129.95, 129.98, 131.10, 131.18, 134.85, 137.35, 138.18, 141.20, 145.84, 152.26, 165.75. ES-MS m/z 554 (M+H). Anal. Calcd. for C$_{33}$H$_{39}$N$_5$O$_3$·0.9CH$_2$Cl$_2$: C, 64.62; H, 6.53; N, 11.11. Found. C, 64.80; H, 6.51; N, 11.15.

EXAMPLE 175

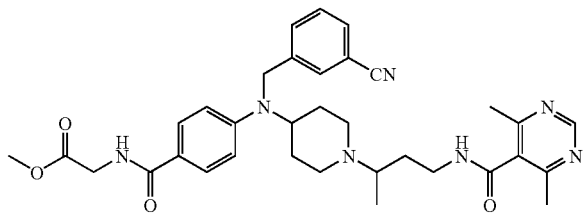

COMPOUND 175: {4-[(3-Cyano-benzyl)-(1-{3-[(4,6-dimethyl-pyrimidine-5-carbonyl)-amino]-1-methyl-propyl}-piperidin-4-yl)-amino]-benzoylamino}-acetic acid methyl ester Using general procedure E, 4-[(3-cyano-benzyl)-(1-{3-[(4,6-dimethyl-pyrimidine-5-carbonyl)-amino]-1-methyl-propyl}-piperidin-4-yl)-amino]-benzoic acid (see EXAMPLE 129) (100 mg, 0.26 mmol) and glycine methyl ester hydrochloride (46 mg, 0.37 mmol) afforded COMPOUND 175 as a white solid (65 mg, 57%). $^1$H NMR (CDCl$_3$) δ 1.04 (d, 3H, J=6.3 Hz), 1.04-1.26 (m, 2H), 1.46-1.62 (m, 1H), 1.67-1.86 (m, 3H), 2.14-2.27 (m, 1H), 2.51 (s, 6H), 2.56-2.65 (m, 1H), 2.70-2.93 (m, 3H), 3.28-3.38 (m, 2H), 3.47-3.53 (m, 1H), 3.67-3.89 (m, 2H), 3.96-4.07 (m, 3H), 4.20, 4.21 (s, 2H), 6.43-6.59 (m, 3H), 7.42-7.58 (m, 4H), 7.64 (d, 3H, J=8.1 Hz), 8.49 (br s, 1H), 8.90 (s, 1H). $^{13}$C NMR (CDCl$_3$) δ 13.50, 14.75, 21.97, 25.65, 28.42, 29.32, 30.43, 30.82, 36.04, 36.33, 39.99, 41.65, 43.55, 44.41, 48.02, 51.89, 52.40, 53.80, 55.71, 56.68, 60.17, 111.77, 112.07, 112.78, 118.78, 122.09, 128.89, 129.50, 129.65, 130.72, 130.84, 131.65, 140.87, 150.78, 157.58, 158.34, 163.12, 166.28, 166.90, 170.80, 181.11. ES-MS m/z 612 (M+H).

EXAMPLE 176

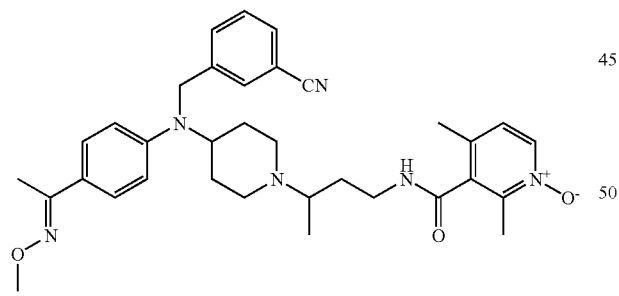

COMPOUND 176: N-[3-(4-{(3-Cyano-benzyl)-[4-(1-methoxyimino-ethyl)-phenyl]-amino}-piperidin-1-yl)-butyl]-2,4-dimethyl-1-oxy-nicotinamide A mixture of COMPOUND 174 (59 mg, 0.11 mmol), NaOAc (170 mg, 2.1 mmol) and methoxylamine hydrochloride (89 mg, 1.1 mmol) in MeOH (1.2 mL) was stirred at room temperature for 3 days to afford COMPOUND 176 as a white solid (51 mg, 83%) following work-up and purification. $^1$H NMR (CDCl$_3$) δ 1.03 (d, 3H, J=6.3 Hz), 1.02-1.26 (m, 2H), 1.53-1.60 (m, 1H), 1.78-1.82 (m, 3H), 2.147 (s, 3H), 2.22 (t, 1H, J=11.4 Hz), 2.29 (s, 3H), 2.46 (s, 3H), 2.59 (t, 1H, J=11.7 Hz), 2.75-2.88 (m, 3H), 3.36-3.38 (m, 1H), 3.68-3.81 (m, 2H), 3.94 (s, 3H), 4.13 (s, 2H), 6.55 (d, 2H, J=8.7 Hz), 6.87 (d, 1H, J=6.9 Hz), 7.44-7.53 (m, 5H), 7.61 (d, 1H, J=7.5 Hz), 7.98 (d, 1H, J=6.3 Hz), 8.41 (br s, 1H). $^{13}$C NMR (CDCl$_3$) δ 12.73, 13.96, 15.46, 18.86, 29.99, 30.69, 32.66, 39.23, 44.83, 48.66, 51.77, 56.60, 58.83, 62.05, 112.23, 112.92, 113.20, 119.31, 125.30, 126.01, 127.62, 129.75, 130.20, 130.59, 130.95, 131.37, 134.90, 137.37, 138.16, 142.13, 145.84, 149.25, 154.72, 156.74. ES-MS m/z 582 (M+H). Anal. Calcd. for C$_{34}$H$_{42}$N$_6$O$_3$.0.4CH$_2$Cl$_2$: C, 67.00; H, 6.99; N, 13.63. Found. C, 67.17; H, 7.03; N, 13.59.

Scheme 9 describes the preparation of Examples 177-192, using various general procedures previously described, and reagents listed below.

Scheme 9 i) R$^3$—NH$_2$, general procedure A
ii) 3-cyanobenzyl bromide
   general procedure H
iii) general procedure C
iv) 2-(3-oxo-butyl)-isoindole-1,3-dione
   general procedure B
v) general procedure D
vi) R$^1$COOH
   general procedure E

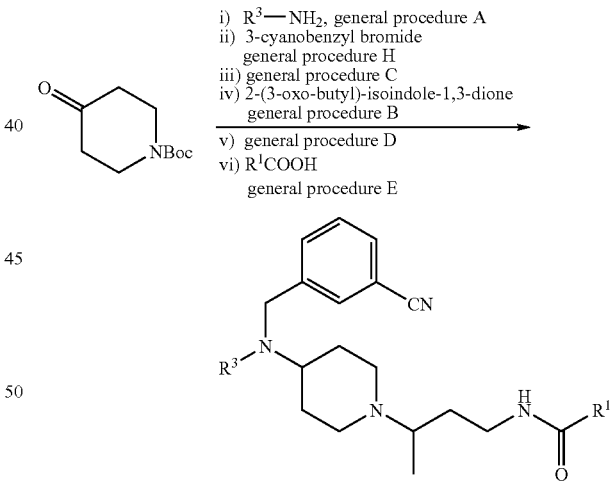

| Example | R$^3$—NH$_2$ | R$^1$COOH |
|---|---|---|
| 177 | 5-aminoindole | 2,6-dimethylbenzoic acid |
| 178 | 5-aminoindole | 4,6-dimethyl-pyrimidine-5-carboxylic acid |
| 179 | 3,4-(methylenedioxy)aniline | 4,6-dimethyl-pyrimidine-5-carboxylic acid |
| 180 | 3,4-(methylenedioxy)aniline | 2,6-dimethylbenzoic acid |

-continued

| Example | R³—NH₂ | R¹COOH |
|---|---|---|
| 181 | 5-amino-2,3-dihydro-benzofuran (Wright, Stephen W.; et al., Tetrahedron Lett., 37, 27, 1996, 4631-4634) | 4,6-dimethyl-pyrimidine-5-carboxylic acid |
| 182 | 5-amino-2,3-dihydro-benzofuran | 2,6-dimethylbenzoic acid |
| 183 | 5-amino-1,3-dihydro-isobenzofuran (Clark, R. L.; et al., J. Med. Chem., 21, 1978, 965-978) | 2,6-dimethylbenzoic acid |
| 184 | benzofuran-5-ylamine (Abramenko, P. I.; et al., Chem. Heterocycl. Cmpd., 11, 1975, 1358-1361) | 4,6-dimethyl-pyrimidine-5-carboxylic acid |
| 185 | benzofuran-5-ylamine | 2,6-dimethylbenzoic acid |
| 186 | 4-aminoveratole | 4,6-dimethyl-pyrimidine-5-carboxylic acid |
| 187 | 4-aminoveratole | 2,6-dimethylbenzoic acid |
| 188 | 1,4-benzodioxan-6-amine | 4,6-dimethyl-pyrimidine-5-carboxylic acid |
| 189 | 1,4-benzodioxan-6-amine | 2-chloro-6-methylbenzoic acid |
| 190 | 1,4-benzodioxan-6-amine | 2,6-dimethylbenzoic acid |
| 191 | 6-methoxy-pyridin-3-ylamine (Nishikawa, Yoshinori; et al., J. Med. Chem., 32, 3, 1989, 583-593) | 4,6-dimethyl-pyrimidine-5-carboxylic acid |
| 192 | 6-methoxy-pyridin-3-ylamine | 2,6-dimethylbenzoic acid |

EXAMPLE 177

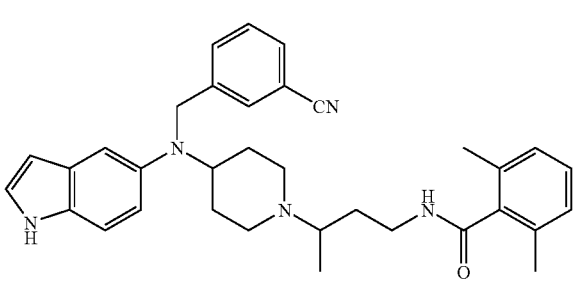

COMPOUND 177: N-(3-{4-[(3-Cyano-benzyl)-(1H-indol-5-yl)-amino]-piperidin-1-yl}-butyl)-2,6-dimethyl-benzamide White solid. ¹H NMR (CDCl₃) δ 0.89-1.17 (m, 2H), 0.99 (d, 3H, J=5.4 Hz), 1.52 (d, 1H, J=13.8 Hz), 1.75-1.78 (m, 3H), 2.07-2.15 (m, 1H), 2.32 (s, 6H), 2.48-2.56 (m, 1H), 2.73-2.94 (m, 3H), 3.25-3.41 (m, 2H), 3.78 (s, 2H), 3.88 (br s, 1H), 6.33 (s, 1H), 6.66 (d, 1H, J=8.7 Hz), 6.90-6.95 (m, 4H), 7.07 (s, 1H), 7.15 (d, 1H, J=8.7 Hz), 7.32-7.37 (m, 1H), 7.43-7.50 (m, 2H), 7.55 (s, 1H), 8.26 (s, 1H), 8.59 (br s, 1H). ¹³C NMR (CDCl₃) δ 13.35, 19.15, 29.14, 30.39, 30.87, 39.88, 43.68, 49.45, 52.21, 59.82, 60.57, 101.80, 108.43, 111.43, 112.09, 114.97, 119.23, 124.82, 127.28, 128.35, 128.41, 128.83, 130.16, 130.81, 131.71, 134.02, 138.53, 142.44, 142.98, 170.01. ES-MS m/z 534 (M+H). Anal. Calcd. for C₃₄H₃₉N₅O.0.7CH₂Cl₂: C, 70.26; H, 6.86; N, 11.81. Found. C, 70.35; H, 6.84; N, 11.98.

EXAMPLE 178

COMPOUND 178: 4,6-Dimethyl-pyrimidine-5-carboxylic acid (3-{4-[(3-cyano-benzyl)-(1H-indol-5-yl)-amino]-piperidin-1-yl}-butyl)-amide White solid. ¹H NMR (CDCl₃) δ 0.87-1.15 (m, 2H), 1.00 (d, 3H, J=6.3 Hz), 1.54 (d, 1H, J=12.0 Hz), 1.79-1.83 (m, 3H), 2.13 (t, 1H, J=12.0 Hz), 2.51 (s, 6H), 2.51-2.57 (m, 1H), 2.72-2.87 (m, 3H), 3.27-3.41 (m, 2H), 3.83-3.88 (m, 1H), 3.88 (s, 2H), 6.37 (s, 1H), 6.67 (d, 1H, J=8.1 Hz), 6.94 (s, 1H), 7.12 (s, 1H), 7.18 (d, 1H, J=8.7 Hz), 7.34-7.39 (m, 1H), 7.45 (d, 1H, J=7.5 Hz), 7.57-7.61 (m, 2H), 8.09 (br s, 1H), 8.81 (s, 1H), 8.84 (br s, 1H). ¹³C NMR (CDCl₃) δ 13.37, 21.94, 29.45, 30.55, 40.21, 43.59, 50.07, 52.09, 59.63, 60.47, 102.10, 109.44, 111.41, 112.21, 115.62, 119.20, 124.79, 128.39, 128.95, 130.33, 130.84, 131.14, 131.82, 142.22, 142.49, 157.52, 163.04, 166.35. ES-MS m/z 536 (M+H). Anal. Calcd.

for C₃₂H₃₇N₇O.0.3CH₂Cl₂: C, 69.13; H, 6.75; N, 17.47. Found. C, 69.38; H, 6.86; N, 17.48.

EXAMPLE 179

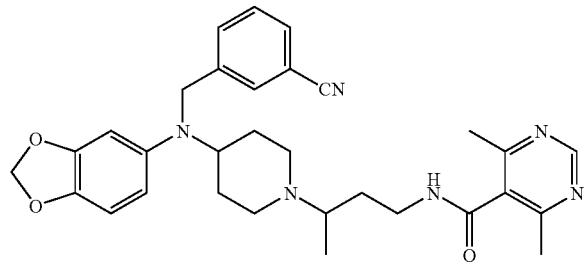

COMPOUND 179: 4,6-Dimethyl-pyrimidine-5-carboxylic acid (3-{4-[benzo[1,3]dioxol-5-yl-(3-cyano-benzyl)-amino]-piperidin-1-yl}-butyl)-amide White solid. $^1$H NMR (CDCl₃) δ 0.82-1.10 (m, 2H), 0.99 (d, 3H, J=6.3 Hz), 1.48-1.55 (m, 1H), 1.75 (m, 3H), 2.12 (t, 1H, J=11.7 Hz), 2.45-2.56 (m, 1H), 2.50 (s, 6H), 2.71-2.86 (m, 3H), 3.26-3.40 (m, 2H), 3.79 (s, 2H), 3.79-3.88 (m, 1H), 5.84 (s, 2H), 6.02 (d, 1H, J=8.4 Hz), 6.24 (s, 1H), 6.59 (d, 1H, J=8.4 Hz), 7.38-7.55 (m, 3H), 8.71 (m, 1H), 8.82 (s, 1H). $^1$H NMR (CDCl₃) δ 13.42, 21.93, 29.35, 30.52, 30.63, 40.12, 43.56, 49.34, 52.00, 58.30, 60.33, 98.77, 100.83, 108.34, 112.43, 119.04, 129.16, 130.33, 130.53, 130.88, 131.35, 140.59, 141.85, 143.92, 148.39, 157.52, 163.04, 166.27. ES-MS m/z 541 (M+H). Anal. Calcd. for C₃₁H₃₆N₆O₃.0.9CH₂Cl₂: C, 62.09; H, 6.17; N, 13.62. Found. C, 62.29; H, 6.05; N, 13.84.

EXAMPLE 180

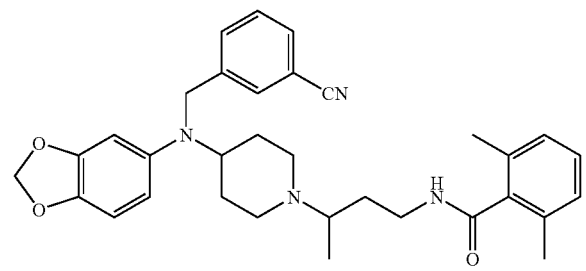

COMPOUND 180: N-(3-{4-[Benzo[1,3]dioxol-5-yl-(3-cyano-benzyl)-amino]-piperidin-1-yl}-butyl)-2,6-dimethyl-benzamide White solid. $^1$H NMR (CDCl₃) δ 0.89-1.21 (m, 2H), 0.99 (d, 3H, J=6.0 Hz), 1.49-1.55 (m, 1H), 1.69-1.81 (m, 3H), 2.11 (t, 1H, J=11.4 Hz), 2.31 (s, 6H), 2.52 (t, 1H, J=11.1 Hz), 2.73-2.89 (m, 3H), 3.23-3.47 (m, 2H), 3.69 (s, 2H), 3.86-3.92 (m, 1H), 5.83 (s, 2H), 6.00 (dd, 1H, J=8.4, 1.8 Hz), 6.23 (s, 1H), 6.58 (d, 1H, J=8.4 Hz), 6.93-7.00 (m, 3H), 7.37-7.52 (m, 4H), 8.43 (m, 1H). $^{13}$C NMR (CDCl₃) δ 13.38, 19.14, 29.09, 30.34, 30.92, 39.83, 43.59, 48.95, 52.13, 58.60, 60.52, 98.45, 100.76, 107.87, 108.30, 112.38, 119.05, 127.24, 128.35, 129.06, 130.35, 130.40, 131.25, 134.05, 138.62, 140.25, 142.23, 144.13, 148.34, 169.85. ES-MS m/z 539 (M+H). Anal. Calcd. for C₃₃H₃₈N₄O₃.0.4CH₂Cl₂: C, 70.05; H, 6.83; N, 9.78. Found. C, 70.30; H, 6.77; N, 9.85.

EXAMPLE 181

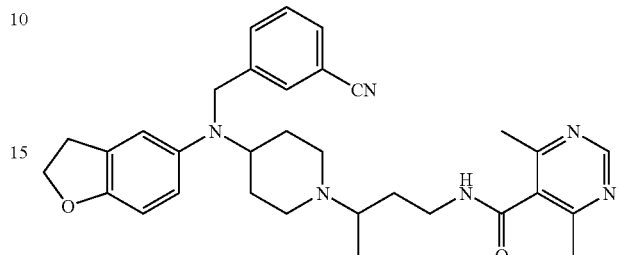

COMPOUND 181: 4,6-Dimethyl-pyrimidine-5-carboxylic acid (3-{4-[(3-cyano-benzyl)-(2,3-dihydro-benzofuran-5-yl)-amino]-piperidin-1-yl}-butyl)-amide White solid. $^1$H NMR (CDCl₃) δ 0.87-1.07 (m, 2H), 0.99 (d, 3H, J=6.3 Hz), 1.54 (d, 1H, J=12.3 Hz), 1.74-1.78 (m, 3H), 2.12 (t, 1H, J=11.4 Hz), 2.51 (s, 6H), 2.50-2.56 (m, 1H), 2.67-2.86 (m, 3H), 3.09 (t, 2H, J=8.4 Hz), 3.30 (m, 2H), 3.79 (s, 2H), 3.79-3.88 (m, 1H), 4.47 (t, 2H, J=8.4 Hz), 6.42 (d, 1H, J=8.4 Hz), 6.56-6.59 (m, 2H), 7.37-7.42 (m, 1H), 7.47-7.55 (m, 3H), 8.77 (br s, 1H), 8.82 (s, 1H). $^{13}$C NMR (CDCl₃) δ 13.39, 21.92, 29.35, 30.25, 30.51, 30.63, 40.06, 43.60, 49.74, 51.95, 58.95, 60.28, 71.07, 109.15, 112.28, 114.95, 117.11, 119.11, 127.79, 129.06, 130.43, 130.59, 130.86, 131.60, 142.19, 142.51, 153.85, 157.49, 163.01, 166.30. ES-MS m/z 539 (M+H). Anal. Calcd. for C₃₂H₃₈N₆O₂.0.5CHCl₃: C, 65.24; H, 6.48; N, 14.04. Found. C, 65.19; H, 6.55; N, 13.93.

EXAMPLE 182

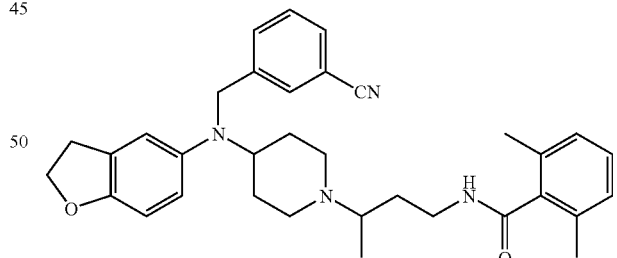

COMPOUND 182: N-(3-{4-[(3-Cyano-benzyl)-(2,3-dihydro-benzofuran-5-yl)-amino]-piperidin-1-yl}-butyl)-2,6-dimethyl-benzamide White solid. $^1$H NMR (CDCl₃) δ 0.88-1.17 (m, 2H), 0.98 (d, 3H, J=6.3 Hz), 1.51 (d, 1H, J=13.8 Hz), 1.66-1.81 (m, 3H), 2.10 (t, 1H, J=11.4 Hz), 2.31 (s, 6H), 2.50 (t, 1H, J=10.8 Hz), 2.72-2.88 (m, 3H), 3.09 (t, 2H, J=8.4 Hz), 3.24-3.31 (m, 2H), 3.69 (s, 2H), 3.86-3.90 (m, 1H), 4.46 (t, 2H, J=8.4 Hz), 6.39 (d, 1H, J=8.7 Hz), 6.56 (m, 2H), 6.92-6.97 (m, 3H), 7.35-7.48

(m, 4H), 8.45 (s, 1H). $^{13}$C NMR (CDCl$_3$) δ 12.41, 18.16, 28.15, 29.32, 29.94, 38.86, 42.66, 48.25, 51.17, 52.50, 58.24, 59.54, 70.05, 108.11, 111.27, 113.35, 115.45, 118.17, 126.26, 126.76, 127.37, 127.99, 129.32, 129.62, 130.52, 133.05, 137.63, 141.63, 141.79, 152.48, 169.90. ES-MS m/z 537 (M+H). Anal. Calcd. for C$_{34}$H$_{40}$N$_4$O$_2$.0.3C$_6$H$_{14}$.0.1CH$_2$Cl$_2$: C, 75.51; H, 7.84; N, 9.81. Found. C, 75.44; H, 7.85; N, 9.81.

EXAMPLE 183

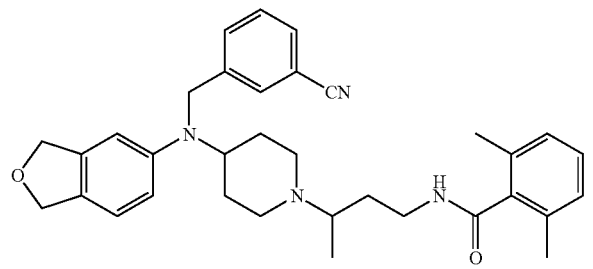

COMPOUND 183: N-(3-{4-[(3-Cyano-benzyl)-(1,3-dihydro-isobenzofuran-5-yl)-amino]-piperidin-1-yl}-butyl)-2,6-dimethyl-benzamide White solid. $^1$H NMR (CDCl$_3$) δ 0.93-1.20 (m, 2H), 1.00 (d, 3H, J=6.6 Hz), 1.51-1.55 (m, 1H), 1.71-1.84 (m, 3H), 2.17 (t, 1H, J=11.4 Hz), 2.31 (s, 6H), 2.57 (t, 1H, J=11.7 Hz), 2.75-2.91 (m, 3H), 3.29 (t, 1H, J=11.4 Hz), 3.56-3.64 (m, 1H), 3.81 (s, 2H), 3.86-3.92 (m, 1H), 4.98 (s, 4H), 6.43-6.47 (m, 2H), 6.93-7.05 (m, 4H), 7.39-7.52 (m, 3H), 8.36 (m, 1H). $^{13}$C NMR (CDCl$_3$) δ 13.83, 19.54, 29.37, 30.74, 31.36, 40.22, 44.01, 48.87, 52.56, 57.41, 60.92, 73.58, 74.03, 106.40, 112.93, 113.68, 119.37, 121.96, 127.68, 128.67, 128.77, 129.61, 130.38, 130.89, 131.30, 134.49, 139.05, 141.09, 142.52, 148.51, 170.23. ES-MS m/z 537 (M+H). Anal. Calcd. for C$_{34}$H$_{40}$N$_4$O$_2$.0.4C$_6$H$_{14}$.0.1CH$_2$Cl$_2$: C, 75.63; H, 7.96; N, 9.67. Found. C, 75.41; H, 7.90; N, 9.70.

EXAMPLE 184

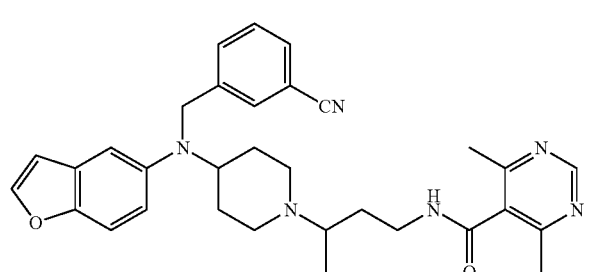

COMPOUND 184: 4,6-Dimethyl-pyrimidine-5-carboxylic acid (3-{4-[benzofuran-5-yl-(3-cyano-benzyl)-amino]-piperidin-1-yl}-butyl)-amide White solid. $^1$H NMR (CDCl$_3$) δ 0.94-1.12 (m, 2H), 1.01 (d, 3H, J=6.6 Hz), 1.47-1.57 (m, 1H), 1.74-1.83 (m, 3H), 2.16 (t, 1H, J=11.4 Hz), 2.51 (s, 6H), 2.56 (t, 1H, J=11.4 Hz), 2.74-2.85 (m, 3H), 3.32 (t, 1H, J=11.1 Hz), 3.48 (m, 1H), 3.82-3.90 (m, 1H), 3.90 (s, 2H), 6.59 (s, 1H), 6.67 (dd, 1H, J=9.0, 1.5 Hz), 7.28 (m, 1H), 7.37-7.58 (m, 5H), 8.74 (br s, 1H), 8.83 (s, 1H). $^{13}$C NMR (CDCl$_3$) δ 13.41, 21.94, 29.33, 30.52, 30.64, 40.09, 43.61, 49.54, 52.03, 58.73, 60.32, 106.43, 107.32, 107.99, 111.56, 112.38, 114.87, 119.05, 128.09, 129.14, 130.48, 130.88, 131.48, 142.05, 144.55, 145.51, 149.53, 157.51, 163.05, 166.30. ES-MS m/z 537 (M+H). Anal. Calcd. for C$_{32}$H$_{36}$N$_6$O$_2$.0.4CH$_2$Cl$_2$: C, 68.20; H, 6.50; N, 14.73. Found. C, 68.32; H, 6.48; N, 14.74.

EXAMPLE 185

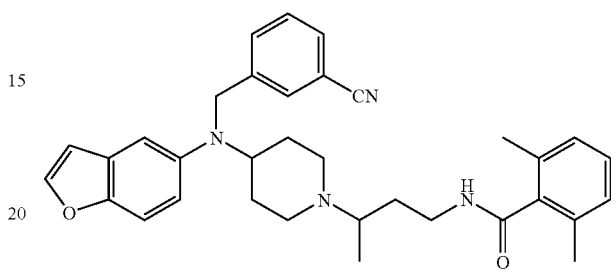

COMPOUND 185: N-(3-{4-[Benzofuran-5-yl-(3-cyano-benzyl)-amino]-piperidin-1-yl}-butyl)-2,6-dimethyl-benzamide White solid. $^1$H NMR (CDCl$_3$) δ 0.97-1.21 (m, 2H), 0.99 (d, 3H, J=6.6 Hz), 1.53 (m, 1H), 1.66-1.78 (m, 3H), 2.14 (t, 1H, J=10.8 Hz), 2.32 (s, 6H), 2.54 (t, 1H, J=11.4 Hz), 2.74-2.90 (m, 3H), 3.28 (t, 1H, J=11.4 Hz), 3.45-3.52 (m, 1H), 3.79 (s, 2H), 3.87-3.93 (m, 1H), 6.58 (s, 1H), 6.66 (d, 1H, J=8.7 Hz), 6.77 (s, 1H), 6.94-7.00 (m, 3H), 7.26 (m, 1H), 7.36-7.41 (m, 1H), 7.46-7.51 (m, 4H), 8.47 (br s, 1H). $^{13}$C NMR (CDCl$_3$) δ 13.81, 19.55, 29.53, 30.79, 31.33, 40.26, 44.04, 49.56, 52.60, 59.43, 60.96, 106.81, 107.80, 111.89, 112.73, 114.91, 119.49, 127.66, 128.45, 128.76, 129.44, 130.77, 130.89, 131.79, 134.46, 139.03, 142.87, 145.13, 145.86, 149.69, 170.27. ES-MS m/z 535 (M+H). Anal. Calcd. for C$_{34}$H$_{38}$N$_4$O$_2$.0.1CH$_2$Cl$_2$: C, 75.40; H, 7.09; N, 10.31. Found. C, 75.68, H, 7.13; N, 10.37.

EXAMPLE 186

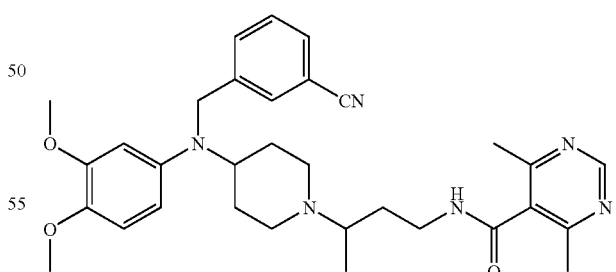

COMPOUND 186: 4,6-Dimethyl-pyrimidine-5-carboxylic acid (3-{4-[(3-cyano-benzyl)-(3,4-dimethoxy-phenyl)-amino]-piperidin-1-yl}-butyl)-amide White solid. $^1$H NMR (CDCl$_3$) δ 0.88-1.09 (m, 5H), 1.49-1.58 (m, 1H), 1.76-1.80 (m, 3H), 2.11-2.18 (m, 1H), 2.52 (s, 6H), 2.52-2.58 (m, 1H), 2.74-2.86 (m, 3H), 3.32-3.40 (m, 2H), 3.68-3.86 (m, 1H), 3.73 (s, 3H), 3.78 (s, 3H), 3.81 (s, 2H), 6.16-6.22 (m, 2H), 6.68 (d, 1H, J=8.7 Hz), 7.39-7.44 (m, 1H), 7.49-7.56 (m, 3H), 8.74 (br s, 1H), 8.83 (s, 1H). $^{13}$C NMR (CDCl$_3$) δ 13.77, 22.29, 29.73, 30.81, 31.14, 40.30, 44.07, 49.60, 52.32, 56.26, 56.78, 58.52, 60.51, 102.59, 108.38, 112.76, 112.97, 119.38, 129.54, 130.78, 130.91, 131.23, 131.78, 142.45, 142.97, 143.30, 149.95, 157.83, 163.45, 166.72. ES-MS m/z 557 (M+H). Anal. Calcd. for C$_{32}$H$_{40}$N$_6$O$_3$.0.8CH$_2$Cl$_2$: C, 63.07; H, 6.71; N, 13.45. Found. C, 62.95; H, 6.60; N, 13.46.

EXAMPLE 187

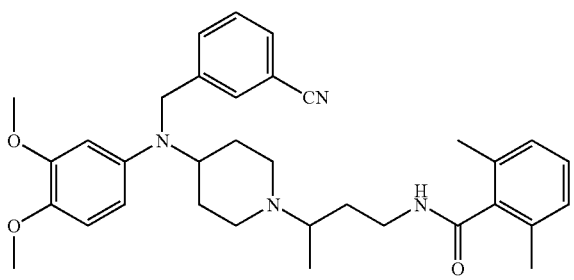

COMPOUND 187: N-(3-{4-[(3-Cyano-benzyl)-(3,4-dimethoxy-phenyl)-amino]-piperidin-1-yl}-butyl)-2,6-dimethyl-benzamide White solid. $^1$H NMR (CDCl$_3$) δ 0.90-1.19 (m, 5H), 1.49-1.54 (m, 1H), 1.71-1.75 (m, 3H), 2.12 (t, 1H, J=10.5 Hz), 2.31 (s, 6H), 2.52 (t, 1H, J=10.8 Hz), 2.74-2.94 (m, 3H), 3.24-3.44 (m, 2H), 3.76 (s, 5H), 3.85 (s, 3H), 3.84-3.92 (m, 1H), 6.13 (d, 1H, J=8.7 Hz), 6.19 (s, 1H), 6.66 (d, 1H, J=7.8 Hz), 6.92 (br s, 3H), 7.36-7.50 (m, 4H), 8.45 (br s, 1H). $^{13}$C NMR (CDCl$_3$) δ 13.81, 19.54, 29.55, 30.78, 31.33, 40.25, 44.04, 49.21, 52.61, 56.22, 56.81, 58.72, 60.96, 102.01, 107.64, 112.78, 112.99, 119.41, 127.64, 128.74, 129.45, 130.08, 130.80, 131.66, 134.45, 139.02, 142.60, 142.92, 143.51, 149.97, 170.25. ES-MS m/z 555 (M+H). Anal. Calcd. for C$_{34}$H$_{42}$N$_4$O$_3$.0.6CH$_2$Cl$_2$: C, 68.61; H, 7.19; N, 9.25. Found. C, 68.81; H, 7.14; N, 9.31.

EXAMPLE 188

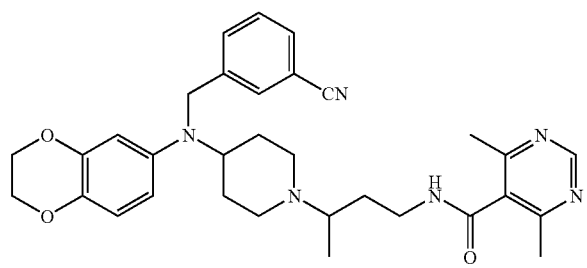

COMPOUND 188: 4,6-Dimethyl-pyrimidine-5-carboxylic acid (3-{4-[(3-cyano-benzyl)-(2,3-dihydro-benzo[1,4]dioxin-6-yl)-amino]-piperidin-1-yl}-butyl)-amide Pale yellow foam. $^1$H NMR (CDCl$_3$) δ 0.80-1.10 (m, 2H), 1.01 (d, 3H, J=6.6 Hz), 1.49-1.59 (m, 1H), 1.69-1.83 (m, 3H), 2.09-2.20 (m, 1H), 2.44-2.60 (m, 1H), 2.51 (s, 6H), 2.69-2.90 (m, 3H), 3.25-3.37 (m, 1H), 3.39-3.50 (m, 1H), 3.79 (s, 2H), 3.82-3.91 (m, 1H), 4.14-4.24 (m, 4H), 6.06-6.16 (m, 2H), 6.66 (d, 1H, J=8.7 Hz), 7.39-7.46 (m, 1H), 7.48-7.58 (m, 3H), 8.74 (br s, 1H), 8.84 (s, 1H). $^{13}$C NMR (CDCl$_3$) δ 13.32, 21.83, 29.12, 30.35, 30.53, 40.01, 43.47, 48.72, 51.94, 57.18, 60.22, 64.08, 64.59, 103.86, 108.27, 112.33, 117.39, 118.98, 129.08, 130.05, 130.40, 130.78, 131.07, 136.16, 142.02, 143.13, 143.75, 157.42, 162.94, 166.18. ESI-MS m/z 555 (MH)$^+$. Anal. Calcd. for C$_{32}$H$_{38}$N$_6$O$_3$.H$_2$O: C, 67.11; H, 7.04; N, 14.67. Found: C, 67.00; H, 6.68; N, 14.40.

EXAMPLE 189

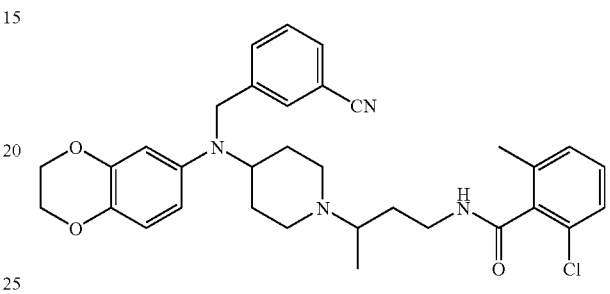

COMPOUND 189: 2-Chloro-N-(3-{4-[(3-cyano-benzyl)-(2,3-dihydro-benzo[1,4]dioxin-6-yl)-amino]-piperidin-1-yl}-butyl)-6-methyl-benzamide Off-white powder. $^1$H NMR (CDCl$_3$) δ 0.91-1.05 (m, 1H), 0.99 (d, 3H, J=6.6 Hz), 1.08-1.22 (m, 1H), 1.47-1.58 (m, 1H), 1.68-1.84 (m, 3H), 2.08-2.17 (m, 1H), 2.35 (s, 3H), 2.48-2.58 (m, 1H), 2.74-2.97 (m, 3H), 3.24-3.35 (m, 1H), 3.39-3.50 (m, 1H), 3.73 (s, 2H), 3.84-3.95 (m, 1H), 4.12-4.22 (m, 4H), 6.06-6.15 (m, 2H), 6.65 (d, 1H, J=8.7 Hz), 6.96-7.05 (m, 2H), 7.10 (d, 1H, J=6.9 Hz), 7.38-7.46 (m, 3H), 7.48-7.53 (m, 1H), 8.61 (br s, 1H). $^{13}$C NMR (CDCl$_3$) δ 13.26, 19.24, 29.14, 30.26, 30.60, 39.95, 43.48, 48.57, 52.05, 57.54, 60.36, 64.06, 64.58, 103.83, 108.26, 112.32, 117.35, 118.94, 126.44, 128.25, 129.05, 129.32, 130.08, 130.33, 130.55, 130.99, 136.02, 137.01, 137.55, 142.32, 143.23, 143.70, 166.65. ESI-MS m/z 573 (MH)$^+$, 575 (MH+2)$^+$. Anal. Calcd. for C$_{33}$H$_{37}$ClN$_4$O$_3$.0.2H$_2$O.0.1CH$_2$Cl$_2$: C, 67.93; H, 6.48; N, 9.57; Cl, 7.27. Found: C, 67.72; H, 6.44; N, 9.54; Cl, 7.58.

EXAMPLE 190

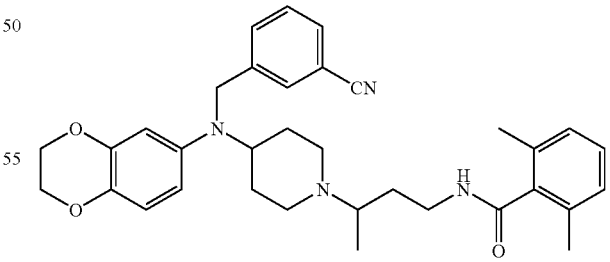

COMPOUND 190: N-(3-{4-[(3-Cyano-benzyl)-(2,3-dihydro-benzo[1,4]dioxin-6-yl)-amino]-piperidin-1-yl}-butyl)-2,6-dimethyl-benzamide White foam. $^1$H NMR (CDCl$_3$) δ 0.86-1.16 (m, 2H), 0.99 (d, 3H, J=6.6 Hz), 1.46-1.57 (m, 1H), 1.65-1.82 (m, 3H), 2.07-2.17 (m, 1H), 2.31 (s, 6H), 2.47-2.58 (m, 1H), 2.69-2.91

(m, 3H), 3.21-3.33 (m, 1H), 3.37-3.49 (m, 1H), 3.69 (s, 2H), 3.84-3.94 (m, 1H), 4.11-4.22 (m, 4H), 6.05-6.14 (m, 2H), 6.64 (d, 1H, J=8.7 Hz), 6.89-7.01 (m, 3H), 7.37-7.53 (m, 4H), 8.45 (br s, 1H). $^{13}$C NMR (CDCl$_3$) δ 13.27, 19.02, 28.88, 30.20, 30.76, 39.74, 43.48, 48.46, 52.07, 57.45, 60.45, 64.04, 64.58, 103.60, 108.05, 112.26, 117.31, 118.98, 127.14, 128.25, 128.98, 130.07, 130.26, 131.00, 133.94, 135.90, 138.52, 142.37, 143.26, 143.69, 169.73. ESI-MS m/z 553 (MH)$^+$. Anal. Calcd. for C$_{34}$H$_{40}$N$_4$O$_3$.0.2CH$_2$Cl$_2$: C, 72.10; H, 7.15; N, 9.83. Found: C, 71.87; H, 7.07; N, 9.71.

EXAMPLE 191

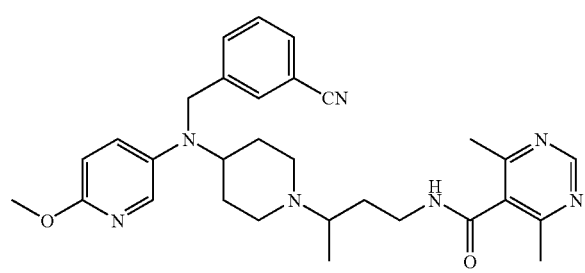

COMPOUND 191: 4,6-Dimethyl-pyrimidine-5-carboxylic acid (3-{4-[(3-cyano-benzyl)-(6-methoxy-pyridin-3-yl)-amino]-piperidin-1-yl}-butyl)-amide White solid. $^1$H NMR (CDCl$_3$) δ 0.85-1.17 (m, 2H), 1.00 (d, 3H, J=6.3 Hz), 1.50-1.62 (m, 1H), 1.72-1.83 (m, 3H), 2.06-2.18 (m, 1H), 2.39-2.58 (m, 1H), 2.51 (s, 6H), 2.71-2.91 (m, 3H), 3.26-3.39 (m, 2H), 3.79-3.90 (m, 6H), 6.58 (d, 1H, J=9.0 Hz), 6.98 (d, 1H, J=8.4 Hz), 7.38-7.56 (m, 5H), 8.57 (br s, 1H), 8.80 (s, 1H). $^{13}$C NMR (CDCl$_3$) δ 13.42, 21.95, 29.32, 30.37, 30.76, 40.03, 43.55, 49.16, 51.87, 53.33, 58.43, 60.20, 110.78, 112.59, 118.92, 128.79, 129.31, 130.37, 130.75, 130.85, 131.45, 134.93, 138.93, 141.19, 157.51, 158.12, 163.06, 166.28. ES-MS m/z 528 (M+H). Anal. Calcd. for C$_{30}$H$_{37}$N$_7$O$_2$.0.1CH$_2$Cl$_2$: C, 67.43; H, 6.99; N, 18.29. Found: C, 67.42; H, 7.03; N, 18.16.

EXAMPLE 192

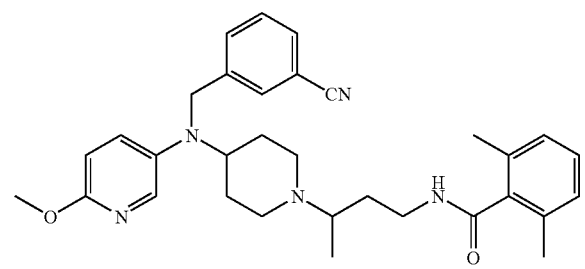

COMPOUND 192: N-(3-{4-[(3-Cyano-benzyl)-(6-methoxy-pyridin-3-yl)-amino]-piperidin-1-yl}-butyl)-2,6-dimethyl-benzamide White solid. $^1$H NMR (CDCl$_3$) δ 0.88-1.23 (m, 2H), 0.98 (d, 3H, J=6.0 Hz), 1.47-1.58 (m, 1H), 1.67-1.80 (m, 3H), 2.04-2.15 (m, 1H), 2.31 (s, 6H), 2.42-2.56 (m, 1H), 2.72-2.92 (m, 3H), 3.32-3.37 (m, 2H), 3.70 (s, 2H), 3.81 (s, 3H), 3.83-3.94 (m, 1H), 6.56 (d, 1H, J=9.3 Hz), 6.89-7.02 (m, 4H), 7.36-7.54 (m, 5H), 8.37 (br s, 1H). $^{13}$C NMR (CDCl$_3$) δ 13.38, 19.14, 29.05, 30.19, 30.98, 39.80, 43.55, 48.73, 52.04, 53.28, 58.75, 60.49, 110.73, 112.52, 118.93, 127.22, 128.35, 128.49, 129.19, 130.43, 130.62, 131.40, 134.06, 134.42, 138.61, 139.10, 141.57, 157.84, 169.83. ES-MS m/z 526 (M+H). Anal. Calcd. for C$_{32}$H$_{39}$N$_5$O$_2$.0.2CH$_2$Cl$_2$: C, 71.27; H, 7.32; N, 12.91. Found: C, 71.31; H, 7.20; N, 12.77.

EXAMPLE 193

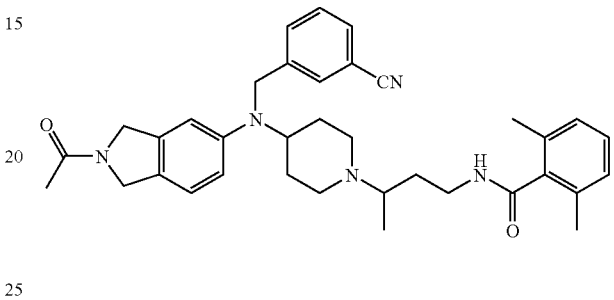

COMPOUND 193: N-(3-{4-[(2-Acetyl-2,3-dihydro-1H-isoindol-5-yl)-(3-cyano-benzyl)-amino]-piperidin-1-yl}-butyl)-2,6-dimethyl-benzamide 4-Nitrophthalimide (8.0 g, 41.6 mmol) in THF (10 mL) was reduced with BH$_3$-THF (1.0M in THF, 111 mL, 111 mmol) at reflux and treated with 6N HCl to afford 5-nitro-2,3-dihydro-1H-isoindole (1.89 g, 28%) after work-up and purification.

To the above amine (1.89 g, 11.5 mmol) in CH$_2$Cl$_2$ (30 mL) was added Boc$_2$O (2.51 g, 11.5 mmol) and the mixture was stirred at room temperature for 5 minutes to afford 5-nitro-1,3-dihydro-isoindole-2-carboxylic acid tert-butyl ester as a white solid (3.04 g, 100%).

A mixture of the above substrate (3.04 g, 11.5 mmol), 10% Pd/C (100 mg), EtOAc (20 mL), MeOH (5 mL) and CH$_2$Cl$_2$ (5 mL) was hydrogenated at 3 atm for 1 h. The mixture was concentrated under reduced pressure and filtered through a silica gel plug to afford 5-amino-1,3-dihydro-isoindole-2-carboxylic acid tert-butyl ester (2.3 g, 85%).

Using general procedure A, the above amine (2.3 g, 9.8 mmol) and 1-CBZ-4-piperidone (2.17 mg, 9.31 mmol) afforded 5-(1-benzyloxycarbonyl-piperidin-4-ylamino)-1,3-dihydro-isoindole-2-carboxylic acid tert-butyl ester (4.28 g, 95%).

A mixture of the above substrate (2.5 g, 5.53 mmol), 10% Pd/C (250 mg), EtOAc (10 mL) and MeOH (5 mL) was hydrogenated at 3 atm for 3 h. The mixture was concentrated under reduced pressure and filtered through Celite® to afford 5-(piperidin-4-ylamino)-1,3-dihydro-isoindole-2-carboxylic acid tert-butyl ester as a yellow solid (1.4 g) that was used in the next reaction without purification.

Using general procedure B with the above amine (1.4 g, 4.4 mmol) and 2-(3-oxo-butyl)-isoindole-1,3-dione (1.91 g, 8.8 mmol) followed by general procedure H with the resulting aniline and 3-cyanobenzyl bromide (612 mg, 3.12 mmol) gave 5-((3-cyano-benzyl)-{1-[3-(1,3-dioxo-1,3-dihydro-isoindol-2-yl)-1-methyl-propyl]-piperidin-4-yl}-amino)-1,3-dihydro-isoindole-2-carboxylic acid tert-butyl ester (1.0 g, 37% over 2 steps).

Using general procedure D with the above substrate (1.08 g, 1.57 mmol), then general procedure E with the resulting amine and 2,6-dimethylbenzoic acid (103 mg, 0.68 mmol) and then using general procedure C afforded N-(3-{4-[(3-cyano-benzyl)-(2,3-dihydro-1H-isoindol-5-yl)-amino]-piperidin-1-yl}-butyl)-2,6-dimethyl-benzamide (230 mg, 54% over 3 steps).

To a solution of the above amine (110 mg, 0.20 mmol) in CH$_2$Cl$_2$ (2 mL) was added Et$_3$N (0.04 mL, 0.29 mmol) followed by acetic anhydride (23 µL, 0.24 mmol) and the mixture was stirred at room temperature overnight to afford COMPOUND 193 as a white solid (90 mg, 87%) after workup and purification. $^1$H NMR (CDCl$_3$) δ 0.90-1.23 (m, 5H), 1.49-1.54 (m, 1H), 1.70-1.74 (m, 3H), 2.09 (s, 3H), 2.09-2.17 (m, 1H), 2.29 (s, 6H), 2.56-2.60 (m, 1H), 2.75-2.90 (m, 3H), 3.24-3.31 (m, 1H), 3.55-3.63 (m, 1H), 3.81 (s, 2H), 3.83-3.89 (m, 1H), 4.62 (s, 2H), 4.64 (s, 2H), 6.39-6.53 (m, 2H), 6.91-7.04 (m, 4H), 7.42 (m, 3H), 7.51 (s, 1H), 8.35 (br s, 1H). $^{13}$C NMR (CDCl$_3$) δ 13.85, 19.54, 22.51, 22.56, 29.37, 30.67, 31.38, 40.13, 44.05, 48.68, 48.74, 51.74, 52.47, 52.57, 53.14, 53.97, 57.24, 57.34, 60.80, 60.85, 107.81, 108.04, 112.95, 113.94, 114.25, 119.32, 123.69, 124.08, 125.62, 126.12, 127.66, 128.76, 129.65, 130.33, 130.94, 131.28, 134.48, 138.01, 138.39, 139.00, 142.28, 148.52, 148.75, 169.81, 169.90, 170.25. ES-MS m/z 578 (M+H). Anal. Calcd. for C$_{36}$H$_{43}$N$_5$O$_2$·1.1CH$_2$Cl$_2$: C, 66.39, H, 6.79; N, 10.43. Found: C, 66.35; H, 6.58; N, 10.52.

EXAMPLE 194

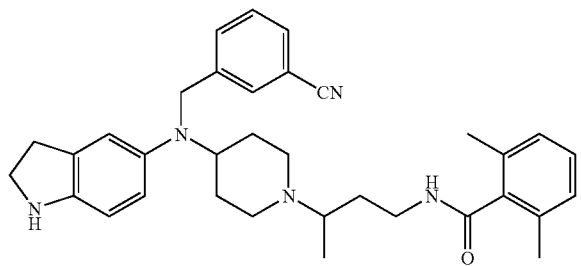

COMPOUND 194: N-(3-{4-[(3-Cyano-benzyl)-(2,3-dihydro-1H-indol-5-yl)-amino]-piperidin-1-yl}-butyl)-2,6-dimethyl-benzamide To 5-nitroindoline (2.0 g, 11.81 mmol) in CH$_2$Cl$_2$ (20 mL) were added Boc$_2$O (2.6 g, 11.9 mmol), Et$_3$N (1.6 mL, 11.8 mmol) and DMAP (20 mg) and the mixture was heated at 40° C. for 48 h. The resulting substrate, 10% Pd/C (200 mg), EtOAc (30 mL) and MeOH (3 mL) was hydrogenated at 2 atm for 2 h. The mixture was concentrated under reduced pressure and filtered through a silica gel plug to afford 5-amino-2,3-dihydro-indole-1-carboxylic acid tert-butyl ester (2.76 g, 100% over 2 steps).

Using general procedure A, the above amine (2.76 g, 11.8 mmol) and 1-CBZ-4-piperidone (2.61 g, 11.2 mmol) gave the crude material that was used in the next reaction without purification.

A mixture of the above substrate, 10% Pd/C (250 mg), EtOAc (20 mL) and MeOH (10 mL) was hydrogenated at 2 atm for 3 h. The mixture was concentrated under reduced pressure and filtered through Celite® to afford 5-(piperidin-4-ylamino)-2,3-dihydro-indole-1-carboxylic acid tert-butyl ester (3.05 g, 81% over 2 steps) following purification.

Using general procedure B with the above amine (3.05 g, 9.6 mmol) and 2-(3-oxo-butyl)-isoindole-1,3-dione (4.17 g, 19.2 mmol) followed by general procedure H with the resulting amine and 3-cyanobenzyl bromide (1.39 g, 7.09 mmol) gave 5-((3-cyano-benzyl)-{1-[3-(1,3-dioxo-1,3-dihydro-isoindol-2-yl)-1-methyl-propyl]-piperidin-4-yl}-amino)-2,3-dihydro-indole-1-carboxylic acid tert-butyl ester (3.24 g, 53% over 2 steps).

Using general procedure D with the above substrate (1.5 g, 2.36 mmol) and then using general procedure E with the resulting amine (490 mg, 0.97 mmol) and 2,6-dimethylbenzoic acid (161 mg, 1.07 mmol) afforded 5-((3-cyano-benzyl)-{1-[3-(2,6-dimethyl-benzoylamino)-1-methyl-propyl]-piperidin-4-yl}-amino)-2,3-dihydro-indole-1-carboxylic acid tert-butyl ester (510 mg, 68% over 2 steps).

The above amide (110 mg, 0.20 mmol) was treated with EtOAc (10 mL) saturated with HCl (g). The mixture was stirred for 1 h then concentrated under reduced pressure. Et$_2$O (20 mL) was added and the precipitate was filtered. The solid was partitioned between 2N NaOH (10 mL) and CH$_2$Cl$_2$ (20 mL). The organic layer was dried (Na$_2$SO$_4$), filtered and concentrated under reduced pressure to afford COMPOUND 194 as a white solid (300 mg, 70%). $^1$H NMR (CDCl$_3$) δ 0.97-1.12 (m, 5H), 1.48-1.53 (m, 1H), 1.69-1.73 (m, 3H), 2.09-2.13 (m, 1H), 2.31 (s, 6H), 2.46-2.53 (m, 1H), 2.71-2.94 (m, 5H), 3.24-3.29 (m, 2H), 3.46 (t, 2H, J=9.0 Hz), 3.67 (s, 2H), 3.87-3.89 (m, 1H), 6.33 (d, 1H, J=6.0 Hz), 6.46 (d, 1H, J=9.0 Hz), 6.54 (s, 1H), 6.93 (m, 3H), 7.34-7.49 (m, 4H), 8.49 (br s, 1H). $^{13}$C NMR (CDCl$_3$) δ 15.13, 20.91, 30.88, 32.24, 32.68, 41.61, 45.40, 49.31, 51.05, 53.95, 60.99, 62.31, 111.87, 113.93, 116.59, 117.99, 120.97, 129.01, 130.12, 130.63, 131.97, 132.46, 132.61, 133.32, 135.78, 140.34, 143.72, 144.65, 146.42, 171.68. ES-MS m/z 536 (M+H). Anal. Calcd. for C$_{34}$H$_{41}$N$_5$O·0.6CH$_2$Cl$_2$: C, 70.83; H, 7.25; N, 11.94. Found: C, 70.53; H, 7.17; N, 11.89.

Scheme 10 describes the preparation of Examples 195-206, using various general procedures previously described, and reagents listed below.

Scheme 10 i) 5-chloro-2-fluorobenzyl bromide
general procedure H
ii) general procedure C
iii) 2-(3-oxo-butyl)-isoindole-1,3-dione, general procedure B
iv) general procedure D
v) 3,5-dichloroisonicotinic acid
general procedure F or R$^1$COOH
general procedure E

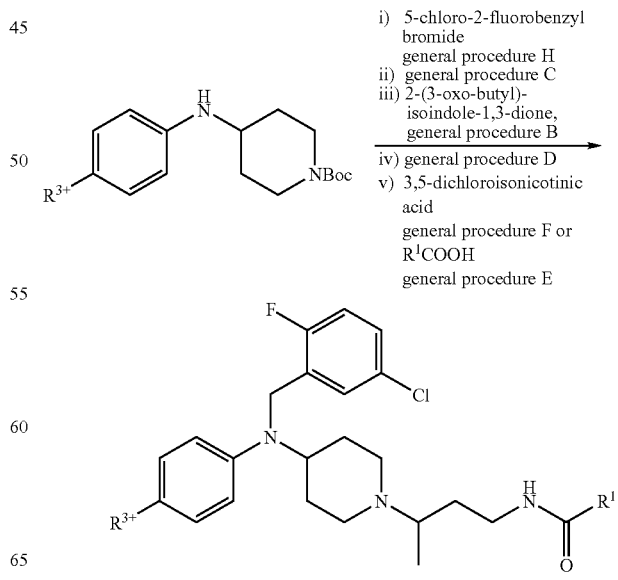

| Example | R³* | R¹COOH |
|---|---|---|
| 195 | CN | 3,5-dichloroisonicotinic acid |
| 196 | CN | 2,4-dimethyl-1-oxy-nicotinic acid |
| 197 | CN | 4,6-dimethyl-pyrimidine-5-carboxylic acid |
| 198 | Cl | 3,5-dichloroisonicotinic acid |
| 199 | CONMe₂ | 4,6-dimethyl-pyrimidine-5-carboxylic acid |
| 200 | CONMe₂ | 2,4-dimethyl-1-oxy-nicotinic acid |
| 201 | OMe | 4,6-dimethyl-pyrimidine-5-carboxylic acid |
| 202 | OMe | 2,4-dimethyl-1-oxy-nicotinic acid |
| 203 | O(CH₂)₂OMe | 4,6-dimethyl-pyrimidine-5-carboxylic acid |
| 204 | O(CH₂)₂OMe | 2,4-dimethyl-1-oxy-nicotinic acid |
| 205 | NHCOMe | 4,6-dimethyl-pyrimidine-5-carboxylic acid |
| 206 | NHCOMe | 2,4-dimethyl-1-oxy-nicotinic acid |

EXAMPLE 195

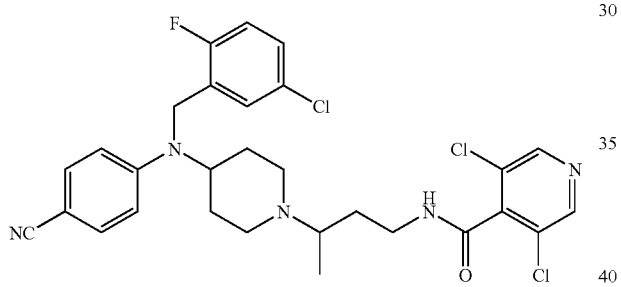

COMPOUND 195: 3,5-Dichloro-N-(3-{4-[(5-chloro-2-fluoro-benzyl)-(4-cyano-phenyl)-amino]-piperidin-1-yl}-butyl)-isonicotinamide White foam. ¹H NMR (CDCl₃) δ 1.03 (d, 3H, J=6.6 Hz), 1.04-1.18 (m, 1H), 1.21-1.35 (m, 1H), 1.54-1.64 (m, 1H), 1.73-1.87 (m, 3H), 2.18-2.27 (m, 1H), 2.55-2.64 (m, 1H), 2.80-2.98 (m, 3H), 3.33-3.44 (m, 1H), 3.69-3.88 (m, 2H), 4.09 (s, 2H), 6.57 (d, 2H, J=8.9 Hz), 6.95 (dd, 1H, J=6.6, 2.4 Hz), 7.08 (dd, 1H, J=9.2, 9.2 Hz), 7.20-7.26 (m, 1H), 7.43 (d, 2H, J=8.9 Hz), 8.29 (br s, 1H), 8.49 (s, 2H). ¹³C NMR (CDCl₃) δ 13.29, 29.17, 30.01, 30.99, 39.30, 42.47 (d, J=5.4 Hz), 43.61, 51.37, 55.62, 59.17, 98.95, 112.30, 116.79 (d, J=22.6 Hz), 119.91, 127.04 (d, J=15.6 Hz), 127.25 (d, J=4.8 Hz), 128.55 (d, J=8.1 Hz), 128.74, 129.46 (d, J=3.8 Hz), 133.56, 142.85, 147.45, 150.86, 158.32 (d, J=246 Hz), 161.51. ESI-MS m/z 588 (MH)⁺, 590 (MH+2)⁺, 592 (MH+4)⁺. Anal. Calcd. for C₂₉H₂₉Cl₃FN₅O.0.2CH₂Cl₂: C, 58.77; H, 4.89; N, 11.56; Cl, 19.89. Found: C, 57.62; H, 4.97; N, 11.46; Cl, 19.63.

EXAMPLE 196

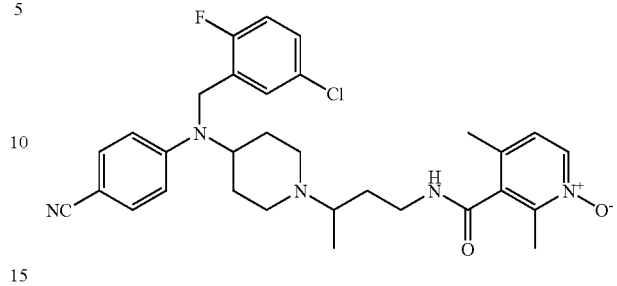

COMPOUND 196: N-(3-{4-[(5-Chloro-2-fluoro-benzyl)-(4-cyano-phenyl)-amino]-piperidin-1-yl}-butyl)-2,4-dimethyl-1-oxy-nicotinamide White solid. ¹H NMR (CDCl₃) δ 1.03 (m, 3H), 1.25-1.64 (m, 3H), 1.79-1.84 (m, 3H), 2.22-2.26 (m, 1H), 2.31 (s, 3H), 2.37 (s, 3H), 2.53-2.60 (m, 1H), 2.76-2.90 (m, 3H), 3.45 (br s, 1H), 3.63-3.76 (m, 2H), 4.30 (s, 2H), 6.59 (d, 2H, J=7.9 Hz), 6.91-7.08 (m, 3H), 7.21 (br s, 1H), 7.43 (d, 2H, J=8.4 Hz), 8.02 (d, 2H, J=9.0 Hz). ¹³C NMR (CDCl₃) δ 13.94, 15.40, 18.90, 29.74, 30.09, 32.94, 38.86, 43.37, 44.91, 51.47, 56.39, 58.50, 99.54, 112.85, 117.22 (d, J=23 Hz), 120.50, 125.30, 127.94, 129.02 (d, J=8 Hz), 130.06, 134.15, 134.85, 137.22, 138.33, 145.95, 151.56, 158.87 (d, J=246 Hz), 165.89. ES-MS m/z 564 (M+H). Anal. Calcd. for C₃₁H₃₅N₅O₂ClF.0.9CH₄O.0.3CH₂Cl₂: C, 62.54; H, 6.39; N, 11.32; Cl, 9.17; F, 3.07. Found: C, 62.67; H, 6.23; N, 10.98; Cl, 9.35; F, 2.75.

EXAMPLE 197

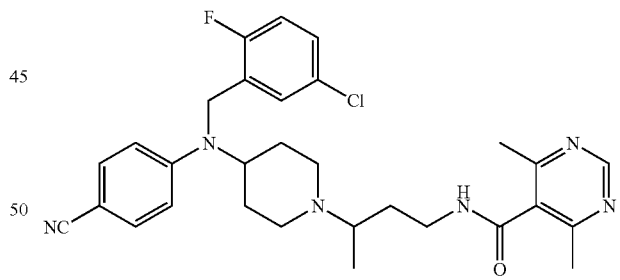

COMPOUND 197: 4,6-Dimethyl-pyrimidine-5-carboxylic acid (3-{4-[(5-chloro-2-fluoro-benzyl)-(4-cyano-phenyl)-amino]-piperidin-1-yl}-butyl)-amide White solid. ¹H NMR (CDCl₃) δ 1.03 (d, 3H, J=5.7 Hz), 1.10-1.36 (m, 2H), 1.60-1.68 (m, 1H), 1.70-1.84 (m, 3H), 2.23 (t, 1H, J=11.7 Hz), 2.50 (s, 6H), 2.59 (t, 1H, J=11.1 Hz), 2.78-2.92 (m, 3H), 3.40 (br s, 1H), 3.70-3.80 (m, 2H), 4.16 (s, 2H), 6.57 (d, 2H, J=8.1 Hz), 6.94-6.97 (m, 1H), 7.03-7.10 (m, 1H), 7.18-7.24 (m, 1H), 7.42 (d, 2H, J=7.9 Hz), 7.70 (br s, 1H), 8.89 (s, 1H). ¹³C NMR (CDCl₃) δ 13.43, 21.99, 29.27, 30.22, 31.58, 39.43, 42.60, 43.79, 51.71, 55.91, 59.42, 99.36, 112.53, 116.97 (d, J=23 Hz), 120.04, 127.39, 128.72 (d, J=8 Hz), 129.62, 133.75, 150.95, 157.73, 158.51 (d, J=246 Hz), 162.99, 166.52. ES-MS m/z 549 (M+H). Anal. Calcd. for $C_{30}H_{34}N_6OClF \cdot 0.3H_2O$: C, 64.98; H, 6.29; N, 15.16; Cl, 6.39; F, 3.43. Found: C, 65.14; H, 6.35; N, 14.96; Cl, 6.41; F, 3.25.

EXAMPLE 198

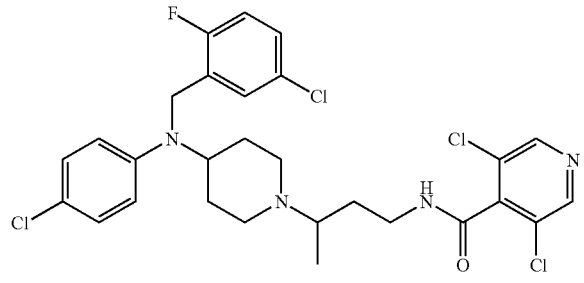

COMPOUND 198: 3,5-Dichloro-N-(3-{4-[(5-chloro-2-fluoro-benzyl)-(4-chloro-phenyl)-amino]-piperidin-1-yl}-butyl)-isonicotinamide White solid. $^1$H NMR (CDCl$_3$) δ 0.98-1.24 (m, 2H), 1.02 (d, 3H, J=6.6 Hz), 1.54-1.59 (m, 1H), 1.73-1.83 (m, 3H), 2.18 (t, 1H, J=11.4 Hz), 2.57 (t, 1H, J=11.7 Hz), 2.79-2.91 (m, 3H), 3.32-3.39 (m, 1H), 3.55-3.63 (m, 1H), 3.87-3.92 (m, 1H), 3.92 (s, 2H), 6.50 (d, 2H, J=8.7 Hz), 7.01-7.12 (m, 4H), 7.18-7.19 (m, 1H), 8.48 (s, 2H), 8.60 (br s, 1H). $^{13}$C NMR (CDCl$_3$) δ 13.35, 29.22, 30.29, 30.68, 40.00, 42.72, 43.57, 51.99, 56.24, 60.12, 114.56, 116.67 (d, J=23 Hz), 122.54, 127.95, 128.33 (d, J=9 Hz), 128.85, 129.15, 129.52, 143.02, 146.67, 147.67, 156.96, 158.59 (d, J=245 Hz), 161.57. ES-MS m/z 597 (M+H). Anal. Calcd. for $C_{28}H_{29}N_4Cl_4OF \cdot 0.2C_3H_7NO$: C, 56.04; H, 5.00; N, 9.60; Cl, 23.13; F, 3.10. Found: C, 55.65; H, 4.98; N, 9.61; Cl, 23.11; F, 2.80.

EXAMPLE 199

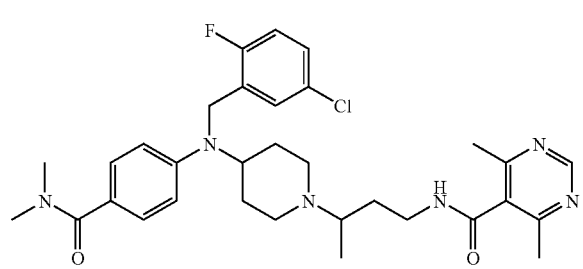

COMPOUND 199: 4,6-Dimethyl-pyrimidine-5-carboxylic acid (3-{4-[(5-chloro-2-fluoro-benzyl)-(4-dimethylcarbamoyl-phenyl)-amino]-piperidin-1-yl}-butyl)-amide White solid. $^1$H NMR (CDCl$_3$) δ 1.02 (d, 3H, J=6.0 Hz), 1.03-1.33 (m, 2H), 1.52-1.64 (m, 1H), 1.69-1.87 (m, 3H), 2.15-2.27 (m, 1H), 2.50 (s, 6H), 2.52-2.63 (m, 1H), 2.73-2.92 (m, 3H), 3.03 (s, 6H), 3.31-3.43 (m, 1H), 3.65-3.83 (m, 2H), 4.08 (s, 2H), 6.54 (d, 2H, J=7.8 Hz), 6.99-7.07 (m, 2H), 7.14-7.21 (m, 1H), 7.24-7.34 (m, 2H), 8.02 (br s, 1H), 8.88 (s, 1H). $^{13}$C NMR (CDCl$_3$) δ 13.88, 22.35, 29.65, 30.66, 31.90, 39.79, 43.11, 44.38, 52.12, 56.30, 59.78, 112.44, 117.08 (d, J=23 Hz), 124.83, 128.25, 128.66, 129.74, 131.05, 149.64, 158.00, 158.95 (d, J=245 Hz), 163.35, 166.93, 172.09. ES-MS m/z 595 (M+H). Anal. Calcd. for $C_{32}H_{40}ClFN_6O_2 \cdot 0.4CH_2Cl_2 \cdot 0.3H_2O$: C, 61.15; H, 6.63; N, 13.04; Cl, 10.40; F, 2.88. Found: C, 61.33; H, 6.58; N, 13.24; Cl, 10.06; F, 2.99.

EXAMPLE 200

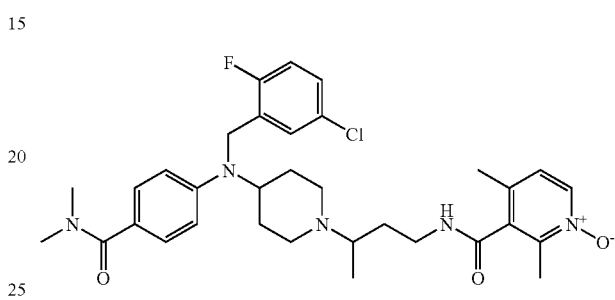

COMPOUND 200: N-(3-{4-[(5-Chloro-2-fluoro-benzyl)-(4-dimethylcarbamoyl-phenyl)-amino]-piperidin-1-yl}-butyl)-2,4-dimethyl-1-oxy-nicotinamide White solid. $^1$H NMR (CDCl$_3$) δ 1.03 (d, 3H, J=6.0 Hz), 1.19-1.45 (m, 2H), 1.54-1.67 (m, 1H), 1.73-1.89 (m, 3H), 2.17-2.30 (m, 1H), 2.30 (s, 3H), 2.35 (s, 3H), 2.51-2.63 (m, 1H), 2.74-2.91 (m, 3H), 3.04 (s, 6H), 3.35-3.48 (m, 1H), 3.62-3.80 (m, 2H), 4.23 (s, 2H), 6.56 (d, 2H, J=8.1 Hz), 6.90 (d, 1H, J=6.0 Hz), 6.98-7.10 (m, 2H), 7.14-7.22 (m, 1H), 7.30 (d, 2H, J=8.1 Hz), 7.99 (d, 1H, J=6.6 Hz), 8.36 (br s, 1H). $^{13}$C NMR (CDCl$_3$) δ 13.88, 15.50, 18.83, 29.73, 30.59, 32.24, 36.87, 39.58, 43.27, 44.53, 52.01, 56.30, 59.39, 112.40, 116.96 (d, J=23 Hz), 125.07 (d, J=18 Hz), 128.45, 128.65, 128.76, 129.01, 129.77, 133.78, 137.00, 138.64, 146.08, 149.67, 165.90, 172.16. ES-MS m/z 610 (M+H). Anal. Calcd. for $C_{33}H_{41}ClFN_5O_3 \cdot 0.3CH_2Cl_2 \cdot 1.1H_2O$: C, 61.02; H, 6.74; N, 10.68; Cl, 8.65; F, 2.90. Found: C, 61.20; H, 6.86; N, 11.08; Cl, 8.31; F, 2.50.

EXAMPLE 201

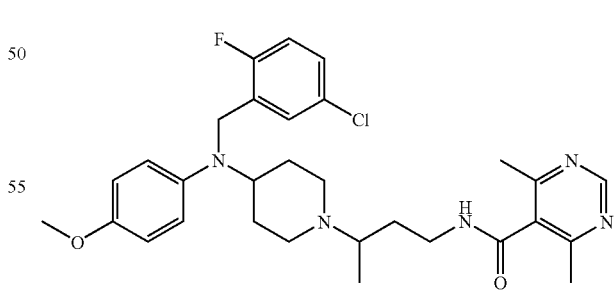

COMPOUND 201: 4,6-Dimethyl-pyrimidine-5-carboxylic acid (3-{4-[(5-chloro-2-fluoro-benzyl)-(4-methoxy-phenyl)-amino]-piperidin-1-yl}-butyl)-amide White solid. $^1$H NMR (CDCl$_3$) δ 0.95-1.20 (m, 2H), 1.01 (d, 3H, J=6.3 Hz), 1.55-1.60 (m, 1H), 1.77-1.81 (m, 3H), 2.14

(t, 1H, J=11.4 Hz), 2.51 (s, 6H), 2.51-2.57 (m, 1H), 2.73-2.84 (m, 3H), 3.34-3.39 (m, 2H), 3.73 (s, 3H), 3.81-3.89 (m, 1H), 3.89 (s, 2H), 6.62 (d, 2H, J=8.4 Hz), 6.74 (d, 2H, J=8.4 Hz), 6.95-7.01 (m, 1H), 7.12-7.19 (m, 2H), 8.35 (br s, 1H), 8.86 (s, 1H). $^{13}$C NMR (CDCl$_3$) δ 13.77, 22.32, 29.76, 30.83, 31.41, 40.24, 43.71, 44.16, 52.35, 55.97, 58.62, 60.37, 114.97, 116.81 (d, J=23 Hz), 118.01, 128.37 (d, J=8 Hz), 129.14 (d, J=4 Hz), 129.43, 129.63, 131.05, 142.72, 153.33, 158.05, 159.21 (d, J=245 Hz), 163.29, 166.87. ES-MS m/z 554 (M+H). Anal. Calcd. for C$_{30}$H$_{37}$N$_5$ClO$_2$F.0.3H$_2$O: C, 64.40; H, 6.77; N, 12.52; Cl, 6.34; F, 3.40. Found: C, 64.45; H, 6.64; N, 12.40; Cl, 6.44; F, 3.61.

EXAMPLE 202

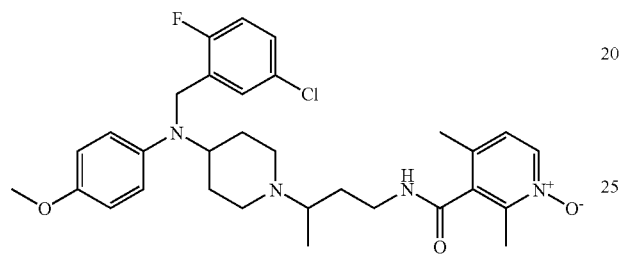

COMPOUND 202: N-(3-{4-[(5-Chloro-2-fluoro-benzyl)-(4-methoxy-phenyl)-amino]-piperidin-1-yl}-butyl)-2,4-dimethyl-1-oxy-nicotinamide White solid. $^1$H NMR (CDCl$_3$) δ 1.01 (d, 3H, J=6.3 Hz), 1.09-1.29 (m, 2H), 1.57-1.62 (m, 1H), 1.80-1.83 (m, 3H), 2.16 (t, 1H, J=12.0 Hz), 2.30 (s, 3H), 2.41 (s, 3H), 2.52 (t, 1H, J=11.4 Hz), 2.74-2.83 (m, 3H), 3.71-3.42 (m, 1H), 3.73 (s, 3H), 3.73-3.79 (m, 1H), 4.03 (s, 2H), 6.63 (d, 2H, J=8.4 Hz), 6.75 (d, 2H, J=8.4 Hz), 6.90 (d, 1H, J=6.3 Hz), 6.94-7.00 (m, 1H), 7.12 (m, 1H), 7.21-7.22 (m, 1H), 8.01 (d, 1H, J=6.3 Hz), 8.45 (br s, 1H). $^{13}$C NMR (CDCl$_3$) δ 13.94, 15.35, 18.86, 30.00, 30.59, 32.72, 39.17, 44.34, 45.02, 51.68, 56.02, 58.34, 58.69, 115.04, 116.69 (d, J=23 Hz), 125.24, 128.29 (d, J=8 Hz), 129.14 (d, J=4 Hz), 129.74, 129.96 (d, J=15 Hz), 134.75, 137.31, 138.25, 143.05, 145.94, 153.05, 159.12 (d, J=245 Hz), 165.82. ES-MS m/z 569 (M+H). Anal. Calcd. for C$_{31}$H$_{38}$N$_4$ClO$_3$F.0.4H$_2$O.0.05CH$_2$Cl$_2$: C, 64.23; H, 6.75; N, 9.65; Cl, 6.72; F, 3.27. Found: C, 64.21; H, 6.72; N, 9.79; Cl, 6.72; F, 3.20.

EXAMPLE 203

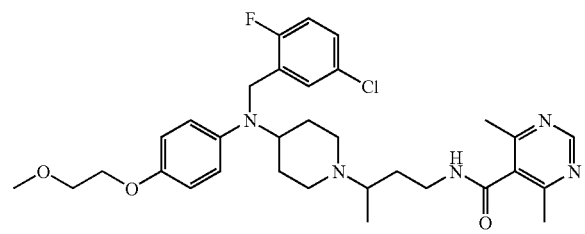

COMPOUND 203: 4,6-Dimethyl-pyrimidine-5-carboxylic acid [3-(4-{(5-chloro-2-fluoro-benzyl)-[4-(2-methoxy-ethoxy)-phenyl]-amino}-piperidin-1-yl)-butyl]-amide Yellow foam. $^1$H NMR (CDCl$_3$) δ 1.01 (d, 3H, J=5.7 Hz), 1.55-1.81 (m, 8H), 2.15 (t, 1H, J=10.2 Hz), 2.51 (s, 6H), 2.74-2.77 (m, 1H), 2.86 (d, 2H, J=9.3 Hz), 3.35-3.38 (m, 1H), 3.42 (s, 3H), 3.70 (s, 2H), 3.81-3.83 (m, 1H), 3.90 (s, 2H), 4.03 (s, 2H), 6.59 (d, 2H, J=8.4 Hz), 6.77 (d, 2H, J=8.7 Hz), 6.98 (t, 1H, J=9.0 Hz), 7.12-7.15 (m, 2H), 8.34 (br s, 1H), 8.86 (s, 1H). $^{13}$C NMR (CDCl$_3$) δ 13.75, 22.34, 29.70, 30.79, 31.41, 40.22, 43.64, 44.15, 52.39, 58.43, 59.57, 60.40, 68.11, 71.56, 115.93, 116.67, 116.98, 117.72, 128.34, 138.45, 129.09, 129.63, 142.94, 146.72, 153.21, 158.08, 163.32. ES-MS m/z 599 [M+H]$^+$. Anal. Calcd. for C$_{32}$H$_{41}$N$_5$O$_3$FCl.0.4H$_2$O: C, 63.49; H, 63.53; N, 11.57; Cl, 5.86; F, 3.14. Found: C, 63.53; H, 6.90; N, 11.19; Cl, 5.74; F, 2.99.

EXAMPLE 204

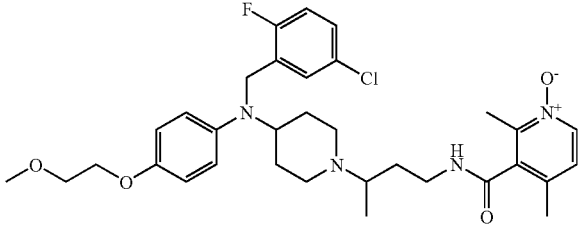

COMPOUND 204: N-[3-(4-{(5-Chloro-2-fluoro-benzyl)-[4-(2-methoxy-ethoxy)-phenyl]-amino}-piperidin-1-yl)-butyl]-2,4-dimethyl-1-oxy-nicotinamide Pale yellow foam. $^1$H NMR (CDCl$_3$) δ 1.00 (d, 3H, J=6.0 Hz), 1.12-1.28 (m, 2H), 1.57-1.60 (m, 1H), 1.79-1.83 (m, 3H), 2.16 (t, 1H, J=11.7 Hz), 2.30 (s, 3H), 2.38 (s, 3H), 2.51 (t, 1H, J=11.4 Hz), 2.73-2.87 (m, 3H), 3.38-3.43 (m, 5H), 3.70-3.73 (m, 3H), 4.02-4.05 (m, 4H), 6.61 (d, 2H, J=8.1 Hz), 6.78 (d, 2H, J=8.1 Hz), 6.89 (d, 1H, J=6.3 Hz), 6.97 (t, 1H, J=9.0 Hz), 7.12 (br s, 1H), 7.20-7.21 (m, 1H), 7.99 (d, 1H, J=6.0 Hz), 8.49 (s, 1H). $^{13}$C NMR (CDCl$_3$) δ 13.45, 15.11, 18.42, 29.53, 30.36, 31.52, 39.46, 43.70, 44.10, 51.72, 53.44, 57.98, 59.18, 67.77, 71.18, 115.60, 116.18, 116.49, 117.18, 124.77, 127.99, 128.05, 128.80, 128.85, 129.20, 129.42, 133.22, 136.60, 138.29, 142.67, 145.69, 151.99, 15.52. ES-MS m/z 614 [M+H]$^+$. Anal. Calcd. for $C_{33}H_{42}N_4O_4FCl.0.1CH_2Cl_2.0.5H_2O$: C, 63.04; H, 6.90; N, 8.88; Cl, 6.75. Found: C, 63.08; H, 6.96; N, 8.76; Cl, 6.62.

EXAMPLE 205

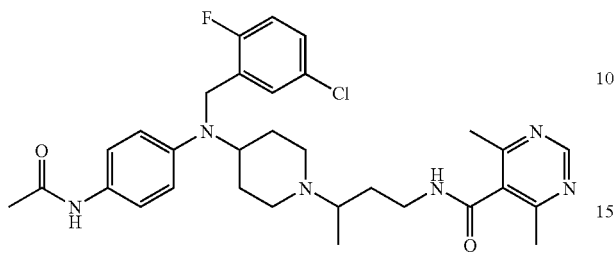

COMPOUND 205: 4,6-Dimethyl-pyrimidine-5-carboxylic acid (3-{4-[(4-acetylamino-phenyl)-(5-chloro-2-fluoro-benzyl)-amino]-piperidin-1-yl}-butyl)-amide White solid. $^1$H NMR (CDCl$_3$) δ 0.93-1.27 (m, 2H), 1.02 (d, 3H, J=6.3 Hz), 1.52-1.62 (m, 1H), 1.70-1.85 (m, 3H), 2.12 (s, 3H), 2.13-2.23 (m, 1H), 2.50 (s, 6H), 2.51-2.61 (m, 1H), 2.72-2.91 (m, 3H), 3.29-3.41 (m, 1H), 3.51-3.62 (m, 1H), 3.75-3.86 (m, 1H), 3.96 (s, 2H), 6.56 (d, 2H, J=8.4 Hz), 6.96-7.05 (m, 2H), 7.07-7.18 (m, 2H), 7.21-7.29 (m, 2H), 8.18 (br s, 1H), 8.86 (s, 1H). $^{13}$C NMR (CDCl$_3$) δ 13.43, 21.93, 24.19, 29.26, 30.31, 31.22, 39.65, 42.77, 43.87, 51.90, 56.86, 59.68, 114.43, 116.54 (d, J=23 Hz), 122.04, 127.89, 128.07, 128.20, 128.77, 128.97, 129.40, 130.64, 145.20, 157.62, 158.67 (d, J=245 Hz), 162.95, 166.51, 168.26. ES-MS m/z 581 (M+H). Anal. Calcd. for $C_{31}H_{38}N_6ClO_2F.0.6CH_2Cl_2$: C, 60.05; H, 6.25; N, 13.30; Cl, 12.34; F, 3.01. Found: C, 59.75; H, 6.28; N, 13.21; Cl, 12.16; F, 2.89.

EXAMPLE 206

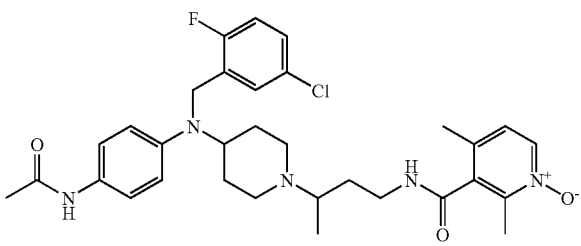

COMPOUND 206: N-(3-{4-[(4-Acetylamino-phenyl)-(5-chloro-2-fluoro-benzyl)-amino]-piperidin-1-yl}-butyl)-2,4-dimethyl-1-oxy-nicotinamide White solid. $^1$H NMR (CDCl$_3$) δ 1.01 (d, 3H, J=6.0 Hz), 1.04-1.35 (m, 2H), 1.53-1.64 (m, 1H), 1.70-1.87 (m, 3H), 2.13 (s, 3H), 2.13-2.23 (m, 1H), 2.29 (s, 3H), 2.40 (s, 3H), 2.47-2.60 (m, 1H), 2.71-2.91 (m, 3H), 3.29-3.42 (m, 1H), 3.44-3.57 (m, 1H), 3.69-3.81 (m, 1H), 4.11 (s, 2H), 6.58 (d, 2H, J=7.5 Hz), 6.88-7.04 (m, 2H), 7.11-7.20 (m, 2H), 7.21-7.32 (m, 3H), 8.02 (d, 1H, J=6.3 Hz), 8.28 (br s, 1H). $^{13}$C NMR (CDCl$_3$) δ 13.53, 15.03, 18.46, 24.17, 29.47, 30.15, 32.13, 38.94, 43.52, 44.47, 51.45, 56.91, 58.58, 114.64, 116.43 (d, J=23 Hz), 122.04, 124.87, 128.07 (d, J=8 Hz), 128.42, 128.99, 129.25, 129.45, 134.26, 136.79, 137.98, 145.24, 145.60, 158.64 (d, J=245 Hz), 165.45, 168.39. ES-MS m/z 596 (M+H). Anal. Calcd. for $C_{32}H_{39}N_5ClO_3F.0.4CH_2Cl_2.0.2H_2O$: C, 61.41; H, 6.39; N, 11.05; Cl, 10.07; F, 3.00. Found: C, 61.47; H, 6.25; N, 10.94; Cl, 9.72; F, 2.86.

EXAMPLE 207

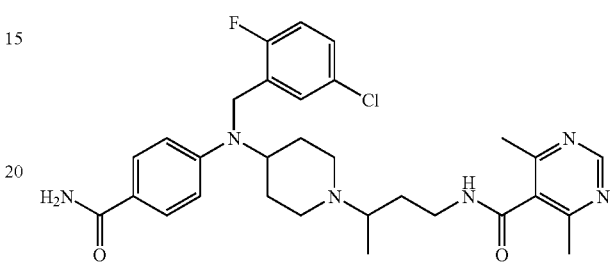

COMPOUND 207: 4,6-Dimethyl-pyrimidine-5-carboxylic acid (3-{4-[(4-carbamoyl-phenyl)-(5-chloro-2-fluoro-benzyl)-amino]-piperidin-1-yl}-butyl)-amide Using general procedure H, 4-(4-methoxycarbonyl-phenylamino)-piperidine-1-carboxylic acid tert-butyl ester (see EXAMPLE 85) (442 mg, 1.32 mmol) and 5-chloro-2-fluorobenzyl bromide (385 mg, 1.72 mmol) gave impure product as an oily, white foam (358 mg).

Using general procedure C with the impure carbamate, then general procedure B with the resulting amine and 2-(3-oxo-butyl)-isoindole-1,3-dione (206 mg, 0.95 mmol) followed by general procedure D gave 4-[[1-(3-amino-1-methyl-propyl)-piperidin-4-yl]-(5-chloro-2-fluoro-benzyl)-amino]-benzoic acid methyl ester as a white foam (138 mg, 23% over 4 steps).

Using general procedure E with the primary amine (69 mg, 0.15 mmol) and 4,6-dimethylpyrimidine-5-carboxylic acid (32 mg, 0.21 mmol) followed by general procedure K gave 4-[(5-chloro-2-fluoro-benzyl)-(1-{3-[(4,6-dimethyl-pyrimidine-5-carbonyl)-amino]-1-methyl-propyl}-piperidin-4-yl)-amino]-benzoic acid as a beige solid (41.6 mg, 47% over 2 steps).

Using general procedure E, the carboxylic acid (41.6 mg, 0.073 mmol) and NH$_4$Cl (10 mg, 0.19 mmol) gave COMPOUND 207 as an off-white solid (30.8 mg, 74%). $^1$H NMR (CDCl$_3$) δ 1.05 (d, 3H, J=6.6 Hz), 1.06-1.20 (m, 1H), 1.23-1.37 (m, 1H), 1.55-1.89 (m, 4H), 2.20-2.31 (m, 1H), 2.51 (s, 6H), 2.56-2.67 (m, 1H), 2.76-2.95 (m, 3H), 3.34-3.46 (m, 1H), 3.71-3.84 (m, 2H), 4.14 (s, 2H), 5.68 (br s, 2H), 6.58 (d, 2H, J=8.6 Hz), 6.99-7.09 (m, 2H), 7.16-7.23 (m, 1H), 7.64 (d, 2H, J=8.6 Hz), 7.90 (br s, 1H), 8.89 (s, 1H). $^{13}$C NMR (CDCl$_3$) δ 13.41, 21.91, 29.21, 30.16, 31.49, 39.32, 42.63 (d, J=4.4 Hz), 43.88, 51.65, 55.83, 59.32, 111.99, 116.74 (d, J=22.9 Hz), 121.45, 127.64 (d, J=4.7 Hz), 127.87 (d, J=15.8 Hz), 128.41 (d, J=8.3 Hz), 129.18, 129.46 (d, J=3.2 Hz), 130.54, 150.87, 157.57, 158.49 (d, J=246 Hz), 162.94, 166.51, 168.99. ESI-MS m/z 567 (MH)$^+$, 569 (MH+2)$^+$.

Anal. Calcd. for $C_{30}H_{36}ClFN_6O_2 \cdot 0.8CH_2Cl_2$: C, 58.25; H, 5.97; N, 13.23; Cl, 14.52. Found: C, 58.12; H, 5.87; N, 12.87; Cl, 14.35.

EXAMPLE 208

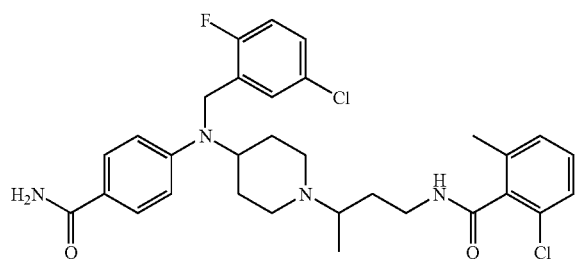

COMPOUND 208: N-(3-{4-[(4-Carbamoyl-phenyl)-(5-chloro-2-fluoro-benzyl)-amino]-piperidin-1-yl}-butyl)-2-chloro-6-methyl-benzamide Using general procedure E with 4-[[1-(3-amino-1-methyl-propyl)-piperidin-4-yl]-(5-chloro-2-fluoro-benzyl)-amino]-benzoic acid methyl ester (see EXAMPLE 207) (69 mg, 0.15 mmol) and 4,6-dimethylpyrimidine-3-carboxylic acid (32 mg, 0.21 mmol) followed by general procedure K gave 4-((5-chloro-2-fluoro-benzyl)-{1-[3-(2-chloro-6-methyl-benzoylamino)-1-methyl-propyl]-piperidin-4-yl}-amino)-benzoic acid as a beige solid (45.9 mg, 51% over 2 steps).

Using general procedure E, the crude carboxylic acid (45.9 mg, 0.078 mmol) and $NH_4Cl$ (13 mg, 0.24 mmol) gave COMPOUND 208 as an off-white solid (27.0 mg, 59%). $^1$H NMR ($CDCl_3$) δ 0.96-1.10 (m, 1H), 1.02 (d, 3H, J=6.6 Hz), 1.14-1.28 (m, 1H), 1.50-1.60 (m, 1H), 1.71-1.86 (m, 3H), 2.16-2.26 (m, 1H), 2.36 (s, 3H), 2.54-2.65 (m, 1H), 2.79-3.00 (m, 3H), 3.26-3.38 (m, 1H), 3.67-3.78 (m, 1H), 3.82-3.93 (m, 1H), 3.97 (s, 2H), 5.64 (br s, 2H), 6.55 (d, 2H, J=8.4 Hz), 6.96-7.01 (m, 1H), 7.03-7.14 (m, 4H), 7.18-7.24 (m, 1H), 7.63 (d, 2H, J=8.4 Hz), 8.42 (br s, 1H). $^{13}$C NMR ($CDCl_3$) δ 13.40, 19.27, 29.05, 30.21, 30.78, 39.86, 42.43 (d, J=4.3 Hz), 43.53, 51.94, 55.96, 60.29, 111.98, 116.62 (d, J=22.9 Hz), 121.44, 126.51, 127.76 (d, J=4.6 Hz), 128.00 (d, J=15.7 Hz), 128.37 (d, J=8.2 Hz), 128.43, 129.17, 129.59 (d, J=1.2 Hz), 130.41, 136.84, 137.37, 150.79, 158.47 (d, J=245 Hz), 166.89, 168.93. ESI-MS m/z 585 $(MH)^+$, 587 $(MH+2)^+$. Anal. Calcd. for $C_{31}H_{35}Cl_2FN_4O_2 \cdot 0.6CH_2Cl_2$: C, 59.63; H, 5.73; N, 8.80; Cl, 17.82. Found: C, 59.44; H, 5.57; N, 8.64; Cl, 17.69.

EXAMPLE 209

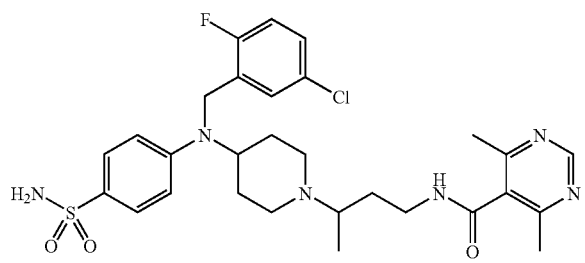

COMPOUND 209: 4,6-Dimethyl-pyrimidine-5-carboxylic acid (3-{4-[(5-chloro-2-fluoro-benzyl)-(4-sulfamoyl-phenyl)-amino]-piperidine-1-yl}-butyl)-amide Using general procedure H, 4-(4-dibenzylsulfamoyl-phenylamino)-piperidine-1-carboxylic acid tert-butyl ester (see EXAMPLE 168) (2.19 g, 4.09 mmol) and 2-fluoro-5-chlorobenzyl bromide (1.37 g, 6.13 mmol) afforded the product as a yellow foam (1.70 g, 61%).

Using general procedure C with the above amine, then general procedure B with the resulting amine and 2-(3-oxo-butyl)-isoindole-1,3-dione and then using general procedure D afforded 4-[[1-(3-amino-1-methyl-propyl)-piperidin-4-yl]-(5-chloro-2-fluoro-benzyl)-amino]-N,N-dibenzyl-benzenesulfonamide as a pale yellow foam (0.66 g, 40% over 3 steps).

Using general procedure E, the amine (320 mg, 0.49 mmol) and 4,6-dimethyl-pyrimidine-5-carboxylic acid (97 mg, 0.64 mmol) afforded 4,6-dimethyl-pyrimidine-5-carboxylic acid (3-{4-[(5-chloro-2-fluoro-benzyl)-(4-dibenzylsulfamoyl-phenyl)-amino]-piperidin-1-yl}-butyl)-amide as a pale yellow oil (137 mg, 36%).

A solution of the above amine (137 mg, 0.18 mmol) in $H_2SO_4$ (conc) (1.5 mL) was stirred for 2 h. Then the mixture was poured into ice (50 mL), basified with $Na_2CO_3$ (s) to pH-9, and extracted with $CH_2Cl_2$ (8×30 mL). The combined organic layers were dried ($MgSO_4$), filtered, and concentrated to afford COMPOUND 209 as a pale yellow foam (41 mg, 37%) after purification. $^1$H NMR ($CDCl_3$) δ 1.04 (d, 3H, J=6.0 Hz), 1.17-1.21 (m, 1H), 1.25-1.32 (m, 1H), 1.59 (br s, 1H), 1.75-1.80 (m, 3H), 2.25 (t, 1H, J=12.0 Hz), 2.51 (s, 6H), 2.61 (t, 1H, J=11.1 Hz), 2.79-2.92 (m, 3H), 3.41 (br s, 1H), 3.76 (br s, 2H), 4.16 (s, 2H), 4.67 (s, 2H), 6.61 (d, 2H, J=8.4 Hz), 6.96 (d, 1H, J=5.7 Hz), 7.07 (t, 1H, J=9.0 Hz), 7.20 (br s, 1H), 7.70 (d, 2H, J=8.4 Hz), 7.79 (br s, 1H), 8.89 (br s, 1H), 8.89 (s, 1H). $^{13}$C NMR ($CDCl_3$) δ 13.83, 22.36, 29.64, 30.63, 31.93, 39.85, 43.04, 44.17, 52.12, 56.47, 59.86, 112.55, 117.19, 117.49, 117.60, 127.84, 128.93, 129.01, 129.10, 151.65, 158.11, 166.90. ES-MS m/z 625 $[M+Na]^+$. Anal. Calcd. for $C_{29}H_{36}N_6O_3SFCl$: C, 51.22; H, 5.78; N, 11.99; S, 4.57; F, 2.71; Cl, 14.16. Found: C, 51.15; H, 5.52; N, 11.98; S, 4.41; F, 2.50; Cl, 14.19.

EXAMPLE 210

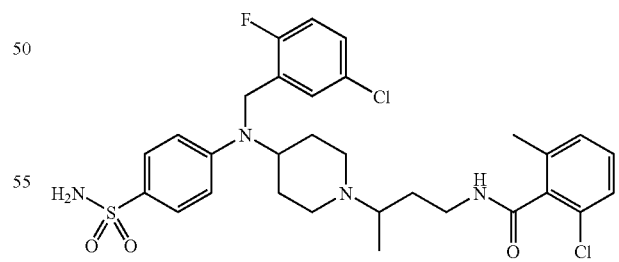

COMPOUND 210: 2-Chloro-N-(3-{4-[(5-chloro-2-fluoro-benzyl)-(4-sulfamoyl-phenyl)-amino]-piperidin-1-yl}-butyl)-6-methyl-benzamide Using general procedure E, 4-[[1-(3-amino-1-methyl-propyl)-piperidin-4-yl]-(5-chloro-2-fluoro-benzyl)-amino]-N,N-dibenzyl-benzenesulfonamide (see EXAMPLE 209) (339 mg, 0.52 mmol) and 2-chloro-6-methylbenzoic acid (116 mg, 0.68 mmol) afforded 2-chloro-N-(3-{4-[(5-chloro-2-fluoro-benzyl)-(4-dibenzylsulfamoyl-phenyl)-amino]-piperidin-1-yl}-butyl)-6-methyl-benzamide as a yellow oil (387 mg, 100%).

A solution of the above amine (387 mg, 0.52 mmol) in H$_2$SO$_4$ (conc) (1.5 mL) was stirred for 1 h. Then the mixture was poured into ice (50 mL), basified with Na$_2$CO$_3$ (s) to pH-9, and extracted with CH$_2$Cl$_2$ (6×30 mL). The combined organic layers were dried (MgSO$_4$), filtered, and concentrated to afford COMPOUND 210 as a pale yellow foam (70 mg, 24%) after purification. $^1$H NMR (CDCl$_3$) δ 1.01 (d, 3H, J=5.7 Hz), 1.19-1.23 (m, 1H), 1.51-1.56 (m, 1H), 1.73-1.77 (m, 3H), 2.20 (t, 1H, J=11.4 Hz), 2.34 (s, 3H), 2.58 (t, 1H, J=11.1 Hz), 2.80-2.94 (m, 4H), 3.31 (t, 1H, J=10.8 Hz), 3.71 (t, 1H, J=10.8 Hz), 3.82-3.86 (m, 1H), 3.97 (s, 2H), 4.89 (br s, 2H), 6.55 (d, 2H, J=8.4 Hz), 6.93 (d, 1H, J=4.5 Hz), 7.04-7.09 (m, 4H), 7.20 (br s, 1H), 7.67 (d, 2H, J=8.1 Hz), 8.36 (br s, 1H). $^{13}$C NMR (CDCl$_3$) & 13.83, 19.70, 29.44, 30.57, 31.24, 40.24, 42.88, 43.93, 53.85, 58.09, 60.64, 112.67, 117.05, 117.35, 125.87, 126.92, 127.79, 127.94, 127.99, 128.80, 128.86, 128.94, 129.05, 129.62, 130.03, 130.83, 131.19, 137.32, 137.77, 151.51, 157.27, 160.52, 167.30. ES-MS m/z 622 [M+H]$^+$. Anal. Calcd. for C$_{30}$H$_{35}$N$_4$O$_3$SFCl.1.0CH$_2$Cl$_2$.0.3H$_2$O: C, 52.30; H, 5.32; N, 7.87; S, 4.50; F, 2.67; Cl, 19.92. Found: C, 52.43; H, 5.14; N, 7.99; S, 4.43; F, 2.65; Cl, 19.75.

EXAMPLE 211

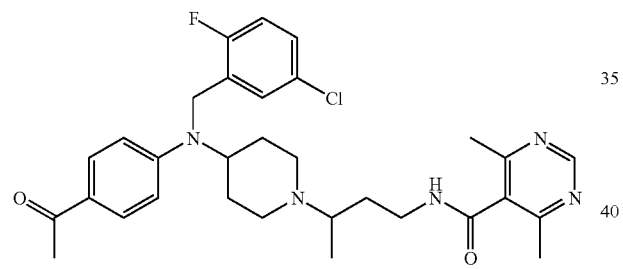

COMPOUND 211: 4,6-Dimethyl-pyrimidine-5-carboxylic acid (3-{4-[(4-acetyl-phenyl)-(5-chloro-2-fluoro-benzyl)-amino]-piperidin-1-yl}-butyl)-amide Using general procedure H, 4-[4-(2-methyl-[1,3]dioxolan-2-yl)-phenylamino]-piperidine-1-carboxylic acid tert-butyl ester (see EXAMPLE 173) (350 mg, 0.97 mmol) and 5-chloro-2-fluorobenzyl bromide (324 mg, 1.5 mmol) afforded 4-{(5-chloro-2-fluoro-benzyl)-[4-(2-methyl-[1,3]dioxolan-2-yl)-phenyl]-amino}-piperidine-1-carboxylic acid tert-butyl ester as a beige solid (316 mg, 65%).

A solution of the above carbamate (315 mg, 0.62 mmol) in 6N HCl (6 mL) was heated at 40° C. for 2 hours. The mixture was cooled to 0° C., basified with 10N NaOH and extracted with CH$_2$Cl$_2$ (3×15 mL). The organic layers were dried (Na$_2$SO$_4$), filtered and concentrated under reduced pressure to give a white solid (233 mg).

Using general procedure B, the above amine and 2-(3-oxo-butyl)-isoindole-1,3-dione (350 mg, 1.6 mmol) gave a pale yellow solid (181 mg).

To a solution of the imide (180 mg) from above in EtOH (2 mL) was added butylamine (0.63 mL, 6.4 mmol) and the solution was heated to reflux overnight to afford 1-{4-[[1-(3-amino-1-methyl-propyl)-piperidin-4-yl]-(5-chloro-2-fluoro-benzyl)-amino]-phenyl}-ethanone as a pale brown solid (82 mg, 31% over 3 steps) after work-up and purification.

Using general procedure E, the above amine (40 mg, 0.093 mmol) and 4,6-dimethyl-pyrimidine-5-carboxylic acid (21 mg, 0.14 mmol) afforded COMPOUND 211 as a white solid (38 mg, 73%). $^1$H NMR (CDCl$_3$) δ 1.04 (d, 3H, J=6.0 Hz), 1.11-1.35 (m, 2H), 1.60-1.63 (m, 1H), 1.76-1.84 (m, 3H), 2.25 (t, 1H, J=11.4 Hz), 2.48 (s, 3H), 2.51 (s, 6H), 2.61 (t, 1H, J=11.7 Hz), 2.78-2.92 (m, 3H), 3.39-3.48 (m, 1H), 3.77-3.81 (m, 2H), 4.16 (s, 2H), 6.58 (d, 2H, J=8.4 Hz), 6.98-7.10 (m, 2H), 7.19-7.26 (m, 1H), 7.79-7.82 (m, 3H), 8.90 (s, 1H). $^{13}$C NMR (CDCl$_3$) δ 13.86, 20.52, 22.33, 26.39, 29.73, 30.65, 32.00, 39.71, 43.02 (d, J=4 Hz), 44.30, 52.02, 56.27, 59.64, 112.05, 117.21 (d, J=23 Hz), 127.04, 127.99 (d, J=3 Hz), 128.20, 128.90 (d, J=8 Hz), 129.94, 131.05, 152.15, 158.01, 158.89 (d, J=246 Hz), 163.34, 166.93. ES-MS m/z 566 (M+H). Anal. Calcd. for C$_{31}$H$_{37}$N$_5$ClO$_2$F.0.3H$_2$O.0.1CH$_2$Cl$_2$: C, 64.40; H, 6.57; N, 12.07; Cl, 7.33; F, 3.28. Found: C, 64.13; H, 6.55; N, 12.07; Cl, 7.60; F, 3.10.

EXAMPLE 212

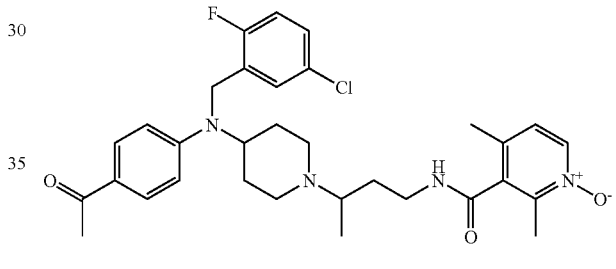

COMPOUND 212: N-(3-{4-[(4-Acetyl-phenyl)-(5-chloro-2-fluoro-benzyl)-amino]-piperidin-1-yl}-butyl)-2,4-dimethyl-1-oxy-nicotinamide Using general procedure E, 1-{4-[[1-(3-amino-1-methyl-propyl)-piperidin-4-yl]-(5-chloro-2-fluoro-benzyl)-amino]-phenyl}-ethanone (see EXAMPLE 211) (40 mg, 0.093 mmol) and 2,4-dimethyl-1-oxy-nicotinic acid (23 mg, 0.14 mmol) afforded COMPOUND 212 as a pale beige solid (37 mg, 69%). $^1$H NMR (CDCl$_3$) δ 1.05 (d, 3H, J=6.0 Hz), 1.25-1.49 (m, 2H), 1.62-1.64 (m, 1H), 1.75-1.83 (m, 3H), 2.27 (t, 1H, J=12.0 Hz), 2.31 (s, 3H), 2.37 (s, 3H) 2.49 (s, 3H), 2.60 (t, 1H, J=11.1 Hz), 2.79-2.92 (m, 3H), 3.45 (br s, 1H), 3.65-3.71 (m, 1H), 3.79-3.86 (m, 1H), 4.32 (s, 2H), 6.59 (d, 2H, J=8.1 Hz), 6.91 (d, 1H, J=6.9 Hz), 7.02-7.08 (m, 2H), 7.19-7.26 (m, 1H), 7.82 (d, 2H, J=7.8 Hz), 8.01 (d, 1H, J=6.6 Hz), 8.13 (br s, 1H). $^{13}$C NMR (CDCl$_3$) δ 14.02, 15.35, 18.89, 23.42, 29.96, 30.48, 33.12, 38.85, 43.42 (d, J=4 Hz), 45.00, 51.46, 56.46, 58.28, 111.95, 117.08 (d, J=23 Hz), 125.28, 126.96, 128.14 (d, J=4 Hz), 128.47, 128.83 (d, J=8 Hz), 129.94, 131.10, 135.00, 137.35, 138.17, 145.92, 152.39, 158.88 (d, J=245 Hz), 165.83. ES-MS m/z 581 (M+H). Anal.

Calcd. for $C_{32}H_{38}N_4ClO_3F \cdot 0.4CH_2Cl_2 \cdot 0.5H_2O$: C, 62.35; H, 6.43; N, 8.98; Cl, 10.23; F, 3.04. Found: C, 62.06; H, 6.43; N, 8.93; Cl, 10.57; F, 2.81.

EXAMPLE 213

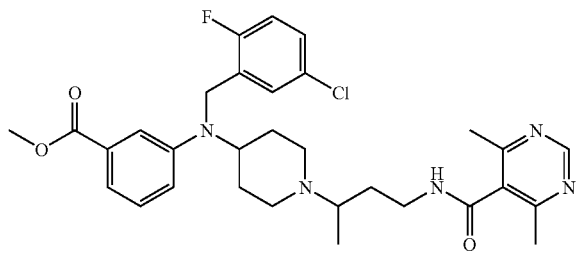

COMPOUND 213: 3-[(5-Chloro-2-fluoro-benzyl)-(1-{3-[(4,6-dimethyl-pyrimidine-5-carbonyl)-amino]-1-methyl-propyl}-piperidin-4-yl)-amino]-benzoic acid methyl ester Using general procedure A with methyl 3-aminobenzoate (2.16 g, 14.3 mmol) and 1-Boc-4-piperidone (2.39 g, 12.0 mmol) followed by general procedure H with the resulting amine and 5-chloro-2-fluorobenzyl bromide (65%, 1.04 g, 3.0 mmol) gave 4-[(5-chloro-2-fluoro-benzyl)-(3-methoxycarbonyl-phenyl)-amino]-piperidine-1-carboxylic acid tert-butyl ester as a white foam (911 mg, 47% over 2 steps).

Using general procedure C with the carbamate (910 mg, 1.91 mmol), then general procedure B with the resulting amine and 2-(3-oxo-butyl)-isoindole-1,3-dione (565 mg, 2.60 mmol) and then using general procedure D gave 3-[[1-(3-amino-1-methyl-propyl)-piperidin-4-yl]-(5-chloro-2-fluoro-benzyl)-amino]-benzoic acid methyl ester as a white foam (473 mg, 56% over 3 steps).

Using general procedure E, the primary amine (236 mg, 0.53 mmol) and 4,6-dimethylpyrimidine-5-carboxylic acid (106 mg, 0.70 mmol) gave COMPOUND 213 as a white foam (228 mg, 74%). $^1$H NMR (CDCl$_3$) δ 0.99-1.13 (m, 1H), 1.04 (d, 3H, J=6.6 Hz), 1.17-1.31 (m, 1H), 1.54-1.65 (m, 1H), 1.72-1.88 (m, 3H), 2.19-2.30 (m, 1H), 2.51 (s, 6H), 2.56-2.67 (m, 1H), 2.74-2.93 (m, 3H), 3.32-3.42 (m, 1H), 3.67-3.86 (m, 2H), 3.88 (s, 3H), 4.04 (s, 2H), 6.70 (d, 1H, J=8.4 Hz), 7.01-7.09 (m, 2H), 7.14-7.23 (m, 2H), 7.35-7.41 (m, 2H), 8.12 (br s, 1H), 8.87 (s, 1H). ESI-MS m/z 582 (MH)$^+$, 584 (MH+2)$^+$.

EXAMPLE 214

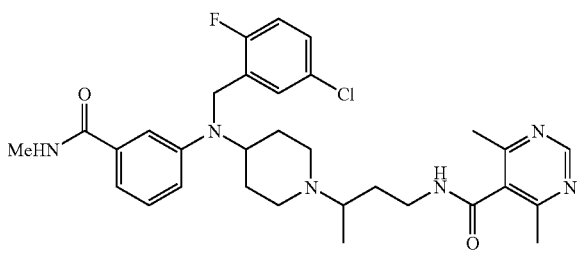

COMPOUND 214: 4,6-Dimethyl-pyrimidine-5-carboxylic acid (3-{4-[(5-chloro-2-fluoro-benzyl)-(3-methylcarbamoyl-phenyl)-amino]-piperidin-1-yl}-butyl)-amide Using general procedure K, 3-[(5-chloro-2-fluoro-benzyl)-(1-{3-[(4,6-dimethyl-pyrimidine-5-carbonyl)-amino]-1-methyl-propyl}-piperidin-4-yl)-amino]-benzoic acid methyl ester (see EXAMPLE 213) (208 mg, 0.36 mmol) gave 3-[(5-chloro-2-fluoro-benzyl)-(1-{3-[(4,6-dimethyl-pyrimidine-5-carbonyl)-amino]-1-methyl-propyl}-piperidin-4-yl)-amino]-benzoic acid as a pale yellow solid (240 mg).

Using general procedure E, the crude carboxylic acid (100 mg, 0.18 mmol) and methylamine hydrochloride (39 mg, 0.58 mmol) gave COMPOUND 214 as an off-white foam (86.4 mg, 84%). $^1$H NMR (CDCl$_3$) δ 0.93-1.10 (m, 1H), 1.02 (d, 3H, J=6.6 Hz), 1.13-1.27 (m, 1H), 1.52-1.63 (m, 1H), 1.71-1.86 (m, 3H), 2.18-2.29 (m, 1H), 2.51 (s, 6H), 2.55-2.66 (m, 1H), 2.71-2.91 (m, 3H), 2.99 (d, 3H, J=3.9 Hz), 3.29-3.41 (m, 1H), 3.68-3.86 (m, 2H), 4.04 (s, 2H), 6.19 (br s, 1H), 6.60 (d, 1H, J=8.1 Hz), 6.95 (d, 1H, J=7.5 Hz), 6.99-7.08 (m, 2H), 7.12-7.20 (m, 2H), 7.25 (d, 1H, J=7.8 Hz), 8.21 (br s, 1H), 8.88 (s, 1H). $^{13}$C NMR (CDCl$_3$) δ 13.44, 21.81, 26.68, 29.19, 30.24, 31.09, 39.48, 42.54 (d, J=4.8 Hz), 43.74, 51.51, 56.06, 59.50, 112.44, 115.03, 116.40, 116.55 (d, J=23.5 Hz), 127.86 (d, J=4.0 Hz), 128.18 (d, J=8.0 Hz), 128.31 (d, J=16.0 Hz), 129.33, 129.41, 130.55, 135.54, 148.28, 157.47, 158.53 (d, J=246 Hz), 162.84, 166.36, 168.61. ESI-MS t/z 581 (MH)$^+$, 583 (MH+2)$^+$. Anal. Calcd. for $C_{31}H_{38}ClFN_6O_2 \cdot 0.7CH_2Cl_2$: C, 59.74; H, 6.22; N, 13.21; Cl, 12.81. Found: C, 59.66; H, 6.22; N, 13.34; Cl, 12.78.

EXAMPLE 215

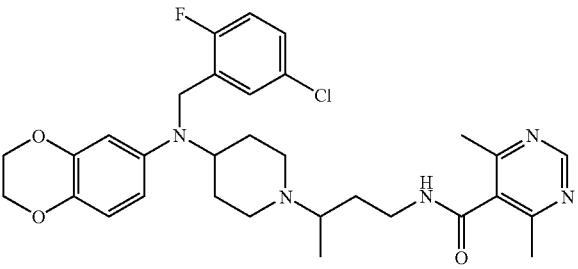

COMPOUND 215: 4,6-Dimethyl-pyrimidine-5-carboxylic acid (3-{4-[(5-chloro-2-fluoro-benzyl)-(2,3-dihydro-benzo[1,4]dioxin-6-yl)-amino]-piperidin-1-yl}-butyl)-amide Using general procedure H, 4-(2,3-dihydro-benzo[1,4]dioxin-6-ylamino)-piperidine-1-carboxylic acid tert-butyl ester (see EXAMPLE 188) (502 mg, 1.50 mmol) and 5-chloro-2-fluoro-benzyl bromide (80%, 630 mg, 2.26 mmol) gave 4-[(5-chloro-2-fluoro-benzyl)-(2,3-dihydro-benzo[1,4]dioxin-6-yl)-amino]-piperidine-1-carboxylic acid tert-butyl ester as a pale yellow foam (676 mg, 94%).

Using general procedure C with the carbamate (676 mg, 1.42 mmol), then general procedure B with the resulting amine and 2-(3-oxo-butyl)-isoindole-1,3-dione (425 mg, 1.96 mmol) and then using general procedure D gave [1-(3-amino-1-methyl-propyl)-piperidin-4-yl]-(5-chloro-2-fluoro-benzyl)-(2,3-dihydro-benzo[1,4]dioxin-6-yl)-amine as a white foam (277 mg, 44% over 3 steps).

Using general procedure E, the primary amine (86 mg, 0.19 mmol) and 4,6-dimethylpyrimidine-5-carboxylic acid (40 mg, 0.26 mmol) gave COMPOUND 215 as a white foam (91.8 mg, 82%). $^1$H NMR (CDCl$_3$) δ 0.90-1.05 (m, 1H), 1.01 (d, 3H, J=6.6 Hz), 1.08-1.21 (m, 1H), 1.52-1.64 (m, 1H), 1.70-1.85 (m, 3H), 2.10-2.21 (m, 1H), 2.44-2.58 (m, 1H), 2.50 (s, 6H), 2.70-2.90 (m, 3H), 3.29-3.48 (m, 2H), 3.77-3.87 (m, 1H), 3.89 (s, 2H), 4.14-4.24 (m, 4H), 6.14 (dd, 1H, J=9.2, 2.3 Hz), 6.18 (s, 1H), 6.67 (d, 1H, J=8.7 Hz), 7.00 (t, 1H, J=8.9 Hz), 7.11-7.18 (m, 2H), 8.25 (br s, 1H), 8.86 (s, 1H). $^{13}$C NMR (CDCl$_3$) δ 13.29, 21.81, 29.14, 30.23, 31.01, 39.63, 43.02 (d, J=3.8 Hz), 43.72, 51.83, 57.37, 59.70, 64.08, 64.58, 103.94, 108.39, 116.36 (d, J=23.3 Hz), 117.34, 127.90 (d, J=8.2 Hz), 128.32 (d, J=4.8 Hz), 129.07 (d, J=15.1 Hz), 129.22, 130.50, 136.16, 143.17, 143.70, 157.53, 158.60 (d, J=245 Hz), 162.77, 166.38. ESI-MS m/z 582 (MH)$^+$, 584 (MH+2)$^+$. Anal. Calcd. for C$_{31}$H$_{37}$ClFN$_5$O$_3$.0.3CH$_2$Cl$_2$: C, 61.87; H, 6.24; N, 11.53; Cl, 9.34. Found: C, 61.57; H, 6.16; N, 11.52; Cl, 9.07.

EXAMPLE 216

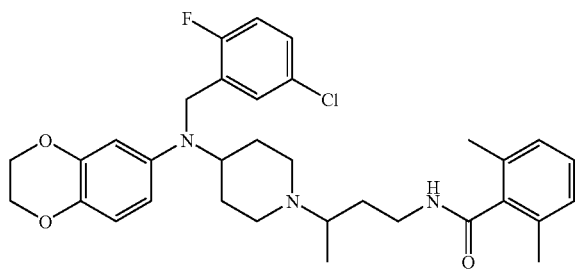

COMPOUND 216: N-(3-{4-[(5-Chloro-2-fluoro-benzyl)-(2,3-dihydro-benzo[1,4]dioxin-6-yl)-amino]-piperidin-1-yl}-butyl)-2,6-dimethyl-benzamide Using general procedure E, [1-(3-amino-1-methyl-propyl)-piperidin-4-yl]-(5-chloro-2-fluoro-benzyl)-(2,3-dihydro-benzo[1,4]dioxin-6-yl)-amine (see EXAMPLE 215) (86 mg, 0.19 mmol) and 2,6-dimethyl-benzoic acid (40 mg, 0.27 mmol) gave COMPOUND 216 as a white foam (94 mg, 84%). $^1$H NMR (CDCl$_3$) δ 0.83-1.14 (m, 2H), 0.98 (d, 3H, J=6.6 Hz), 1.47-1.57 (m, 1H), 1.66-1.81 (m, 3H), 2.06-2.17 (m, 1H), 2.30 (s, 6H), 2.46-2.57 (m, 1H), 2.69-2.90 (m, 3H), 3.22-3.33 (m, 1H), 3.36-3.47 (m, 1H), 3.75 (s, 2H), 3.81-3.93 (m, 1H), 4.12-4.23 (m, 4H), 6.07-6.17 (m, 2H), 6.66 (d, 1H, J=8.7 Hz), 6.87-7.04 (m, 4H), 7.10-7.18 (m, 2H), 8.36 (s, 1H). $^{13}$C NMR (CDCl$_3$) δ 13.25, 18.99, 28.82, 30.02, 30.90, 39.54, 42.59 (d, J=3.8 Hz), 43.57, 52.01, 57.47, 60.23, 64.04, 64.56, 103.36, 107.81, 116.24 (d, J=23.2 Hz), 117.28, 127.13, 127.77 (d, J=8.1 Hz), 128.32 (d, J=5.5 Hz), 128.35, 129.20 (d, J=3.2 Hz), 129.35 (d, J=15.3 Hz), 133.61, 135.82, 138.27, 143.27, 143.66, 158.57 (d, J=245 Hz), 169.89. ESI-MS m/z 580 (MH)$^+$, 582 (MH+2)$^+$. Anal. Calcd. for C$_{33}$H$_{39}$ClFN$_3$O$_3$.0.3H$_2$O.0.2CH$_2$Cl$_2$: C, 66.55; H, 6.72; N, 7.02; Cl, 7.70. Found: C, 66.44; H, 6.60; N, 7.12; Cl, 7.74.

EXAMPLE 217

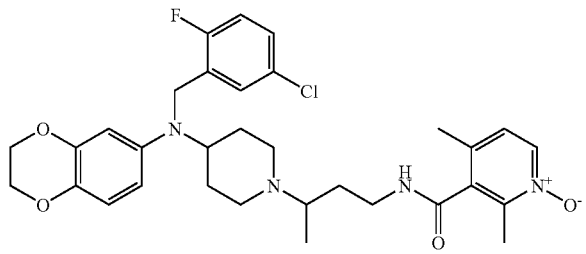

COMPOUND 217: N-(3-{4-[(5-Chloro-2-fluoro-benzyl)-(2,3-dihydro-benzo[1,4]dioxin-6-yl)-amino]-piperidin-1-yl}-butyl)-3,5-dimethyl-1-oxy-isonicotin-amide Using general procedure E, 1-(3-amino-1-methyl-propyl)-piperidin-4-yl]-(5-chloro-2-fluoro-benzyl)-(2,3-dihydro-benzo[1,4]dioxin-6-yl)-amine (see EXAMPLE 215) (86 mg, 0.19 mmol) and 3,5-dimethyl-1-oxy-isonicotinic acid (44 mg, 0.26 mmol) gave COMPOUND 217 as a white foam (85.6 mg, 75%). $^1$H NMR (CDCl$_3$) δ 1.02 (d, 3H, J=6.6 Hz), 1.12-1.38 (m, 2H), 1.54-1.65 (m, 1H), 1.74-1.88 (m, 3H), 2.13-2.24 (m, 1H), 2.30 (s, 3H), 2.35 (s, 3H), 2.47-2.58 (m, 1H), 2.71-2.90 (m, 3H), 3.34-3.54 (m, 2H), 3.64-3.76 (m, 1H), 4.08 (s, 2H), 4.14-4.24 (m, 4H), 6.13-6.22 (m, 2H), 6.69 (d, 1H, J=8.4 Hz), 6.89 (d, 1H, J=6.6 Hz), 6.98 (t, 1H, J=8.9 Hz), 7.11-7.23 (m, 2H), 7.97 (d, 1H, J=6.6 Hz), 8.51 (br s, 1H). $^{13}$C NMR (CDCl$_3$) δ 13.50, 14.87, 18.40, 29.42, 30.03, 32.33, 38.61, 43.62 (d, J=3.9 Hz), 44.60, 51.18, 57.19, 58.11, 64.10, 64.63, 103.38, 107.87, 116.24 (d, J=23.6 Hz), 117.40, 124.76, 127.84 (d, J=8.5 Hz), 128.38 (d, J=4.5 Hz), 129.30 (d, J=2.9 Hz), 129.45 (d, J=15.5 Hz), 134.31, 135.90, 136.86, 137.73, 143.53, 143.75, 145.45, 158.54 (d, J=245 Hz), 165.33. ESI-MS m/z 597 (MH)$^+$, 599 (MH+2)$^+$. Anal. Calcd. for C$_{32}$H$_{38}$ClFN$_4$O$_4$.0.5CH$_2$Cl$_2$.0.3H$_2$O: C, 60.52; H, 6.19; N, 8.69; Cl, 10.99. Found: C, 60.48; H, 6.10; N, 8.70; Cl, 10.90.

EXAMPLE 218

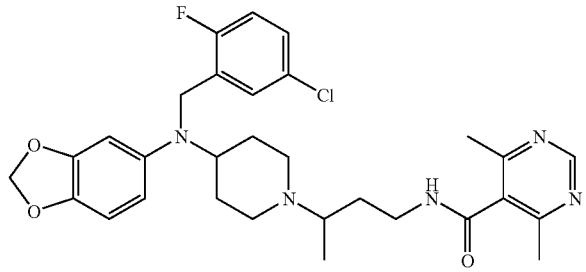

COMPOUND 218: 4,6-Dimethyl-pyrimidine-5-carboxylic acid (3-{4-[benzo[1,3]dioxol-5-yl-(5-chloro-2-fluoro-benzyl)-amino]-piperidin-1-yl}-butyl)-amide Using general procedure H with 4-(benzo[1,3]dioxol-5-ylamino)-piperidine-1-carboxylic acid tert-butyl ester (see EXAMPLE 179) (320 mg, 1.0 mmol) and 2-fluoro-5-chlorobenzyl bromide (291 mg, 1.3 mmol) and then using general procedure C afforded benzo[1,3]dioxol-5-yl-(5-chloro-2-fluoro-benzyl)-piperidin-4-yl-amine as a white solid (323 mg, 89% over 2 steps).

Using general procedure B with the above secondary amine (323 mg, 0.89 mmol) and 2-(3-oxo-butyl)-isoindole-1,3-dione (387 mg, 1.78 mmol) and then using general procedure D afforded [1-(3-amino-1-methyl-propyl)-piperidin-4-yl]-benzo[1,3]dioxol-5-yl-(5-chloro-2-fluoro-benzyl)-amine as a white solid (220 mg, 57% over 2 steps).

Using general procedure E, the above amine (60 mg, 0.14 mmol) and 4,6-dimethyl-pyrimidine-5-carboxylic acid (23 mg, 0.15 mmol) afforded COMPOUND 218 as a white solid (69 mg, 88%). $^1$H NMR (CDCl$_3$) δ 0.89-1.20 (m, 2H), 1.00 (d, 3H, J=6.3 Hz), 1.54-1.61 (m, 1H), 1.71-1.84 (m, 3H), 2.08-2.19 (m, 1H), 2.51 (s, 6H), 2.50-2.58 (m, 1H), 2.70-2.89 (m, 3H), 3.28-3.40 (m, 2H), 3.75-3.87 (m, 1H), 3.88 (s, 2H), 5.86 (s, 2H), 6.08 (d, 1H, J=8.4 Hz), 6.29 (s, 1H), 6.61 (d, 1H, J=8.4 Hz), 6.94-7.03 (m, 1H), 7.10-7.19 (m, 2H), 8.30 (br s, 1H), 8.86 (s, 1H). $^{13}$C NMR (CDCl$_3$) δ 13.77, 22.30, 29.77, 30.81, 31.43, 40.18, 43.91, 44.16, 52.29, 58.88, 60.27, 99.37, 101.19, 108.69, 108.92, 116.87 (d, J=23 Hz), 128.45 (d, J=8 Hz), 129.03 (d, J=4 Hz), 129.16, 129.50 (d, J=21 Hz), 131.02, 141.02, 144.33, 148.71, 158.03, 159.18 (d, J=245 Hz), 163.29, 166.86. ES-MS m/z 568 (M+H). Anal. Calcd. for C$_{30}$H$_{35}$N$_5$ClO$_3$F.0.3CH$_2$Cl$_2$: C, 61.31; H, 6.04; N, 11.80; Cl, 9.56; F, 3.20. Found: C, 61.34; H, 6.04; N, 11.70; Cl, 9.17; F, 3.22.

Scheme 11 describes the preparation of Examples 219-226, using various general procedures previously described, and reagents listed below.

Scheme 11

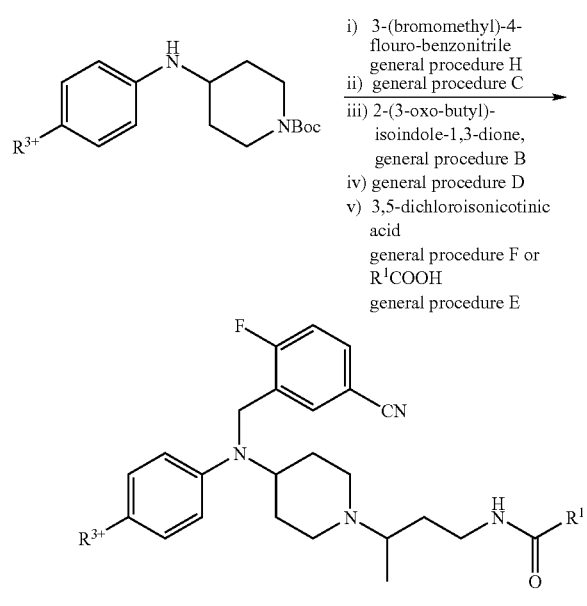

i) 3-(bromomethyl)-4-flouro-benzonitrile
general procedure H
ii) general procedure C
iii) 2-(3-oxo-butyl)-isoindole-1,3-dione,
general procedure B
iv) general procedure D
v) 3,5-dichloroisonicotinic acid
general procedure F or
R$^1$COOH
general procedure E

| Example | R$^3$* | R$^1$COOH |
|---|---|---|
| 219 | CN | 3,5-dichloroisonicotinic acid |
| 220 | Br | 2,4-dimethyl-1-oxy-nicotinic acid |
| 221 | OMe | 4,6-dimethyl-pyrimidine-5-carboxylic acid |
| 222 | OMe | 2,4-dimethyl-1-oxy-nicotinic acid |
| 223 | O(CH$_2$)$_2$OMe | 4,6-dimethyl-pyrimidine-5-carboxylic acid |
| 224 | O(CH$_2$)$_2$OMe | 2,4-dimethyl-1-oxy-nicotinic acid |
| 225 | NHCOMe | 4,6-dimethyl-pyrimidine-5-carboxylic acid |
| 226 | NHCOMe | 2,4-dimethyl-1-oxy-nicotinic acid |

EXAMPLE 219

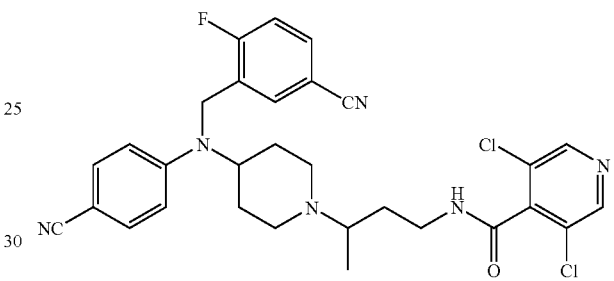

COMPOUND 219: 3,5-Dichloro-N-(3-{4-[(5-cyano-2-fluoro-benzyl)-(4-cyano-phenyl)-amino]-piperidin-1-yl}-butyl)-isonicotinamide A solution of 4-fluoro-3-methyl-benzonitrile (Khanna, Ish K., *J. Med. Chem.*, 40, 11, 1997, 1634-1647) (0.70 g, 5.2 mmol), NBS (1.10 g, 6.2 mmol) and benzoyl peroxide (223 mg, 0.92 mmol) in CCl$_4$ (35 mL) was stirred at reflux under nitrogen for 3 hours. To the reaction was added additional NBS (0.53 g, 2.98 mmol) and 1,1'-azobis(cyclohexanecarbonitrile) (180 mg, 0.74 mmol), and the reaction was heated at reflux for a further 1.5 hours. The reaction mixture was cooled on ice and filtered with suction through a glass frit. The filtrate was dried (Na$_2$SO$_4$), filtered and concentrated under reduced pressure to give a mixture of 3-(bromomethyl)-4-fluoro-benzonitrile and unreacted 1,1'-azobis(cyclohexanecarbonitrile) (660 mg) following purification.

COMPOUND 219 was isolated as a white powder. $^1$H NMR (CDCl$_3$) δ 1.04 (d, 3H, J=6.6 Hz), 1.05-1.18 (m, 1H), 1.21-1.34 (m, 1H), 1.53-1.64 (m, 1H), 1.73-1.86 (m, 3H), 2.18-2.29 (m, 1H), 2.56-2.66 (m, 1H), 2.79-2.99 (m, 3H), 3.33-3.45 (m, 1H), 3.71-3.87 (m, 2H), 4.13 (s, 2H), 6.55 (d, 2H, J=8.7 Hz), 7.22-7.34 (m, 2H), 7.44 (d, 2H, J=8.7 Hz), 7.58-7.65 (m, 1H), 8.15 (br s, 1H), 8.48 (s, 2H). $^{13}$C NMR (CDCl$_3$) δ 13.38, 29.35, 30.25, 31.01, 39.65, 42.28 (d, J=4.8 Hz), 43.55, 51.62, 55.80, 59.62, 99.87, 108.86 (d, J=3.5 Hz), 112.46, 117.04 (d, J=22.3 Hz), 117.93, 119.77, 127.52 (d, J=15.5 Hz), 128.91, 132.02 (d, J=5.6 Hz), 133.40 (d, J=9.3 Hz), 133.84, 142.95, 147.62, 150.57, 161.50, 162.37 (d, J=256 Hz). ESI-MS m/z 579 (MH)$^+$, 581 (MH+2)$^+$. Anal.

Calcd. for C₃₀H₂₉Cl₂FN₆O.0.4CH₂Cl₂.0.2H₂O: C, 59.17; H, 4.93; N, 13.62; Cl, 16.09. Found: C, 59.11; H, 4.92; N, 13.32; Cl, 16.19.

EXAMPLE 220

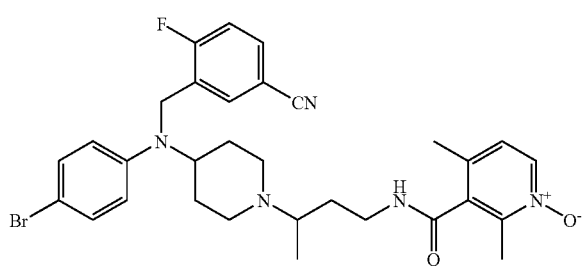

COMPOUND 220: N-(3-{4-[(4-Bromo-phenyl)-(5-cyano-2-fluoro-benzyl)-amino]-piperidin-1-yl}-butyl)-2,4-dimethyl-1-oxy-nicotinamide White solid. ¹H NMR (CDCl₃) δ 1.04 (d, 3H, J=6.0 Hz), 1.24-1.42 (m, 2H), 1.58-1.64 (m, 1H), 1.76-1.80 (m, 3H), 2.19-2.30 (m, 1H), 2.30 (s, 3H), 2.36 (s, 3H), 2.57 (t, 1H, J=12.0 Hz), 2.78-2.90 (m, 3H), 3.40-3.46 (m, 1H), 3.63-3.69 (m, 2H), 4.22 (s, 2H), 6.47 (d, 2H, J=8.2 Hz), 6.91 (d, 1H, J=6.7 Hz), 7.16-7.24 (m, 3H), 7.46 (d, 1H, J=5.9 Hz), 7.50-7.60 (m, 1H), 7.98 (d, 1H, J=6.3 Hz), 8.15 (br s, 1H). ES-MS m/z 608 (M+H).

EXAMPLE 221

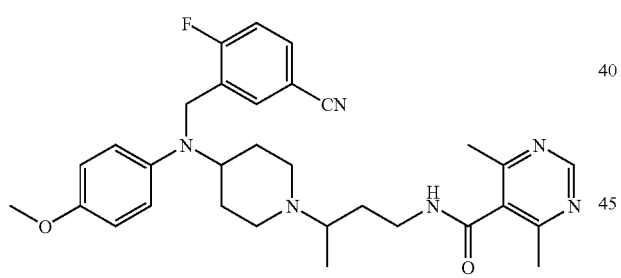

COMPOUND 221: 4,6-Dimethyl-pyrimidine-5-carboxylic acid (3-{4-[(5-cyano-2-fluoro-benzyl)-(4-methoxy-phenyl)-amino]-piperidin-1-yl}-butyl)-amide White solid. ¹H NMR (CDCl₃) δ 0.94-1.16 (m, 2H), 1.01 (d, 3H, J=6.3 Hz), 1.54-1.58 (m, 1H), 1.77-1.81 (m, 3H), 2.14 (t, 1H, J=12.0 Hz), 2.50 (s, 6H), 2.53 (t, 1H, J=12.6 Hz), 2.74-2.84 (m, 3H), 3.29-3.41 (m, 2H), 3.72 (s, 3H), 3.80-3.86 (m, 1H), 3.91 (s, 2H), 6.61 (d, 2H, J=8.1 Hz), 6.74 (d, 2H, J=8.1 Hz), 7.12-7.18 (m, 1H), 7.50-7.56 (m, 2H), 8.36 (br s, 1H), 8.83 (s, 1H). ¹³C NMR (CDCl₃) δ 13.41, 21.95, 29.43, 30.48, 30.94, 39.93, 42.81, 43.72, 51.94, 55.58, 58.81, 60.08, 108.42, 114.67, 116.52 (d, J=23 Hz), 118.21, 118.40, 129.37 (d, J=15 Hz), 130.72, 132.65 (d, J=15 Hz), 133.63 (d, J=6 Hz), 141.49, 153.38, 157.61, 162.76 (d, J=255 Hz), 162.97, 166.41. ES-MS m/z 545 (M+H). Anal. Calcd. for C₃₁H₃₇N₆O₂F.0.5H₂O: C, 67.25; H, 6.92; N, 15.18; F, 3.43. Found: C, 67.32; H, 6.77; N, 15.22; F, 3.47.

EXAMPLE 222

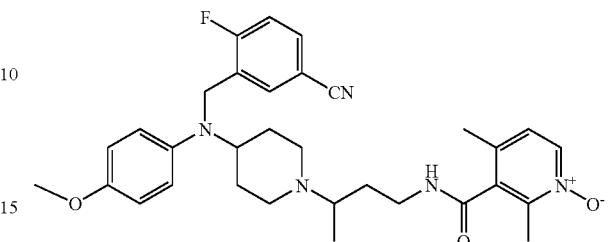

COMPOUND 222: N-(3-{4-[(5-Cyano-2-fluoro-benzyl)-(4-methoxy-phenyl)-amino]-piperidin-1-yl}-butyl)-2,4-dimethyl-1-oxy-nicotinamide White solid. ¹H NMR (CDCl₃) δ 1.02 (d, 3H, J=6.0 Hz), 1.25-1.42 (m, 2H), 1.57-1.64 (m, 1H), 1.80-1.83 (m, 3H), 2.19 (t, 1H, J=11.4 Hz), 2.28 (s, 3H), 2.30 (s, 3H), 2.51 (t, 1H, J=10.2 Hz), 2.76-2.87 (m, 3H), 3.41-3.45 (m, 2H), 3.62-3.68 (m, 1H), 3.73 (s, 3H), 4.18 (s, 2H), 6.64 (d, 2H, J=8.1 Hz), 6.76 (d, 2H, J=7.8 Hz), 6.88 (d, 1H, J=6.3 Hz), 7.09-7.15 (m, 1H), 7.47-7.53 (m, 1H), 7.60 (d, 1H, J=6.3 Hz), 7.91 (d, 1H, J=6.3 Hz), 8.61 (br s, 1H). ¹³C NMR (CDCl₃) δ 13.53, 15.05, 18.47, 29.66, 30.34, 32.07, 39.01, 43.57, 44.41, 51.39, 55.62, 58.61, 108.45, 114.72, 116.41 (d, J=23 Hz), 117.88, 118.41, 124.79, 129.73 (d, J=15 Hz), 132.62 (d, J=9 Hz), 133.66 (d, J=6 Hz), 133.93, 136.82, 137.99, 142.05, 145.61, 153.23, 162.70 (d, J=255 Hz), 165.44. ES-MS m/z 560 (M+H). Anal. Calcd. for C₃₂H₃₈N₅O₃F.1.2H₂O: C, 66.12; H, 7.00; N, 12.05; F, 3.27. Found: C, 66.13; H, 6.74; N, 11.95; F, 3.17.

EXAMPLE 223

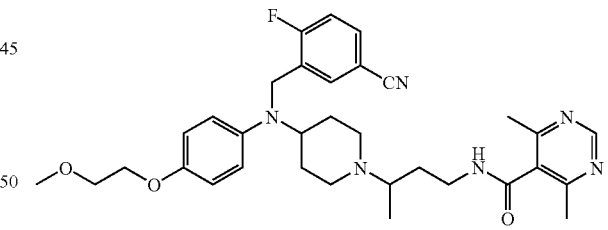

COMPOUND 223: 4,6-Dimethyl-pyrimidine-5-carboxylic acid [3-(4-{(5-cyano-2-fluoro-benzyl)-[4-(2-methoxy-ethoxy)-phenyl]-amino}-piperidin-1-yl)-butyl]-amide Yellow foam. ¹H NMR (CDCl₃) δ 1.02 (d, 2H, J=3.0 Hz), 1.57-1.60 (m, 1H), 1.80 (br d, 2H, J=9.9 Hz), 2.17 (br t, 1H), 2.61 (s, 6H), 2.51-2.55 (m, 2H), 2.72-2.79 (m, 4H), 3.36 (br s, 1H), 3.42 (s, 3H), 3.69 (s, 2H), 3.79 (br s, 1H), 3.93 (s, 2H), 4.02 (s, 2H), 6.59 (d, 2H, J=8.1 Hz), 6.76 (d, 2H, J=7.8 Hz), 7.14 (t, 1H, J=8.7 Hz), 7.52 (br s, 2H), 8.32 (br s, 1H), 8.83 (s, 1H). ¹³C NMR (CDCl₃) δ 13.76, 22.35, 29.69, 30.70, 31.42, 40.13, 43.23, 44.18, 52.29, 58.90, 59.57, 60.35, 68.09, 71.51, 108.80, 116.00, 116.76, 117.07, 118.28, 118.76, 129.62, 131.06, 132.99, 133.12, 133.94, 142.39, 152.88, 157.99, 161.45, 163.35, 164.83, 166.87. ES-MS m/z 589 [M+H]+. Anal. Calcd. for $C_{33}H_{41}N_6O_3F \cdot 0.3H_2O \cdot 0.2CH_2Cl_2$: C, 65.25; H, 6.93; N, 13.75; F, 3.11. Found: C, 65.21; H, 6.93; N, 13.73; F, 2.98.

EXAMPLE 224

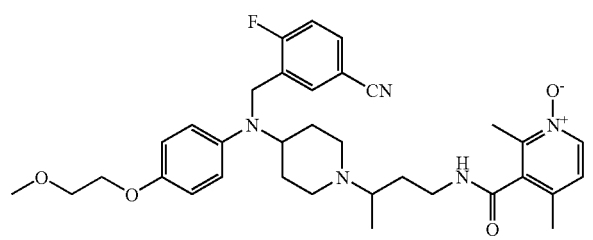

COMPOUND 224: N-[3-(4-{(5-Cyano-2-fluoro-benzyl)-[4-(2-methoxy-ethoxy)-phenyl]-amino}-piperidin-1-yl)-butyl]-2,4-dimethyl-1-oxy-nicotinamide Yellow foam. $^1$H NMR (CDCl$_3$) δ 1.01 (d, 3H, J=6.0 Hz), 1.28-1.42 (m, 3H), 1.59-1.61 (m, 1H), 1.79-1.83 (m, 3H), 2.16-2.19 (m, 1H), 2.26 (s, 3H), 2.29 (s, 3H), 2.50 (t, 1H, J=10.8 Hz), 2.80-2.86 (m, 3H), 3.41-3.45 (m, 4H), 3.59-3.63 (m, 1H), 3.69 (s, 2H), 4.02 (d, 2H, J=3.6 Hz), 4.19 (s, 2H), 6.62 (d, 2H, J=8.4 Hz), 6.77 (d, 2H, J=8.1 Hz), 6.87 (d, 1H, J=6.3 Hz), 7.11 (t, 1H, J=9.0 Hz), 7.49 (br s, 1H), 7.58 (d, 1H, J=6.0 Hz), 7.90 (d, 1H, J=6.3 Hz), 8.61 (br s, 1H). $^{13}$C NMR (CDCl$_3$) δ 13.91, 15.41, 18.86, 29.99, 30.62, 32.56, 36.88, 43.97, 44.89, 51.68, 58.71, 58.85, 59.55, 68.14, 71.52, 116.06, 116.65, 116.95, 117.87, 118.78, 125.22, 130.20, 132.99, 134.99, 134.57, 137.22, 138.34, 142.69, 14597, 152.66, 161.37, 162.90, 164.75, 165.84. ES-MS nz/z 603 [M+H]+. Anal. Calcd. for $C_{34}H_{42}N_5O_4F \cdot 0.4CH_2Cl_2$: C, 64.79; H, 6.76; N, 10.98; F, 2.98. Found: C, 64.54; H, 6.85; N, 10.80; F, 2.95.

EXAMPLE 225

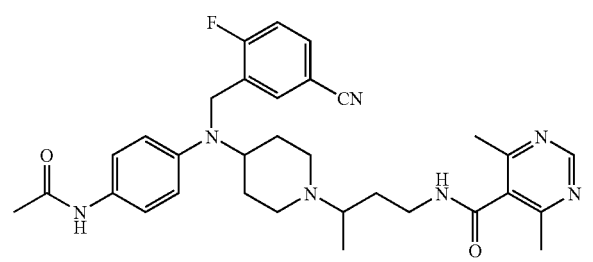

COMPOUND 225: 4,6-Dimethyl-pyrimidine-5-carboxylic acid (3-{4-[(4-acetylamino-phenyl)-(5-cyano-2-fluoro-benzyl)-amino]-piperidin-1-yl}-butyl)-amide White solid. $^1$H NMR (CDCl$_3$) δ 0.93-1.26 (m, 2H), 1.02 (d, 3H, J=6.0 Hz), 1.52-1.61 (m, 1H), 1.72-1.85 (m, 3H), 2.12 (s, 3H), 2.13-2.25 (m, 1H), 2.50 (s, 6H), 2.51-2.62 (m, 1H), 2.73-2.92 (m, 3H), 3.30-3.42 (m, 1H), 3.51-3.64 (m, 1H), 3.75-3.87 (m, 1H), 3.99 (s, 2H), 6.55 (d, 2H, J=8.1 Hz), 7.01 (s, 1H), 7.15-7.29 (m, 3H), 7.44-7.57 (m, 2H), 8.18 (br s, 1H), 8.84 (s, 1H). $^{13}$C NMR (CDCl$_3$) δ 13.47, 21.94, 24.22, 29.37, 30.35, 31.21, 39.64, 42.42, 43.87, 51.82, 57.27, 59.67, 108.48, 114.89, 116.66 (d, J=23 Hz), 118.29, 121.97, 129.17 (d, J=15 Hz), 129.38, 130.67, 132.84 (d, J=9 Hz), 133.05 (d, J=6 Hz), 144.71, 157.56, 162.64 (d, J=256 Hz), 162.99, 166.46, 168.27. ES-MS m/z 572 (M+H). Anal. Calcd. for $C_{32}H_{38}N_7O_2F \cdot 0.4CH_2Cl_2$: C, 64.25; H, 6.46; N, 16.19; F, 3.14. Found: C, 64.48; H, 6.57; N, 16.19; F, 3.10.

EXAMPLE 226

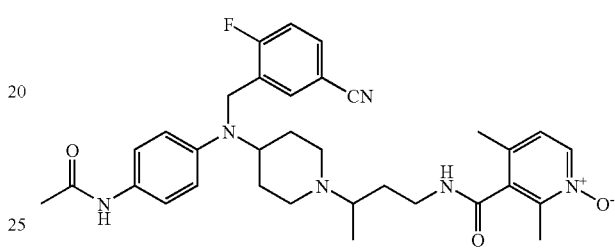

COMPOUND 226: N-(3-{4-[(4-Acetylamino-phenyl)-(5-cyano-2-fluoro-benzyl)-amino]-piperidin-1-yl}-butyl)-2,4-dimethyl-1-oxy-nicotinamide White solid. $^1$H NMR (CDCl$_3$) δ 1.02 (d, 3H, J=6.0 Hz), 1.07-1.36 (m, 2H), 1.54-1.65 (m, 1H), 1.71-1.87 (m, 3H), 2.14 (s, 3H), 2.15-2.24 (m, 1H), 2.30 (s, 3H), 2.38 (s, 3H), 2.47-2.59 (m, 1H), 2.72-2.90 (m, 3H), 3.31-3.56 (m, 2H), 3.67-3.79 (m, 1H), 4.18 (s, 2H), 6.58 (d, 2H, J=8.1 Hz), 6.93 (d, 1H, =6.3 Hz), 7.11-7.20 (m, 1H), 7.22-7.28 (m, 2H), 7.36 (s, 1H), 7.49-7.57 (m, 2H), 8.01 (d, 1H, J=6.6 Hz), 8.18 (br s, 1H). $^{13}$C NMR (CDCl$_3$) δ 13.95, 15.42, 18.86, 24.58, 29.96, 30.57, 32.67, 39.20, 43.69, 44.92, 51.71, 57.69, 58.78, 108.91, 115.53, 116.93 (d, J=23 Hz), 118.71, 122.36, 125.27, 129.76, 129.96, 133.17 (d, J=9 Hz), 133.56 (d, J=6 Hz), 134.79, 137.22, 138.30, 145.17, 145.96, 162.99 (d, J=255 Hz), 165.82, 168.77. ES-MS m/z 587 (M+H). Anal. Calcd. for $C_{33}H_{39}N_6O_3F \cdot 0.9CH_2Cl_2$: C, 61.40; H, 6.20; N, 12.67; F, 2.86. Found: C, 61.17; H, 6.11; N, 12.51; F, 2.81.

EXAMPLE 227

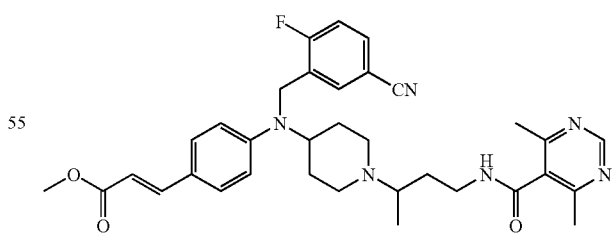

COMPOUND 227: (E)-3-{4-[(5-Cyano-2-fluoro-benzyl)-(1-{3-[(4,6-dimethyl-pyrimidine-5-carbonyl)-amino]-1-methyl-propyl}-piperidin-4-yl)-amino]-phenyl}-acrylic acid methyl ester Using general procedure A, (E)-3-(4-amino-phenyl)-acrylic acid methyl ester (Ono, Shin'ichiro; et al., *Chem.*

*Pharm. Bull.*, 47, 12, 1999, 1694-1712) (1.00 g, 5.64 mmol) and 1-Boc-4-piperidone (1.19 g, 5.93 mmol) gave the crude amine.

Using general procedure G, 4-fluoro-3-hydroxymethyl-benzonitrile (311 mg, 1.98 mmol) gave the crude mesylate as a yellow oil. Using general procedure H, the resulting yellow oil and the above amine (550 mg, 1.53 mmol) gave 4-{(5-cyano-2-fluoro-benzyl)-[4-((E)-2-methoxycarbonyl-vinyl)-phenyl]-amino}-piperidine-1-carboxylic acid tert-butyl ester as a yellow foam (1.56 g, 56% over 2 steps).

Using general procedure C with the above carbamate (320 mg, 0.648 mmol), then general procedure B with the resulting amine and 2-(3-oxo-butyl)-isoindole-1,3-dione (266 mg, 1.22 mmol) and then using general procedure D gave (E)-3-{4-[[1-(3-amino-1-methyl-propyl)-piperidin-4-yl]-(5-cyano-2-fluoro-benzyl)-amino]-phenyl}-acrylic acid methyl ester as a yellow oil (106 mg, 35% over 3 steps).

Using general procedure E, the above amine (51 mg, 0.11 mmol) and 4,6-dimethyl-pyrimidine-5-carboxylic acid (20 mg, 0.13 mmol) gave COMPOUND 227 as a yellow foam (65 mg, 98%) (91:8, trans/cis isomers). $^1$H NMR (CDCl$_3$) δ 0.98-1.30 (m, 2H), 1.04 (d, 3H, J=6.6 Hz), 1.60 (m, 1H), 1.77 (m, 3H), 2.25 (m, 1H), 2.50 (s, 6H), 2.61 (m, 1H), 2.78-2.95 (m, 3H), 3.39 (m, 1H), 3.77 (m, 5H), 4.14 (s, 2H), 6.22 (d, 1H, J=15.9 Hz), 6.54 (d, 2H, J=8.7 Hz), 7.24 (m, 1H), 7.35 (d, 2H, J=8.7 Hz), 7.40 (dd, 1H, J=6.9, 2.1 Hz), 7.58 (m, 2H), 7.89 (m, 1H), 8.87 (s, 1H). ES-MS m/z 599 (M+H).

EXAMPLE 228

COMPOUND 228: 4-{4-[(5-Cyano-2-fluoro-benzyl)-(1-{3-[(4,6-dimethyl-pyrimidine-5-carbonyl)-amino]-1-methyl-propyl}-piperidin-4-yl)-amino]-phenoxy}-benzoic acid Using general procedure H, 4-[4-(4-methoxycarbonyl-phenoxy)-phenylamino]-piperidine-1-carboxylic acid tert-butyl ester (see EXAMPLE 96) (430 mg, 1.04 mmol) and 2-fluoro-5-cyanobenzyl bromide (289 mg, 1.35 mmol) afforded 4-{(5-cyano-2-fluoro-benzyl)-[4-(4-methoxycarbonyl-phenoxy)-phenyl]-amino}-piperidine-1-carboxylic acid tert-butyl ester as a white solid (520 mg, 89%).

Using general procedure C with the above substrate (515 mg, 0.92 mmol), then general procedure B with the resulting amine and 2-(3-oxo-butyl)-isoindole-1,3-dione (398 mg, 1.83 mmol) and then using general procedure D afforded 4-{4-[[1-(3-amino-1-methyl-propyl)-piperidin-4-yl]-(5-cyano-2-fluoro-benzyl)-amino]-phenoxy}-benzoic acid methyl ester as a white solid (230 mg, 48% over 3 steps).

Using general procedure E with the above amine (90 mg, 0.17 mmol) and 4,6-dimethyl-pyrimidine-5-carboxylic acid (29 mg, 0.19 mmol) and then using general procedure K with the resulting ester afforded COMPOUND 228 as a white solid (40 mg, 36% over 2 steps). $^1$H NMR (CDCl$_3$) δ 1.14-1.26 (m, 3H), 1.67-2.19 (m, 4H), 2.40-2.59 (m, 1H), 2.48 (s, 6H), 2.73-2.85 (m, 1H), 3.01-3.17 (m, 3H), 3.32-3.36 (m, 2H), 3.38-3.51 (m, 1H), 3.58-3.75 (m, 2H), 4.20-4.35 (m, 2H), 6.69 (d, 2H, J=8.4 Hz), 6.82-6.92 (m, 4H), 7.10-7.18 (m, 1H), 7.49-7.61 (m, 2H), 7.71 (d, 2H, J=7.8 Hz), 8.41 (br s, 1H), 8.87 (s, 1H). $^{13}$C NMR (CDCl$_3$) δ 12.80, 22.42, 27.60, 28.02, 32.11, 38.06, 44.46, 51.32, 53.84, 56.22, 58.67, 108.95, 116.92, 117.30, 118.65, 121.60, 127.77, 129.38 (d, J=15 Hz), 130.85, 131.82, 133.35, 144.82, 148.94, 157.73, 161.83, 163.01 (d, J=256 Hz), 163.50, 167.60, 171.81. ES-MS m/z

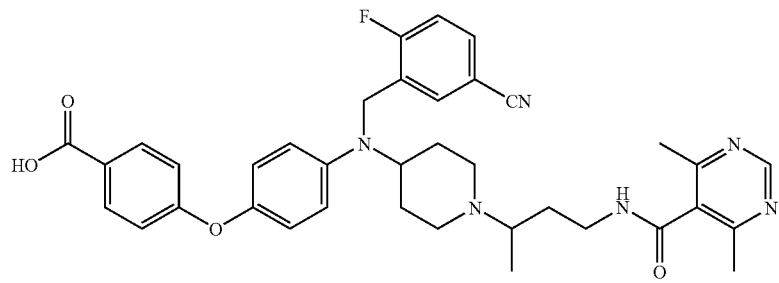

651 (M+H). Anal. Calcd. for $C_{37}H_{39}N_6O_4F \cdot 1.1CH_2Cl_2$: C, 61.49; H, 5.58; N, 11.29; F, 2.55. Found: C, 61.44; H, 5.70; N, 11.14; F, 2.38.

EXAMPLE 229

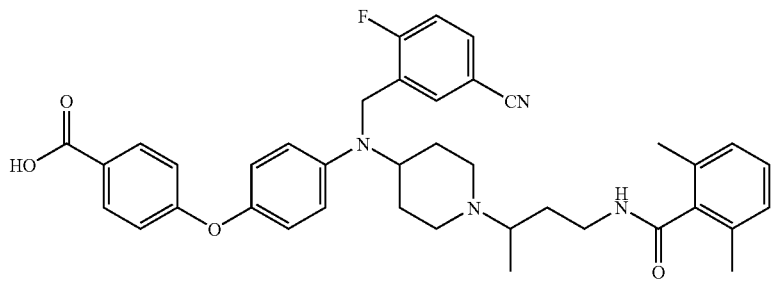

COMPOUND 229: 4-[4-((5-Cyano-2-fluoro-benzyl)-{1-[3-(2,6-dimethyl-benzoylamino)-1-methyl-propyl]-piperidin-4-yl}-amino)-phenoxy]-benzoic acid Using general procedure E with 4-{4-[[1-(3-amino-1-methyl-propyl)-piperidin-4-yl]-(5-cyano-2-fluoro-benzyl)-amino]-phenoxy}-benzoic acid methyl ester (see EXAMPLE 228) (90 mg, 0.17 mmol) and 2,6-dimethylbenzoic acid (29 mg, 0.19 mmol) followed by general procedure K with the resulting ester afforded COMPOUND 229 as a white solid (58 mg, 53% over 2 steps). $^1$H NMR (CDCl$_3$) δ 1.06-1.16 (m, 3H), 1.53-1.69 (m, 1H), 1.78-2.04 (m, 3H), 2.28 (s, 6H), 2.32-2.45 (m, 1H), 2.63-2.75 (m, 1H), 2.92-3.18 (m, 3H), 3.29-3.45 (m, 2H), 3.57-3.82 (m, 3H), 4.11 (s, 2H), 6.58-6.65 (m, 2H), 6.82-7.03 (m, 7H), 7.12-7.21 (m, 1H), 7.50-7.85 (m, 2H), 7.79-8.01 (m, 3H). $^{13}$C NMR (CDCl$_3$) δ 11.81, 18.19, 26.45, 27.05, 30.35, 36.88, 42.30, 43.32, 49.61, 55.06, 57.96, 107.47, 114.99, 115.37, 115.81, 117.29, 120.17, 125.91, 126.28, 127.40, 128.17 (d, J=15 Hz), 130.59, 131.94, 132.92, 136.93, 143.59, 147.04, 160.57, 161.58 (d, J=256 Hz), 169.66, 170.16. ES-MS m/z 649 (M+H). Anal. Calcd. for $C_{39}H_{41}N_4O_4F \cdot 0.9CH_2Cl_2$: C, 66.08; H, 5.95; N, 7.73; F, 2.62. Found: C, 66.11; H, 6.08; N, 7.64; F, 2.48.

EXAMPLE 230

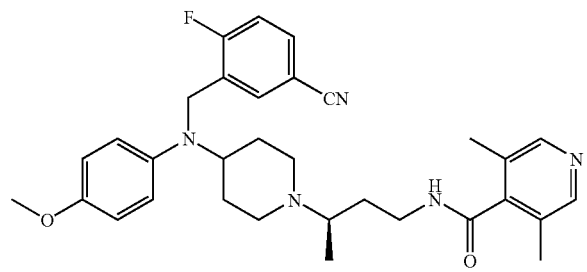

COMPOUND 230: N—((R)-3-{4-[(5-Cyano-2-fluoro-benzyl)-(4-methoxy-phenyl)-amino]-piperidin-1-yl}-butyl)-3,5-dimethyl-isonicotinamide Using general procedure A with p-anisidine (738 mg, 6.00 mmol) and (R)-3-(4-oxo-piperidin-1-yl)-butyronitrile (1.11 g, 6.67 mmol) followed by general procedure J gave [1-((R)-3-amino-1-methyl-propyl)-piperidin-4-yl]-(4-methoxy-phenyl)-amine as an orange oil (1.43 g, 86% over 2 steps).

Using general procedure F, 3,5-dimethylisonicotinic acid (227 mg, 1.5 mmol) and the above amine (275 mg, 1.0 mmol) afforded N-{(R)-3-[4-(4-methoxy-phenylamino)-piperidin-1-yl]-butyl}-3,5-dimethyl-isonicotinamide as a white solid (164 mg, 42%).

Using general procedure G, 4-fluoro-3-hydroxymethyl-benzonitrile (81 mg, 0.54 mmol) gave the crude material that was used in the next reaction without purification. Using general procedure H, the above aniline (169 mg, 0.411 mmol) and the above mesylate (142 mg) afforded COMPOUND 230 as a white solid (20 mg, 9%). $^1$H NMR (CDCl$_3$) δ 0.80-1.23 (m, 5H), 1.50-1.58 (m, 1H), 1.74-1.76 (m, 3H), 2.11-2.17 (m, 1H), 2.29 (s, 6H), 2.50-2.56 (m, 1H), 2.73-2.83 (m, 3H), 3.26-3.43 (m, 2H), 3.72 (s, 3H), 3.75-3.87 (m, 3H), 6.59 (d, 2H, J=7.8 Hz), 6.74 (d, 2H, J=7.8 Hz), 7.13-7.18 (m, 1H), 7.51-7.54 (m, 2H), 8.21-8.25 (m, 3H). $^{13}$C NMR (CDCl$_3$) δ 13.74, 16.33, 29.59, 30.71, 31.56, 39.93, 43.17, 44.08, 52.36, 55.99, 58.81, 60.54, 108.76, 115.09, 116.92 (d, J=23 Hz), 118.05, 118.84, 128.66, 130.03, 133.03 (d, J=9 Hz), 133.95, 142.32, 145.44, 149.00, 153.58, 164.87, 167.68. ES-MS m/z 545 (M+H).

EXAMPLE 231

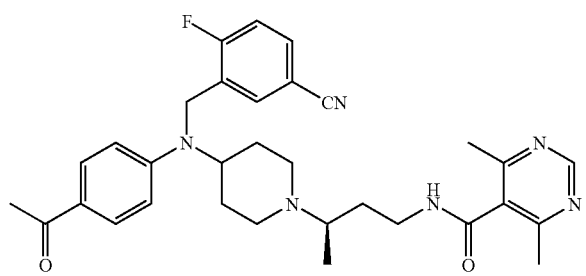

COMPOUND 231: 4,6-Dimethyl-pyrimidine-5-carboxylic acid ((R)-3-{4-[(4-acetyl-phenyl)-(5-cyano-2-fluoro-benzyl)-amino]-piperidin-1-yl}-butyl)-amide Using general procedure A with 4-(2-methyl-[1,3]dioxolan-2-yl)-phenylamine (see EXAMPLE 173) (500 mg, 2.79 mmol) and (R)-3-(4-oxo-piperidin-1-yl)-butyronitrile (487 mg, 2.93 mmol), then general procedure J and then using general procedure E with the resulting amine and 4,6-dimethyl-pyrimidine-5-carboxylic acid (123 mg, 0.81 mmol) afforded 4,6-dimethyl-pyrimidine-5-carboxylic acid ((R)-3-{4-[4-(2-methyl-[1,3]dioxolan-2-yl)-phenylamino]-piperidin-1-yl}-butyl)-amide as a pale beige solid (315 mg, 29% over 3 steps).

Using general procedure G, 4-fluoro-3-hydroxymethyl-benzonitrile (61 mg, 0.39 mmol) gave the crude mesylate. Using general procedure H, 4,6-dimethyl-pyrimidine-5-carboxylic acid ((R)-3-{4-[4-(2-methyl-[1,3]dioxolan-2-yl)-phenylamino]-piperidin-1-yl}-butyl)-amide (150 mg, 0.32 mmol) and the above mesylate (95 mg) afforded a pale yellow solid (73 mg, 38%).

The above substrate (73 mg, 0.12 mmol) in 6N HCl (2.5 mL) was heated at 40° C. for 3 hours to afford COMPOUND 231 as a white solid (41 mg, 23% over 2 steps) after basic work-up and purification. $^1$H NMR (CDCl$_3$) δ 1.05 (d, 3H, J=6.9 Hz), 1.09-1.35 (m, 2H), 1.54-1.64 (m, 1H), 1.72-1.88 (m, 3H), 2.21-2.31 (m, 1H), 2.49 (s, 3H), 2.50 (s, 6H), 2.57-2.67 (m, 1H), 2.76-2.94 (m, 3H), 3.33-3.46 (m, 1H), 3.71-3.88 (m, 2H), 4.21 (s, 2H), 6.55 (d, 2H, J=9.0 Hz), 7.21-7.28 (m, 1H), 7.34-7.38 (m, 1H), 7.56-7.62 (m, 1H), 7.77-7.83 (m, 3H), 8.88 (s, 1H). $^{13}$C NMR (CDCl$_3$) δ 13.51, 21.96, 26.06, 29.45, 30.34, 31.59, 39.35, 42.32, 42.37, 43.87, 51.59, 55.96, 59.29, 108.73 (d, J=3 Hz), 111.73, 116.94 (d, J=23 Hz), 118.06, 127.07, 127.63 (d, J=16 Hz), 130.61, 130.74, 132.29 (d, J=6 Hz), 133.24 (d, J=9 Hz), 151.35, 157.60, 162.46 (d, J=256 Hz), 163.00, 166.49, 196.31. ES-MS m/z 557 (M+H). Anal. Calcd. for $C_{32}H_{37}N_6O_2F \cdot 0.4CH_2Cl_2$: C, 65.89; H, 6.45; N, 14.23; F, 3.22. Found: C, 65.98; H, 6.49; N, 14.15; F, 3.17.

EXAMPLE 232

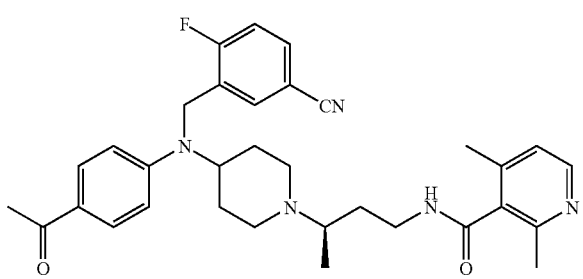

COMPOUND 232: N—((R)-3-{4-[(4-Acetyl-phenyl)-(5-cyano-2-fluoro-benzyl)-amino]-piperidin-1-yl}-butyl)-2,4-dimethyl-nicotinamide Using general procedure E, [1-((R)-3-amino-1-methyl-propyl)-piperidin-4-yl]-[4-(2-methyl-[1,3]dioxolan-2-yl)-phenyl]-amine (see EXAMPLE 231) (94 mg, 0.28 mmol) and 2,4-dimethyl-1-oxy-nicotinic acid (70 mg, 0.42 mmol) afforded 2,4-dimethyl-N-((R)-3-{4-[4-(2-methyl-[1,3]dioxolan-2-yl)-phenylamino]-piperidin-1-yl}-butyl)-1-oxy-nicotinamide as a white solid (98 mg, 73%).

Using general procedure G, 4-fluoro-3-hydroxymethyl-benzonitrile (71 mg, 0.45 mmol) gave the crude mesylate. Using general procedure H, 2,4-dimethyl-N-((R)-3-{4-[4-(2-methyl-[1,3]dioxolan-2-yl)-phenylamino]-piperidin-1-yl}-butyl)-1-oxy-nicotinamide (157 mg, 0.33 mmol) and the above mesylate (97 mg) afforded N—[(R)-3-(4-{(5-cyano-2-fluoro-benzyl)-[4-(2-methyl-[1,3]dioxolan-2-yl)-phenyl]-amino}-piperidin-1-yl)-butyl]-2,4-dimethyl-nicotinamide as a brown oil (60 mg, 30%).

The above substrate (60 mg, 0.10 mmol) in 6N HCl (2 mL) was heated at 40° C. for 3 hours to afford COMPOUND 232 as a white solid (22 mg, 39%) after basic work-up and purification. $^1$H NMR (CDCl$_3$) δ 1.00-1.30 (m, 2H), 1.04 (d, 3H, J=6.6 Hz), 1.52-164 (m, 1H), 1.72-1.84 (m, 3H), 2.19-2.29 (m, 1H), 2.31 (s, 3H), 2.48 (s, 3H), 2.53 (s, 3H), 2.55-2.66 (m, 1H), 2.76-2.95 (m, 3H), 3.30-3.42 (m, 1H), 3.75-3.86 (m, 2H), 4.13 (s, 2H), 6.53 (d, 2H, J=9.0 Hz), 6.92 (d, 1H, J=5.1 Hz), 7.21-7.28 (m, 1H), 7.32-7.37 (m, 1H), 7.56-7.62 (m, 1H), 7.80 (d, 2H, J=9.0 Hz), 7.91 (br s, 1H), 8.27 (d, 1H, J=6.0 Hz). $^{13}$C NMR (CDCl$_3$) δ 13.50, 18.80, 22.28, 26.06, 29.26, 30.33, 31.37, 39.48, 42.30, 43.73, 51.73, 56.01, 59.78, 108.83, 111.75, 116.89 (d, J=23 Hz), 118.05, 122.44, 127.10, 128.18 (d, J=16 Hz), 130.73, 132.37 (d, J=6 Hz), 133.21 (d, J=9 Hz), 133.62, 143.74, 148.90, 151.28, 154.20, 162.43 (d, J=256 Hz), 168.21, 196.27. ES-MS m/z 556 (M+H). Anal. Calcd. for C$_{33}$H$_{38}$N$_5$O$_2$F.0.3CH$_2$Cl$_2$: C, 68.82; H, 6.69; N, 12.05; F, 3.27. Found: C, 68.54; H, 6.67; N, 11.71; F, 3.25.

EXAMPLE 233

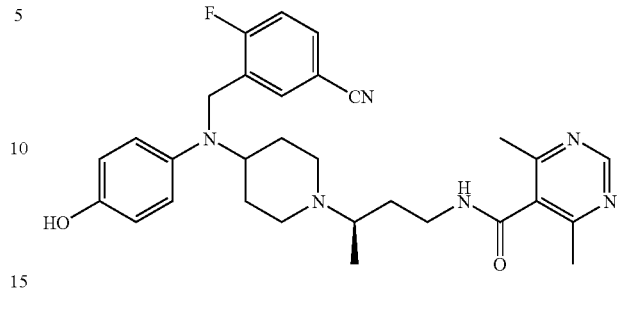

COMPOUND 233: 4,6-Dimethyl-pyrimidine-5-carboxylic acid ((R)-3-{4-[(5-cyano-2-fluoro-benzyl)-(4-hydroxy-phenyl)-amino]-piperidin-1-yl}-butyl)-amide Using general procedure A with 4-(tert-butyl-dimethyl-silanyloxy)-phenylamine (Swenton, John S.; et al., *J. Org. Chem.*, 54, 1, 1989, 51-58) (1.28 g, 5.73 mmol) and (R)-3-(4-oxo-piperidin-1-yl)-butyronitrile (1.05 g, 6.32 mmol) followed by general procedure J gave [1-((R)-3-amino-1-methyl-propyl)-piperidin-4-yl]-[4-(tert-butyl-dimethyl-silanyloxy)-phenyl]-amine as a yellow oil (1.81 g, 84% over 2 steps).

To a solution of the above amine (1.81 g, 4.79 mmol) in THF cooled to 0° C. was added a solution of Boc$_2$O (1.15 g, 5.27 mmol) in THF (20 mL). The solution was warmed to room temperature and stirred for 14 hours then concentrated to give ((R)-3-{4-[4-(tert-butyl-dimethyl-silanyloxy)-phenylamino]-piperidin-1-yl}-butyl)-carbamic acid tert-butyl ester as a yellow oil (2.26 g, 99%) after purification.

Using general procedure G, 4-fluoro-3-hydroxymethyl-benzonitrile (883 mg, 5.84 mmol) gave the crude mesylate as a yellow oil. Using general procedure H, the resulting yellow oil and the above amine (1.86 g, 3.89 mmol) gave ((R)-3-{4-[[4-(tert-butyl-dimethyl-silanyloxy)-phenyl]-(5-cyano-2-fluoro-benzyl)-amino]-piperidin-1-yl}-butyl)-carbamic acid tert-butyl ester as a yellow foam (1.56 g, 66%).

Using general procedure C with the carbamate from above (1.56 g, 2.55 mmol) then using general procedure E with the resulting amine (500 mg, 0.979 mmol) and 4,6-dimethyl-pyrimidine-5-carboxylic acid (179 mg, 1.18 mmol) gave 4,6-dimethyl-pyrimidine-5-carboxylic acid ((R)-3-{4-[[4-(tert-butyl-dimethyl-silanyloxy)-phenyl]-(5-cyano-2-fluoro-benzyl)-amino]-piperidin-1-yl}-butyl)-amide as a yellow foam (553 mg, 88% over 2 steps).

To a solution of the above substrate (553 mg, 0.857 mmol) in THF (8 mL) cooled to 0° C. was added TBAF (1.0M in THF, 0.90 mL, 0.90 mmol) and the solution was stirred at 0° C. for 15 minutes. TBAF (1.0M in THF, 0.20 mL, 0.20 mmol) was added and the solution stirred at 0° C. for 5 minutes. Aqueous work-up and purification gave COMPOUND 233 as a yellow foam (393 mg, 86%). $^1$H NMR (CDCl$_3$) δ 0.88-1.16 (m, 2H), 1.00 (d, 3H, J=6.6 Hz), 1.53-1.81 (m, 5H), 2.13 (m, 1H), 2.50 (s, 6H), 2.53 (m, 1H), 2.67-2.87 (m, 3H), 3.22-3.37 (m, 2H), 3.88 (m, 1H), 3.92 (s, 2H), 5.72 (br s, 1H), 6.57 (d, 2H, J=9.0 Hz), 6.66 (d, 2H, J=9.0 Hz), 7.13 (m, 1H), 7.50 (m, 1H), 7.56 (m, 2H), 8.37 (m, 1H), 8.86 (s, 1H). ES-MS m/z 531 (M+H).

EXAMPLE 234

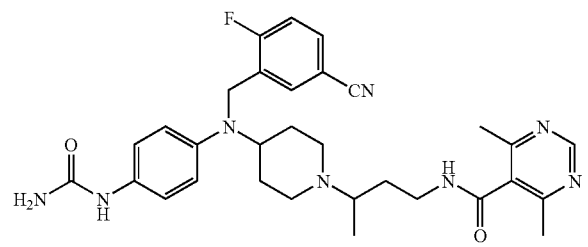

COMPOUND 234: 4,6-Dimethyl-pyrimidine-5-carboxylic acid (3-{4-[(5-cyano-2-fluoro-benzyl)-(4-ureido-phenyl)-amino]-piperidin-1-yl}-butyl)-amide COMPOUND 225 (78 mg, 0.14 mmol), MeOH (1.5 mL) and 6N HCl (0.5 mL) were stirred at room temperature for 18 hours to afford a white solid after basic work-up and purification.

To the aniline (43 mg, 0.08 mmol) in AcOH (0.25 mL) and H$_2$O (0.5 mL) was added NaOCN (11 mg, 0.16 mmol) in H$_2$O (0.5 mL) and the mixture was stirred at room temperature overnight to afford COMPOUND 234 as a white solid (24 mg, 31% over 2 steps) after work-up and purification. $^1$H NMR (CDCl$_3$) δ 0.94-1.26 (m, 2H), 1.03 (d, 3H, J=6.6 Hz), 1.53-1.64 (m, 1H), 1.72-1.86 (m, 3H), 2.15-2.26 (m, 1H), 2.50 (s, 6H), 2.52-2.63 (m, 1H), 2.74-2.93 (m, 3H), 3.30-3.42 (m, 1H), 3.54-3.66 (m, 1H), 3.75-3.86 (m, 1H), 4.04 (s, 2H), 4.61 (s, 2H), 6.26 (s, 1H), 6.55 (d, 2H, J=9.0 Hz), 7.08 (d, 2H, J=8.7 Hz), 7.17-7.24 (m, 1H), 7.43-7.48 (m, 1H), 7.53-7.59 (m, 1H), 8.10 (br s, 1H), 8.85 (s, 1H). $^{13}$C NMR (CDCl$_3$) δ 13.45, 21.94, 29.35, 30.34, 31.26, 39.60, 42.65, 43.87, 51.78, 57.13, 59.62, 108.54, 115.23, 116.74 (d, J=23 Hz), 118.32, 124.92, 128.90, 128.10, 130.66, 132.86, 132.98, 145.33, 157.56, 157.71, 162.63 (d, J=256 Hz), 163.01, 166.48. ES-MS m/z 573 (M+H). Anal. Calcd. for C$_{31}$H$_{37}$FN$_8$O$_2$.0.4CH$_2$Cl$_2$.0.1H$_2$O: C, 61.98; H, 6.29; N, 18.42. Found: C, 62.25; H, 6.42; N, 18.28.

EXAMPLE 235

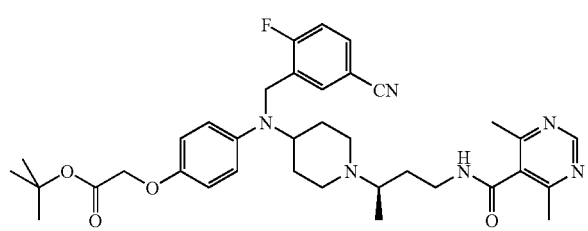

COMPOUND 235: {4-[(5-Cyano-2-fluoro-benzyl)-(1-{(R)-3-[(4,6-dimethyl-pyrimidine-5-carbonyl)-amino]-1-methyl-propyl}-piperidin-4-yl)-amino]-phenoxy}-acetic acid tert-butyl ester A mixture of COMPOUND 233 (100 mg, 0.188 mmol), t-butyl bromoacetate (37 mg, 0.19 mmol) and K$_2$CO$_3$ (39 mg, 0.28 mmol) in DMF (1.9 mL) were heated at 80° C. for 18 h to give COMPOUND 235 as a yellow foam (88 mg, 72%) following work-up and purification. $^1$H NMR (CDCl$_3$) δ 0.92-1.03 (m, 1H), 1.01 (d, 3H, J=6.6 Hz), 1.08-1.20 (m, 1H), 1.46 (s, 9H), 1.52-1.63 (m, 1H), 1.76 (m, 3H), 2.16 (m, 1H), 2.50 (s, 6H), 2.54 (m, 1H), 2.68-2.95 (m, 3H), 3.31-3.46 (m, 2H), 3.82 (m, 1H), 3.92 (s, 2H), 4.41 (s, 2H), 6.58 (m, 2H), 6.73 (m, 2H), 7.16 (m, 1H), 7.51 (m, 2H), 8.30 (m, 1H), 8.83 (s, 1H). ES-MS m/z 645 (M+H).

EXAMPLE 236

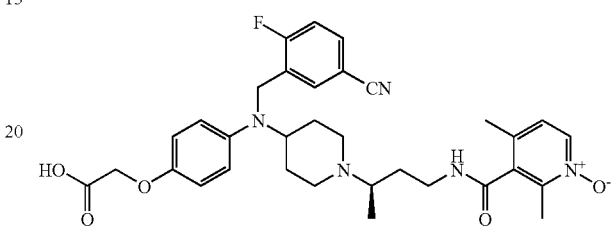

COMPOUND 236: {4-[(5-Cyano-2-fluoro-benzyl)-(1-{(R)-3-[(2,4-dimethyl-1-oxy-pyridine-3-carbonyl)-amino]-1-methyl-propyl}-piperidin-4-yl)-amino]-phenoxy}-acetic acid Using general procedure E, 3-({[1-((R)-3-amino-1-methyl-propyl)-piperidin-4-yl]-[4-(tert-butyl-dimethyl-silanyloxy)-phenyl]-amino}-methyl)-4-fluoro-benzonitrile (see EXAMPLE 233) (400 mg, 0.783 mmol) and 2,4-dimethyl-1-oxy-nicotinic acid (157 mg, 0.939 mmol) gave N—((R)-3-{4-[[4-(tert-butyl-dimethyl-silanyloxy)-phenyl]-(5-cyano-2-fluoro-benzyl)-amino]-piperidin-1-yl}-butyl)-2,4-dimethyl-1-oxy-nicotinamide as a yellow foam (240 mg, 46%).

To a solution of the above substrate (240 mg, 0.364 mmol) in THF (4 mL) cooled to 0° C. was added TBAF (1.0M in THF, 0.40 mL, 0.40 mmol) and the solution was stirred at 0° C. for 20 minutes. Aqueous work-up and purification gave a yellow foam (181 mg).

A mixture of the above alcohol (181 mg), methyl bromoacetate (56 mg, 0.37 mmol) and K$_2$CO$_3$ (92 mg, 0.67 mmol) in DMF (3.3 mL) were heated at 80° C. for 13 h to give {4-[(5-cyano-2-fluoro-benzyl)-(1-{(R)-3-[(2,4-dimethyl-1-oxy-pyridine-3-carbonyl)-amino]-1-methyl-propyl}-piperidin-4-yl)-amino]-phenoxy}-acetic acid methyl ester as a yellow foam (70 mg, 31% over 2 steps) following work-up and purification.

Using general procedure K, the above substrate (44 mg, 0.071 mmol) gave COMPOUND 236 as a colourless solid (20 mg, 47%). $^1$H NMR (CD$_3$OD) δ 1.43 (d, 3H, J=6.3 Hz), 1.61 (m, 3H), 2.19 (m, 3H), 2.35 (s, 3H), 2.47 (s, 3H), 3.28 (m, 2H), 3.55 (m, 5H), 4.44 (s, 2H), 4.52 (s, 2H), 6.84 (d, 2H, J=9.0 Hz), 6.93 (d, 2H, J=8.7 Hz), 7.25 (m, 1H), 7.33 (d, 1H, J=6.6 Hz), 7.61-7.69 (m, 2H), 8.28 (d, 1H, J=6.6 Hz). $^1$H NMR (CDCl$_3$+CD$_3$OD) δ 12.86, 15.36, 18.89, 26.41, 29.97, 31.49, 36.47, 46.60, 59.99, 66.29, 108.44, 116.09, 116.90, 117.21, 119.05, 125.55, 133.67, 136.28, 136.93, 138.99, 142.31, 166.87. ES-MS m/z 604 (M+H).

EXAMPLE 237

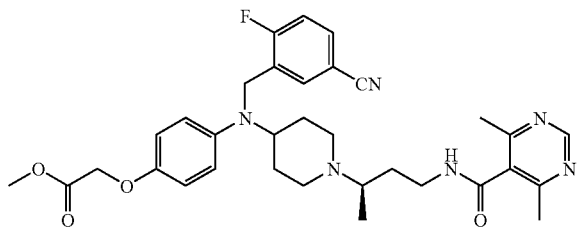

COMPOUND 237: {4-[(5-Cyano-2-fluoro-benzyl)-(1-{(R)-3-[(4,6-dimethyl-pyrimidine-5-carbonyl)-amino]-1-methyl-propyl}-piperidin-4-yl)-amino]-phenoxy}-acetic acid methyl ester A mixture of COMPOUND 233 (91 mg, 0.17 mmol), methyl bromoacetate (29 mg, 0.19 mmol) and $K_2CO_3$ (47 mg, 0.34 mmol) in DMF (1.7 mL) were heated at 80° C. for 25 h to give COMPOUND 237 as a yellow foam (90 mg, 87%) after work-up and purification. $^1$H NMR (CDCl$_3$) δ 0.93-1.25 (m, 2H), 1.01 (d, 3H, J=6.9 Hz), 1.58 (m, 1H), 1.76 (m, 3H), 2.16 (m, 1H), 2.50 (s, 6H), 2.55 (m, 1H), 2.68-2.88 (m, 3H), 3.31-3.53 (m, 2H), 3.78 (s, 3H), 3.82 (m, 1H), 3.93 (s, 2H), 4.54 (s, 2H), 6.57 (m, 2H), 6.76 (m, 2H), 7.17 (m, 1H), 7.52 (m, 2H), 8.28 (m, 1H), 8.83 (s, 1H). ES-MS m/z 603 (M+H).

EXAMPLE 238

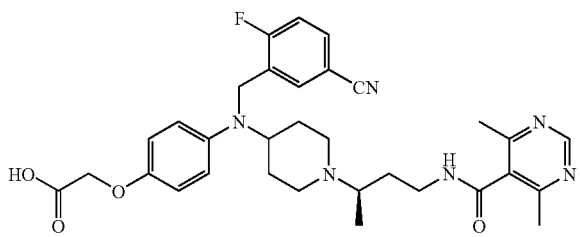

COMPOUND 238: {4-[(5-Cyano-2-fluoro-benzyl)-(1-{(R)-3-[(4,6-dimethyl-pyrimidine-5-carbonyl)-amino]-1-methyl-propyl}-piperidin-4-yl)-amino]-phenoxy}-acetic acid Using general procedure K, COMPOUND 237 (83 mg, 0.14 mmol) gave COMPOUND 238 as a yellow foam (73 mg, 90%). $^1$H NMR (CD$_3$OD) δ 1.41 (d, 3H, J=6.6 Hz), 1.83-2.05 (m, 5H), 2.23 (m, 1H), 2.48 (s, 6H), 3.10-3.24 (m, 2H), 3.35-3.59 (m, 5H), 3.75 (m, 1H), 4.30 (s, 2H), 4.33 (s, 2H), 6.82 (m, 4H), 7.24 (m, 1H), 7.62 (m, 2H), 8.88 (s, 1H). $^1$H NMR (CDCl$_3$+CD$_3$OD) δ 11.91, 22.05, 24.72, 26.46, 29.71, 31.55, 39.07, 36.18, 44.66, 58.40, 66.77, 108.44, 115.26, 116.67, 116.97, 118.23, 130.24, 113.04, 141.15, 157.31, 163.18, 167.48, 167.57, 174.77. ES-MS m/z 589 (M+H). Anal. Calcd. for $C_{32}H_{37}N_6FO_4 \cdot 2.5CH_4O$: C, 61.96; H, 7.08; N, 12.57; F, 2.84. Found: C, 62.21; H, 6.84; N, 12.23; F, 2.58.

EXAMPLE 239

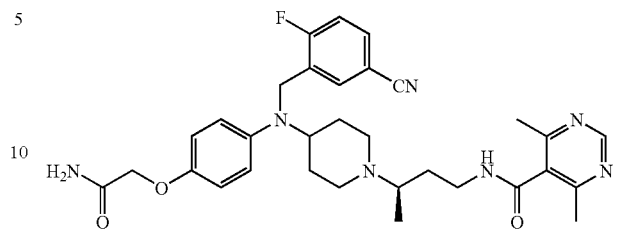

COMPOUND 239: 4,6-Dimethyl-pyrimidine-5-carboxylic acid ((R)-3-{4-[(4-carbamoylmethoxy-phenyl)-(5-cyano-2-fluoro-benzyl)-amino]-piperidin-1-yl}-butyl)-amide COMPOUND 237 (74 mg, 0.12 mmol) was dissolved in MeOH (15 mL) and NH$_3$(g) was passed through the solution for 10 minutes. The mixture was stirred at room temperature for 1 h then concentrated to give COMPOUND 239 as a yellow foam (72 mg, 100%). $^1$H NMR (CDCl$_3$) δ 0.92-1.25 (m, 2H), 1.02 (d, 3H, J=6.6 Hz), 1.59 (m, 1H), 1.71-1.82 (m, 3H), 2.17 (m, 1H), 2.50 (s, 6H), 2.55 (m, 1H), 2.75-2.90 (m, 3H), 3.31-3.46 (m, 2H), 3.83 (m, 1H), 3.97 (s, 2H), 4.41 (s, 2H), 5.60 (br s, 1H), 6.60 (d, 2H, J=9.0 Hz), 6.76 (d, 2H, J=9.0 Hz), 7.17 (m, 1H), 7.52 (m, 2H), 8.23 (m, 1H), 8.84 (s, 1H). $^{13}$C NMR (CDCl$_3$) δ 13.42, 21.92, 29.40, 30.42, 31.08, 39.81, 42.94, 43.79, 51.92, 58.25, 59.94, 67.83, 108.52, 115.69, 116.49, 116.80, 117.52, 118.34, 129.01, 129.21, 130.68, 132.73, 132.86, 133.32, 133.39, 142.87, 150.71, 157.58, 161.04, 162.97, 164.43, 166.40, 171.31. ES-MS m/z 588 (M+H). Anal. Calcd. for $C_{32}H_{38}N_7FO_3 \cdot 1.2CH_4O$: C, 63.69; H, 6.89; N, 15.66; F, 3.03. Found: C, 63.77; H, 6.68; N, 15.53; F, 2.87.

EXAMPLE 240

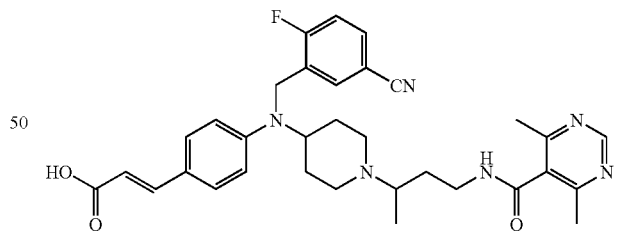

COMPOUND 240: (E)-3-{4-[(5-Cyano-2-fluoro-benzyl)-(1-{3-[(4,6-dimethyl-pyrimidine-5-carbonyl)-amino]-1-methyl-propyl}-piperidin-4-yl)-amino]-phenyl}-acrylic acid Using general procedure K, COMPOUND 227 (54 mg, 0.090 mmol) gave COMPOUND 240 as a yellow foam (52 mg, 98%) (78:18, trans/cis isomers). $^1$H NMR (CD$_3$OD) δ 1.48 (d, 3H, J=6.6 Hz), 1.95 (m, 1H), 2.16 (m, 5H), 2.50 (s, 6H), 3.35-3.62 (m, 7H), 4.44 (m, 1H), 4.65 (s, 2H), 6.26 (d, 1H, J=15.6 Hz), 6.85 (d, 2H, J=9.0 Hz), 7.35 (m, 1H), 7.48 (m, 3H), 7.57 (d, 1H, J=15.9 Hz), 7.70 (m, 1H), 8.90 (s, 1H). $^{13}$C NMR (CDCl$_3$+CD$_3$OD) δ 12.83, 22.23, 26.13, 26.35, 30.02, 31.83, 36.37, 43.25, 46.20, 51.07, 53.35, 53.82, 60.07, 108.81, 113.63, 114.56, 117.27, 117.57, 118.50, 125.02, 128.59, 128.79, 129.78, 130.48, 132.47, 133.07, 133.62, 145.46, 149.57, 157.54, 161.26, 163.62, 168.02, 170.09. ES-MS m/z 585 (M+H). Anal. Calcd. for C$_{33}$H$_{37}$N$_6$FO$_3$.0.4C$_6$H$_{14}$.1.5CH$_2$Cl$_2$: C, 59.37; H, 6.16; N, 11.26; F, 2.54. Found: C, 59.47; H, 6.52; N, 11.48; F, 2.35.

EXAMPLE 241

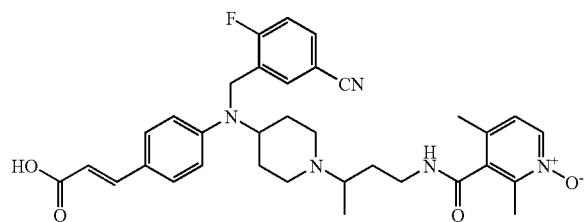

COMPOUND 241: (E)-3-{4-[(5-Cyano-2-fluoro-benzyl)-(1-{3-[(2,4-dimethyl-1-oxy-pyridine-3-carbonyl)-amino]-1-methyl-propyl}-piperidin-4-yl)-amino]-phenyl}-acrylic acid Using general procedure E with (E)-3-{4-[[1-(3-amino-1-methyl-propyl)-piperidin-4-yl]-(5-cyano-2-fluoro-benzyl)-amino]-phenyl}-acrylic acid methyl ester (see EXAMPLE 227) (55 mg, 0.12 mmol) and 2,4-dimethyl-1-oxy-nicotinic acid (24 mg, 0.14 mmol) followed by general procedure K with the resulting ester gave COMPOUND 241 as a yellow foam (56 mg, 90% over 2 steps) (86:11, trans/cis isomers). $^1$H NMR (CD$_3$OD) δ 1.48 (d, 3H, J=6.3 Hz), 1.95 (m, 1H), 2.23 (m, 5H), 2.36 (s, 3H), 2.48 (s, 3H), 3.35-3.62 (m, 7H), 4.45 (m, 1H), 4.66 (s, 2H), 6.26 (d, 1H, J=15.9 Hz), 6.85 (d, 2H, J=8.7 Hz), 7.32 (m, 2H), 7.54 (m, 3H), 7.57 (d, 1H, J=15.9 Hz), 7.71 (m, 1H), 8.28 (d, 1H, J=6.6 Hz). $^1$H NMR (CDCl$_3$+CD$_3$OD) δ 12.05, 14.24, 17.70, 25.05, 28.70, 29.80, 35.18, 41.91, 45.90, 51.84, 52.51, 58.89, 107.40, 112.31, 113.17, 117.16, 123.60, 124.39, 127.37, 129.14, 131.20, 132.28, 135.05, 136.79, 137.84, 144.19, 145.37, 148.31, 165.47, 168.87. ES-MS m/z 600 (M+H). Anal. Calcd. for C$_{34}$H$_{38}$N$_5$FO$_4$.5.0CH$_4$O.4.2H$_2$O.2.7CH$_2$Cl$_2$: C, 47.03; H, 6.80; N, 6.58; F, 1.78. Found: C, 47.15; H, 6.74; N, 6.77; F, 1.39.

EXAMPLE 242

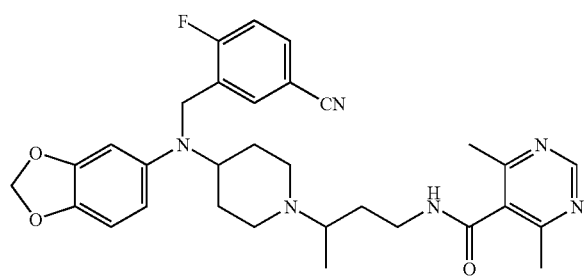

COMPOUND 242: 4,6-Dimethyl-pyrimidine-5-carboxylic acid (3-{4-[benzo[1,3]dioxol-5-yl-(5-cyano-2-fluoro-benzyl)-amino]-piperidin-1-yl}-butyl)-amide Using general procedure H, 4-(benzo[1,3]dioxol-5-ylamino)-piperidine-1-carboxylic acid tert-butyl ester (see EXAMPLE 179) (320 mg, 1.0 mmol) and 2-fluoro-5-cyanobenzyl bromide (278 mg, 1.3 mmol) afforded a white syrup (449 mg).

Using general procedure C with the above substrate (449 mg), then general procedure B with the resulting amine and 2-(3-oxo-butyl)-isoindole-1,3-dione (343 mg, 1.58 mmol) and then using general procedure D afforded 3-({[1-(3-amino-1-methyl-propyl)-piperidin-4-yl]-benzo[1,3]dioxol-5-yl-amino}-methyl)-4-fluoro-benzonitrile as a white solid (162 mg, 38% over 4 steps).

Using general procedure E, the above primary amine (40 mg, 0.09 mmol) and 4,6-dimethyl-pyrimidine-5-carboxylic acid (15.8 mg, 0.10 mmol) afforded COMPOUND 242 as a white solid (46 mg, 87%). $^1$H NMR (CDCl$_3$) δ 0.89-1.23 (m, 2H), 1.01 (d, J=6.3 Hz), 1.51-1.61 (m, 1H), 1.69-1.85 (m, 3H), 2.09-2.20 (m, 1H), 2.51 (s, 6H), 2.50-2.59 (m, 1H), 2.70-2.91 (m, 3H), 3.28-3.41 (m, 2H), 2.76-3.88 (m, 1H), 3.91 (s, 2H), 5.87 (s, 2H), 6.07 (d, 1H, J=8.4 Hz), 6.29 (s, 1H), 6.61 (d, 1H, J=8.7 Hz), 7.11-7.20 (m, 1H), 7.48-7.56 (m, 2H), 8.30 (br s, 1H), 8.84 (s, 1H). $^{13}$C NMR (CDCl$_3$) δ 13.80, 22.30, 29.84, 30.82, 31.44, 40.13, 43.45, 44.16, 52.19, 59.36, 60.21, 99.74, 101.30, 108.73, 109.40, 116.95 (d, J=23 Hz), 118.75, 129.54 (d, J=15 Hz), 131.06, 133.10 (d, J=9 Hz), 133.87 (d, J=6 Hz), 141.46, 143.82, 148.82, 157.94, 163.11 (d, J=256 Hz), 163.32, 166.80. ES-MS m/z 559 (M+H). Anal. Calcd. for C$_{31}$H$_{35}$N$_6$O$_3$F.0.1CH$_2$Cl$_2$: C, 65.86; H, 6.26; N, 14.82; F, 3.35. Found: C, 65.57; H, 6.30; N, 14.45; F, 3.32.

EXAMPLE 243

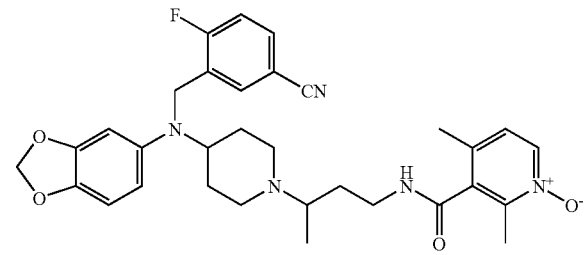

COMPOUND 243: N-(3-{4-[Benzo[1,3]dioxol-5-yl-(5-cyano-2-fluoro-benzyl)-amino]-piperidin-1-yl}-butyl)-2,4-dimethyl-1-oxy-nicotinamide Using general procedure E, 3-({[1-(3-amino-1-methyl-propyl)-piperidin-4-yl]-benzo[1,3]dioxol-5-yl-amino}-methyl)-4-fluoro-benzonitrile (see EXAMPLE 242) (40 mg, 0.09 mmol) and 2,4-dimethyl-1-oxy-nicotinic acid (17.4 mg, 0.10 mmol) afforded COMPOUND 243 as a white solid (40 mg, 74%). $^1$H NMR (CDCl$_3$) δ 1.01 (d, 3H, J=6.0 Hz), 1.11-1.39 (m, 2H), 1.53-1.66 (m, 1H), 1.74-1.87 (m, 3H), 2.12-2.23 (m, 1H), 2.31 (s, 3H), 2.37 (s, 3H), 2.46-2.57 (m, 1H), 3.72-3.90 (m, 3H), 3.33-3.46 (m, 2H), 3.63-3.76 (m, 1H), 4.11 (s, 2H), 5.87 (s, 2H), 6.09 (d, 1H, J=8.7 Hz), 6.31 (s, 1H), 6.62 (d, 1H, J=8.1 Hz), 6.91 (d, 1H, J=6.0 Hz), 7.09-7.18 (m, 1H), 7.48-7.59 (m, 2H), 7.98 (d, 1H, J=6.3 Hz), 8.38 (br s, 1H). $^{13}$C NMR (CDCl$_3$) δ 13.95, 15.38, 18.87, 30.07, 30.65, 32.78, 39.11, 44.10, 44.97, 51.59, 58.60, 59.09, 99.20, 101.26, 108.74, 108.83, 116.84 (d, J=23 Hz), 118.78, 125.23, 129.92 (d, J=15 Hz), 133.07 (d, J=9 Hz), 133.88 (d, J=6 Hz), 134.79, 137.31, 138.22, 141.15, 144.18, 145.95, 148.86, 163.05 (d, J=255 Hz), 165.80. ES-MS m/z 574 (M+H). Anal. Calcd. for C$_{32}$H$_{36}$N$_5$O$_4$F.0.8CH$_2$Cl$_2$: C, 61.40; H, 5.91; N, 10.92; F, 2.96. Found: C, 61.67; H, 6.04; N, 10.72; F, 2.70.

EXAMPLE 244

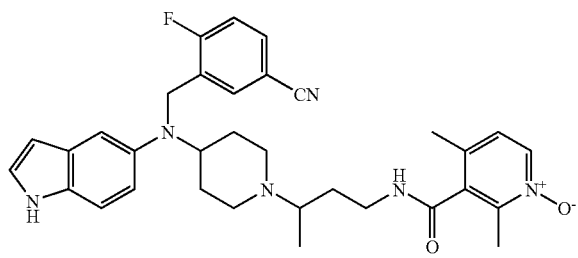

COMPOUND 244: N-(3-{4-[(5-Cyano-2-fluoro-benzyl)-(1H-indol-5-yl)-amino]-piperidin-1-yl}-butyl)-2,4-dimethyl-1-oxy-nicotinamide Using general procedure G, 4-fluoro-3-hydroxymethyl-benzonitrile (302 mg, 2.0 mmol) gave the crude mesylate. Using general procedure H, 4-(1H-indol-5-ylamino)-piperidine-1-carboxylic acid tert-butyl ester (see EXAMPLE 177) (486 mg, 1.54 mmol) and the above mesylate (448 mg) afforded 4-[(5-cyano-2-fluoro-benzyl)-(1H-indol-5-yl)-amino]-piperidine-1-carboxylic acid tert-butyl ester as a white solid (401 mg, 58%).

Using general procedure C with the above carbamate (400 mg, 0.891 mmol), then general procedure B with the resulting amine and 2-(3-oxo-butyl)-isoindole-1,3-dione (386 mg, 1.78 mmol) followed by general procedure D afforded 3-{[[1-(3-amino-1-methyl-propyl)-piperidin-4-yl]-(1H-indol-5-yl)-amino]-methyl}-4-fluoro-benzonitrile as a white solid (92 mg, 26% over 3 steps).

Using general procedure E, the above amine (45 mg, 0.11 mmol) and 2,4-dimethyl-1-oxy-nicotinic acid (22 mg, 0.13 mmol) afforded COMPOUND 244 as a white solid (20 mg, 32%). $^1$H NMR (CDCl$_3$) δ 1.02 (d, 3H, J=5.4 Hz), 1.20-1.30 (m, 2H), 1.58-1.64 (m, 1H), 1.84-1.89 (m, 3H), 2.18-2.24 (m, 1H), 2.27 (s, 3H), 2.36 (s, 3H), 2.47-2.55 (m, 1H), 2.75-2.85 (m, 3H), 3.28-3.35 (m, 2H), 3.67-3.74 (m, 1H), 4.20 (s, 2H), 6.39 (s, 1H), 6.74 (d, 1H, J=8.7 Hz), 6.81 (d, 1H, J=6.6 Hz), 7.04-7.22 (m, 4H), 7.42-7.46 (m, 1H), 7.68-7.72 (m, 1H), 7.95 (d, 1H, J=6.6 Hz), 8.38 (br s, 1H), 8.57 (br s, 1H). $^{13}$C NMR (CDCl$_3$) δ 12.38, 14.09, 17.42, 28.63, 29.29, 30.43, 38.23, 43.28, 43.71, 50.54, 58.23, 59.23, 101.12, 107.24, 110.02, 110.48, 114.03 (d, J=14 Hz), 115.28 (d, J=23 Hz), 115.84, 117.49, 123.73, 123.92, 127.35, 131.35, 131.48, 132.63, 133.20, 135.56, 137.17, 140.48, 144.64, 161.89 (d, J=255 Hz), 164.53. ES-MS m/z 569 (M+H). Anal. Calcd. for C$_{33}$H$_{37}$N$_6$O$_2$F.0.5CH$_2$Cl$_2$.1.2CH$_4$O: C, 64.16; H, 6.64; N, 12.94; F, 2.92. Found: C, 64.27; H, 6.39; N, 12.74; F, 2.43.

EXAMPLE 245

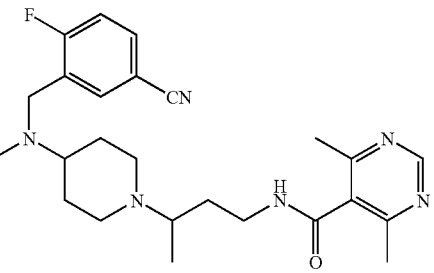

COMPOUND 245: 4,6-Dimethyl-pyrimidine-5-carboxylic acid (3-{4-[(5-cyano-2-fluoro-benzyl)-(1H-indol-5-yl)-amino]-piperidin-1-yl}-butyl)-amide Using general procedure E, 3-{[[1-(3-amino-1-methyl-propyl)-piperidin-4-yl]-(1H-indol-5-yl)-amino]-methyl}-4-fluoro-benzonitrile (see EXAMPLE 244) (45 mg, 0.11 mmol) and 4,6-dimethyl-pyrimidine-5-carboxylic acid (20 mg, 0.13 mmol) afforded COMPOUND 245 as a white solid (35 mg, 60%). $^1$H NMR (CDCl$_3$) δ 0.88-1.25 (m, 5H), 1.54-1.64 (m, 1H), 1.76-1.92 (m, 3H), 2.13-2.20 (m, 1H), 2.51 (s, 6H), 2.51-2.57 (m, 1H), 2.69-2.84 (m, 3H), 3.31-3.37 (m, 2H), 3.82-3.85 (m, 1H), 3.98 (s, 2H), 6.39 (s, 1H), 6.72 (d, 1H, J=8.6 Hz), 7.00 (s, 1H), 7.08-7.14 (m, 2H), 7.21 (d, 1H, J=8.6 Hz), 7.43-7.45 (m, 1H), 7.65 (d, 1H, J=6.4 Hz), 8.02 (s, 1H), 8.50 (br s, 1H), 8.83 (s, 1H). $^{13}$C NMR (CDCl$_3$) δ 13.74, 22.36, 29.89, 30.88, 31.26, 40.33, 43.81, 44.17, 52.34, 60.54, 60.81, 102.63, 108.63, 110.70, 111.94, 116.61, 116.72, 116.92, 118.91, 125.26, 128.77, 131.10, 132.79, 134.50, 157.98, 163.38. ES-MS m/z 554 (M+H). Anal. Calcd. for C$_{32}$H$_{36}$N$_7$OF.0.2CH$_2$Cl$_2$: C, 67.77; H, 6.43; N, 17.18; F, 3.33. Found: C, 68.16; H, 6.64; N, 16.86; F, 3.05.

EXAMPLE 246

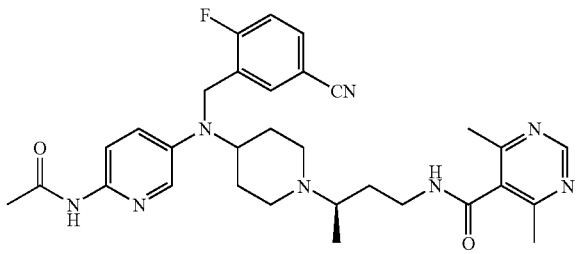

COMPOUND 246: 4,6-Dimethyl-pyrimidine-5-carboxylic acid ((R)-3-{4-[(6-acetylamino-pyridin-3-yl)-(5-cyano-2-fluoro-benzyl)-amino]-piperidin-1-yl}-butyl)-amide Using general procedure A with N-(5-amino-pyridin-2-yl)-acetamide (Bae, Jong Woo; et al., *Tetrahedron Lett.*, 41, 2, 2000, 175-178) (1.00 g, 6.62 mmol) and (R)-3-(4-oxo-piperidin-1-yl)-butyronitrile (1.16 g, 6.95 mmol) and then using general procedure J afforded N-{5-[1-((R)-3-amino-1-methyl-propyl)-piperidin-4-ylamino]-pyridin-2-yl}-acetamide as a white solid (1.05 g, 52% over 2 steps).

Using general procedure E, the above primary amine (400 mg, 1.31 mmol) and 4,6-dimethyl-pyrimidine-5-carboxylic acid (219 mg, 1.44 mmol) afforded 4,6-dimethyl-pyrimidine-5-carboxylic acid {(R)-3-[4-(6-acetylamino-pyridin-3-ylamino)-piperidin-1-yl]-butyl}-amide as a white solid (523 mg, 91%).

Using general procedure G, 4-fluoro-3-hydroxymethyl-benzonitrile (300 mg, 1.91 mmol) gave the crude mesylate. Using general procedure H, 4,6-dimethyl-pyrimidine-5-carboxylic acid {(R)-3-[4-(6-acetylamino-pyridin-3-ylamino)-piperidin-1-yl]-butyl}-amide (500 mg, 1.14 mmol) and the above mesylate (340 mg) afforded COMPOUND 246 as a white solid (150 mg, 23%). $^1$H NMR (CDCl$_3$) δ 0.98-1.30 (m, 2H), 1.03 (d, 3H, J=6.6 Hz), 1.53-1.62 (m, 1H), 1.71-1.86 (m, 3H), 2.15 (s, 3H), 2.16-2.25 (m, 1H), 2.51 (s, 6H), 2.52-2.63 (m, 1H), 2.75-2.94 (m, 3H), 3.31-3.43 (m, 1H), 3.48-3.59 (m, 1H), 3.74-3.86 (m, 1H), 4.02 (s, 2H), 6.99 (dd, 1H, J=9.3, 3.0 Hz), 7.17-7.24 (m, 1H), 7.44-7.48 (m, 1H), 7.53-7.59 (m, 1H), 7.63 (d, 1H, J=2.7 Hz), 7.76 (s, 1H), 7.96-8.05 (m, 2H), 8.84 (s, 1H). $^{13}$C NMR (CDCl$_3$) δ 13.49, 21.95, 24.39, 29.36, 30.22, 31.39, 39.51, 42.21, 43.82, 51.65, 57.56, 59.50, 108.75 (d, J=3 Hz), 114.74, 116.89 (d, J=23 Hz), 118.07, 124.58, 128.25 (d, J=15 Hz), 130.67, 132.73 (d, J=6 Hz), 133.16 (d, J=9 Hz), 134.31, 140.17, 143.87, 157.57, 162.34 (d, J=256 Hz), 163.01, 166.44, 168.26. ES-MS m/z 573 (M+H). Anal. Calcd. for C$_{31}$H$_{37}$FN$_8$O$_2$.0.4CH$_2$Cl$_2$.0.5H$_2$O: C, 61.26; H, 6.35; N, 18.20; F, 3.09. Found: C, 61.65; H, 6.46; N, 18.19; F, 3.03.

EXAMPLE 247

A mixture of the alcohol from above (791 mg), (S)-BINAP (135 mg, 0.217 mmol), Pd(OAc)$_2$ (48 mg, 0.21 mmol), and K$_2$CO$_3$ (602 mg, 4.36 mmol) in degassed toluene (7 mL) was heated to 110° C. for 40 h. The mixture was allowed to cool to room temperature, filtered and concentrated to give 4-[2-(4-trifluoromethoxy-phenyl)-2,3-dihydro-benzofuran-2-yl]-piperidine-1-carboxylic acid tert-butyl ester as a colourless foam (375 mg, 50%) after purification.

Using general procedure C with the carbamate from above (375 mg, 0.809 mmol), then general procedure I with the resulting amine and then using general procedure J gave a 1:1 diastereomeric mixture of 3-{4-[2-(4-trifluoromethoxy-phenyl)-2,3-dihydro-benzofuran-2-yl]-piperidin-1-yl}-butylamine as a colourless oil (138 mg, 81% over 3 steps).

Using general procedure F, 3,5-dichloroisonicotinic acid (51 mg, 0.27 mmol) and the amine from above (77 mg, 0.18 mmol) in THF (2 mL) gave a 1:1 diastereomeric mixture of COMPOUND 247 (71 mg, 66%). $^1$H NMR (CDCl$_3$) δ 0.57-1.32 (m, 12H), 1.47-2.00 (m, 10H), 2.24-2.41 (m, 2H), 2.68-2.88 (m, 6H), 3.13-3.39 (m, 6H), 3.87 (m, 2H), 6.84 (m, 4H), 7.11 (m, 8H), 7.29 (m, 4H), 8.58 (s, 2H), 8.60 (s, 2H), 8.88 (d, 1H, J=5.7 Hz), 9.01 (br s, 1H). $^{13}$C NMR (CDCl$_3$) δ 13.00, 13.32, 26.32, 26.78, 26.92, 27.57, 29.89, 30.55, 39.57, 40.10, 40.19, 40.31, 43.94, 44.12, 46.98, 52.51, 60.31, 60.67, 91.88, 92.04, 109.22, 120.60, 124.63, 125.46, 126.66, 126.80, 128.26, 129.01, 143.16, 143.72, 143.92, 147.67, 148.08, 158.78, 161.49, 161.72. ES-MS m/z 608 (M+H). Anal. Calcd. for C$_{30}$H$_{30}$N$_3$Cl$_2$F$_3$O$_3$: C, 59.22; H, 4.97; N, 6.91; Cl, 11.65; F, 9.37. Found: C, 59.37; H, 5.03; N, 6.84; Cl, 11.58; F, 9.33.

Scheme 12 describes the preparation of Examples 248-255, using various general procedures previously described, and reagents listed below.

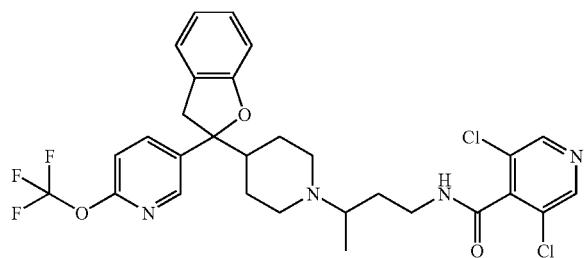

COMPOUND 247: 3,5-Dichloro-N-(3-{4-[2-(4-trifluoromethoxy-phenyl)-2,3-dihydro-benzofuran-2-yl]-piperidin-1-yl}-butyl)-isonicotinamide To a solution of 4-[hydroxy-(4-trifluoromethoxy-phenyl)-methyl]-piperidine-1-carboxylic acid tert-butyl ester (see EXAMPLE 32) (604 mg, 1.61 mmol) in CH$_2$Cl$_2$ (8 mL) was added SiO$_2$ (2 g) followed by PCC (1.04 g, 4.82 mmol), and the mixture was stirred at room temperature for 3 h to give 4-(4-trifluoromethoxy-benzoyl)-piperidine-1-carboxylic acid tert-butyl ester as colourless crystals (601 mg, 100%) after purification.

A mixture of 2-bromobenzyl bromide (805 mg, 3.22 mmol), Mg turnings (180 mg, 7.40 mmol), and iodine (cat.) in Et$_2$O (16 mL) was heated to reflux until the reaction was initiated (indicated by decolourization) then stirred at room temperature for 2 h. The mixture was added to a solution of the ketone from above (601 mg, 1.61 mmol) in Et$_2$O (1 mL) then stirred for 19 h. Aqueous work-up and purification gave a colourless oil (791 mg).

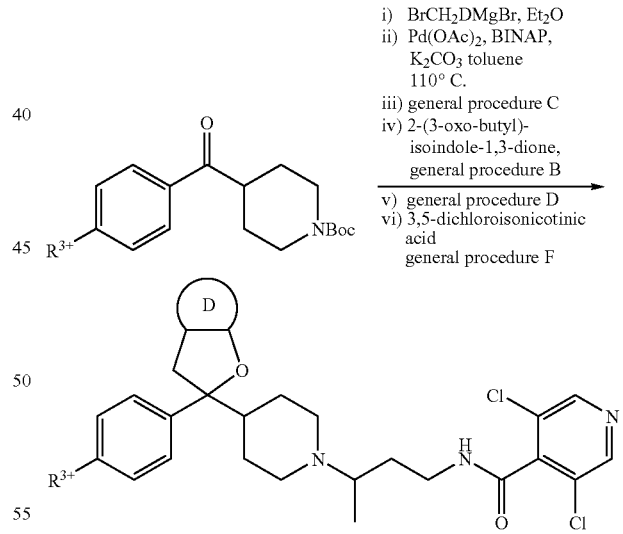

Scheme 12 i) BrCH$_2$DMgBr, Et$_2$O
ii) Pd(OAc)$_2$, BINAP, K$_2$CO$_3$ toluene 110° C.
iii) general procedure C
iv) 2-(3-oxo-butyl)-isoindole-1,3-dione, general procedure B
v) general procedure D
vi) 3,5-dichloroisonicotinic acid general procedure F

| Example | R$^{3*}$ | BrCH$_2$DBr |
|---|---|---|
| 248 | CF$_3$ | 2-bromobenzyl bromide |
| 249 | SO$_2$Me | 2-bromobenzyl bromide |
| 250 | SO$_2$NHMe | 2-bromobenzyl bromide |
| 251 | CF$_3$ | 1-bromo-2-bromomethyl-3-fluoro-benzene (Dewar, M. J. S.; Grisdale, P. J., J. Org. Chem., 28, 1963, 1759-1762) |

217

-continued

| Example | R³* | BrCH₂DBr |
|---|---|---|
| 252 | OCF₃ | 1-bromo-2-bromomethyl-3-fluoro-benzene |
| 253 | SO₂Me | 1-bromo-2-bromomethyl-3-fluoro-benzene |
| 254 | SO₂NHMe | 1-bromo-2-bromomethyl-3-fluoro-benzene |
| 255 | CF₃ | 2-bromo-1-bromomethyl-4-fluoro-benzene (Musso, David L.; et al., J. Med. Chem., 46, 3, 2003, 409-416) (800 mg, 2.99 mmol) |

EXAMPLE 248

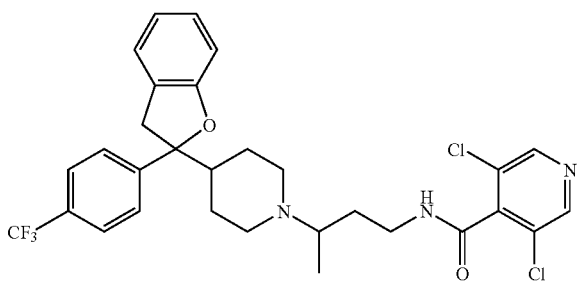

COMPOUND 248: 3,5-Dichloro-N-(3-{4-[2-(4-trifluoromethyl-phenyl)-2,3-dihydrobenzofuran-2-yl]-piperidin-1-yl}-butyl)-isonicotinamide White solid. ¹H NMR (CDCl₃) δ 0.59-0.73 (m, 1H), 0.94 (t, 3H, J=7.5 Hz), 0.91-0.96 (m, 1H), 1.04-1.24 (m, 2H), 1.47-2.02 (m, 4H), 2.24-2.42 (m, 1H), 2.66-2.89 (m, 3H), 3.16-3.38 (m, 3H), 3.75-3.97 (m, 1H), 6.80-6.90 (m, 2H), 7.07 (t, 1H, J=6 Hz), 7.17 (t, 1H, J=7.5 Hz), 7.38 (t, 2H, J=10.5 Hz), 7.57 (t, 2H, J=6.0 Hz), 8.59 (d, 2H, J=6.0 Hz), 8.83-8.97 (br s, 1H). ¹³C NMR (CDCl₃) δ 13.34, 13.70, 26.63, 27.17, 27.23, 30.31, 31.02, 40.21, 40.51, 40.64, 44.33, 44.54, 47.23, 52.78, 52.56, 60.60, 61.02, 92.33, 92.48, 109.65, 109.70, 121.10, 122.66, 125.01, 125.57, 125.68, 125.99, 126.12, 126.26, 128.71, 129.39, 129.87, 143.52, 148.05, 149.60, 146.78, 159.03, 159.14, 161.87, 162.14. ES-MS m/z 592.8 (M+H). Anal. Calcd. for C₃₀H₃₀N₃Cl₂O₂F₃: C, 60.82; H, 5.10; N, 7.09; Cl, 11.97; F, 9.62. Found: C, 60.94; H, 5.23; N, 7.09; Cl, 12.08; F, 9.50.

EXAMPLE 249

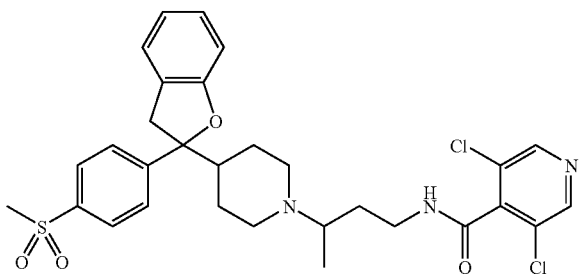

218

COMPOUND 249: 3,5-Dichloro-N-(3-{4-[2-(4-methanesulfonyl-phenyl)-2,3-dihydro-benzofuran-2-yl]-piperidin-1-yl}-butyl)-isonicotinamide White foam. ¹H NMR (CDCl₃) δ 0.60-0.90 (m, 2H), 0.91-0.96 (m, 3H) 1.01-1.21 (m, 1H), 1.43-1.80 (m, 5H), 1.82-2.02 (m, 1H), 2.20-2.44 (m, 1H), 2.64-2.91 (m, 3H), 3.03 (s, 3H), 3.15-3.44 (m, 2H), 3.73-3.40 (m, 1H), 6.80-6.92 (m, 2H), 7.03-7.11 (m, 1H), 7.12-7.20 (m, 1H), 7.46, 7.49 (d, 2H, J=8.4 Hz), 7.88, 7.89 (d, 2H, J=8.4 Hz), 8.57, 8.60 (s, 2H), 8.79, 8.92 (br s, 1H). ¹³C NMR (CDCl₃) δ 13.01, 13.34, 14.20, 21.07, 26.22, 26.79, 27.55, 29.92, 30.64, 39.89, 40.10, 40.30, 43.88, 44.11, 44.46, 46.79, 52.30, 52.41, 53.45, 60.16, 60.40, 60.61, 91.93, 92.06, 109.36, 109.41, 120.88, 124.63, 125.08, 126.31, 126.43, 127.37, 128.43, 129.02, 139.22, 143.16, 147.67, 151.69, 151.86, 158.52, 158.62, 161.44, 161.73. ES-MS m/z 626 (M+Na). Anal. Calcd. for C₃₀H₃₃N₃Cl₂O₄S·0.8CH₂Cl₂·0.2H₂O: C, 54.88; H, 5.23; N, 6.23; Cl, 18.93; S, 4.76. Found: C, 55.08; H, 5.28; N, 6.46; Cl, 18.69; S, 4.77.

EXAMPLE 250

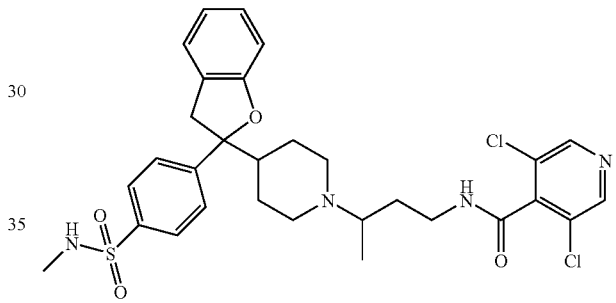

COMPOUND 250: 3,5-Dichloro-N-(3-{4-[2-(4-methylsulfamoyl-phenyl)-2,3-dihydro-benzofuran-2-yl]-piperidin-1-yl}-butyl)-isonicotinamide To a solution of 4-[hydroxy-(4-methylsulfamoyl-phenyl)-methyl]-piperidine-1-carboxylic acid tert-butyl ester (see EXAMPLE 33) (530 mg, 1.38 mmol) in CH₂Cl₂ (10 ml) were added PCC (900 mg, 4.1 mmol) followed by SiO₂ (1.5 g). The resultant mixture was stirred at room temperature overnight to give 4-(4-methylsulfamoyl-benzoyl)-piperidine-1-carboxylic acid tert-butyl ester (420 mg, 80%) as a colourless oil after purification.

COMPOUND 250 was isolated as a white foam. ¹H NMR (CDCl₃) δ 0.60-0.72 (m, 1H), 0.75-1.30 (m, 6H), 1.40-2.04 (m, 6H), 2.24-2.48 (m, 1H), 2.53-2.99 (m, 3H), 3.63 (d, 3H, J=3.0 Hz), 3.05-3.45 (m, 3H), 3.70-3.80 (m, 0.5H), 3.85-4.00 (m, 0.5H), 4.68 (q, 1H, J=6.0 Hz), 2.83-6.90 (m, 2H), 7.08-7.23 (m, 2H), 7.39-7.45 (m, 2H), 7.80 (d, 2H, J=6.0 Hz), 8.57 (s, 1H), 8.59 (s, 1H), 8.80 (s, 0.5H), 8.99 (s, 0.5H). ¹³C NMR (CDCl₃) δ 13.0, 13.32, 26.19, 26.77, 27.51, 29.34, 29.93, 30.61, 39.87, 40.06, 40.16, 40.28, 43.94, 44.16, 46.84, 52.27, 52.36, 53.46, 60.07, 60.51, 91.96, 92.10, 92.78, 109.29, 109.34, 113.89, 120.78, 124.63, 125.24, 126.04, 126.17, 126.60, 127.11, 127.76, 128.36, 129.00, 137.61, 143.11, 147.63, 150.31, 150.49, 158.55, 158.65, 161.50, 161.78. ES-MS m/z 618.6 (M+H). Anal. Calcd. for C$_{30}$H$_{34}$Cl$_2$N$_4$O$_4$S.0.3CH$_2$Cl$_2$: C, 56.59; H, 5.42; N, 8.71; Cl, 14.33; S, 4.99. Found: C, 55.65; H, 5.56; N, 8.60; Cl, 14.05; S, 4.94.

EXAMPLE 251

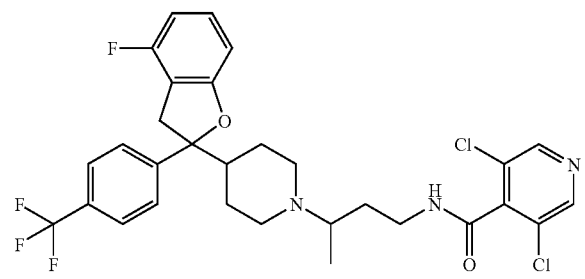

COMPOUND 251: 3,5-Dichloro-N-(3-{4-[4-fluoro-2-(4-trifluoromethyl-phenyl)-2,3-dihydro-benzofuran-2-yl]-piperidin-1-yl}-butyl)-isonicotinamide Colourless foam. $^1$H NMR (CDCl$_3$) δ 0.59-1.24 (m, 12H), 1.43-2.02 (m, 10H), 2.23-2.43 (m, 2H), 2.67-2.90 (m, 6H), 3.21-3.44 (m, 6H), 3.76-3.97 (m, 2H), 6.55 (m, 2H), 6.68 (m, 2H), 7.12 (m, 2H), 7.37 (m, 4H), 7.59 (d, 4H, J=7.8 Hz), 8.58 (s, 2H), 8.60 (s, 2H), 8.79 (d, 1H, J=5.7 Hz), 8.87 (br s, 1H). $^{13}$C NMR (CDCl$_3$) δ 13.00, 13.31, 26.16, 26.76, 27.54, 30.04, 30.63, 36.84, 37.22, 40.13, 43.87, 44.11, 46.85, 52.36, 60.22, 60.61, 93.31, 93.45, 105.26, 107.62, 107.89, 111.80, 112.08, 122.20, 125.28, 125.47, 125.60, 128.98, 129.30, 129.72, 129.84, 143.10, 147.68, 148.58, 148.75, 157.38, 160.65, 160.89, 161.48, 161.72. ES-MS m/z 610 (M+H). Anal. Calcd. for C$_{30}$H$_{29}$N$_3$Cl$_2$F$_4$O$_2$.0.2C$_3$H$_7$NO.0.1CH$_2$Cl$_2$.0.1C$_6$H$_{14}$: C, 58.54; H, 5.02; N, 6.98; Cl, 12.15; F, 11.83. Found: C, 58.82; H, 4.86; N, 7.00; Cl, 11.79; F, 11.61.

EXAMPLE 252

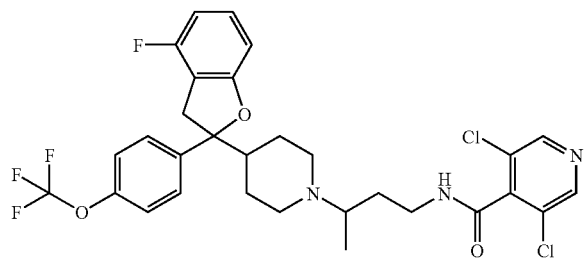

COMPOUND 252: 3,5-Dichloro-N-(3-{4-[4-fluoro-2-(4-trifluoromethoxy-phenyl)-2,3-dihydro-benzofuran-2-yl]-piperidin-1-yl}-butyl)-isonicotinamide Colourless foam. $^1$H NMR (CDCl$_3$) δ 0.58-1.29 (m, 12H), 1.37-1.97 (m, 10H), 2.24-2.43 (m, 2H), 2.68-2.89 (m, 6H), 3.13-3.39 (m, 6H), 3.74-3.97 (m, 2H), 6.55 (m, 2H), 6.66 (m, 2H), 7.08-7.18 (m, 6H), 7.27 (m, 4H), 8.58 (s, 2H), 8.60 (s, 2H), 8.81 (m, 1H), 8.88 (m, 1H). $^{13}$C NMR (CDCl$_3$) δ 13.01, 13.31, 26.23, 26.79, 27.55, 30.08, 30.58, 36.65, 37.10, 40.16, 43.91, 44.12, 46.99, 52.41, 60.27, 60.60, 93.28, 93.44, 105.21, 107.53, 107.80, 111.96, 112.23, 120.69, 126.54, 126.68, 128.98, 129.65, 129.76, 143.12, 143.31, 147.69, 148.22, 157.43, 160.70, 160.84, 160.94, 161.50, 161.70. ES-MS m/z 626 (M+H). Anal. Calcd. for C$_{30}$H$_{29}$N$_3$Cl$_2$F$_4$O$_3$: C, 57.52; H, 4.67; N, 6.71; Cl, 11.32; F, 12.13. Found: C, 57.26; H, 4.56; N, 6.62; Cl, 11.65; F, 11.84.

EXAMPLE 253

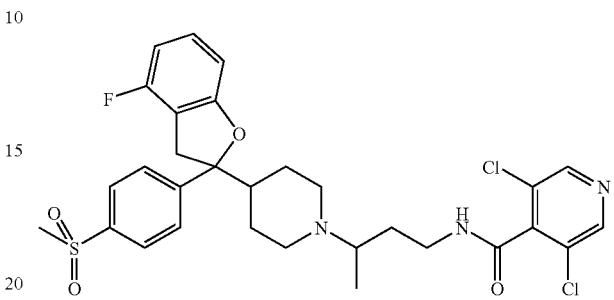

COMPOUND 253: 3,5-Dichloro-N-(3-{4-[4-fluoro-2-(4-methanesulfonyl-phenyl)-2,3-dihydro-benzofuran-2-yl]-piperidin-1-yl}-butyl)-isonicotinamide Colourless foam. $^1$H NMR (CDCl$_3$) δ 0.62-1.24 (m, 12H), 1.48-2.06 (m, 10H), 2.23-2.43 (m, 2H), 2.55-2.89 (m, 6H), 3.03 (s, 6H), 3.21-4.06 (m, 8H), 6.56 (m, 2H), 6.69 (m, 2H), 7.13 (m, 2H), 7.46 (m, 4H), 7.90 (m, 4H), 8.57 (s, 2H), 8.59 (s, 2H), 8.68 (m, 1H), 8.77 (m, 1H). $^{13}$C NMR (CDCl$_3$) δ 12.99, 13.29, 23.39, 26.12, 26.69, 26.76, 27.50, 30.19, 30.74, 33.25, 36.93, 37.28, 40.06, 43.88, 44.13, 44.45, 46.80, 52.22, 52.30, 60.00, 60.42, 67.39, 93.30, 93.44, 98.39, 105.34, 107.77, 108.04, 111.65, 111.93, 126.19, 126.31, 127.48, 128.99, 129.85, 129.96, 139.47, 143.10, 147.67, 151.00, 151.16, 157.36, 160.64, 160.75, 161.47, 161.72. ES-MS m/z 620 (M+H). Anal. Calcd. for C$_{30}$H$_{32}$N$_3$Cl$_2$FSO$_4$.0.1CH$_2$Cl$_2$.0.6CH$_4$O: C, 56.88; H, 5.38; N, 6.48; Cl, 12.03; F, 2.93; S, 4.95. Found: C, 57.00; H, 5.46; N, 6.24; Cl, 11.65; F, 2.63; S, 4.68.

EXAMPLE 254

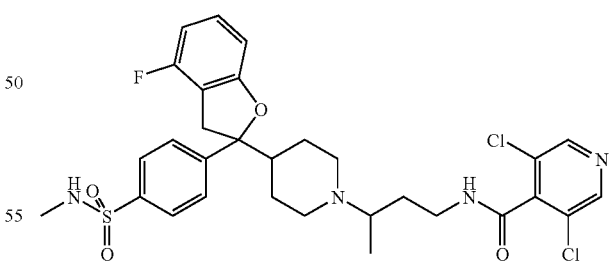

COMPOUND 254: 3,5-Dichloro-N-(3-{4-[4-fluoro-2-(4-methylsulfamoyl-phenyl)-2,3-dihydro-benzofuran-2-yl]-piperidin-1-yl}-butyl)-isonicotinamide Yellow foam. $^1$H NMR (CDCl$_3$) δ 0.65-2.07 (m, 22H), 2.27-2.44 (m, 2H), 2.65-2.91 (m, 12H), 3.16-3.46 (m, 6H), 3.70-3.90 (m, 2H), 4.52 (m, 2H), 6.56 (m, 2H), 6.69 (m, 2H), 7.13 (m, 2H), 7.41 (m, 4H), 7.82 (d, 4H, J=8.1 Hz), 8.58 (s, 2H), 8.60 (s, 2H), 8.74 (m, 1H), 8.81 (m, 1H). $^{13}$C NMR (CDCl$_3$) δ 13.00, 13.29, 26.09, 26.70, 27.48, 29.39, 29.71, 30.13, 30.31, 30.65, 36.86, 37.23, 40.06, 43.91, 44.14, 46.85, 52.33, 60.14, 60.53, 93.31, 93.45, 105.31, 107.72, 107.99, 111.73, 112.01, 125.52, 125.94, 126.07, 127.26, 129.00, 129.82, 129.93, 137.93, 143.13, 147.67, 149.64, 149.83, 157.37, 160.66, 160.78, 160.88, 161.50, 161.73. ES-MS m/z 635 (M+H).

EXAMPLE 255

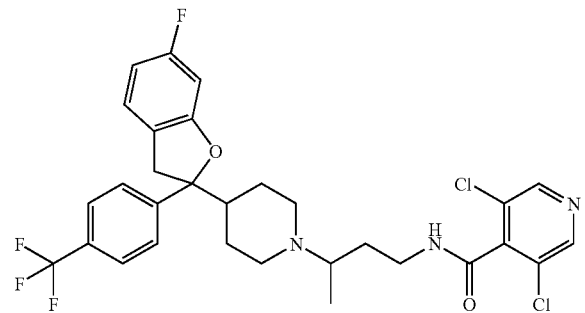

COMPOUND 255: 3,5-Dichloro-N-(3-{4-[6-fluoro-2-(4-trifluoromethyl-phenyl)-2,3-dihydro-benzofuran-2-yl]-piperidin-1-yl}-butyl)-isonicotinamide Colourless foam. $^1$H NMR (CDCl$_3$) δ 0.58-1.27 (m, 12H), 1.48-2.00 (m, 10H), 2.24-2.42 (m, 2H), 2.67-2.88 (m, 6H), 3.11-3.39 (m, 6H), 3.76-3.97 (m, 2H), 6.57 (m, 4H), 6.98 (m, 2H), 7.36 (m, 4H), 7.58 (d, 4H, J=7.8 Hz), 8.58 (s, 2H), 8.60 (s, 2H), 8.79 (d, 1H, J=4.8 Hz), 8.92 (br s, 1H). $^{13}$C NMR (CDCl$_3$) δ 13.01, 13.32, 26.20, 26.70, 26.81, 27.47, 29.93, 30.61, 39.04, 39.47, 40.11, 40.26, 43.88, 44.09, 46.88, 52.32, 52.40, 60.20, 60.61, 93.75, 93.88, 97.62, 97.97, 107.17, 107.48, 120.80, 124.75, 124.89, 125.24, 125.49, 125.62, 129.03, 129.66, 143.12, 147.64, 148.89, 159.68, 161.44, 161.72, 164.84. ES-MS m/z 612 (M+H). Anal. Calcd. for C$_{30}$H$_{29}$N$_3$Cl$_2$F$_4$O$_2$.0.3C$_3$H$_7$NO.0.1CH$_2$Cl$_2$.0.1C$_6$H$_{14}$: C, 58.44; H, 5.07; N, 7.12; Cl, 12.01; F, 11.70. Found: C, 58.70; H, 4.87; N, 7.06; Cl, 11.64; F, 11.57.

EXAMPLE 256

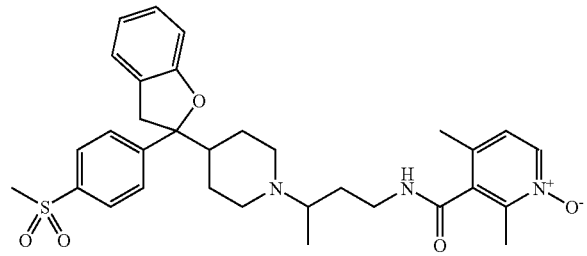

COMPOUND 256: N-(3-{4-[2-(4-Methanesulfonyl-phenyl)-2,3-dihydro-benzofuran-2-yl]-piperidin-1-yl}-butyl)-2,4-dimethyl-1-oxy-nicotinamide Using general procedure E, 3-{4-[2-(4-methanesulfonyl-phenyl)-2,3-dihydro-benzofuran-2-yl]-piperidin-1-yl}-butylamine (see EXAMPLE 249) (26 mg, 0.060 mmol) and 2,4-dimethyl-1-oxy-nicotinic acid (11 mg, 0.067 mmol) afforded a 1:1 diastereomeric mixture of COMPOUND 256 (32 mg, 92%) as a white foam. $^1$H NMR (CDCl$_3$) δ 0.80-1.15 (m, 2H), 0.93, 0.95 (d, 3H, J=6.7 Hz), 1.42-1.96 (m, 7H), 2.26 (s, 3H), 2.40 (s, 3H), 2.59-2.85 (m, 3H), 3.03 (s, 3H), 3.22-3.48 (m, 3H), 3.63-3.82 (m, 1H), 6.79-6.86 (m, 1H), 6.89-6.97 (m, 2H), 7.05-7.20 (m, 2H), 7.55, 7.58 (d, 2H, J=8.0 Hz), 7.89 (d, 2H, J=8.4 Hz), 8.08, 8.12 (d, 1H, J=6.5 Hz), 8.34, 8.42 (br s, 1H). $^{13}$C NMR (CDCl$_3$) δ 13.24, 13.40, 15.11, 18.43, 22.62, 26.36, 26.90, 27.51, 31.63, 31.87, 39.17, 39.86, 40.14, 44.48, 44.78, 47.01, 51.88, 53.45, 58.95, 59.15, 92.27, 92.40, 109.40, 120.81, 124.62, 124.86, 125.29, 125.36, 126.60, 126.69, 127.27, 128.37, 133.85, 136.70, 138.13, 139.16, 145.54, 151.47, 151.58, 158.54, 158.60, 165.39, 165.50. ES-MS m/z 626 (M+Na). Anal. Calcd. for C$_{32}$H$_{39}$N$_3$O$_5$S.0.1CH$_2$Cl$_2$.1.3H$_2$O: C, 63.24; H, 6.91; N, 6.89; S, 5.26. Found: C, 62.92; H, 6.91; N, 7.26; S, 5.04.

EXAMPLE 257

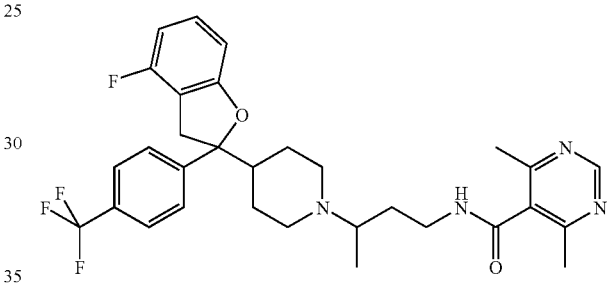

COMPOUND 257: 4,6-Dimethyl-pyrimidine-5-carboxylic acid (3-{4-[4-fluoro-2-(4-trifluoromethyl-phenyl)-2,3-dihydro-benzofuran-2-yl]-piperidin-1-yl}-butyl)-amide Using general procedure E, 3-{4-[4-fluoro-2-(4-trifluoromethyl-phenyl)-2,3-dihydro-benzofuran-2-yl]-piperidin-1-yl}-butylamine (see EXAMPLE 251) (60 mg, 0.14 mmol) and 4,6-dimethyl-pyrimidine-5-carboxylic acid (42 mg, 0.28 mmol) afforded COMPOUND 257 as a white solid (32 mg, 41%). $^1$H NMR (CDCl$_3$) δ 0.62-0.92 (m, 2H), 0.92-0.97 (m, 3H), 1.09-1.23 (m, 1H), 1.50-1.55 (m, 1H), 1.69-1.78 (m, 2H), 1.84-2.02 (m, 2H), 2.24-2.45 (m, 1H), 2.50 (s, 6H), 2.61-2.86 (m, 3H), 3.17-3.47 (m, 3H), 3.70-4.00 (m, 1H), 6.51-6.57 (m, 1H), 6.84, 6.89 (d, 1H, J=8.1 Hz), 7.10-7.17 (m, 1H), 7.36-7.43 (m, 2H), 7.58-7.62 (m, 2H), 8.44, 8.59 (m, 1H), 9.04, 9.09 (s, 1H). $^{13}$C NMR (CDCl$_3$) δ 14.55, 14.95, 23.47, 27.69, 28.14, 28.30, 29.01, 31.91, 32.79, 38.48, 38.90, 41.46, 41.67, 45.53, 45.79, 48.46, 48.52, 53.92, 54.00, 61.60, 62.16, 94.67, 94.84, 107.08, 109.15, 109.42, 113.35, 113.62, 123.78, 126.91, 127.05, 127.16, 127.39, 131.29, 131.40, 131.48, 132.30, 150.24, 150.40, 158.92, 159.20, 162.19, 162.56, 164.50, 167.87, 168.26. ES-MS m/z 571 (M+H). Anal. Calcd. for C$_{31}$H$_{34}$N$_4$O$_2$F$_4$.0.5H$_2$O: C, 64.24; H, 6.09; N, 9.67. Found: C, 64.25; H, 6.00; N, 9.68.

Scheme 13 describes the preparation of Examples 258-260, using general procedures E or F, and reagents listed below.

Scheme 13

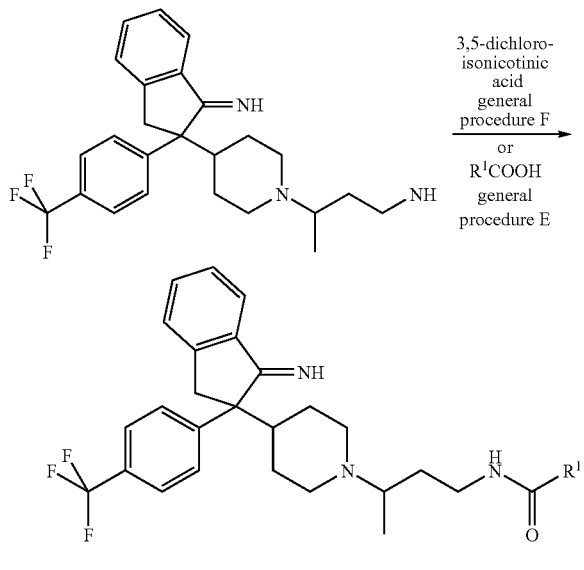

| Example | R¹COOH |
|---|---|
| 258 | 3,5-dichloroisonicotinic acid |
| 259 | 4,6-dimethyl-pyrimidine-5-carboxylic acid |
| 260 | 2,4-dimethyl-1-oxy-nicotinic acid |

EXAMPLE 258

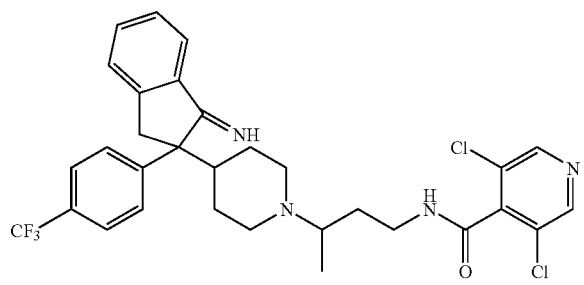

COMPOUND 258: 3,5-Dichloro-N-(3-{4-[1-imino-2-(4-trifluoromethyl-phenyl)-indan-2-yl]-piperidin-1-yl}-butyl)-isonicotinamide To a solution of 4-[hydroxy-(4-trifluoromethyl-phenyl)-methyl]-piperidine-1-carboxylic acid tert-butyl ester (990 mg, 2.75 mmol), acetone cyanohydrin (913 mg, 10.73 mmol) and Ph₃P (2.5 g, 9.63 mmol) in THF (25 mL) was added DIAD (2.2 g, 10.94 mmol) in THF (10 mL) over 5 hours at 0° C. and the resulting mixture was stirred for another 72 hours at room temperature. Standard work-up and purification afforded 4-[cyano-(4-trifluoromethyl-phenyl)-methyl]-piperidine-1-carboxylic acid tert-butyl ester (539 mg, 53%) as a white foam.

To a solution of the above nitrile (280 mg, 0.76 mmol) in THF at −78° C. was added freshly prepared LDA (0.32M, 2.6 mL, 0.83 mmol). The resulting mixture was stirred for 30 min. at −78° C. and 2-bromobenzyl bromide (570 mg, 2.28 mmol) in THF (1 mL) was added. The reaction was stirred for 3 hours at 0° C. and quenched with saturated aqueous NH₄Cl (20 mL) to give 4-[2-(2-bromo-phenyl)-1-cyano-1-(4-trifluoromethyl-phenyl)-ethyl]-piperidine-1-carboxylic acid tert-butyl ester (264 mg, 65%) as a white foam after work-up and purification.

To a solution of the above bromo-adduct (262 mg, 0.48 mmol) in THF (5 mL) cooled to −78° C. was added t-BuLi (1.7M in hexane, 0.62 mL, 1.05 mmol) and the resulting mixture was stirred for 1 h at −78° C. and quenched with saturated aqueous NH₄Cl (20 mL) to give 4-[1-imino-2-(4-trifluoromethyl-phenyl)-indan-2-yl]-piperidine-1-carboxylic acid tert-butyl ester (190 mg, 86%) as a white foam following work-up and purification.

Using general procedure C with the above carbamate, then general procedure I with the resulting amine followed by general procedure J gave 2-[1-(3-amino-1-methyl-propyl)-piperidin-4-yl]-1-imino-2-(4-trifluoromethyl-phenyl)-indan (47 mg, 53% over 3 steps) as a white foam.

Using general procedure F, 3,5-dichloroisonicotinic acid (25 mg, 0.13 mmol) and the above amine (47 mg, 0.11 mmol) afforded COMPOUND 258 (16 mg, 24%) as a mixture of two diastereomers. ¹H NMR (CDCl₃) δ 0.51-0.86 (m, 1H), 0.90 (d, 3H, J=6 Hz), 1.46-1.84 (m, 5H), 2.09-2.14 (m, 1H), 2.32-2.54 (m, 3H), 2.68-2.85 (m, 3H), 3.05 (t, 1H, J=15 Hz), 3.22-3.25 (m, 1H), 3.89-3.97 (m, 1H), 7.30-7.35 (m, 1H), 7.48-7.54 (m, 7H), 8.55 (d, 2H, J=12 Hz), 9.48-9.65 (m, 1H). ¹³C NMR (CDCl₃) δ 13.24, 13.35, 27.22, 27.47, 28.02, 28.31, 29.37, 29.79, 36.33, 40.58, 40.73, 44.00, 44.12, 52.68, 52.81, 53.44, 57.54, 60.83, 61.03, 121.66, 122.24, 125.34, 125.84, 126.94, 127.64, 128.61, 129.27, 132.83, 135.48, 143.49, 146.76, 147.64, 161.29, 161.52, 184.21. ES-MS m/z 627 (M+Na).

EXAMPLE 259

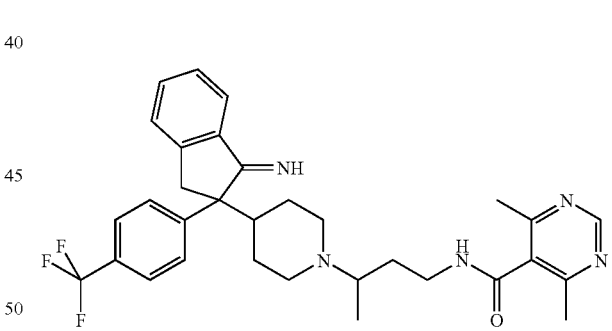

COMPOUND 259: 4,6-Dimethyl-pyrimidine-5-carboxylic acid (3-{4-[1-imino-2-(4-trifluoromethyl-phenyl)-indan-2-yl]-piperidin-1-yl}-butyl)-amide White solid. ¹H NMR (CDCl₃) δ 0.62-0.82 (m, 2H), 0.96 (d, 3H, J=6.0 Hz), 1.31-1.55 (m, 3H), 1.67-1.79 (m, 1H), 1.97-2.37 (m, 2H), 2.43-2.53 (m, 2H), 2.48, 2.50 (s, 6H), 2.64-2.84 (m, 3H), 3.07-3.32 (m, 3H), 3.75-3.89 (m, 1H), 7.29-7.58 (m, 8H), 8.95, 9.03 (s, 1H), 9.16, 9.71 (br s, 1H). ¹³C NMR (CDCl₃) δ 13.64, 13.73, 22.31, 27.56, 27.79, 28.45, 28.67, 30.27, 36.57, 40.97, 44.19, 44.57, 53.14, 53.32, 53.83, 57.95, 61.40, 122.00, 122.64, 125.60, 126.28, 127.51, 127.95, 129.36, 131.40, 133.18, 135.89, 146.75, 157.91, 157.98, 163.50, 166.55, 166.74, 184.60. ES-MS m/z 564

(M+H). Anal. Calcd. for $C_{32}H_{36}N_5OF_3 \cdot 0.7H_2O$: C, 66.70; H, 6.54; N, 12.15; F, 9.89. Found: C, 66.73; H, 6.41; N, 12.01; F, 9.83.

EXAMPLE 260

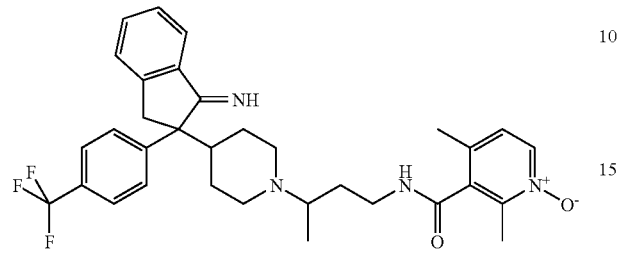

COMPOUND 260: N-(3-{4-[1-Imino-2-(4-trifluoromethyl-phenyl)-indan-2-yl]-piperidin-1-yl}-butyl)-2,4-dimethyl-1-oxy-nicotinamide White solid. $^1$H NMR (CDCl$_3$) δ 0.62-0.77 (m, 2H), 0.97 (d, 3H, J=5.4 Hz), 1.35-1.60 (m, 4H), 1.69-1.76 (m, 1H), 2.04-2.14 (m, 1H), 2.25, 2.27 (s, 3H), 2.43-2.54 (m, 1H), 2.51 (s, 3H), 2.64-2.76 (m, 4H), 3.22-3.32 (m, 2H), 3.80-3.87 (m, 1H), 6.89, 6.95 (d, 1H, J=6.6 Hz), 7.31-7.36 (m, 1H), 7.49-7.62 (m, 6H), 8.14, 8.20 (d, 1H, J=6.6 Hz), 9.00 (br s, 1H), 9.92 (br s, 1H). $^{13}$C NMR (CDCl$_3$) δ 13.72, 15.61, 18.77, 27.56, 27.88, 28.33, 28.66, 30.90, 37.62, 40.50, 44.88, 52.93, 53.82, 57.99, 60.70, 122.11, 125.15, 125.61, 126.38, 127.60, 127.92, 133.10, 133.97, 137.25, 138.53, 145.98, 146.74, 147.55, 165.69, 165.79. ES-MS m/z 579 (M+H). Anal. Calcd. for $C_{33}H_{37}N_4O_2F_3 \cdot 0.1H_2O \cdot 0.5CH_2Cl_2$: C, 64.59; H, 6.18; N, 8.99; F, 9.15. Found: C, 64.76; H, 6.23; N, 8.98; F, 9.05.

Scheme 14 describes the preparation of Examples 261-263, using general procedures E or F, and reagents listed below.

Scheme 14

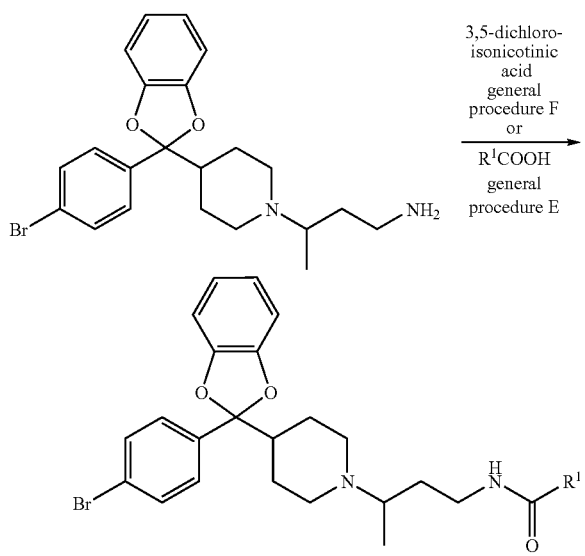

| Example | R$^1$COOH |
|---------|-----------|
| 261 | 3,5-dichloroisonicotinic acid |
| 262 | 2,4-dimethyl-1-oxy-nicotinic acid |
| 263 | 4,6-dimethyl-pyrimidine-5-carboxylic acid |

EXAMPLE 261

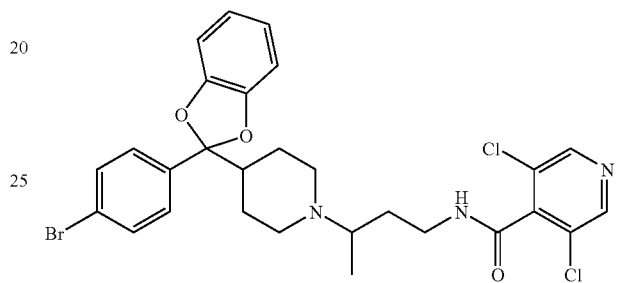

COMPOUND 261: N-(3-{4-[2-(4-Bromo-phenyl)-benzo[1,3]dioxol-2-yl]-piperidin-1-yl}-butyl)-3,5-dichloro-isonicotinamide A mixture of (4-bromophenyl)-piperidin-4-yl-methanone (536 mg, 2.00 mmol), catechol (880 mg, 8.00 mmol) and p-TsOH.H$_2$O (760 mg, 4.00 mmol) in xylene (20 mL) was heated at reflux with a Dean-Stark apparatus to remove water for 68 hours. Standard work-up and purification gave 4-[2-(4-bromophenyl)-benzo[1,3]dioxol-2-yl]-piperidine (629 mg, 87%) as a yellow foam.

Using general procedure B with the above amine (400 mg, 1.11 mmol) and 2-(3-oxo-butyl)-isoindole-1,3-dione (482 mg, 2.22 mmol) and then using general procedure D gave 3-{4-[2-(4-bromophenyl)-benzo[1,3]dioxol-2-yl]-piperidin-1-yl}-butylamine (284 mg, 59% over 2 steps) as a colorless oil.

COMPOUND 261 was isolated as a white foam. $^1$H NMR (CDCl$_3$) δ 0.75-1.07 (m, 2H), 0.95 (d, 3H, J=6.6 Hz), 1.43-1.61 (m, 3H), 1.72-1.98 (m, 3H), 2.36 (t, 1H, J=11.7 Hz), 2.74 (d, 1H, J=10.5 Hz), 2.81-2.86 (m, 2H), 3.30 (t, 1H, J=12 Hz) 3.86-3.93 (m, 1H), 6.78-6.84 (m, 4H), 7.23 (d, 2H, J=8.4 Hz), 7.46 (d, 2H, J=8.4 Hz), 8.59 (s, 2H), 9.16 and 9.18 (br s, 1H). $^{13}$C NMR(CDCl$_3$) δ 14.6, 27.1, 21.6, 31.4, 41.6, 44.9, 46.5, 53.4, 62.0, 110.0, 119.0, 122.9, 124.3, 128.7, 130.3, 132.6, 140.2, 144.5, 148.2, 148.3, 149.0, 163.0. ES-MS m/z 606 (M+H). Anal. Calcd. for $C_{28}H_{28}BrCl_2N_3O_3 \cdot 0.3CH_2Cl_2 \cdot 0.3C_6H_{14}$: C, 55.05; H, 5.03; N, 6.40; Br, 12.17; Cl, 14.04. Found: C, 55.32; H, 4.80; N, 6.70; Br, 12.12; Cl, 13.75.

EXAMPLE 262

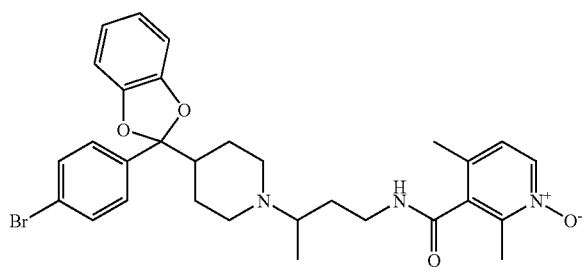

COMPOUND 262: N-(3-{4-[2-(4-Bromo-phenyl)-benzo [1,3]dioxol-2-yl]-piperidin-1-yl}-butyl)-2,4-dimethyl-1-oxy-nicotinamide White solid. $^1$H NMR (CDCl$_3$) δ 0.96 (d, 3H, J=6.6 Hz), 1.01-1.29 (m, 2H), 1.51-1.65 (m, 2H), 1.71-1.84 (m, 1H), 1.91-2.03 (m, 3H), 2.28 (s, 3H), 2.32 (s, 3H), 3.32-2.37 (m, 1H), 2.69-2.80 (m, 3H), 3.21-3.38 (m, 1H), 3.66-3.70 (m, 1H), 6.74-6.86 (m, 4H), 6.90 (d, 1H, J=6.6 Hz), 7.32 (d, 2H, J=8.4 Hz), 7.46 (d, 2H, J=8.4 Hz), 8.02 (d, 1H, J=6.6 Hz), 8.68 (br s, 1H). $^{13}$C NMR (CDCl$_3$) δ 13.68, 15.46, 18.83, 26.20, 26.70, 32.17, 39.58, 44.73, 45.90, 52.01, 59.53, 108.92, 108.95, 118.38, 121.91, 123.30, 125.15, 127.93, 131.60, 134.28, 137.12, 138.47, 139.21, 145.98, 147.38, 147.43, 165.85. ES-MS m/z 580 (M+H). Anal. Calcd. for C$_{30}$H$_{34}$N$_3$O$_4$Br.1.5H$_2$O: C, 59.31; H, 6.14; N, 6.92. Found: C, 59.28; H, 5.81; N, 6.62.

EXAMPLE 263

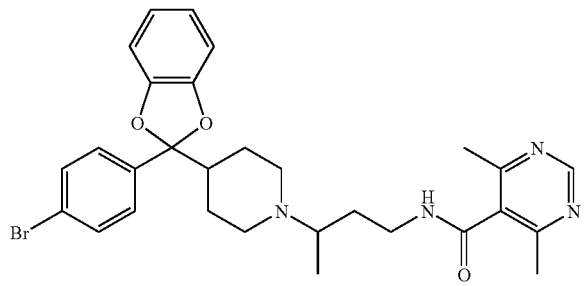

COMPOUND 263: 4,6-Dimethyl-pyrimidine-5-carboxylic acid (3-{4-[2-(4-bromo-phenyl)-benzo[1,3]dioxol-2-yl]-piperidin-1-yl}-butyl)-amide White solid. $^1$H NMR (CDCl$_3$) δ 0.71-1.08 (m, 2H), 0.93 (d, 3H, J=6.6 Hz), 1.44-1.59 (m, 2H), 1.65-1.79 (m, 1H), 1.82-1.99 (m, 3H), 2.32-2.39 (m, 1H), 2.50 (s, 6H), 2.65-2.78 (m, 3H), 3.21-3.29 (m, 1H), 3.82-3.91 (m, 1H), 6.74-6.93 (m, 4H), 7.24 (d, 2H, J=8.4 Hz), 7.46 (d, 2H, J=8.4 Hz), 8.77-8.78 (m, 1H), 9.04 (s, 1H). $^{13}$C NMR (CDCl$_3$) δ 13.99, 22.68, 26.36, 27.00, 31.42, 40.95, 44.39, 45.98, 52.92, 61.46, 109.39, 109.47, 118.38, 122.31, 123.72, 128.16, 128.42, 132.08, 139.60, 147.68, 147.78, 158.43, 163.67, 167.27. ES-MS m/z 565 (M+H). Anal. Calcd. for C$_{29}$H$_{33}$N$_4$O$_3$Br.0.2H$_2$O: C, 61.20; H, 5.92; N, 9.84. Found: C, 61.21; H, 5.97; N, 9.56.

Scheme 15 describes the preparation of Examples 264-270, using general procedures E or F, and reagents listed below.

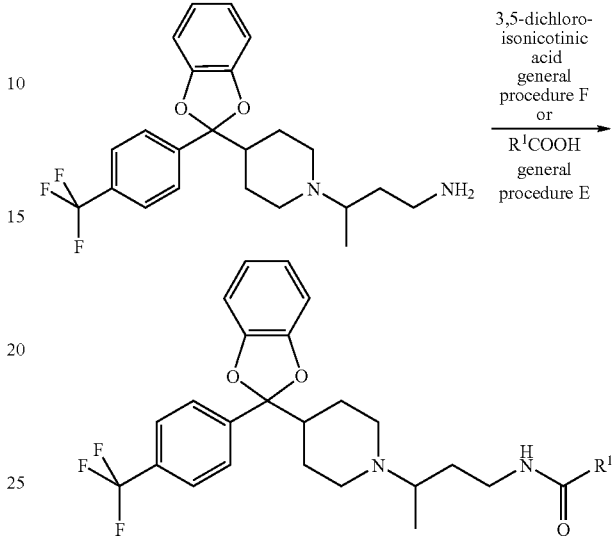

Scheme 15

| Example | R$^1$COOH |
|---|---|
| 264 | 3,5-dichloroisonicotinic acid |
| 265 | 2,4-dimethyl-1-oxy-nicotinic acid |
| 266 | 4,6-dimethyl-pyrimidine-5-carboxylic acid |
| 267 | 2,6-dimethylbenzoic acid |
| 268 | 2,4-dimethylnicotinic acid |
| 269 | 2-chloro-6-methylbenzoic acid |
| 270 | 3,5-dimethylisonicotinic acid |

EXAMPLE 264

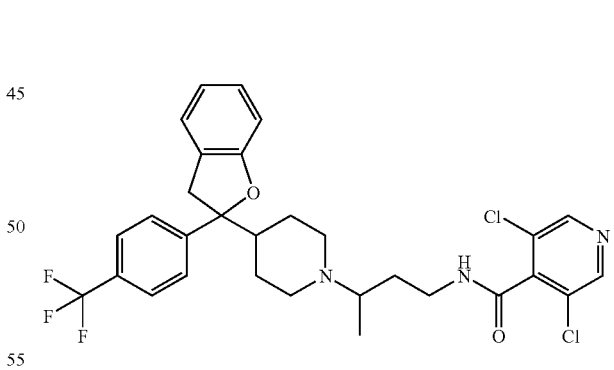

COMPOUND 264: 3,5-Dichloro-N-(3-{4-[2-(4-trifluoromethyl-phenyl)-benzo[1,3]dioxol-2-yl]-piperidin-1-yl}-butyl)-isonicotinamide A mixture of 4-(4-trifluorobenzoyl)-piperidine-1-carboxylic acid tert-butyl ester (357 mg, 1.00 mmol), catechol (440 mg, 4.00 mmol) and p-TsOH.H$_2$O (380 mg, 2.00 mmol) in xylene (10 mL) was heated at reflux using a Dean-Stark apparatus to remove water for 47 hours. Standard work-up and purification gave 4-[2-(4-trifluoromethyl-phenyl)-benzo [1,3]dioxol-2-yl]-piperidine (164 mg, 47%) as a yellow foam.

Using general procedure B with the above amine (115 mg, 0.330 mmol) and 2-(3-oxo-butyl)-isoindole-1,3-dione (143 mg, 0.660 mmol) and then using general procedure D gave 3-{4-[2-(4-trifluoromethyl-phenyl)-benzo[1,3]dioxol-2-yl]-piperidin-1-yl}-butylamine (96 mg, 69% over 2 steps) as a colorless oil.

COMPOUND 264 was isolated as a white foam. $^1$H NMR (CDCl$_3$) δ 0.77-1.15 (m, 2H), 0.95 (d, 3H, J=6.6 Hz), 1.48-1.59 (m, 3H), 1.70-1.82 (m, 1H), 2.37 (t, 1H, J=11.7 Hz), 2.74 (d, 1H, J=11.4 Hz), 2.81-2.88 (m, 2H), 3.30 (t, 1H, J=12 Hz), 3.86-3.94 (m, 1H), 6.78-6.87 (m, 4H), 7.50 (d, 2H, J=8.4 Hz), 7.60 (d, 2H, J=8.4 Hz), 8.60 (s, 2H), 9.12 and 9.14 (br s, 1H). $^{13}$C NMR (CDCl$_3$) δ 13.2, 25.7, 26.3, 30.1, 40.3, 43.6, 45.1, 52.0, 60.6, 108.7, 121.7, 123.9 (q, J=270.7 Hz), 125.1 (q, J=3.4 Hz), 126.1, 129.0, 130.9 (q, J=32.3 Hz), 143.2, 143.8, 146.76, 146.83, 147.6, 161.6. ES-MS m/z 595 (M+H). Anal. Calcd. for C$_{29}$H$_{28}$Cl$_2$F$_3$N$_3$O$_3$: C, 58.59; H, 4.75; N, 7.07; Cl, 11.93; F, 9.59. Found: C, 58.47; H, 4.77; N, 6.91; Cl, 11.96; F, 9.46.

EXAMPLE 265

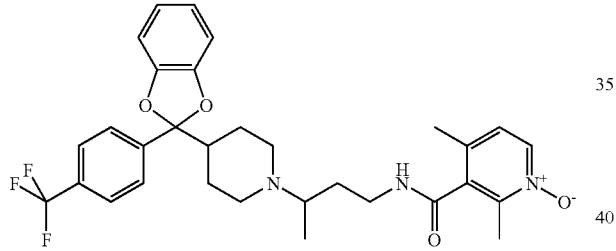

COMPOUND 265: 2,4-Dimethyl-1-oxy-N-(3-{4-[2-(4-trifluoromethyl-phenyl)-benzo[1,3]dioxol-2-yl]-piperidin-1-yl}-butyl)-nicotinamide White solid. $^1$H NMR (CDCl$_3$) δ0.96 (d, 3H, J=6.6 Hz), 0.97-1.26 (m, 2H), 1.49-1.61 (m, 3H), 1.68-1.83 (m, 1H), 1.91-2.04 (m, 2H), 2.29 (s, 3H), 2.31-2.42 (m, 1H), 2.44 (s, 3H), 2.67-2.84 (m, 3H), 2.36-3.39 (m, 1H), 3.73-3.84 (m, 1H), 6.76-6.90 (m, 4H), 6.93 (d, 1H, J=6.6 Hz), 7.54-7.63 (m, 4H), 8.13 (d, 1H, J=6.6 Hz), 8.48 (br s, 1H). $^{13}$C NMR (CDCl$_3$) δ 13.35, 15.02, 18.45, 25.80, 26.25, 32.07, 38.96, 44.52, 45.56, 51.44, 58.80, 108.58, 117.82, 121.60, 124.79, 123.92 (q, J=272 Hz), 125.06 (q, J=3 Hz), 126.30, 130.85 (q, J=32 Hz), 134.15, 136.87, 137.95, 143.78, 145.55, 146.93, 146.97, 165.43. ES-MS m/z 570 (M+H). Anal. Calcd. for C$_{31}$H$_{34}$N$_3$O$_4$F$_3$.1.1H$_2$O.0.1CH$_2$Cl$_2$: C, 62.47; H, 6.14; N, 7.03. Found: C, 62.66; H, 6.14; N, 7.12.

EXAMPLE 266

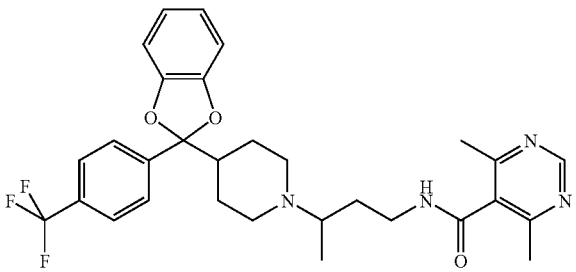

COMPOUND 266: 4,6-Dimethyl-pyrimidine-5-carboxylic acid (3-{4-[2-(4-trifluoromethyl-phenyl)-benzo[1,3]dioxol-2-yl]-piperidin-1-yl}-butyl)-amide White solid. $^1$H NMR (CDCl$_3$) δ 0.74-1.12 (m, 2H), 0.95 (d, 3H, J=6.9 Hz), 1.42-1.58 (m, 3H), 1.66-1.81 (m, 1H), 1.86-1.99 (m, 2H), 2.33-2.43 (m, 1H), 2.52 (s, 6H), 2.65-2.86 (m, 3H), 3.22-3.33 (m, 1H), 3.86-3.97 (m, 1H), 6.76-6.83 (m, 2H), 6.84-6.91 (m, 1H), 6.93-6.99 (m, 1H), 7.51 (d, 2H, J=8.1 Hz), 7.62 (d, 2H, J=8.4 Hz), 8.76 (br s, 1H), 9.07 (s, 1H). $^{13}$C NMR (CDCl$_3$) δ 13.20, 21.91, 25.52, 26.16, 30.68, 40.18, 43.59, 45.16, 52.14, 60.72, 108.68, 108.76, 117.32, 121.65, 123.89 (q, J=272 Hz), 125.17 (q, J=3 Hz), 126.12, 130.84, 130.93 (q, J=32 Hz), 143.72, 146.80, 146.90, 157.67, 162.93, 166.49. ES-MS m/z 555 (M+H). Anal. Calcd. for C$_{30}$H$_{33}$N$_4$O$_3$F$_3$.0.15CH$_2$Cl$_2$: C, 63.80; H, 5.91; N, 9.87. Found: C, 63.86; H, 6.01; N, 9.54.

EXAMPLE 267

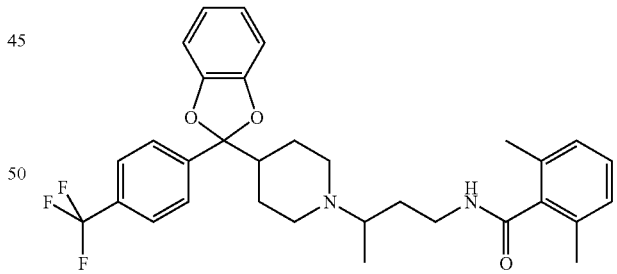

COMPOUND 267: 2,6-Dimethyl-N-(3-{4-[2-(4-trifluoromethyl-phenyl)-benzo[1,3]dioxol-2-yl]-piperidin-1-yl}-butyl)-benzamide White foam. $^1$H NMR (CDCl$_3$) δ 0.94 (d, 3H, J=6.6 Hz), 0.95-1.06 (m, 1H), 1.13-1.26 (m, 1H), 1.44-1.78 (m, 4H), 1.88-1.99 (m, 2H), 2.28-2.38 (m, 1H), 2.31 (s, 6H), 2.67-2.79

(m, 3H), 3.25-3.35 (m, 1H), 3.73-3.83 (m, 1H), 6.76-6.79 (m, 4H), 7.04 (d, 2H, J=7.5 Hz), 7.16-7.21 (m, 1H), 7.49-7.60 (m, 5H). ES-MS m/z 553 (M+H).

EXAMPLE 268

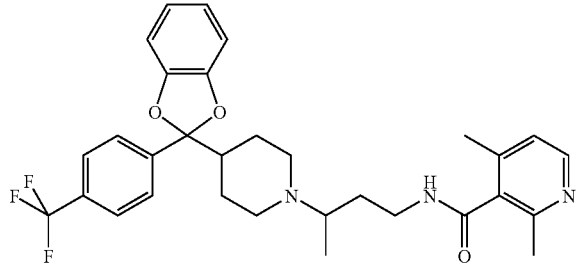

COMPOUND 268: 2,4-Dimethyl-N-(3-{4-[2-(4-trifluoromethyl-phenyl)-benzo[1,3]dioxol-2-yl]-piperidin-1-yl}-butyl)-nicotinamide White foam. $^1$H NMR (CDCl$_3$) δ 0.85-0.98 (m, 1H), 0.95 (d, 3H, J=6.6 Hz), 1.05-1.18 (m, 1H), 1.46-1.58 (m, 3H), 1.67-1.81 (m, 1H), 1.88-1.99 (m, 2H), 2.31 (s, 3H), 2.36 (t, 1H, J=12.3 Hz), 2.55 (s, 3H), 2.68-2.81 (m, 3H), 3.25-3.35 (m, 1H), 3.80-3.89 (m, 1H), 6.76-6.86 (m, 4H), 7.00 (d, 1H, J=5.1 Hz), 7.51 (d, 2H, J=8.1 Hz), 7.60 (d, 2H, J=8.4 Hz), 8.09 (br s, 1H), 8.43 (d, 1H, J=5.1 Hz). ES-MS m/z 554 (M+H).

EXAMPLE 269

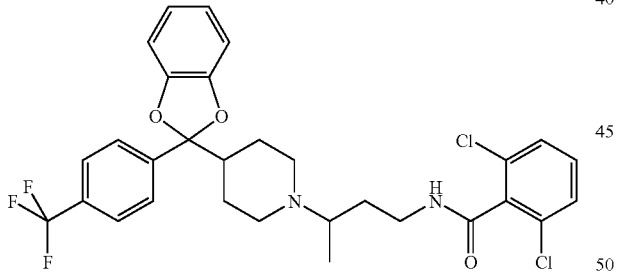

COMPOUND 269: 2-Chloro-6-methyl-N-(3-{4-[2-(4-trifluoromethyl-phenyl)-benzo[1,3]dioxol-2-yl]-piperidin-1-yl}-butyl)-benzamide White foam. $^1$H NMR (CDCl$_3$) δ 0.90-1.03 (m, 1H), 0.93 (d, 3H, J=6.6 Hz), 1.10-1.23 (m, 1H), 1.46-1.59 (m, 3H), 1.68-1.80 (m, 1H), 1.87-1.90 (m, 2H), 2.29-2.37 (m, 1H), 2.35 (s, 3H), 2.70-2.84 (m, 3H), 3.25-3.35 (m, 1H), 3.75-3.85 (m, 1H), 6.73-6.79 (m, 4H), 7.10-7.22 (m, 3H), 7.51 (d, 2H, J=8.1 Hz), 7.58 (d, 2H, J=8.4 Hz), 7.97 (br s, 1H). ES-MS m/z 573 (M+H).

EXAMPLE 270

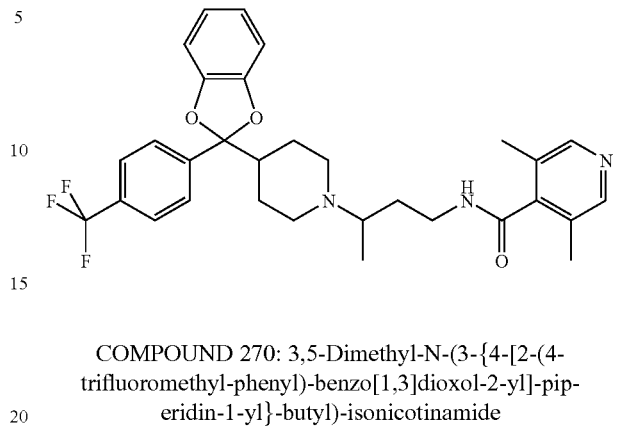

COMPOUND 270: 3,5-Dimethyl-N-(3-{4-[2-(4-trifluoromethyl-phenyl)-benzo[1,3]dioxol-2-yl]-piperidin-1-yl}-butyl)-isonicotinamide White foam. $^1$H NMR (CDCl$_3$) δ 0.94 (d, 3H, J=6.6 Hz), 0.79-0.92 (m, 1H), 1.01-1.51 (m, 1H), 1.42-1.59 (m, 2H), 1.66-1.80 (m, 2H), 1.88-1.99 (m, 1H), 2.29 (s, 6H), 2.36 (t, 1H, J=11.4 Hz), 2.67-2.81 (m, 3H), 3.23-3.30 (m, 1H), 3.80-3.90 (m, 1H), 6.75-6.89 (m, 4H), 7.51 (d, 2H, J=8.4 Hz), 7.60 (d, 2H, J=8.4 Hz), 8.32 (br s, 1H), 8.38 (s, 2H). ES-MS m/z 554 (M+H).

EXAMPLE 271

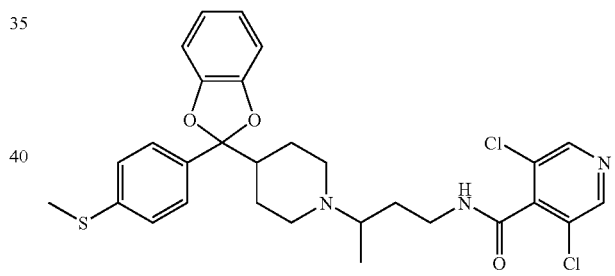

COMPOUND 271: 3,5-Dichloro-N-(3-{4-[2-(4-methylsulfanyl-phenyl)-benzo[1,3]dioxol-2-yl]-piperidin-1-yl}-butyl)-isonicotinamide A solution of 4-(4-methylsulfanyl-benzoyl)-piperidine-1-carboxylic acid tert-butyl ester (see EXAMPLE 28) (335 mg, 1.0 mmol), catechol (440 mg, 4.00 mmol) and p-TsOH.H$_2$O (380 mg, 2.00 mmol) in xylene (10 mL) was heated at reflux under a Dean-Stark trap for 45 hours. Standard work-up and purification gave 4-[2-(4-methylsulfanyl-phenyl)-benzo[1,3]dioxol-2-yl]-piperidine as a white solid (286 mg, 87%).

Using general procedure B with the above amine (65 mg, 0.20 mmol) and 2-(3-oxo-butyl)-isoindole-1,3-dione (86 mg, 0.40 mmol) and then using general procedure D afforded 3-{4-[2-(4-methylsulfanyl-phenyl)-benzo[1,3]dioxol-2-yl]-piperidin-1-yl}-butylamine as a white solid (42 mg, 53% over 2 steps).

Using general procedure F, 3,5-dichloroisonicotinic acid (41 mg, 0.21 mmol) and the above amine (42 mg, 0.11 mmol)

gave COMPOUND 271 as a white solid (57 mg, 93%). $^1$H NMR (CDCl$_3$) δ 0.79-1.04 (m, 2H), 0.95 (d, 3H, J=6.3 Hz), 1.41-1.94 (m, 6H), 2.37 (t, 1H, J=12.0 Hz), 2.46 (s, 3H), 2.73-2.88 (m, 3H), 3.30 (t, 1H, J=12.0 Hz), 3.89 (m, 1H), 6.77-6.85 (m, 4H), 7.19 (d, 2H, J=8.4 Hz), 7.27 (d, 2H, J=7.4 Hz), 8.59 (s, 2H), 9.24 (br s, 1H). $^{13}$C NMR (CDCl$_3$) δ 13.58, 15.81, 26.13, 26.70, 30.41, 40.66, 44.01, 45.57, 52.50, 61.05, 108.97, 118.43, 121.79, 126.10, 126.41, 129.30, 136.70, 139.81, 143.51, 147.45, 147.54, 148.03, 162.05. ES-MS m/z 573 (M+2). Anal. Calcd. for $C_{29}H_{31}N_3Cl_2O_3S \cdot 0.5CH_2Cl_2$: C, 57.61; H, 5.24; N, 6.83. Found: C, 57.43; H, 5.27; N, 6.78.

$C_{29}H_{31}N_3Cl_2O_4S \cdot 0.96CH_2Cl_2$: C, 53.70, H, 4.95; N, 6.27; Cl, 20.74; S, 4.78. Found: C, 53.44; H, 4.89; N, 6.28; Cl, 20.56; S, 4.65.

EXAMPLE 273

EXAMPLE 272

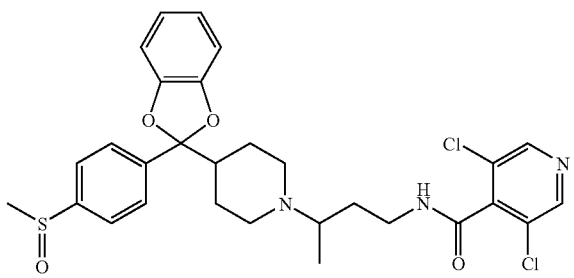

COMPOUND 272: 3,5-Dichloro-N-(3-{4-[2-(4-methanesulfinyl-phenyl)-benzo[1,3]dioxol-2-yl]-piperidin-1-yl}-butyl)-isonicotinamide A solution of 4-[2-(4-methylsulfanyl-phenyl)-benzo[1,3]dioxol-2-yl]-piperidine (see EXAMPLE 271) (220 mg, 0.673 mmol), Boc$_2$O (161 mg, 0.74 mmol) and Et$_3$N (0.14 mL, 1.01 mmol) in CH$_2$Cl$_2$ (5 mL) was stirred at room temperature for 1.5 hours. Standard work-up and purification afforded 4-[2-(4-methylsulfanyl-phenyl)-benzo[1,3]dioxol-2-yl]-piperidine-1-carboxylic acid tert-butyl ester as a white solid (270 mg, 94%).

To the above thiol (270 mg, 0.632 mmol) in Et$_2$O (5 mL) cooled to 0° C. was added hydrogen peroxide (50%, 0.22 mL, 3.16 mmol) and the mixture was stirred at 0° C. for 2.5 hours. Work-up and purification afforded 4-[2-(4-methanesulfinyl-phenyl)-benzo[1,3]dioxol-2-yl]-piperidine-1-carboxylic acid tert-butyl ester as a white solid (283 mg, 100%).

Using general procedure C with the above carbamate (116 mg, 0.26 mmol), then general procedure B with the resulting amine and 2-(3-oxo-butyl)-isoindole-1,3-dione (114 mg, 0.53 mmol) and then using general procedure D afforded 3-{4-[2-(4-methanesulfinyl-phenyl)-benzo[1,3]dioxol-2-yl]-piperidin-1-yl}-butylamine as a white solid (80 mg, 74% over 3 steps).

Using general procedure F, 3,5-dichloroisonicotinic acid (74 mg, 0.39 mmol) and the above amine (80 mg, 0.19 mmol) gave COMPOUND 272 as a white solid (99 mg, 86%). $^1$H NMR (CDCl$_3$) δ 0.80-1.12 (m, 2H), 0.95 (d, 3H, J=6.6 Hz), 1.48-1.60 (m, 3H), 1.72-1.98 (m, 3H), 2.37 (t, 1H, J=11.4 Hz), 2.69 (s, 3H), 2.73-2.87 (m, 3H), 3.30 (t, 1H, J=11.4 Hz), 3.86-3.92 (m, 1H), 6.78-6.88 (m, 4H), 7.53 (d, 2H, J=8.4 Hz), 6.62 (d, 2H, J=8.4 Hz), 8.59 (s, 2H), 9.13 (br s, 1H). $^{13}$C NMR (CDCl$_3$) δ 13.62, 26.06, 26.62, 30.51, 31.98, 40.58, 44.02, 44.19, 45.57, 52.33, 60.89, 109.09, 117.91, 122.03, 123.82, 127.11, 129.34, 143.50, 146.69, 147.20, 147.28, 148.01, 161.99. ES-MS m/z 588 (M+H). Anal. Calcd. for

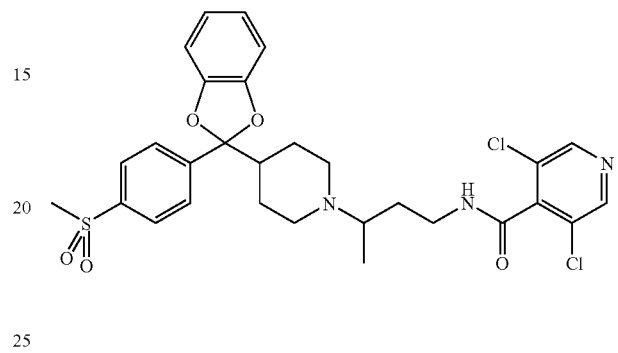

COMPOUND 273: 3,5-Dichloro-N-(3-{4-[2-(4-methanesulfonyl-phenyl)-benzo[1,3]dioxol-2-yl]-piperidin-1-yl}-butyl)-isonicotinamide To 4-[2-(4-methylsulfanyl-phenyl)-benzo[1,3]dioxol-2-yl]-piperidine-1-carboxylic acid tert-butyl ester (see EXAMPLE 272) (166 mg, 0.375 mmol) in MeOH (5 mL) cooled to 0° C. was added OXONE® (461 mg, 0.75 mmol) and the mixture was stirred at room temperature for 2 hours. A second aliquot of OXONE® (461 mg, 0.75 mmol) was added and the mixture stirred at room temperature for 24 hours. Standard work-up gave 4-[2-(4-methanesulfonyl-phenyl)-benzo[1,3]dioxol-2-yl]-piperidine-1-carboxylic acid tert-butyl ester as a white solid (172 mg, 100%).

Using general procedure C with the above carbamate (170 mg, 0.37 mmol), then using general procedure B with the resulting amine and 2-(3-oxo-butyl)-isoindole-1,3-dione (70 mg, 0.32 mmol) followed by general procedure D gave 3-{4-[2-(4-methanesulfonyl-phenyl)-benzo[1,3]dioxol-2-yl]-piperidin-1-yl}-butylamine as a white solid (46 mg, 68% over 3 steps).

Using general procedure F, 3,5-dichloroisonicotinic acid (41 mg, 0.21 mmol) and the above amine (46 mg, 0.11 mmol) gave COMPOUND 273 as a white solid (55 mg, 85%). $^1$H NMR (CDCl$_3$) δ 0.84-1.08 (m, 2H), 0.96 (d, 3H, J=6.0 Hz), 1.41-1.59 (m, 3H), 1.75-1.98 (m, 3H), 2.38 (t, 1H, J=11.1 Hz), 2.74-2.85 (m, 3H), 3.02 (s, 3H), 3.31 (t, 1H, J=12.0 Hz), 3.88 (m, 1H), 6.80-6.88 (m, 4H), 7.59 (d, 2H, J=8.4 Hz), 7.92 (d, 2H, J=8.4 Hz), 8.60 (s, 2H), 9.09 (br s, 1H). $^{13}$C NMR (CDCl$_3$) δ 13.20, 25.56, 26.15, 30.10, 40.20, 43.55, 44.38, 44.98, 51.93, 60.57, 108.82, 117.13, 121.82, 126.82, 127.30, 128.97, 140.91, 143.14, 145.95, 146.62, 146.68, 147.63, 161.59. ES-MS m/z 606 (M+3). Anal. Calcd. for $C_{29}H_{31}N_3Cl_2O_5S \cdot 0.1CH_2Cl_2$: C, 52.26; H, 4.82; N, 6.09; Cl, 20.57; S, 4.65. Found: C, 52.23; H, 4.79; N, 6.05; Cl, 20.85; S, 4.54.

EXAMPLE 274

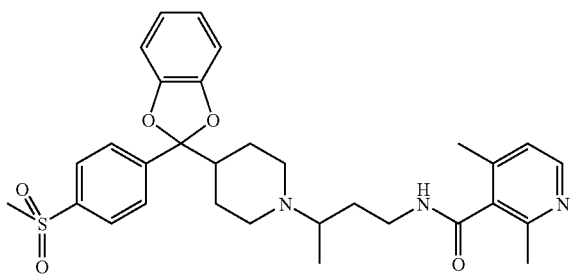

COMPOUND 274: N-(3-{4-[2-(4-Methanesulfonyl-phenyl)-benzo[1,3]dioxol-2-yl]-piperidin-1-yl}-butyl)-2,4-dimethyl-nicotinamide Using general procedure E, 3-{4-[2-(4-methanesulfonyl-phenyl)-benzo[1,3]dioxol-2-yl]-piperidin-1-yl}-butylamine (see EXAMPLE 273) (139 mg, 0.32 mmol) and 2,4-dimethylnicotinic acid (53 mg, 0.35 mmol) afforded COMPOUND 274 as a white solid (59 mg, 32%). $^1$H NMR (CDCl$_3$) δ 0.84-1.19 (m, 2H), 0.95 (d, 3H, J=6.6 Hz), 1.45-1.62 (m, 3H), 1.66-1.79 (m, 1H), 1.89-1.99 (m, 2H), 2.31 (s, 3H), 2.36 (t, 1H, J=11.7 Hz), 2.54 (s, 3H), 2.68-2.81 (m, 3H), 3.02 (s, 3H), 3.26-3.34 (m, 1H), 3.49 (s, 2H), 3.80-3.89 (m, 1H), 6.78-6.88 (m, 3H), 7.00 (d, 1H, J=4.8 Hz), 7.60 (d, 2H, J=8.1 Hz), 7.91 (d, 2H, J=7.8 Hz), 8.05 (br s, 1H), 8.42 (d, 1H, J=4.8 Hz). $^{13}$C NMR (CDCl$_3$) δ 13.58, 19.20, 22.67, 25.88, 26.50, 31.68, 40.00, 44.24, 44.80, 45.65, 52.34, 60.55, 109.09, 117.67, 122.11, 122.92, 127.29, 127.63, 134.00, 141.22, 144.09, 146.41, 147.20, 149.23, 154.55, 168.70. ES-MS m/z 564 (M+H). Anal. Calcd. for C$_{31}$H$_{37}$N$_3$O$_5$S.1.0CH$_2$Cl$_2$.0.3H$_2$O: C, 58.77; H, 6.10; N, 6.42. Found: C, 58.42; H, 5.79; N, 6.37.

EXAMPLE 275

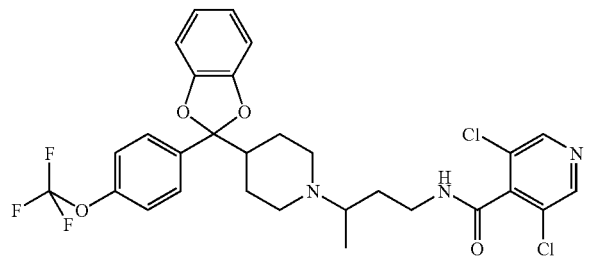

COMPOUND 275: 3,5-Dichloro-N-(3-{4-[2-(4-trifluoromethoxy-phenyl)-benzo[1,3]dioxol-2-yl]-piperidin-1-yl}-butyl)-isonicotinamide A solution of 4-(4-trifluoromethoxy-benzoyl)-piperidine-1-carboxylic acid tert-butyl ester (see EXAMPLE 247) (373 mg, 1.0 mmol), catechol (440 mg, 4.0 mmol) and p-TsOH.H$_2$O (380 mg, 2.0 mmol) in xylene (10 mL) was heated at reflux under a Dean-Stark trap for 44 hours. Standard work-up and purification gave 4-[2-(4-trifluoromethoxy-phenyl)-benzo[1,3]dioxol-2-yl]-piperidine as a white solid (260 mg, 71%).

Using general procedure B with the above amine (260 mg, 0.712 mmol) and 2-(3-oxo-butyl)-isoindole-1,3-dione (309 mg, 1.42 mmol) and then using general procedure D gave 3-{4-[2-(4-trifluoromethoxy-phenyl)-benzo[1,3]dioxol-2-yl]-piperidin-1-yl}-butylamine as a white solid (193 mg, 63% over 2 steps).

Using general procedure F, 3,5-dichloroisonicotinic acid (62 mg, 0.32 mmol) and the above amine (75 mg, 0.16 mmol) gave COMPOUND 275 as a white solid (68 mg, 64%). $^1$H NMR (CDCl$_3$) δ 0.78-1.10 (m, 2H), 0.95 (d, 3H, J=6.6 Hz), 1.48-1.61 (m, 3H), 1.73-1.99 (m, 3H), 2.38 (t, 1H, J=11.1 Hz), 2.73-2.87 (m, 3H), 3.31 (t, 1H, J=11.1 Hz), 3.86-3.93 (m, 1H), 6.78-6.86 (m, 4H), 7.17 (d, 2H, J=8.1 Hz), 7.40 (d, 2H, J=8.4 Hz), 8.59 (s, 2H), 9.18 (br s, 1H). $^{13}$C NMR (CDCl$_3$) δ 13.60, 26.08, 26.66, 30.41, 40.71, 43.98, 45.65, 52.43, 61.03, 109.07, 117.94, 120.76 (q, J=258 Hz), 120.85, 121.98, 127.61, 129.34, 138.84, 143.55, 147.24, 147.32, 148.02, 149.79, 162.01. ES-MS m/z 611 (M+H). Anal. Calcd. for C$_{29}$H$_{28}$N$_3$Cl$_2$O$_4$F$_3$.0.3CH$_2$Cl$_2$.0.2C$_6$H$_{14}$: C, 56.09; H, 4.85; N, 6.43; Cl, 14.11; F, 8.73. Found: C, 56.15; H, 4.60; N, 6.57; Cl, 14.06; F, 8.73.

EXAMPLE 276

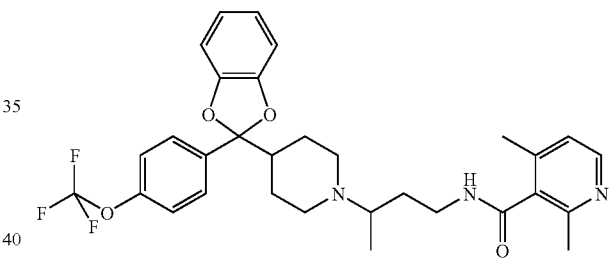

COMPOUND 276: 2,4-Dimethyl-N-(3-{4-[2-(4-trifluoromethoxy-phenyl)-benzo[1,3]dioxol-2-yl]-piperidin-1-yl}-butyl)-nicotinamide Using general procedure E, 3-{4-[2-(4-trifluoromethoxy-phenyl)-benzo[1,3]dioxol-2-yl]-piperidin-1-yl}-butylamine (see EXAMPLE 275) (135 mg, 0.31 mmol) and 2,4-dimethylnicotinic acid (51 mg, 0.34 mmol) afforded COMPOUND 276 (55 mg, 31%). $^1$H NMR (CDCl$_3$) δ 0.83-1.17 (m, 2H), 0.95 (d, 3H, J=6.6 Hz), 1.46-1.63 (m, 3H), 1.67-1.80 (m, 1H), 1.86-1.99 (m, 2H), 2.31 (s, 3H), 2.33-2.40 (m, 1H), 2.54 (s, 3H), 2.67-2.81 (m, 3H), 3.25-3.35 (m, 1H), 3.79-3.89 (m, 1H), 6.76-6.86 (m, 4H), 6.99 (d, 1H, J=5.1 Hz), 7.17 (d, 2H, J=8.1 Hz), 7.40-7.44 (m, 2H), 8.11 (br s, 1H), 8.42 (d, 1H, J=4.8 Hz). $^{13}$C NMR (CDCl$_3$) δ 13.57, 19.19, 22.63, 25.94, 26.56, 31.64, 40.02, 44.32, 45.92, 52.42, 60.54, 108.92, 118.07, 120.78, 121.86, 122.91, 127.68, 133.99, 138.89, 144.02, 147.35, 149.21, 149.76, 154.55, 168.73. ES-MS m/z 570 (M+H). Anal. Calcd. for C$_{31}$H$_{34}$N$_3$F$_3$O$_4$.0.28CH$_2$Cl$_2$: C, 63.31; H, 5.87; N, 7.08. Found: C, 63.01; H, 5.88; N, 7.47.

EXAMPLE 277

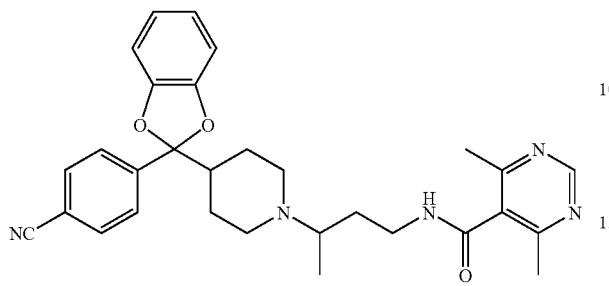

COMPOUND 277: 4,6-Dimethyl-pyrimidine-5-carboxylic acid (3-{4-[2-(4-cyano-phenyl)-benzo[1,3]dioxol-2-yl]-piperidin-1-yl}-butyl)-amide 4-(4-Bromo-benzoyl)-piperidine-1-carboxylic acid tert-butyl ester (5.3 g, 13 mmol), catechol (5.73 g, 52 mmol), p-TsOH.H$_2$O (4.95 g, 26 mmol) and xylene (65 mL) were heated at 180° C. for 24 hours using a Dean-Stark apparatus to remove water. Work-up and purification gave the desired amine.

The above secondary amine (4.92 g), Boc$_2$O (4.48 g, 20.49 mmol), Et$_3$N (2.85 mL, 20.49 mmol) and THF (46 mL) were stirred at room temperature for 2.5 hours. Standard work-up and purification afforded 4-[2-(4-bromo-phenyl)-benzo[1,3]dioxol-2-yl]-piperidine-1-carboxylic acid tert-butyl ester as a white solid (4.06 g, 68% over 2 steps).

The above bromide (2.0 g, 4.34 mmol), Zn(CN)$_2$ (306 mg, 2.60 mmol), DPPF (240 mg, 0.43 mmol) and degassed DMF (22 mL) were flushed with N$_2$. Pd$_2$(dba)$_3$ (199 mg, 0.22 mmol) was added and the mixture was flushed with N$_2$ for an additional 5 minutes. The reaction mixture was heated at 130° C. overnight to afford 4-[2-(4-cyano-phenyl)-benzo[1,3]dioxol-2-yl]-piperidine-1-carboxylic acid tert-butyl ester as a white solid (1.49 g, 85%) after work-up and purification.

Using general procedure C with the above substrate (1.49 g, 3.67 mmol), then general procedure B with the resulting amine and 2-(3-oxo-butyl)-isoindole-1,3-dione (1.09 g, 5.02 mmol) and then using general procedure D afforded 4-{2-[1-(3-amino-1-methyl-propyl)-piperidin-4-yl]-benzo[1,3]dioxol-2-yl}-benzonitrile as a colourless oil (370 mg, 37% over 3 steps).

Using general procedure E, the above amine (99 mg, 0.26 mmol) and 4,6-dimethyl-pyrimidine-5-carboxylic acid (44 mg, 0.29 mmol) afforded COMPOUND 277 as a white foam (120 mg, 89%). $^1$H NMR (CDCl$_3$) δ 0.74-1.11 (m, 2H), 0.95 (d, 3H, J=6.6 Hz), 1.41-1.55 (m, 3H), 1.67-1.81 (m, 1H), 1.86-1.99 (m, 2H), 2.34-2.44 (m, 1H), 2.52 (s, 6H), 2.67-2.82 (m, 3H), 3.23-3.30 (m, 1H), 3.86-3.94 (m, 1H), 6.77-6.83 (m, 2H), 6.86-6.90 (m, 1H), 6.94-6.97 (m, 1H), 7.51 (d, 2H, J=7.8 Hz), 7.65 (d, 2H, J=8.1 Hz), 8.68-8.70 (m, 1H), 9.06 (s, 1H). ES-MS m/z 512 (M+H).

EXAMPLE 278

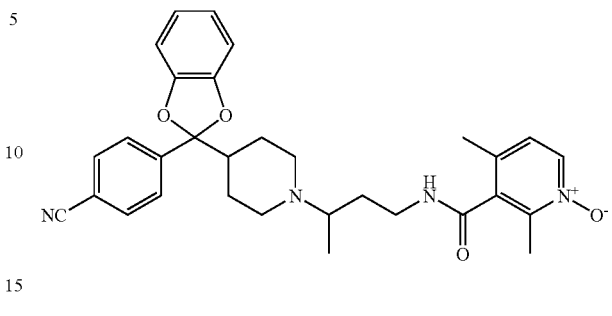

COMPOUND 278: N-(3-{4-[2-(4-Cyano-phenyl)-benzo[1,3]dioxol-2-yl]-piperidin-1-yl}-butyl)-2,4-dimethyl-1-oxy-nicotinamide Using general procedure E, 4-{2-[1-(3-amino-1-methyl-propyl)-piperidin-4-yl]-benzo[1,3]dioxol-2-yl}-benzonitrile (see EXAMPLE 277) (96 mg, 0.25 mmol) and 2,4-dimethyl-1-oxy-nicotinic acid (47 mg, 0.28 mmol) afforded COMPOUND 278 as a white foam (126 mg, 94%). $^1$H NMR (CDCl$_3$) δ 0.90-1.23 (m, 2H), 0.96 (d, 3H, J=6.6 Hz), 1.51-1.82 (m, 3H), 1.91-2.03 (m, 2H), 2.29 (s, 3H), 2.32-2.40 (m, 1H), 2.43 (s, 3H), 2.69-2.82 (m, 3H), 3.28-3.38 (m, 1H), 3.72-3.82 (m, 1H), 6.77-6.88 (m, 4H), 6.94 (d, 1H, J=6.6 Hz), 7.55-7.58 (m, 2H), 7.63-7.66 (m, 2H), 8.12 (d, 1H, J=6.6 Hz), 8.40 (br s, 1H). ES-MS m/z 527 (M+H).

EXAMPLE 279

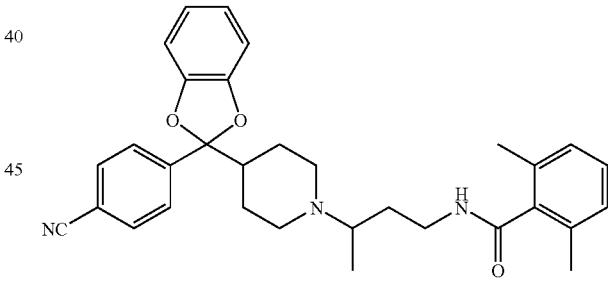

COMPOUND 279: N-(3-{4-[2-(4-Cyano-phenyl)-benzo[1,3]dioxol-2-yl]-piperidin-1-yl}-butyl)-2,6-dimethyl-benzamide Using general procedure E, 4-{2-[1-(3-amino-1-methyl-propyl)-piperidin-4-yl]-benzo[1,3]dioxol-2-yl}-benzonitrile (see EXAMPLE 277) (64 mg, 0.17 mmol) and 2,6-dimethyl-benzoic acid (28 mg, 0.19 mmol) afforded COMPOUND 279 as a white foam (65 mg, 75%). $^1$H NMR (CDCl$_3$) δ0.93 (d, 3H, J=6.6 Hz), 0.94-1.23 (m, 2H), 1.42-1.58 (m, 3H), 1.65-1.78 (m, 1H), 1.86-1.98 (m, 2H), 2.28-2.36 (m, 1H), 2.31 (s, 6H), 2.68-2.79 (m, 3H), 3.26-3.36 (m, 1H), 3.71-3.82 (m, 1H), 6.76-6.80 (m, 4H), 7.03 (d, 2H, J=7.8 Hz), 7.15-7.20 (m, 1H), 7.43 (br s, 1H), 7.51-7.53 (m, 2H), 7.61-7.64 (m, 2H). ES-MS m/z 510 (M+H).

EXAMPLE 280

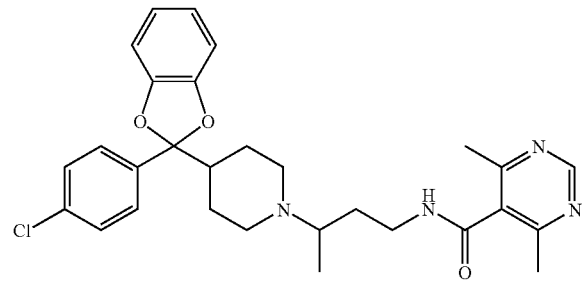

COMPOUND 280: 4,6-Dimethyl-pyrimidine-5-carboxylic acid (3-{4-[2-(4-chloro-phenyl)-benzo [1,3] dioxol-2-yl]-piperidin-1-yl}-butyl)-amide To a solution of 4-bromochlorobenzene (1.35 g, 7.03 mmol) in THF (30 mL) cooled to −78° C. was added n-BuLi (2.5M in THF, 3.00 mL, 7.5 mmol) and the mixture was stirred at −78° C. for 30 minutes. TMEDA (1.06 mL, 7.02 mmol) and 4-formyl-piperidine-1-carboxylic acid tert-butyl ester (1.00 g, 4.69 mmol) in THF (10 mL) were added and the mixture stirred at −78° C. for 3 hours. The reaction was quenched with saturated aqueous $NH_4Cl$ (30 mL) and after work-up and purification afforded 4-[(4-chloro-phenyl)-hydroxy-methyl]-piperidine-1-carboxylic acid tert-butyl ester as a white solid (450 mg, 30%).

A mixture of the above alcohol (450 mg, 1.38 mmol), $SiO_2$ (1.50 g) and PCC (895 mg, 4.15 mmol) in $CH_2Cl_2$ (25 mL) was stirred at room temperature for 1 hour to afford 4-(4-chloro-benzoyl)-piperidine-1-carboxylic acid tert-butyl ester as a yellow solid (440 mg, 99%) after purification.

The above ketone (450 mg, 1.39 mmol), catechol (614 mg, 5.58 mmol), p-TsOH.$H_2O$ (529 mg, 2.78 mmol), toluene (5 mL) and xylene (15 mL) were heated at 185° C. overnight using a Dean-Stark apparatus to remove water. Work-up and purification afforded 4-[2-(4-chloro-phenyl)-benzo[1,3]dioxol-2-yl]-piperidine as a pink oil (221 mg, 50%).

Using general procedure B with the above amine (221 mg, 0.70 mmol) and 2-(3-oxo-butyl)-isoindole-1,3-dione (305 mg, 1.40 mmol) and then using general procedure D afforded 3-{4-[2-(4-chloro-phenyl)-benzo[1,3]dioxol-2-yl]-piperidin-1-yl}-butylamine as a colourless oil (185 mg, 68% over 2 steps).

Using general procedure E, the above amine (86 mg, 0.22 mmol) and 4,6-dimethyl-pyrimidine-5-carboxylic acid (37 mg, 0.24 mmol) afforded COMPOUND 280 as a white foam (100 mg, 86%). $^1$H NMR (CDCl$_3$) δ 0.71-0.85 (m, 1H), 0.95 (d, 3H, J=6.6 Hz), 0.96-1.09 (m, 1H), 1.45-1.61 (m, 3H), 1.67-1.80 (m, 1H), 1.85-1.98 (m, 2H), 2.37 (td, 1H, J=11.4, 2.1 Hz), 2.51 (s, 6H), 2.67-2.83 (m, 3H), 3.22-3.32 (m, 1H), 3.86-3.95 (m, 1H), 6.75-6.81 (m, 2H), 6.82-6.88 (m, 1H), 6.91-6.95 (m, 1H), 7.29-7.33 (m, 4H), 8.76-8.78 (m, 1H), 9.06 (s, 1H). $^{13}$C NMR (CDCl$_3$) δ 13.58, 22.29, 25.97, 26.63, 30.99, 40.61, 43.97, 45.64, 52.59, 61.16, 108.99, 109.08, 117.95, 121.90, 127.44, 128.73, 158.06, 163.28. ES-MS m/z 521 (M+H). Anal. Calcd. for $C_{29}H_{33}N_4ClO_3$.0.05$CH_2Cl_2$: C, 66.42; H, 6.35; N, 10.67. Found: C, 66.32; H, 6.43; N, 10.49.

EXAMPLE 281

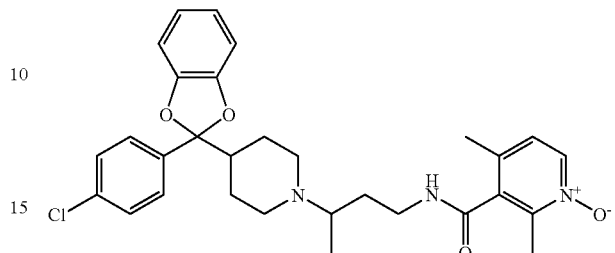

COMPOUND 281: N-(3-{4-[2-(4-Chloro-phenyl)-benzo[1,3]dioxol-2-yl]-piperidin-1-yl}-butyl)-2,4-dimethyl-1-oxy-nicotinamide Using general procedure E, 3-{4-[2-(4-chloro-phenyl)-benzo[1,3]dioxol-2-yl]-piperidin-1-yl}-butylamine (see EXAMPLE 280) (86 mg, 0.22 mmol) and 2,4-dimethyl-1-oxy-nicotinic acid (41 mg, 0.25 mmol) afforded COMPOUND 281 as a white foam (63 mg, 53%). $^1$H NMR (CDCl$_3$) δ 0.87-1.00 (m, 1H), 0.95 (d, 3H, J=6.6 Hz), 1.06-1.19 (m, 1H), 1.50-1.81 (m, 4H), 1.89-2.02 (m, 2H), 2.28 (s, 3H), 2.37 (td, 1H, J=12.0, 1.8 Hz), 2.46 (s, 3H), 2.68-2.81 (m, 3H), 3.26-3.36 (m, 1H), 3.76-3.86 (m, 1H), 6.76-6.88 (m, 4H), 6.93 (d, 1H, J=6.6 Hz), 7.29-7.38 (m, 4H), 8.15 (d, 1H, J=6.6 Hz), 8.45 (br s, 1H). $^{13}$C NMR (CDCl$_3$) δ 13.59, 15.58, 18.78, 26.11, 26.73, 31.53, 40.12, 44.32, 45.80, 52.40, 60.42, 108.96, 109.03, 111.56, 121.93, 125.04, 127.56, 128.69, 133.34, 138.75, 165.91. ES-MS m/z 536 (M+H). Anal. Calcd. for $C_{30}H_{34}N_3ClO_4$.0.2$CH_2Cl_2$: C, 65.59; H, 6.27; N, 7.60. Found: C, 65.73; H, 6.55; N, 7.45.

EXAMPLE 282

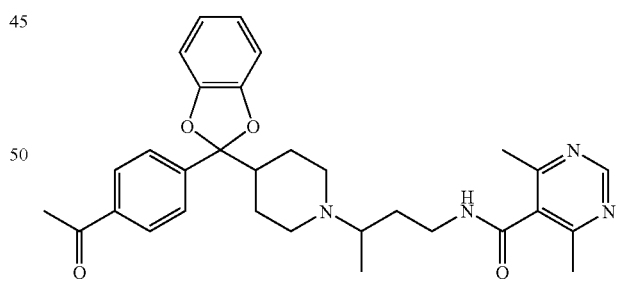

COMPOUND 282: 4,6-Dimethyl-pyrimidine-5-carboxylic acid (3-{4-[2-(4-acetyl-phenyl)-benzo[1,3]dioxol-2-yl]-piperidin-1-yl}-butyl)-amide To a solution of 4-[2-(4-bromo-phenyl)-benzo[1,3]dioxol-2-yl]-piperidine-1-carboxylic acid tert-butyl ester (see EXAMPLE 277) (742 mg, 1.61 mmol) in $Et_2O$ (20 mL) cooled to −78° C. was added BuLi (2.5M in Hexanes, 0.80 mL, 2.0 mmol) and the mixture was stirred at −10° C. for 1 hour. The mixture was cooled to −78° C., acetaldehyde (0.5 mL) was added and the mixture was warmed to room temperature and stirred for 30 minutes. Work-up and purification gave the desired substrate. To the substrate in CH$_2$Cl$_2$ (3 mL) were added H$_{20}$ (2 drops) and TFA (1 mL) and the mixture was stirred at room temperature for 1 hour to afford 1-[4-(2-piperidin-4-yl-benzo[1,3]dioxol-2-yl)-phenyl]-ethanol as a pale yellow solid (170 mg, 32% over 2 steps) after basic work-up and purification.

Using general procedure B with the above amine (166 mg, 0.510 mmol) and 2-(3-oxo-butyl)-isoindole-1,3-dione (222 mg, 1.03 mmol) and then using general procedure D afforded 1-(4-{2-[1-(3-amino-1-methyl-propyl)-piperidin-4-yl]-benzo[1,3]dioxol-2-yl}-phenyl)-ethanol as a colourless oil (139 mg, 69% over 2 steps).

Using general procedure E, the above amine (139 mg, 0.351 mmol) and 4,6-dimethyl-pyrimidine-5-carboxylic acid (59 mg, 0.38 mmol) afforded the desired amide, which was subsequently oxidized with MnO$_2$ (1.05 g, 12.1 mmol) to afford COMPOUND 282 as a white solid (86 mg, 52% over 2 steps) following filtration through Celite® and purification. $^1$H NMR (CDCl$_3$) δ 0.76-1.10 (m, 2H), 0.94 (d, 3H, J=6.6 Hz), 1.44-1.61 (m, 3H), 1.94 (t, 2H, J=11.7 Hz), 2.38 (t, 1H, J=11.4 Hz), 2.51 (s, 6H), 2.58 (s, 3H), 2.67-2.80 (m, 3H), 3.23-3.31 (m, 1H), 3.86-3.93 (m, 1H), 6.78-6.79 (m, 2H), 6.86-6.87 (m, 1H), 6.94-6.97 (m, 1H), 7.48 (d, 2H, J=8.1 Hz), 7.93 (d, 2H, J=8.1 Hz), 8.75-8.77 (m, 1H), 9.07 (s, 1H). $^{13}$C NMR (CDCl$_3$) δ 13.39, 22.10, 25.74, 26.36, 26.90, 30.87, 40.37, 43.79, 45.30, 52.35, 60.93, 108.83, 108.92, 117.74, 121.79, 126.13, 128.37, 131.02, 137.52, 144.87, 147.07, 147.17, 157.86, 163.11, 166.69, 197.84. ES-MS m/z 529 (M+H). Anal. Calcd. for C$_{31}$H$_{36}$N$_4$O$_4$.0.15CH$_2$Cl$_2$: C, 69.11; H, 6.76; N, 10.35. Found: C, 69.08; H, 6.83; N, 10.32.

EXAMPLE 283

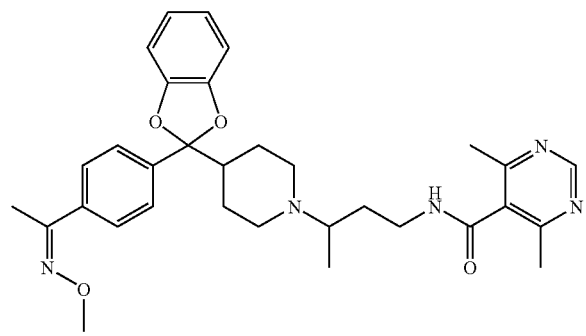

COMPOUND 283: 4,6-Dimethyl-pyrimidine-5-carboxylic acid [3-(4-{2-[4-(1-methoxyimino-ethyl)-phenyl]-benzo[1,3]dioxol-2-yl}-piperidin-1-yl)-butyl]-amide To a solution of COMPOUND 282 (47 mg, 0.089 mmol) in MeOH (4 mL) was added methoxylamine hydrochloride (19 mg, 0.22 mmol) and NaOAc (21 mg, 0.25 mmol) and the mixture was stirred at room temperature overnight. Standard work-up and purification afforded COMPOUND 283 as a white solid (38 mg, 75%). $^1$H NMR (CDCl$_3$) δ 0.76-0.81 (m, 1H), 0.94 (d, 3H, J=6.6 Hz), 1.01-1.06 (m, 1H), 1.45-1.75 (m, 4H), 1.88-1.96 (m, 2H), 2.19 (s, 3H), 2.37 (t, 1H, J=10.7 Hz), 2.51 (s, 6H), 2.66-2.82 (m, 3H), 3.22-3.30 (m, 1H), 3.84-3.94 (m, 1H), 3.98 (s, 3H), 6.75-6.78 (m, 2H), 6.84-6.87 (m, 1H), 6.93-6.96 (m, 1H), 7.37 (d, 2H, J=8.4 Hz), 7.61 (d, 2H, J=8.4 Hz), 8.82-8.83 (m, 1H), 9.08 (s, 1H). $^{13}$C NMR (CDCl$_3$) δ 12.63, 13.18, 21.54, 21.89, 25.60, 26.25, 30.62, 40.22, 43.57, 45.17, 52.24, 60.78, 61.77, 62.00, 108.53, 108.63, 117.87, 121.39, 125.35, 125.69, 125.79, 127.78, 130.82, 137.07, 140.48, 147.05, 147.16, 154.18, 157.68, 162.88, 166.51. ES-MS m/z 558 (M+H). Anal. Calcd. for C$_{32}$H$_{39}$N$_5$O$_4$.0.15CH$_2$Cl$_2$: C, 67.70; H, 6.94; N, 12.28. Found: C, 67.71; H, 7.06; N, 12.16.

EXAMPLE 284

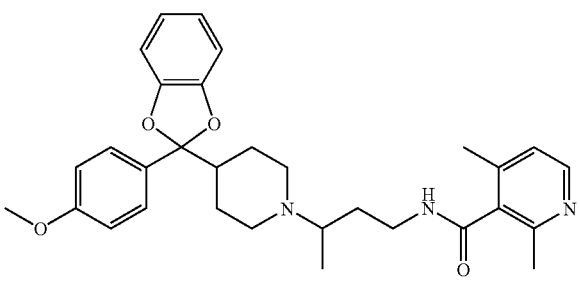

COMPOUND 284: N-(3-{4-[2-(4-Methoxy-phenyl)-benzo[1,3]dioxol-2-yl]-piperidin-1-yl}-butyl)-2,4-dimethyl-nicotinamide To a solution of 4-bromoanisole (5.00 g, 26.70 mmol) in THF (100 mL) at −78° C. was added n-BuLi (1.9M in hexanes, 14 mL, 26.7 mmol). After the solution was stirred at −78° C. for 45 minutes, TMEDA (4.03 mL, 26.7 mmol) was added followed by a solution of 4-formyl-piperidine-1-carboxylic acid tert-butyl ester (4.76 g, 22.3 mmol) in THF (20 mL), and the mixture was stirred at −78° C. for 1 hour. The reaction was quenched with saturated aqueous NH$_4$Cl and after work-up and purification gave 4-[hydroxy-(4-methoxy-phenyl)-methyl]-piperidine-1-carboxylic acid tert-butyl ester (3.40 g, 47%) as a white foam.

To a solution of the above alcohol (3.40 g, 10.6 mmol) in CH$_2$Cl$_2$ (50 mL) at room temperature was added SiO$_2$ (13.60 g) and PCC (6.84 g, 31.70 mmol). The resulting mixture was stirred under N$_2$ for 2 hours to afford 4-(4-methoxy-benzoyl)-piperidine-1-carboxylic acid tert-butyl ester as a yellow solid (3.00 g, 88%) after purification.

A solution of the above ketone (957 mg, 3.00 mmol), catechol (660 mg, 6.00 mmol) and p-TsOH.H$_2$O (1.14 g, 6.00 mmol) in xylene (20 mL) was heated at reflux using a Dean-Stark apparatus to remove water for 24 hours. Standard work-up and purification gave 4-[2-(4-methoxy-phenyl)-benzo[1,3]dioxol-2-yl]-piperidine as a pale yellow oil (335 mg, 36%).

Using general procedure B with the above amine (335 mg, 1.02 mmol) and 2-(3-oxo-butyl)-isoindole-1,3-dione (837 mg, 2.56 mmol) and then using general procedure D afforded 3-{4-[2-(4-methoxy-phenyl)-benzo[1,3]dioxol-2-yl]-piperidin-1-yl}-butylamine as a colourless oil (240 mg, 62% over 2 steps).

Using general procedure E, the above amine (50 mg, 0.13 mmol) and 2,4-dimethylnicotinic acid (24 mg, 0.16 mmol) afforded COMPOUND 284 as a white solid (45 mg, 66%). $^1$H NMR (CDCl$_3$) δ 0.84-0.93 (m, 1H), 0.94 (d, 3H, J=6.6 Hz), 1.02-1.15 (m, 1H), 1.46-1.61 (m, 3H), 1.66-1.79 (m, 1H), 1.86-1.98 (m, 2H), 2.31 (s, 3H), 2.35 (td, 1H, J=12.0, 2.1 Hz), 2.54 (s, 3H), 2.66-2.81 (m, 3H), 3.24-3.34 (m, 1H), 3.79 (s, 3H), 3.81-3.90 (m, 1H), 6.73-6.86 (m, 6H), 6.99 (d, 1H, J=5.1 Hz), 7.28-7.31 (m, 2H), 8.19 (br s, 1H), 8.43 (d, 1H, J=5.1 Hz). $^{13}$C NMR (CDCl$_3$) δ 13.36, 18.98, 22.42, 25.86, 26.49, 31.36, 39.87, 44.14, 45.83, 52.33, 55.44, 60.39, 108.54, 113.52, 118.64, 121.35, 122.73, 127.05, 132.05, 133.77, 143.73, 147.47, 147.56, 149.00, 154.31, 159.93, 168.55. ES-MS m/z 516 (M+H). Anal. Calcd. for C$_{31}$H$_{37}$N$_3$O$_4$.0.1CH$_2$Cl$_2$: C, 71.27; H, 7.15; N, 8.02. Found: C, 71.13; H, 7.25; N, 8.00.

EXAMPLE 285

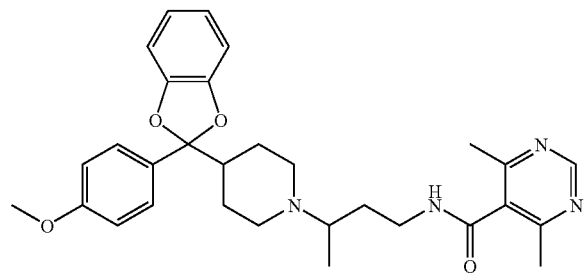

COMPOUND 285: 4,6-Dimethyl-pyrimidine-5-carboxylic acid (3-{4-[2-(4-methoxy-phenyl)-benzo[1,3]dioxol-2-yl]-piperidin-1-yl}-butyl)-amide Using general procedure E, 3-{4-[2-(4-methoxy-phenyl)-benzo[1,3]dioxol-2-yl]-piperidin-1-yl}-butylamine (see EXAMPLE 284) (50 mg, 0.13 mmol) and 4,6-dimethyl-pyrimidine-5-carboxylic acid (24 mg, 0.16 mmol) afforded COMPOUND 285 as a white solid (42 mg, 63%). $^1$H NMR (CDCl$_3$) δ 0.70-0.84 (m, 1H), 0.94 (d, 3H, J=6.6 Hz), 0.95-1.08 (m, 1H), 1.45-1.63 (m, 3H), 1.66-1.80 (m, 1H), 1.86-1.98 (m, 2H), 2.38 (t, 1H, J=11.4 Hz), 2.52 (s, 6H), 2.66-2.84 (m, 3H), 3.22-3.31 (m, 1H), 3.79 (s, 3H), 3.87-3.97 (m, 1H), 6.74-6.79 (m, 2H), 6.83-6.88 (m, 3H), 6.91-6.94 (m, 1H), 7.29 (d, 2H, J=9.0 Hz), 8.86-8.88 (m, 1H), 9.08 (s, 1H). $^{13}$C NMR (CDCl$_3$) δ 13.37, 22.07, 25.89, 26.55, 30.77, 40.43, 43.83, 45.63, 52.47, 55.45, 60.96, 108.65, 108.73, 113.61, 118.42, 121.44, 126.99, 131.00, 131.96, 147.38, 147.50, 157.84, 159.96, 163.05, 166.71. ES-MS m/z 517 (M+H). Anal. Calcd. for C$_{30}$H$_{36}$N$_4$O$_4$.0.1CH$_2$Cl$_2$: C, 68.85; H, 6.95; N, 10.67. Found: C, 69.00; H, 7.03; N, 10.76.

EXAMPLE 286

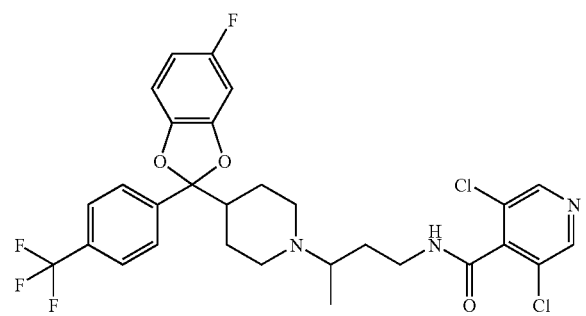

COMPOUND 286: 3,5-Dichloro-N-(3-{4-[5-fluoro-2-(4-trifluoromethyl-phenyl)-benzo[1,3]dioxol-2-yl]-piperidin-1-yl}-butyl)-isonicotinamide A solution of 4-(4-trifluorobenzoyl)-piperidine-1-carboxylic acid tert-butyl ester (179 mg, 0.50 mmol), 4-fluorocatechol (275 mg, 2.00 mmol) and p-TsOH.H$_2$O (190 mg, 1.00 mmol) in xylene (5 mL) was heated at reflux under a Dean-Stark trap for 64.5 hours. Standard work-up and purification gave 4-[5-fluoro-2-(4-trifluoromethyl-phenyl)-benzo[1,3]dioxol-2-yl]-piperidine as a pale yellow oil (59 mg, 32%).

Using general procedure B with the above amine (59 mg, 0.16 mmol) and 2-(3-oxo-butyl)-isoindole-1,3-dione (70 mg, 0.32 mmol) and then using general procedure D gave 3-{4-[5-fluoro-2-(4-trifluoromethyl-phenyl)-benzo[1,3]dioxol-2-yl]-piperidin-1-yl}-butylamine as a white solid (35 mg, 51% over 2 steps).

Using general procedure F, 3,5-dichloroisonicotinic acid (31.6 mg, 0.164 mmol) and the above amine (36 mg) gave COMPOUND 286 as a white solid (41 mg, 82%). $^1$H NMR (CDCl$_3$) δ 0.84-1.08 (m, 2H), 0.95 (d, 3H, J=6.6 Hz), 1.48-1.98 (m, 6H), 2.37 (t, 1H, J=11.4 Hz), 2.74-2.88 (m, 3H), 3.31 (t, 1H, J=11.4 Hz), 3.89 (m, 1H), 6.48 (m, 1H), 6.57-6.66 (m, 1H), 6.69-6.81 (m, 1H), 7.47 (d, 2H, J=8.4 Hz), 7.61 (d, 2H, J=8.1 Hz), 8.59 (s, 2H), 9.10 (br s, 1H). $^{13}$C NMR (CDCl$_3$) δ 13.21, 25.56, 25.66, 26.13, 26.26, 30.06, 30.93, 40.28, 43.54, 45.06, 51.95, 53.45, 60.62, 98.21 (d, J=27 Hz), 106.92 (d, J=24 Hz), 108.08 (d, J=10 Hz), 118.94, 121.69, 123.82 (d, J=272 Hz), 125.20, 125.24, 126.05, 128.41, 131.13 (q, J=33 Hz), 143.17, 143.29, 147.27, 147.61, 157.92 (d, J=239 Hz), 161.57. ES-MS m/z 612 (M+H). Anal. Calcd. for C$_{29}$H$_{27}$N$_3$Cl$_2$O$_3$F$_4$.0.2CH$_2$Cl$_2$.0.1C$_6$H$_{14}$: C, 56.10; H, 4.55; N, 6.59; Cl, 13.34; F, 11.91. Found: C, 56.22; H, 4.50; N, 6.48; Cl, 13.05; F, 11.59.

EXAMPLE 287

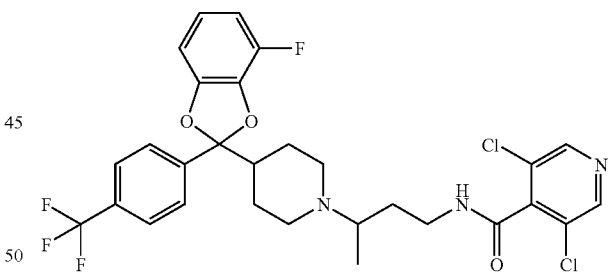

COMPOUND 287: 3,5-Dichloro-N-(3-{4-[4-fluoro-2-(4-trifluoromethyl-phenyl)-benzo[1,3]dioxol-2-yl]-piperidin-1-yl}-butyl)-isonicotinamide A solution of 4-(4-trifluorobenzoyl)-piperidine-1-carboxylic acid tert-butyl ester (357 mg, 1.00 mmol), 3-fluorocatechol (512 mg, 4.00 mmol) and p-TsOH.H$_2$O (380 mg, 2.00 mmol) in xylene (10 mL) was heated at reflux under a Dean-Stark trap for 43 hours. Standard work-up and purification gave 4-[4-fluoro-2-(4-trifluoromethyl-phenyl)-benzo[1,3]dioxol-2-yl]-piperidine as a pale yellow oil (18 mg, 3%).

Using general procedure B with the above amine (18 mg, 0.049 mmol) and 2-(3-oxo-butyl)-isoindole-1,3-dione (21 mg, 0.098 mmol) and then using general procedure D afforded 3-{4-[4-fluoro-2-(4-trifluoromethyl-phenyl)-benzo[1,3]dioxol-2-yl]-piperidin-1-yl}-butylamine as a white solid (11 mg, 52% over 2 steps).

Using general procedure F, 3,5-dichloroisonicotinic acid (12 mg, 0.063 mmol) and the above amine (11 mg, 0.025 mmol) gave COMPOUND 287 as a white solid (10 mg, 63%). $^1$H NMR (CDCl$_3$) δ 0.84-1.07 (m, 2H), 0.95 (d, 3H, J=6.6 Hz), 1.44-1.79 (m, 5H), 1.94-2.04 (m, 1H), 2.33-2.43 (m, 1H), 2.69-2.85 (m, 3H), 3.31 (t, 1H, J=11.7 Hz), 3.86-3.93 (m, 1H), 6.60-6.79 (m, 3H), 7.51 (d, 2H, J=8.1 Hz), 7.62 (d, 2H, J=8.4 Hz), 8.59 (s, 2H), 8.90, 9.01 (m, 1H). $^{13}$C NMR (CDCl$_3$) δ 13.19, 25.48, 25.82, 26.07, 26.41, 30.17, 30.36, 40.19, 40.26, 43.54, 45.09, 51.93, 52.05, 60.61, 104.90, 110.36 (d, J=16 Hz), 119.47, 121.89 (d, J=7 Hz), 125.23, 125.61, 126.08, 126.37, 128.93, 131.24 (d, J=32 Hz), 133.35, 133.53, 142.99, 143.09, 146.36 (d, J=246 Hz), 147.67, 149.44, 161.61. ES-MS m/z 612 (M+H). Anal. Calcd. for C$_{29}$H$_{27}$N$_3$Cl$_2$O$_3$F$_4$·0.2C$_6$H$_{14}$: C, 57.61; H, 4.77; N, 6.67. Found: C, 57.59; H, 4.73; N, 6.58.

EXAMPLE 288

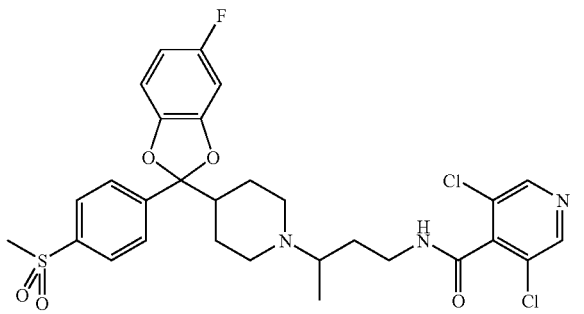

COMPOUND 288: 3,5-Dichloro-N-(3-{4-[5-fluoro-2-(4-methanesulfonyl-phenyl)-benzo[1,3]dioxol-2-yl]-piperidin-1-yl}-butyl)-isonicotinamide A solution of 4-(4-methylsulfanyl-benzoyl)-piperidine-1-carboxylic acid tert-butyl ester (see EXAMPLE 28) (168 mg, 0.50 mmol), 4-fluorocatechol (128 mg, 2.0 mmol) and p-TsOH.H$_2$O (190 mg, 1.0 mmol) in xylene (50 mL) was heated at reflux under a Dean-Stark trap for 41 hours. Standard work-up and purification gave 4-[5-fluoro-2-(4-methylsulfanyl-phenyl)-benzo[1,3]dioxol-2-yl]-piperidine as a white solid (58 mg, 34%).

A solution of the above thiol (29 mg, 0.084 mmol), Boc$_2$O (20 mg, 0.092 mmol) and Et$_3$N (18 µL, 0.13 mmol) in CH$_2$Cl$_2$ (0.5 mL) was stirred at room temperature for 1 hour. Work-up and purification afforded 4-[5-fluoro-2-(4-methylsulfanyl-phenyl)-benzo[1,3]dioxol-2-yl]-piperidine-1-carboxylic acid tert-butyl ester as a white solid (36 mg, 97%).

To the above thiol (36 mg, 0.082 mmol) in Et$_2$O (1 mL) cooled to 0° C. was added hydrogen peroxide (50%, 28 µL, 0.82 mmol) and the mixture was stirred at 0° C. for 2 hours. Work-up and purification afforded a white solid (35 mg, 90%).

To the above sulfoxide (35 mg, 0.076 mmol) in MeOH (1 mL) cooled to 0° C. was added OXONE® (186 mg, 0.303 mmol) and the mixture was stirred at room temperature for 21 hours. Work-up and purification gave 4-[5-fluoro-2-(4-methanesulfonyl-phenyl)-benzo[1,3]dioxol-2-yl]-piperidine-1-carboxylic acid tert-butyl ester as a white solid (36 mg, 100%).

Using general procedure C with the above carbamate (36 mg, 0.075 mmol), and then general procedure B with the resulting amine and 2-(3-oxo-butyl)-isoindole-1,3-dione (32 mg, 0.15 mmol) and then using general procedure D gave 3-{4-[5-fluoro-2-(4-methanesulfonyl-phenyl)-benzo[1,3]dioxol-2-yl]-piperidin-1-yl}-butylamine as a white solid (24 mg, 85% over 3 steps).

Using general procedure F, 3,5-dichloroisonicotinic acid (27 mg, 0.14 mmol) and the above amine (18 mg, 0.047 mmol) gave COMPOUND 288 as a white solid (25 mg, 100%). $^1$H NMR (CDCl$_3$) δ 0.85-1.05 (m, 2H), 0.96 (d, 3H, J=6.3 Hz), 1.44-1.62 (m, 3H), 1.76-1.96 (m, 3H), 2.37 (m, 1H), 2.75-2.85 (m, 3H), 3.03 (s, 3H), 3.32 (t, 1H, J=11.7 Hz), 3.87 (m, 1H), 6.46-6.52 (m, 1H), 6.58-6.66 (m, 1H), 6.71-6.79 (m, 1H), 7.56 (d, 2H, J=8.4 Hz), 7.93 (d, 2H, J=8.1 Hz), 8.58 (s, 2H), 9.04 (br s, 1H). $^{13}$C NMR (CDCl$_3$) δ 13.60, 25.98, 26.45, 40.62, 43.91, 44.76, 45.35, 52.26, 60.95, 98.69 (d, J=28 Hz), 107.48 (d, J=24 Hz), 108.61 (d, J=7 Hz), 119.08, 127.14, 127.77, 129.40, 141.53, 143.35, 143.55, 145.87, 147.64, 148.00, 158.36 (d, J=239 Hz), 161.95. ES-MS m/z 623 (M+2). Anal. Calcd. for C$_{29}$H$_{30}$N$_3$Cl$_2$O$_5$FS·0.8CH$_2$Cl$_2$: C, 51.84; H, 4.61; N, 6.09. Found: C, 51.79; H, 4.61; N, 5.98.

EXAMPLE 289

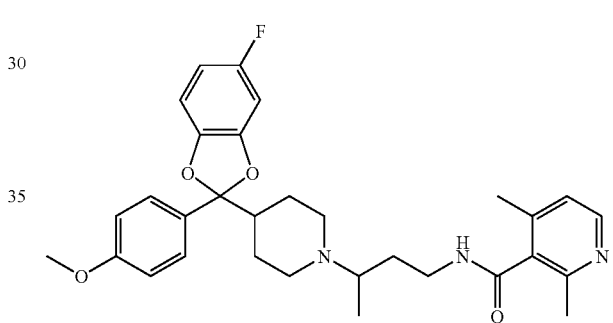

COMPOUND 289: N-(3-{4-[5-Fluoro-2-(4-methoxy-phenyl)-benzo[1,3]dioxol-2-yl]-piperidin-1-yl}-butyl)-2,4-dimethyl-nicotinamide A solution of 4-(4-methoxy-benzoyl)-piperidine-1-carboxylic acid tert-butyl ester (see EXAMPLE 284) (638 mg, 2.00 mmol), 4-fluorocatechol (512 mg, 4.00 mmol) and p-TsOH.H$_2$O (760 mg, 4.00 mmol) in xylene (20 mL) was heated at reflux using a Dean-Stark apparatus to remove water for 52 hours. Standard work-up and purification gave 4-[5-fluoro-2-(4-methoxy-phenyl)-benzo[1,3]dioxol-2-yl]-piperidine as a pale yellow oil (220 mg, 33%).

Using general procedure I the above amine (220 mg, 0.669 mmol) afforded the nitrile, which was subsequently reduced with BH$_3$-THF (1.0M in THF, 1.72 mL, 1.72 mmol) in THF (4 mL) at reflux and treated with ethylenediamine (1.5 mL) to give 3-{4-[5-fluoro-2-(4-methoxy-phenyl)-benzo[1,3]dioxol-2-yl]-piperidin-1-yl}-butylamine as a white solid (169 mg, 74%) following work-up and purification.

Using general procedure E, the above amine (50 mg, 0.15 mmol) and 2,4-dimethylnicotinic acid (27 mg, 0.18 mmol) afforded COMPOUND 289 as a pale yellow solid (51 mg, 62%). $^1$H NMR (CDCl$_3$) δ 0.88-1.17 (m, 2H), 0.96 (d, 3H, J=6.6 Hz), 1.46-1.62 (m, 2H), 1.73-1.77 (m, 1H), 1.88-2.01 (m, 2H), 2.31 (s, 3H), 2.32-2.41 (m, 2H), 2.54 (s, 3H), 2.69-

2.82 (m, 3H), 3.29-3.33 (m, 1H), 3.73 (s, 3H), 3.79-3.88 (m, 1H), 6.39-6.46 (m, 1H), 6.54, 6.58 (dd, 1H, J=8.4, 2.7 Hz), 6.64-6.73 (m, 1H), 6.84-6.87 (m, 2H), 6.98 (d, 1H, J=5.1 Hz), 7.26-7.30 (m, 2H), 8.13 (br s, 1H), 8.41, 8.42 (d, 1H, J=5.1 Hz). $^{13}$C NMR (CDCl$_3$) δ 13.32, 19.00, 22.42, 25.64, 25.71, 26.26, 26.35, 31.39, 31.45, 39.72, 44.17, 45.69, 52.20, 55.47, 60.30, 97.84, 98.23, 106.46 (d, 1H, J=24 Hz), 107.78 (d, 1H, J=10 Hz), 113.62, 120.19, 122.72, 127.01, 131.53, 133.77, 143.86, 148.16, 148.97, 154.33, 157.93 (d, J=238 Hz), 160.10, 168.58. ES-MS m/z 534 (M+H). Anal. Calcd. for C$_{31}$H$_{36}$N$_3$O$_4$F.0.45CH$_2$Cl$_2$: C, 66.06; H, 6.50; N, 7.35. Found: C, 66.04; H, 6.53; N, 7.26.

EXAMPLE 290

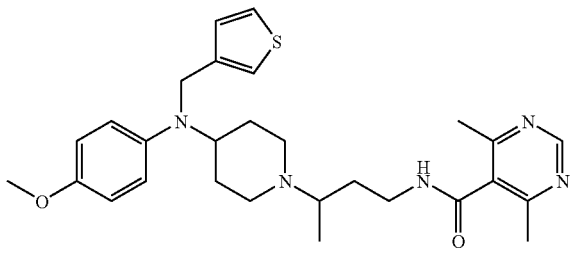

COMPOUND 290: 4,6-Dimethyl-pyrimidine-5-carboxylic acid (3-{4-[(4-methoxy-phenyl)-thiophen-3-ylmethyl-amino]-piperidin-1-yl}-butyl)-amide Using general procedure A, 4-methoxyphenylamine (246 mg, 2.00 mmol) and 1-Boc-4-piperidone (418 mg, 2.10 mmol) gave 4-(4-methoxyphenylamino)-piperidine-1-carboxylic acid tert-butyl ester as a pale yellow oil (612 mg, 100%).

Using general procedure C with the above aniline (706 mg, 2.30 mmol), then general procedure I with the resulting amine and then using general procedure J afforded [1-(3-amino-1-methyl-propyl)-piperidin-4-yl]-(4-methoxy-phenyl)-amine as a white solid (538 mg, 85% over 3 steps).

Using general procedure E, the above amine (538 mg, 1.94 mmol) and 4,6-dimethyl-pyrimidine-5-carboxylic acid (325 mg, 2.13 mmol) afforded 4,6-dimethyl-pyrimidine-5-carboxylic acid {3-[4-(4-methoxy-phenylamino)-piperidin-1-yl]-butyl}-amide as a white solid (638 mg, 80%).

Using general procedure H, the above amine (88 mg, 0.20 mmol) and 3-(bromomethyl)thiophene (80 mg) afforded COMPOUND 290 as a brown solid (56 mg, 54%). $^1$H NMR (CDCl$_3$) δ 0.88-1.14 (m, 2H), 1.00 (d, 3H, J=6.9 Hz), 1.51-1.56 (m, 1H), 1.73-1.78 (m, 3H), 2.08-2.16 (m, 1H), 2.45-2.57 (m, 1H), 2.52 (s, 6H), 2.72-2.87 (m, 3H), 3.25-3.41 (m, 2H), 3.73 (s, 3H), 3.77 (s, 2H), 3.84-3.94 (m, 1H), 6.61-6.64 (m, 2H), 6.72-6.75 (m, 2H), 6.99-7.00 (m, 2H), 7.24-7.26 (m, 1H), 8.85-8.87 (m, 2H). $^{13}$C NMR (CDCl$_3$) δ 13.76, 22.31, 29.64, 30.94, 40.67, 43.96, 46.54, 52.56, 56.06, 57.61, 60.96, 114.92, 117.08, 121.18, 125.91, 127.21, 131.26, 142.22, 143.46, 152.69, 158.01, 163.39, 166.76. ES-MS m/z 508 (M+H). Anal. Calcd. for C$_{28}$H$_{37}$N$_5$O$_2$S.0.73H$_2$O: C, 64.57; H, 7.44; N, 13.45; S, 6.16. Found: C, 64.61; H, 7.21; N, 13.32; S, 5.87.

EXAMPLE 291

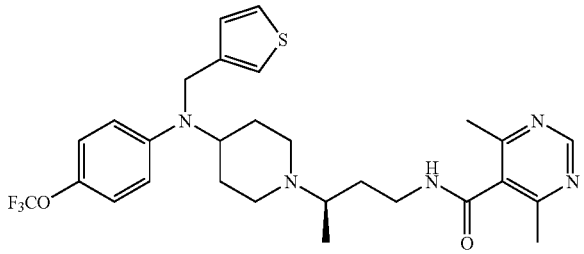

COMPOUND 291: 4,6-Dimethyl-pyrimidine-5-carboxylic acid ((R)-3-{4-[thiophen-3-ylmethyl-(4-trifluoromethoxy-phenyl)-amino]-piperidin-1-yl}-butyl)-amide Using general procedure A with 4-(trifluoromethoxy)-aniline (0.21 mL, 1.55 mmol) and (R)-3-(4-oxo-piperidin-1-yl]-butyronitrile (310 mg, 1.87 mmol) followed by general procedure J afforded [1-((R)-3-amino-1-methyl-propyl)-piperidin-4-yl]-(4-trifluoromethoxy-phenyl)-amine as a white solid (277 mg, 55% over 2 steps).

Using general procedure E, the above amine (121 mg, 0.34 mmol) and 4,6-dimethyl-pyrimidine-5-carboxylic acid (57 mg, 0.37 mmol) afforded 3,6-dimethyl-pyrimidine-5-carboxylic acid {(R)-3-[4-(4-trifluoromethoxy-phenylamino)-piperidin-1-yl]-butyl}-amide as a pale yellow foam (123 mg, 78%).

A solution of the above amide (123 mg, 0.26 mmol) and 3-(bromomethyl)thiophene (56 mg, 0.32 mmol) in CH$_3$CN (3 mL) was stirred overnight. Standard work-up and purification afforded COMPOUND 291 as a white foam (15 mg, 10%). $^1$H NMR (CDCl$_3$) δ 1.01 (d, 3H, J=9.0 Hz), 1.77 (d, 4H, J=9.0 Hz), 2.16 (t, 1H, J=12.0 Hz), 2.52 (s, 6H), 2.59 (d, 1H, J=9.0 Hz), 2.73-2.78 (m, 1H), 2.83-2.90 (m, 2H), 3.33 (td, 1H, J=9.0, 3.0 Hz), 3.55 (td, 1H, J=9.0, 3.0 Hz), 3.84 (s, 2H), 3.86-3.91 (m, 1H), 6.57 (d, 2H, J=9.0 Hz), 6.96-7.02 (m, 4H), 7.30 (dd, 1H, J=6.0, 3.0 Hz), 8.71 (d, 1H, J=3.0 Hz), 8.88 (s, 1H). ES-MS m/z 562 [M+H]$^+$.

EXAMPLE 292

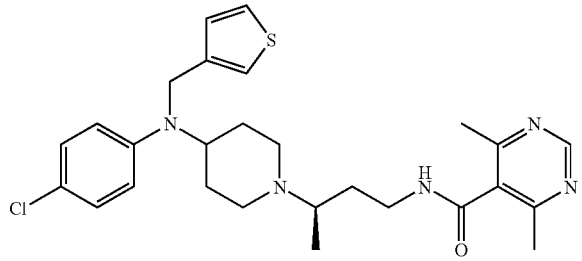

COMPOUND 292: 4,6-Dimethyl-pyrimidine-5-carboxylic acid ((R)-3-{4-[(4-chloro-phenyl)-thiophen-3-ylmethyl-amino]-piperidin-1-yl}-butyl)-amide Using general procedure A with 4-chloroaniline (230 mg, 1.80 mmol) and (R)-3-(4-oxo-piperidin-1-yl)-butyronitrile (263 mg, 1.58 mmol), then general procedure J and then using general procedure E with the resulting amine and 4,6-dimethyl-pyrimidine-5-carboxylic acid (100 mg, 0.66 mmol) afforded 4,6-dimethyl-pyrimidine-5-carboxylic acid {(R)-3-[4-(4-chloro-phenylamino)-piperidin-1-yl]-butyl}-amide (237 mg, 35% over 3 steps).

A solution of the above aniline (119 mg, 0.29 mmol) and 3-(bromomethyl)thiophene (61 mg, 0.34 mmol) in $CH_3CN$ (5 mL) was stirred at room temperature overnight to afford COMPOUND 292 as a white solid (34 mg, 23%) following work-up and purification. $^1H$ NMR ($CDCl_3$) δ 0.89-1.19 (m, 2H), 1.01 (d, 3H, J=6.6 Hz), 1.54-1.58 (m, 1H), 1.73-1.80 (m, 3H), 2.16 (t, 1H, J=12.3 Hz), 2.52 (s, 6H), 2.56 (t, 1H, J=12.3 Hz), 2.73-2.89 (m, 3H), 3.28-3.36 (m, 1H), 3.49-3.57 (m, 1H), 3.82 (s, 2H), 3.84-3.92 (m, 1H), 6.54 (d, 2H, J=8.7 Hz), 6.98-7.01 (m, 2H), 7.06-7.09 (m, 2H), 7.28 (dd, 1H, J=4.8, 3.0 Hz), 8.71 (br s, 1H), 8.88 (s, 1H). ES-MS m/z 512 (M+H).

EXAMPLE 293

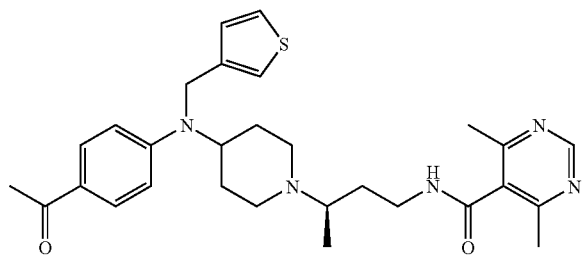

COMPOUND 293: 4,6-Dimethyl-pyrimidine-5-carboxylic acid ((R)-3-{4-[(4-acetyl-phenyl)-thiophen-3-ylmethyl-amino]-piperidin-1-yl}-butyl)-amide To a solution of [1-((R)-3-amino-1-methyl-propyl)-piperidin-4-yl]-[4-(2-methyl-[1,3]dioxolan-2-yl)-phenyl]-amine (see EXAMPLE 231) (386 mg, 1.16 mmol) in MeOH (5 mL) and THF (5 mL) was added $Boc_2O$ (300 mg, 1.4 mmol) and the mixture was stirred at room temperature for 1.5 hours to afford a yellow foam (284 mg) following purification.

Using general procedure H, the above aniline and 3-(bromomethyl)thiophene (177 mg, 1.0 mmol) afforded [(R)-3-(4-{[4-(2-methyl-[1,3]dioxolan-2-yl)-phenyl]-thiophen-3-ylmethyl-amino}-piperidin-1-yl)-butyl]-carbamic acid tert-butyl ester (168 mg, 54% over 2 steps).

To a solution of the above substrate (168 mg, 0.32 mmol) in MeOH (1.5 mL) was added 4N HCl (1.5 mL) and the mixture was stirred at room temperature for 3 hours. After basic work-up, general procedure C was used to afford 1-(4-{[1-((R)-3-amino-1-methyl-propyl)-piperidin-4-yl]-thiophen-3-ylmethyl-amino}-phenyl)-ethanone as a pale yellow foam (132 mg).

Using general procedure E, the above amine (132 mg, 0.34 mmol) and 4,6-dimethyl-pyrimidine-5-carboxylic acid (54 mg, 0.35 mmol) afforded COMPOUND 293 as a yellow oil (44 mg, 38% over 3 steps). $^1H$ NMR ($CDCl_3$) δ 1.04 (d, 3H, J=6.3 Hz), 1.53-1.82 (m, 5H), 2.23 (t, 1H, J=12.3 Hz), 2.47 (s, 3H), 2.52 (s, 6H), 2.61 (t, 1H, J=11.4 Hz), 2.78-2.93 (m, 3H), 3.31-3.39 (m, 1H), 3.48 (s, 2H), 3.70-3.87 (m, 2H), 4.00 (s, 1H), 6.61 (d, 2H, J=9.0 Hz), 6.98-7.01 (m, 2H), 7.31 (dd, 1H, J=5.1, 3.0 Hz), 7.79 (d, 2H, J=9.0 Hz), 8.55 (br s, 1H), 8.91 (s, 1H). ES-MS m/z 520 (M+H).

EXAMPLE 294

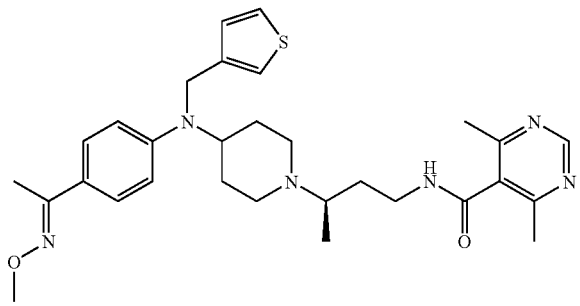

COMPOUND 294: 4,6-Dimethyl-pyrimidine-5-carboxylic acid [(R)-3-(4-{[4-(1-methoxyimino-ethyl)-phenyl]-thiophen-3-ylmethyl-amino}-piperidin-1-yl)-butyl]-amide To a solution of COMPOUND 293 in MeOH (3 mL) were added methoxyamine hydrochloride (15 mg, 0.18 mmol) followed by NaOAc (14 mg, 0.17 mmol) and the mixture was stirred at room temperature overnight to afford COMPOUND 294 as a clear oil (31 mg, 82%) after work-up and purification. $^1H$ NMR ($CDCl_3$) δ 0.95-1.17 (m, 2H), 1.02 (d, 3H, J=6.6 Hz), 1.52-1.58 (m, 1H), 1.74-1.79 (m, 3H), 2.14 (s, 3H), 2.17 (t, 1H, J=11.7 Hz), 2.52 (s, 6H), 2.57 (t, 1H, J=11.4 Hz), 2.73-2.89 (m, 3H), 3.28-3.36 (m, 1H), 3.59-3.68 (m, 1H), 3.88 (s, 3H), 3.94 (s, 3H), 6.60 (d, 2H, J=9.0 Hz), 6.98-7.03 (m, 2H), 7.28 (dd, 1H, J=4.8, 3.0 Hz), 7.45 (d, 2H, J=9.0 Hz), 8.71 (br s, 1H), 8.89 (s, 1H). ES-MS m/z 549 (M+H).

EXAMPLE 295

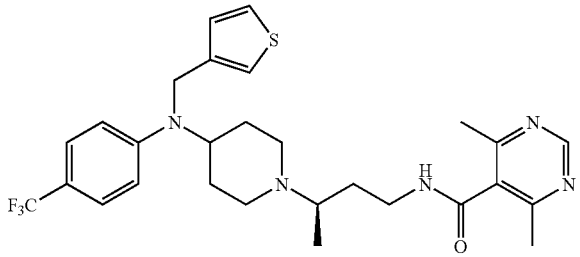

COMPOUND 295: 4,6-Dimethyl-pyrimidine-5-carboxylic acid ((R)-3-{4-[thiophen-3-ylmethyl-(4-trifluoromethyl-phenyl)-amino-piperidin-1-yl}-butyl)-amide Using general procedure A with 4-(trifluoromethyl)aniline (0.19 mL, 1.51 mmol) and (R)-3-(4-oxo-piperidin-1-yl)-butyronitrile (302 mg, 1.82 mmol) followed by general procedure J afforded [1-((R)-3-amino-1-methyl-propyl)-piperidin-4-yl]-(4-trifluoromethyl-phenyl)-amine as a pale blue solid (232 mg, 49% over 2 steps).

Using general procedure E, the above amine (104 mg, 0.33 mmol) and 4,6-dimethyl-pyrimidine-5-carboxylic acid (55 mg, 0.36 mmol) afforded 4,6-dimethyl-pyrimidine-5-carboxylic acid {(R)-3-[4-(4-trifluoromethyl-phenylamino)-piperidin-1-yl]-butyl}-amide as a pale yellow foam (114 mg, 77%).

A mixture of the above amide (79 mg, 0.18 mmol), 3-(bromomethyl)thiophene (37 mg, 0.21 mmol), and 2,2,6,6-tetramethylpiperidine (60 μL, 0.35 mmol) in CH$_3$CN (2 mL) was stirred at 80° C. overnight. Then more 3-(bromomethyl)thiophene (37 mg, 0.21 mmol) and 2,2,6,6-tetramethylpiperidine (60 mL), 0.35 mmol) was added and after 3 h afforded COMPOUND 295 as a yellow foam (13 mg, 14%) following purification. $^1$H NMR (CDCl$_3$) δ 1.00 (d, 3H, J=6.0 Hz), 1.15-1.18 (m, 1H), 1.54-1.58 (m, 2H), 1.78 (d, 3H, J=9.0 Hz), 2.19 (t, 1H, J=9.0 Hz), 2.52 (s, 6H), 2.59 (td, 1H, J=12.0, 3.0 Hz), 2.86-2.91 (m, 3H), 3.33 (td, 1H, J=9.0, 3.0 Hz), 3.66 (td, 1H, J=6.0, 3.0 Hz), 3.83-3.90 (m, 1H), 3.92 (s, 2H), 6.64 (d, 2H, J=9.0 Hz), 7.01 (dd, 2H, J=6.0, 3.0 Hz), 7.31 (dd, 1H, J=6.0, 3.0 Hz), 7.37 (d, 2H, J=9.0 Hz), 8.61 (dd, 1H, J=3.0 Hz), 8.90 (s, 1H). ES-MS m/z 546 [M+H]$^+$.

EXAMPLE 296

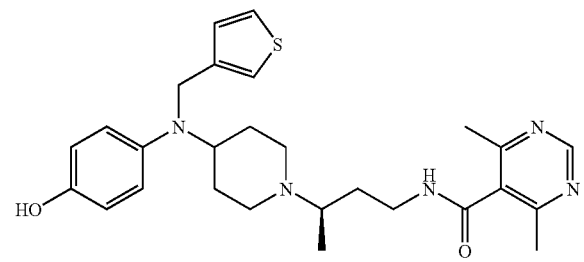

COMPOUND 296: 4,6-Dimethyl-pyrimidine-5-carboxylic acid ((R)-3-{4-[(4-hydroxy-phenyl)-thiophen-3-ylmethyl-amino]-piperidin-1-yl}-butyl)-amide Using general procedure E, [1-((R)-3-amino-1-methyl-propyl)-piperidin-4-yl]-[4-(tert-butyl-dimethyl-silanyloxy)-phenyl]-amine (see EXAMPLE 233) (940 mg, 2.5 mmol) and 4,6-dimethyl-pyrimidine-5-carboxylic acid (490 mg, 3.2 mmol) afforded 4,6-dimethyl-pyrimidine-5-carboxylic acid ((R)-3-{4-[4-(tert-butyl-dimethyl-silanyloxy)-phenylamino]-piperidin-1-yl}-butyl)-amide as a peach solid (790 mg, 62%).

Using general procedure H, the above aniline (790 mg, 1.5 mmol) and 3-(bromomethyl)thiophene (410 mg, 2.3 mmol) afforded 4,6-dimethyl-pyrimidine-5-carboxylic acid [(R)-3-(4-{[4-(tert-butyl-dimethyl-silanyloxy)-phenyl]-thiophen-3-ylmethyl-amino}-piperidin-1-yl)-butyl]-amide as a brown solid (117 mg, 12%).

To a solution of the above amine (115 mg, 0.19 mmol) in THF (2 mL) cooled to 0° C. was added TBAF (1.0M in THF, 0.23 mL, 0.23 mmol) and the mixture was stirred at 0° C. for 30 minutes. Aqueous work-up and purification afforded COMPOUND 296 as a pale brown solid (76 mg, 81%). $^1$H NMR (CDCl$_3$) δ 0.86-1.11 (m, 2H), 0.99 (d, 3H, J=6.6 Hz), 1.52-1.77 (m, 4H), 2.10 (t, 1H, J=11.4 Hz), 2.47-2.52 (m, 1H), 2.51 (s, 6H), 2.71-2.85 (m, 3H), 3.26-3.33 (m, 2H), 3.78 (s, 2H), 3.85-3.91 (m, 1H), 6.55-6.66 (m, 4H), 6.98 (d, 2H, J=3.9 Hz), 7.22-7.24 (m, 1H), 8.81-8.83 (m, 1H), 8.86 (s, 1H). ES-MS m/z 494 (M+H).

EXAMPLE 297

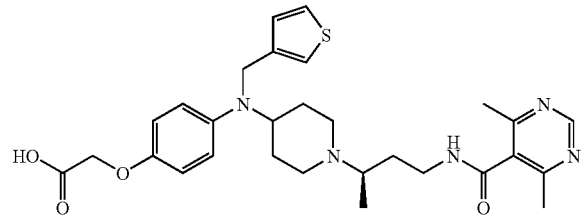

COMPOUND 297: {4-[(1-{(R)-3-[(4,6-Dimethyl-pyrimidine-5-carbonyl)-amino]-1-methyl-propyl}-piperidin-4-yl)-thiophen-3-ylmethyl-amino]-phenoxy}-acetic acid A mixture of COMPOUND 296 (290 mg, 0.59 mmol), methyl bromoacetate (141 mg, 0.92 mmol) and K$_2$CO$_3$ (123 mg, 0.89 mmol) in DMF (5.8 mL) was heated at 80° C. overnight to afford {4-[(1-{(R)-3-[(4,6-dimethyl-pyrimidine-5-carbonyl)-amino]-1-methyl-propyl}-piperidin-4-yl)-thiophen-3-ylmethyl-amino]-phenoxy}-acetic acid methyl ester as a brown oil (145 mg, 42%) following work-up and purification.

Using general procedure K, the above substrate (85 mg, 0.15 mmol) gave COMPOUND 297 as a white solid (95 mg). $^1$H NMR (CD$_3$OD) δ 1.44 (d, 3H, J=6.6 Hz), 1.92-2.00 (m, 3H), 2.20-2.24 (m, 3H), 2.50 (s, 6H), 3.20-3.30 (m, 1H), 3.42-3.51 (m, 6H), 3.80-3.86 (m, 1H), 4.43 (s, 2H), 4.58 (s, 2H), 6.85 (d, 2H, J=8.7 Hz), 6.96-6.99 (m, 3H), 7.14 (s, 1H), 7.30 (dd, 1H, J=4.8, 3.0 Hz), 7.90 (s, 1H), 8.90 (s, 1H). ES-MS m/z 552 (M+H).

EXAMPLE 298

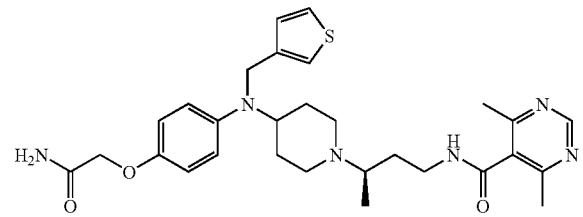

COMPOUND 298: 4,6-Dimethyl-pyrimidine-5-carboxylic acid ((R)-3-{4-[(4-carbamoylmethoxy-phenyl)-thiophen-3-ylmethyl-amino]-piperidin-1-yl}-butyl)-amide NH$_3$ (g) was bubbled through a solution of {4-[(1-{(R)-3-[(4,6-dimethyl-pyrimidine-5-carbonyl)-amino]-1-methyl-propyl}-piperidin-4-yl)-thiophen-3-ylmethyl-amino]-phenoxy}-acetic acid methyl ester (see EXAMPLE 297) (54 mg, 0.095 mmol) in MeOH (10 mL) for 10 minutes. The mixture was stirred at room temperature for 1 hour and concentrated under reduced pressure to give COMPOUND 298 as a pale brown solid (52 mg, 100%). ¹H NMR (CDCl₃) δ 0.89-1.12 (m, 2H), 1.00 (d, 3H, J=6.3 Hz), 1.52-1.63 (m, 1H), 1.74-1.78 (m, 3H), 2.13 (t, 1H, J=11.4 Hz), 2.51 (s, 6H), 2.51-2.57 (m, 1H), 2.72-2.84 (m, 3H), 3.27-3.40 (m, 2H), 3.79 (s, 2H), 3.85-3.89 (m, 1H), 4.40 (s, 2H), 5.59 (br s, 1H), 6.59-6.76 (m, 5H), 6.99 (s, 2H), 8.78 (br s, 1H), 8.86 (s, 1H). ES-MS m/z 551 (M+H).

EXAMPLE 299

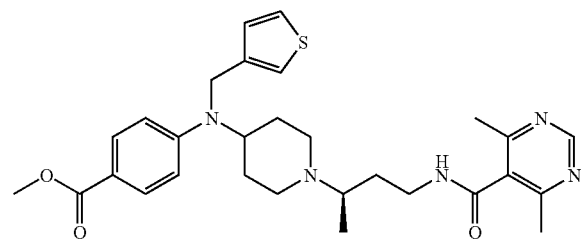

COMPOUND 299: 4-[(1-{(R)-3-[(4,6-Dimethyl-pyrimidine-5-carbonyl)-amino]-1-methyl-propyl}-piperidin-4-yl)-thiophen-3-ylmethyl-amino]-benzoic acid methyl ester Using general procedure A with methyl 4-aminobenzoate (507 mg, 3.35 mmol) and (R)-3-(4-oxo-piperidin-1-yl)-butyronitrile (669 mg, 4.03 mmol) followed by general procedure J afforded 4-[1-((R)-3-amino-1-methyl-propyl)-piperidin-4-ylamino]-benzoic acid methyl ester as a white foam (390 mg, 38% over 2 steps).

Using general procedure E, the above amine (390 mg, 1.28 mmol) and 4,6-dimethyl-pyrimidine-5-carboxylic acid (214 mg, 1.41 mmol) afforded 4-(1-{(R)-3-[(4,6-dimethyl-pyridimine-5-cabonyl)-amino]-1-methyl-propyl}-piperidin-4-ylamino]-benzoic acid methyl ester as a white foam (373 mg, 66%).

A solution of the above amide (373 mg, 0.85 mmol), 3-(bromomethyl)thiophene (180 mg, 1.02 mmol), and 2,2,6,6-tetramethylpiperidine (0.29 mL, 1.70 mmol) in CH₃CN (5 mL) was heated at 80° C. overnight. Then more 3-(bromomethyl)thiophene (180 mg, 1.02 mmol) and 2,2,6,6-tetramethylpiperidine (0.29 mL, 1.70 mmol) was added and the mixture was heated at 80° C. overnight to afford COMPOUND 299 as a yellow oil (61 mg, 13%) following work-up and purification. ¹H NMR (CDCl₃) δ 0.98-1.25 (m, 2H), 1.02 (d, 3H, J=6.6 Hz), 1.53-1.59 (m, 1H), 1.76-1.79 (m, 3H), 2.19 (t, 1H, J=11.4 Hz), 2.53 (s, 6H), 2.59 (t, 1H, J=10.5 Hz), 2.75-2.91 (m, 3H), 3.30-3.37 (m, 1H), 3.66-3.74 (m, 1H), 3.83 (s, 3H), 3.83-3.90 (m, 1H), 8.94-3.95 (m, 2H), 6.59 (d, 2H, J=9.0 Hz), 6.99-7.02 (m, 2H), 7.30 (dd, 1H, J=4.8, 3.0 Hz), 7.82 (d, 2H, J=9.0 Hz), 8.62-8.64 (m, 1H), 8.92 (s, 1H). ES-MS m/z 536 (M+H).

EXAMPLE 300

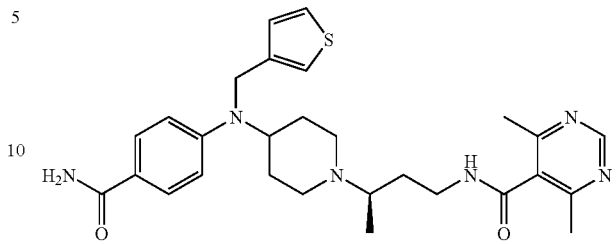

COMPOUND 300: 4,6-Dimethyl-pyrimidine-5-carboxylic acid ((R)-3-{4-[(4-carbamoyl-phenyl)-thiophen-3-ylmethyl-amino]-piperidin-1-yl}-butyl)-amide Using general procedure K with COMPOUND 299 (61 mg, 0.11 mmol) followed by general procedure E with the resulting acid and ammonium chloride (10 mg, 0.18 mmol) afforded COMPOUND 300 as a pale yellow foam (21 mg, 35%, over 2 steps). ¹H NMR (CDCl₃) δ 1.03 (d, 3H, J=6.0 Hz), 1.15-1.25 (m, 1H), 1.54-1.58 (m, 2H), 1.78 (d, 3H, J=9.0 Hz), 2.20-2.23 (m, 1H), 2.53 (s, 6H), 2.60 (td, 1H, J=9.0, 3.0 Hz), 2.86-2.96 (m, 3H), 3.33 (td, 1H, J=9.0, 3.0 Hz), 3.69 (td, 1H, J=9.0, 3.0 Hz), 3.84-3.86 (m, 1H), 3.94 (s, 2H), 6.62 (d, 2H, J=9.0 Hz), 6.99-7.02 (m, 2H), 7.31 (dd, 1H, J=6.0, 3.0 Hz), 7.63 (d, 2H, J=9.0 Hz), 8.68 (d, 1H, J=3.0 Hz), 8.91 (s, 1H). ES-MS m/z 521 [M+H]⁺.

EXAMPLE 301

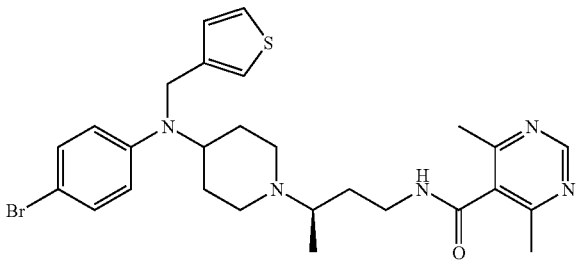

COMPOUND 301: 4,6-Dimethyl-pyrimidine-5-carboxylic acid ((R)-3-{4-[(4-bromo-phenyl)-thiophen-3-ylmethyl-amino]-piperidin-1-yl}-butyl)-amide Using general procedure A with 4-bromoaniline (969 mg, 5.63 mmol) and (R)-3-(4-oxo-piperidin-1-yl)-butyronitrile (936 mg, 5.63 mmol) gave the nitrile, which was subsequently reduced with BH₃-THF (1.0M in THF, 14.7 mL, 14.7 mmol) in THF (30 mL) at reflux and treated with 6N HCl (10 mL) to afford [1-((R)-3-amino-1-methyl-propyl)-piperidin-4-yl]-(4-bromo-phenyl)-amine as a white solid (750 mg, 28% over 2 steps) following basic work-up and purification.

Using general procedure E, the above primary amine (542 mg, 1.66 mmol) and 4,6-dimethyl-pyrimidine-5-carboxylic acid (328 mg, 2.16 mmol) afforded 4,6-dimethyl-pyrimidine-5-carboxylic acid {(R)-3-[4-(4-bromo-phenylamino)-piperidin-1-yl]-butyl}-amide (237 mg, 96%).

A solution of the above aniline (95 mg, 0.21 mmol) and 3-(bromomethyl)thiophene (56 mg, 0.32 mmol) in $CH_3CN$ (10 mL) was stirred at room temperature overnight to afford COMPOUND 301 as a white solid (27 mg, 24%) following purification. $^1H$ NMR ($CDCl_3$) δ 0.89-1.18 (m, 2H), 1.02 (d, 3H, J=6.6 Hz), 1.51-1.62 (m, 1H), 1.73-1.80 (m, 3H), 2.16 (t, 1H, J=11.4 Hz), 2.52 (s, 6H), 2.56 (t, 1H, J=12.0 Hz), 2.73-2.86 (m, 3H), 3.28-3.36 (m, 1H), 3.49-3.58 (m, 1H), 3.83 (s, 2H), 3.83-3.92 (m, 1H), 6.49 (d, 2H, J=9.0 Hz), 6.98-7.00 (m, 2H), 7.21 (d, 2H, J=9.0 Hz), 7.28 (dd, 1H, J=4.8, 3.0 Hz), 8.69 (br s, 1H), 8.88 (s, 1H). $^{13}C$ NMR ($CDCl_3$) δ 13.79, 22.32, 29.49, 30.76, 31.02, 40.61, 43.92, 45.61, 52.57, 56.23, 60.89, 115.15, 121.09, 126.43, 126.73, 132.21, 158.03. ES-MS m/z 556 (M+H). Anal. Calcd. for $C_{27}H_{34}N_5BrOS \cdot 0.5CH_2Cl_2 \cdot 0.6H_2O$: C, 54.16; H, 5.98; N, 11.48. Found: C, 54.54; H, 5.95; N, 11.11.

EXAMPLE 302

Using general procedure E, the above amine (238 mg, 0.6 mmol) and 4,6-dimethyl-pyrimidine-5-carboxylic acid (110 mg, 0.7 mmol) afforded 4-[4-(1-{(R)-3-[(4,6-dimethyl-pyrimidine-5-carbonyl)-amino]-1-methyl-propyl}-piperidin-4-ylamino)-phenoxy]-benzoic acid methyl ester as a white solid (309 mg, 97%).

Using general procedure H with the above aniline (309 mg, 0.60 mmol) and 3-(bromomethyl)thiophene (165 mg, 0.93 mmol) followed by general procedure K with the resulting ester afforded COMPOUND 302 as a white solid (149 mg, 42% over 2 steps). $^1H$ NMR ($CD_3OD$) δ 1.13 (d, 3H, J=6.3 Hz), 1.58-1.80 (m, 3H), 1.86-2.01 (m, 3H), 2.41-2.49 (m, 1H), 2.49 (s, 6H), 2.59-2.70 (m, 1H), 2.83-3.03 (m, 3H), 3.37-3.59 (m, 2H), 3.64-3.77 (m, 1H), 4.35 (s, 2H), 6.76-6.88 (m, 6H), 6.99 (d, 1H, J=4.2 Hz), 7.07-7.09 (m, 1H), 7.31 (dd, 1H, J=4.8, 3.0 Hz), 7.87 (d, 2H, J=8.7 Hz), 8.86 (s, 1H). $^{13}C$ NMR ($CD_3OD$) δ 14.49, 22.23, 30.83, 31.12, 33.62, 39.34,

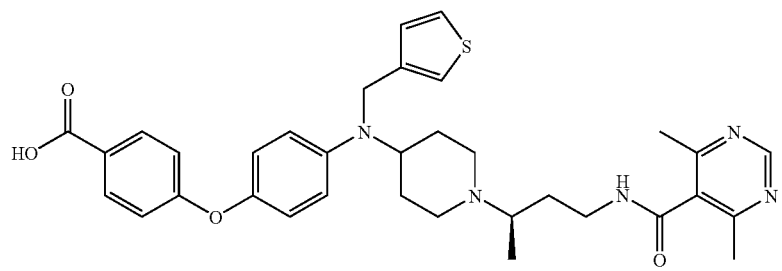

COMPOUND 302: 4-{4-[(1-{(R)-3-[(4,6-Dimethyl-pyrimidine-5-carbonyl)-amino]-1-methyl-propyl}-piperidin-4-yl)-thiophen-3-ylmethyl-amino]-phenoxy}-benzoic acid Using general procedure A with 4-(4-amino-phenoxy)-benzoic acid methyl ester (see EXAMPLE 96) (300 mg, 1.2 mmol) and (R)-3-(4-oxo-piperidin-1-yl)-butyronitrile (225 mg, 1.4 mmol) followed by general procedure J gave a green oil, which was subsequently treated with a solution of NaCN (175 mg) in $H_2O$ (5 mL) and MeOH (5 mL). The mixture was stirred at room temperature for 20 minutes to afford 4-{4-[1-((R)-3-amino-1-methyl-propyl)-piperidin-4-ylamino]-phenoxy}-benzoic acid methyl ester as a white solid (238 mg, 48% over 2 steps) following work-up and purification.

47.35, 47.66, 51.76, 58.36, 59.13, 117.13, 117.42, 122.20, 122.44, 127.08, 128.15, 132.58, 143.74, 147.70, 148.94, 158.60, 162.93, 165.04, 169.09, 175.54. ES-MS m/z 614 (M+H). Anal. Calcd. for $C_{34}H_{39}N_5O_4S \cdot 1.4CH_2Cl_2$: C, 58.03; H, 5.75; N, 9.56. Found: C, 58.05; H, 5.56; N, 9.73.

EXAMPLE 303

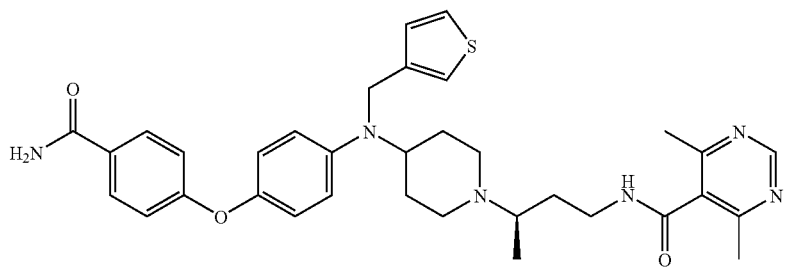

COMPOUND 303: 4,6-Dimethyl-pyrimidine-5-carboxylic acid [(R)-3-(4-{[4-(4-carbamoyl-phenoxy)-phenyl]-thiophen-3-ylmethyl-amino}-piperidin-1-yl)-butyl]-amide Using general procedure E, COMPOUND 302 (103 mg, 0.17 mmol) and ammonium chloride (23 mg, 0.42 mmol)

afforded COMPOUND 303 as a white solid (160 mg, 100%). ¹H NMR (CDCl₃) δ 0.87-1.21 (m, 2H), 1.01 (d, 3H, J=6.0 Hz), 1.49-1.60 (m, 1H), 1.71-1.85 (m, 3H), 2.11-2.22 (m, 1H), 2.53 (s, 6H), 2.55-2.62 (m, 1H), 2.71-2.92 (m, 3H), 3.25-3.38 (m, 1H), 3.48-3.61 (m, 1H), 3.82-3.94 (m, 1H), 3.83 (s, 2H), 5.77 (br s, 2H), 6.62 (d, 1H, J=8.1 Hz), 6.87 (d, 2H, J=8.4 Hz), 6.92 (d, 2H, J=8.4 Hz), 7.04 (d, 1H, J=3.3 Hz), 7.26-7.32 (m, 1H), 7.73 (d, 2H, J=7.8 Hz), 8.81 (br s, 1H), 8.89 (s, 1H). ¹³C NMR (CDCl₃) δ 13.80, 22.33, 29.50, 30.86, 31.03, 40.62, 43.96, 46.17, 52.59, 56.51, 60.90, 114.86, 116.77, 121.09, 121.80, 126.32, 126.87, 129.62, 131.31, 141.91, 146.46, 158.01, 162.73, 163.46, 166.72, 169.17. ES-MS m/z 613 (M+H). Anal. Calcd. for $C_{34}H_{40}N_6O_3S \cdot 0.3CH_2Cl_2$: C, 64.55; H, 6.41; N, 13.17. Found: C, 64.29; H, 6.38; N, 12.96.

EXAMPLE 304

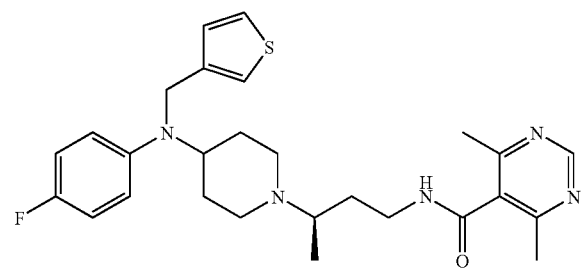

COMPOUND 304: 4,6-Dimethyl-pyrimidine-5-carboxylic acid ((R)-3-{4-[(4-fluoro-phenyl)-thiophen-3-ylmethyl-amino]-piperidin-1-yl}-butyl)-amide Using general procedure A with 4-fluoroaniline (328 mg, 2.95 mmol) and (R)-3-(4-oxo-piperidin-1-yl)-butyronitrile (500 mg, 3.01 mmol) followed by general procedure J gave the amine, which was subsequently treated with Boc₂O (680 mg, 3.12 mmol) in THF (20 mL) to afford the aniline after purification.

A solution of the above aniline (850 mg) and 3-(bromomethyl)thiophene (658 mg, 3.72 mmol) in CH₃CN (30 mL) was stirred at 60° C. for several hours. Standard work-up and purification afforded ((R)-3-{4-[(4-fluoro-phenyl)-thiophen-3-ylmethyl-amino]-piperidin-1-yl}-butyl)-carbamic acid tert-butyl ester as a white solid (657 mg, 48% over 3 steps).

Using general procedure C, the above substrate (657 mg, 1.43 mmol) gave [1-((R)-3-amino-1-methyl-propyl)-piperidin-4-yl]-(4-fluoro-phenyl)-thiophen-3-ylmethyl-amine (484 mg, 94%).

Using general procedure E, the above primary amine (120 mg, 0.33 mmol) and 4,6-dimethyl-pyrimidine-5-carboxylic acid (56 mg, 0.37 mmol) afforded COMPOUND 304 as a white solid (71 mg, 44%). ¹H NMR (CDCl₃) δ 0.87-1.17 (m, 2H), 1.01 (d, 3H, J=6.6 Hz), 1.51-1.59 (m, 1H), 1.72-1.80 (m, 3H), 2.14 (t, 1H, J=11.1 Hz), 2.52 (s, 6H), 2.54 (t, 1H, J=11.1 Hz), 2.73-2.88 (m, 3H), 3.27-3.49 (m, 2H), 3.80 (s, 2H), 3.84-3.92 (m, 1H), 6.55-6.59 (m, 2H), 6.81-6.88 (m, 2H), 6.98-7.00 (m, 2H), 7.26-7.28 (m, 1H), 8.77 (br s, 1H), 8.86 (s, 1H). ¹³C NMR (CDCl₃) δ 13.79, 22.33, 29.47, 30.72, 31.02, 40.57, 43.93, 45.62, 52.55, 56.20, 60.85, 109.14, 115.13, 116.05, 121.08, 124.31, 126.43, 126.73, 127.32, 131.26, 132.20, 141.37, 147.95, 158.01, 163.45, 166.73. ES-MS m/z 496 (M+H). Anal. Calcd. for $C_{27}H_{34}N_5FOS \cdot 0.3CH_2Cl_2$: C, 62.92; H, 6.69; N, 13.44. Found: C, 63.08; H, 6.69; N, 13.28.

EXAMPLE 305

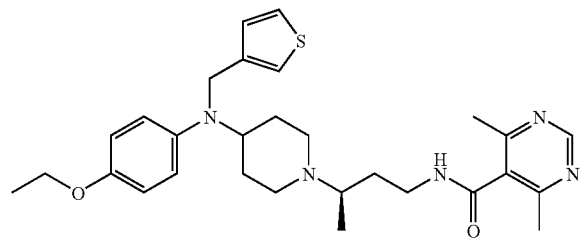

COMPOUND 305: 4,6-Dimethyl-pyrimidine-5-carboxylic acid ((R)-3-{4-[(4-ethoxy-phenyl)-thiophen-3-ylmethyl-amino]-piperidin-1-yl}-butyl)-amide Using general procedure A with p-phenetidine (137 mg, 1.20 mmol) and (R)-3-(4-oxo-piperidin-1-yl)-butyronitrile (166 mg, 1.20 mmol) followed by general procedure J gave [1-((R)-3-amino-1-methyl-propyl)-piperidin-4-yl]-(4-ethoxy-phenyl)-amine (251 mg).

Using general procedure E, the above amine (291 mg, 0.86 mmol) and 4,6-dimethyl-pyrimidine-5-carboxylic acid (144 mg, 0.95 mmol) afforded 4,6-dimethyl-pyrimidine-5-carboxylic acid {(R)-3-[4-(4-ethoxy-phenylamino)-piperidin-1-yl]-butyl}-amide as a white solid (268 mg, 64% over 3 steps).

A solution of the above aniline (70 mg, 0.17 mmol) and 3-(bromomethyl)thiophene (58 mg, 0.33 mmol) in CH₃CN (1.7 mL) was stirred at room temperature overnight. Standard work-up and purification afforded COMPOUND 305 as a white solid (66 mg, 77%). ¹H NMR (CDCl₃) δ 0.93-1.10 (m, 2H), 1.00 (d, 3H, J=6.3 Hz), 1.35 (t, 3H, J=6.69 Hz), 1.50-1.56 (m, 1H), 1.74-1.78 (m, 3H), 2.09-2.15 (m, 1H), 2.52 (s, 6H), 2.52-2.54 (m, 1H), 2.73-2.87 (m, 3H), 3.31-3.37 (m, 1H), 3.77 (s, 2H), 3.79-3.90 (m, 1H), 3.93 (q, 2H, J=6.6 Hz), 6.61 (d, 2H, J=9.0 Hz), 6.73 (d, 2H, J=9.0 Hz), 6.99-7.00 (m, 2H), 7.23-7.26 (m, 1H), 8.83-8.86 (m, 2H). ¹³C NMR (CDCl₃) δ 13.35, 14.99, 21.92, 29.20, 30.46, 30.57, 40.21, 43.59, 46.19, 52.13, 57.11, 60.52, 63.90, 115.31, 116.65, 120.80, 125.51, 126.83, 130.86, 141.86, 143.01, 151.61, 157.61, 163.00, 166.39. ES-MS m/z 522 (M+H). Anal. Calcd. for $C_{29}H_{39}N_5O_2S \cdot 0.1C_6H_{14} \cdot 0.1CH_2Cl_2$: C, 66.20; H, 7.59; N, 13.00. Found: C, 66.40; H, 7.61; N, 12.72.

EXAMPLE 306

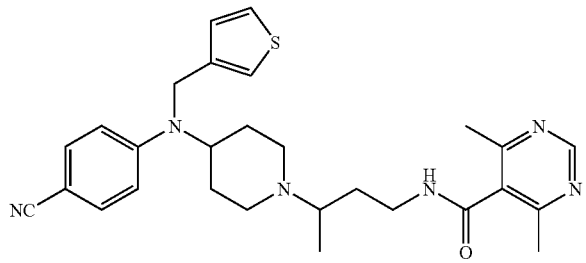

259

COMPOUND 306: 4,6-Dimethyl-pyrimidine-5-carboxylic acid (3-{4-[(4-cyano-phenyl)-thiophen-3-ylmethyl-amino]-piperidin-1-yl}-butyl)-amide To a solution of 4-(4-cyano-phenylamino)-piperidine-1-carboxylic acid tert-butyl ester (see EXAMPLE 106) (1.17 g, 3.89 mmol) in THF (20 mL) cooled to −78° C. was added KHMDS (0.5M, 12.0 mL, 6.0 mmol) and the mixture was stirred at −78° C. for 20 minutes. The reaction was quenched with 3-(bromomethyl)thiophene (1.06 g, 5.99 mmol) and warmed to room temperature to afford 4-[(4-cyano-phenyl)-thiophen-3-ylmethyl-amino]-piperidine-1-carboxylic acid tert-butyl ester (941 mg, 61%) following work-up and purification.

Using general procedure C with the above substrate (941 mg, 2.37 mmol), then general procedure B with the resulting amine and 2-(3-oxo-butyl)-isoindole-1,3-dione (998, 4.60 mmol) and then using general procedure D gave 4-{[1-(3-amino-1-methyl-propyl)-piperidin-4-yl]-thiophen-3-ylmethyl-amino}-benzonitrile (367 mg, 42% over 3 steps).

Using general procedure E, the above amine (132 mg, 0.36 mmol) and 4,6-dimethyl-pyrimidine-5-carboxylic acid (60 mg, 0.39 mmol) afforded COMPOUND 306 as a white solid (63 mg, 35%). $^1$H NMR (CDCl$_3$) δ 0.95-1.25 (m, 2H), 1.02 (d, 3H, J=6.6 Hz), 1.52-1.60 (m, 1H), 1.71-1.80 (m, 3H), 2.18 (t, 1H, J=12.3 Hz), 2.52 (s, 6H), 2.58 (t, 1H, J=12.0 Hz), 2.74-2.91 (m, 3H), 3.29-3.39 (m, 1H), 3.61-3.71 (m, 1H), 3.81-3.89 (m, 1H), 3.95 (s, 2H), 6.60 (d, 2H, J=9.0 Hz), 6.96-7.00 (m, 2H), 7.32 (dd, 1H, J=4.8, 3.0 Hz), 7.40 (d, 2H, J=8.7 Hz), 8.49 (br s, 1H), 8.91 (s, 1H). $^{13}$C NMR (CDCl$_3$) δ 13.82, 22.33, 29.60, 30.70, 31.23, 40.38, 43.92, 45.42, 52.29, 55.90, 60.56, 98.70, 112.65, 120.70, 121.19, 126.42, 126.90, 131.25, 133.95, 140.01, 151.65, 158.00, 163.50, 166.71. ES-MS m/z 503 (M+H). Anal. Calcd. for $C_{28}H_{34}N_6OS.0.2CH_2Cl_2$: C, 65.18; H, 6.67; N, 16.17. Found: C, 64.81; H, 6.71; N, 16.00.

EXAMPLE 307

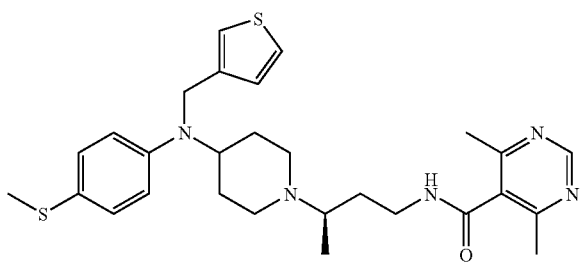

COMPOUND 307: 4,6-Dimethyl-pyrimidine-5-carboxylic acid ((R)-3-{4-[(4-methylsulfanyl-phenyl)-thiophen-3-ylmethyl-amino]-piperidin-1-yl}-butyl)-amide Using general procedure A, (R)-3-(4-oxo-piperidin-1-yl)-butyronitrile (1.00 g, 6.00 mmol) and 4-(methylthio)aniline afforded (R)-3-[4-(4-methylsulfanyl-phenylamino)-piperidin-1-yl]-butyronitrile as a brown oil (1.55 g, 89%).

Using general procedure H, the above aniline (1.55 g, 5.37 mmol) and 3-(bromomethyl)thiophene (1.23 g, 6.96 mmol) afforded the nitrile, which was subsequently reduced with LiAlH$_4$ (516 mg, 13.6 mmol) in Et$_2$O (34 mL) to afford [1-((R)-3-amino-1-methyl-propyl)-piperidin-4-yl]-(4-methylsulfanyl-phenyl)-thiophen-3-ylmethyl-amine as a colourless oil (1.22 g, 58% over 2 steps) following a Feiser work-up and purification.

Using general procedure E, the above amine (392 mg, 1.00 mmol) and 4,6-dimethyl-pyrimidine-5-carboxylic acid (190 mg, 1.25 mmol) afforded COMPOUND 307 as a white solid (367 mg, 70%). $^1$H NMR (CDCl$_3$) δ 0.88-1.18 (m, 2H), 1.02 (d, 3H, J=6.6 Hz), 1.52-1.58 (m, 1H), 1.74-1.79 (m, 3H), 2.16 (t, 1H, J=11.1 Hz), 2.39 (s, 3H), 2.52 (s, 6H), 2.56 (t, 1H, J=11.4 Hz), 2.73-2.89 (m, 3H), 3.28-3.36 (m, 1H), 3.52-3.60 (m, 1H), 3.83 (s, 2H), 3.86-3.93 (m, 1H), 6.58 (d, 2H, J=9.0 Hz), 7.00-7.02 (m, 2H), 7.18 (d, 2H, J=9.0 Hz), 7.26-7.29 (m, 1H), 8.73 (br s, 1H), 8.81 (s, 1H). $^{13}$C NMR (CDCl$_3$) δ 13.80, 19.32, 22.31, 29.50, 30.78, 31.05, 40.54, 43.98, 45.73, 52.55, 55.12, 60.81, 114.19, 121.04, 124.33, 126.29, 126.81, 131.57, 134.98, 141.73, 147.81, 158.00, 163.42, 166.74. ES-MS m/z 524 (M+H). Anal. Calcd. for $C_{28}H_{37}N_5OS_2.0.5CH_2Cl_2$: C, 60.46; H, 6.76; N, 12.37. Found: C, 60.61; H, 6.74; N, 12.24.

EXAMPLE 308

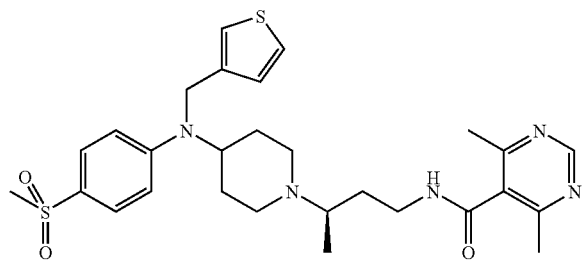

COMPOUND 308: 4,6-Dimethyl-pyrimidine-5-carboxylic acid ((R)-3-{4-[(4-methanesulfonyl-phenyl)-thiophen-3-ylmethyl-amino]-piperidin-1-yl}-butyl)-amide To a solution of COMPOUND 307 (273 mg, 0.522 mmol) in MeOH (5 mL) cooled to −15° C. was added a solution of OXONE® (1.41 g, 2.30 mmol) in H$_2$O (5 mL) and the mixture was stirred at −15° C. for 15 minutes. Standard work-up and purification afforded COMPOUND 308 as a white solid (69 mg, 23%). $^1$H NMR (CDCl$_3$) δ 0.96-1.25 (m, 2H), 1.03 (d, 3H, J=6.6 Hz), 1.54-1.61 (m, 1H), 1.71-1.84 (m, 3H), 2.21 (t, 1H, J=10.2 Hz), 2.53 (s, 6H), 2.60 (t, 1H, J=11.1 Hz), 2.77-2.92 (m, 3H), 2.99 (s, 3H), 3.31-3.38 (m, 1H), 3.66-3.74 (m, 1H), 3.82-3.89 (m, 1H), 3.98 (s, 2H), 6.67 (d, 2H, J=9.0 Hz), 6.98-7.01 (m, 2H), 7.32 (dd, 1H, J=5.1, 3.0 Hz), 7.66 (d, 2H, J=9.0 Hz), 8.49-8.50 (m, 1H), 8.92 (s, 1H). $^{13}$C NMR (CDCl$_3$) δ 13.85, 22.35, 29.53, 30.67, 31.23, 40.34, 43.92, 45.40, 45.54, 52.25, 55.99, 60.54, 112.25, 121.23, 126.45, 126.93, 129.57, 130.66, 131.26, 139.96, 152.59, 157.99, 163.51, 166.72. ES-MS m/z 556 (M+H). Anal. Calcd. for $C_{28}H_{37}N_5O_3S_2.0.6H_2O$: C, 59.36; H, 6.80; N, 12.36; S, 11.32. Found: C, 59.38; H, 6.74; N, 12.07; S, 11.22.

Scheme 16 describes the preparation of Examples 309-317, using general procedure E, and reagents listed below.

Scheme 16

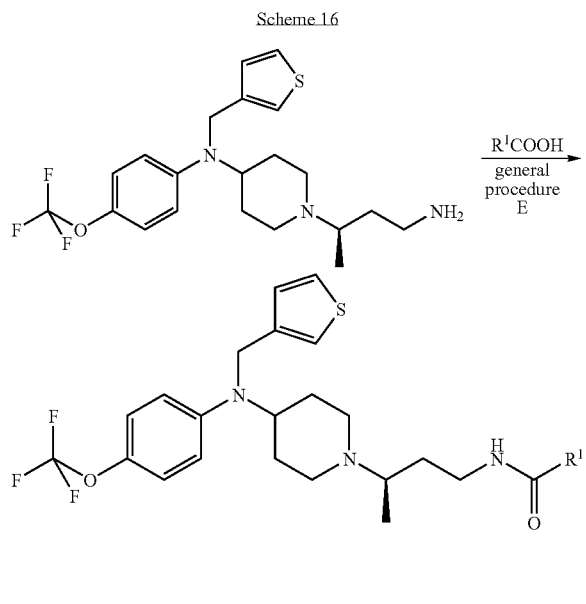

| Example | R¹COOH |
|---|---|
| 309 | 3,5-dimethylisonicotinic acid |
| 310 | 2,6-dimethylbenzoic acid |
| 311 | 2-chloro-6-methylbenzoic acid |
| 312 | 3,5-dimethylisoxazole-4-carboxylic acid |
| 313 | 1,3,5-trimethyl-1H-pyrazole-4-carboxylic acid |
| 314 | 2,4-dimethyl-1-oxy-nicotinic acid |
| 315 | 2,6-dimethyl-4-pyridin-4-yl-benzoic acid |
| 316 | 2,4-dimethylnicotinic acid |
| 317 | 2,4-dimethyl-thiophene-3-carboxylic acid |

EXAMPLE 309

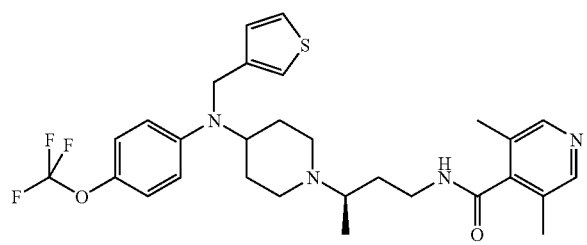

COMPOUND 309: 3,5-Dimethyl-N-((R)-3-{4-[thiophen-3-ylmethyl-(4-trifluoromethoxy-phenyl)-amino]-piperidin-1-yl}-butyl)-isonicotinamide Using general procedure A, (R)-3-(4-oxo-piperidin-1-yl)-butyronitrile (2.0 g, 12 mmol) and 4-(trifluoromethoxy) aniline (1.34 mL, 10.0 mmol) gave (R)-3-[4-(4-trifluoromethoxy-phenylamino)-piperidin-1-yl]-butyronitrile as a pale yellow solid (3.7 g, 94%).

Using general procedure H, the above nitrile (3.7 g, 11 mmol) and 3-(bromomethyl)thiophene (2.0 g, 11 mmol) gave the nitrile, which was subsequently reduced with LiAlH$_4$ (780 mg, 20.5 mmol) in Et$_2$O (35 mL) to afford [1-((R)-3-amino-1-methyl-propyl)-piperidin-4-yl]-thiophen-3-ylmethyl-(4-trifluoromethoxy-phenyl)-amine as a colourless oil (1.71 g, 80%) after a Feiser work-up and purification.

COMPOUND 309 was isolated as a white foam. $^1$H NMR (CDCl$_3$) δ 0.89-1.20 (m, 5H), 1.53-1.58 (m, 1H), 1.73-1.81 (m, 3H), 2.14-2.24 (m, 1H), 2.28 (s, 6H), 2.54-2.61 (m, 1H), 2.76-2.88 (m, 3H), 3.27-3.34 (m, 1H), 3.52-3.59 (m, 1H), 3.74 (s, 2H), 3.85-3.91 (m, 1H), 6.54 (d, 2H, J=8.4 Hz), 6.96-7.00 (m, 4H), 7.29 (dd, 1H, J=4.8, 3.0 Hz), 8.28 (s, 2H), 8.72 (br s, 1H). ES-MS m/z 561 (M+H).

EXAMPLE 310

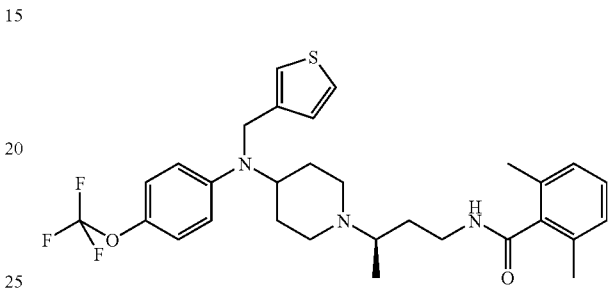

COMPOUND 310: 2,6-Dimethyl-N-((R)-3-{4-[thiophen-3-ylmethyl-(4-trifluoromethoxy-phenyl)-amino]-piperidin-1-yl}-butyl)-benzamide White solid. $^1$H NMR (CDCl$_3$) δ 0.96-1.20 (m, 2H), 1.00 (d, 3H, J=6.6 Hz), 1.50-1.56 (m, 1H), 1.70-1.80 (m, 3H), 2.14 (t, 1H, J=10.5 Hz), 2.32 (s, 6H), 2.54 (t, 1H, J=11.4 Hz), 2.74-2.90 (m, 3H), 3.24-3.32 (m, 1H), 3.48-3.56 (m, 1H), 3.75 (s, 2H), 3.86-3.94 (m, 1H), 6.55 (d, 2H, J=9.0 Hz), 6.89-7.10 (m, 7H), 7.29 (dd, 1H, J=4.8, 3.0 Hz), 8.42-8.44 (m, 1H). ES-MS m/z 560 (M+H).

EXAMPLE 311

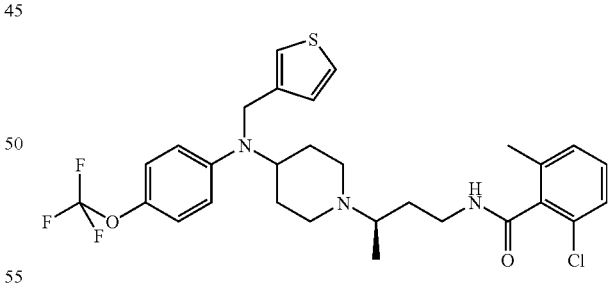

COMPOUND 311: 2-Chloro-6-methyl-N-((R)-3-{4-[thiophen-3-ylmethyl-(4-trifluoromethoxy-phenyl)-amino]-piperidin-1-yl}-butyl)-benzamide White solid. $^1$H NMR (CDCl$_3$) δ 0.99-1.27 (m, 2H), 1.00 (d, 3H, J=6.6 Hz), 1.49-1.57 (m, 1H), 1.72-1.84 (m, 3H), 2.14 (t, 1H, J=11.7 Hz), 2.36 (s, 3H), 2.55 (t, 1H, J=10.5 Hz), 2.79-2.96 (m, 3H), 3.17-3.35 (m, 1H), 3.50-3.58 (m, 1H), 3.78 (s, 2H), 3.87-3.94 (m, 1H), 6.56 (d, 2H, J=9.3 Hz), 6.87

(d, 1H, J=5.1 Hz), 6.91-7.14 (m, 6H), 7.29 (dd, 1H, J=4.8, 3.0 Hz), 8.63-8.65 (m, 1H). ES-MS m/z 580 (M+H).

EXAMPLE 312

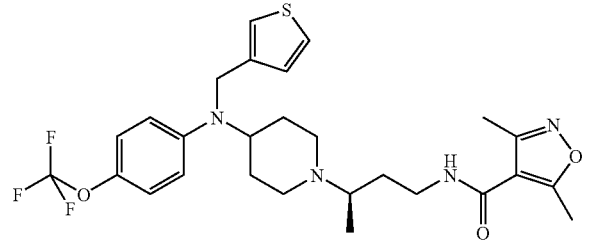

COMPOUND 312: 3,5-Dimethyl-isoxazole-4-carboxylic acid ((R)-3-{4-[thiophen-3-ylmethyl-(4-trifluoromethoxy-phenyl)-amino]-piperidin-1-yl}-butyl)-amide White solid. $^1$H NMR(CDCl$_3$) δ 1.01 (d, 3H, J=6.6 Hz), 1.34-1.46 (m, 1H), 1.52-1.61 (m, 2H), 1.68-1.84 (m, 3H), 2.19 (t, 1H, J=11.7 Hz), 2.39 (s, 3H), 2.52-2.59 (m, 1H), 2.54 (s, 3H), 2.79-2.88 (m, 3H), 3.37-3.43 (m, 1H), 3.55-3.67 (m, 2H), 4.29 (s, 2H), 6.64 (d, 2H, J=9.3 Hz), 6.90 (br s, 1H), 6.98-7.03 (m, 4H), 7.29 (dd, 1H, J=4.8, 3.0 Hz). ES-MS nz/z 551 (M+H).

EXAMPLE 313

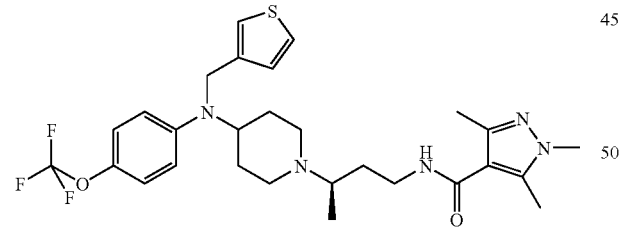

COMPOUND 313: 1,3,5-Trimethyl-1H-pyrazole-4-carboxylic acid ((R)-3-{4-[thiophen-3-ylmethyl-(4-trifluoromethoxy-phenyl)-amino]-piperidin-1-yl}-butyl)-amide White solid. $^1$H NMR (CDCl$_3$) δ 1.00 (d, 3H, J=6.6 Hz), 1.48-1.82 (m, 7H), 2.20 (t, 1H, J=10.8 Hz), 2.37 (s, 3H), 2.44 (s, 3H), 2.51 (t, 1H, J=11.7 Hz), 2.74-2.87 (m, 3H), 3.40-3.65 (m, 3H), 3.68 (s, 3H), 4.34 (s, 2H), 6.32-6.34 (m, 1H), 6.65 (d, 2H, J=9.3 Hz), 6.97-7.03 (m, 3H), 7.28 (dd, 1H, J=5.1, 3.0 Hz). ES-MS m/z 564 (M+H).

EXAMPLE 314

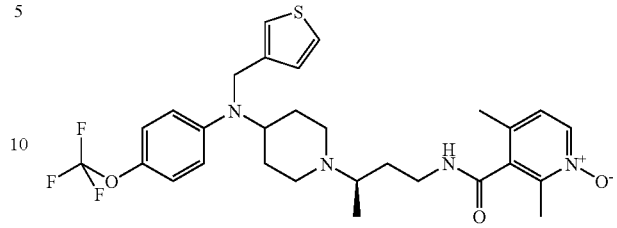

COMPOUND 314: 2,4-Dimethyl-1-oxy-N-((R)-3-{4-[thiophen-3-ylmethyl-(4-trifluoromethoxy-phenyl)-amino]-piperidin-1-yl}-butyl)-nicotinamide White solid. $^1$H NMR (CDCl$_3$) δ 0.97-1.28 (m, 2H), 1.02 (d, 3H, J=6.9 Hz), 1.54-1.60 (m, 1H), 1.71-1.79 (m, 3H), 2.19 (t, 1H, J=10.5 Hz), 2.28 (s, 3H), 2.54 (s, 3H), 2.61 (t, 1H, J=11.4 Hz), 2.79-2.90 (m, 3H), 3.33-3.37 (m, 1H), 3.54-3.59 (m, 1H), 3.79-3.86 (m, 1H), 4.00 (s, 2H), 6.59 (d, 2H, J=9.0 Hz), 6.81 (d, 1H, J=6.9 Hz), 6.98-7.03 (m, 4H), 7.30 (dd, 1H, J=4.8, 3.0 Hz), 7.98 (d, 1H, J=6.6 Hz), 8.59-8.60 (m, 1H). ES-MS m/z 577 (M+H).

EXAMPLE 315

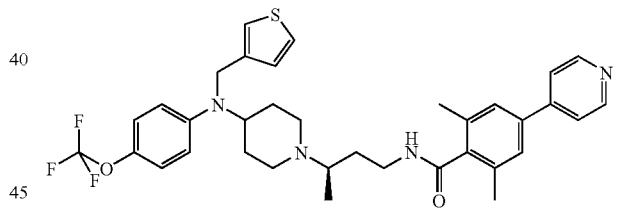

COMPOUND 315: 2,6-Dimethyl-4-pyridin-4-yl-N-((R)-3-{4-[thiophen-3-ylmethyl-(4-trifluoromethoxy-phenyl)-amino]-piperidin-1-yl}-butyl)-benzamide White solid. $^1$H NMR (CDCl$_3$) δ 1.01-1.31 (m, 2H), 1.02 (d, 3H, J=6.6 Hz), 1.54-1.58 (m, 1H), 1.73-1.85 (m, 3H), 2.17 (t, 1H, J=11.1 Hz), 2.41 (s, 6H), 2.60 (t, 1H, J=12.3 Hz), 2.77-2.93 (m, 3H), 3.29-3.37 (m, 1H), 3.49-3.57 (m, 1H), 3.72 (s, 2H), 3.85-3.94 (m, 1H), 6.49 (d, 2H, J=9.3 Hz), 6.58 (d, 1H, J=4.8 Hz), 6.89 (d, 1H, J=1.5 Hz), 6.96 (d, 2H, J=8.7 Hz), 7.16 (dd, 1H, J=4.8, 3.0 Hz), 7.30 (s, 2H), 7.44-7.46 (m, 2H), 8.31-8.33 (m, 1H), 8.66 (d, 2H, J=6.0 Hz). ES-MS m/z 637 (M+H).

EXAMPLE 316

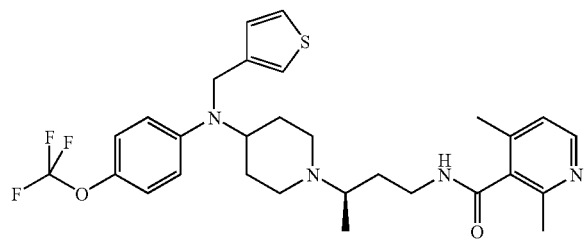

COMPOUND 316: 2,4-Dimethyl-N-((R)-3-{4-[thiophen-3-ylmethyl-(4-trifluoromethoxy-phenyl)-amino]-piperidin-1-yl}-butyl)-nicotinamide Using general procedure G, COMPOUND 314 afforded COMPOUND 316 as a white foam. $^1$H NMR (CDCl$_3$) δ 1.01 (d, 3H, J=6.6 Hz), 1.11-1.29 (m, 2H), 1.51-1.59 (m, 1H), 1.71-1.83 (m, 3H), 2.17 (t, 1H, J=11.1 Hz), 2.29 (s, 3H), 2.51-2.60 (m, 1H), 2.54 (s, 3H), 2.76-2.91 (m, 3H), 3.27-3.35 (m, 1H), 3.51-3.58 (m, 1H), 3.82 (s, 2H), 3.81-3.88 (m, 1H), 6.56 (d, 2H, J=9.3 Hz), 6.86 (d, 1H, J=5.1 Hz), 6.95-6.99 (m, 4H), 7.28 (dd, 1H, J=4.8, 3.0 Hz), 8.26 (d, 1H, J=5.1 Hz), 8.55 (br s, 1H). ES-MS m/z 561 (M+H).

EXAMPLE 317

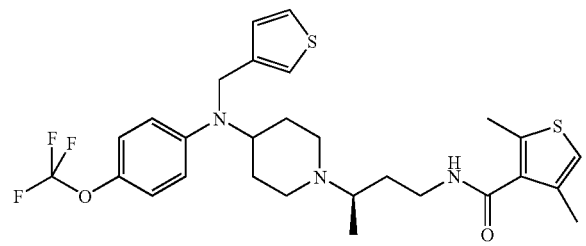

COMPOUND 317: 2,4-Dimethyl-thiophene-3-carboxylic acid ((R)-3-{4-[thiophen-3-ylmethyl-(4-trifluoromethoxy-phenyl)-amino]-piperidin-1-yl}-butyl)-amide To a solution of 3-bromo-4-methylthiophene (500 mg, 2.82 mmol) in Et$_2$O (10 mL) cooled to −78° C. was added t-BuLi (1.7M in Et$_2$O, 3.7 mL, 6.36 mmol). CO$_2$ (g) was bubbled through the solution at −78° C. for 20 minutes and while the solution was warmed to room temperature. The reaction was quenched with H$_2$O (10 mL) to afford 4-methyl-thiophene-3-carboxylic acid as a pale grey solid (240 mg, 60%) following an acidic work-up and purification.

To a solution of the above acid (390 mg, 2.75 mmol) in THF (10 mL) cooled to −78° C. was added n-BuLi (2.5M in THF, 2.75 mL, 6.05 mmol) and the mixture was stirred −78° C. for 30 minutes. MeI (0.43 mL, 6.9 mmol) was added slowly at −78° C. and the mixture was stirred at room temperature overnight. The reaction was quenched with H$_2$O (15 mL) to afford 2,4-dimethyl-thiophene-3-carboxylic acid as a pale grey solid (344 mg, 80%) following an acidic work-up and purification.

COMPOUND 317 was isolated as a white foam. $^1$H NMR (CDCl$_3$) δ 1.00 (d, 3H, J=6.6 Hz), 1.14-1.45 (m, 2H), 1.48-1.56 (m, 1H), 1.69-1.83 (m, 3H), 2.17 (t, 1H, J=11.4 Hz), 2.21 (s, 3H), 2.47 (s, 3H), 2.56 (t, 1H, J=11.1 Hz), 2.78-2.90 (m, 3H), 3.23-3.32 (m, 1H), 3.55-3.64 (m, 1H), 3.76-3.86 (m, 1H), 4.09 (s, 2H), 6.55 (s, 1H), 6.60 (d, 2H, J=9.3 Hz), 6.94-7.01 (m, 4H), 7.28 (dd, 1H, J=4.8, 3.3 Hz), 7.64-7.95 (m, 1H). ES-MS m/z 566 (M+H).

Scheme 17 describes the preparation of Examples 318-326, using general procedure E, and reagents listed below.

Scheme 17

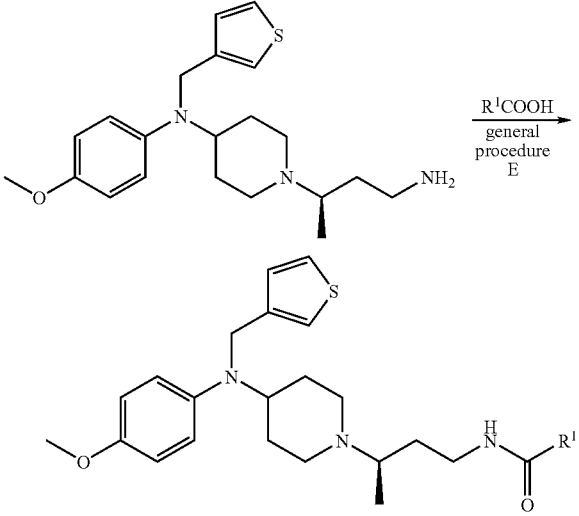

| Example | R$^1$COOH |
|---|---|
| 318 | 2,6-dimethylbenzoic acid |
| 319 | 2-chloro-6-methylbenzoic acid |
| 320 | 1,3,5-trimethyl-1H-pyrazole-4-carboxylic acid |
| 321 | 2,4-dimethylnicotinic acid |
| 322 | 2,4-dimethyl-1-oxy-nicotinic acid |
| 323 | 3,5-dichloroisonicotinic acid |
| 324 | 3,5-dimethylisoxazole-4-carboxylic acid |
| 325 | 3,5-dimethylisonicotinic acid |
| 326 | 2,4-dimethyl-thiophene-3-carboxylic acid |

EXAMPLE 318

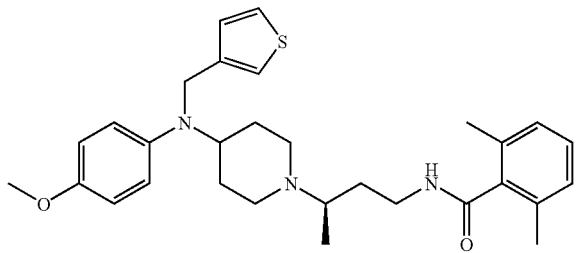

COMPOUND 318: N—((R)-3-{4-[(4-Methoxy-phenyl)-thiophen-3-ylmethyl-amino]-piperidin-1-yl}-butyl)-2,6-dimethyl-benzamide Using general procedure H, (R)-3-[4-(4-methoxy-phenylamino)-piperidin-1-yl]-butyronitrile (see EXAMPLE 230) (8.18 g, 30.1 mmol) and 3-(bromomethyl)thiophene (5.33 g, 30.1 mmol) gave the nitrile, which was subsequently reduced with LiAlH$_4$ (3.15 g, 83.2 mmol) in Et$_2$O (66 mL) to afford [1-((R)-3-amino-1-methyl-propyl)-piperidin-4-yl]-(4-methoxy-phenyl)-thiophen-3-ylmethyl-amine as a yellow oil (6.23 g, 80%) after a Feiser work-up and purification.

COMPOUND 318 was isolated as a yellow foam. $^1$H NMR (CDCl$_3$) δ 0.91-1.20 (m, 2H), 0.98 (d, 3H, J=6.6 Hz), 1.47-1.55 (m, 1H), 1.68-1.82 (m, 3H), 2.10 (t, 1H, J=11.4 Hz), 2.32 (s, 6H), 2.51 (t, 1H, J=11.4 Hz), 2.72-2.88 (m, 3H), 3.23-3.43 (m, 2H), 3.70 (s, 2H), 3.71 (s, 3H), 3.85-3.94 (m, 1H), 6.58-6.62 (m, 2H), 6.71-6.74 (m, 2H), 6.89-6.94 (m, 3H), 6.96 (s, 1H), 7.05 (dd, 1H, J=8.4, 6.3 Hz), 7.24 (dd, 1H, J=5.1, 3.3 Hz), 8.49 (br s, 1H). ES-MS m/z 506 (M+H).

EXAMPLE 319

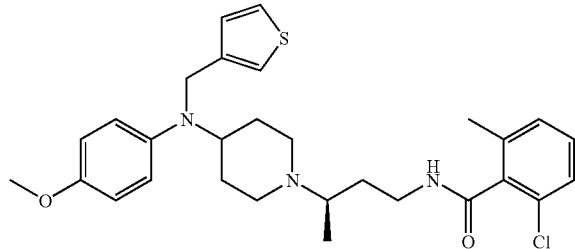

COMPOUND 319: 2-Chloro-N-((R)-3-{4-[(4-methoxy-phenyl)-thiophen-3-ylmethyl-amino]-piperidin-1-yl}-butyl)-6-methyl-benzamide Yellow foam. $^1$H NMR (CDCl$_3$) δ 0.94-1.25 (m, 2H), 0.99 (d, 3H, J=6.3 Hz), 1.47-1.55 (m, 1H), 1.71-1.83 (m, 3H), 2.11 (t, 1H, J=11.7 Hz), 1.59 (s, 3H), 2.51 (t, 1H, J=11.7 Hz), 2.76-2.92 (m, 3H), 3.29-3.39 (m, 2H), 3.71 (s, 5H), 3.86-3.95 (m, 1H), 6.58-6.63 (m, 2H), 6.70-6.74 (m, 2H), 6.88 (dd, 1H, J=4.8, 1.5 Hz), 6.91-6.92 (m, 1H), 7.02-7.04 (m, 2H), 7.09-7.13 (m, 1H), 7.24 (dd, 1H, J=4.8, 3.0 Hz), 8.74 (br s, 1H). ES-MS m/z 526 (M+H).

EXAMPLE 320

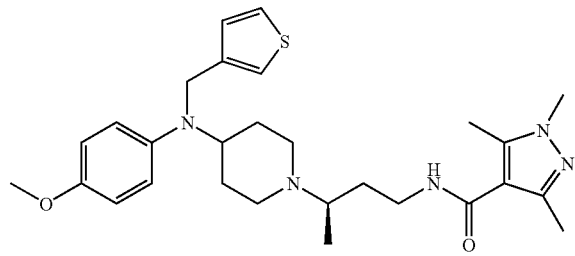

COMPOUND 320: 1,3,5-Trimethyl-1H-pyrazole-4-carboxylic acid ((R)-3-{4-[(4-methoxy-phenyl)-thiophen-3-ylmethyl-amino]-piperidin-1-yl}-butyl)-amide Colourless oil. $^1$H NMR (CDCl$_3$) δ 1.02 (d, 3H, J=6.3 Hz), 1.51-1.87 (m, 3H), 2.21 (t, 1H, J=12.0 Hz), 2.36 (s, 3H), 2.43 (s, 3H), 2.52 (t, 1H, J=11.7 Hz), 2.80-2.88 (m, 3H), 3.42-3.53 (m, 3H), 3.66 (s, 3H), 3.73 (s, 3H), 4.26 (s, 2H), 6.45 (br s, 1H), 6.69-6.78 (m, 4H), 6.96-7.00 (m, 2H), 7.22 (dd, 1H, J=4.8, 3.0 Hz). ES-MS m/z 510 (M+H).

EXAMPLE 321

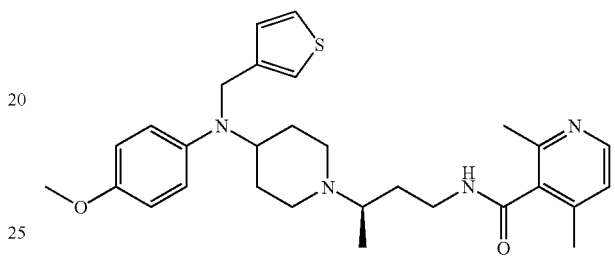

COMPOUND 321: N—((R)-3-{4-[(4-Methoxy-phenyl)-thiophen-3-ylmethyl-amino]-piperidin-1-yl}-butyl)-2,4-dimethyl-nicotinamide Colourless oil. $^1$H NMR (CDCl$_3$) δ 0.91-1.23 (m, 2H), 1.01 (d, 3H, J=6.6 Hz), 1.51-1.57 (m, 1H), 1.71-1.83 (m, 3H), 2.14 (t, 1H, J=12.3 Hz), 2.30 (s, 3H), 2.50-2.57 (m, 1H), 2.55 (s, 3H), 2.74-2.86 (m, 3H), 3.31-3.39 (m, 2H), 3.71 (s, 3H), 3.74 (s, 2H), 3.84-3.91 (m, 1H), 6.60-6.63 (m, 2H), 6.72-6.74 (m, 2H), 6.86 (d, 1H, J=5.1 Hz), 6.94-6.96 (m, 2H), 7.24 (dd, 1H, J=4.8, 3.0 Hz), 8.25 (d, 1H, J=5.4 Hz), 8.66 (br s, 1H). ES-MS m/z 507 (M+H).

EXAMPLE 322

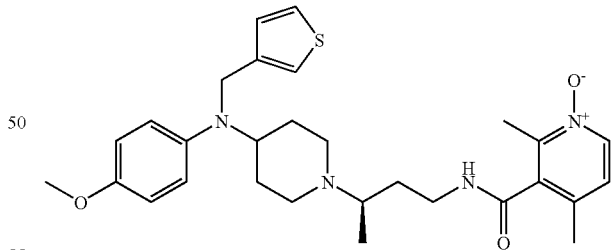

COMPOUND 322: N—((R)-3-{4-[(4-Methoxy-phenyl)-thiophen-3-ylmethyl-amino]-piperidin-1-yl}-butyl)-2,4-dimethyl-1-oxy-nicotinamide Pale yellow oil. $^1$H NMR (CDCl$_3$) δ 1.01 (d, 3H, J=6.3 Hz), 1.12-1.37 (m, 2H), 1.53-1.62 (m, 1H), 1.78-1.84 (m, 3H), 2.17 (t, 1H, J=12.0 Hz), 2.28 (s, 3H), 2.38 (s, 3H), 2.52 (t, 1H, J=11.7 Hz), 2.75-2.88 (m, 3H), 3.35-3.41 (m, 3H), 3.71 (s, 3H), 3.71-3.76 (m, 1H), 4.00 (s, 2H), 6.64-6.68 (m, 2H), 6.71-6.76 (m, 2H), 6.80 (d, 1H, J=6.6 Hz), 6.96-7.01 (m, 2H), 2.24 (dd, 1H, J=4.8, 3.0 Hz), 7.92 (d, 1H, J=6.6 Hz), 8.82-8.85 (m, 1H). ES-MS m/z 524 (M+H).

EXAMPLE 323

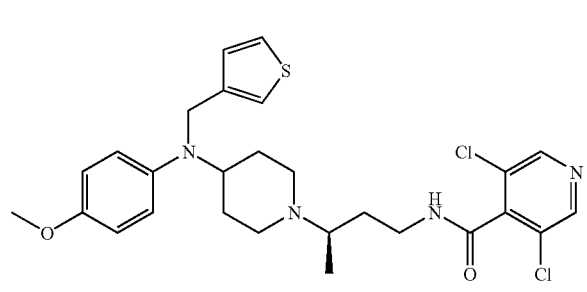

COMPOUND 323: 3,5-Dichloro-N-((R)-3-{4-[(4-methoxy-phenyl)-thiophen-3-ylmethyl-amino]-piperidin-1-yl}-butyl)-isonicotinamide Pale yellow oil. ¹H NMR (CDCl₃) δ 0.92-1.23 (m, 2H), 0.99 (d, 3H, J=6.6 Hz), 1.47-1.55 (m, 1H), 1.72-1.83 (m, 3H), 2.12 (t, 1H, J=11.4 Hz), 2.51 (t, 1H, J=12.3 Hz), 2.76-2.92 (m, 3H), 3.27-3.42 (m, 2H), 3.71 (s, 3H), 3.76 (s, 2H), 3.81-3.88 (m, 1H), 6.60-6.64 (m, 2H), 6.70-6.74 (m, 2H), 6.93-6.96 (m, 2H), 2.25 (dd, 1H, J=4.8, 3.0 Hz), 8.46 (s, 2H), 9.14-9.16 (m, 1H). ES-MS m/z 547 (M+H).

EXAMPLE 324

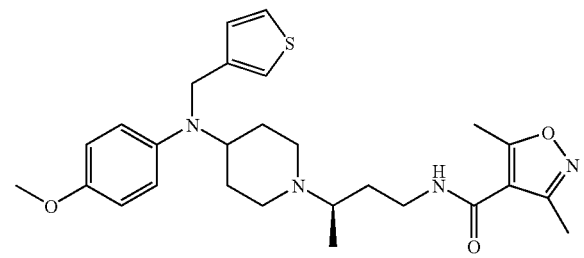

COMPOUND 324: 3,5-Dimethyl-isoxazole-4-carboxylic acid ((R)-3-{4-[(4-methoxy-phenyl)-thiophen-3-ylmethyl-amino]-piperidin-1-yl}-butyl)-amide Pale yellow oil. ¹H NMR (CDCl₃) δ 0.99 (d, 3H, J=6.3 Hz), 1.29-1.61 (m, 3H), 1.68-1.88 (m, 3H), 2.16 (t, 1H, J=11.1 Hz), 2.36 (s, 3H), 2.47-2.54 (m, 1H), 2.49 (s, 3H), 2.76-2.85 (m, 3H), 3.32-3.46 (m, 2H), 3.52-3.62 (m, 1H), 3.73 (s, 3H), 4.22 (s, 2H), 6.69-6.78 (m, 4H), 6.96-7.00 (m, 2H), 7.03-7.06 (m, 1H), 7.22 (dd, 1H, J=4.8, 3.0 Hz). ES-MS m/z 497 (M+H).

EXAMPLE 325

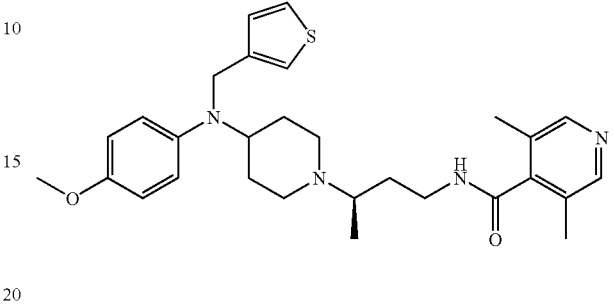

COMPOUND 325: N—((R)-3-{4-[(4-Methoxy-phenyl)-thiophen-3-ylmethyl-amino]-piperidin-1-yl}-butyl)-3,5-dimethyl-isonicotinamide Colourless oil. ¹H NMR (CDCl₃) δ 0.86-1.16 (m, 2H), 1.00 (d, 3H, J=6.3 Hz), 1.50-1.57 (m, 1H), 1.70-1.80 (m, 3H), 2.13 (t, 1H, J=11.4 Hz), 2.28 (s, 3H), 2.54 (t, 1H, J=11.4 Hz), 2.73-2.88 (m, 3H), 3.25-3.44 (m, 2H), 3.69 (s, 2H), 3.71 (s, 3H), 3.84-3.92 (m, 1H), 6.59 (d, 2H, J=9.0 Hz), 6.70-6.75 (m, 2H), 6.96-7.00 (m, 1H), 7.25 (dd, 1H, J=4.8, 3.0 Hz), 8.29 (s, 2H), 8.76 (br s, 1H). ES-MS nz/z 507 (M+H).

EXAMPLE 326

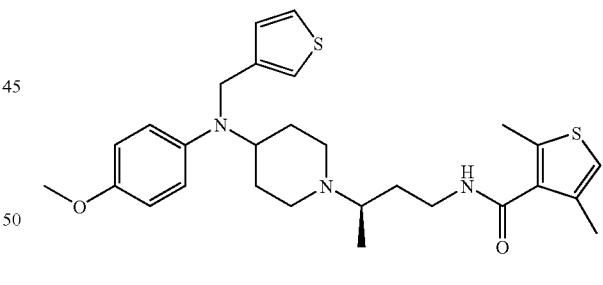

COMPOUND 326: 2,4-Dimethyl-thiophene-3-carboxylic acid ((R)-3-{4-[(4-methoxy-phenyl)-thiophen-3-ylmethyl-amino]-piperidin-1-yl}-butyl)-amide Colourless oil. ¹H NMR (CDCl₃) δ 0.99 (d, 3H, J=6.6 Hz), 1.10-1.42 (m, 2H), 1.48-1.55 (m, 1H), 1.70-1.81 (m, 3H), 2.13 (t, 1H, J=12.0 Hz), 2.08 (s, 3H), 2.47 (s, 3H), 2.52 (t, 1H, J=12.0 Hz), 2.75-2.88 (m, 3H), 3.23-3.32 (m, 1H), 3.39-3.49 (m, 1H), 3.72 (s, 3H), 3.76-3.85 (m, 1H), 4.03 (s, 2H), 6.55 (d, 1H, J=0.9 Hz), 6.64-6.67 (m, 2H), 6.74-6.77 (m, 2H), 6.94-6.98 (m, 2H), 7.24 (dd, 1H, J=4.8, 3.3 Hz), 7.98 (br s, 1H). ES-MS m/z 512 (M+H).

EXAMPLE 327

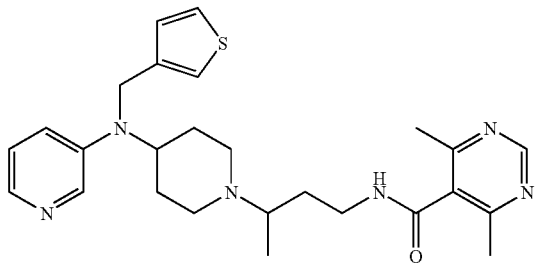

COMPOUND 327: 4,6-Dimethyl-pyrimidine-5-carboxylic acid {3-[4-(pyridin-3-yl-thiophen-3-ylmethyl-amino)-piperidin-1-yl]-butyl}-amide Using general procedure A, 3-aminopyridine (1.43 g, 1.01 mmol) and 1-Boc-4-piperidone (3.0 g, 1.0 mmol) afforded 4-(pyridin-3-ylamino)-piperidine-1-carboxylic acid tert-butyl ester as a white solid (3.15 g, 92%).

To a solution of 3-thiophenecarboxylic acid (300 mg, 2.34 mmol) in $CH_2Cl_2$ (15 mL) and DMF (catalytic) cooled to 0° C. was added oxalyl chloride (0.65 mL, 7.34 mmol). The mixture was stirred at room temperature for 1 hour. The mixture was concentrated and dried in vacuo for 10 minutes to yield a pale yellow solid. A solution of the above amine (584 mg, 2.11 mmol) in pyridine (10 mL) and DMAP (catalytic) were added and the mixture was heated to 70° C. overnight to give the crude material which was used in the next reaction without purification.

Using general procedure C, the above substrate afforded thiophene-3-carboxylic acid piperidin-4-yl-pyridin-3-yl-amide as a white solid (261 mg, 39% over 2 steps).

Using general procedure I, the above amine (261 mg, 0.91 mmol) gave the nitrile, which was subsequently reduced with $BH_3$-THF (1M in THF, 3.4 mL, 3.4 mmol) in THF (5 mL) at reflux and treated with 6N HCl (1.7 mL) to afford [1-(3-amino-1-methyl-propyl)-piperidin-4-yl]-pyridin-3-yl-thiophen-3-ylmethyl-amine as a white solid (86 mg) following basic work-up and purification.

Using general procedure E, the above amine (86 mg) and 4,6-dimethyl-pyrimidine-5-carboxylic acid (57 mg, 0.37 mmol) afforded COMPOUND 327 as a white solid (46 mg, 10% over 3 steps). $^1$H NMR (CDCl$_3$) δ 0.96-1.34 (m, 2H), 1.01 (d, 3H, J=6.6 Hz), 1.51-1.59 (m, 1H), 1.71-1.79 (m, 3H), 2.16 (t, 1H, J=11.4 Hz), 2.50 (s, 6H), 2.52-2.74 (m, 1H), 2.78-2.89 (m, 3H), 3.28-3.36 (m, 1H), 3.60 (tt, 1H, J=11.7, 3.6 Hz), 3.79-3.86 (m, 1H), 3.88 (s, 2H), 6.84 (dd, 1H, J=8.4, 2.1 Hz), 6.97-7.04 (m, 3H), 7.28 (dd, 1H, J=4.8, 3.3 Hz), 7.90 (d, 1H, J=4.2 Hz), 8.04 (d, 1H, J=3.0 Hz), 8.67-8.68 (m, 1H), 8.85 (s, 1H). $^{13}$C NMR (CDCl$_3$) δ 13.84, 22.33, 29.52, 30.68, 31.14, 40.46, 43.94, 45.24, 52.39, 55.85, 60.68, 120.04, 121.17, 123.94, 126.60, 126.65, 131.27, 135.81, 138.63, 140.82, 144.77, 157.99, 163.45, 166.73. ES-MS m/z 479 (M+H). Anal. Calcd. for $C_{26}H_{34}N_6OS.0.9H_2O$: C, 63.10; H, 7.29; N, 16.98. Found: C, 63.11; H, 7.08; N, 16.90.

EXAMPLE 328

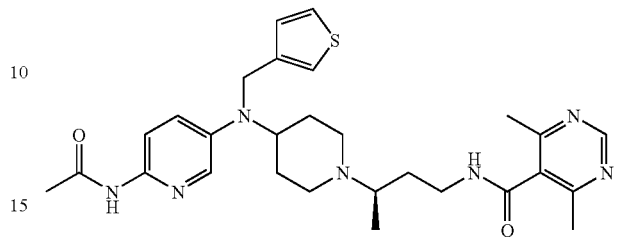

COMPOUND 328: 4,6-Dimethyl-pyrimidine-5-carboxylic acid ((R)-3-{4-[(6-acetylamino-pyridin-3-yl)-thiophen-3-ylmethyl-amino]-piperidin-1-yl}-butyl)-amide Using general procedure H, 4,6-dimethyl-pyrimidine-5-carboxylic acid {(R)-3-[4-(6-acetylamino-pyridin-3-ylamino)-piperidin-1-yl]-butyl}-amide (see EXAMPLE 246) (343 mg, 0.780 mmol) and 3-(bromomethyl)thiophene (207 mg) gave COMPOUND 328 as a yellow foam (86 mg, 21%). $^1$H NMR (CDCl$_3$) δ 0.94-1.22 (m, 2H), 1.01 (d, 3H, J=6.6 Hz), 1.55 (m, 1H), 1.75 (m, 3H), 2.10 (s, 3H), 2.19 (m, 1H), 2.51 (s, 6H), 2.55 (m, 1H), 2.73-2.89 (m, 3H), 3.32 (m, 1H), 3.48 (m, 1H), 3.84 (s, 2H), 3.87 (m, 1H), 7.49 (m, 3H), 7.27 (m, 1H), 7.65 (d, 1H, J=3.0 Hz), 7.93 (d, 1H, J=9.3 Hz), 8.06 (s, 1H), 8.63 (m, 1H), 8.83 (s, 1H). $^{13}$C NMR (CDCl$_3$) δ 13.82, 22.33, 24.81, 29.56, 30.68, 31.10, 40.51, 53.91, 45.47, 52.40, 56.77, 60.75, 114.94, 121.30, 123.84, 126.63, 126.71, 131.23, 133.74, 140.77, 142.05, 143.02, 158.01, 163.43, 166.72, 168.47. ES-MS m/z 536 (M+H). Anal. Calcd. for $C_{28}H_{37}N_7SO_2.1.1CH_2Cl_2$: C, 55.56; H, 6.28; N, 15.58; S, 5.10. Found: C, 55.76; H, 6.30; N, 15.63; S, 5.27.

EXAMPLE 329

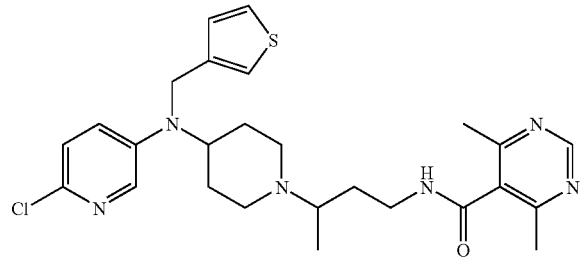

COMPOUND 329: 4,6-Dimethyl-pyrimidine-5-carboxylic acid (3-{4-[(6-chloro-pyridin-3-yl)-thiophen-3-ylmethyl-amino]-piperidin-1-yl}-butyl)-amide Using general procedure A with 5-amino-2-chloropyridine (254 mg, 1.98 mmol) and 1-Boc-4-piperidone (590 mg, 2.96 mmol), then general procedure H with the resulting amine and 3-(bromomethyl)thiophene (517 mg) and then using general procedure C gave (6-chloro-pyridin-3-yl)-piperidin-4-yl-thiophen-3-ylmethyl-amine as a green oil (65 mg, 10% over 3 steps).

Using general procedure B with the amine from above (65 mg, 0.21 mmol) and 2-(3-oxo-butyl)-isoindole-1,3-dione (115 mg, 0.529 mmol) and then using general procedure D gave [1-(3-amino-1-methyl-propyl)-piperidin-4-yl]-(6-chloro-pyridin-3-yl)-thiophen-3-ylmethyl-amine as a yellow oil (60 mg, 75% over 2 steps).

Using general procedure E, the above amine (60 mg, 0.16 mmol) and 4,6-dimethyl-pyrimidine-5-carboxylic acid (29 mg, 0.19 mmol) gave COMPOUND 329 as a colourless foam (71 mg, 88%). $^1$H NMR (CDCl$_3$) δ 0.96-1.24 (m, 2H), 1.01 (d, 3H, J=6.6 Hz), 1.55 (m, 1H), 1.76 (m, 3H), 2.16 (m, 1H), 2.51 (s, 6H), 2.55 (m, 1H), 2.72-2.90 (m, 3H), 3.33 (m, 1H), 3.53 (m, 1H), 3.82 (m, 1H), 3.87 (s, 2H), 6.83 (dd, 1H, J=9.0, 3.3 Hz), 6.96 (d, 2H, J=4.2 Hz), 7.02 (d, 1H, J=9.0 Hz), 7.30 (m, 1H), 7.76 (d, 1H, J=3.0 Hz), 8.53 (m, 1H), 8.84 (s, 1H). $^{13}$C NMR (CDCl$_3$) δ 13.47, 21.95, 29.14, 30.22, 30.83, 40.02, 43.54, 44.91, 51.93, 55.94, 60.23, 120.91, 123.07, 123.87, 126.09, 126.54, 130.85, 134.43, 138.67, 139.77, 143.54, 157.61, 163.08, 166.33. ES-MS m/z 513 (M+H). Anal. Calcd. for C$_{26}$H$_{33}$N$_6$SClO.0.1CH$_2$Cl$_2$.0.3H$_2$O: C, 59.49; H, 6.46; N, 15.95; S, 6.08; Cl, 8.07. Found: C, 59.55; H, 6.38; N, 15.69; S, 6.06; Cl, 8.02.

EXAMPLE 330

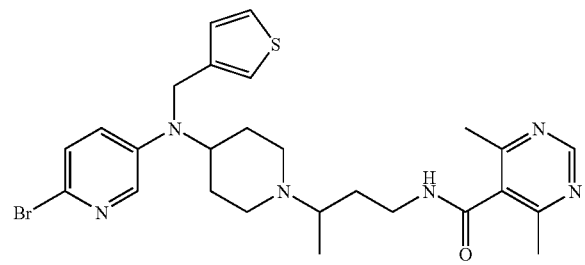

COMPOUND 330: 4,6-Dimethyl-pyrimidine-5-carboxylic acid (3-{4-[(6-bromo-pyridin-3-yl)-thiophen-3-ylmethyl-amino]-piperidin-1-yl}-butyl)-amide Using general procedure A, 5-amino-2-bromopyridine (Binz; v, Schickh, Chem. Ber., 68, 1935, 315-321) (308 mg, 1.78 mmol) and 1-Boc-4-piperidone (317 mg, 1.59 mmol) gave 4-(6-bromo-pyridin-3-ylamino)-piperidine-1-carboxylic acid tert-butyl ester as a yellow solid (326 mg, 58%).

A solution of the secondary amine (152 mg, 0.43 mmol) in THF (3.0 mL) was cooled to −78° C. under nitrogen and KHMDS (0.5M in toluene, 1.3 mL, 0.65 mmol) was added. The resulting orange solution was stirred for 15 minutes, and then a solution of 3-(bromomethyl)thiophene (117 mg, 0.66 mmol) in THF (1.5 mL) was added. The reaction was stirred for another 1.5 hours while warming to room temperature to give 4-[(6-bromo-pyridin-3-yl)-thiophen-3-ylmethyl-amino]-piperidine-1-carboxylic acid tert-butyl ester as a pale yellow solid (159 mg, 82%) following work-up and purification.

Using general procedure C with the tert-butyl carbamate (149 mg, 0.33 mmol), then general procedure B with the resulting amine and 2-(3-oxo-butyl)-isoindole-1,3-dione (128 mg, 0.59 mmol) followed by general procedure D gave [1-(3-amino-1-methyl-propyl)-piperidin-4-yl]-(6-bromo-pyridin-3-yl)-thiophen-3-ylmethyl-amine as a colourless oil (43.4 mg, 31% over 3 steps).

Using general procedure E, the primary amine (43.4 mg, 0.10 mmol) and 4,6-dimethylpyrimidine-5-carboxylic acid (22 mg, 0.14 mmol) gave COMPOUND 330 as a white foam (35.7 mg, 63%). $^1$H NMR (CDCl$_3$) δ 0.95-1.27 (m, 2H), 1.03 (d, 3H, J=6.6 Hz), 1.52-1.64 (m, 1H), 1.71-1.84 (m, 3H), 2.12-2.24 (m, 1H), 2.52 (s, 6H), 2.53-2.63 (m, 1H), 2.73-2.95 (m, 3H), 3.29-3.41 (m, 1H), 3.49-3.60 (m, 1H), 3.79-3.91 (m, 1H), 3.88 (s, 2H), 6.76 (dd, 1H, J=8.8, 3.2 Hz), 6.97 (d, 2H, J=4.4 Hz), 7.17 (d, 1H, J=8.9 Hz), 7.31 (t, 1H, J=3.9 Hz), 7.80 (d, 1H, J=2.9 Hz), 8.49 (br s, 1H), 8.86 (s, 1H). $^{13}$C NMR (CDCl$_3$) δ 13.40, 21.91, 29.02, 30.07, 30.83, 39.86, 43.52, 44.80, 51.84, 55.74, 60.10, 120.86, 122.88, 126.01, 126.52, 127.48, 127.95, 130.77, 135.06, 139.60, 143.86, 157.55, 163.01, 166.30. ESI-MS m/z 557 (MH)$^+$, 559 (MH+2)$^+$. Anal. Calcd. for C$_{26}$H$_{33}$BrN$_6$OS.0.3CH$_2$Cl$_2$: C, 54.18; H, 5.81; N, 14.41. Found: C, 54.45; H, 5.92; N, 14.20.

EXAMPLE 331

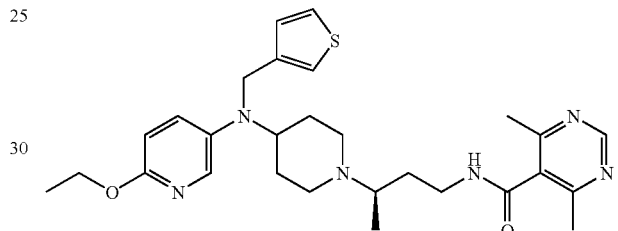

COMPOUND 331: 4,6-Dimethyl-pyrimidine-5-carboxylic acid ((R)-3-{4-[(6-ethoxy-pyridin-3-yl)-thiophen-3-ylmethyl-amino]-piperidin-1-yl}-butyl)-amide Using general procedure A with 6-ethoxy-pyridin-3-ylamine (Nishikawa, Yoshinori; et al., J. Med. Chem., 32, 3, 1989, 583-593) (210 mg, 1.52 mmol) and (R)-3-(4-oxo-piperidin-1-yl)-butyronitrile (278 mg, 1.67 mmol) followed by general procedure J afforded [1-((R)-3-amino-1-methyl-propyl)-piperidin-4-yl]-(6-ethoxy-pyridin-3-yl)-amine as a white solid (365 mg, 83% over 2 steps).

Using general procedure E, the above amine (147 mg, 0.50 mmol) and 4,6-dimethyl-pyrimidine-5-carboxylic acid (92 mg, 0.60 mmol) afforded 4,6-dimethyl-pyrimidine-5-carboxylic acid {(R)-3-[4-(6-ethoxy-pyridin-3-ylamino)-piperidin-1-yl]-butyl}-amide as a white solid (189 mg, 88%).

Using general procedure H, the above aniline (189 mg, 0.44 mmol) and 3-(bromomethyl)thiophene (126 mg, 0.71 mmol) afforded COMPOUND 331 as a white solid (40 mg, 17%). $^1$H NMR (CDCl$_3$) δ 0.86-1.18 (m, 2H), 0.99 (d, 3H, J=6.0 Hz), 1.34 (t, 3H, J=6.9 Hz), 1.49-1.64 (m, 1H), 1.69-1.83 (m, 3H), 2.04-2.17 (m, 1H), 2.43-2.54 (m, 1H), 2.51 (s, 6H), 2.69-2.91 (m, 3H), 3.23-3.38 (m, 2H), 3.78 (s, 2H), 3.80-3.92 (m, 1H), 4.23 (q, 2H, J=6.9 Hz), 6.55 (d, 1H, J=8.7 Hz), 6.93-7.03 (m, 3H), 7.22-7.26 (m, 1H), 7.59 (d, 1H, J=2.4 Hz), 8.69 (br s, 1H), 8.83 (s, 1H). $^{13}$C NMR (CDCl$_3$) δ 13.75, 15.17, 22.31, 29.65, 30.75, 31.07, 40.51, 43.95, 46.45, 52.31, 57.95, 60.75, 61.85, 110.95, 121.49, 126.23, 127.12, 128.73, 131.21, 134.74, 139.95, 141.25, 157.78, 157.99, 163.38, 166.75. ES-MS m/z 523 (M+H). Anal. Calcd. for $C_{28}H_{38}N_6O_2S \cdot 0.1CH_2Cl_2$: C, 63.54; H, 7.25; N, 15.82. Found: C, 63.42; H, 7.55; N, 15.56.

Scheme 18 describes the preparation of Examples 332-338, using general procedures E or F, and reagents listed below.

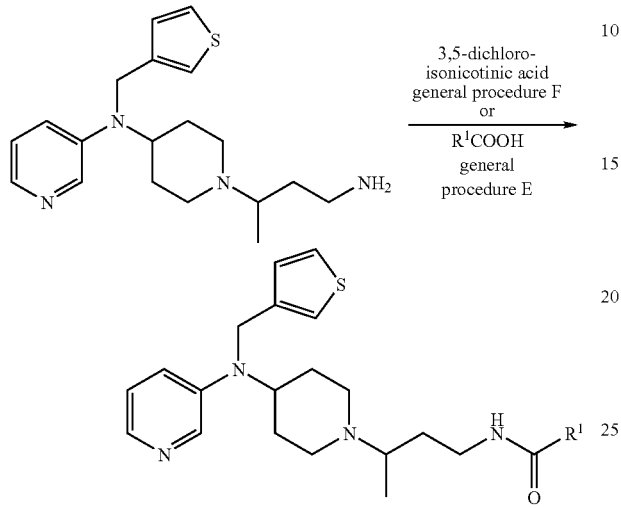

| Example | R¹COOH |
|---------|--------|
| 332 | 2,6-dimethylbenzoic acid |
| 333 | 2-chloro-6-methylbenzoic acid |
| 334 | 2,4-dimethylnicotinic acid |
| 335 | 2,4-dimethyl-1-oxy-nicotinic acid |
| 336 | 3,5-dichloroisonicotinic acid |
| 337 | 3,5-dimethylisonicotinic acid |
| 338 | 2,4-dimethyl-thiophene-3-carboxylic acid |

EXAMPLE 332

COMPOUND 332: 2,6-Dimethyl-N-{3-[4-(pyridin-3-yl-thiophen-3-ylmethyl-amino)-piperidin-1-yl]butyl}-benzamide Yellow oil. $^1$H NMR (CDCl$_3$) δ 0.98 (d, 3H, J=6.6 Hz), 0.99-1.26 (m, 2H), 1.47-1.55 (m, 1H), 1.68-1.81 (m, 3H), 2.14 (t, 1H, J=11.4 Hz), 2.50 (s, 6H), 2.53 (t, 1H, J=11.4 Hz), 2.73-2.89 (m, 3H), 3.22-3.32 (m, 1H), 3.51-3.61 (m, 1H), 3.82 (s, 2H), 3.81-3.90 (m, 1H), 6.81-7.06 (m, 7H), 7.27 (dd, 1H, J=4.8, 3.0 Hz), 7.88 (d, 1H, J=4.2 Hz), 8.03 (d, 1H, J=2.7 Hz), 8.41-8.43 (m, 1H). ES-MS m/z 477 (M+H).

EXAMPLE 333

COMPOUND 333: 2-Chloro-6-methyl-N-{3-[4-(pyridin-3-yl-thiophen-3-ylmethyl-amino)-piperidin-1-yl]-butyl}-benzamide Yellow oil. $^1$H NMR (CDCl$_3$) δ 0.98-1.31 (m, 5H), 1.48-1.55 (m, 1H), 1.71-1.82 (m, 3H), 2.14 (t, 1H, J=11.4 Hz), 2.24-2.35 (m, 1H), 2.30, 2.34 (s, 3H), 2.54 (d, 3H, J=12.3 Hz), 2.78-2.90 (m, 3H), 3.33-3.34 (m, 1H), 3.51-3.62 (m, 1H), 3.77, 3.80 (s, 2H), 3.81-3.91 (m, 1H), 6.81-7.11 (m, 7H), 7.26-7.29 (m, 1H), 7.88 (d, 1H, J=4.5 Hz), 8.04 (br s, 1H), 8.42-8.44, 8.62-8.64 (m, 1H). ES-MS m/z 497 (M+H).

EXAMPLE 334

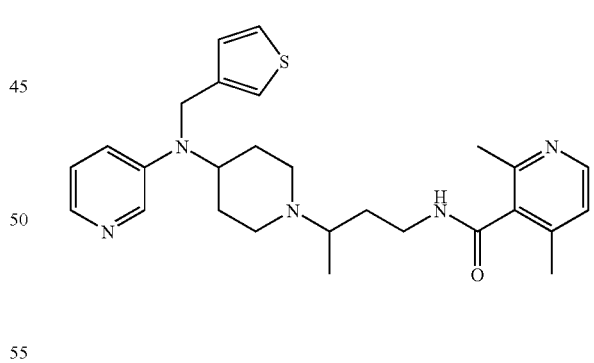

COMPOUND 334: 2,4-Dimethyl-N-{3-[4-(pyridin-3-yl-thiophen-3-ylmethyl-amino)-piperidin-1-yl]-butyl}-nicotinamide Yellow foam. $^1$H NMR (CDCl$_3$) δ 0.96-1.25 (m, 2H), 0.99 (d, 3H, J=6.6 Hz), 1.48-1.57 (m, 1H), 1.69-1.80 (m, 3H), 2.15 (t, 1H, J=12.0 Hz), 2.28 (s, 3H), 2.50-2.58 (m, 1H), 2.52 (s, 3H), 2.73-2.89 (m, 3H), 3.25-3.34 (m, 1H), 3.52-3.65 (m, 1H), 3.78-3.88 (m, 1H), 3.82 (s, 2H), 6.81-6.85 (m, 2H), 6.92-6.95 (m, 2H), 7.00 (dd, 1H, J=8.4, 4.5 Hz), 7.27 (dd, 1H, J=4.8, 3.0 Hz), 7.87 (dd, 1H, J=4.5, 0.9 Hz), 8.03 (d, 1H, J=3.0 Hz), 8.23 (d, 1H, J=5.1 Hz), 8.56-8.58 (m, 1H). ES-MS m/z 478 (M+H).

EXAMPLE 335

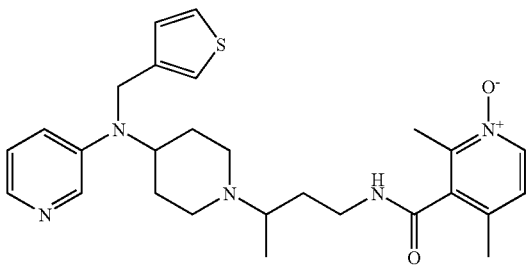

COMPOUND 335: 2,4-Dimethyl-1-oxy-N-{3-[4-(pyridin-3-yl-thiophen-3-ylmethyl-amino)-piperidin-1-yl]-butyl}-nicotinamide Yellow foam. ¹H NMR (CDCl₃) δ 1.01 (d, 3H, J=6.6 Hz), 1.29-1.64 (m, 3H), 1.75-1.87 (m, 3H), 2.17-2.25 (m, 1H), 2.27 (s, 3H), 2.30 (s, 3H), 2.53 (t, 1H, J=12.0 Hz), 2.76-2.89 (m, 3H), 3.35-3.45 (m, 1H), 3.60-3.68 (m, 2H), 4.18 (s, 2H), 6.80 (d, 1H, J=6.6 Hz), 6.86-6.90 (m, 1H), 6.94-7.04 (m, 4H), 7.25-7.27 (m, 1H), 7.85-7.89 (m, 2H), 8.07 (d, 1H, J=2.7 Hz), 8.80-8.83 (m, 1H). ES-MS m/z 494 (M+H).

EXAMPLE 336

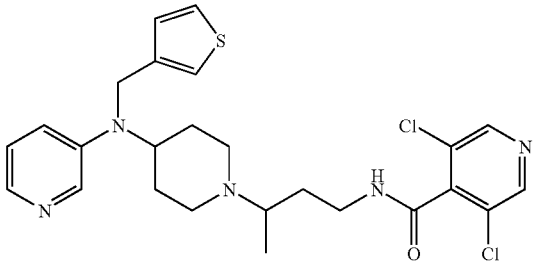

COMPOUND 336: 3,5-Dichloro-N-{3-[4-(pyridin-3-yl-thiophen-3-ylmethyl-amino)-piperidin-1-yl]-butyl}-isonicotinamide Yellow foam. ¹H NMR (CDCl₃) δ 1.01 (d, 3H, J=6.6 Hz), 1.04-1.33 (m, 2H), 1.50-1.58 (m, 1H), 1.72-1.85 (m, 3H), 2.18 (t, 1H, J=12.0 Hz), 2.56 (t, 1H, J=11.4 Hz), 2.79-2.94 (m, 3H), 3.30-3.39 (m, 1H), 3.56-3.68 (m, 1H), 3.78-3.87 (m, 1H), 3.84 (s, 2H), 6.81-6.85 (m, 1H), 6.91-6.94 (m, 2H), 7.00 (dd, 1H, J=8.4, 4.8 Hz), 7.29 (dd, 1H, J=4.8, 3.0 Hz), 7.88 (d, 1H, J=4.2 Hz), 8.03 (d, 1H, J=2.7 Hz), 8.43 (s, 2H), 8.97-8.99 (m, 1H). ES-MS m/z 518 (M+H).

EXAMPLE 337

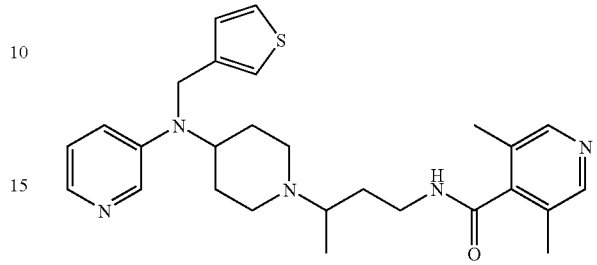

COMPOUND 337: 3,5-Dimethyl-N-{3-[4-(pyridin-3-yl-thiophen-3-ylmethyl-amino)-piperidin-1-yl]-butyl}-isonicotinamide Yellow foam. ¹H NMR (CDCl₃) δ 0.93-1.24 (m, 2H), 1.01 (d, 3H, J=6.6 Hz), 1.50-1.58 (m, 1H), 1.70-1.83 (m, 3H), 2.17 (t, 1H, J=11.7 Hz), 2.27 (s, 6H), 2.57 (t, 1H, J=11.7 Hz), 2.75-2.91 (m, 3H), 3.26-3.35 (m, 1H), 3.55-3.65 (m, 1H), 3.77 (s, 2H), 3.81-3.91 (m, 1H), 6.81 (ddd, 1H, J=8.7, 3.0, 1.2 Hz), 6.93-7.03 (m, 3H), 7.29 (dd, 1H, J=4.8, 3.0 Hz), 7.90 (d, 1H, J=3.6 Hz), 7.90 (s, 1H), 8.27 (s, 2H), 8.64-8.65 (m, 1H). ES-MS m/z 478 (M+H).

EXAMPLE 338

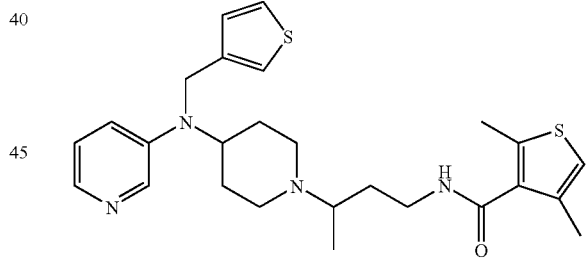

COMPOUND 338: 2,4-Dimethyl-thiophene-3-carboxylic acid {3-[4-(pyridin-3-yl-thiophen-3-ylmethyl-amino)-piperidin-1-yl]-butyl}-amide Colourless oil. ¹H NMR (CDCl₃) δ 1.00 (d, 3H, J=6.6 Hz), 1.16-1.57 (m, 2H), 1.69-1.83 (m, 3H), 2.12-2.20 (m, 1H), 2.20 (s, 3H), 2.46 (s, 3H), 2.56 (t, 1H, J=12.0 Hz), 2.78-2.90 (m, 3H), 3.23-3.33 (m, 1H), 3.59-3.68 (m, 1H), 3.75-3.84 (m, 1H), 4.11 (s, 2H), 6.88 (ddd, 1H, J=9.3, 3.0, 1.2 Hz), 6.92-6.95 (m, 2H), 7.03 (dd, 1H, J=8.4, 4.5 Hz), 7.27 (dd, 1H, J=4.8, 1.6 Hz), 7.87-7.92 (m, 2H), 8.09 (d, 1H, J=2.7 Hz). ES-MS m/z 483 (M+H).

Scheme 19 describes the preparation of Examples 339-341, using general procedure E, and reagents listed below.

Scheme 19

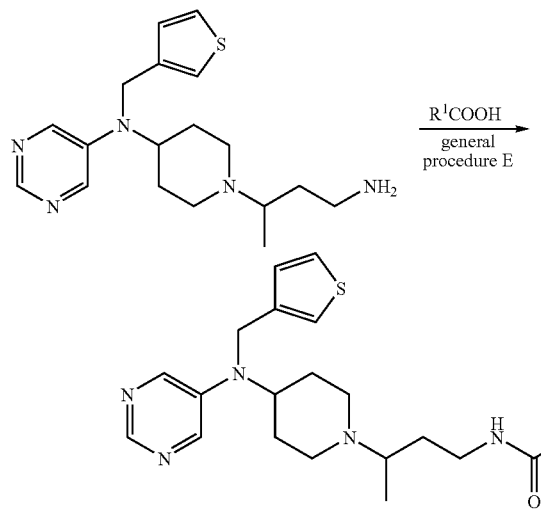

| Example | R¹COOH |
|---|---|
| 339 | 4,6-dimethyl-pyrimidine-5-carboxylic acid |
| 340 | 2,4-dimethyl-1-oxy-nicotinic acid |
| 341 | 2,6-dimethylbenzoic acid |

EXAMPLE 339

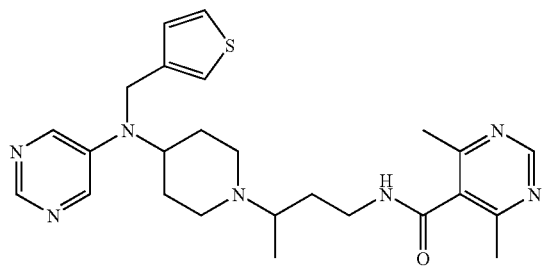

COMPOUND 339: 4,6-Dimethyl-pyrimidine-5-carboxylic acid {3-[4-(pyrimidin-5-yl-thiophen-3-ylmethyl-amino)-piperidin-1-yl]-butyl}-amide A mixture of 5-bromopyrimidine (325 mg, 2.04 mmol), 4-amino-1-Boc-piperidine (425 mg, 2.12 mmol), Pd$_2$(dba)$_3$ (41 mg, 0.045 mmol), (±)-BINAP (78 mg, 0.13 mmol) and t-BuONa (210 mg, 2.19 mmol) in freshly degassed toluene (7.0 mL) was stirred at 85° C. under argon for 2 hours. Basic work-up and purification gave 4-(pyrimidin-5-ylamino)-piperidine-1-carboxylic acid tert-butyl ester as a pale brown solid (415 mg, 73%).

A solution of the secondary amine (406 mg, 1.46 mmol) in THF (10 mL) was cooled to −78° C. under nitrogen and KHMDS (0.5M in toluene, 4.2 mL, 2.1 mmol) was added. The resulting orange solution was stirred for 10 minutes, and then a solution of 3-(bromomethyl)thiophene (379 mg, 2.14 mmol) in THF (5 mL) was added. The reaction was stirred for another 1.5 hours while warming to room temperature to give 4-(pyrimidin-5-yl-thiophen-3-ylmethyl-amino)-piperidine-1-carboxylic acid tert-butyl ester as an orange foam (461 mg, 84%) after work-up and purification.

Using general procedure C with the tert-butyl carbamate (461 mg, 1.23 mmol), then general procedure B with the resulting amine and 2-(3-oxo-butyl)-isoindole-1,3-dione (428 mg, 1.97 mmol) and then using general procedure D gave 2-{3-[4-(pyrimidin-5-yl-thiophen-3-ylmethyl-amino)-piperidin-1-yl]-butyl}-isoindole-1,3-dione as a yellow oil (214 mg, 54% over 3 steps).

COMPOUND 339 was isolated as a white foam. $^1$H NMR (CDCl$_3$) δ 1.02-1.15 (m, 1H), 1.03 (d, 3H, J=6.6 Hz), 1.17-1.31 (m, 1H), 1.53-1.62 (m, 1H), 1.72-1.85 (m, 3H), 2.20 (td, 1H, J=11.7, 1.5 Hz), 2.53 (s, 6H), 2.59 (td, 1H, J=11.7, 1.8 Hz), 2.76-2.96 (m, 3H), 3.31-3.41 (m, 1H), 3.60 (tt, 1H, J=11.7, 3.9 Hz), 3.80-3.90 (m, 1H), 3.95 (s, 2H), 6.98-7.00 (m, 2H), 7.33 (dd, 1H, J=4.7, 3.5 Hz), 8.12 (s, 2H), 8.41 (br s, 1H), 8.55 (s, 1H), 8.86 (s, 1H). $^{13}$C NMR (CDCl$_3$) δ 13.32, 21.77, 28.97, 29.90, 30.95, 39.55, 43.44, 44.17, 51.53, 55.04, 59.65, 120.84, 125.77, 126.66, 130.63, 138.93, 140.63, 141.60, 147.42, 157.41, 162.86, 166.19. ESI-MS m/z 480 (MH)$^+$. Anal. Calcd. for C$_{25}$H$_{33}$N$_7$OS.0.8CH$_2$Cl$_2$: C, 56.59; H, 6.37; N, 17.91. Found: C, 56.24; H, 6.45; N, 17.94.

EXAMPLE 340

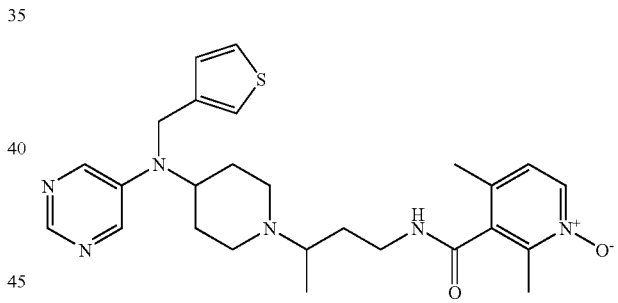

COMPOUND 340: 2,4-Dimethyl-1-oxy-N-{3-[4-(pyrimidin-5-yl-thiophen-3-ylmethyl-amino)-piperidin-1-yl]-butyl}-nicotinamide White foam. $^1$H NMR (CDCl$_3$) δ 1.04 (d, 3H, J=6.5 Hz), 1.27-1.52 (m, 2H), 1.57-1.67 (m, 1H), 1.75-1.90 (m, 3H), 2.24 (td, 1H, J=11.6, 1.5 Hz), 2.30 (s, 3H), 2.38 (s, 3H), 2.59 (td, 1H, J=11.6, 1.8 Hz), 2.78-2.97 (m, 3H), 3.36-3.47 (m, 1H), 3.59-3.78 (m, 2H), 4.19 (s, 2H), 6.82 (d, 1H, J=6.6 Hz), 6.97 (dd, 1H, J=4.8, 1.2 Hz), 7.02 (dd, 1H, J=3.0, 1.2 Hz), 7.33 (dd, 1H, J=4.8, 3.1 Hz), 7.91 (d, 1H, J=6.6 Hz), 8.14 (s, 2H), 8.54 (s, 1H), 8.55 (br s, 1H). $^{13}$C NMR (CDCl$_3$) δ 13.42, 14.82, 18.30, 29.35, 29.83, 32.41, 38.41, 44.25, 44.41, 50.96, 55.48, 57.92, 120.83, 124.71, 125.80, 126.57, 134.44, 136.85, 137.52, 139.23, 140.67, 141.69, 145.27, 147.31,

EXAMPLE 341

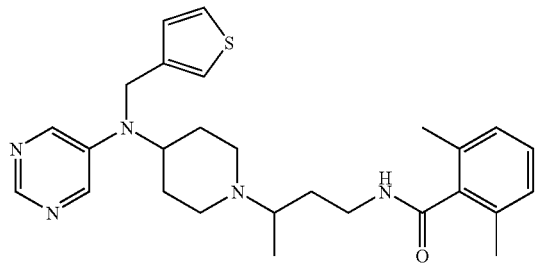

COMPOUND 341: 2,6-Dimethyl-N-{3-[4-(pyrimidin-5-yl-thiophen-3-ylmethyl-amino)-piperidin-1-yl]-butyl}-benzamide White foam. $^1$H NMR(CDCl$_3$) δ 1.01 (d, 3H, J=6.6 Hz), 1.02-1.15 (m, 1H), 1.18-1.31 (m, 1H), 1.50-1.59 (m, 1H), 1.69-1.84 (m, 3H), 2.17 (td, 1H, J=11.8, 1.6 Hz), 2.32 (s, 6H), 2.61 (td, 1H, J=11.6, 1.5 Hz), 2.76-2.97 (m, 3H), 3.25-3.35 (m, 1H), 3.56 (tt, 1H, J=11.6, 3.7 Hz), 3.81 (s, 2H), 3.84-3.94 (m, 1H), 6.88 (dd, 1H, J=5.0, 1.4 Hz), 6.92 (dd, 1H, J=3.2, 1.4 Hz), 6.94 (d, 2H, J=8.1 Hz), 7.05 (dd, 1H, J=8.4, 6.9 Hz), 7.32 (dd, 1H, J=5.0, 3.2 Hz), 8.09 (s, 2H), 8.32 (br s, 1H), 8.52 (s, 1H). $^{13}$C NMR (CDCl$_3$) δ 13.35, 19.03, 28.72, 29.87, 30.92, 39.57, 43.39, 44.12, 51.76, 55.28, 60.26, 120.80, 125.77, 126.54, 127.20, 128.32, 133.85, 138.46, 139.24, 140.76, 141.64, 147.41, 169.76. ESI-MS m/z 478 (MH)$^+$. Anal. Calcd. for C$_{27}$H$_{35}$N$_5$OS.0.4CH$_2$Cl$_2$: C, 64.32; H, 7.05; N, 13.69. Found: C, 64.47; H, 7.06; N, 13.59.

EXAMPLE 342

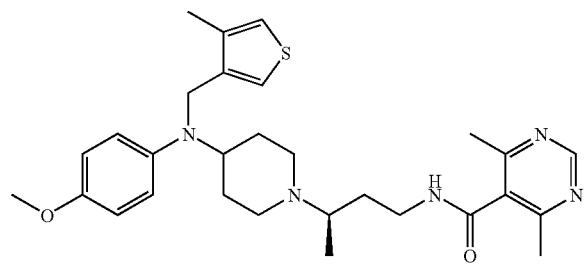

COMPOUND 342: 4,6-Dimethyl-pyrimidine-5-carboxylic acid ((R)-3-{4-[(4-methoxy-phenyl)-(4-methyl-thiophen-3-ylmethyl)-amino]-piperidin-1-yl}-butyl)-amide To a solution of 3-bromo-4-methylthiophene (500 mg, 2.82 mmol) in THF (5 mL) cooled to −78° C. was added n-BuLi (2.0M in Hexanes, 1.69 mL, 3.39 mmol). The mixture was stirred at −78° C. for 1 hour. DMF (0.26 mL, 3.39 mmol) was added and the mixture stirred at −78° C. for 30 minutes and at room temperature for 2 hours to give the aldehyde, which was subsequently reduced with NaBH$_4$ (76 mg, 2.0 mmol) in MeOH (2 mL) to afford (4-methyl-thiophen-3-yl)-methanol as a white solid (105 mg, 29% over 2 steps) after work-up.

To a solution of the above alcohol (105 mg, 0.82 mmol) in CH$_2$Cl$_2$ (1 mL) was added PPh$_3$ (215 mg, 0.82 mmol) then carbon tetrabromide (272 mg, 0.82 mmol) and the solution was stirred at room temperature for 30 minutes. The mixture was concentrated under reduced pressure and the residue washed with Hexanes (3×5 mL). The combined organic extracts were concentrated under reduced pressure to give 3-bromomethyl-4-methyl-thiophene as a colourless liquid (209 mg, 79%).

Using general procedure E, [1-((R)-3-amino-1-methyl-propyl)-piperidin-4-yl]-(4-methoxy-phenyl)-amine (see EXAMPLE 230) (1.59 g, 5.48 mmol) and 4,6-dimethyl-pyrimidine-5-carboxylic acid (834 mg, 5.48 mmol) afforded 4,6-dimethyl-pyrimidine-5-carboxylic acid {(R)-3-[4-(4-methoxy-phenylamino)-piperidin-1-yl]-butyl}-amide as a white solid (2.07 g, 83%).

Using general procedure H, the above amide (62 mg, 0.15 mmol) and the above bromide (97 mg, 0.30 mmol) gave COMPOUND 342 as a yellow solid (54 mg, 68%). $^1$H NMR (CDCl$_3$) δ 1.06 (d, 3H, J=4.8 Hz), 1.59-1.63 (m, 2H), 1.83-2.02 (m, 4H), 2.19-2.29 (m, 1H), 2.24 (s, 3H), 2.51 (s, 6H), 2.59 (m, 1H), 2.84-2.91 (m, 3H), 3.38 (m, 1H), 3.73 (s, 3H), 3.76-3.82 (m, 1H), 3.86 (s, 2H), 6.63 (d, 2H, J=8.7 Hz), 6.74 (d, 2H, J=9.0 Hz), 6.85-6.89 (m, 2H), 8.17 (br s, 1H), 8.78 (s, 1H). $^{13}$C NMR (CDCl$_3$) δ 13.63, 14.94, 22.43, 29.52, 31.60, 39.88, 44.52, 46.70, 52.33, 56.00, 58.06, 60.28, 114.82, 118.47, 121.82, 122.69, 130.92, 136.16, 139.89, 143.17, 153.23, 157.97, 163.28, 167.07. ES-MS m/z 522 (M+H). Anal. Calcd. for C$_{29}$H$_{39}$N$_5$O$_2$S.0.5CH$_2$Cl$_2$: C, 62.80; H, 7.15; N, 12.41; S, 5.68. Found: C, 63.16; H, 7.30; N, 12.12; S, 6.39.

EXAMPLE 343

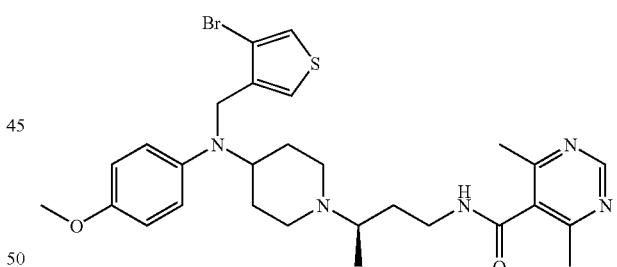

COMPOUND 343: 4,6-Dimethyl-pyrimidine-5-carboxylic acid ((R)-3-{4-[(4-bromo-thiophen-3-ylmethyl)-(4-methoxy-phenyl)-amino]-piperidin-1-yl}-butyl)-amide A mixture of 3-bromo-4-methylthiophene (177 mg, 1.00 mmol), benzoyl peroxide (10 mg, 0.04 mmol) and CCl$_4$ (2 mL) was heated to reflux. NBS (125 mg, 0.70 mmol) and benzoyl peroxide (10 mg, 0.04 mmol) were added and the mixture was heated to reflux for 2 hours to give 3-bromomethyl-4-methyl-thiophene as a colourless liquid (206 mg) after standard work-up and purification.

Using general procedure H, 4,6-dimethyl-pyrimidine-5-carboxylic acid {(R)-3-[4-(4-methoxy-phenylamino)-piperidin-1-yl]-butyl}-amide (see EXAMPLE 342) (74 mg, 0.18 mmol) and the above bromide (154 mg) gave COMPOUND 343 as a white solid (24 mg, 23%). $^1$H NMR (CDCl$_3$) δ 1.01 (d, 3H, J=6.6 Hz), 1.02-1.26 (m, 2H), 1.55-1.62 (m, 1H), 1.72-1.81 (m, 3H), 2.15 (t, 1H, J=10.2 Hz), 2.48-2.55 (m, 1H), 2.51 (s, 6H), 2.73-2.87 (m, 3H), 3.31-3.38 (m, 2H), 3.73 (s, 3H), 3.75-3.84 (m, 1H), 3.92 (s, 2H), 6.61-6.69 (m, 2H), 6.71-6.77 (m, 2H), 0.93 (d, 1H, J=3.6 Hz), 7.26 (d, 1H, J=3.6 Hz), 7.97 (br s, 1H), 8.85 (s, 1H). $^{13}$C NMR (CDCl$_3$) δ 13.73, 22.35, 30.16, 31.00, 31.84, 40.00, 44.38, 47.35, 52.28, 56.01, 58.50, 60.05, 110.44, 114.90, 118.24, 123.31, 123.48, 130.96, 139.43, 142.94, 153.23, 158.07, 163.28, 166.96. ES-MS m/z 586 (M+H). Anal. Calcd. for C$_{28}$H$_{36}$N$_5$O$_2$SBr.0.6CH$_2$Cl$_2$: C, 53.88; H, 5.88; N, 10.98; S, 5.03. Found: C, 54.08; H, 5.72; N, 10.87; S, 5.30.

EXAMPLE 344

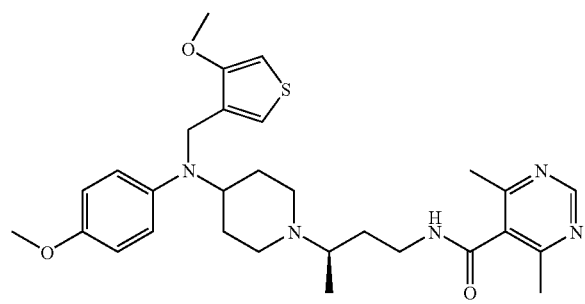

COMPOUND 344: 4,6-Dimethyl-pyrimidine-5-carboxylic acid ((R)-3-{4-[(4-methoxy-phenyl)-(4-methoxy-thiophen-3-ylmethyl)-amino]-piperidin-1-yl}-butyl)-amide 4-Methylthiophene-3-carboxylic acid (158 mg, 1.00 mmol) was reduced with BH$_3$-THF (1.0M in THF, 3.0 mL, 3.0 mmol) in THF (2 mL) at room temperature and treated with MeOH to give (4-methoxy-thiophen-3-yl)-methanol as an oil (144 mg, 100%) after work-up.

To a solution of phosphorous tribromide (271 mg, 1.00 mmol) in CH$_2$Cl$_2$ (1.5 mL) cooled to 0° C. was added a solution of the above alcohol (144 mg, 1.00 mmol) in CH$_2$Cl$_2$ (1.5 mL) and the solution was stirred at 0° C. for 5 minutes to give 3-bromomethyl-4-methoxy-thiophene as an oil (200 mg, 97%) after work-up.

Using general procedure H, 4,6-dimethyl-pyrimidine-5-carboxylic acid {(R)-3-[4-(4-methoxy-phenylamino)-piperidin-1-yl]-butyl}-amide (see EXAMPLE 342) (62 mg, 0.15 mmol) and the above bromide (62 mg, 0.30 mmol) gave COMPOUND 344 as a white solid (36 mg, 44%). $^1$H NMR (CDCl$_3$) δ 0.98-1.28 (m, 2H), 1.00 (d, 3H, J=6.6 Hz), 1.54-1.62 (m, 1H), 1.69-1.80 (m, 3H), 2.14 (t, 1H, J=10.2 Hz), 2.49-2.55 (m, 1H), 2.50 (s, 6H), 2.71-2.85 (m, 3H), 3.32-3.42 (m, 2H), 3.72 (s, 3H), 3.76-3.86 (m, 1H), 3.80 (s, 2H), 3.90 (s, 3H), 6.20 (d, 1H, J=3.3 Hz), 6.61-6.69 (m, 2H), 6.71-6.78 (m, 3H), 8.14 (m, 1H), 8.85 (s, 1H). $^{13}$C NMR (CDCl$_3$) δ 13.73, 22.30, 29.87, 30.87, 31.71, 40.01, 44.34, 44.46, 52.35, 56.06, 57.63, 57.82, 60.05, 96.59, 114.89, 117.09, 121.61, 130.96, 132.06, 143.36, 152.56, 155.98, 158.05, 163.22, 166.99. ES-MS m/z 538 (M+H). Anal. Calcd. for C$_{29}$H$_{39}$N$_5$O$_3$S.0.2CH$_2$Cl$_2$.0.4C$_4$H$_8$O$_2$: C, 62.71; H, 7.28; N, 11.87. Found: C, 62.74; H, 6.99; N, 11.82.

EXAMPLE 345

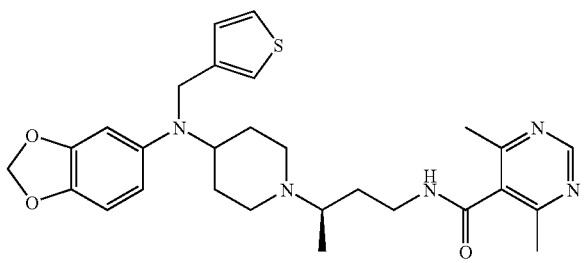

COMPOUND 345: 4,6-Dimethyl-pyrimidine-5-carboxylic acid {(R)-3-[4-(benzo[1,3]dioxol-5-yl-thiophen-3-ylmethyl-amino)-piperidin-1-yl]-butyl}-amide Using general procedure A with 3,4-(methylenedioxy) aniline (250 mg, 1.8 mmol) and (R)-3-(4-oxo-piperidin-1-yl)-butyronitrile (329 mg, 2.0 mmol) followed by general procedure J gave a green oil, which was subsequently treated with a solution of NaCN (175 mg) in H$_2$O (5 mL) and MeOH (5 mL) to afford [1-((R)-3-amino-1-methyl-propyl)-piperidin-4-yl]-benzo[1,3]dioxol-5-yl-amine as a white solid (281 mg, 68% over 2 steps) after work-up and purification.

Using general procedure E, the above amine (281 mg, 1.0 mmol) and 4,6-dimethyl-pyrimidine-5-carboxylic acid (176 mg, 1.2 mmol) afforded 4,6-dimethyl-pyrimidine-5-carboxylic acid {(R)-3-[4-(benzo[1,3]dioxol-5-ylamino)-piperidin-1-yl]-butyl}-amide as a white solid (377 mg, 92%).

Using general procedure H, the above aniline (377 mg, 0.90 mmol) and 3-(bromomethyl)thiophene (251 mg, 1.4 mmol) afforded COMPOUND 345 as a white solid (302 mg, 83%). $^1$H NMR (CDCl$_3$) δ 0.81-1.14 (m, 2H), 0.98 (d, 3H, J=6.3 Hz), 1.49-1.63 (m, 1H), 1.68-1.82 (m, 3H), 2.05-2.16 (m, 1H), 2.46-2.57 (m, 1H), 2.50 (s, 6H), 2.68-2.89 (m, 3H), 3.23-3.38 (m, 2H), 3.76 (s, 2H), 3.80-3.94 (m, 1H), 5.83 (s, 2H), 6.08 (dd, 1H, J=8.7, 2.4 Hz), 6.29 (d, 1H, J=2.4 Hz), 6.60 (d, 1H, J=8.7 Hz), 6.96-7.00 (m, 2H), 7.22-7.27 (m, 1H), 8.80 (br s, 1H), 8.84 (s, 1H). $^{13}$C NMR (CDCl$_3$) δ 13.76, 22.30, 29.67, 30.92, 30.97, 40.63, 43.96, 46.77, 52.52, 57.94, 60.91, 98.65, 101.05, 107.99, 108.63, 121.22, 126.00, 127.15, 131.24, 140.30, 141.95, 145.09, 148.63, 158.01, 163.39, 166.75. ES-MS m/z 522 (M+H). Anal. Calcd. for C$_{28}$H$_{35}$N$_5$O$_3$S.0.3C$_4$H$_8$O$_2$.0.1H$_2$O: C, 63.78; H, 6.89; N, 12.74. Found: C, 63.76; H, 6.88; N, 12.67.

EXAMPLE 346

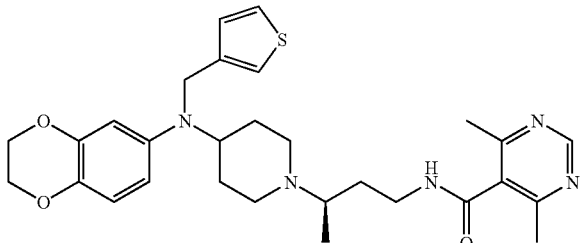

285

COMPOUND 346: 4,6-Dimethyl-pyrimidine-5-carboxylic acid ((R)-3-{4-[(2,3-dihydro-benzo[1,4]dioxin-6-yl)-thiophen-3-ylmethyl-amino]-piperidin-1-yl}-butyl)-amide Using general procedure A with 1,4-benzodioxan-6-amine (170 mg, 1.1 mmol) and (R)-3-(4-oxo-piperidin-1-yl)-butyronitrile (206 mg, 1.2 mmol) followed by general procedure J gave a green oil, which was subsequently treated with a solution of NaCN (175 mg) in $H_2O$ (5 mL) and MeOH (5 mL) and stirred at room temperature for 20 minutes. Work-up and purification afforded [1-((R)-3-amino-1-methyl-propyl)-piperidin-4-yl]-(2,3-dihydro-benzo[1,4]dioxin-6-yl)-amine as a white solid (245 mg, 71% over 2 steps).

Using general procedure E, the above amine (110 mg, 0.4 mmol) and 4,6-dimethyl-pyrimidine-5-carboxylic acid (66 mg, 0.4 mmol) afforded 4,6-dimethyl-pyrimidine-5-carboxylic acid {(R)-3-[4-(2,3-dihydro-benzo[1,4]dioxin-6-ylamino)-piperidin-1-yl]-butyl}-amide as a white solid (160 mg, 100%).

Using general procedure H, the above aniline (160 mg, 0.36 mmol) and 3-(bromomethyl)thiophene (103 mg, 0.58 mmol) afforded COMPOUND 346 as a white solid (35 mg, 18%). $^1$H NMR (CDCl$_3$) δ 0.82-1.15 (m, 2H), 0.99 (d, 3H, J=6.6 Hz), 1.48-1.58 (m, 1H), 1.67-1.83 (m, 3H), 2.06-2.17 (m, 1H), 2.43-2.57 (m, 1H), 2.51 (s, 6H), 2.67-2.89 (m, 3H), 3.23-3.45 (m, 2H), 3.75 (s, 2H), 3.80-3.93 (m, 1H), 4.12-4.22 (m, 4H), 6.13-6.21 (m, 2H), 6.65 (d, 1H, J=8.4 Hz), 6.96-7.01 (m, 2H), 7.22-7.26 (m, 1H), 8.81 (br s, 1H), 8.84 (s, 1H). $^{13}$C NMR (CDCl$_3$) δ 13.75, 22.30, 29.51, 30.84, 30.95, 40.65, 43.95, 46.28, 52.60, 57.07, 60.93, 64.60, 65.11, 103.71, 108.40, 117.72, 121.05, 126.01, 127.04, 131.25, 136.04, 142.26, 144.11, 144.34, 158.01, 163.39, 166.76. ES-MS m/z 536 (M+H). Anal. Calcd. for $C_{29}H_{37}N_5O_3S·0.1CH_2Cl_2$: C, 64.23; H, 6.89; N, 12.87. Found: C, 64.13; H, 7.01; N, 12.55.

EXAMPLE 347

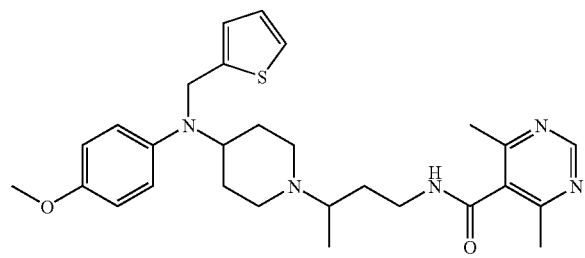

COMPOUND 347: 4,6-Dimethyl-pyrimidine-5-carboxylic acid (3-{4-[(4-methoxy-phenyl)-thiophen-2-ylmethyl-amino]-piperidin-1-yl}-butyl)-amide Using general procedure C, 4-(4-methoxy-phenylamino)-piperidine-1-carboxylic acid tert-butyl ester (see EXAMPLE 119) (706 mg, 2.30 mmol) afforded (4-methoxy-phenyl)-piperidin-4-yl-amine as a sticky white solid (423 mg, 89%).

Using general procedure I with the above amine (423 mg, 2.05 mmol) and then using general procedure J afforded [1-(3-amino-1-methyl-propyl)-piperidin-4-yl]-(4-methoxy-phenyl)-amine as a white solid (538 mg, 95% over 2 steps).

Using general procedure E, the above amine (538 mg, 1.94 mmol) and 4,6-dimethyl-pyrimidine-5-carboxylic acid (325 mg, 2.13 mmol) afforded 4,6-dimethyl-pyrimidine-5-car-

286 boxylic acid {3-[4-(4-methoxy-phenylamino)-piperidin-1-yl]-butyl}-amide as a white solid (638 mg, 80%).

A mixture of 2-thiophenemethanol (0.4 mL, 4.2 mmol), carbon tetrabromide (1.4 g, 4.2 mmol) and $CH_2Cl_2$ (20 mL) was stirred at room temperature for 3 hours to give the crude material after work-up.

Using general procedure H, the above amine (84 mg, 0.20 mmol) and the above bromide (70 mg) afforded COMPOUND 347 as a pale brown solid (71 mg, 70%). $^1$H NMR (CDCl$_3$) δ 0.87-0.97 (m, 1H), 1.00 (d, 3H, J=6.6 Hz), 1.06-1.18 (m, 1H), 1.52-1.54 (m, 1H), 1.70-1.83 (m, 3H), 2.11 (t, 1H, J=11.4 Hz), 2.48-2.55 (m, 1H), 2.52 (s, 6H), 2.73-2.87 (m, 3H), 3.27-3.35 (m, 2H), 3.73 (s, 3H), 3.85-3.89 (m, 1H), 3.95 (s, 2H), 6.69-6.76 (m, 4H), 6.89-6.93 (m, 2H), 7.12 (dd, 1H, J=5.1, 1.2 Hz), 8.77-8.78 (m, 1H), 8.82 (s, 1H). $^{13}$C NMR (CDCl$_3$) δ 13.78, 22.34, 29.85, 31.03, 40.62, 44.00, 46.59, 52.42, 55.97, 58.27, 60.88, 114.77, 118.87, 124.24, 127.05, 131.21, 142.96, 145.63, 153.48, 158.03, 163.35, 166.81. ES-MS m/z 508 (M+H). Anal. Calcd. for $C_{28}H_{37}N_5O_2S·0.51CH_4O$: C, 65.35; H, 7.51; N, 13.36; S, 6.12. Found: C, 65.64; H, 7.22; N, 12.97; S, 6.25.

EXAMPLE 348

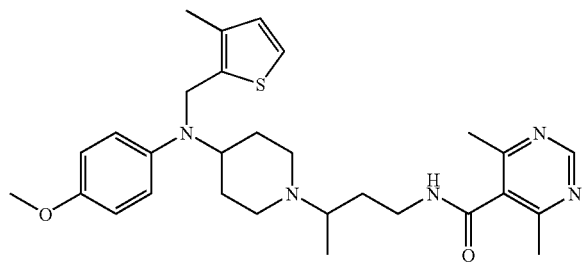

COMPOUND 348: 4,6-Dimethyl-pyrimidine-5-carboxylic acid (3-{4-[(4-methoxy-phenyl)-(3-methyl-thiophen-2-ylmethyl)-amino]-piperidin-1-yl}-butyl)-amide To a solution of 3-methyl-2-thiophenecarboxaldehyde (374 mg, 2.97 mmol) in MeOH (10 mL) cooled to 0° C. was added NaBH$_4$ (230 mg, 5.97 mmol) and the mixture was stirred at 0° C. for 2 hours. Aqueous work-up gave (3-methyl-thiophen-2-yl)-methanol.

A mixture of the above alcohol (271 mg), carbon tetrabromide (702 mg, 2.12 mmol), PPh$_3$ (555 mg, 2.12 mmol) and $CH_2Cl_2$ (10 mL) was stirred at room temperature for 30 minutes. The mixture was concentrated under reduced pressure and the crude material was used in the next reaction without purification.

Using general procedure H, 4,6-dimethyl-pyrimidine-5-carboxylic acid {3-[4-(4-methoxy-phenylamino)-piperidin-1-yl]-butyl}-amide (see EXAMPLE 347) (77 mg, 0.19 mmol) and the above bromide (excess) afforded COMPOUND 348 as a yellow solid (41 mg, 42%). $^1$H NMR (CDCl$_3$) δ 0.89-1.20 (m, 2H), 1.00 (d, 3H, J=6.6 Hz), 1.52-1.56 (m, 1H), 1.71-1.85 (m, 3H), 2.08-2.15 (m, 1H), 2.21 (s, 3H), 2.48-2.53 (m, 1H), 2.51 (s, 6H), 2.73-2.86 (m, 3H), 3.20-3.36 (m, 2H), 3.73 (s, 3H), 3.83-3.89 (m, 1H), 3.90 (s, 2H), 6.66-6.79 (m, 5H), 7.01 (d, 1H, J=5.1 Hz), 8.55 (br s, 1H), 8.75 (s, 1H). $^{13}$C NMR (CDCl$_3$) δ 13.35, 13.81, 21.93, 29.67, 30.57, 30.90, 40.03, 43.74, 45.06, 51.90, 55.51, 58.40, 60.24, 114.27, 119.73, 122.50, 129.92, 130.72, 132.21, 138.35, 142.51, 153.54, 157.54, 162.86, 166.47. ES-MS m/z 544 (M+Na). Anal. Calcd. for $C_{29}H_{39}N_5O_2S.0.3C_4H_8O_2$: C, 66.17; H, 7.61; N, 12.78; S, 5.85. Found: C, 66.28; H, 7.49; N, 12.50; S, 6.54.

EXAMPLE 349

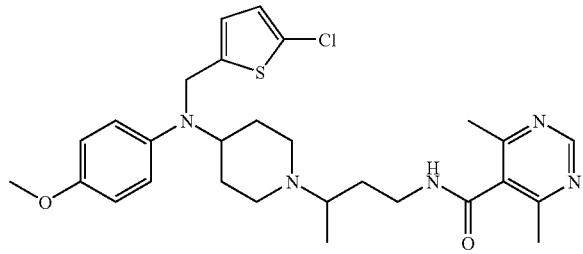

COMPOUND 349: 4,6-Dimethyl-pyrimidine-5-carboxylic acid (3-{4-[(5-chloro-thiophen-2-ylmethyl)-(4-methoxy-phenyl)-amino]-piperidin-1-yl}-butyl)-amide 5-Chlorothiophene-2-carboxylic acid (436 mg, 2.6 mmol) was reduced with $BH_3$-THF (1M in THF, 3.2 mL, 3.2 mmol) in THF (10 mL) at room temperature to give (5-chloro-thiophen-2-yl)-methanol after work-up.

A mixture of the above alcohol (179 mg), carbon tetrabromide (401 mg, 1.21 mmol), $PPh_3$ (317 g, 1.21 mmol) and $CH_2Cl_2$ (10 mL) was stirred at room temperature for 1 hour. The mixture was diluted with Hexanes, filtered and concentrated under reduced pressure. The crude material was used in the next reaction without purification.

Using general procedure H, 4,6-dimethyl-pyrimidine-5-carboxylic acid {3-[4-(4-methoxy-phenylamino)-piperidin-1-yl]-butyl}-amide (see EXAMPLE 347) (75 mg, 0.18 mmol) and the above bromide (58 mg) afforded COMPOUND 349 as a yellow solid (53 mg, 54%). $^1$H NMR ($CDCl_3$) δ 0.82-1.13 (m, 2H), 0.98 (d, 3H, J=6.6 Hz), 1.50-1.56 (m, 1H), 1.69-1.80 (m, 4H), 2.08 (t, 1H, J=10.5 Hz), 2.46-2.52 (m, 1H), 2.51 (s, 6H), 2.71-2.85 (m, 3H), 3.19-3.34 (m, 2H), 3.73 (s, 3H), 3.82-3.89 (m, 1H), 3.83 (s, 2H), 6.66 (d, 1H, J=3.9 Hz), 6.70 (d, 1H, J=3.9 Hz), 6.73-6.76 (m, 4H), 8.75-8.77 (m, 1H), 8.86 (s, 1H). $^{13}$C NMR ($CDCl_3$) δ 13.77, 22.32, 29.76, 30.89, 31.00, 40.59, 43.94, 46.84, 52.33, 55.92, 58.81, 60.81, 114.76, 119.69, 123.33, 126.08, 128.38, 131.23, 142.53, 144.63, 153.94, 157.98, 163.39, 166.74. ES-MS m/z 542 (M+H). Anal. Calcd. for $C_{28}N_{36}N_5ClO_2S.0.5H_2O$: C, 61.02; H, 6.77; N, 12.71; Cl, 6.43; S, 5.82. Found: 61.19; H, 6.60; N, 12.45; Cl, 7.01; S, 5.79.

EXAMPLE 350

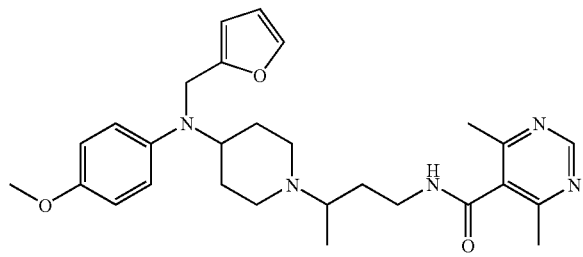

COMPOUND 350: 4,6-Dimethyl-pyrimidine-5-carboxylic acid (3-{4-[furan-2-ylmethyl-(4-methoxy-phenyl)-amino]-piperidin-1-yl}-butyl)-amide Using general procedure H, 4,6-dimethyl-pyrimidine-5-carboxylic acid {3-[4-(4-methoxy-phenylamino)-piperidin-1-yl]-butyl}-amide (see EXAMPLE 347) (89 mg, 0.22 mmol) and 2-bromomethyl-1-furan (Murakarni, Teiichi; et al., *Synthesis*, 4, 2002, 479-482) (100 mg) afforded COMPOUND 350 as a yellow solid (48 mg, 44%). $^1$H NMR ($CDCl_3$) δ 0.88-1.14 (m, 2H), 1.00 (d, 3H, J=6.6 Hz), 1.52-1.58 (m, 1H), 1.71-1.80 (m, 3H), 2.11 (t, 1H, J=10.2 Hz), 2.47-2.54 (m, 1H), 2.53 (s, 6H), 2.72-2.88 (m, 3H), 3.24-3.36 (m, 2H), 3.74 (s, 3H), 3.79 (s, 2H), 3.83-3.92 (m, 1H), 6.01 (d, 1H, J=3.3 Hz), 6.26 (dd, 1H, J=3.3, 1.8 Hz), 6.68-6.77 (m, 4H), 7.34 (s, 1H), 8.75-8.77 (m, 1H), 8.84 (s, 1H). $^{13}$C NMR ($CDCl_3$) δ 13.37, 21.93, 29.60, 30.63, 40.18, 43.63, 44.28, 51.87, 55.61, 57.24, 60.39, 106.99, 110.20, 114.38, 118.17, 130.80, 141.34, 142.73, 152.96, 153.51, 157.67, 162.91, 166.45. ES-MS m/z 492 (M+H). Anal. Calcd. for $C_{28}H_{37}N_5O_3.0.5H_2O$: C, 67.18; H, 7.65; N, 13.99. Found: C, 67.16; H, 7.44; N, 13.79.

EXAMPLE 351

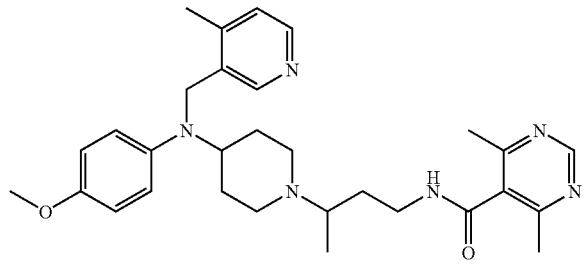

COMPOUND 351: 4,6-Dimethyl-pyrimidine-5-carboxylic acid (3-{4-[(4-methoxy-phenyl)-(4-methyl-pyridin-3-ylmethyl)-amino]-piperidin-1-yl 1-butyl)-amide Using general procedure F with 4-methylnicotinic acid hydrochloride (277 mg, 1.60 mmol) and 4-(4-methoxy-phenylamino)-piperidine-1-carboxylic acid tert-butyl ester (see EXAMPLE 119) (350 mg, 1.14 mmol) and then using general procedure C afforded N-(4-methoxy-phenyl)-4-methyl-N-piperidin-4-yl-nicotinamide as a white solid (181 mg, 49% over 2 steps).

Using general procedure I, the above secondary amine (181 mg, 0.56 mmol) afforded the nitrile, which was subsequently reduced with $BH_3$-THF (2.1 mL, 2.1 mmol) in THF (3.5 mL) at reflux and treated with 6N HCl to afford [1-(3-amino-1-methyl-propyl)-piperidin-4-yl]-(4-methoxy-phenyl)-(4-methyl-pyridin-3-ylmethyl)-amine as a white solid (71 mg, 32% over 2 steps) after basic work-up and purification.

Using general procedure E, the above amine (31 mg, 0.08 mmol) and 4,6-dimethyl-pyrimidine-5-carboxylic acid (14 mg, 0.09 mmol) afforded COMPOUND 351 as a white solid (25 mg, 61%). $^1$H NMR ($CDCl_3$) δ 0.91-1.25 (m, 2H), 0.98 (d, 3H, J=6.3 Hz), 1.49-1.59 (m, 1H), 1.67-1.85 (m, 3H), 2.06-2.16 (m, 1H), 2.35 (s, 3H), 2.43-2.57 (m, 1H), 2.48 (s, 6H), 2.67-2.87 (m, 3H), 3.16-3.38 (m, 2H), 3.70 (s, 3H), 3.72-3.83 (m, 3H), 3.91 (s, 2H), 6.60 (d, 2H, J=9.0 Hz), 6.70 (d, 2H, J=9.0 Hz), 7.01 (d, 1H, J=5.1 Hz), 8.23 (s, 1H), 8.26 (d, 1H, J=5.1 Hz), 8.32 (br s, 1H), 8.77 (s, 1H). $^{13}$C NMR (CDCl$_3$) δ 13.77, 19.18, 22.33, 30.05, 30.70, 30.91, 31.51, 33.85, 40.15, 44.28, 47.75, 52.16, 53.83, 55.92, 59.29, 60.22, 114.76, 120.49, 125.47, 131.08, 133.36, 142.59, 145.67, 148.39, 149.60, 154.14, 157.87, 163.31, 166.85. ES-MS m/z 517 (M+H). Anal. Calcd. for C$_{30}$H$_{40}$N$_6$O$_2$.0.1CH$_2$Cl$_2$.0.4H$_2$O: C, 67.91; H, 7.76; N, 15.79. Found: C, 67.53; H, 7.78; N, 15.56.

EXAMPLE 352

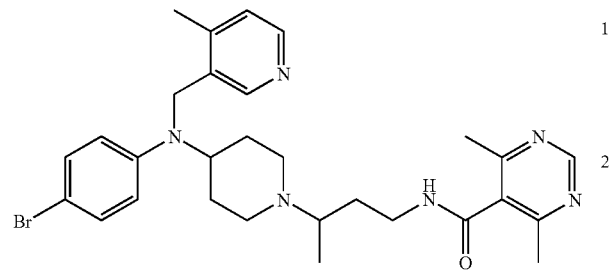

COMPOUND 352: 4,6-Dimethyl-pyrimidine-5-carboxylic acid (3-{4-[(4-bromo-phenyl)-(4-methyl-pyridin-3-ylmethyl)-amino]-piperidin-1-yl}-butyl)-amide Using general procedure A, 1-Boc-4-piperidone (2.42 g, 12.1 mmol) and aniline (1.0 mL, 11.0 mmol) gave 4-phenylamino-piperidine-1-carboxylic acid tert-butyl ester as a white solid (2.82 g, 93%).

Using general procedure F, 4-methylnicotinic acid hydrochloride (421 mg, 2.43 mmol) and the secondary aniline (559 mg, 2.02 mmol) gave 4-[(4-methyl-pyridine-3-carbonyl)-phenyl-amino]-piperidine-1-carboxylic acid tert-butyl ester as an orange foam (438 mg, 55%).

Using general procedure C, the tert-butyl carbamate (438 mg, 1.11 mmol) gave the amide, which was subsequently reduced with BH$_3$-THF (1.0M in THF, 2.5 mL, 2.5 mmol) in THF (6 mL) at reflux and then treated with 6M HCl to give (4-methyl-pyridin-3-ylmethyl)-phenyl-piperidin-4-yl-amine as a white solid (191 mg, 57% over 2 steps) after basic work-up and purification.

A solution of the amine (115 mg, 0.41 mmol), Boc$_2$O (106 mg, 0.49 mmol) and NEt$_3$ (0.08 mL, 0.6 mmol) in CH$_2$Cl$_2$ (2.5 mL) was stirred at room temperature for 1 hour. Standard work-up and purification gave 4-[(4-methyl-pyridin-3-ylmethyl)-phenyl-amino]-piperidine-1-carboxylic acid tert-butyl ester as a white solid (142 mg, 91%).

To a 0° C. solution of the aniline (141 mg, 0.37 mmol) in CHCl$_3$ (1.5 mL) was added dropwise a suspension of NBS (67 mg, 0.38 mmol) in CHCl$_3$ (2.5 mL) and the resulting solution was stirred at 0° C. for 2 hours to give 4-[(4-bromo-phenyl)-(4-methyl-pyridin-3-ylmethyl)-amino]-piperidine-1-carboxylic acid tert-butyl ester as a beige solid (163 mg, 96%) after work-up and purification.

Using general procedure C with the tert-butyl carbamate (163 mg, 0.35 mmol), then general procedure B with the resulting amine and 2-(3-oxo-butyl)-isoindole-1,3-dione (144 mg, 0.66 mmol) and then using general procedure D gave [1-(3-amino-1-methyl-propyl)-piperidin-4-yl]-(4-bromo-phenyl)-(4-methyl-pyridin-3-ylmethyl)-amine as a white foam (85.9 mg, 57% over 3 steps).

Using general procedure E, the primary amine (85.9 mg, 0.20 mmol) and 4,6-dimethylpyrimidine-5-carboxylic acid (41 mg, 0.27 mmol) gave COMPOUND 352 as a white foam (97.5 mg, 87%). $^1$H NMR (CDCl$_3$) δ 1.02-1.30 (m, 2H), 1.03 (d, 3H, J=6.6 Hz), 1.53-1.63 (m, 1H), 1.71-1.90 (m, 3H), 2.17-2.25 (m, 1H), 2.39 (s, 3H), 2.51 (s, 6H), 2.53-2.61 (m, 1H), 2.72-2.91 (m, 3H), 3.32-3.43 (m, 1H), 3.59 (tt, 1H, J=11.3, 3.3 Hz), 3.73-3.84 (m, 1H), 4.03 (s, 2H), 6.43 (d, 2H, J=9.0 Hz), 7.10 (d, 1H, J=4.8 Hz), 7.21 (d, 2H, J=9.0 Hz), 7.91 (br s, 1H), 8.23 (s, 1H), 8.35 (d, 1H, J=4.8 Hz), 8.79 (s, 1H). $^{13}$C NMR (CDCl$_3$) δ 13.38, 18.55, 21.86, 29.27, 30.11, 31.51, 39.20, 44.00, 45.23, 51.58, 56.58, 59.11, 109.56, 115.50, 125.00, 130.56, 131.82, 132.12, 144.31, 147.16, 147.66, 147.98, 157.32, 162.84, 166.37. ESI-MS m/z 565 (MH)$^+$, 567 (MH+2)$^+$. Anal. Calcd. for C$_{29}$H$_{37}$BrN$_6$O.0.6H$_2$O.0.3CH$_2$Cl$_2$: C, 58.47; H, 6.50; N, 13.96. Found: C, 58.53; H, 6.54; N, 13.88.

EXAMPLE 353

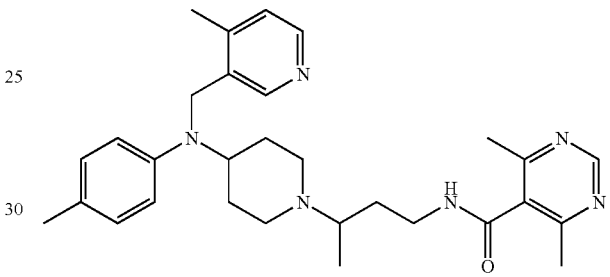

COMPOUND 353: 4,6-Dimethyl-pyrimidine-5-carboxylic acid (3-{4-[(4-methyl-pyridin-3-ylmethyl)-p-tolyl-amino]-piperidin-1-yl}-butyl)-amide Using general procedure A, 1-Boc-4-piperidone (665 mg, 3.34 mmol) and p-toluidine (322 mg, 3.01 mmol) gave 4-p-tolylamino-piperidine-1-carboxylic acid tert-butyl ester as an off-white solid (842 mg, 96%).

Using general procedure F, 4-methylnicotinic acid hydrochloride (601 mg, 3.46 mmol) and the secondary aniline (810 mg, 2.79 mmol) gave 4-[(4-methyl-pyridine-3-carbonyl)-p-tolyl-amino]-piperidine-1-carboxylic acid tert-butyl ester as a pale orange solid (921 mg, 81%).

Using general procedure C, the tert-butyl carbamate (921 mg, 2.25 mmol) gave the amide, which was subsequently reduced with BH$_3$-THF (1.0M in THF, 6.0 mL, 6.0 mmol) in THF (8 mL) at reflux then treated with 6M HCl (14 mL) to give (4-methyl-pyridin-3-ylmethyl)-piperidin-4-yl-p-tolyl-amine as a colourless oil (536 mg, 82% over 2 steps) following basic work-up and purification.

Using general procedure B with the piperidine (268 mg, 0.91 mmol) and 2-(3-oxo-butyl)-isoindole-1,3-dione (401 mg, 1.85 mmol) and then using general procedure D gave [1-(3-amino-1-methyl-propyl)-piperidin-4-yl]-(4-methyl-pyridin-3-ylmethyl)-p-tolyl-amine as a colourless oil (180 mg, 54%).

Using general procedure E, the primary amine (90 mg, 0.25 mmol) and 4,6-dimethylpyrimidine-5-carboxylic acid (46 mg, 0.30 mmol) gave COMPOUND 353 as a white foam (97.5 mg, 79%). $^1$H NMR (CDCl$_3$) δ 0.95-1.27 (m, 2H), 1.01 (d, 3H, J=6.6 Hz), 1.52-1.62 (m, 1H), 1.72-1.90 (m, 3H), 2.14-2.24 (m, 1H), 2.21 (s, 3H), 2.38 (s, 3H), 2.50 (s, 6H), 2.55 (td, 1H, J=11.7, 1.8 Hz), 2.70-2.89 (m, 3H), 3.30-3.40 (m, 1H), 3.52 (tt, 1H, J=11.6, 3.3 Hz), 3.75-3.85 (m, 1H), 3.98 (s, 2H), 6.51 (d, 2H, J=8.5 Hz), 6.95 (d, 2H, J=8.5 Hz), 7.06 (d, 1H, J=5.3 Hz), 8.12 (br s, 1H), 8.28 (s, 1H), 8.32 (d, 1H, J=5.3 Hz), 8.77 (s, 1H). $^{13}$C NMR (CDCl$_3$) δ 13.36, 18.56, 20.13, 21.79, 29.29, 30.16, 31.35, 39.25, 44.05, 45.75, 51.59, 57.01, 59.20, 115.15, 124.86, 127.42, 129.57, 130.56, 132.96, 144.46, 146.01, 147.66, 148.16, 157.26, 162.77, 166.38. ESI-MS m/z 501 (MH)$^+$. Anal. Calcd. for C$_{30}$H$_{40}$N$_6$O.0.3CH$_2$Cl$_2$: C, 69.17; H, 7.78; N, 15.97. Found: C, 68.92; H, 7.82; N, 15.95.

EXAMPLE 354

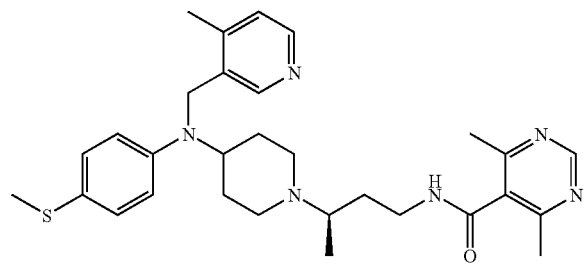

COMPOUND 354: 4,6-Dimethyl-pyrimidine-5-carboxylic acid ((R)-3-{4-[(4-methyl-pyridin-3-ylmethyl)-(4-methylsulfanyl-phenyl)-amino]-piperidin-1-yl}-butyl)-amide Using general procedure F, 4-methylnicotinic acid hydrochloride (363 mg, 2.09 mmol) and (R)-3-[4-(4-methylsulfanyl-phenylamino)-piperidin-1-yl]-butyronitrile (see EXAMPLE 307) (304 mg, 0.93 mmol) afforded N-[1-((R)-2-cyano-1-methyl-ethyl)-piperidin-4-yl]-4-methyl-N-(4-methylsulfanyl-phenyl)-nicotinamide as a brown oil (256 mg, 70%).

The above amide (276 mg, 0.70 mmol) in THF (10 mL) was reduced with BH$_3$-THF (1.0M in THF, 4.2 mL, 4.2 mmol) at reflux and treated with 6N HCl (8 mL) to afford [1-((R)-3-amino-1-methyl-propyl)-piperidin-4-yl]-(4-methyl-pyridin-3-ylmethyl)-(4-methylsulfanyl-phenyl)-amine as a clear oil (203 mg, 70%) after basic work-up and purification.

Using general procedure E, the above amine (104 mg, 0.27 mmol) and 4,6-dimethyl-pyrimidine-5-carboxylic acid (58 mg, 0.38 mmol) afforded COMPOUND 354 as a clear oil (100 mg, 90%). $^1$H NMR (CDCl$_3$) δ 1.02 (d, 3H, J=6.6 Hz), 1.12-1.39 (m, 2H), 1.53-1.62 (m, 1H), 1.75-1.88 (m, 3H), 2.23 (t, 1H, J=11.1 Hz), 2.36 (s, 3H), 2.37 (s, 3H), 2.48 (s, 6H), 2.75-2.88 (m, 3H), 3.32-3.42 (m, 1H), 3.57-3.77 (m, 2H), 4.06 (s, 2H), 6.51 (d, 2H, J=8.7 Hz), 7.07 (d, 1H, J=4.8 Hz), 7.12-7.16 (m, 2H), 7.99 (br s, 1H), 8.22 (s, 1H), 8.30 (d, 1H, J=4.8 Hz), 8.77 (s, 1H). ES-MS m/z 533 (M+H).

EXAMPLE 355

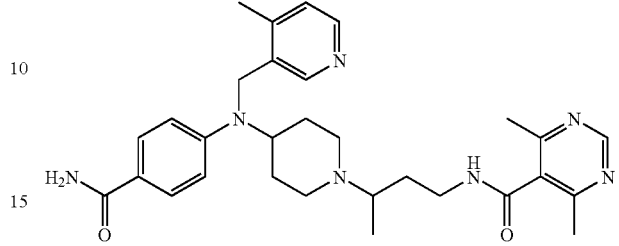

COMPOUND 355: 4,6-Dimethyl-pyrimidine-5-carboxylic acid (3-{4-[(4-carbamoyl-phenyl)-(4-methyl-pyridin-3-ylmethyl)-amino]-piperidin-1-yl}-butyl)-amide To a mixture of 4-[(4-bromo-phenyl)-(4-methyl-pyridin-3-ylmethyl)-amino]-piperidine-1-carboxylic acid tert-butyl ester (see EXAMPLE 352) (232 mg, 0.50 mmol), Zn(CN)$_2$ (66 mg, 0.56 mmol), Pd$_2$(dba)$_3$ (53 mg, 0.058 mmol) and DPPF (56 mg, 0.10 mmol) was added freshly degassed DMF (2.5 mL). The reaction was flushed with argon, heated to 130° C. and stirred under argon for 16 hours giving a black foam (268 mg) after work-up.

Using general procedure C, the crude product gave 4-[(4-methyl-pyridin-3-ylmethyl)-piperidin-4-yl-amino]-benzonitrile as a brown foam (101 mg, 65%) following purification.

A solution of the above substrate (336 mg, 1.10 mmol) and NaOH (420 mg, 10.5 mmol) in 1:1 EtOH/H$_2$O (10 mL) was stirred at reflux for 20 hours. Once cooled, the solution was neutralized with 4M HCl (3 mL) and the mixture was concentrated under reduced pressure, giving a dark brown solid. To a solution of this material in MeOH (20 mL) was added concentrated H$_2$SO$_4$ (1 mL) and the reaction was stirred at reflux for 3 hours to give 4-[(4-methyl-pyridin-3-ylmethyl)-piperidin-4-yl-amino]-benzoic acid methyl ester as a light brown foam (135 mg, 36%) along with 4-[(4-methyl-pyridin-3-ylmethyl)-piperidin-4-yl-amino]-benzamide as a light brown foam (98 mg, 27%) after basic work-up and purification.

Using general procedure B with the primary amide (98 mg, 0.30 mmol) and 2-(3-oxo-butyl)-isoindole-1,3-dione (136 mg, 0.63 mmol) and then using general procedure D gave 4-[[1-(3-amino-1-methyl-propyl)-piperidin-4-yl]-(4-methyl-pyridin-3-ylmethyl)-amino]-benzamide as a pale yellow foam (43.6 mg, 37% over 2 steps).

Using general procedure E, the primary amine (21.8 mg, 0.055 mmol) and 4,6-dimethylpyrimidine-5-carboxylic acid (12 mg, 0.079 mmol) gave COMPOUND 355 as a beige solid (22.6 mg, 77%). $^1$H NMR (CDCl$_3$) δ 1.04 (d, 3H, J=6.6 Hz), 1.08-1.37 (m, 2H), 1.54-1.83 (m, 2H), 1.84-1.93 (m, 2H), 2.26 (t, 1H, J=11.5 Hz), 2.41 (s, 3H), 2.50 (s, 6H), 2.61 (t, 1H, J=11.5 Hz), 2.74-2.92 (m, 3H), 3.34-3.45 (m, 1H), 3.71-3.83 (m, 2H), 4.17 (s, 2H), 5.63 (br s, 2H), 6.54 (d, 2H, J=8.7 Hz), 7.12 (d, 1H, J=4.8 Hz), 7.61 (d, 2H, J=8.7 Hz), 7.75 (br s, 1H), 8.19 (s, 1H), 8.37 (d, 1H, J=4.8 Hz), 8.82 (s, 1H). $^{13}$C NMR (CDCl$_3$) δ 13.48, 18.60, 21.93, 29.39, 30.22, 31.64, 39.23, 44.10, 45.01, 51.56, 56.02, 59.12, 112.09, 121.32, 125.12, 129.16, 130.60, 131.73, 144.25, 147.38, 148.24, 150.96, 157.41, 162.96, 166.46, 169.02. ESI-MS m/z 530 (MH)+.
Anal. Calcd. for $C_{30}H_{39}N_7O_2 \cdot 0.9CH_2Cl_2$: C, 61.23; H, 6.78; N, 16.18. Found: C, 61.43; H, 6.77; N, 15.81.

EXAMPLE 356

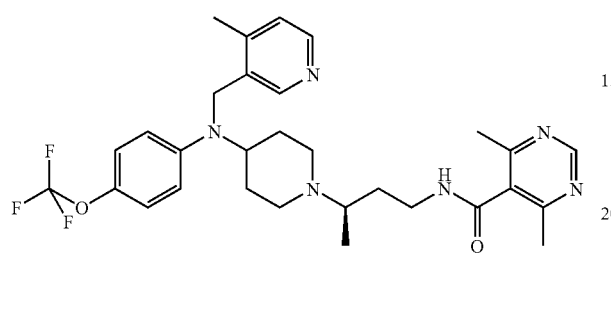

Scheme 20

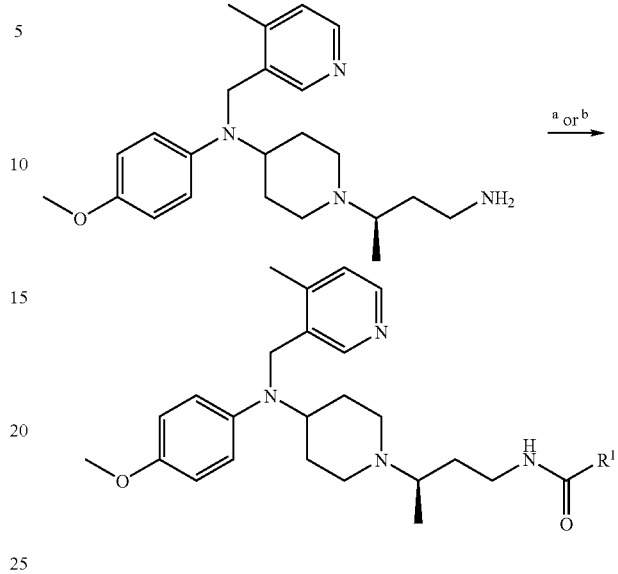

COMPOUND 356: 4,6-Dimethyl-pyrimidine-5-carboxylic acid ((R)-3-{4-[(4-methyl-pyridin-3-ylmethyl)-(4-trifluoromethoxy-phenyl)-amino]-piperidin-1-yl}-butyl)-amide To a solution of (R)-3-[4-(4-trifluoromethoxy-phenylamino)-piperidin-1-yl]-butyronitrile (see EXAMPLE 309) (601 mg, 1.84 mmol) and 4-methyl-3-pyridinecarboxaldehyde (Konno, Katsuhiro; et al., Heterocycles, 30, 1, 1990, 247-251) (475 mg, 3.93 mmol) in 1,2-dichloroethane (10 mL) was added NaBH(OAc)$_3$ (754 mg, 3.56 mmol) and the reaction stirred at 60° C. overnight. Purification gave the desired nitrile, which was subsequently reduced with BH$_3$-THF (1.0M in THF, 1.0 mL, 1.0 mmol) in THF (6 mL) at reflux and then treated with 6N HCl (2 mL) to give the desired primary amine (25 mg, 3% over 2 steps) as a clear oil after basic work-up.

Using general procedure E, the amine from above (25 mg, 0.057 mmol) and 4,6-dimethyl-pyrimidine-5-carboxylic acid (25 mg, 0.16 mmol) gave COMPOUND 356 (22 mg, 68%) as a white solid. $^1$H NMR (CDCl$_3$) δ 1.01 (d, 3H, J=6 Hz), 1.65-1.89 (m, 6H), 2.19-2.26 (m, 1H), 2.40 (s, 3H), 2.51 (s, 6H), 2.51-2.61 (m, 1H), 2.76-2.88 (m, 3H), 3.35-3.40 (m, 1H), 3.58-3.63 (m, 1H), 3.75-3.81 (m, 1H), 4.05 (s, 2H), 6.52 (d, 2H, J=9 Hz), 6.99 (d, 2H, J=9 Hz), 7.10 (d, 1H, J=4.8 Hz), 7.91 (br s, 1H), 8.25 (s, 1H), 8.37 (d, 1H, J=4.8 Hz), 8.80 (s, 1H). $^{13}$C NMR (CDCl$_3$) δ 13.78, 19.06, 22.38, 29.60, 30.50, 31.86, 39.79, 44.40, 45.89, 52.22, 57.01, 59.88, 113.83, 114.65, 119.31, 122.66, 125.53, 131.01, 132.58, 141.00, 144.82, 147.37, 148.18, 148.64, 157.87, 163.38, 166.89. ES-MS m/z 571 (M+H). Anal. Calcd. for $C_{30}H_{37}N_6O_2F_3 \cdot 0.1H_2O \cdot 1.1CH_3OH$: C, 60.99; H, 6.82; N, 13.68; F, 9.28. Found: C, 61.25; H, 6.52; N, 13.31; F, 9.52.

Scheme 20 describes the preparation of Examples 357-365, using general procedures E or F, and reagents listed below.

| Example | R$^1$COOH |
|---|---|
| 357$^a$ (racemic) | 3,5-dimethylisonicotinic acid |
| 358$^b$ | 2,6-dimethylbenzoic acid |
| 359$^b$ | 2,4-dimethylnicotinic acid |
| 360$^b$ | 2-amino-6-methylbenzoic acid |
| 361$^b$ | 2-chloro-6-methylbenzoic acid |
| 362$^a$ | 3,5-dichloroisonicotinic acid |
| 363$^b$ (racemic) | 2,6-dimethyl-4-pyridin-4-yl-benzoic acid |
| 364$^b$ | 2,4-dimethyl-thiophene-3-carboxylic acid |
| 365$^b$ | 2,4-dimethyl-1-oxy-nicotinic acid |

$^a$general procedure F
$^b$general procedure E

EXAMPLE 357

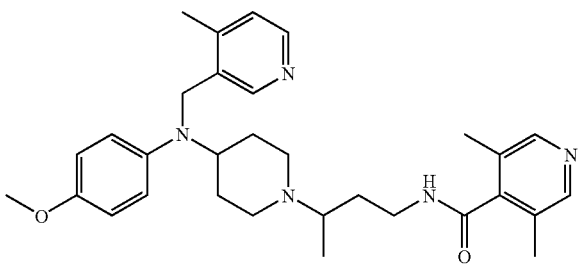

COMPOUND 357: N-(3-{4-[(4-Methoxy-phenyl)-(4-methyl-pyridin-3-ylmethyl)-amino]-piperidin-1-yl}-butyl)-3,5-dimethyl-isonicotinamide White solid. $^1$H NMR (CDCl$_3$) δ 0.81-1.21 (m, 2H), 0.99 (d, 3H, J=6.6 Hz), 1.49-1.61 (m, 1H), 1.67-1.85 (m, 3H), 2.06-2.17 (m, 1H), 2.27 (s, 6H), 2.34 (s, 3H), 2.43-2.54 (m, 1H), 2.68-2.87 (m, 3H), 3.19-3.37 (m, 2H), 3.71 (s, 3H), 3.72-3.86 (m, 1H), 3.89 (s, 2H), 6.59 (d, 2H, J=9.0 Hz), 6.71

(d, 2H, J=9.0 Hz), 7.03 (d, 1H, J=4.8 Hz), 8.10 (br s, 1H), 8.22 (s, 2H), 8.25 (s, 1H), 8.29 (d, 1H, J=4.8 Hz). $^{13}$C NMR (CDCl$_3$) δ 13.76, 16.32, 19.17, 30.05, 30.94, 31.66, 39.81, 44.30, 47.57, 52.18, 55.94, 58.97, 60.27, 114.79, 119.94, 125.46, 128.72, 133.52, 142.68, 145.42, 145.53, 148.35, 148.94, 149.49, 153.92, 167.68. ES-MS m/z 516 (M+H). Anal. Calcd. for C$_{31}$H$_{41}$N$_5$O$_2$.0.1CH$_2$Cl$_2$.0.5C$_4$H$_8$O$_2$: C, 69.96; H, 8.02; N, 12.32. Found: C, 69.80; H, 8.01; N, 12.39.

EXAMPLE 358

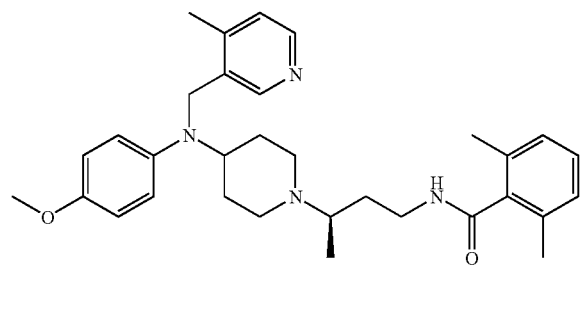

COMPOUND 358: N—((R)-3-{4-[(4-Methoxy-phenyl)-(4-methyl-pyridin-3-ylmethyl)-amino]-piperidin-1-yl}-butyl)-2,6-dimethyl-benzamide Using general procedure F, 4-methylnicotinic acid hydrochloride (578 mg, 3.33 mmol) and (R)-3-[4-(4-methoxy-phenylamino)-piperidin-1-yl]-butyronitrile (see EXAMPLE 230) (700 mg, 2.56 mmol) afforded the amide, which was subsequently reduced with BH$_3$-THF (1.0M in THF, 10.0 mL, 10.0 mmol) in THF (17 mL) at reflux and then treated with 6N HCl (6.7 mL, 40.1 mmol) to afford [1-((R)-3-amino-1-methyl-propyl)-piperidin-4-yl]-(4-methoxy-phenyl)-(4-methyl-pyridin-3-ylmethyl)-amine as a white solid (526 mg, 53% over 2 steps) after basic work-up and purification.

COMPOUND 358 was isolated as a white solid. $^1$H NMR (CDCl$_3$) δ 0.97 (d, 3H, J=6.6 Hz), 1.00-1.33 (m, 2H), 1.47-1.61 (m, 1H), 1.70-1.83 (m, 3H), 2.04-2.15 (m, 1H), 2.30 (s, 9H), 2.42-2.52 (m, 1H), 2.68-2.88 (m, 3H), 3.19-3.36 (m, 2H), 3.69 (s, 3H), 3.75-3.88 (m, 2H), 6.60 (d, 2H, J=8.4 Hz), 6.69 (d, 2H, J=8.4 Hz), 6.85-6.91 (m, 3H), 7.01 (d, 1H, J=4.8 Hz), 7.94 (br s, 1H), 8.26 (s, 1H), 8.29 (d, 1H, J=5.1 Hz). ES-MS m/z 515 (M+H).

EXAMPLE 359

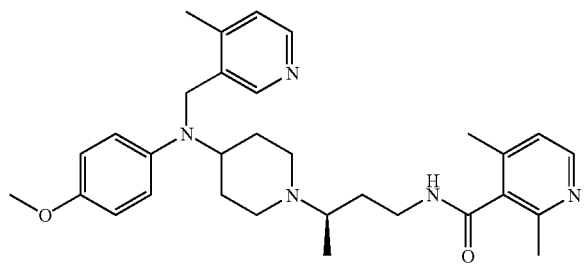

COMPOUND 359: N—((R)-3-{4-[(4-Methoxy-phenyl)-(4-methyl-pyridin-3-ylmethyl)-amino]-piperidin-1-yl}-butyl)-2,4-dimethyl-nicotinamide White solid. $^1$H NMR (CDCl$_3$) δ 0.90-1.27 (m, 2H), 0.99 (d, 3H, J=2.2 Hz), 1.49-1.84 (m, 4H), 2.06-2.17 (m, 1H), 2.30 (s, 3H), 2.35 (s, 3H), 2.42-2.57 (m, 1H), 2.54 (s, 3H), 2.68-2.89 (m, 3H), 3.17-3.38 (m, 2H), 3.71 (s, 3H), 3.77-3.91 (m, 3H), 6.61 (d, 2H, J=8.7 Hz), 6.70 (d, 2H, J=8.7 Hz), 6.83 (d, 1H, J=5.1 Hz), 7.03 (d, 1H, J=4.5 Hz), 8.09-8.17 (m, 2H), 8.26 (s, 1H), 8.30 (d, 1H, J=4.8 Hz). ES-MS m/z 516 (M+H).

EXAMPLE 360

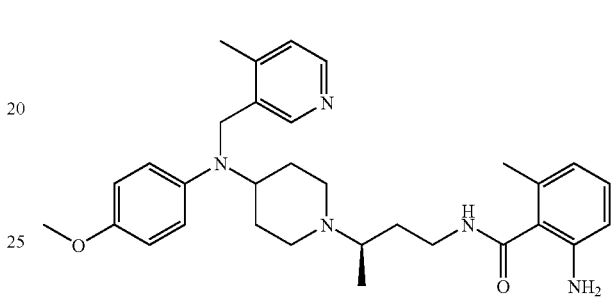

COMPOUND 360: 2-Amino-N-((R)-3-{4-[(4-methoxy-phenyl)-(4-methyl-pyridin-3-ylmethyl)-amino]-piperidin-1-yl}1-butyl)-6-methyl-benzamide White solid. $^1$H NMR (CDCl$_3$) δ 0.97 (d, 3H, J=4.8 Hz), 1.11-1.44 (m, 2H), 1.46-1.59 (m, 1H), 1.67-1.93 (m, 3H), 2.03-2.16 (m, 1H), 2.29 (s, 3H), 2.31 (s, 3H), 2.40-2.53 (m, 1H), 2.70-2.90 (m, 3H), 3.21-3.36 (m, 2H), 3.70 (s, 3H), 3.72-3.86 (m, 1H), 3.93 (s, 2H), 4.04 (s, 2H), 6.38-6.47 (m, 2H), 6.58-6.81 (m, 5H), 6.98-7.05 (m, 1H), 7.85 (br s, 1H), 8.25-8.33 (m, 2H). ES-MS m/z 516 (M+H).

EXAMPLE 361

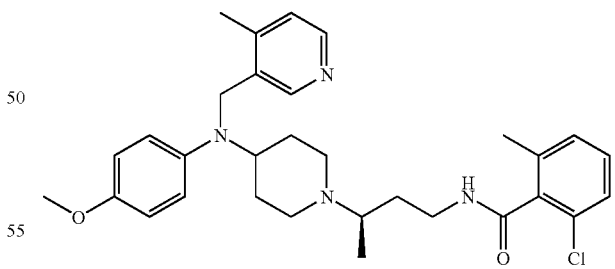

COMPOUND 361: 2-Chloro-N-((R)-3-{4-[(4-methoxy-phenyl)-(4-methyl-pyridin-3-ylmethyl)-amino]-piperidin-1-yl}-butyl)-6-methyl-benzamide White solid. $^1$H NMR (CDCl$_3$) δ 0.84-1.18 (m, 5H), 1.49-1.61 (m, 1H), 1.72-1.89 (m, 3H), 2.04-2.17 (m, 1H), 2.30 (s, 1H), 2.35 (s, 1H), 2.42-2.56 (m, 1H), 2.73-2.95 (m, 3H), 3.19-3.39 (m, 2H), 3.70 (s, 3H), 3.77-3.91 (m, 3H), 6.61 (d, 2H, J=7.8 Hz), 6.69 (d, 0.2H, J=7.8 Hz), 6.86-7.10 (m, 4H), 8.19 (br s, 1H), 8.23-8.32 (m, 2H). ES-MS m/z 535 (M+H).

EXAMPLE 362

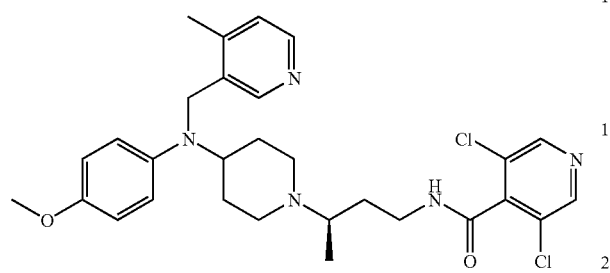

COMPOUND 362: 3,5-Dichloro-N-((R)-3-{4-[(4-methoxy-phenyl)-(4-methyl-pyridin-3-ylmethyl)-amino]-piperidin-1-yl}-butyl)-isonicotinamide White solid. $^1$H NMR (CDCl$_3$) δ 0.92-1.22 (m, 2H), 0.99 (d, 3H, J=6.0 Hz), 1.48-1.58 (m, 1H), 1.76-1.89 (m, 3H), 2.05-2.16 (m, 1H), 2.41 (s, 3H), 2.44-2.55 (m, 1H), 2.73-2.93 (m, 3H), 3.13-3.24 (m, 1H), 3.28-3.41 (m, 1H), 3.73 (s, 3H), 3.78-3.92 (m, 1H), 3.91 (s, 2H), 6.61 (d, 2H, J=8.7 Hz), 6.71 (d, 2H, J=8.4 Hz), 7.01-7.06 (m, 1H), 8.24-8.33 (m, 2H), 8.43 (s, 2H), 8.61 (br s, 1H). ES-MS m/z 556 (M+H).

EXAMPLE 363

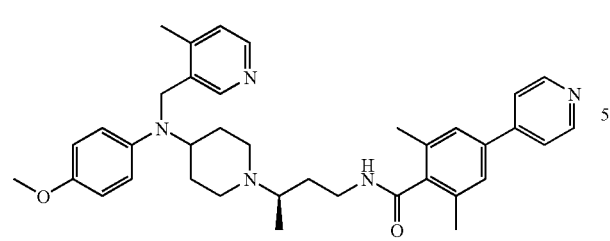

COMPOUND 363: N—((R)-3-{4-[(4-Methoxy-phenyl)-(4-methyl-pyridin-3-ylmethyl)-amino]-piperidin-1-yl}-butyl)-2,6-dimethyl-4-pyridin-4-yl-benzamide White foam. $^1$H NMR (CDCl$_3$) δ 0.83-1.38 (m, 5H), 1.59-1.88 (m, 4H), 2.09-2.19 (m, 4H), 2.41 (s, 6H), 2.47-2.58 (m, 1H), 2.77-2.91 (m, 3H), 3.25-3.42 (m, 2H), 3.69 (s, 3H), 3.77-3.91 (m, 3H), 6.58-6.69 (m, 4H), 6.84-6.85 (m, 1H), 7.27 (s, 2H), 7.34 (d, 2H, J=5.1 Hz), 7.76 (br s, 1H), 8.20-8.23 (m, 2H), 8.56 (d, 2H, J=5.4 Hz). ES-MS m/z 592 (M+H).

EXAMPLE 364

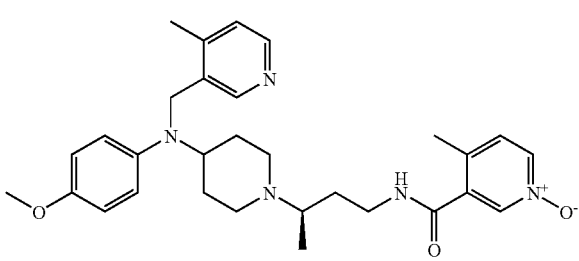

COMPOUND 364: 2,4-Dimethyl-thiophene-3-carboxylic acid ((R)-3-{4-[(4-methoxy-phenyl)-(4-methyl-pyridin-3-ylmethyl)-amino]-piperidin-1-yl}-butyl)-amide White foam. $^1$H NMR (CDCl$_3$) δ 0.99 (d, 3H, J=6.6 Hz), 1.18-1.59 (m, 3H), 1.72-1.87 (m, 3H), 2.10-2.18 (m, 1H), 2.21 (s, 3H), 2.35 (s, 3H), 2.46 (s, 3H), 2.46-2.53 (m, 1H), 2.75-2.85 (m, 3H), 3.27-3.36 (m, 2H), 3.69-3.77 (m, 1H), 3.71 (s, 3H), 4.08 (s, 2H), 6.52 (s, 1H), 6.63-6.74 (m, 4H), 7.03 (d, 1H, J=5.1 Hz), 7.41 (br s, 1H), 8.30-8.32 (m, 2H). ES-MS m/z 521 (M+H).

EXAMPLE 365

COMPOUND 365: N—((R)-3-{4-[(4-Methoxy-phenyl)-(4-methyl-pyridin-3-ylmethyl)-amino]-piperidin-1-yl}-butyl)-2,4-dimethyl-1-oxy-nicotinamide White solid. $^1$H NMR (CDCl$_3$) δ 1.05 (d, 3H, J=6.3 Hz), 1.29-1.53 (m, 2H), 1.58-1.67 (m, 2H), 1.85-1.92 (m, 3H), 2.18-2.26 (m, 1H), 2.28 (s, 3H), 2.35 (s, 6H), 2.48-2.58 (m, 1H), 2.80-2.92 (m, 3H), 3.25-3.45 (m, 2H), 3.62-3.70 (m, 1H), 3.72 (s, 3H), 4.10 (s, 2H), 6.66-6.75 (m, 4H), 6.83 (d, 1H, J=6.6 Hz), 7.03 (d, 1H, J=4.8 Hz), 7.90 (d, 1H, J=6.6 Hz), 8.30 (s, 2H), 8.41 (br s, 1H). ES-MS m/z 532 (M+H).

EXAMPLE 366

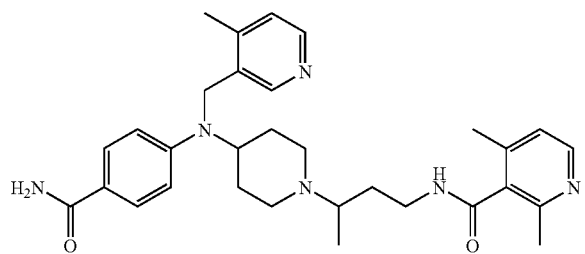

COMPOUND 366: N-(3-{4-[(4-Carbamoyl-phenyl)-(4-methyl-pyridin-3-ylmethyl)-amino]-piperidin-1-yl}-butyl)-2,4-dimethyl-nicotinamide Using general procedure E, 4-[[1-(3-amino-1-methyl-propyl)-piperidin-4-yl]-(4-methyl-pyridin-3-ylmethyl)-amino]-benzamide (see EXAMPLE 355) (21.8 mg, 0.055 mmol) and 2,4-dimethylnicotinic acid hydrochloride (15 mg, 0.080 mmol) gave COMPOUND 366 as an off-white solid (24.6 mg, 84%). $^1$H NMR (CDCl$_3$) δ 1.03 (d, 3H, J=6.6 Hz), 1.09-1.38 (m, 2H), 1.53-1.63 (m, 1H), 1.72-1.90 (m, 3H), 2.24 (t, 1H, J=11.0 Hz), 2.29 (s, 3H), 2.39 (s, 3H), 2.53 (s, 3H), 2.59 (t, 1H, J=11.0 Hz), 2.74-2.93 (m, 3H), 3.31-3.42 (m, 1H), 3.71-3.84 (m, 2H), 4.12 (s, 2H), 5.64 (br s, 2H), 6.53 (d, 2H, J=8.9 Hz), 6.84 (d, 1H, J=5.0 Hz), 7.12 (d, 1H, J=4.9 Hz), 7.61 (d, 2H, J=8.9 Hz), 7.65 (br s, 1H), 8.18 (s, 1H), 8.18 (d, 1H, J=5.0 Hz), 8.37 (d, 1H, J=4.9 Hz). $^{13}$C NMR (CDCl$_3$) δ 13.44, 18.65, 18.72, 22.26, 29.28, 30.17, 31.72, 39.11, 44.05, 44.86, 51.61, 56.13, 59.29, 112.07, 121.24, 122.44, 125.08, 129.13, 131.84, 133.50, 143.83, 144.19, 147.41, 148.19, 148.63, 150.95, 154.03, 168.20, 169.02. ESI-MS m/z 529 (MH)$^+$. Anal. Calcd. for $C_{31}H_{40}N_6O_2 \cdot 0.6CH_2Cl_2$: C, 65.48; H, 7.16; N, 14.50. Found: C, 65.26; H, 7.46; N, 14.25.

EXAMPLE 367 mL) followed by general procedure C afforded [1-((R)-3-amino-1-methyl-propyl)-piperidin-4-yl]-[4-(tert-butyl-dimethyl-silanyloxy)-phenyl]-(4-methyl-pyridin-3-ylmethyl)-amine (130 mg, 17% over 2 steps) as a white foam.

Using general procedure E, the amine (136 mg, 0.28 mmol) and 2,4-dimethyl-nicotinic acid (69 mg, 0.37 mmol) gave N—((R)-3-{4-[[4-(tert-butyl-dimethyl-silanyloxy)-phenyl]-(4-methyl-pyridin-3-ylmethyl)-amino]-piperidin-1-yl}-butyl)-2,4-dimethyl-nicotinamide (165 mg, 99%).

To a solution of the above substrate (165 mg, 0.27 mmol) in THF (2 mL) at 0° C. was added TBAF (1M, 0.27 mmol) and the reaction mixture was stirred for 1 h at room temperature to give N—((R)-3-{4-[(4-hydroxy-phenyl)-(4-methyl-pyridin-3-ylmethyl)-amino]-piperidin-1-yl}-butyl)-2,4-dimetyl-nicotinamide (100 mg, 74%) as a white foam after purification.

To the above alcohol (100 mg, 0.2 mmol), ethyl glycolate (100 µL, 1.05 mmol) and Ph$_3$P (277 mg, 1.06 mmol) in THF (3 mL) cooled to 0° C. was added DIAD (204 µL, 1.05 mmol) and reaction mixture was stirred for 1 h at room temperature to give the desired product as a yellow foam following purification.

The intermediate above was subjected to MeOH sat. NH$_3$ and the mixture was stirred for 3 h at room temperature. The mixture was concentrated under reduced pressure and the crude material was purified to give COMPOUND 367 (25 mg, 22%) as a white foam. $^1$H NMR (CDCl$_3$) δ 0.98 (d, 3H, J=4.5 Hz), 0.98-0.99 (m, 1H), 1.15-1.26 (m, 1H), 1.5-1.58 (m, 1H), 1.69-1.82 (m, 2H), 2.03 (br s, 1H), 2,15 (t, 1H, J=5.4 Hz), 2.28 (s, 3H), 2.35 (s, 3H), 2.51 (s, 1H), 2.46-2.72 (m, 1H), 2.76-2.82 (m, 3H), 3.28-3.37 (m, 2H), 3.77-3.84 (m, 1H), 3.89 (s, 2H), 4.37 (s, 2H), 6.57 (d, 2H, J=9 Hz), 5.90 (br s, 1H), 6.66 (br s, 1H), 6.74 (d, 2H, J=9 Hz), 6.82 (d, 1H, J=4.8 Hz), 7.04 (d, 1H, J=5.1 Hz), 8.04 (br s, 1H), 8.12 (d, 1H, J=6 Hz), 8.23 (s, 1H), 8.30 (d, 1H, J=6 Hz). $^{13}$C NMR (CDCl$_3$) δ 13.78, 19.16, 19.22, 22.65, 29.80, 30.68, 31.74, 39.97, 44.32, 46.75, 52.29, 57.61, 58.90, 60.26, 68.20, 115.81, 118.78, 122.82, 125.50, 133.22, 134.00, 143.92, 144.20, 145.37, 148.45, 149.08, 149.18, 151.00, 154.44, 168.56, 171.77. ES-MS 12/z 560.0 (M+1).

EXAMPLE 368

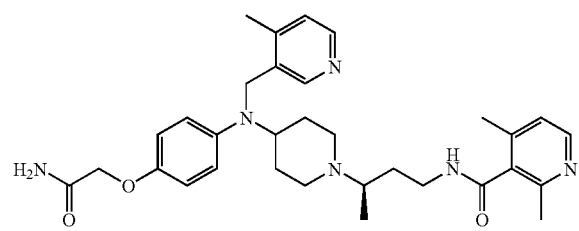

COMPOUND 367: N—((R)-3{4-[(4-Carbamoyl-methoxy-phenyl)-(4-methyl-pyridin-3-ylmethyl)-amino]-piperidin-1-yl}-butyl)-2,4-dimethyl-nicotinamide Using general procedure A with ((R)-3-{4-[4-(tert-butyl-dimethyl-silanyloxy)-phenylamino]-piperidin-1-yl}-butyl)-carbamic acid tert-butyl ester (see EXAMPLE 233) (796 mg, 2.10 mmol) and 4-methyl-3-pyridinecarboxaldehyde (see EXAMPLE 356) (367 mg, 3.00 mmol) in ClCH$_2$CH$_2$Cl (6

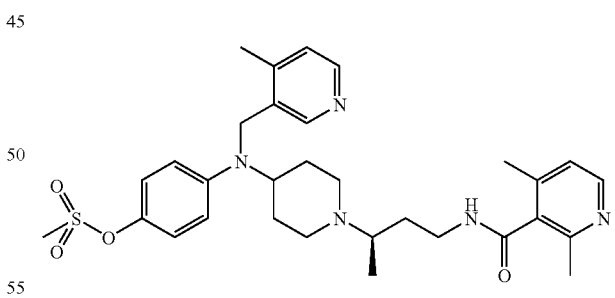

COMPOUND 368: Methanesulfonic acid 4-[(1-{(R)-3-[(2,4-dimethyl-pyridine-3-carbonyl)-amino]-1-methyl-propyl}-piperidin-4-yl)-(4-methyl-pyridin-3-ylmethyl)-amino]-phenyl ester Using general procedure G, N—((R)-3-{4-[(4-hydroxy-phenyl)-(4-methyl-pyridin-3-ylmethyl)-amino]-piperidin-1-yl}-butyl)-2,4-dimetyl-nicotinamide (see EXAMPLE 368) (46 mg, 0.09 mmol) gave COMPOUND 368 (6 mg, 11%) as a white foam. $^1$H NMR (CDCl$_3$) δ 1.02 (d, 3H, J=6.6 Hz), 1.07-1.12 (m, 1H), 1.17-1.32 (m, 2H), 1.67-1.82 (m, 2H), 2.17-2.21 (m, 1H), 2.30 (s, 3H), 2.38 (s, 3H), 2.54 (s, 3H), 2.54-2.57 (m, 2H), 2.76-2.89 (m, 3H), 3.05 (s, 3H), 3.33-3.38 (m, 1H), 3.58-3.65 (m, 1H), 3.70-3.83 (m, 1H), 4.05 (s, 2H), 6.47 (d, 2H, J=9 Hz), 6.84 (d, 1H, J=5.1 Hz), 7.02 (d, 2H, J=9 Hz), 7.01-7.03 (m, 1H), 7.11 (d, 1H, J=6 Hz), 7.69-7.70 (m, 1H), 8.15 (d, 1H, J=5.1 Hz), 8.24 (s, 1H), 8.36 (d, 1H, J=6 Hz). $^{13}$C NMR (CDCl3) δ 13.82, 19.15, 22.72, 29.64, 30.59, 32.00, 37.15, 39.75, 44.36, 45.61, 52.23, 57.23, 59.99, 114.59, 122.86, 123.16, 123.35, 125.56, 133.97, 140.76, 144.23, 144.72, 147.83, 148.16, 148.62, 149.10, 154.47, 168.60. ES-MS m/z 580.4 (M+1).

EXAMPLE 369

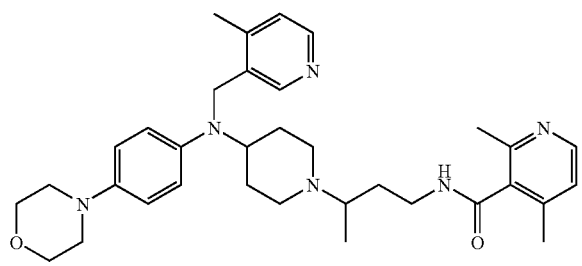

COMPOUND 369: 2,4-Dimethyl-N-(3-{4-[(4-methyl-pyridin-3-ylmethyl)-(4-morpholin-4-yl-phenyl)-amino]-piperidin-1-yl}-butyl)-nicotinamide A solution of 4-[(4-bromo-phenyl)-(4-methyl-pyridin-3-ylmethyl)-amino]-piperidine-1-carboxylic acid tert-butyl ester (see EXAMPLE 352) (300 mg, 0.630 mmol), Pd(OAc)$_2$ (7.10 mg, 0.0315 mmol), potassium tert-butoxide (106 mg, 0.945 mmol), morpholine (50.0 μL, 0.573 mmol) and tri(tert-butyl)phosphine (128 mg, 0.0315 mmol) in degassed toluene (2.2 mL) was stirred at 100° C. for 16 hours under nitrogen. Standard work-up and purification gave 4-[(4-methyl-pyridin-3-ylmethyl)-(4-morpholin-4-yl-phenyl)-amino]-piperidine-1-carboxylic acid tert-butyl ester as a white solid (191 mg, 74%).

Using general procedure C with the tert-butyl carbamate (191 mg, 0.422 mmol), then general procedure I with the resulting amine and then using general procedure J gave [1-(3-amino-1-methyl-propyl)-piperidin-4-yl]-(4-methyl-pyridin-3-ylmethyl)-(4-morpholin-4-yl-phenyl)-amine as a white foam (51.5 mg, 19% over 3 steps).

Using general procedure E, the primary amine (36.1 mg, 0.0824 mmol) and 4,6-dimethylpyrimidine-5-carboxylic acid (18.5 mg, 0.0989 mmol) afforded COMPOUND 369 as a white foam (22.5 mg, 48%). $^1$H NMR (CDCl$_3$) δ 1.00 (d, 3H, J=6.0 Hz), 1.71-1.84 (m, 9H), 2.31 (s, 3H), 2.36 (s, 3H), 2.51-2.54 (m, 4H), 2.73-2.82 (m, 3H), 3.00 (t, 4H, J=4.7 Hz), 3.35-3.38 (m, 2H), 3.82 (t, 4H, J=4.7 Hz), 3.90 (s, 2H), 6.59 (d, 2H, J=8.7 Hz), 6.75 (d, 2H, J=8.7 Hz), 6.83 (d, 1H, J=4.2 Hz), 7.05 (d, 1H, J=4.5 Hz), 8.14 (d, 1H, J=4.5 Hz), 8.27 (s, 1H), 8.31 (d, 1H, J=4.5 Hz). $^{13}$C NMR (CDCl$_3$) δ 13.73, 19.18, 19.26, 22.71, 29.72, 30.63, 31.75, 39.94, 44.36, 45.67, 46.63, 50.86, 52.35, 58.83, 66.29, 67.42, 114.41, 117.76, 118.46, 122.85, 125.44, 129.64, 133.56, 142.89, 144.16, 145.32, 148.34, 149.14, 149.32, 154.51. ESI-MS m/z 571 (MH)$^+$. Anal. Calcd. for C$_{34}$H$_{46}$N$_6$O$_2$.0.4H$_2$O.1.3CH$_3$OH: C, 67.77; H, 8.31; N, 13.43. Found: C, 67.73; H, 8.06; N, 13.18.

EXAMPLE 370

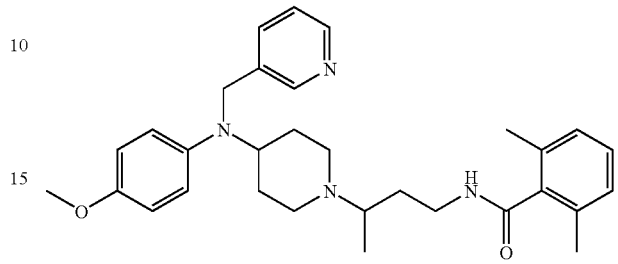

COMPOUND 370: N-(3-{4-[(4-Methoxy-phenyl)-pyridin-3-ylmethyl-amino]-piperidin-1-yl}-butyl)-2,6-dimethyl-benzamide Using general procedure H, 4-(4-methoxy-phenylamino)-piperidine-1-carboxylic acid tert-butyl ester (see EXAMPLE 119) (585 mg, 1.90 mmol) and 3-picolyl chloride hydrobromide (1.9 g, 9.5 mmol) afforded a white solid (575 mg).

Using general procedure C with the above substrate (575 mg), then general procedure B with 2-(3-oxo-butyl)-isoindole-1,3-dione (136 mg, 0.63 mmol) and then using general procedure D afforded [1-(3-amino-1-methyl-propyl)-piperidin-4-yl]-pyridin-(4-methoxy-phenyl)-amine as a colourless syrup (90 mg, 58% over 3 steps).

Using general procedure E, the above amine (46 mg, 0.13 mmol) and 2,6-dimethylbenzoic acid (21 mg, 0.14 mmol) afforded COMPOUND 370 as a white solid (31 mg, 49%). $^1$H NMR (CDCl$_3$) δ 0.91-1.28 (m, 2H), 0.98 (d, 3H, J=5.7 Hz), 1.49-1.54 (m, 1H), 1.70-1.74 (m, 3H), 2.10 (t, 1H, J=12.0 Hz), 2.31 (s, 6H), 2.51 (t, 1H, J=11.1 Hz), 2.73-2.85 (m, 3H), 3.22-3.41 (m, 2H), 3.69 (s, 5H), 3.88-3.90 (m, 1H), 6.58 (d, 2H, J=7.8 Hz), 6.70 (d, 2H, J=8.4 Hz), 6.91-6.95 (m, 3H), 7.16-7.20 (m, 1H), 7.47 (d, 1H, J=7.5 Hz), 8.45 (s, 2H), 8.52 (br s, 1H). $^{13}$C NMR (CDCl$_3$) δ 13.73, 19.14, 29.07, 30.37, 30.91, 39.93, 43.60, 47.01, 52.27, 55.60, 58.49, 60.69, 114.52, 117.27, 123.24, 127.27, 128.44, 134.00, 134.56, 136.00, 138.61, 142.62, 148.04, 148.92, 152.55, 169.90. ES-MS m/z 501 (M+H). Anal. Calcd. for C$_{31}$H$_{40}$N$_4$O$_2$.0.2H$_2$O: C, 73.31; H, 8.10; N, 11.03. Found: C, 73.39; H, 8.06; N, 11.13.

EXAMPLE 371

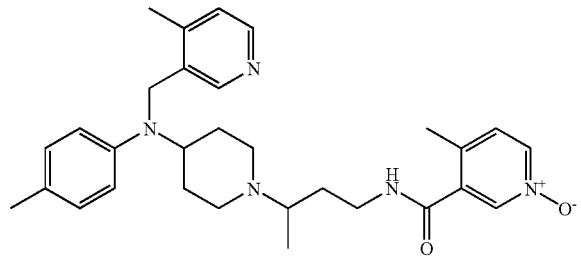

COMPOUND 371: 2,4-Dimethyl-N-(3-{4-[(4-methyl-pyridin-3-ylmethyl)-p-tolyl-amino]-piperidin-1-yl}-butyl)-1-oxy-nicotinamide Using general procedure E, [1-(3-amino-1-methyl-propyl)-piperidin-4-yl]-(4-methyl-pyridin-3-ylmethyl)-p-tolyl-amine (see EXAMPLE 353) (90 mg, 0.25 mmol) and 2,4-dimethyl-1-oxy-nicotinic acid (52 mg, 0.31 mmol) gave COMPOUND 371 as a white foam (55.0 mg, 43%). $^1$H NMR (CDCl$_3$) δ 1.02 (d, 3H, J=6.6 Hz), 1.21-1.47 (m, 2H), 1.55-1.66 (m, 1H), 1.75-1.93 (m, 3H), 2.17-2.27 (m, 1H), 2.21 (s, 3H), 2.28 (s, 3H), 2.36 (s, 6H), 2.48-2.58 (m, 1H), 2.72-2.89 (m, 3H), 3.35-3.48 (m, 1H), 3.51-3.61 (m, 1H), 3.63-3.73 (m, 1H), 4.14 (s, 2H), 6.55 (d, 2H, J=8.4 Hz), 6.79 (d, 1H, J=6.6 Hz), 6.96 (d, 2H, J=8.4 Hz), 7.06 (d, 1H, J=5.4 Hz), 7.85 (d, 1H, J=6.6 Hz), 8.19 (br s, 1H), 8.32 (s, 1H), 8.33 (d, 1H, J=5.4 Hz). $^{13}$C NMR (CDCl$_3$) δ 13.56, 14.91, 18.39, 18.54, 20.17, 29.61, 30.06, 32.57, 38.48, 44.86, 46.10, 51.11, 56.97, 57.90, 114.83, 124.76, 124.86, 127.13, 129.64, 133.28, 134.45, 136.87, 137.60, 144.34, 145.42, 146.34, 147.81, 148.32, 165.36. ESI-MS m/z 516 (MH)$^+$. Anal. Calcd. for C$_{31}$H$_{41}$N$_5$O$_2$·0.7CH$_2$Cl$_2$: C, 66.20; H, 7.43; N, 12.18. Found: C, 65.94; H, 7.39; N, 12.18.

EXAMPLE 372

Cell Fusion Assay

The assay measures the ability of a test compound to inhibit gp120 and CD4/CCR5-dependent cell-cell fusion. The assay uses two cell lines, 1) CHO-tat cell line that expresses the viral gp120 from a R5 using virus (JR-FL) and the HIV tat proteins, 2) P4-CCR5 cell line that expresses human CD4 and CCR5 on the surface and carries β-galactosidase construct under the control of the retroviral promotor LTR. Once fusion of these two cell lines occurs, the tat protein from the CHO cell line trans-activates the reporter gene O-galactosidase in the P4-CCR5 cell line. In a 96 well format, 1×10$^4$ cells of each cell line are plated per well in the presence or absence of test compound. The cells are then incubated at 37° C., 5% CO$_2$ for 18-24 hours. The β-galactosidase activity in each well is measured by the addition of a luminescence substrate (Gal-Screen substrate, Applied Biosystems) and luminescence monitored with a Victor 2 plate reader (Wallac). The ability of test compounds to inhibit fusion is indicated by a decrease in β-galactosidase activity. Results are reported as the concentration of test compound required to inhibit 50% of the β-galactosidase activity in the test controls.

When tested in the assay described above, many compounds of the invention exhibited IC$_{50}$'s in the range of 0.01 nM to 100 nM.

EXAMPLE 373

Assay for Inhibition of RANTES Binding to HEK293F.CCR5 Cells

For the competition binding studies, a concentration range of antagonist was incubated for 45 minutes at room temperature in binding buffer (50 mM HEPES, 5 mM MgCl$_2$, 1 mM CaCl$_2$, 0.2% BSA pH 7.4) with 8 μg of HEK293F.CCR5 cell membrane and 50 pM $^{125}$I-RANTES (Perkin Elmer, 81400 GBq/mmol) in Milipore GF-B filter plates. Unbound $^{125}$I-RANTES was removed by washing with cold 50 mM HEPES, 0.5 M NaCl pH 7.4. Compounds were tested at a concentration range of 10000-0.6 nM. The 50% inhibitory concentration (IC$_{50}$ value) was defined as the concentration of test compound required to inhibit RANTES binding by 50% relative to untested controls.

When tested in the assay described above, the compounds of the invention exhibited IC$_{50}$'s in the range of 1 nM to 500 nM.

EXAMPLE 374

Assay for Inhibition of HIV-1 Using PBMC and R5

Performed as described in literature (Inhibition of T-tropic HIV strains by selective antagonization of the chemokine receptor CXCR4. 1997—D. Schols, S. Struyf, J. Van Damme, J. A. Esté, G. Henson & E. De Clercq. J. Exp. Med. 186, 1383-1388.)

The method were as follows:

PBMC from healthy donors were isolated by density gradient centrifugation and stimulated with PHA at 1 μg/ml (Sigma Chemical Co., Bornem, Belgium) for 3 days at 37° C. The activated cells (PHA-stimulated blasts) were washed three times with PBS, and viral infections were performed. The cells were seeded in 48-well plates (5×10$^5$ cells per well in 200 uL culture medium) and pre-incubated for 15 min with compounds at different concentrations. Then 500 pg p24 viral Ag/well of CCR5-using viruses was added. The HIV-1 R5 strains BaL, SF-162, ADA, and JR-FL were all obtained through the Medical Research Council AIDS reagent project (Herts, UK).

HIV-infected or mock-infected PHA-stimulated blasts were then further cultured in the presence of 25 U/ml of IL-2 and supernatant was collected at days 8-10, and HIV-1 core antigen in the culture supernatant was analyzed by the p24 Ag ELISA kit from DuPont-Merck Pharmaceutical Co. (Wilmington, Del.).

When tested in the assay described above, many compounds of the invention exhibited IC$_{50}$'s in the range of 0.01 nM to 50 μM.

The invention claimed is:
1. A compound or a pharmaceutically acceptable salt thereof, having the formula:

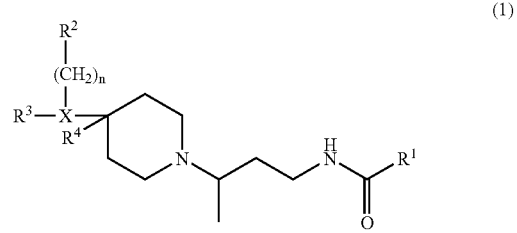

(1)

where
n is 0 or 1;
R$^1$ is pyridinyl or pyrimidinyl, each optionally substituted by one or more halogen, alkyl, amine or heteroaryl;
R$^2$ is phenyl, pyridinyl, thiazolyl, furanyl, or thiophenyl, each of which is optionally linked to one or more C1-C6 alkyl, alkoxy, trifluoromethyl, carboxylalkyl, cyano, or halogen;
R$^3$ is phenyl, pyridinyl, thiazolyl, oxazolyl, pyrimidinyl, indolyl, indolinyl, isoindolinyl, 1,3-benzodioxolyl, 1,4-benzodioxanyl, benzofuranyl, 2,3-dihydroxybenzofuranyl or phthalanyl, each of which is optionally linked to one or more C1-C6 alkyl, trifluoromethyl, oxotrifluoromethyl, carboxylalkyl, cyano, halogen, sulfanyl, SO$_2$R$^9$, where R$^9$ is alkyl, amine or amino alkyl, C(O)R$^{10}$, where R$^{10}$ is alkyl, amine, morpholine, NMe$_2$, N(OMe)Me, NHPh, piperidine, NHMe, piperazine, NHCH$_2$C(O)OMe or PhC(O)OH, OR$^{11}$, where R$^{11}$ is H, alkyl, (CH$_2$)$_2$OMe, CH$_2$C(O)NH$_2$, CH$_2$C(O)NHNH$_2$, CH$_2$C(O)OCMe$_3$, CH$_2$C(O)OMe, CH$_2$C(O)OH, PhC(O)OH, PhC(O)NH$_2$, SO$_2$Me, C(O)Me, C(O)OMe, C(O)NEt$_2$, C(O)NMe$_2$ or

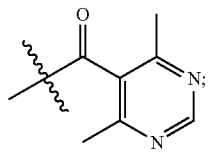

NHR$^{12}$, where R$^{12}$ is H, C(O)Me, C(O)CF$_3$, SO$_2$Me, C(O)NH$_2$, C(O)NMe$_2$ or

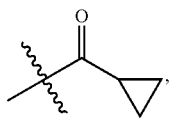

NO$_2$, CH$_2$PhC(O)OH, SOMe, CH$_2$NHC(O)Me, morpholine, CH=CHC(O)OMe, CH=CHC(O)OH,

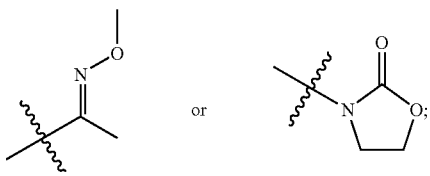

and

R$^4$ is hydrogen or alkyl.

2. The compound of claim 1, where R$^4$ is hydrogen.

3. A pharmaceutical composition comprising the compound of claim 1 and a pharmaceutically acceptable carrier.

4. A compound or a pharmaceutically acceptable salt thereof, selected from the group consisting of N-(3-{4-[(4-Bromo-phenyl)-(3-chloro-benzyl)-amino]-piperidin-1-yl}-butyl)-3,5-dichloro-isonicotinamide (62);

N-(3-{4-[Benzyl-(4-cyano-phenyl)-amino]-piperidin-1-yl}-butyl)-3,5-dichloro-isonicotinamide (63);

3,5-Dichloro-N-(3-{4-[(4-cyano-phenyl)-(3-fluoro-benzyl)-amino]-piperidin-1-yl}-butyl)-isonicotinamide (64);

3,5-Dichloro-N-(3-{4-[(3-chloro-benzyl)-(4-cyano-phenyl)-amino]-piperidin-1-yl}-butyl)-isonicotinamide (65);

3,5-Dichloro-N-(3-{4-[(4-cyano-phenyl)-(3-methyl-benzyl)-amino]-piperidin-1-yl}-butyl)-isonicotinamide (66);

N-(3-{4-[Benzyl-(4-trifluoromethyl-phenyl)-amino]-piperidin-1-yl}-butyl)-3,5-dichloro-isonicotinamide (67);

3,5-Dichloro-N-(3-{4-[(3-fluoro-benzyl)-(4-trifluoro-methyl-phenyl)-amino]-piperidin-1-yl}-butyl)-isonicotinamide (68);

3,5-Dichloro-N-(3-{4-[(3-chloro-benzyl)-(4-trifluoromethyl-phenyl)-amino]-piperidin-1-yl}-butyl)-isonicotinamide (69);

N-(3-{4-[Benzyl-(4-trifluoromethoxy-phenyl)-amino]-piperidin-1-yl}-butyl)-3,5-dichloro-isonicotinamide (70);

3,5-Dichloro-N-(3-{4-[(3-methyl-benzyl)-(4-trifluoromethoxy-phenyl)-amino]-piperidin-1-yl}-butyl)-isonicotinamide (71);

3,5-Dichloro-N-(3-{4-[(3-fluoro-benzyl)-(4-methylsulfanyl-phenyl)-amino]-piperidin-1-yl}-butyl)-isonicotinamide (72);

3,5-Dichloro-N-(3-{4-[(3-chloro-benzyl)-(4-methylsulfanyl-phenyl)-amino]-piperidin-1-yl}-butyl)-isonicotinamide (73);

3,5-Dichloro-N-(3-{4-[(3-methyl-benzyl)-(4-methylsulfanyl-phenyl)-amino]-piperidin-1-yl}-butyl)-isonicotinamide (74);

3,5-Dichloro-N-(3-{4-[(3-chloro-benzyl)-(4-methanesulfonyl-phenyl)-amino]-piperidin-1-yl}-butyl)-isonicotinamide (75);

3,5-Dichloro-N-(3-{4-[(4-methanesulfonyl-phenyl)-(3-methyl-benzyl)-amino]-piperidin-1-yl}-butyl)-isonicotinamide (76);

3,5-Dichloro-N-(3-{4-[(3-fluoro-benzyl)-(4-methoxy-phenyl)-amino]-piperidin-1-yl}-butyl)-isonicotinamide (77);

3,5-Dichloro-N-(3-{4-[(3-chloro-benzyl)-(4-methoxy-phenyl)-amino]-piperidin-1-yl}-butyl)-isonicotinamide (78);

N-(3-{4-Benzyl-(4-methylsulfamoyl-phenyl)-amino]-piperidin-1-yl}-butyl)-3,5-dichloro-isonicotinamide (79);

Methanesulfonic acid 4-[benzyl-(1-{3-[(3,5-dichloro-pyridine-4-carbonyl)-amino]-1-methyl-propyl}-piperidin-4-yl)-amino]-phenyl ester (80);

N-(3-{4-[Benzyl-(4-nitro-phenyl)-amino]-piperidin-1-yl}-butyl)-3,5-dichloro-isonicotinamide (81);

3,5-Dichloro-N-(3-{4-[(3-chloro-benzyl)-(4-nitro-phenyl)-amino]-piperidin-1-yl}-butyl)-isonicotinamide (82);

N-(3-{4-[Benzyl-(4-sulfamoyl-phenyl)-amino]-piperidin-1-yl}-butyl)-3,5-dichloro-isonicotinamide (83);

4,6-Dimethyl-pyrimidine-5-carboxylic acid (3-{4-[(3-fluoro-benzyl)-(4-nitro-phenyl)-amino]-piperidin-1-yl}-butyl)-amide (84);

4,6-Dimethyl-pyrimidine-5-carboxylic acid (3-{4-[(4-cyano-phenyl)-(3-fluoro-benzyl)-amino]-piperidin-1-yl}-butyl)-amide (95);

4-{4-[Benzyl-(1-{3-[(4,6-dimethyl-pyrimidine-5-carbonyl)-amino]-1-methyl-propyl}-piperidin-4-yl)-amino]-phenoxy}-benzoic acid (96);

4-{4-[Benzyl-(1-{1-methyl-3-[(4-methyl-pyridine-3-carbonyl)-amino]-propyl}-piperidin-4-yl)-amino]-phenoxyl}-benzoic acid (99);

4-{4-[Benzyl-(1-{3-[(4,6-dimethyl-pyrimidine-5-carbonyl)-amino]-1-methyl-propyl}-piperidin-4-yl)-amino]-benzyl}-benzoic acid (102);

N-(3-{4-[(4-Bromo-phenyl)-(3-cyano-benzyl)-amino]-piperidin-1-yl}-butyl)-3,5-dichloro-isonicotinamide (103);

3,5-Dichloro-N-(3-{4-[(3-cyano-benzyl)-(4-trifluoro-methyl-phenyl)-amino]-piperidin-1-yl}-butyl)-isonicotinamide (104);

3,5-Dichloro-N-(3-{4-[(3-cyano-benzyl)-(4-methylsulfanyl-phenyl)-amino]-piperidin-1-yl}-butyl)-isonicotinamide (105);

3,5-Dichloro-N-(3-{4-[(3-cyano-benzyl)-(4-cyano-phenyl)-amino]-piperidin-1-yl}-butyl)-isonicotinamide (106);

4-[(3-Cyano-benzyl)-(1-{3-[(3,5-dichloro-pyridine-4-carbonyl)-amino]-1-methyl-propyl}-piperidin-4-yl)-amino]-benzoic acid methyl ester (107);

3,5-Dichloro-N-(3-{4-[(4-chloro-phenyl)-(3-cyano-benzyl)-amino]-piperidin-1-yl}-butyl)-isonicotinamide (108);

4,6-Dimethyl-pyrimidine-5-carboxylic acid (3-{4-[(4-acetylamino-phenyl)-(3-cyano-benzyl)-amino]-piperidin-1-yl}-butyl)-amide (111);

4,6-Dimethyl-pyrimidine-5-carboxylic acid [3-(4-{(3-cyano-benzyl)-[4-(2-methoxy-ethoxy)-phenyl]-amino}-piperidin-1-yl)-butyl]-amide (114);

4,6-Dimethyl-pyrimidine-5-carboxylic acid (3-{4-[(3-cyano-benzyl)-(4-hydrazinocarbonylmethoxy-phenyl)-amino]-piperidin-1-yl}-butyl)-amide (116);

4,6-Dimethyl-pyrimidine-5-carboxylic acid (3-{4-[(3-cyano-benzyl)-(4-methanesulfonylamino-phenyl)-amino]-piperidin-1-yl}-butyl)-amide (118);

4,6-Dimethyl-pyrimidine-5-carboxylic acid (3-{4-[(3-cyano-benzyl)-(4-methoxy-phenyl)-amino]-piperidin-1-yl}-butyl)-amide (119);

4,6-Dimethyl-pyrimidine-5-carboxylic acid (3-{4-[(3-cyano-benzyl)-(4-trifluoromethoxy-phenyl)-amino]-piperidin-1-yl}-butyl)-amide (123);

3,5-Dichloro-N-(3-{4-[(3-cyano-benzyl)-(4-methanesulfinyl-phenyl)-amino]-piperidin-1-yl}-butyl)-isonicotinamide (125);

3,5-Dichloro-N-(3-{4-[(3-cyano-benzyl)-(4-methanesulfonyl-phenyl)-amino]-piperidin-1-yl}-butyl)-isonicotinamide (126);

3,5-Dichloro-N-(3-{4-[(3-cyano-benzyl)-(4-nitro-phenyl)-amino]-piperidin-1-yl}-butyl)-isonicotinamide (127);

3,5-Dichloro-N-(3-{4-[(3-cyano-benzyl)-(4-dimethylcarbamoyl-phenyl)-amino]-piperidin-1-yl}-butyl)-isonicotinamide (128);

4,6-Dimethyl-pyrimidine-5-carboxylic acid (3-{4-[(3-cyano-benzyl)-(4-dimethylcarbamoyl-phenyl)-amino]-piperidin-1-yl}-butyl)-amide (129);

4,6-Dimethyl-pyrimidine-5-carboxylic acid (3-{4-[(3-cyano-benzyl)-(4-methylcarbamoyl-phenyl)-amino]-piperidin-1-yl}-butyl)-amide (133);

4,6-Dimethyl-pyrimidine-5-carboxylic acid [3-(4-{(3-cyano-benzyl)-[4-(piperazine-1-carbonyl)-phenyl]-amino}-piperidin-1-yl)-butyl]-amide (135);

4,6-Dimethyl-pyrimidine-5-carboxylic acid 4-[(3-cyano-benzyl)-(1-{3-[(4,6-dimethyl-pyrimidine-5-carbonyl)-amino]-1-methyl-propyl}-piperidin-4-yl)-amino]-phenyl ester (136);

Acetic acid 4-[(3-cyano-benzyl)-(1-{3-[(4,6-dimethyl-pyrimidine-5-carbonyl)-amino]-1-methyl-propyl}-piperidin-4-yl)-amino]-phenyl ester (138);

Carbonic acid 4-[(3-cyano-benzyl)-(1-{3-[(4,6-dimethyl-pyrimidine-5-carbonyl)-amino]-1-methyl-propyl}-piperidin-4-yl)-amino]-phenyl ester methyl ester (140);

{4-[(Cyano-benzyl)-(1-{3-[(4,6-dimethyl-pyrimidine-5-carbonyl)-amino]-1-methyl-propyl}-piperidin-4-yl)-amino-phenoxy}-acetic acid tert-butyl ester (144);

Dimethyl-carbamic acid 4-[(3-cyano-benzyl)-(1-{3-[(4,6-dimethyl-pyrimidine-5-carbonyl)-amino]-1-methyl-propyl}-piperidin-4-yl)-amino]-phenyl ester (146);

{4-[(3-Cyano-benzyl)-(1-{3-[(4,6-dimethyl-pyrimidine-5-carbonyl)-amino]-1-methyl-propyl}-piperidin-4-yl)-amino]-phenoxyl-acetic acid methyl ester (148);

{4-[(3-Cyano-benzyl)-(1-{3-[(4,6-dimethyl-pyrimidine-5-carbonyl)-amino]-1-methyl-propyl}-piperidin-4-yl)-amino]-phenoxyl-acetic acid (150);

4,6-Dimethyl-pyrimidine-5-carboxylic acid (3-{4-[(3-cyano-benzyl)-(4-methylsulfamoyl-phenyl)-amino]-piperidin-1-yl}-butyl)-amide (152);

4,6-Dimethyl-pyrimidine-5-carboxylic acid [3-(4-{(3-cyano-benzyl)-[4-(cyclopropanecarbonyl-amino)-phenyl]-amino}-piperidin-1-yl)-butyl]-amide (154);

4,6-Dimethyl-pyrimidine-5-carboxylic acid [3-(4-{(3-cyano-benzyl)-[4-(2,2,2-trifluoro-acetylamino)-phenyl]-amino}-piperidin-1-yl)-butyl]-amide (157);

4,6-Dimethyl-pyrimidine-5-carboxylic acid (3-{4-[(3-cyano-benzyl)-(4-ureido-phenyl)-amino]-piperidin-1-yl}-butyl)-amide (159);

4,6-Dimethyl-pyrimidine-5-carboxylic acid [3-(4-{(3-cyano-benzyl)-[4-(2-oxo-oxazolidin-3-yl)-phenyl]-amino}-piperidin-1-yl)-butyl]-amide (161);

4-{4-[(3-Cyano-benzyl)-(1-{3-[(4,6-dimethyl-pyrimidine-5-carbonyl)-amino]-1-methyl-propyl}-piperidin-4-yl)-amino]-phenoxyl{-benzoic acid (162);

4,6-Dimethyl-pyrimidine-5-carboxylic acid (3-{4-[(4-carbamoyl-phenyl)-(3-cyano-benzyl)-amino]-piperidin-1-yl}-butyl)-amide (164);

4,6-Dimethyl-pyrimidine-5-carboxylic acid [3-(4-{(3-cyano-benzyl)-[4-(morpholine-4-carbonyl)-phenyl]-amino}-piperidin-1-yl)-butyl]-amide (167);

4,6-Dimethyl-pyrimidine-5-carboxylic acid (3-{4-[(3-cyano-benzyl]-(4-sulfamoyl-phenyl)-amino]-piperidine-1-yl}-butyl)-amide (168);

Methanesulfonic acid 4-[(3-cyano-benzyl)-(1-{3-[(4,6-dimethyl-pyrimidine-5-carbonyl)-amino]-1-methyl-propyl}-piperidin-4-yl)-amino]-phenyl ester (169);

4,6-Dimethyl-pyrimidine-5-carboxylic acid (3-{4-[[4-(acetylamino-methyl)-phenyl]-(3-cyano-benzyl)-amino]-piperidin-1-yl}-butyl)-amide (171);

4,6-Dimethyl-pyrimidine-5-carboxylic acid (3-{4-[(4-acetyl-phenyl)-(3-cyano-benzyl)-amino]-piperidin-1-yl}-butyl)-amide (173);

{4-[(3-Cyano-benzyl)-(1-{3-[(4,6-dimethyl-pyrimidine-5-carbonyl)-amino]-1-methyl-propyl}-piperidin-4-yl)-amino]-benzoylamino}-acetic acid methyl ester (175);

4,6-Dimethyl-pyrimidine-5-carboxylic acid (3-{4-[(3-cyano-benzyl)-(1H-indol-5-yl)-amino]-piperidin-1-yl}-butyl)-amide (178);

4,6-Dimethyl-pyrimidine-5-carboxylic acid (3-{4-[benzo[1,3]dioxol-5-yl-(3-cyano-benzyl)-amino]-piperidin-1-yl}-butyl)-amide (179);

4,6-Dimethyl-pyrimidine-5-carboxylic acid (3-{4-[(3-cyano-benzyl)-(2,3-dihydro-benzofuran-5-yl)-amino]-piperidin-1-yl}-butyl)-amide (181);

4,6-Dimethyl-pyrimidine-5-carboxylic acid (3-{4-[benzofuran-5-yl-(3-cyano-benzyl)-amino]-piperidin-1-yl}-butyl)-amide (184);

4,6-Dimethyl-pyrimidine-5-carboxylic acid (3-{4-[(3-cyano-benzyl)-(3,4-dimethoxy-phenyl)-amino]-piperidin-1-yl}-butyl)-amide (186);

4,6-Dimethyl-pyrimidine-5-carboxylic acid (3-{4-[(3-cyano-benzyl)-(2,3-dihydro-benzo[1,4]dioxin-6-yl)-amino]-piperidin-1-yl}-butyl)-amide (188);

4,6-Dimethyl-pyrimidine-5-carboxylic acid (3-{4-[(3-cyano-benzyl)-(6-methoxy-pyridin-3-yl)-amino]-piperidin-1-yl}-butyl)-amide (191);

3,5-Dichloro-N-(3-{4-[(5-chloro-2-fluoro-benzyl)-(4-cyano-phenyl)-amino]-piperidin-1-yl}-butyl)-isonicotinamide (195);

4,6-Dimethyl-pyrimidine-5-carboxylic acid (3-{4-[(5-chloro-2-fluoro-benzyl)-(4-cyano-phenyl)-amino]-piperidin-1-yl}-butyl)-amide (197);

3,5-Dichloro-N-(3-{4-[(5-chloro-2-fluoro-benzyl)-(4-chloro-phenyl)-amino]-piperidin-1-yl}-butyl)-isonicotinamide (198);

4,6-Dimethyl-pyrimidine-5-carboxylic acid (3-{4-[(5-chloro-2-fluoro-benzyl)-(4-dimethylcarbamoyl-phenyl)-amino]-piperidin-1-yl}-butyl)-amide (199);

4,6-Dimethyl-pyrimidine-5-carboxylic acid (3-{4-[(5-chloro-2-fluoro-benzyl)-(4-methoxy-phenyl)-amino]-piperidin-1-yl}-butyl)-amide (201);

4,6-Dimethyl-pyrimidine-5-carboxylic acid [3-(4-{(5-chloro-2-fluoro-benzyl)-[4-(2-methoxy-ethoxy)-phenyl]-amino}-piperidin-1-yl)-butyl]-amide (203);

4,6-Dimethyl-pyrimidine-5-carboxylic acid (3-{4-[(4-acetylamino-phenyl)-(5-chloro-2-fluoro-benzyl)-amino]-piperidin-1-yl}-butyl)-amide (205);

4,6-Dimethyl-pyrimidine-5-carboxylic acid (3-{4-[(4-carbamoyl-phenyl)-(5-chloro-2-fluoro-benzyl)-amino]-piperidin-1-yl}-butyl)-amide (207);

4,6-Dimethyl-pyrimidine-5-carboxylic acid (3-{4-[(5-chloro-2-fluoro-benzyl)-(4-sulfamoyl-phenyl)-amino]-piperidine-1-yl}-butyl)-amide (209);

4,6-Dimethyl-pyrimidine-5-carboxylic acid (3-{4-[(4-acetyl-phenyl)-(5-chloro-2-fluoro-benzyl)-amino]-piperidin-1-yl}-butyl)-amide (211);

3-[(5-Chloro-2-fluoro-benzyl)-(1-{3-[(4,6-dimethyl-pyrimidine-5-carbonyl)-amino]-1-methyl-propyl}-piperidin-4-yl)-amino]-benzoic acid methyl ester (2{3);

4,6-Dimethyl-pyrimidine-5-carboxylic acid (3-{4-[(5-chloro-2-fluoro-benzyl)-(3-methylcarbamoyl-phenyl)-amino]-piperidin-1-yl}-butyl)-amide (214);

4,6-Dimethyl-pyrimidine-5-carboxylic acid (3-{4-[(5-chloro-2-fluoro-benzyl)-(2,3-dihydro-benzo[1,4]dioxin-6-yl)-amino]-piperidin-1-yl}-butyl)-amide (215);

4,6-Dimethyl-pyrimidine-5-carboxylic acid (3-{4-[benzo[1,3]dioxol-5-yl-(5-chloro-2-fluoro-benzyl)-amino]-piperidin-1-yl}-butyl)-amide (218);

3,5-Dichloro-N-(3-{4-[(5-cyano-2-fluoro-benzyl)-(4-cyano-phenyl)-amino]-piperidin-1-yl}-butyl)-isonicotinamide (219);

4,6-Dimethyl-pyrimidine-5-carboxylic acid (3-{4-[(5-cyano-2-fluoro-benzyl)-(4-methoxy-phenyl)-amino]-piperidin-1-yl}-butyl)-amide (221);

4,6-Dimethyl-pyrimidine-5-carboxylic acid [3-(4-{(5-cyano-2-fluoro-benzyl)-[4-(2-methoxy-ethoxy)-phenyl]-amino}-piperidin-1-yl)-butyl]-amide (223);

4,6-Dimethyl-pyrimidine-5-carboxylic acid (3-{4-[(4-acetylamino-phenyl)-(5-cyano-2-fluoro-benzyl)-amino]-piperidin-1-yl}-butyl)-amide (225);

(E)-3-{4-[(5-Cyano-2-fluoro-benzyl)-(1-{3-[(4,6-dimethyl-pyrimidine-5-carbonyl)-amino]-1-methyl-propyl}-piperidin-4-yl)-amino]-phenyl 1-acrylic acid methyl ester (227);

4-{4-[(5-Cyano-2-fluoro-benzyl)-(1-{3-[(4,6-dimethyl-pyrimidine-5-carbonyl)-amino]-1-methyl-propyl}-piperidin-4-yl)-amino]-phenoxy}-benzoic acid (228);

N-((R)-3-{4-[(5-Cyano-2-fluoro-benzyl)-(4-methoxy-phenyl)-amino]-piperidin-1-yl}-butyl)-3,5-dimethyl-isonicotinamide (230);

4,6-Dimethyl-pyrimidine-5-carboxylic acid ((R)-3-{4-[(4-acetyl-phenyl)-(5-cyano-2-fluoro-benzyl)-amino]-piperidin-1-yl}-butyl)-amide (231);

N-((R)-3-{4-[(4-Acetyl-phenyl)-(5-cyano-2-fluoro-benzyl)-amino]-piperidin-1-yl}-butyl)-2,4-dimethyl-nicotinamide (232);

4,6-Dimethyl-pyrimidine-5-carboxylic acid ((R)-3-{4-[(5-cyano-2-fluoro-benzyl)-(4-hydroxy-phenyl)-amino]-piperidin-1-yl}-butyl)-amide (233);

4,6-Dimethyl-pyrimidine-5-carboxylic acid (3-{4-[(5-cyano-2-fluoro-benzyl)-(4-ureido-phenyl)-amino]-piperidin-1-yl}-butyl)-amide (234);

{4-[(5-Cyano-2-fluoro-benzyl)-(1-{(R)-3-[(4,6-dimethyl-pyrimidine-5-carbonyl)-amino]-1-methyl-propyl}-piperidin-4-yl)-amino]-phenoxy}-acetic acid tert-butyl ester (235);

{4-[(5-Cyano-2-fluoro-benzyl)-(1-{(R)-3-[(4,6-dimethyl-pyrimidine-5-carbonyl)-amino]-1-methyl-propyl}-piperidin-4-yl)-amino]-phenoxy}-acetic acid methyl ester (237);

{4-[(5-Cyano-2-fluoro-benzyl)-(1-{(R)-3-[(4,6-dimethyl-pyrimidine-5-carbonyl)-amino]-1-methyl-propyl}-piperidin-4-yl)-amino]-phenoxy}-acetic acid (238); 4,6-Dimethyl-pyrimidine-5-carboxylic acid ((R)-3-{4-[(4-carbamoylmethoxy-phenyl)-(5-cyano-2-fluoro-benzyl)-amino]-piperidin-1-yl}-butyl)-amide (239);

(E)-3-{4-[(5-Cyano-2-fluoro-benzyl)-(1-{3-[(4,6-dimethyl-pyrimidine-5-carbonyl)-amino]-1-methyl-propyl}-piperidin-4-yl)-amino]-phenyl}-acrylic acid (240);

4,6-Dimethyl-pyrimidine-5-carboxylic acid (3-{4-[benzo[1,3]dioxol-5-yl-(5-cyano-2-fluoro-benzyl)-amino]-piperidin-1-yl}-butyl)-amide (242);

4,6-Dimethyl-pyrimidine-5-carboxylic acid (3-{4-[(5-cyano-2-fluoro-benzyl)-(1H-indol-5-yl)-amino]-piperidin-1-yl}-butyl)-amide (245);

4,6-Dimethyl-pyrimidine-5-carboxylic acid ((R)-3-{4-[(6-acetylamino-pyridin-3-yl)-(5-cyano-2-fluoro-benzyl)-amino]-piperidin-1-yl}-butyl)-amide (246);

4,6-Dimethyl-pyrimidine-5-carboxylic acid (3-{4-[(4-methoxy-phenyl)-thiophen-3-ylmethyl-amino]-piperidin-1-yl}-butyl)-amide (290);

4,6-Dimethyl-pyrimidine-5-carboxylic acid (3-{4-[thiophen-3-ylmethyl-(4-trifluoromethoxy-phenyl)-amino]-piperidin-1-yl}-butyl)-amide (291);

4,6-Dimethyl-pyrimidine-5-carboxylic acid ((R)-3-{4-[(4-chloro-phenyl)-thiophen-3-ylmethyl-amino]-piperidin-1-yl}-butyl)-amide (292);

4,6-Dimethyl-pyrimidine-5-carboxylic acid ((R)-3-{4-[(4-acetyl-phenyl)-thiophen-3-ylmethyl-amino]-piperidin-1-yl}-butyl)-amide (293);

4,6-Dimethyl-pyrimidine-5-carboxylic acid [(R)-3-(4-{[4-(1-methoxyimino-ethyl)-phenyl]-thiophen-3-ylmethyl-amino}-piperidin-1-yl)-butyl]-amide (294);

4,6-Dimethyl-pyrimidine-5-carboxylic acid (3-{4-[thiophen-3-ylmethyl-(4-trifluoromethyl-phenyl)-amino-piperidin-1-yl}-butyl)-amide (295);

4,6-Dimethyl-pyrimidine-5-carboxylic acid ((R)-3-{4-[(4-hydroxy-phenyl)-thiophen-3-ylmethyl-amino]-piperidin-1-yl}-butyl)-amide (296);

{4-[(1-{(R)-3-[(4,6-Dimethyl-pyrimidine-5-carbonyl)-amino]-1-methyl-propyl}-piperidin-4-yl)-thiophen-3-ylmethyl-amino]-phenoxy}-acetic acid (297);

4,6-Dimethyl-pyrimidine-5-carboxylic acid ((R)-3-{4-[(4-carbamoylmethoxy-phenyl)-thiophen-3-ylmethyl-amino]-piperidin-1-yl}-butyl)-amide (298);

4-[(1-{(R)-3-[(4,6-Dimethyl-pyrimidine-5-carbonyl)-amino]-1-methyl-propyl}-piperidin-4-yl)-thiophen-3-ylmethyl-amino]-benzoic acid methyl ester (299);

4,6-Dimethyl-pyrimidine-5-carboxylic acid (3-{4-[(4-carbamoyl-phenyl)-thiophen-3-ylmethyl-amino]-piperidin-1-yl}-butyl)-amide (300);

4,6-Dimethyl-pyrimidine-5-carboxylic acid ((R)-3-{4-[(4-bromo-phenyl)-thiophen-3-ylmethyl-amino]-piperidin-1-yl}-butyl)-amide (301);

4-{4-[(1-{(R)-3-[(4,6-Dimethyl-pyrimidine-5-carbonyl)-amino]-1-methyl-propyl}-piperidin-4-yl)-thiophen-3-ylmethyl-amino]-phenoxy}-benzoic acid (302);

4,6-Dimethyl-pyrimidine-5-carboxylic acid [(R)-3-(4-{[4-(4-carbamoyl-phenoxy)-phenyl]-thiophen-3-ylmethyl-amino}-piperidin-1-yl)-butyl]-amide (303);

4,6-Dimethyl-pyrimidine-5-carboxylic acid ((R)-3-{4-[(4-fluoro-phenyl)-thiophen-3-ylmethyl-amino]-piperidin-1-yl}-butyl)-amide (304);

4,6-Dimethyl-pyrimidine-5-carboxylic acid ((R)-3-{4-[(4-ethoxy-phenyl)-thiophen-3-ylmethyl-amino]-piperidin-1-yl}-butyl)-amide (305);

4,6-Dimethyl-pyrimidine-5-carboxylic acid (3-{4-[(4-cyano-phenyl)-thiophen-3-ylmethyl-amino]-piperidin-1-yl}-butyl)-amide (306);

4,6-Dimethyl-pyrimidine-5-carboxylic acid ((R)-3-{4-[(4-methylsulfanyl-phenyl)-thiophen-3-ylmethyl-amino]-piperidin-1-yl}-butyl)-amide (307);

4,6-Dimethyl-pyrimidine-5-carboxylic acid ((R)-3-{4-[(4-methanesulfonyl-phenyl)-thiophen-3-ylmethyl-amino]-piperidin-1-yl}-butyl)-amide (308);

3,5-Dimethyl-N-((R)-3-{4-[thiophen-3-ylmethyl-(4-trifluoromethoxy-phenyl)-amino]-piperidin-1-yl}-butyl)-isonicotinamide (309);

2,4-Dimethyl-N-((R)-3-{4-[thiophen-3-ylmethyl-(4-trifluoromethoxy-phenyl)-amino]-piperidin-1-yl}-butyl)-nicotinamide (316);

N-((R)-3-{4-[(4-Methoxy-phenyl)-thiophen-3-ylmethyl-amino]-piperidin-1-yl}-butyl)-2,4-dimethyl-nicotinamide (321);

3,5-Dichloro-N-((R)-3-{4-[(4-methoxy-phenyl)-thiophen-3-ylmethyl-amino]-piperidin-1-yl}-butyl)-isonicotinamide (323);

N-((R)-3-{4-[(4-Methoxy-phenyl)-thiophen-3-ylmethyl-amino]-piperidin-1-yl}-butyl)-3,5-dimethyl-isonicotinamide (325);

4,6-Dimethyl-pyrimidine-5-carboxylic acid {3-[4-(pyridin-3-yl-thiophen-3-ylmethyl-amino)-piperidin-1-yl]-butyl}-amide (327);

4,6-Dimethyl-pyrimidine-5-carboxylic acid ((R)-3-{4-[(6-acetylamino-pyridin-3-yl)-thiophen-3-ylmethyl-amino]-piperidin-1-yl}-butyl)-amide (328);

4,6-Dimethyl-pyrimidine-5-carboxylic acid (3-{4-[(6-chloro-pyridin-3-yl)-thiophen-3-ylmethyl-amino]-piperidin-1-yl}-butyl)-amide (329);

4,6-Dimethyl-pyrimidine-5-carboxylic acid (3-{4-[(6-bromo-pyridin-3-yl)-thiophen-3-ylmethyl-amino]-piperidin-1-yl}-butyl)-amide (330);

4,6-Dimethyl-pyrimidine-5-carboxylic acid ((R)-3-{4-[(6-ethoxy-pyridin-3-yl)-thiophen-3-ylmethyl-amino]-piperidin-1-yl}-butyl)-amide (331);

2,4-Dimethyl-N-{3-[4-(pyridin-3-yl-thiophen-3-ylmethyl-amino)-piperidin-1-yl]-butyl}-nicotinamide (334);

3,5-Dichloro-N-{3-[4-(pyridin-3-yl-thiophen-3-ylmethyl-amino)-piperidin-1-yl]-butyl}-isonicotinamide (336);

3,5-Dimethyl-N-{3-[4-(pyridin-3-yl-thiophen-3-ylmethyl-amino)-piperidin-1-yl]-butyl}-isonicotinamide (337);

4,6-Dimethyl-pyrimidine-5-carboxylic acid {3-[4-(pyrimidin-5-yl-thiophen-3-ylmethyl-amino)-piperidin-1-yl]-butyl}-amide (339);

4,6-Dimethyl-pyrimidine-5-carboxylic acid ((R)-3-{4-[(4-methoxy-phenyl)-(4-methyl-thiophen-3-ylmethyl)-amino]-piperidin-1-yl}-butyl)-amide (342);

4,6-Dimethyl-pyrimidine-5-carboxylic acid ((R)-3-{4-[(4-bromo-thiophen-3-ylmethyl)-(4-methoxy-phenyl)-amino]-piperidin-1-yl}-butyl)-amide (343);

4,6-Dimethyl-pyrimidine-5-carboxylic acid ((R)-3-{4-[(4-methoxy-phenyl)-(4-methoxy-thiophen-3-ylmethyl)-amino]-piperidin-1-yl}-butyl)-amide (344);

4,6-Dimethyl-pyrimidine-5-carboxylic acid {(R)-3-[4-(benzo[1,3]dioxol-5-yl-thiophen-3-ylmethyl-amino)-piperidin-1-yl]-butyl}-amide (345);

4,6-Dimethyl-pyrimidine-5-carboxylic acid ((R)-3-{4-[(2,3-dihydro-benzo[1,4]dioxin-6-yl)-thiophen-3-ylmethyl-amino]-piperidin-1-yl}-butyl)-amide (346);

4,6-Dimethyl-pyrimidine-5-carboxylic acid (3-{4-[(4-methoxy-phenyl)-thiophen-2-ylmethyl-amino]-piperidin-1-yl}-butyl)-amide (347);

4,6-Dimethyl-pyrimidine-5-carboxylic acid (3-{4-[(4-methoxy-phenyl)-(3-methyl-thiophen-2-ylmethyl)-amino]-piperidin-1-yl}-butyl)-amide (348);

4,6-Dimethyl-pyrimidine-5-carboxylic acid (3-{4-[(5-chloro-thiophen-2-ylmethyl)-(4-methoxy-phenyl)-amino]-piperidin-1-yl}-butyl)-amide (349);

4,6-Dimethyl-pyrimidine-5-carboxylic acid (3-{4-[furan-2-ylmethyl-(4-methoxy-phenyl)-amino]-piperidin-1-yl}-butyl)-amide (350);

4,6-Dimethyl-pyrimidine-5-carboxylic acid (3-{4-[(4-methoxy-phenyl)-(4-methyl-pyridin-3-ylmethyl)-amino]-piperidin-1-yl}-butyl)-amide (351);

4,6-Dimethyl-pyrimidine-5-carboxylic acid (3-{4-[(4-bromo-phenyl)-(4-methyl-pyridin-3-ylmethyl)-amino]-piperidin-1-yl}-butyl)-amide (352);

4,6-Dimethyl-pyrimidine-5-carboxylic acid (3-{4-[(4-methyl-pyridin-3-ylmethyl)-p-tolyl-amino]-piperidin-1-yl}-butyl)-amide (353);

4,6-Dimethyl-pyrimidine-5-carboxylic acid ((R)-3-{4-[(4-methyl-pyridin-3-ylmethyl)-(4-methylsulfanyl-phenyl)-amino]-piperidin-1-yl}-butyl)-amide (354);

4,6-Dimethyl-pyrimidine-5-carboxylic acid (3-{4-[(4-carbamoyl-phenyl)-(4-methyl-pyridin-3-ylmethyl)-amino]-piperidin-1-yl}-butyl)-amide (355);

4,6-Dimethyl-pyrimidine-5-carboxylic acid ((R)-3-{4-[(4-methyl-pyridin-3-ylmethyl)-(4-trifluoromethoxy-phenyl)-amino]-piperidin-1-yl}-butyl)-amide (356);

N-(3-{4-[(4-Methoxy-phenyl)-(4-methyl-pyridin-3-ylmethyl)-amino]-piperidin-1-yl}-butyl)-3,5-dimethyl-isonicotinamide (357);

N-((R)-3-{4-[(4-Methoxy-phenyl)-(4-methyl-pyridin-3-ylmethyl)-amino]-piperidin-1-yl}-butyl)-2,4-dimethyl-nicotinamide (359);

3,5-Dichloro-N-((R)-3-{4-[(4-methoxy-phenyl)-(4-methyl-pyridin-3-ylmethyl)-amino]-piperidin-1-yl}-butyl)-isonicotinamide (362);

N-(3-{4-[(4-Carbamoyl-phenyl)-(4-methyl-pyridin-3-ylmethyl)-amino]-piperidin-1-yl}-butyl)-2,4-dimethyl-nicotinamide (366);

N-((R)-3 {4-[(4-Carbamoylmethoxy-phenyl)-(4-methylpyridin-3-ylmethyl)-amino]-piperidin-1-yl}-butyl)-2,4-dimethyl-nicotinamide (367);

Methanesulfonic acid 4-[(1-{(R)-3-[(2,4-dimethyl-pyridine-3-carbonyl)-amino]-1-methyl-propyl}-piperidin-4-yl)-(4-methyl-pyridin-3-ylmethyl)-amino]-phenyl ester (368); and 2,4-Dimethyl-N-(3-{4-[(4-methyl-pyridin-3-ylmethyl)-(4-morpholin-4-yl-phenyl)-amino]-piperidin-1-yl}-butyl)-nicotinamide (369).

5. A pharmaceutical composition comprising the compound of claim 4 and a pharmaceutically acceptable carrier.

6. The compound of claim 1, wherein $R^3$ is indolyl, 1,3-benzodioxolyl, 1,4-benzodioxanyl, or benzofuranyl.

* * * * *